US012642768B2

(12) United States Patent
Yang et al.

(10) Patent No.: US 12,642,768 B2
(45) Date of Patent: *Jun. 2, 2026

(54) LIPID NANOPARTICLES

(71) Applicants: Beijing Jitai Life Sciences Ltd, Beijing (CN); Hangzhou Jitai Life Sciences Ltd, Hangzhou (CN); Metis TechBio Co., Ltd., Beijing (CN)

(72) Inventors: Liu Yang, Beijing (CN); Le Yin, Beijing (CN); Andong Liu, Beijing (CN); Lin Zhang, Beijing (CN); Caida Lai, Hangzhou (CN); Wenshou Wang, Hangzhou (CN)

(73) Assignees: Beijing Jitai Life Sciences Ltd, Beijing (CN); Hangzhou Jitai Life Sciences Ltd, Hangzhou (CN); Metis TechBio Co., Ltd., Beijing (CN)

( * ) Notice: Subject to any disclaimer, the term of this patent is extended or adjusted under 35 U.S.C. 154(b) by 520 days.

This patent is subject to a terminal disclaimer.

(21) Appl. No.: 18/150,528

(22) Filed: Jan. 5, 2023

(65) Prior Publication Data

US 2023/0346702 A1 Nov. 2, 2023

(30) Foreign Application Priority Data

Apr. 29, 2022 (CN) ........................ 202210478132.X
Apr. 29, 2022 (CN) ........................ 202210478559.X
Oct. 26, 2022 (CN) ........................ 202211319726.2
Nov. 14, 2022 (CN) ........................ 202211419648.3

(51) Int. Cl.
*A61K 9/1271* (2025.01)

(52) U.S. Cl.
CPC .................................. *A61K 9/1271* (2013.01)

(58) Field of Classification Search
None
See application file for complete search history.

(56) References Cited

U.S. PATENT DOCUMENTS

| | | | | |
|---|---|---|---|---|
| 11,246,933 | B1 | 2/2022 | Maier et al. | |
| 12,162,819 | B2 * | 12/2024 | Zhang | C07C 275/16 |
| 2015/0306039 | A1 * | 10/2015 | Akinc | A61K 9/0019 514/786 |
| 2019/0022247 | A1 | 1/2019 | Ansell et al. | |
| 2019/0374646 | A1 * | 12/2019 | Maier | C07C 211/10 |
| 2020/0254086 | A1 * | 8/2020 | Hoge | A61K 39/12 |
| 2020/0306191 | A1 | 10/2020 | Schariter et al. | |

FOREIGN PATENT DOCUMENTS

| | | | |
|---|---|---|---|
| CN | 110520409 | A | 11/2019 |
| CN | 111315359 | A | 6/2020 |
| CN | 111417621 | A | 7/2020 |
| CN | 113164379 | A | 7/2021 |
| CN | 113908292 | A | 1/2022 |
| CN | 114073677 | A | 2/2022 |
| CN | 115850104 | A | 3/2023 |
| CN | 115887674 | A | 4/2023 |
| CN | 116348147 | A | 6/2023 |
| CN | 116969851 | A | 10/2023 |
| CN | 117243922 | A | 12/2023 |
| WO | 2013086322 | A1 | 6/2013 |
| WO | 2013086354 | A1 | 6/2013 |
| WO | 2014089239 | A1 | 6/2014 |
| WO | 2021/030701 | A1 | 2/2021 |
| WO | 2021204175 | A1 | 10/2021 |
| WO | 2022/013443 | A1 | 1/2022 |
| WO | 2022/076547 | A1 | 4/2022 |
| WO | 2022204288 | A1 | 9/2022 |
| WO | 2023086465 | A1 | 5/2023 |
| WO | 2024026482 | A1 | 2/2024 |

OTHER PUBLICATIONS

Soohyung Park, Yeol Kyo Choi, Seonghoon Kim, Jumin Lee, and Wonpil Im. "CHARMM-GUI Membrane Builder for Lipid Nanoparticles with Ionizable Cationic Lipids and PEGylated Lipids." Journal of Chemical Information and Modeling, vol. 61, 2021, pp. 5192-5202 and 14 supplemental pages (Year: 2021).*

Maier et al., "Biodegradable Lipids Enabling Rapidly Eliminated Lipid Nanoparticles for Systemic Delivery of RNAi Therapeutics," Mol Therapy (2013) vol. 21, No. 8, pp. 1570-1578.

International Search Report and Written Opinion in International Patent Application No. PCT/CN2022/136858 dated Feb. 27, 2023.

International Search Report and Written Opinion in International Patent Application No. PCT/CN2022/136859 dated Jan. 18, 2023.

International Search Report and Written Opinion from PCT/CN2025/079791, mailed May 13, 2025, Chinese with machine translation.

International Search Report and Written Opinion from PCT/CN2025/079792, mailed Jun. 13, 2025, Chinese with machine translation.

* cited by examiner

*Primary Examiner* — Isaac Shomer
(74) *Attorney, Agent, or Firm* — K&L Gates LLP

(57) ABSTRACT

The present disclosure provides a lipid nanoparticle wherein the lipid ingredient comprises a compound of formula (IV). The present disclosure also provides a method of preparing the lipid nanoparticle, a pharmaceutical composition of the lipid nanoparticle, and use of the lipid nanoparticle and pharmaceutical compositions in the delivery of nucleic acids.

(IV)

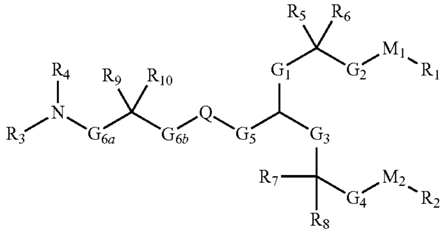

35 Claims, No Drawings

LIPID NANOPARTICLES

CROSS REFERENCE TO RELATED APPLICATIONS

The present application claims the priority of the Chinese Patent Application No. 202210478559.X filed on Apr. 29, 2022, Chinese Patent Application No. 202210478132.X filed on Apr. 29, 2022, Chinese Patent Application No. 202211319726.2 filed on Oct. 26, 2022, and Chinese Patent Application No. 202211419648.3 filed on Nov. 14, 2022. The Chinese Patent Applications mentioned above are incorporated herein by reference as part of the disclosure of the present application.

FIELD OF THE INVENTION

The present disclosure relates to a new lipid nanoparticle wherein the lipid ingredient comprises a new class of ionizable cationic lipid compound, or pharmaceutically acceptable salts, isotopic variants, tautomers or stereoisomers thereof. The present disclosure also relates to a method of preparing the lipid nanoparticle, a pharmaceutical composition comprising the lipid nanoparticle, and use of the lipid nanoparticle or the pharmaceutical composition in the delivery of biologically active substances such as nucleic acids (e.g., mRNA, miRNA, siRNA, saRNA, ASO, and DNA, etc.).

BACKGROUND OF THE INVENTION

Gene therapy refers to the introduction of exogenous genes into target cells to correct or compensate for genetic defects or abnormalities within the cell, so as to achieve the purpose of treatment. In the past few decades, research related to the treatment of clinical diseases through gene therapy has received more and more attention. Especially in recent years, siRNA-related drugs and mRNA vaccines have been approved by the FDA for clinical treatment, which has further promoted research and related investment in the field of gene therapy.

Due to their unique nature, nucleic acid drugs are able to act on non-druggable targets that are difficult to be acted upon by conventional small molecule chemical drugs, proteins or antibodies, and have significant applications values in the treatment or prevention of diseases such as tumors, infectious diseases and genetic diseases.

However, nucleic acid substances are easily degraded by nucleases in organisms, and nucleic acid substances themselves are negatively charged, which makes it difficult for them to enter the cell through the cell membrane. Thus, delivery technology is a major challenge in nucleic acid drug development.

As a nucleic acid delivery material, lipid nanoparticles (LNP) are one of the most important nucleic acid delivery systems with the advantages of easy to prepare, good biodegradability, no immunogenicity and good safety. The nucleic acid vaccine developed by Moderna and BioNTech uses LNP as the delivery system, and the main components of LNP include cationic lipids, cholesterol, neutral lipids and polyethylene glycol-conjugated lipids. Among them, cationic lipid molecules are the core of LNP delivery system, and their molecular structure plays a decisive role in the delivery efficiency, targeting, and formulation stability, and the like, of the entire liposome nanoparticles.

Due to the different requirements of the delivery system for the delivery of different kinds of nucleic acid substances and the specific delivery of different targets, in order to meet the different needs of gene therapy, further development of new lipid molecules and continuous improvement of LNP technology are needed to obtain new LNP formulations with good nucleic acid delivery efficiency.

SUMMARY OF THE INVENTION

The present disclosure develops a new class of lipid nanoparticles that can be used to deliver various biologically active substances with high delivery efficiency.

In one aspect, the present disclosure provides a nanoparticle composition, comprising a lipid ingredient, and optionally comprising a load;

wherein the lipid ingredient comprises the following components in the molar percentages:

Ionizable cationic lipids 20 mol %-85 mol %;

Structure lipids 10 mol %-75 mol %;

Neutral lipids 1.0 mol %-30 mol %;

Polymer lipids 0.25 mol %-10 mol %;

wherein the ionizable cationic lipid is the compound of formula (IV), or a pharmaceutically acceptable salt, isotopic variant, tautomer or stereoisomer thereof, (IV)

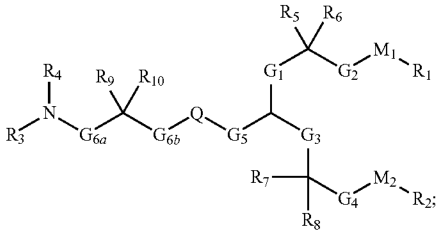

wherein, $M_1$ and $M_2$ are independently selected from —C(O)O—, —O—, —SC(O)O—, —OC(O)NR$_a$—, —NR$_a$C(O)NR$_a$—, —OC(O)S—, —OC(O)O—, —NR$_a$C(O)O—, —OC(O)—, —SC(O)—, —C(O)S—, —NR$_a$—, —C(O)NR$_a$—, —NR$_a$C(O)—, —NR$_a$C(O)S—, —SC(O)NR$_a$—, —C(O)—, —OC(S)—, —C(S)O—, —OC(S)NR$_a$—, —NR$_a$C(S)O—, —S—S— and —S(O)$_{0-2}$—;

Q is selected from a chemical bond, —C(O)O—, —O—, —SC(O)O—, —OC(O)NR$_b$—, —NR$_b$C(O)NR$_b$—, —OC(O)S—, —OC(O)O—, —NR$_b$C(O)O—, —OC(O)—, —SC(O)—, —C(O)S—, —NR$_b$—, —C(O)NR$_b$—, —NR$_b$C(O)—, —NR$_b$C(O)S—, —SC(O)NR$_b$—, —C(O)—, —OC(S)—, —C(S)O—, —OC(S)NR$_b$—, —NR$_b$C(S)O—, —S—S—, —S(O)$_{0-2}$—, phenylene and pyridylidene, wherein, the phenylene or pyridylidene is optionally substituted with one or more R*;

$G_5$ is a chemical bond or $C_{1-8}$ alkylene, which is optionally substituted with one or more R**;

$G_{6a}$ and $G_{6b}$ are independently a chemical bond or $C_{1-7}$ alkylene, which is optionally substituted with one or more R**;

$G_{6a}$ and $G_{6b}$ have a total length of 0, 1, 2, 3, 4, 5, 6 or 7 carbon atoms;

$R_9$, $R_{10}$ and R** are independently H, $C_{1-8}$ alkyl, -$L_c$-OR$_c$, -$L_c$-SR$_c$ or -$L_c$-NR$_c$R'$_c$;

$G_1$, $G_2$, $G_3$ and $G_4$ are independently a chemical bond, $C_{1-13}$ alkylene, $C_{2-13}$ alkenylene or $C_{2-13}$ alkynylene, which is optionally substituted with one or more $R^s$;

$G_1$ and $G_2$ have a total length of 3, 4, 5, 6, 7, 8, 9, 10, 11, 12 or 13 carbon atoms;

$G_3$ and $G_4$ have a total length of 3, 4, 5, 6, 7, 8, 9, 10, 11, 12 or 13 carbon atoms;

$R_3$ and $R_4$ are independently H, $C_{1-10}$ alkyl, $C_{1-10}$ haloalkyl, $C_{2-10}$ alkenyl, $C_{2-10}$ alkynyl, 3- to 14-membered cycloalkyl, 3- to 14-membered heterocyclyl, $C_{6-10}$ aryl or 5- to 14-membered heteroaryl, which is optionally substituted with one or more R*;

or, $R_3$ and $R_4$ are taken together with the N atom to which they are attached to form 3- to 14-membered heterocyclyl, which is optionally substituted with one or more R*;

or, $R_4$ and $R_9$ are taken together with the atoms to which they are attached to form 3- to 14-membered heterocyclyl or 5- to 14-membered heteroaryl, which is optionally substituted with one or more R*;

R* is independently H, halogen, cyano, $C_{1-10}$ alkyl, $C_{1-10}$ haloalkyl, $-L_b-OR_b$, $-L_b-SR_b$ or $-L_b-NR_bR'_b$;

$R_5$, $R_6$, $R_7$ and $R_8$ are independently $C_{1-8}$ alkyl, which is optionally substituted with one or more R*;

$R_1$ and $R_2$ are independently $C_{4-20}$ alkyl, $C_{4-20}$ alkenyl or $C_{4-20}$ alkynyl, which is optionally substituted with one or more R, and wherein one or more methylene units are optionally and independently replaced with —NR"—;

$R^s$ is independently H, $C_{1-14}$ alkyl, $-L_d-OR_d$, $-L_d-SR_d$ or $-L_d-NR_dR'_d$;

R is independently H, $C_{1-20}$ alkyl, $-L_a-OR_a$, $-L_a-SR_a$ or $-L_a-NR_aR'_a$;

R" is independently H or $C_{1-20}$ alkyl;

$L_a$ and $L_e$ are independently a chemical bond or $C_{1-20}$ alkylene;

$L_b$ and $L_f$ are independently a chemical bond or $C_{1-10}$ alkylene;

$L_c$ is independently a chemical bond or $C_{1-8}$ alkylene;

$L_d$ is independently a chemical bond or $C_{1-14}$ alkylene;

$R_a$ and $R'_a$ are independently selected from H, $C_{1-20}$ alkyl, 3- to 14-membered cycloalkyl, and 3- to 14-membered heterocyclyl, which are optionally substituted with one or more of the following substituents: H, $C_{1-20}$ alkyl, $-L_e-OR_e$, $-L_e-SR_e$ and $-L_e-NR_eR'_e$;

$R_b$ and $R'_b$ are independently selected from H, $C_{1-10}$ alkyl, 3- to 14-membered cycloalkyl, and 3- to 14-membered heterocyclyl, which are optionally substituted with one or more of the following substituents: H, $C_{1-10}$ alkyl, $-L_f-OR_f$, $-L_f-SR_f$ and $-L_f-NR_fR'_f$;

$R_c$ and $R'_c$ are independently H or $C_{1-8}$ alkyl;

$R_d$ and $R'_d$ are independently H or $C_{1-14}$ alkyl;

$R_e$ and $R'_e$ are independently H or $C_{1-20}$ alkyl;

$R_f$ and $R'_f$ are independently H or $C_{1-10}$ alkyl.

U.S. Ser. No. 11/246,933B1 discloses that the incorporation of the biodegradable group(s) into the tail chain of a lipid compound in a lipid nanoparticle results in faster metabolism and removal of the lipid from the body following delivery of the active agent to a target area. As a result, these lipids which contain the biodegradable groups have lower toxicity than similar lipids without the biodegradable groups. The tail chain of the cationic lipid compound of the present disclosure has biodegradable group(s), thereby has superior toxicity profile to similar lipids without biodegradable groups, such as DLin-MC3-DMA.

In another aspect, the present disclosure provides a method of preparing the nanoparticle composition comprising: mixing the components of the lipid ingredient, and then with a load.

In another aspect, the present disclosure provides a pharmaceutical composition, comprising the nanoparticle composition of the present disclosure, and optionally pharmaceutically acceptable excipient(s), such as carrier(s), adjuvant(s) or vehicle(s).

In another aspect, the present disclosure provides the use of a nanoparticle composition of the present disclosure, or a pharmaceutical composition of the present disclosure in the manufacture of a medicament for treating, diagnosing, or preventing a disease.

In another aspect, the present disclosure provides the use of a nanoparticle composition of the present disclosure, or a pharmaceutical composition of the present disclosure in the manufacture of a medicament for delivering a load.

In another aspect, the present disclosure provides a method of treating, diagnosing, or preventing a disease in a subject, comprising administering to the subject a nanoparticle composition of the present disclosure, or a pharmaceutical composition of the present disclosure.

In another aspect, the present disclosure provides a nanoparticle composition of the present disclosure, or a pharmaceutical composition of the present disclosure, for use in treating, diagnosing, and/or preventing a disease.

In another aspect, the present disclosure provides a method of delivering a load in a subject, comprising administering to the subject a nanoparticle composition of the present disclosure, or a pharmaceutical composition of the present disclosure.

In another aspect, the present disclosure provides a nanoparticle composition of the present disclosure, or a pharmaceutical composition of the present disclosure, for use in delivering a load.

In a specific embodiment, the load is selected from one or more of therapeutic agents, prophylactic agents, and diagnostic agents; alternatively, the therapeutic agent, prophylactic agent, or diagnostic agent is a nucleic acid.

In a more specific embodiment, the nucleic acid is selected from one or more of ASO, RNA and DNA.

In a more specific embodiment, the RNA is selected from one or more of interfering RNA (RNAi), small interfering RNA (siRNA), short hairpin RNA (shRNA), antisense RNA (aRNA), messenger RNA (mRNA), modified messenger RNA (mmRNA), long non-coding RNA (lncRNA), microRNA (miRNA), small activating RNA (saRNA), multimeric coding nucleic acid (MCNA), polymeric coding nucleic acid (PCNA), guide RNA (gRNA), CRISPRRNA (crRNA) and nucleases, alternatively mRNA, more alternatively modified mRNA.

Terminology

Chemical Terminology

Terminology of specific functional groups and chemical terms are described in more detail below.

When a range of values is listed, it is intended to encompass each value and sub-range within the range. For example, "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

"$C_{1-28}$ alkyl" refers to a radical of a linear or branched, saturated hydrocarbon group having 1 to 28 carbon atoms. In some embodiments, $C_{4-28}$ alkyl, $C_{4-24}$ alkyl, $C_{4-20}$ alkyl, $C_{8-10}$ alkyl, $C_{2-8}$ alkyl, $C_{7-9}$ alkyl, $C_{4-6}$ alkyl, $C_{1-20}$ alkyl, $C_{1-14}$ alkyl, $C_{2-14}$ alkyl, $C_{1-13}$ alkyl, $C_{1-12}$ alkyl, $C_{1-10}$ alkyl, $C_{1-8}$ alkyl, $C_{1-7}$ alkyl, $C_{2-7}$ alkyl, $C_{1-6}$ alkyl, $C_{1-5}$ alkyl, $C_5$ alkyl, $C_{1-4}$ alkyl, $C_{2-4}$ alkyl, $C_{1-3}$ alkyl, $C_{2-3}$ alkyl, $C_{1-2}$ alkyl and Me are alternative. Examples of $C_{1-6}$ alkyl include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me ($—CH_3$), Et ($—CH_2CH_3$), iPr ($—CH(CH_3)_2$), nPr ($—CH_2CH_2CH_3$), n-Bu ($—CH_2CH_2CH_2CH_3$) or i-Bu ($—CH_2CH(CH_3)_2$).

"$C_{2-20}$ alkenyl" refers to a radical of a linear or branched hydrocarbon group having 2 to 20 carbon atoms and at least one carbon-carbon double bond. "$C_{4-28}$ alkenyl" refers to a radical of a linear or branched hydrocarbon group having 4 to 28 carbon atoms and at least one carbon-carbon double bond. In some embodiments, $C_{4-20}$ alkenyl, $C_{2-13}$ alkenyl, $C_{2-10}$ alkenyl, $C_{2-6}$ alkenyl, and $C_{2-4}$ alkenyl is alternative. Examples of $C_{2-6}$ alkenyl include vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"$C_{2-20}$ alkynyl" refers to a radical of a linear or branched hydrocarbon group having 2 to 20 carbon atoms, at least one carbon-carbon triple bond and optionally one or more carbon-carbon double bonds. "$C_{4-28}$ alkynyl" refers to a radical of a linear or branched hydrocarbon group having 4 to 28 carbon atoms, at least one carbon-carbon triple bond and optionally one or more carbon-carbon double bonds. In some embodiments, $C_{4-20}$ alkynyl, $C_{2-13}$ alkynyl, $C_{2-10}$ alkynyl, $C_{2-6}$ alkynyl, and $C_{2-4}$ alkynyl is alternative. Examples of $C_{2-6}$ alkynyl include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. The term "$C_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"$C_{1-20}$ alkylene" refers to a divalent group formed by removing another hydrogen of the $C_{1-20}$ alkyl, and can be substituted or unsubstituted. In some embodiments, $C_{4-20}$ alkylene, $C_{8-10}$ alkylene, $C_{2-8}$ alkylene, $C_{7-9}$ alkylene, $C_{4-6}$ alkylene, $C_{1-20}$ alkylene, $C_{1-14}$ alkylene, $C_{2-14}$ alkylene, $C_{1-13}$ alkylene, $C_{1-12}$ alkylene, $C_{1-10}$ alkylene, $C_{1-8}$ alkylene, $C_{1-7}$ alkylene, $C_{2-7}$ alkylene, $C_{1-6}$ alkylene, $C_{1-8}$ alkylene, $C_5$ alkylene, $C_{1-4}$ alkylene, $C_{2-4}$ alkylene, $C_{1-3}$ alkylene, $C_{2-3}$ alkylene, $C_{1-2}$ alkylene, and methylene are alternative. The unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene ($—CH_2CH_2CH_2CH_2CH_2CH_2—$), etc. Examples of substituted alkylene groups, such as those substituted with one or more alkyl (methyl) groups, include, but are not limited to, substituted methylene ($—CH(CH_3)—$, $—C(CH_3)_2—$), substituted ethylene ($—CH(CH_3)CH_2—$, $—CH_2CH(CH_3)—$, $—C(CH_3)_2CH_2—$, $—CH_2C(CH_3)_2—$), substituted propylene ($—CH(CH_3)CH_2CH_2—$, $—CH_2CH(CH_3)CH_2—$, $—CH_2CH_2CH(CH_3)—$, $—C(CH_3)_2CH_2CH_2—$, $—CH_2C(CH_3)_2CH_2—$, $—CH_2CH_2C(CH_3)_2—$), etc.

"$C_{2-13}$ alkenylene" refers to a $C_{2-13}$ alkenyl group wherein another hydrogen is removed to provide a divalent radical of alkenylene, and which may be substituted or unsubstituted. In some embodiments, $C_{2-10}$ alkenyl, $C_{2-6}$ alkenyl, and $C_{2-4}$ alkenylene is yet alternative. Exemplary unsubstituted alkenylene groups include, but are not limited to, ethylene ($—CH{=}CH—$) and propenylene (e.g., $—CH{=}CHCH_2—$, $—CH_2—CH{=}CH—$). Exemplary substituted alkenylene groups, e.g., substituted with one or more alkyl (methyl) groups, include but are not limited to, substituted ethylene ($—C(CH_3){=}CH—$, $—CH{=}C(CH_3)—$), substituted propylene (e.g., $—C(CH_3){=}CHCH_2—$, $—CH{=}C(CH_3)CH_2—$, $—CH{=}CHCH(CH_3)—$, $—CH{=}CHC(CH_3)_2—$, $—CH(CH_3)—CH{=}CH—$, $—C(CH_3)_2—CH{=}CH—$, $—CH_2—C(CH_3){=}CH—$, $—CH_2—CH{=}C(CH_3)—$), and the like.

"$C_{2-13}$ alkynylene" refers to a $C_{2-13}$ alkynyl group wherein another hydrogen is removed to provide a divalent radical of alkynylene, and which may be substituted or unsubstituted. In some embodiments, $C_{2-10}$ alkynylene, $C_{2-6}$ alkynylene, and $C_{2-4}$ alkynylene is yet alternative. Exemplary alkynylene groups include, but are not limited to, ethynylene ($—C{\equiv}C—$), substituted or unsubstituted propynylene ($—C{\equiv}CCH_2—$), and the like.

"$C_{0-6}$ alkylene" refers to the chemical bond and the "$C_{1-6}$ alkylene" described above, "$C_{0-4}$ alkylene" refers to the chemical bond and the "$C_{1-4}$ alkylene" described above.

The term "variable A and variable B have a total length of x carbon atoms" means that the total number of carbon atoms of the main chain in the group represented by variable A and the number of carbon atoms of the main chain in the group represented by variable B is x.

"Halo" or "halogen" refers to fluorine (F), chlorine (Cl), bromine (Br) and iodine (I).

Thus, "$C_{1-10}$ haloalkyl" refers to the above "$C_{1-10}$ alkyl", which is substituted by one or more halogen. In some embodiments, $C_{1-6}$ haloalkyl and $C_{1-4}$ haloalkyl is yet alternative, and still alternatively $C_{1-2}$ haloalkyl. Exemplary haloalkyl groups include, but are not limited to, $—CF_3$, $—CH_2F$, $—CHF_2$, $—CHFCH_2F$, $—CH_2CHF_2$, $—CF_2CF_3$, $—CCl_3$, $—CH_2Cl$, $—CHCl_2$, 2,2,2-trifluoro-1,1-dimethyl-ethyl, and the like. The haloalkyl can be substituted at any available point of attachment, for example, with 1 to 5 substituents, 1 to 3 substituents or 1 substituent.

"$C_{3-14}$ cycloalkyl" or "3- to 14-membered cycloalkyl" refers to a radical of a non-aromatic cyclic hydrocarbon group having from 3 to 14 ring carbon atoms and zero heteroatoms, optionally wherein 1, 2 or 3 double or triple bonds are contained. In some embodiments, 3- to 10-membered cycloalkyl, 5- to 10-membered cycloalkyl, 3- to 8-membered cycloalkyl, 3- to 7-membered cycloalkyl, 3- to 6-membered cycloalkylare yet alternative, and still alternatively 5- to 7-membered cycloalkyl, 4- to 6-membered cycloalkyl, 5- to 6-membered cycloalkyl, 5-membered cycloalkyl, and 6-membered cycloalkyl. The cycloalkyl also includes a ring system in which the cycloalkyl ring described above is fused with one or more aryl or heteroaryl groups, wherein the point of attachment is on the cycloalkyl ring, and in such case, the number of carbon atoms continues to represent the number of carbon atoms in the cycloalkyl system. The cycloalkyl further comprises the cycloalkyl described above, in which the substituents on any non-adjacent carbon atoms are connected to form a bridged ring, together forming a polycyclic alkane sharing two or more carbon atoms. The cycloalkyl further comprises the cycloalkyl described above, in which the substituents on the same carbon atom are connected to form a ring, together forming a polycyclic alkane sharing one carbon atom. Exemplary cycloalkyl groups include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc. The cycloalkyl can be substituted with one or more substituents, for example, with 1 to 5 substituents, 1 to 3 substituents or 1 substituent.

"$C_{3-10}$ cycloalkylene" refers to a divalent radical formed by removing another hydrogen of $C_{3-10}$ cycloalkyl group and may be substituted or unsubstituted. In some embodiments, $C_{3-6}$ cycloalkylene and $C_{3-4}$ cycloalkylene groups are particularly alternative, especially alternatively cyclopropylene.

"3- to 14-membered heterocyclyl" refers to a saturated or unsaturated radical of 3- to 14-membered non-aromatic ring system having ring carbon atoms and 1 to 5 ring heteroatoms, wherein each of the heteroatoms is independently selected from nitrogen, oxygen, sulfur, boron, phosphorus and silicon, optionally wherein 1, 2 or 3 double or triple bonds are contained. In the heterocyclyl containing one or more nitrogen atoms, the point of attachment can be a carbon or nitrogen atom as long as the valence permits. In some embodiments, 3- to 10-membered heterocyclyl is alternative, which is a radical of 3- to 10-membered non-aromatic ring system having ring carbon atoms and 1 to 5 ring heteroatoms; in some embodiments, 5- to 10-membered heterocyclyl is alternative, which is a radical of 5- to 10-membered non-aromatic ring system having ring carbon atoms and 1 to 5 ring heteroatoms; in some embodiments, 3- to 8-membered heterocyclyl is alternative, which is a radical of 3- to 8-membered non-aromatic ring system having ring carbon atoms and 1 to 4 ring heteroatoms; in some embodiments, 3- to 7-membered heterocyclyl is alternative, which is a radical of 3- to 7-membered non-aromatic ring system having ring carbon atoms and 1 to 4 ring heteroatoms; 5- to 7-membered heterocyclyl is alternative, which is a radical of 5- to 7-membered non-aromatic ring system having ring carbon atoms and 1 to 3 ring heteroatoms; 3- to 6-membered heterocyclyl is alternative, which is a radical of 3- to 6-membered non-aromatic ring system having ring carbon atoms and 1 to 3 ring heteroatoms; 4- to 6-membered heterocyclyl is alternative, which is a radical of 4- to 6-membered non-aromatic ring system having ring carbon atoms and 1 to 3 ring heteroatoms; 5- to 6-membered heterocyclyl is more alternative, which is a radical of 5- to 6-membered non-aromatic ring system having ring carbon atoms and 1 to 3 ring heteroatoms; 5-membered heterocyclyl is more alternative, which is a radical of 5-membered non-aromatic ring system having ring carbon atoms and 1 to 3 ring heteroatoms; 6-membered heterocyclyl is more alternative, which is a radical of 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the heterocyclyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. The heterocyclyl further comprises the heterocyclyl described above, in which the substituents on any non-adjacent carbon or nitrogen atoms are connected to form a bridge ring, together forming a polycyclic heteroalkane sharing two or more carbon or nitrogen atoms. The heterocyclyl further comprises the heterocyclyl described above, in which the substituents on the same carbon atom are connected to form a ring, together forming a polycyclic heteroalkane sharing one carbon atom. Exemplary 3-membered heterocyclyl groups containing one heteroatom include, but are not limited to, aziridinyl, oxiranyl and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothienyl, pyrrolidinyl, dihydropyrrolyl and pyrrolyl-2,5-dione. Exemplary 5-membered heterocyclyl groups containing two heteroatoms include, but are not limited to, pyrazolidyl, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocyclyl groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6,6-bicyclic heterocyclyl herein) include, but are not limited to, tetrahydroquinolinyl, tetrahydroisoquinolinyl, etc. The heterocyclyl further includes the heterocyclyl described above sharing one or two atoms with a cycloalkyl, heterocyclyl, aryl or heteroaryl to form a bridged or spiro ring, as long as the valence permits, where the shared atom may be carbon or nitrogen atoms. The heterocyclyl further includes the heterocyclyl described above, which optionally can be substituted with one or more substituents, e.g., with 1 to 5 substituents, 1 to 3 substituents or 1 substituent.

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared $\pi$ electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl, e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system. The aryl can be substituted with one or more substituents, for example, with 1 to 5 substituents, 1 to 3 substituents or 1 substituent.

"5- to 14-membered heteroaryl" refers to a radical of 5- to 14-membered monocyclic or bicyclic 4n+2 aromatic ring system (e.g., having 6, 10 or 14 shared R electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. heteroaryl bicyclic systems may include one or more heteroatoms in one or two rings. heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 10-membered heteroaryl groups are alternative, which are radicals of 5- to 10-membered monocyclic or bicyclic 4n+2 aromatic ring systems having ring carbon atoms and 1-4 ring heteroatoms. In other embodiments, 5- to 6-membered heteroaryl groups are yet alternative, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (such as, 1,2,4-oxadiazolyl), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl or pyridonyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6,6-bicyclic heteroaryl groups include, but are not limited to, naphthyridinyl, pteridinyl, quinolyl, isoquinolyl, cinnolinyl, quinoxalinyl, phthalazinyl and quinazolinyl. The heteroaryl can be substituted with one or more substituents, for example, with 1 to 5 substituents, 1 to 3 substituents or 1 substituent.

"Hydroxyalkyl" refers to an alkyl group that is substituted with one or more hydroxyl groups.

"Alkoxy" refers to an oxyether form of a linear or branched-chain alkyl group, i.e., an —O-alkyl group. Similarly, "methoxy" refers to —O—CH$_3$.

"Optionally substituted with" means that it can be substituted with the specified substituents or unsubstituted.

The divalent groups formed by removing another hydrogen from the groups defined above such as alkyl, alkenyl, alkynyl, cycloalkyl, heterocyclyl, aryl and heteroaryl are collectively referred to as "-ylene". Ring-forming groups such as cycloalkyl, heterocyclyl, aryl and heteroaryl are collectively referred to as "cyclic groups".

alkyl, alkenyl, alkynyl, cycloalkyl, heterocyclyl, aryl and heteroaryl as defined herein are optionally substituted groups.

Exemplary substituents on carbon atoms include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(═O)R$^{aa}$, —CO$_2$H, —CHO, —C(OR$^{cc}$)$_2$, —CO$_2$R$^{aa}$, —OC(═O)R$^{aa}$, —OCO$_2$R$^{aa}$, —C(═O)N(R$^{bb}$)$_2$, —OC(═O)N(R$^{bb}$)$_2$, —NR$^{bb}$C(═O)R$^{aa}$, —NR$^{bb}$CO$_2$R$^{aa}$, —NR$^{bb}$C(═O)N(R$^{bb}$)$_2$, —C(═NR$^{bb}$)R$^{aa}$, —C(═NR$^{bb}$)OR$^{aa}$, —OC(═NR$^{bb}$)R$^{aa}$, —OC(═NR$^{bb}$)OR$^{aa}$, —C(═NR$^{bb}$)N(R$^{bb}$)$_2$, —OC(═NR$^{bb}$)N(R$^{bb}$)$_2$, —NR$^{bb}$C(═NR$^{bb}$)N(R$^{bb}$)$_2$, —C(═O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(═O)R$^{aa}$, —OS(═O)R$^{aa}$, —Si(R$^{aa}$)$_3$, —OSi(R$_a$)$_3$, —C(═S)N(R$^{bb}$)$_2$, —C(═O)SR$^{aa}$, —C(═S)SR$^{aa}$, —SC(═S)SR$^{aa}$, —SC(═O)SR$_a$, —OC(═O)SR$^{aa}$, —SC(═O)OR$^{aa}$, —SC(═O)R$^{aa}$, —P(═O)$_2$R$^{aa}$, —OP(═O)$_2$R$^{aa}$, —P(═O)(R$^{aa}$)$_2$, —OP(═O)(R$^{aa}$)$_2$, —OP(═O)(OR$^{cc}$)$_2$, —P(═O)$_2$N(R$^{bb}$)$_2$, —OP(═O)$_2$N(R$^{bb}$)$_2$, —P(═O)(NR$^{bb}$)$_2$, —OP(═O)(NR$^{bb}$)$_2$, —NR$^{bb}$P(═O)(OR")$_2$, —NR$^{bb}$P(═O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, cycloalkyl, heterocyclyl, aryl and heteroaryl, wherein each of the alkyl, alkenyl, alkynyl, cycloalkyl, heterocyclyl, aryl and heteroaryl is independently substituted with 0, 1, 2, 3, 4 or 5 R$^{dd}$ groups;

or two geminal hydrogen on a carbon atom are replaced with ═O, ═S, ═NN(R$^{bb}$)$_2$, ═NNR$^{bb}$C(═O)R$_a$, ═NNR$^{bb}$C(═O)OR$^{aa}$, ═NNR$^{bb}$S(═O)$_2$R$^{aa}$, ═NR$^{bb}$ or ═NOR$^{cc}$ groups;

each of the R$^{aa}$ is independently selected from alkyl, haloalkyl, alkenyl, alkynyl, cycloalkyl, heterocyclyl, aryl and heteroaryl, or two of the R$^{aa}$ groups are combined to form a heterocyclyl or heteroaryl ring, wherein each of the alkyl, alkenyl, alkynyl, cycloalkyl, heterocyclyl, aryl and heteroaryl is independently substituted with 0, 1, 2, 3, 4 or 5 R$_{dd}$ groups;

each of the R$^{bb}$ is independently selected from hydrogen, —OH, —OR$^{aa}$, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R$^{aa}$, —P(═O)(R$^{aa}$)$_2$, —P(═O)$_2$N(R$^{cc}$)$_2$, —P(═O)(NR$^{cc}$)$_2$, alkyl, haloalkyl, alkenyl, alkynyl, cycloalkyl, heterocyclyl, aryl and heteroaryl, or two R$_{bb}$ groups are combined to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 R$^{dd}$ groups;

each of the R$^{cc}$ is independently selected from hydrogen, alkyl, haloalkyl, alkenyl, alkynyl, cycloalkyl, heterocyclyl, aryl and heteroaryl, or two R$^{cc}$ groups are combined to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 R$^{dd}$ groups;

each of the R$^{dd}$ is independently selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(═O)R$^{ee}$, —CO$_2$H, —CO$_2$R$^{ee}$, —OC(═O)R$^{ee}$, —OCO$_2$R$^{ee}$, —C(═O)N(R$^{ff}$)$_2$, —OC(═O)N(R$^{ff}$)$_2$, —NR$^{ff}$C(═O)R$^{ee}$, —NR$^{ff}$CO$_2$R$^{ee}$, —NR$^{ff}$C(═O)N(R$^{ff}$)$_2$, —C(═NR$^{ff}$)OR$^{ee}$, —OC(═NR$^{ff}$)R$^{ee}$, —OC(═NR$^{ff}$)OR$^{ee}$, —C(═NR$^{ff}$)N(R$_f$)$_2$, —OC(═NR$^{ff}$)N(R$_f$)$_2$, —NR$^{ff}$C(═NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(═O)

$R^{ee}$, $—Si(R^{ee})_3$, $—OSi(R^{ee})_3$, $—C(=S)N(R^{ff})_2$, $—C(=O)SR^{ee}$, $—C(=S)SR^{ee}$, $—SC(=S)SR^{ee}$, $—P(=O)_2R^{ee}$, $—P(=O)(R^{ee})_2$, $—OP(=O)(R^{ee})_2$, $—OP(=O)(OR^{ee})_2$, alkyl, haloalkyl, alkenyl, alkynyl, cycloalkyl, heterocyclyl, aryl, heteroaryl, wherein each of the alkyl, alkenyl, alkynyl, cycloalkyl, heterocyclyl, aryl and heteroaryl is independently substituted with 0, 1, 2, 3, 4 or 5 $R^{gg}$ groups, or two geminal $R^{dd}$ substituents can be combined to form =O or =S;

each of the $R^{ee}$ is independently selected from alkyl, haloalkyl, alkenyl, alkynyl, cycloalkyl, aryl, heterocyclyl, and heteroaryl, wherein each of the alkyl, alkenyl, alkynyl, cycloalkyl, heterocyclyl, aryl and heteroaryl is independently substituted with 0, 1, 2, 3, 4 or 5 $R^{gg}$ groups;

each of the $R^{ff}$ is independently selected from hydrogen, alkyl, haloalkyl, alkenyl, alkynyl, cycloalkyl, heterocyclyl, aryl and heteroaryl, or two $R^{ff}$ groups are combined to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 $R^{gg}$ groups;

each of the $R^{gg}$ is independently selected from halogen, —CN, $—NO_2$, $—N_3$, $—SO_2H$, $—SO_3H$, —OH, $—OC_{1-6}$ alkyl, $—ON(C_{1-6}$ alkyl$)_2$, $—N(C_{1-6}$ alkyl$)_2$, $—N(C_{1-6}$ alkyl$)_3{}^+X^-$, $—NH(C_{1-6}$ alkyl$)_2{}^+X^-$, $—NH_2(C_{1-6}$ alkyl$)^+X^-$, $—NH_3{}^+X^-$, $—N(OC_{1-6}$ alkyl$)(C_{1-6}$ alkyl), $—N(OH)(C_{1-6}$ alkyl), —NH(OH), —SH, $—SC_{1-6}$ alkyl, $—SS(C_{1-6}$ alkyl), $—C(=O)(C_{1-6}$ alkyl), $—CO_2H$, $—CO_2(C_{1-6}$ alkyl), $—OC(=O)(C_{1-6}$ alkyl), $—OCO_2(C_{1-6}$ alkyl), $—C(=O)NH_2$, $—C(=O)N(C_{1-6}$ alkyl$)_2$, $—OC(=O)NH(C_{1-6}$ alkyl), $—NHC(=O)(C_{1-6}$ alkyl), $—N(C_{1-6}$ alkyl$)C(=O)(C_{1-6}$ alkyl), $—NHCO_2(C_{1-6}$ alkyl), $—NHC(=O)N(C_{1-6}$ alkyl$)_2$, $—NHC(=O)NH(C_{1-6}$ alkyl), $—NHC(=O)NH_2$, $—C(=NH)O(C_{1-6}$ alkyl), $—OC(=NH)(C_{1-6}$ alkyl), $—OC(=NH)OC_{1-6}$ alkyl, $—C(=NH)N(C_{1-6}$ alkyl$)_2$, $—C(=NH)NH(C_{1-6}$ alkyl), $—C(=NH)NH_2$, $—OC(=NH)N(C_{1-6}$ alkyl$)_2$, $—OC(NH)NH(C_{1-6}$ alkyl), $—OC(NH)NH_2$, $—NHC(NH)N(C_{1-6}$ alkyl$)_2$, $—NHC(=NH)NH_2$, $—NHSO_2(C_{1-6}$ alkyl), $—SO_2N(C_{1-6}$ alkyl$)_2$, $—SO_2NH(C_{1-6}$ alkyl), $—SO_2NH_2$, $—SO_2C_{1-6}$ alkyl, $—SO_2OC_{1-6}$ alkyl, $—OSO_2C_{1-6}$ alkyl, $—SOC_{1-6}$ alkyl, $—Si(C_{1-6}$ alkyl$)_3$, $—OSi(C_{1-6}$ alkyl$)_3$, $—C(=S)N(C_{1-6}$ alkyl$)_2$, $C(=S)NH(C_{1-6}$ alkyl), $C(=S)NH_2$, $—C(=O)S(C_{1-6}$ alkyl), $—C(=S)SC_{1-6}$ alkyl, $—SC(=S)SC_{1-6}$ alkyl, $—P(=O)_2(C_{1-6}$ alkyl), $—P(=O)(C_{1-6}$ alkyl$)_2$, $—OP(=O)(C_{1-6}$ alkyl$)_2$, $—OP(=O)(OC_{1-6}$ alkyl$)_2$, $C_{1-6}$ alkyl, $C_{1-6}$ haloalkyl, $C_2$-$C_6$ alkenyl, $C_2$-$C_6$ alkynyl, $C_3$-$C_7$ cycloalkyl, $C_6$-$C_{10}$ aryl, $C_3$-$C_7$ heterocyclyl, $C_5$-$C_{10}$ heteroaryl; or two geminal $R^{gg}$ substituents may combine to form =O or =S; wherein $X^-$ is a counterion.

Exemplary substituents on nitrogen atoms include, but are not limited to, hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{bb})R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)_2R^{aa}$, $—P(=O)(R^{aa})_2$, $—P(=O)_2N(R^{cc})_2$, $—P(=O)(NR^{cc})_2$, alkyl, haloalkyl, alkenyl, alkynyl, cycloalkyl, heterocyclyl, aryl and heteroaryl, or two $R^{cc}$ groups attached to a nitrogen atom combine to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 $R^{dd}$ groups, and wherein $R^{aa}$, $R^{bb}$, $R^{cc}$ and $R^{dd}$ are as described herein.

"Nucleic acids" refers to single- or double-stranded deoxyribonucleic acid (DNA) or ribonucleic acid (RNA) molecules and their heterozygous molecules. Examples of nucleic acid molecules include, but are not limited to, messenger RNA (mRNA), microRNA (miRNA), small interfering RNA (siRNA), self-amplified RNA (saRNA), and antisense oligonucleotides (ASO), etc. Nucleic acids may be further chemically modified, and the chemical modifier selected from one of, or a combination of: pseudouridine, N1-methyl-pseudouridine, 5-methoxyuridine, and 5-methylcytosine. mRNA molecules contain protein coding regions and may further contain expression regulatory sequences. Typical expression regulatory sequences include, but are not limited to, 5' cap, 5' untranslated region (5' UTR), 3' untranslated region (3' UTR), polyadenylate sequence (PolyA), miRNA binding sites.

"Cationic lipids" refers to lipid molecules that is capable of being positively charged at physiological pH conditions. In some embodiments, the cationic lipid is an amino lipid.

"Neutral lipids" refers to lipid molecules that is not charged at a particular pH, such as physiological pH conditions. Examples of neutral lipids include, but are not limited to 1,2-distearoyl-sn-glycero-3-phosphocholine (DSPC), 1,2-dimyristoyl-sn-glycero-3-phosphocholine (DMPC), 1,2-dioleoyl-sn-glycero-3-phosphocholine (DOPC), 1,2-dipalmitoyl-sn-glycero-3-phosphocholine (DPPC), 1-palmitoyl-2-oleoyl-sn-glycero-3-phosphocholine (POPC), 1,2-dioleoyl-sn-glycero-3-phosphoethanolamine (DOPE), 1,2-dimyristoyl-sn-glycero-3-phosphoethanolamine (DMPE), 1-palmitoyl-2-oleoyl-sn-glycero-3-phosphoethanolamine (POPE), and 1,2-dipalmitoyl-sn-glycero-3-phosphoethanolamine (DPPE).

"Structure lipids" refers to lipids that enhance the stability of nanoparticles by filling the gaps between lipids, commonly such as steroids. The steroid is a compound having a perhydrocyclopentanophenanthrene carbon framework. In an alternative embodiment, the steroid is cholesterol, sitosterol, coprosterol, fucosterol, brassicasterol, ergosterol, tomatine, ursolic acid, α-tocopherol, stigmasterol, avenasterol, ergocalciferol or campesterol.

"Polymer lipids" refers to molecules containing a polymer moiety and a lipid moiety. In some embodiments, the polymer lipid is a polyethylene glycol (PEG) lipid. Other lipids that can reduce aggregation, such as products of compounds having uncharged, hydrophilic, space-barrier moieties coupled with lipid may also be used.

"Lipid nanoparticles" refers to particles containing lipid components of nanoscale size.

"Biodegradable groups" refers to functional groups that contain biodegradable bonds, such as esters, disulfide bonds and amides, etc. Biodegradation may affect the process of removing compounds from the body. The biodegradable groups of the present disclosure are oriented from the head to the tail in ionizable lipid molecules.

Other Terminology

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term “pharmaceutically acceptable salt” as used herein refers to those carboxylate and amino acid addition salts of the compounds of the present disclosure, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N,N'-dibenzylethylenediamine, chloroprocaine, choline, diethanolamine, ethylenediamine, N-methylglucamine and procaine.

The base addition salt of the acidic compound can be prepared by contacting the free acid form with a sufficient amount of the required base to form a salt in a conventional manner. The free acid can be regenerated by contacting the salt form with an acid in a conventional manner and then isolating the free acid. The free acid forms are somewhat different from their respective salt forms in their physical properties, such as solubility in polar solvents. But for the purposes of the present disclosure, the salts are still equivalent to their respective free acids.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., “Pharmaceutical Salts,” J. Pharm. Sci., 1977; 66: 1-19 for reference).

“Subjects” to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms “human”, “patient” and “subject” can be used interchangeably herein.

“Disease”, “disorder”, and “condition” can be used interchangeably herein.

Unless otherwise indicated, the term “treatment” as used herein includes the effect on a subject who is suffering from a particular disease, disorder, or condition, which reduces the severity of the disease, disorder, or condition, or delays or slows the progression of the disease, disorder or condition (“therapeutic treatment”). The term also includes the effect that occurs before the subject begins to suffer from a specific disease, disorder or condition (“prophylactic treatment”).

Generally, the “effective amount” of a pharmaceutical composition refers to an amount sufficient to elicit a target biological response. As understood by those skilled in the art, the effective amount of the pharmaceutical composition of the disclosure can vary depending on the following factors, such as the desired biological endpoint, the pharmacokinetics of the pharmaceutical composition, the diseases being treated, the mode of administration, and the age, health status and symptoms of the subjects. The effective amount includes therapeutically effective amount and prophylactically effective amount.

Unless otherwise indicated, the “therapeutically effective amount” of the pharmaceutical composition as used herein is an amount sufficient to provide therapeutic benefits in the course of treating a disease, disorder or condition, or to delay or minimize one or more symptoms associated with the disease, disorder or condition. The therapeutically effective amount of a pharmaceutical composition refers to the amount of the therapeutic agent that, when used alone or in combination with other therapies, provides a therapeutic benefit in the treatment of a disease, disorder or condition. The term “therapeutically effective amount” can include an amount that improves the overall treatment, reduces or avoids the symptoms or causes of the disease or condition, or enhances the therapeutic effect of other therapeutic agents.

Unless otherwise indicated, the “prophylactically effective amount” of the pharmaceutical composition as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a pharmaceutical composition refers to the amount of a therapeutic agent that, when used alone or in combination with other agents, provides a prophylactic benefit in the prevention of a disease, disorder or condition. The term “prophylactically effective amount” can include an amount that improves the overall prevention, or an amount that enhances the prophylactic effect of other preventive agents.

“Combination” and related terms refer to the simultaneous or sequential administration of the pharmaceutical compositions of the present disclosure and other therapeutic agents. For example, the pharmaceutical compositions of the present disclosure can be administered simultaneously or sequentially in separate unit dosage with other therapeutic agents, or simultaneously in a single unit dosage with other therapeutic agents.

DETAILED DESCRIPTION OF THE INVENTION

As used herein, “compounds of the present disclosure” refers to the following compounds of formula (IV), formula (V), formula (VI), formula (VII), and the like, pharmaceutically acceptable salts, isotopic variants, tautomers or stereoisomers thereof.

In the present disclosure, compounds are named using standard nomenclature. For compounds having an asymmetric center, it should be understood, unless otherwise stated, that all optical isomers and mixtures thereof are included. Furthermore, unless otherwise specified, all isomer compounds and carbon-carbon double bonds included in the present disclosure may occur in the form of Z and E. Compounds which exist in different tautomeric forms, one of which is not limited to any particular tautomer, but is intended to cover all tautomeric forms.

In one embodiment, the present disclosure relates to a nanoparticle composition, comprising a lipid ingredient, and optionally comprising a load;

wherein the lipid ingredient comprises the following components in the molar percentages:

Ionizable cationic lipids 20 mol %-85 mol %;

Structure lipids 10 mol %-75 mol %;

Neutral lipids 1.0 mol %-30 mol %;

Polymer lipids 0.25 mol %-10 mol %;

wherein the ionizable cationic lipid is the compound of formula (IV), or a pharmaceutically acceptable salt, isotopic variant, tautomer or stereoisomer thereof, (IV)

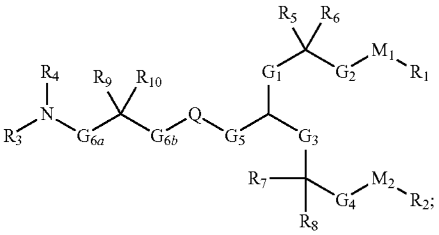

wherein, $M_1$ and $M_2$ are independently selected from —C(O)O—, —O—, —SC(O)O—, —OC(O)$NR_a$—, —$NR_a$C(O)$NR_a$—, —OC(O)S—, —OC(O)O—, —$NR_a$C(O)O—, —OC(O)—, —SC(O)—, —C(O)S—, —$NR_a$—, —C(O)$NR_a$—, —$NR_a$C(O)—, —$NR_a$C(O)S—, —SC(O)$NR_a$—, —C(O)—, —OC(S)—, —C(S)O—, —OC(S)$NR_a$—, —$NR_a$C(S)O—, —S—S— and —S$(O)_{0-2}$—;

Q is selected from a chemical bond, —C(O)O—, —O—, —SC(O)O—, —OC(O)$NR_b$—, —$NR_b$C(O)$NR_b$—, —OC(O)S—, —OC(O)O—, —$NR_b$C(O)O—, —OC(O)—, —SC(O)—, —C(O)S—, —$NR_b$—, —C(O)$NR_b$—, —$NR_b$C(O)—, —$NR_b$C(O)S—, —SC(O)$NR_b$—, —C(O)—, —OC(S)—, —C(S)O—, —OC(S)$NR_b$—, —$NR_b$C(S)O—, —S—S—, —S$(O)_{0-2}$—, phenylene and pyridylidene, wherein, the phenylene or pyridylidene is optionally substituted with one or more R*;

$G_5$ is a chemical bond or $C_{1-8}$ alkylene, which is optionally substituted with one or more R**;

$G_{6a}$ and $G_{6b}$ are independently a chemical bond or $C_{1-7}$ alkylene, which is optionally substituted with one or more R**;

$G_{6a}$ and $G_{6b}$ have a total length of 0, 1, 2, 3, 4, 5, 6 or 7 carbon atoms;

$R_9$, $R_{10}$ and R** are independently H, $C_{1-8}$ alkyl, -$L_c$-$OR_c$, -$L_c$-$SR_c$ or -$L_c$-$NR_cR'_c$;

$G_1$, $G_2$, $G_3$ and $G_4$ are independently a chemical bond, $C_{1-13}$ alkylene, $C_{2-13}$ alkenylene or $C_{2-13}$ alkynylene, which is optionally substituted with one or more $R^s$;

$G_1$ and $G_2$ have a total length of 3, 4, 5, 6, 7, 8, 9, 10, 11, 12 or 13 carbon atoms;

$G_3$ and $G_4$ have a total length of 3, 4, 5, 6, 7, 8, 9, 10, 11, 12 or 13 carbon atoms;

$R_3$ and $R_4$ are independently H, $C_{1-10}$ alkyl, $C_{1-10}$ haloalkyl, $C_{2-10}$ alkenyl, $C_{2-10}$ alkynyl, 3- to 14-membered cycloalkyl, 3- to 14-membered heterocyclyl, $C_{6-10}$ aryl or 5- to 14-membered heteroaryl, which is optionally substituted with one or more R*;

or, $R_3$ and $R_4$ are taken together with the N atom to which they are attached to form 3- to 14-membered heterocyclyl, which is optionally substituted with one or more R*;

or, $R_4$ and $R_9$ are taken together with the atoms to which they are attached to form 3- to 14-membered heterocyclyl or 5- to 14-membered heteroaryl, which is optionally substituted with one or more R*;

R* is independently H, halogen, cyano, $C_{1-10}$ alkyl, $C_{1-10}$ haloalkyl, -$L_b$-$OR_b$, -$L_b$-$SR_b$ or -$L_b$-$NR_bR'_b$;

$R_5$, $R_6$, $R_7$ and $R_8$ are independently $C_{1-8}$ alkyl, which is optionally substituted with one or more R*;

$R_1$ and $R_2$ are independently $C_{4-20}$ alkyl, $C_{4-20}$ alkenyl or $C_{4-20}$ alkynyl, which is optionally substituted with one or more R, and wherein one or more methylene units are optionally and independently replaced with —NR"—;

$R^s$ is independently H, $C_{1-14}$ alkyl, -$L_d$-$OR_d$, -$L_d$-$SR_d$ or -$L_d$-$NR_dR'_d$;

R is independently H, $C_{1-20}$ alkyl, -$L_a$-$OR_a$, -$L_a$-$SR_a$ or -$L_a$-$NR_aR'_a$;

R" is independently H or $C_{1-20}$ alkyl;

$L_a$ and $L_e$ are independently a chemical bond or $C_{1-20}$ alkylene;

$L_b$ and $L_f$ are independently a chemical bond or $C_{1-10}$ alkylene;

$L_e$ is independently a chemical bond or $C_{1-8}$ alkylene;

$L_a$ is independently a chemical bond or $C_{1-14}$ alkylene;

$R_a$ and $R'_a$ are independently selected from H, $C_{1-20}$ alkyl, 3- to 14-membered cycloalkyl, and 3- to 14-membered heterocyclyl, which are optionally substituted with one or more of the following substituents: H, $C_{1-20}$ alkyl, -$L_e$-$OR_e$, -$L_e$-$SR_e$ and -$L_e$-$NR_eR'_e$;

$R_b$ and $R'_b$ are independently selected from H, $C_{1-10}$ alkyl, 3- to 14-membered cycloalkyl, and 3- to 14-membered heterocyclyl, which are optionally substituted with one or more of the following substituents: H, $C_{1-10}$ alkyl, -$L_f$-$OR_f$, -$L_f$-$SR_f$ and -$L_f$-$NR_fR'_f$;

$R_e$ and $R'_e$ are independently H or $C_{1-8}$ alkyl;

$R_d$ and $R'_a$ are independently H or $C_{1-14}$ alkyl;

$R_e$ and $R'_e$ are independently H or $C_{1-20}$ alkyl;

$R_f$ and $R'_f$ are independently H or $C_{1-10}$ alkyl.

$M_1$ and $M_2$

In one embodiment, $M_1$ is —C(O)O—; in another embodiment, $M_1$ is —O—; in another embodiment, $M_1$ is —SC(O)O—; in another embodiment, $M_1$ is —OC(O)$NR_a$—; in another embodiment, $M_1$ is —$NR_a$C(O)$NR_a$—; in another embodiment, $M_1$ is —OC(O)S—; in another embodiment, $M_1$ is —OC(O)O—; in another embodiment, $M_1$ is —$NR_a$C(O)O—; in another embodiment, $M_1$ is —OC(O)—; in another embodiment, $M_1$ is —SC(O)—; in another embodiment, $M_1$ is —C(O)S—; in another embodiment, $M_1$ is —$NR_a$—; in another embodiment, $M_1$ is —C(O)$NR_a$—; in another embodiment, $M_1$ is —$NR_a$C(O)—; in another embodiment, $M_1$ is —$NR_a$C(O)S—; in another embodiment, $M_1$ is —SC(O)$NR_a$—; in another embodiment, $M_1$ is —C(O)—; in another embodiment, $M_1$ is —OC(S)—; in another embodiment, $M_1$ is —C(S)O—; in another embodiment, $M_1$ is —OC(S)$NR_a$—; in another embodiment, $M_1$ is —$NR_a$C(S)O—; in another embodiment, $M_1$ is —S—S—; in another embodiment, $M_1$ is —$S(O)_{0-2}$—.

In one embodiment, $M_2$ is —C(O)O—; in another embodiment, $M_2$ is —O—; in another embodiment, $M_2$ is —SC(O)O—; in another embodiment, $M_2$ is —OC(O)$NR_a$—; in another embodiment, $M_2$ is —$NR_a$C(O)$NR_a$—; in another embodiment, $M_2$ is —OC(O)S—; in another embodiment, $M_2$ is —OC(O)O—; in another embodiment, $M_2$ is —$NR_a$C(O)O—; in another embodiment, $M_2$ is —OC(O)—; in another embodiment, $M_2$ is —SC(O)—; in another embodiment, $M_2$ is —C(O)S—; in another embodiment, $M_2$ is —$NR_a$—; in another embodiment, $M_2$ is —C(O)$NR_a$—; in another embodiment, $M_2$ is —$NR_a$C(O)—; in another embodiment, $M_2$ is —$NR_a$C(O)S—; in another embodiment, $M_2$ is —SC(O)$NR_a$—; in another embodiment, $M_2$ is —C(O)—; in another embodiment, $M_2$ is —OC(S)—; in another embodiment, $M_2$ is —C(S)O—; in another embodiment, $M_2$ is —OC(S)$NR_a$—; in another embodiment, $M_2$ is —$NR_a$C(S)O—; in another embodiment, $M_2$ is —S—S—; in another embodiment, $M_2$ is —$S(O)_{0-2}$—.

In a more specific embodiment, $M_1$ and $M_2$ are independently selected from —C(O)O—, —SC(O)O—, —OC(O)$NR_a$—, —$NR_a$C(O)$NR_a$—, —OC(O)S—, —OC(O)O—, —$NR_a$C(O)O—, —C(O)S—, —C(O)$NR_a$—, —$NR_a$C(O)S—, —SC(O)$NR_a$—, —C(S)O—, —OC(S)$NR_a$— and —$NR_a$C(S)O—; in another more specific embodiment, $M_1$ and $M_2$ are independently selected from —C(O)O—, —C(O)S—, —C(O)$NR_a$—, and —C(S)O—; in another more specific embodiment, $M_1$ and $M_2$ are independently —C(O)O—, —C(O)S— or —C(O)$NR_a$—.

Q

In one embodiment, Q is a chemical bond; in another embodiment, Q is —C(O)O—; in another embodiment, Q is —O—; in another embodiment, Q is —SC(O)O—; in another embodiment, Q is —OC(O)$NR_b$—; in another embodiment, Q is —$NR_b$C(O)$NR_b$—; in another embodiment, Q is —OC(O)S—; in another embodiment, Q is —OC(O)O—; in another embodiment, Q is —$NR_b$C(O)O—; in another embodiment, Q is —OC(O)—; in another embodiment, Q is —SC(O)—; in another embodiment, Q is —C(O)S—; in another embodiment, Q is —$NR_b$—; in another embodiment, Q is —C(O)$NR_b$—; in another embodiment, Q is —$NR_b$C(O)—; in another embodiment, Q is —$NR_b$C(O)S—; in another embodiment, Q is —SC(O)$NR_b$—; in another embodiment, Q is —C(O)—; in another embodiment, Q is —OC(S)—; in another embodiment, Q is —C(S)O—; in another embodiment, Q is —OC(S)$NR_b$—; in another embodiment, Q is —$NR_b$C(S)O—; in another embodiment, Q is —S—S—; in another embodiment, Q is —$S(O)_{0-2}$—; in another embodiment, Q is phenylene; in another embodiment, Q is pyridylidene; in another embodiment, the phenylene or pyridylidene is optionally substituted with one or more R*.

In a more specific embodiment, Q is selected from a chemical bond, —C(O)O—, —O—, —SC(O)O—, —OC(O)$NR_b$—, —$NR_b$C(O)$NR_b$—, —OC(O)S—, —OC(O)O—, —$NR_b$C(O)O—, —OC(O)—, —SC(O)—, —C(O)S—, —$NR_b$—, —C(O)$NR_b$—, —$NR_b$C(O)—, —$NR_b$C(O)S—, —SC(O)$NR_b$—, —C(O)—, —OC(S)—, —C(S)O—, —OC(S)$NR_b$—, —$NR_b$C(S)O—, —S—S—, and —$S(O)_{0-2}$—; in another more specific embodiment, Q is selected from —C(O)O—, —O—, —SC(O)O—, —OC(O)NH—, —NHC(O)NH—, —OC(O)S—, —OC(O)O—, —NHC(O)O—, —OC(O)—, —SC(O)—, —C(O)S—, —NH—, —C(O)NH—, —NHC(O)—, —NHC(O)S—, —SC(O)NH—, —C(O)—, —OC(S)—, —C(S)O—, —OC(S)NH— and —NHC(S)O—; in another more specific embodiment, Q is selected from —C(O)O—, —O—, —SC(O)O—, —OC(O)NH—, —NHC(O)NH—, —OC(O)S—, —OC(O)O— and —NHC(O)O—; in another more specific embodiment, Q is —C(O)O—.

$G_5$

In one embodiment, $G_5$ is a chemical bond; in another embodiment, $G_5$ is $C_{1-8}$ alkylene; in another embodiment, $G_5$ is optionally substituted with one or more R**.

$G_{6a}$ and $G_{6b}$

In one embodiment, $G_{6a}$ is a chemical bond; in another embodiment, $G_{6a}$ is $C_{1-7}$ alkylene; in another embodiment, $G_{6a}$ is $C_{1-5}$ alkylene; in another embodiment, $G_{6a}$ is $C_{1-4}$ alkylene; in another embodiment, $G_{6a}$ is $C_{1-4}$ linear alkylene; in another embodiment, $G_{6a}$ is $(CH_2)_2$—; in another embodiment, $G_{6a}$ is optionally substituted with one or more R; in another embodiment, $G_{6a}$ is optionally substituted with 1, 2, 3 or 4 R.

In one embodiment, $G_{6b}$ is a chemical bond; in another embodiment, $G_{6b}$ is $C_{1-7}$ alkylene; in another embodiment, $G_{6b}$ is $C_{1-5}$ alkylene; in another embodiment, $G_{6b}$ is $C_{1-2}$ alkylene; in another embodiment, $G_{6b}$ is methylene; in another embodiment, $G_{6b}$ is optionally substituted with one or more R; in another embodiment, $G_{6b}$ is optionally substituted with 1, 2, 3 or 4 R; in another embodiment, $G_{6b}$ is optionally substituted with 1 or 2 R**.

In one embodiment, $G_{6a}$ and $G_{6b}$ have a total length of 0 carbon atoms; in another embodiment, $G_{6a}$ and $G_{6b}$ have a total length of 1 carbon atom; in another embodiment, $G_{6a}$ and $G_{6b}$ have a total length of 2 carbon atoms; in another embodiment, $G_{6a}$ and $G_{6b}$ have a total length of 3 carbon atoms; in another embodiment, $G_{6a}$ and $G_{6b}$ have a total length of 4 carbon atoms; in another embodiment, $G_{6a}$ and $G_{6b}$ have a total length of 5 carbon atoms; in another embodiment, $G_{6a}$ and $G_{6b}$ have a total length of 6 carbon atoms; in another embodiment, $G_{6a}$ and $G_{6b}$ have a total length of 7 carbon atoms.

In a more specific embodiment, $G_{6a}$ and $G_{6b}$ are independently a chemical bond or $C_{1-5}$ alkylene, which is optionally substituted with 1, 2, 3 or 4 R**; $G_{6a}$ and $G_{6b}$ have a total length of 0, 1, 2, 3, 4 or 5 carbon atoms.

In another more specific embodiment, $G_{6a}$ is a chemical bond or $C_{1-4}$ alkylene, which is optionally substituted with 1, 2, 3 or 4 R; $G_{6b}$ is a chemical bond or $C_{1-2}$ alkylene, which is optionally substituted with 1 or 2 R; $G_{6a}$ and $G_{6b}$ have a total length of 0, 1, 2, 3 or 4 carbon atoms.

In another more specific embodiment, $G_{6a}$ is a chemical bond or $C_{1-4}$ alkylene, alternatively $C_{2-4}$ alkylene, alternatively $C_{2-3}$ alkylene, more alternatively —$(CH_2)_2$—; $G_{6b}$ is a chemical bond or methylene; $G_{6a}$ and $G_{6b}$ have a total length of 0, 1, 2, 3 or 4 carbon atoms, alternatively 1, 2, 3 or 4 carbon atoms, alternatively 2 or 3 carbon atoms.

In another more specific embodiment, $G_{6a}$ is a chemical bond or $C_{1-4}$ linear alkylene, alternatively $C_{2-4}$ linear alkylene, alternatively $C_{2-3}$ linear alkylene, more alternatively —$(CH_2)_2$—; $G_{6b}$ is a chemical bond or methylene; $G_{6a}$ and $G_{6b}$ have a total length of 0, 1, 2, 3 or 4 carbon atoms, alternatively 1, 2, 3 or 4 carbon atoms, alternatively 2 or 3 carbon atoms.

$R_9$

In one embodiment, $R_9$ is H; in another embodiment, $R_9$ is $C_{1-8}$ alkyl; in another embodiment, $R_9$ is -$L_c$-$OR_c$; in another embodiment, $R_9$ is -$L_c$-$SR_c$; in another embodiment, $R_9$ is -$L_c$-$NR_cR'_c$; in another embodiment, $R_9$ is $C_{1-6}$ alkyl.

In a more specific embodiment, $R_9$ is H, $C_{1-6}$ alkyl, $-L_c-OR_c$ or $-L_c-NR_cR'_c$; in another more specific embodiment, $R_9$ is H or $C_{1-6}$ alkyl; in another more specific embodiment, $R_9$ is H.

$R_{10}$

In one embodiment, $R_{10}$ is H; in another embodiment, $R_{10}$ is $C_{1-8}$ alkyl; in another embodiment, $R_{10}$ is $-L_c-OR_c$; in another embodiment, $R_{10}$ is $-L_c-SR_c$; in another embodiment, $R_{10}$ is $-L_c-NR_cR'_c$.

In a more specific embodiment, $R_{10}$ is H, $C_{1-6}$ alkyl, $-L_c-OR_c$ or $-L_c-NR_cR'_c$; in another more specific embodiment, $R_{10}$ is H.

R**

In one embodiment, R is H; in another embodiment, R is $C_{1-8}$ alkyl; in another embodiment, R is $-L_c-OR_c$; in another embodiment, R is $-L_c-SR_c$; in another embodiment, R is $-L_c-NR_cR'_c$; in another embodiment, R is $C_{1-6}$ alkyl.

In a more specific embodiment, R is H, $C_{1-6}$ alkyl, $-L_c-OR_c$ or $-L_c-NR_cR'_c$; in another more specific embodiment, R is H or $C_{1-6}$ alkyl; in another more specific embodiment, R** is H.

$G_1$, $G_2$, $G_3$ and $G_4$

In one embodiment, $G_1$ is a chemical bond; in another embodiment, $G_1$ is $C_{1-13}$ alkylene; in another embodiment, $G_1$ is $C_{2-13}$ alkenylene; in another embodiment, $G_1$ is $C_{2-13}$ alkynylene; in another embodiment, $G_1$ is optionally substituted with one or more $R^s$.

In one embodiment, $G_2$ is a chemical bond; in another embodiment, $G_2$ is $C_{2-13}$ alkylene; in another embodiment, $G_2$ is $C_{2-13}$ alkenylene; in another embodiment, $G_2$ is $C_{2-13}$ alkynylene; in another embodiment, $G_2$ is optionally substituted with one or more $R^s$.

In one embodiment, $G_1$ and $G_2$ have a total length of 3 carbon atoms; in another embodiment, $G_1$ and $G_2$ have a total length of 4 carbon atoms; in another embodiment, $G_1$ and $G_2$ have a total length of 5 carbon atoms; in another embodiment, $G_1$ and $G_2$ have a total length of 6 carbon atoms; in another embodiment, $G_1$ and $G_2$ have a total length of 7 carbon atoms; in another embodiment, $G_1$ and $G_2$ have a total length of 8 carbon atoms; in another embodiment, $G_1$ and $G_2$ have a total length of 9 carbon atoms; in another embodiment, $G_1$ and $G_2$ have a total length of 10 carbon atoms; in another embodiment, $G_1$ and $G_2$ have a total length of 11 carbon atoms; in another embodiment, $G_1$ and $G_2$ have a total length of 12 carbon atoms; in another embodiment, $G_1$ and $G_2$ have a total length of 13 carbon atoms.

In a more specific embodiment, $-G_1-C(R_5R_6)-G_2-$ is

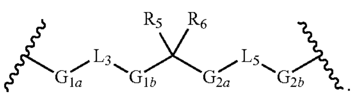

In one embodiment, $G_{1a}$ is a chemical bond; in another embodiment, $G_{1a}$ is $C_{1-7}$ alkylene; in another embodiment, $G_{1a}$ is $-CH_2-$; in another embodiment, $G_{1a}$ is $-(CH_2)_2-$; in another embodiment, $G_{1a}$ is $-(CH_2)_3-$; in another embodiment, $G_{1a}$ is $-(CH_2)_4-$; in another embodiment, $G_{1a}$ is $-(CH_2)_5-$; in another embodiment, $G_{1a}$ is $-(CH_2)_6-$; in another embodiment, $G_{1a}$ is optionally substituted with 1, 2, 3, 4 or 5 $R^s$.

In one embodiment, $G_{1b}$ is a chemical bond; in another embodiment, $G_{1b}$ is $C_{1-7}$ alkylene; in another embodiment, $G_{1b}$ is $C_{1-3}$ alkylene; in another embodiment, $G_{1b}$ is $-CH_2-$; in another embodiment, $G_{1b}$ is $-(CH_2)_2-$; in another embodiment, $G_{1b}$ is $-(CH_2)_3-$; in another embodiment, $G_{1b}$ is optionally substituted with 1, 2, 3, 4 or 5 $R^s$.

In one embodiment, $G_{2a}$ is a chemical bond; in another embodiment, $G_{2a}$ is $C_{1-7}$ alkylene; in another embodiment, $G_{2a}$ is $C_{1-3}$ alkylene; in another embodiment, $G_{2a}$ is optionally substituted with 1, 2, 3, 4 or 5 $R^s$.

In one embodiment, $G_{2b}$ is a chemical bond; in another embodiment, $G_{2b}$ is $C_{1-7}$ alkylene; in another embodiment, $G_{2b}$ is $C_{1-4}$ alkylene; in another embodiment, $G_{2b}$ is $-CH_2-$; in another embodiment, $G_{2b}$ is $-(CH_2)_2-$; in another embodiment, $G_{2b}$ is $-(CH_2)_3-$; in another embodiment, $G_{2b}$ is optionally substituted with 1, 2, 3, 4 or 5 $R^s$.

In a more specific embodiment, $G_{1a}$, $G_{1b}$, $G_{2a}$ and $G_{2b}$ have a total length of 1, 2, 3, 4, 5, 6 or 7 carbon atoms; in another more specific embodiment, $G_{1a}$, $G_{1b}$, $G_{2a}$ and $G_{2b}$ have a total length of 1, 2, 3, 4, 5 or 6 carbon atoms.

In one embodiment, one of $L_3$ and $L_5$ is $-(CR^sR^{s'})_2-$, and the other is a chemical bond; in another embodiment, one of $L_3$ and $L_5$ is $-(CHR^s)_2-$, and the other is a chemical bond; in another embodiment, one of $L_3$ and $L_5$ is $-CH{=}CH-$, and the other is a chemical bond; in another embodiment, one of $L_3$ and $L_5$ is $-C{\equiv}C-$, and the other is a chemical bond.

In one embodiment, $G_3$ is a chemical bond; in another embodiment, $G_3$ is $C_{1-13}$ alkylene; in another embodiment, $G_3$ is $C_{2-13}$ alkenylene; in another embodiment, $G_3$ is $C_{2-13}$ alkynylene; in another embodiment, $G_3$ is optionally substituted with one or more $R^s$.

In one embodiment, $G_4$ is a chemical bond; in another embodiment, $G_4$ is $C_{2-13}$ alkylene; in another embodiment, $G_4$ is $C_{2-13}$ alkenylene; in another embodiment, $G_4$ is $C_{2-13}$ alkynylene; in another embodiment, $G_4$ is optionally substituted with one or more $R^s$.

In one embodiment, $G_3$ and $G_4$ have a total length of 3 carbon atoms; in another embodiment, $G_3$ and $G_4$ have a total length of 4 carbon atoms; in another embodiment, $G_3$ and $G_4$ have a total length of 5 carbon atoms; in another embodiment, $G_3$ and $G_4$ have a total length of 6 carbon atoms; in another embodiment, $G_3$ and $G_4$ have a total length of 7 carbon atoms; in another embodiment, $G_3$ and $G_4$ have a total length of 8 carbon atoms; in another embodiment, $G_3$ and $G_4$ have a total length of 9 carbon atoms; in another embodiment, $G_3$ and $G_4$ have a total length of 10 carbon atoms; in another embodiment, $G_3$ and $G_4$ have a total length of 11 carbon atoms; in another embodiment, $G_3$ and $G_4$ have a total length of 12 carbon atoms; in another embodiment, $G_3$ and $G_4$ have a total length of 13 carbon atoms.

In a more specific embodiment, $-G_3-C(R_7R_8)-G_4-$ is

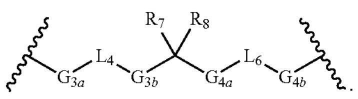

In one embodiment, $G_{3a}$ is a chemical bond; in another embodiment, $G_{3a}$ is $C_{1-7}$ alkylene; in another embodiment, $G_{3a}$ is $-CH_2-$; in another embodiment, $G_{3a}$ is $-(CH_2)_2-$; in another embodiment, $G_{3a}$ is $-(CH_2)_3-$; in another embodiment, $G_{3a}$ is $-(CH_2)_4-$; in another embodiment, $G_{3a}$ is $-(CH_2)_5-$; in another embodiment, $G_{3a}$ is $-(CH_2)_6-$; in another embodiment, $G_{3a}$ is optionally substituted with 1, 2, 3, 4 or 5 $R^s$.

In one embodiment, $G_{3b}$ is a chemical bond; in another embodiment, $G_{3b}$ is $C_{1-7}$ alkylene; in another embodiment, $G_{3b}$ is $C_{1-3}$ alkylene; in another embodiment, $G_{3b}$ is $-CH_2-$; in another embodiment, $G_{3b}$ is $-(CH_2)_2-$; in another embodiment, $G_{3b}$ is —$(CH_2)_3$—; in another embodiment, $G_{3b}$ is optionally substituted with 1, 2, 3, 4 or 5 $R^s$.

In one embodiment, $G_{4a}$ is a chemical bond; in another embodiment, $G_{4a}$ is $C_{1-7}$ alkylene; in another embodiment, $G_{4a}$ is $C_{1-3}$ alkylene; in another embodiment, $G_{4a}$ is optionally substituted with 1, 2, 3, 4 or 5 $R^s$.

In one embodiment, $G_{4b}$ is a chemical bond; in another embodiment, $G_{4b}$ is $C_{1-7}$ alkylene; in another embodiment, $G_{4b}$ is $C_{1-4}$ alkylene; in another embodiment, $G_{4b}$ is —$CH_2$—; in another embodiment, $G_{4b}$ is —$(CH_2)_2$—; in another embodiment, $G_{4b}$ is —$(CH_2)_3$—; in another embodiment, $G_{4b}$ is optionally substituted with 1, 2, 3, 4 or 5 $R^s$;

In a more specific embodiment, $G_{3a}$, $G_{3b}$, $G_{4a}$ and $G_{4b}$ have a total length of 1, 2, 3, 4, 5, 6 or 7 carbon atoms; in another more specific embodiment, $G_{3a}$, $G_{3b}$, $G_{4a}$ and $G_{4b}$ have a total length of 1, 2, 3, 4, 5 or 6 carbon atoms.

In one embodiment, one of $L_4$ and $L_6$ is —$(CR^sR^{s'})_2$—, and the other is a chemical bond; in another embodiment, one of $L_4$ and $L_6$ is —$(CHR^s)_2$—, and the other is a chemical bond; in another embodiment, one of $L_4$ and $L_6$ is —CH═CH—, and the other is a chemical bond; in another embodiment, one of $L_4$ and $L_6$ is —C≡C—, and the other is a chemical bond.

In a more specific embodiment, one of $L_3$ and $L_5$, or one of $L_4$ and $L_6$ is —$(CHR^s)_2$—, —CH═CH— or —C≡C—, and the other is a chemical bond;

- $G_{1a}$ and $G_{3a}$ are independently a chemical bond or $C_{1-7}$ alkylene;
- $G_{1b}$ and $G_{3b}$ are independently a chemical bond or $C_{1-3}$ alkylene;
- $G_{2a}$ and $G_{4a}$ are independently a chemical bond or $C_{1-3}$ alkylene;
- $G_{2b}$ and $G_{4b}$ are independently a chemical bond or $C_{1-4}$ alkylene;
- $G_{1a}$, $G_{1b}$, $G_{2a}$ and $G_{2b}$ have a total length of 1, 2, 3, 4, 5, 6 or 7 carbon atoms;
- $G_{3a}$, $G_{3b}$, $G_{4a}$ and $G_{4b}$ have a total length of 1, 2, 3, 4, 5, 6 or 7 carbon atoms.

In another more specific embodiment, one of $L_3$ and $L_5$, or one of $L_4$ and $L_6$ is —$(CH_2)_2$—, —CH═CH— or —C≡C—, and the other is a chemical bond;

- $G_{1a}$ and $G_{3a}$ are independently a chemical bond, —$CH_2$—, —$(CH_2)_2$—, —$(CH_2)_3$—, —$(CH_2)_4$—, —$(CH_2)_5$— or —$(CH_2)_6$—;
- $G_{1b}$ and $G_{3b}$ is a chemical bond;
- $G_{2a}$ and $G_{4a}$ is a chemical bond;
- $G_{2b}$ and $G_{4b}$ are independently a chemical bond, —$CH_2$—, —$(CH_2)_2$— or —$(CH_2)_3$—;
- $G_{1a}$, $G_{1b}$, $G_{2a}$ and $G_{2b}$ have a total length of 1, 2, 3, 4, 5 or 6 carbon atoms;
- $G_{3a}$, $G_{3b}$, $G_{4a}$ and $G_{4b}$ have a total length of 1, 2, 3, 4, 5 or 6 carbon atoms.

Alternatively, $R^s$ and $R^{s'}$ are independently H, $C_{1-10}$ alkyl, -$L_d$-$OR_d$ or -$L_d$-$NR_dR'_d$; alternatively H or $C_{1-6}$ alkyl; more alternatively H.

In a more specific embodiment, -$G_{1a}$-$L_3$-$G_{1b}$- or -$G_{3a}$-$L_4$-$G_{3b}$- is independently selected from: —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_3$—CH═CH—, —$(CH_2)_3$—C≡C—, —$(CH_2)_2$—CH═CH— and —$(CH_2)_2$—C≡C—.

In a more specific embodiment, -$G_{2a}$-$L_5$-$G_{2b}$- or -$G_{4a}$-$L_6$-$G_{4b}$- is independently selected from: a chemical bond, —$CH_2$—, —$(CH_2)_2$—, —$(CH_2)_3$—, —CH═CH—$CH_2$—, —C≡C— and —C≡C—$CH_2$—.

In a more specific embodiment,

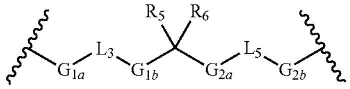

or

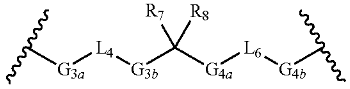

have a total length of 4, 5, 6, 7, 8 or 9 carbon atoms.

In a more specific embodiment,

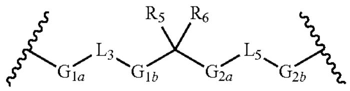

or

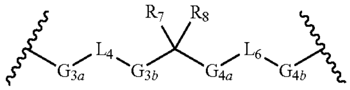

is independently selected from: —$(CH_2)_3$—$C(CH_3)_2$—, —$(CH_2)_4$—$C(CH_3)_2$—, —$(CH_2)_5$—$C(CH_3)_2$—, —$(CH_2)_6$—$C(CH_3)_2$—, —$(CH_2)_7$—$C(CH_3)_2$—, —$(CH_2)_5$—$C(CH_3)_2$—, —$(CH_2)_3$—CH═CH—$C(CH_3)_2$—, —$(CH_2)_3$—C≡C—$C(CH_3)_2$—, —$(CH_2)_4$—$C(CH_3)_2$—$CH_2$—, —$(CH_2)_3$ —$C(CH_3)_2$—$(CH_2)_2$—, —$(CH_2)_2$—$C(CH_3)_2$—$(CH_2)_3$—, —$(CH_2)_2$—CH═CH—$C(CH_3)_2$—$CH_2$—, —$(CH_2)_2$—$C(CH_3)_2$—C≡C—$CH_2$—, —$(CH_2)_2$—$C(CH_3)_2$—CH═CH—$CH_2$—, —$(CH_2)_2$—C≡C—$C(CH_3)_2$—$CH_2$— and —$(CH_2)_3$—$C(CH_3)_2$—C≡C—; in another more specific embodiment,

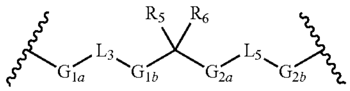

or

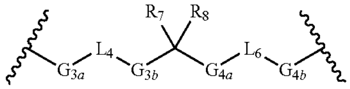

is independently selected from —$(CH_2)_4$—$C(CH_3)_2$—, —$(CH_2)_5$—$C(CH_3)_2$— and —$(CH_2)_6$—$C(CH_3)_2$—; in another more specific embodiment,

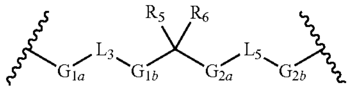

or

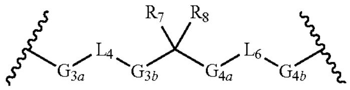

is —$(CH_2)_5$—$C(CH_3)_2$—.

$R_3$ and $R_4$

In one embodiment, $R_3$ is H; in another embodiment, $R_3$ is $C_{1-10}$ alkyl; in another embodiment, $R_3$ is $C_{1-10}$ haloalkyl; in another embodiment, $R_3$ is $C_{2-10}$ alkenyl; in another embodiment, $R_3$ is $C_{2-10}$ alkynyl; in another embodiment, $R_3$ is 3- to 14-membered cycloalkyl; in another embodiment, $R_3$ is 3- to 14-membered heterocyclyl; in another embodiment, $R_3$ is $C_{6-10}$ aryl; in another embodiment, $R_3$ is 5- to 14-membered heteroaryl; in another embodiment, $R_3$ is $C_{1-6}$ alkyl; in another embodiment, $R_3$ is $C_{1-6}$ haloalkyl; in another embodiment, $R_3$ is 3- to 10-membered cycloalkyl; in another embodiment, $R_3$ is 3- to 10-membered heterocyclyl; in another embodiment, $R_3$ is 3- to 7-membered cycloalkyl; in another embodiment, $R_3$ is 3- to 7-membered heterocyclyl; in another embodiment, $R_3$ is Me; in another embodiment, $R_3$ is $—CH_2CH_3$; in another embodiment, $R_3$ is $—CH_2CH_2OH$; in another embodiment, $R_3$ is $—CH(CH_3)_2$; in another embodiment, $R_3$ is substituted with one or more R*; in another embodiment, $R_3$ is optionally substituted with 1, 2, 3, 4 or 5 R*.

In one embodiment, $R_4$ is H; in another embodiment, $R_4$ is $C_{1-10}$ alkyl; in another embodiment, $R_4$ is $C_{1-10}$ haloalkyl; in another embodiment, $R_4$ is $C_{2-10}$ alkenyl; in another embodiment, $R_4$ is $C_{2-10}$ alkynyl; in another embodiment, $R_4$ is 3- to 14-membered cycloalkyl; in another embodiment, $R_4$ is 3- to 14-membered heterocyclyl; in another embodiment, $R_4$ is $C_{6-10}$ aryl; in another embodiment, $R_4$ is 5- to 14-membered heteroaryl; in another embodiment, $R_4$ is $C_{1-6}$ alkyl; in another embodiment, $R_4$ is $C_{1-6}$ haloalkyl; in another embodiment, $R_4$ is 3- to 10-membered cycloalkyl; in another embodiment, $R_4$ is 3- to 10-membered heterocyclyl; in another embodiment, $R_4$ is 3- to 7-membered cycloalkyl; in another embodiment, $R_4$ is 3- to 7-membered heterocyclyl; in another embodiment, $R_4$ is Me; in another embodiment, $R_4$ is substituted with one or more R*; in another embodiment, $R_4$ is optionally substituted with 1, 2, 3, 4 or 5 R*.

In one embodiment, $R_3$, $R_4$ are taken together with the N atom to which they are attached to form 3- to 14-membered heterocyclyl; in another embodiment, $R_3$, $R_4$ are taken together with the N atom to which they are attached to form 3- to 10-membered heterocyclyl; in another embodiment, $R_3$, $R_4$ are taken together with the N atom to which they are attached to form 3- to 7-membered heterocyclyl; in another embodiment, $R_3$, $R_4$ are taken together with the N atom to which they are attached to form 5- to 7-membered heterocyclyl; in another embodiment, $R_3$, $R_4$ are taken together with the N atom to which they are attached to form 4- to 6-membered heterocyclyl; in another embodiment, $R_3$, $R_4$ are taken together with the N atom to which they are attached to form 5-membered heterocyclyl; in another embodiment, $R_3$, $R_4$ are taken together with the N atom to which they are attached to form

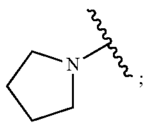 [SMILES: *N1CCCC1]

in another embodiment, $R_3$, $R_4$ are taken together with the N atom to which they are attached to form

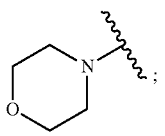 [SMILES: *N1CCOCC1]

in another embodiment, $R_3$, $R_4$ are taken together with the N atom to which they are attached to form

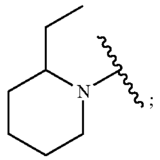 [SMILES: *N1CCCCC1CC]

in another embodiment, $R_3$, $R_4$ are taken together with the N atom to which they are attached to form

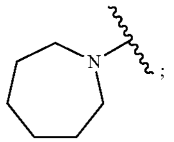 [SMILES: *N1CCCCCC1]

in another embodiment, the heterocyclyl formed by $R_3$ and $R_4$ taken together with the N atom to which they are attached is optionally substituted with one or more R*; in another embodiment, the heterocyclyl formed by $R_3$ and $R_4$ taken together with the N atom to which they are attached is optionally substituted with 1, 2, 3, 4 or 5 R*.

In one embodiment, $R_4$, $R_9$ are taken together with the atom to which they are attached to form 3- to 14-membered heterocyclyl or 5- to 14-membered heteroaryl; in another embodiment, $R_4$, $R_9$ are taken together with the atom to which they are attached to form 3- to 10-membered heterocyclyl; in another embodiment, $R_4$, $R_9$ are taken together with the atom to which they are attached to form 3- to 7-membered heterocyclyl; in another embodiment, $R_4$, $R_9$ are taken together with the atom to which they are attached to form 6-membered heterocyclyl; in another embodiment, $R_4$, $R_9$ are taken together with the atom to which they are attached to form

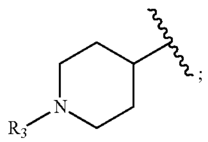

in another embodiment, the heterocyclyl formed by $R_4$ and $R_9$ taken together with the atom to which they are attached is optionally substituted with one or more R*; in another embodiment, the heterocyclyl formed by $R_4$ and $R_9$ taken together with the atom to which they are attached is optionally substituted with 1, 2, 3, 4 or 5 R*.

In a more specific embodiment, $R_3$ and $R_4$ are independently H, $C_{1-6}$ alkyl, $C_{1-6}$ haloalkyl, 3- to 10-membered cycloalkyl or 3- to 10-membered heterocyclyl, which is optionally substituted with 1, 2, 3, 4 or 5 R*;

or, $R_3$ and $R_4$ are taken together with the N atom to which they are attached to form 3- to 10-membered heterocyclyl, which is optionally substituted with 1, 2, 3, 4 or 5 R*;

or, $R_4$ and $R_9$ are taken together with the atoms to which they are attached to form 3- to 10-membered heterocyclyl, which is optionally substituted with 1, 2, 3 or 4 R*.

In another more specific embodiment, $R_3$ and $R_4$ are independently H, $C_{1-6}$ alkyl, $C_{1-6}$ haloalkyl, 3- to 7-membered cycloalkyl or 3- to 7-membered heterocyclyl, which is optionally substituted with 1, 2, 3, 4 or 5 R*;

or, $R_3$ and $R_4$ are taken together with the N atom to which they are attached to form 3- to 7-membered heterocyclyl, which is optionally substituted with 1, 2, 3, 4 or 5 R*;

or, $R_4$ and $R_9$ are taken together with the atoms to which they are attached to form 3- to 7-membered heterocyclyl, which is optionally substituted with 1, 2, 3, 4 or 5 R*.

In a more specific embodiment, $R_3$ and $R_4$ are independently $C_{1-6}$ alkyl, which is optionally substituted with 1, 2, 3, 4 or 5 R*;

or, $R_3$ and $R_4$ are taken together with the N atom to which they are attached to form 5- to 7-membered heterocyclyl, alternatively 4- to 6-membered heterocyclyl, more alternatively 5-membered heterocyclyl, which is optionally substituted with 1, 2, 3, 4 or 5 R*;

or, $R_4$ and $R_9$ are taken together with the atoms to which they are attached to form 6-membered heterocyclyl, which is optionally substituted with 1, 2, 3, 4 or 5 R*.

In a more specific embodiment, $R_3$ is Me, $-CH_2CH_3$, $-CH_2CH_2OH$ or $-CH(CH_3)_2$, alternatively Me, $-CH_2CH_3$ or $-CH(CH_3)_2$, more alternatively Me or $-CH_2CH_3$; $R_4$ is Me;

or, $R_3$ and $R_4$ are taken together with the N atom to which they are attached to form

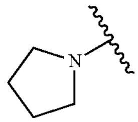
,
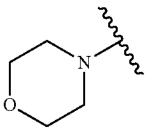
,
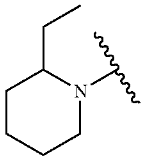
or
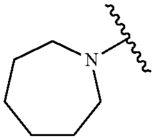
, alternatively

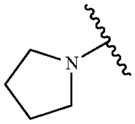
or
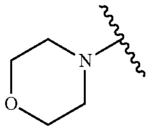
, more alternatively

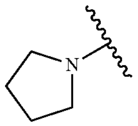
;

or, $R_4$ and $R_9$ are taken together with the atoms to which they are attached to form

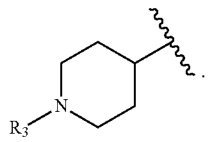
.

R*

In one embodiment, R* is H; in another embodiment, R* is halogen; in another embodiment, R* is cyano; in another embodiment, R* is $C_{1-10}$ alkyl; in another embodiment, R* is $C_{1-10}$ haloalkyl; in another embodiment, R* is $-L_b-OR_b$; in another embodiment, R* is $-L_b-SR_b$; in another embodiment, R* is $-L_b-NR_bR'_b$; in another embodiment, R* is $C_{1-6}$ alkyl; in another embodiment, R* is $C_{1-6}$ haloalkyl; in another embodiment, R* is $-OR_b$.

In a more specific embodiment, R* is independently H, halogen, cyano, $C_{1-6}$ alkyl, $C_{1-6}$ haloalkyl, $-L_b-OR_b$ or $-L_b-NR_bR'_b$; in another more specific embodiment, R* is independently H, $C_{1-6}$ alkyl, $C_{1-6}$ haloalkyl or $-OR_b$; in another more specific embodiment, R* is independently H, halogen, $C_{1-6}$ alkyl or $C_{1-6}$ haloalkyl; in another more specific embodiment, R* is independently H, $C_{1-6}$ alkyl or $C_{1-6}$ haloalkyl; in another more specific embodiment, R* is H, Me or OH; in another more specific embodiment, R* is H or Me.

$R_5$, $R_6$, $R_7$ and $R_8$

In one embodiment, $R_5$ is $C_{1-8}$ alkyl; in another embodiment, $R_5$ is $C_{1-6}$ alkyl; in another embodiment, $R_5$ is $C_{1-3}$ alkyl; in another embodiment, $R_5$ is Me; in another embodiment, $R_5$ is optionally substituted with one or more R*; in another embodiment, $R_5$ is optionally substituted with 1, 2, 3, 4 or 5 R*.

In one embodiment, $R_6$ is $C_{1-8}$ alkyl; in another embodiment, $R_6$ is $C_{1-6}$ alkyl; in another embodiment, $R_6$ is $C_{1-3}$ alkyl; in another embodiment, $R_6$ is Me; in another embodiment, $R_6$ is optionally substituted with one or more R*; in another embodiment, $R_6$ is optionally substituted with 1, 2, 3, 4 or 5 R*.

In one embodiment, $R_7$ is $C_{1-8}$ alkyl; in another embodiment, $R_7$ is $C_{1-6}$ alkyl; in another embodiment, $R_7$ is $C_{1-3}$ alkyl; in another embodiment, $R_7$ is Me; in another embodiment, $R_7$ is optionally substituted with one or more R*; in another embodiment, $R_7$ is optionally substituted with 1, 2, 3, 4 or 5 R*.

In one embodiment, $R_8$ is $C_{1-8}$ alkyl; in another embodiment, $R_8$ is $C_{1-6}$ alkyl; in another embodiment, $R_8$ is $C_{1-3}$ alkyl; in another embodiment, $R_8$ is Me; in another embodiment, $R_8$ is optionally substituted with one or more R*; in another embodiment, $R_8$ is optionally substituted with 1, 2, 3, 4 or 5 R*.

$R_1$ and $R_2$

In one embodiment, $R_1$ is $C_{4-20}$ alkyl; in another embodiment, $R_1$ is $C_{4-20}$ alkenyl; in another embodiment, $R_1$ is $C_{4-20}$ alkynyl; in another embodiment, $R_1$ is optionally substituted with one or more R; in another embodiment, one or more methylene units in $R_1$ are optionally and independently replaced by $-NR''-$.

In a more specific embodiment, $R_1$ is $-G_7-L_1-G_8-H$.

In one embodiment, $G_7$ is a chemical bond; in another embodiment, $G_7$ is $C_{1-12}$ alkylene; in another embodiment, $G_7$ is $C_{1-6}$ alkylene; in another embodiment, $G_7$ is $C_{1-8}$ alkylene; in another embodiment, $G_7$ is $C_{1-5}$ linear alkylene; in another embodiment, $G_7$ is $-CH_2-$; in another embodiment, $G_7$ is $-(CH_2)_2-$; in another embodiment, $G_7$ is $-(CH_2)_4-$; in another embodiment, $G_7$ is $-(CH_2)_5-$; in another embodiment, $G_7$ is optionally substituted with 1, 2, 3, 4, 5 or 6 R; in another embodiment, 1, 2 or 3 methylenes in $G_7$ are optionally and independently substituted with 1 R; in another embodiment, 1 or 2 methylenes in $G_7$ are optionally and independently substituted with 1 R; in another embodiment, the methylene of $G_7$ that is collected to $M_1$ is not substituted with R.

In one embodiment, $G_8$ is a chemical bond; in another embodiment, $G_8$ is $C_{1-12}$ alkylene; in another embodiment, $G_8$ is $C_{1-10}$ alkylene; in another embodiment, $G_8$ is $C_{1-8}$ alkylene; in another embodiment, $G_8$ is $C_{1-8}$ linear alkylene; in another embodiment, $G_8$ is $—(CH_2)_2—$; in another embodiment, $G_8$ is $—(CH_2)_4—$; in another embodiment, $G_8$ is $—(CH_2)_6—$; in another embodiment, $G_8$ is $—(CH_2)_7—$; in another embodiment, $G_8$ is $—(CH_2)_5—$; in another embodiment, $G_8$ is optionally substituted with 1, 2, 3, 4, 5 or 6 R; in another embodiment, 1, 2 or 3 methylenes in $G_8$ are optionally and independently substituted with 1 R; in another embodiment, 1 or 2 alkylene in $G_8$ are optionally and independently substituted with 1 R.

In one embodiment, $G_7$ and $G_8$ have a total length of 4 carbon atoms; in another embodiment, $G_7$ and $G_8$ have a total length of 5 carbon atoms; in another embodiment, $G_7$ and $G_8$ have a total length of 6 carbon atoms; in another embodiment, $G_7$ and $G_8$ have a total length of 7 carbon atoms; in another embodiment, $G_7$ and $G_8$ have a total length of 8 carbon atoms; in another embodiment, $G_7$ and $G_8$ have a total length of 9 carbon atoms; in another embodiment, $G_7$ and $G_8$ have a total length of 10 carbon atoms; in another embodiment, $G_7$ and $G_8$ have a total length of 11 carbon atoms; in another embodiment, $G_7$ and $G_8$ have a total length of 12 carbon atoms.

In a more specific embodiment, $G_7$ and $G_8$ have a total length of 6, 7, 8, 9 or 10 carbon atoms.

In a more specific embodiment, $G_7$ and $G_8$ have a total length of 6, 7 or 8 carbon atoms.

In one embodiment, $L_1$ is $—(CRR')_2—$; in another embodiment, $L_1$ is $—CH{=}CH—$; in another embodiment, $L_1$ is $—C{\equiv}C—$; in another embodiment, $L_1$ is $—NR''—$; in another embodiment, $L_1$ is $—(CHR)_2—$.

In one embodiment, $R_2$ is $C_{4-20}$ alkyl; in another embodiment, $R_2$ is $C_{4-20}$ alkenyl; in another embodiment, $R_2$ is $C_{4-20}$ alkynyl; in another embodiment, $R_2$ is optionally substituted with one or more R; in another embodiment, one or more methylene units in $R_2$ are optionally and independently replaced by $—NR''—$.

In a more specific embodiment, $R_2$ is $-G_9-L_2-G_{10}-H$.

In one embodiment, $G_9$ is a chemical bond; in another embodiment, $G_9$ is $C_{1-12}$ alkylene; in another embodiment, $G_9$ is $C_{1-6}$ alkylene; in another embodiment, $G_9$ is $C_{1-5}$ alkylene; in another embodiment, $G_9$ is $C_{1-5}$ linear alkylene; in another embodiment, $G_9$ is $—CH_2—$; in another embodiment, $G_9$ is $—(CH_2)_2—$; in another embodiment, $G_9$ is $—(CH_2)_4—$; in another embodiment, $G_9$ is $—(CH_2)_5—$; in another embodiment, $G_9$ is optionally substituted with 1, 2, 3, 4, 5 or 6 R; in another embodiment, 1, 2 or 3 methylenes in $G_9$ are optionally and independently substituted with 1 R; in another embodiment, 1 or 2 methylenes in $G_9$ are optionally and independently substituted with 1 R; in another embodiment, the methylene of $G_9$ that is collected to $M_2$ is not substituted with R.

In one embodiment, $G_{10}$ is a chemical bond; in another embodiment, $G_{10}$ is $C_{1-12}$ alkylene; in another embodiment, $G_{10}$ is $C_{1-10}$ alkylene; in another embodiment, $G_{10}$ is $C_{1-8}$ alkylene; in another embodiment, $G_{10}$ is $C_{1-8}$ linear alkylene; in another embodiment, $G_{10}$ is $—(CH_2)_2—$; in another embodiment, $G_{10}$ is $—(CH_2)_4—$; in another embodiment, $G_{10}$ is $—(CH_2)_6—$; in another embodiment, $G_{10}$ is $—(CH_2)_7—$; in another embodiment, $G_{10}$ is $—(CH_2)_8—$; in another embodiment, $G_{10}$ is optionally substituted with 1, 2, 3, 4, 5 or 6 R; in another embodiment, 1, 2 or 3 methylenes in $G_{10}$ are optionally and independently substituted with 1 R; in another embodiment, 1 or 2 methylenes in $G_{10}$ are optionally and independently substituted with 1 R.

In one embodiment, $G_9$ and $G_{10}$ have a total length of 4 carbon atoms; in another embodiment, $G_9$ and $G_{10}$ have a total length of 5 carbon atoms; in another embodiment, $G_9$ and $G_{10}$ have a total length of 6 carbon atoms; in another embodiment, $G_9$ and $G_{10}$ have a total length of 7 carbon atoms; in another embodiment, $G_9$ and $G_{10}$ have a total length of 8 carbon atoms; in another embodiment, $G_9$ and $G_{10}$ have a total length of 9 carbon atoms; in another embodiment, $G_9$ and $G_{10}$ have a total length of 10 carbon atoms; in another embodiment, $G_9$ and $G_{10}$ have a total length of 11 carbon atoms; in another embodiment, $G_9$ and $G_{10}$ have a total length of 12 carbon atoms.

In a more specific embodiment, $G_9$ and $G_{10}$ have a total length of 6, 7, 8, 9 or 10 carbon atoms.

In a more specific embodiment, $G_9$ and $G_{10}$ have a total length of 6, 7 or 8 carbon atoms.

In one embodiment, $L_2$ is $—(CRR')_2—$; in another embodiment, $L_2$ is $—CH{=}CH—$; in another embodiment, $L_2$ is $—C{\equiv}C—$; in another embodiment, $L_2$ is $—NR''—$; in another embodiment, $L_1$ is $—(CHR)_2—$.

In a more specific embodiment, $L_1$ and $L_2$ are independently $—(CRR')_2—$, $—CH{=}CH—$, $—C{\equiv}C—$ or $—NR''—$;

- $G_7$, $G_8$, $G_9$ and $G_{10}$ are independently a chemical bond or $C_{1-12}$ alkylene, which is optionally substituted with 1, 2, 3, 4, 5 or 6 R;
- $G_7$ and $G_8$ have a total length of 4, 5, 6, 7, 8, 9, 10, 11 or 12 carbon atoms;
- $G_9$ and $G_{10}$ have a total length of 4, 5, 6, 7, 8, 9, 10, 11 or 12 carbon atoms;
- 1, 2 or 3 methylenes in $G_7$, $G_8$, $G_9$ or $G_{10}$ are optionally and independently substituted with 1 R;
- R' is independently H, $C_{1-20}$ alkyl, $-L_a-OR_a$ or $-L_a-NR_aR'_a$.

In another more specific embodiment, $L_1$ and $L_2$ are independently $—(CHR)_2—$, $—CH{=}CH—$, $—C{\equiv}C—$ or $—NR''—$;

- $G_7$ and $G_9$ are independently a chemical bond or $C_{1-6}$ alkylene;
- $G_8$ and $G_{10}$ are independently $C_{1-10}$ alkylene;
- $G_7$ and $G_8$ have a total length of 4, 5, 6, 7, 8, 9 or 10 carbon atoms;
- $G_9$ and $G_{10}$ have a total length of 4, 5, 6, 7, 8, 9 or 10 carbon atoms;
- 1, 2 or 3 methylenes in $G_7$, $G_8$, $G_9$ or $G_{10}$ are optionally and independently substituted with 1 R.

In another more specific embodiment, $L_1$ and $L_2$ are independently $—(CHR)_2—$, $—CH{=}CH—$, $—C{\equiv}C—$ or $—NR''—$;

- $G_7$ and $G_9$ are independently a chemical bond or $C_{1-5}$ alkylene, alternatively a chemical bond or $C_{1-5}$ linear alkylene;
- $G_8$ and $G_{10}$ are independently $C_{1-8}$ alkylene, alternatively $C_{1-8}$ linear alkylene;
- $G_7$ and $G_8$ have a total length of 4, 5, 6, 7, 8, 9, 10 carbon atoms, alternatively 6, 7, 8, 9, 10 carbon atoms;
- $G_9$ and $G_{10}$ have a total length of 4, 5, 6, 7, 8, 9, 10 carbon atoms, alternatively 6, 7, 8, 9, 10 carbon atoms;
- 1 or 2 methylenes in $G_7$, $G_8$, $G_9$ or $G_{10}$ are optionally and independently substituted with 1 R.

Alternatively, the methylene collected to $M_1$ and $M_2$ is not substituted with R.

In another more specific embodiment, $L_1$ and $L_2$ are independently $-(CHR)_2-$, $-CH{=}CH-$, $-C{\equiv}C-$ or $-NR''-$;

$G_7$ and $G_9$ are independently a chemical bond, $-CH_2-$, $-(CH_2)_2-$, $-(CH_2)_4-$ or $-(CH_2)_5-$;

$G_8$ and $G_{10}$ are independently $-(CH_2)_2-$, $-(CH_2)_4-$, $-(CH_2)_6-$, $-(CH_2)_7-$ or $-(CH_2)_8-$;

$G_7$ and $G_8$ have a total length of 4, 5, 6, 7, 8, 9, 10 carbon atoms, alternatively 6, 7, 8, 9, 10 carbon atoms;

$G_9$ and $G_{10}$ have a total length of 4, 5, 6, 7, 8, 9, 10 carbon atoms, alternatively 6, 7, 8, 9, 10 carbon atoms;

1 or 2 methylenes in $G_7$, $G_8$, $G_9$ or $G_{10}$ are optionally and independently substituted with 1 R.

Alternatively, the methylene collected to $M_1$ and $M_2$ is not substituted with R.

In another more specific embodiment, $-G_7-L_1-G_8-H$ or $-G_9-L_2-G_{10}-H$ is independently selected from: $-(CH_2)_5CH_3$, $-(CH_2)_6CH_3$, $-(CH_2)_7CH_3$, $-(CH_2)_8CH_3$, $-(CH_2)_9CH_3$, $-(CH_2)_{10}CH_3$, $-(CH_2)_{11}CH_3$, $-CH_2-C{\equiv}C-(CH_2)_5CH_3$, $-CH_2-C{\equiv}C-(CH_2)_6CH_3$, $-(CH_2)_2-C{\equiv}C-(CH_2)_5CH_3$, $-(CH_2)_4-C{\equiv}C-(CH_2)_3CH_3$, $-CH_2-CH{=}CH-(CH_2)_5CH_3$, $-CH_2-CH{=}CH-(CH_2)_6CH_3$, $-(CH_2)_2-CH{=}CH-(CH_2)_5CH_3$, $-(CH_2)_4-CH{=}CH-(CH_2)_3CH_3$, $-(CH_2)_5-CH{=}CH-CH_2CH_3$,

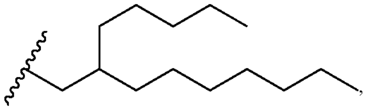,

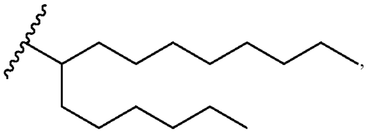,

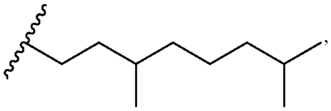,

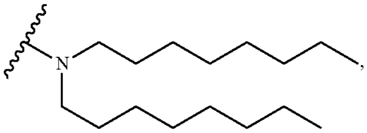,

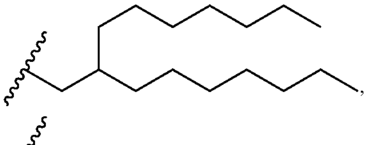,

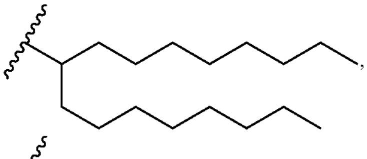,

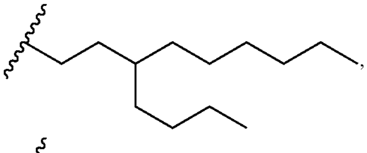,

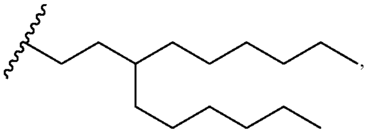,

-continued

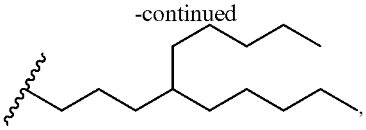,

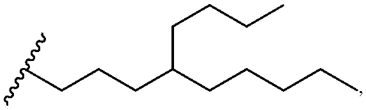,

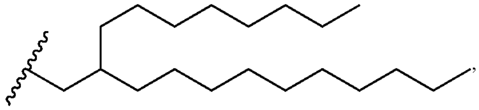,

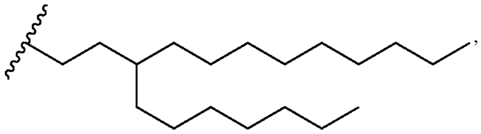,

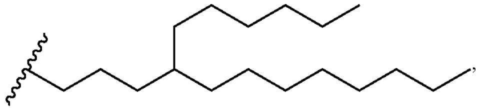,

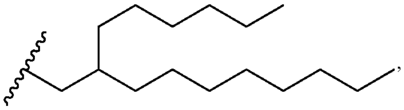,

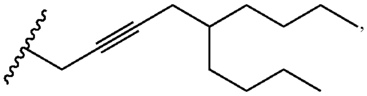,

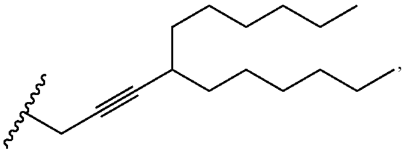,

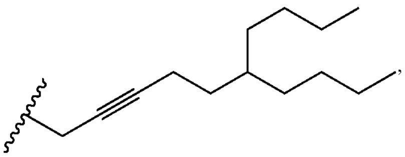,

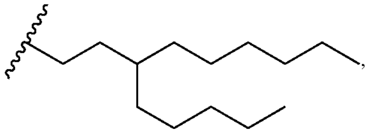, and

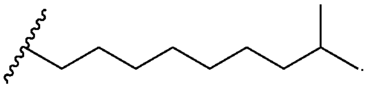.

$R^s$

In one embodiment, $R^s$ is H; in another embodiment, $R^s$ is $C_{1-14}$ alkyl; in another embodiment, $R^s$ is $-L_d-OR_d$; in another embodiment, $R^s$ is $-L_d-SR_d$; in another embodiment, $R^s$ is $-L_d-NR_dR'_d$; in another embodiment, $R^s$ is $C_{1-10}$ alkyl; in another embodiment, $R^s$ is $C_{1-6}$ alkyl.

In a more specific embodiment, $R^s$ is H, $C_{1-10}$ alkyl, $-L_d-OR_d$ or $-L_d-NR_dR'_d$; in another more specific embodiment, $R^s$ is H or $C_{1-6}$ alkyl.

R

In one embodiment, R is H; in another embodiment, R is $C_{1-20}$ alkyl; in another embodiment, R is $-L_a-OR_a$; in another embodiment, R is $-L_a-SR_a$; in another embodiment, R is $-L_a-NR_aR'_a$; in another embodiment, R is $C_{1-10}$ alkyl; in another embodiment, R is $C_{1-8}$ alkyl; in another embodiment, R is $C_{1-8}$ linear alkyl.

In a more specific embodiment, R is H, Me, $-(CH_2)_3CH_3$, $-(CH_2)_4CH_3$, $-(CH_2)_5CH_3$, $-(CH_2)_6CH_3$ or $-(CH_2)_7CH_3$.

R"

In one embodiment, R" is H; in another embodiment, R" is $C_{1-20}$ alkyl; in another embodiment, R" is $C_{1-14}$ alkyl; in another embodiment, R" is $C_{1-10}$ alkyl; in another embodiment, R" is $C_{7-9}$ alkyl; in another embodiment, R" is $-(CH_2)_7CH_3$.

$L_a$ and $L_e$

In one embodiment, $L_a$ and $L_e$ are independently a chemical bond; in another embodiment, $L_a$ and $L_e$ are independently $C_{1-20}$ alkylene; in another embodiment, $L_a$ and $L_e$ are independently $C_{1-14}$ alkylene; in another embodiment, $L_a$ and $L_e$ are independently $C_{1-10}$ alkylene.

$L_b$ and $L_f$

In one embodiment, $L_b$ and $L_f$ are independently a chemical bond; in another embodiment, $L_b$ and $L_f$ are independently $C_{1-10}$ alkylene; in another embodiment, $L_b$ and $L_f$ are independently $C_{1-6}$ alkylene.

$L_c$

In one embodiment, $L_c$ is a chemical bond; in another embodiment, $L_c$ is $C_{1-8}$ alkylene; in another embodiment, $L_c$ is $C_{1-6}$ alkylene.

$L_d$

In one embodiment, $L_d$ is a chemical bond; in another embodiment, $L_d$ is $C_{1-14}$ alkylene; in another embodiment, $L_d$ is $C_{1-10}$ alkylene.

$R_a$ and $R'_a$

In one embodiment, $R_a$ is H; in another embodiment, $R_a$ is $C_{1-20}$ alkyl; in another embodiment, $R_a$ is 3- to 14-membered cycloalkyl; in another embodiment, $R_a$ is 3- to 14-membered heterocyclyl; in another embodiment, $R_a$ is $C_{1-14}$ alkyl; in another embodiment, $R_a$ is $C_{1-10}$ alkyl; in another embodiment, $R_a$ is $C_{8-10}$ alkyl; in another embodiment, $R_a$ is $C_{8-10}$ linear alkyl; in another embodiment, $R_a$ is $-(CH_2)_8CH_3$; in another embodiment, $R_a$ is optionally substituted with one or more of the following substituents: H, $C_{1-20}$ alkyl, $-L_e-OR_e$, $-L_e-SR_e$ and $-L_e-NR_eR'_e$.

In one embodiment, $R'_a$ is H; in another embodiment, $R'_a$ is $C_{1-20}$ alkyl; in another embodiment, $R'_a$ is 3- to 14-membered cycloalkyl; in another embodiment, $R'_a$ is 3- to 14-membered heterocyclyl; in another embodiment, $R'_a$ is $C_{1-14}$ alkyl; in another embodiment, $R'_a$ is $C_{1-10}$ alkyl; in another embodiment, $R'_a$ is $C_{8-10}$ alkyl; in another embodiment, $R'_a$ is $C_{8-10}$ linear alkyl; in another embodiment, $R'_a$ is $-(CH_2)_8CH_3$; in another embodiment, $R'_a$ is optionally substituted with one or more of the following substituents: H, $C_{1-20}$ alkyl, $-L_e-OR_e$, $-L_e-SR_e$ and $-L_e-NR_eR'_e$.

$R_b$ and $R'_b$

In one embodiment, $R_b$ is H; in another embodiment, $R_b$ is $C_{1-10}$ alkyl; in another embodiment, $R_b$ is 3- to 14-membered cycloalkyl; in another embodiment, $R_b$ is 3- to 14-membered heterocyclyl; in another embodiment, $R_b$ is $C_{1-6}$ alkyl; in another embodiment, $R_b$ is 3- to 10-membered cycloalkyl; in another embodiment, $R_b$ is 3- to 10-membered heterocyclyl; in another embodiment, $R_b$ is optionally substituted with one or more of the following substituents: H, $C_{1-10}$ alkyl, $-L_f-OR_f$, $-L_f-SR_f$ and $-L_f-NR_fR'_f$.

In one embodiment, $R'_b$ is H; in another embodiment, $R'_b$ is $C_{1-10}$ alkyl; in another embodiment, $R'_b$ is 3- to 14-membered cycloalkyl; in another embodiment, $R'_b$ is 3- to 14-membered heterocyclyl; in another embodiment, $R'_b$ is $C_{1-6}$ alkyl; in another embodiment, $R'_b$ is 3- to 10-membered cycloalkyl; in another embodiment, $R'_b$ is 3- to 10-membered heterocyclyl; in another embodiment, $R_b$ is optionally substituted with one or more of the following substituents: H, $C_{1-10}$ alkyl, $-L_f-OR_f$, $-L_f-SR_f$ and $-L_f-NR_fR'_f$.

$R_c$ and $R'_c$

In one embodiment, $R_c$ is H; in another embodiment, $R_c$ is $C_{1-8}$ alkyl; in another embodiment, $R_c$ is $C_{1-6}$ alkyl.

In one embodiment, $R'_c$ is H; in another embodiment, $R'_c$ is $C_{1-8}$ alkyl; in another embodiment, $R'_c$ is $C_{1-6}$ alkyl.

$R_d$ and $R'_d$

In one embodiment, $R_d$ is H; in another embodiment, $R_d$ is $C_{1-14}$ alkyl; in another embodiment, $R_d$ is $C_{1-10}$ alkyl. In one embodiment, $R'_d$ is H; in another embodiment, $R'_d$ is $C_{1-14}$ alkyl; in another embodiment, $R'_d$ is $C_{1-10}$ alkyl.

$R_e$ and $R'_e$

In one embodiment, $R_e$ is H; in another embodiment, $R_e$ is $C_{1-20}$ alkyl.

In one embodiment, $R'_e$ is H; in another embodiment, $R'_e$ is $C_{1-20}$ alkyl.

$R_f$ and $R'_f$

In one embodiment, $R_f$ is H; in another embodiment, $R_f$ is $C_{1-10}$ alkyl.

In one embodiment, $R'_f$ is H; in another embodiment, $R'_f$ is $C_{1-10}$ alkyl.

Any of the above technical solutions in any specific embodiment or any combination thereof may be combined with any technical solution or any combination thereof in other specific embodiments. For example, any technical solution of Q, or any combination thereof, may be combined with any technical solution of $M_1$, $M_2$, $G_5$, $G_{6a}$, $G_{6b}$, $R_9$, $R_{10}$, R**, $G_1$, $G_2$, $G_3$, $G_4$, $R_1$, $R_2$, $R_3$, $R_4$, $R_5$, $R_6$, $R_7$, $R_8$, R, R", $R^s$, $Ar_2$, $L_a$, $L_e$, $L_b$, $L_f$, $L_c$, $L_d$, $R_a$, $R'_a$, $R_b$, $R'_b$, $R_c$, $R'_c$, $R_d$, $R'_d$, $R_e$, $R'_e$, $R_f$ and $R'_f$, or any combination thereof. The present disclosure is intended to include all of these combinations of technical solutions and, for reasons of space, will not be listed.

Technical solution 1: In a more specific embodiment, the present disclosure provides a nanoparticle composition, comprising a lipid ingredient, and optionally comprising a load;

wherein the lipid ingredient comprises the following components in the molar percentages:

Ionizable cationic lipids 20 mol %-85 mol %;

Structure lipids 10 mol %-75 mol %;

Neutral lipids 1.0 mol %-30 mol %;

Polymer lipids 0.25 mol %-10 mol %;

wherein the ionizable cationic lipid is a compound of formula (IV), or a pharmaceutically acceptable salt, isotopic variant, tautomer or stereoisomer thereof:

(IV)

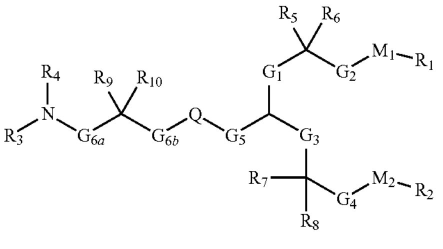

wherein, $M_1$ and $M_2$ are independently selected from —C(O)O—, —O—, —SC(O)O—, —OC(O)$NR_a$—, —$NR_a$C(O)$NR_a$—, —OC(O)S—, —OC(O)O—, —$NR_a$C(O)O—, —OC(O)—, —SC(O)—, —C(O)S—, —$NR_a$—, —C(O)$NR_a$—, —$NR_a$C(O)—, —$NR_a$C(O)S—, —SC (O)$NR_a$—, —C(O)—, —OC(S)—, —C(S)O—, —OC(S)$NR_a$—, —$NR_a$C(S)O—, —S—S— and —$S(O)_{0-2}$—;

Q is selected from a chemical bond, —C(O)O—, —O—, —SC(O)O—, —OC(O)$NR_b$—, —$NR_b$C(O)$NR_b$—, —OC(O)S—, —OC(O)O—, —$NR_b$C(O)O—, —OC(O)—, —SC(O)—, —C(O)S—, —$NR_b$—, —C(O)$NR_b$—, —$NR_b$C(O)—, —$NR_b$C(O)S—, —SC(O)$NR_b$—, —C(O)—, —OC(S)—, —C(S)O—, —OC(S)$NR_b$—, —$NR_b$C(S)O—, —S—S—, —$S(O)_{0-2}$—, phenylene and pyridylidene, wherein, the phenylene or pyridylidene is optionally substituted with one or more R*;

$G_5$ is a chemical bond or $C_{1-8}$ alkylene, which is optionally substituted with one or more R**;

$G_{6a}$ and $G_{6b}$ are independently a chemical bond or $C_{1-7}$ alkylene, which is optionally substituted with one or more R**;

$G_{6a}$ and $G_{6b}$ have a total length of 0, 1, 2, 3, 4, 5, 6 or 7 carbon atoms;

$R_9$, $R_{10}$ and R** are independently H, $C_{1-8}$ alkyl, -$L_c$-$OR_c$, -$L_c$-$SR_c$ or -$L_c$-$NR_cR'_c$;

$G_1$, $G_2$, $G_3$ and $G_4$ are independently a chemical bond, $C_{1-13}$ alkylene, $C_{2-13}$ alkenylene or $C_{2-13}$ alkynylene, which is optionally substituted with one or more $R^s$;

$G_1$ and $G_2$ have a total length of 3, 4, 5, 6, 7, 8, 9, 10, 11, 12 or 13 carbon atoms;

$G_3$ and $G_4$ have a total length of 3, 4, 5, 6, 7, 8, 9, 10, 11, 12 or 13 carbon atoms;

$R_3$ and $R_4$ are independently H, $C_{1-10}$ alkyl, $C_{1-10}$ haloalkyl, $C_{2-10}$ alkenyl, $C_{2-10}$ alkynyl, 3- to 14-membered cycloalkyl, 3- to 14-membered heterocyclyl, $C_{6-10}$ aryl or 5- to 14-membered heteroaryl, which is optionally substituted with one or more R*;

or, $R_3$ and $R_4$ are taken together with the N atom to which they are attached to form 3- to 14-membered heterocyclyl, which is optionally substituted with one or more R*;

or, $R_4$ and $R_9$ are taken together with the atoms to which they are attached to form 3- to 14-membered heterocyclyl or 5- to 14-membered heteroaryl, which is optionally substituted with one or more R*;

R* is independently H, halogen, cyano, $C_{1-10}$ alkyl, $C_{1-10}$ haloalkyl, -$L_b$-$OR_b$, -$L_b$-$SR_b$ or -$L_b$-$NR_bR'_b$;

$R_5$, $R_6$, $R_7$ and $R_8$ are independently $C_{1-8}$ alkyl, which is optionally substituted with one or more R*;

$R_1$ and $R_2$ are independently $C_{4-20}$ alkyl, $C_{4-20}$ alkenyl or $C_{4-20}$ alkynyl, which is optionally substituted with one or more R, and wherein one or more methylene units are optionally and independently replaced with —NR"—;

$R^s$ is independently H, $C_{1-14}$ alkyl, -$L_d$-$OR_d$, -$L_d$-$SR_d$ or -$L_d$-$NR_dR'_d$;

R is independently H, $C_{1-20}$ alkyl, -$L_a$-$OR_a$, -$L_a$-$SR_a$ or -$L_a$-$NR_aR'_a$;

R" is independently H or $C_{1-20}$ alkyl;

$L_a$ and $L_e$ are independently a chemical bond or $C_{1-20}$ alkylene;

$L_b$ and $L_f$ are independently a chemical bond or $C_{1-10}$ alkylene;

$L_c$ is independently a chemical bond or $C_{1-8}$ alkylene;

$L_d$ is independently a chemical bond or $C_{1-14}$ alkylene;

$R_a$ and $R'_a$ are independently selected from H, $C_{1-20}$ alkyl, 3- to 14-membered cycloalkyl, and 3- to 14-membered heterocyclyl, which are optionally substituted with one or more of the following substituents: H, $C_{1-20}$ alkyl, -$L_e$-$OR_e$, -$L_e$-$SR_e$ and -$L_e$-$NR_eR'_e$;

$R_b$ and $R'_b$ are independently selected from H, $C_{1-10}$ alkyl, 3- to 14-membered cycloalkyl, and 3- to 14-membered heterocyclyl, which are optionally substituted with one or more of the following substituents: H, $C_{1-10}$ alkyl, -$L_f$-$OR_f$, -$L_f$-$SR_f$ and -$L_f$-$NR_fR'_f$;

$R_c$ and $R'_c$ are independently H or $C_{1-8}$ alkyl;

$R_d$ and $R'_d$ are independently H or $C_{1-14}$ alkyl;

$R_e$ and $R'_e$ are independently H or $C_{1-20}$ alkyl;

$R_f$ and $R'_f$ are independently H or $C_{1-10}$ alkyl.

Technical solution 2: In a more specific embodiment, the present disclosure provides a nanoparticle composition as described above, wherein the lipid ingredient comprises the following components in the molar percentages:

Ionizable cationic lipids 25 mol %-65 mol %;
Structure lipids 25 mol %-70 mol %;
Neutral lipids 1 mol %-25 mol %;
Polymer lipids 0.5 mol %-8 mol %.

Alternatively, the lipid ingredient comprises the following components in the molar percentages:

Ionizable cationic lipids 30 mol %-60 mol %;
Structure lipids 27.5 mol %-66 mol %;
Neutral lipids 1.5 mol %-20 mol %;
Polymer lipids 1 mol %-5 mol %.

Alternatively, the lipid ingredient comprises the following components in the molar percentages:

Ionizable cationic lipids 30 mol %-50 mol %;
Structure lipids 30.5 mol %-66 mol %;
Neutral lipids 1.5 mol %-20 mol %;
Polymer lipids 1 mol %-5 mol %.

Technical solution 3: In a more specific embodiment, the present disclosure provides a nanoparticle composition as described above, wherein in the compound of formula (IV), $M_1$ and $M_2$ are independently selected from —C(O)O—, —SC(O)O—, —OC(O)$NR_a$—, —$NR_a$C(O)$NR_a$—, —OC(O)S—, —OC(O)O—, —$NR_a$C(O)O—, —C(O)S—, —C(O)$NR_a$—, —$NR_a$C(O)S—, —SC(O)$NR_a$—, —C(S)O—, —OC(S)$NR_a$— and —$NR_a$C(S)O—; alternatively —C(O)O—, —C(O)S—, —C(O)$NR_a$—, and —C(S)O—; alternatively —C(O)O—, —C(O)S— and —C(O)$NR_a$—.

Technical solution 4: In a more specific embodiment, the present disclosure provides a nanoparticle composition as described above, wherein in the compound of formula (IV), Q is selected from a chemical bond, —C(O)O—, —O—, —SC(O)O—, —OC(O)$NR_b$—, —$NR_b$C(O)$NR_b$—, —OC(O)S—, —OC(O)O—, —$NR_b$C(O)O—, —OC(O)—, —SC(O)—, —C(O)S—, —$NR_b$—, —C(O)$NR_b$—, —$NR_b$C(O)—, —$NR_b$C(O)S—, —SC(O)$NR_b$—, —C(O)—, —OC(S)—, —C(S)O—, —OC(S)$NR_b$—, —$NR_b$C(S)O—, —S—S—, and —$S(O)_{0-2}$—; alternatively —C(O)O—, —O—, —SC(O)O—, —OC(O)NH—, —NHC(O)NH—, —OC(O)S—, —OC(O)O—, —NHC(O)O—, —OC(O)—, —SC(O)—, —C(O)S—, —NH—, —C(O)NH—, —NHC(O)—, —NHC(O)S—, —SC(O)NH—, —C(O)—, —OC(S)—, —C(S)O—, —OC(S)NH— and —NHC(S)O—; alternatively —C(O)O—, —O—, —SC(O)O—, —OC(O)NH—, —NHC(O)NH—, —OC(O)S—, —OC(O)O— and —NHC(O)O—; more alternatively —C(O)O—.

Technical solution 5: In a more specific embodiment, the present disclosure provides a nanoparticle composition as described above, wherein in the compound of formula (IV), $G_5$ is a chemical bond.

Technical solution 6: In a more specific embodiment, the present disclosure provides a nanoparticle composition as described above, wherein in the compound of formula (IV), $G_{6a}$ and $G_{6b}$ are independently a chemical bond or $C_{1-5}$ alkylene, which is optionally substituted with 1, 2, 3 or 4 R**;

$G_{6a}$ and $G_{6b}$ have a total length of 0, 1, 2, 3, 4 or 5 carbon atoms.

Alternatively, $G_{6a}$ is a chemical bond or $C_{1-4}$ alkylene, which is optionally substituted with 1, 2, 3 or 4 R**;

$G_{6b}$ is a chemical bond or $C_{1-2}$ alkylene, which is optionally substituted with 1 or 2 R**;

$G_{6a}$ and $G_{6b}$ have a total length of 0, 1, 2, 3 or 4 carbon atoms.

Alternatively, $G_{6a}$ is a chemical bond or $C_{1-4}$ alkylene, alternatively $C_{2-4}$ alkylene, alternatively $C_{2-3}$ alkylene, more alternatively $-(CH_2)_2-$;

$G_{6b}$ is a chemical bond or methylene;

$G_{6a}$ and $G_{6b}$ have a total length of 0, 1, 2, 3 or 4 carbon atoms, alternatively 1, 2, 3 or 4 carbon atoms, alternatively 2 or 3 carbon atoms.

Alternatively, $G_{6a}$ is a chemical bond or $C_{1-4}$ linear alkylene, alternatively $C_{2-4}$ linear alkylene, alternatively $C_{2-3}$ linear alkylene, more alternatively $-(CH_2)_2-$;

$G_{6b}$ is a chemical bond or methylene;

$G_{6a}$ and $G_{6b}$ have a total length of 0, 1, 2, 3 or 4 carbon atoms, alternatively 1, 2, 3 or 4 carbon atoms, alternatively 2 or 3 carbon atoms.

Technical solution 7: In a more specific embodiment, the present disclosure provides a nanoparticle composition as described above, wherein in the compound of formula (IV), $R_9$ and R** are independently H, $C_{1-6}$ alkyl, $-L_c-OR_c$ or $-L_c-NR_cR'_c$, $R_{10}$ is H.

Alternatively, $R_9$ and R** are independently H or $C_{1-6}$ alkyl, $R_{10}$ is H.

Alternatively, $R_9$, R** and $R_{10}$ are H.

Technical solution 8: In a more specific embodiment, the present disclosure provides a nanoparticle composition as described above wherein in the compound of formula (IV), $-G_1-C(R_5R_6)-G_2-$ is

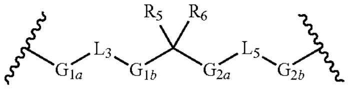, $-G_3-C(R_7R_8)-G_4-$ is

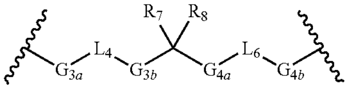;

wherein, one of $L_3$ and $L_5$, or one of $L_4$ and $L_6$ is $-(CR^sR^{s'})_2-$, $-CH{=}CH-$ or $-C{\equiv}C-$, and the other is a chemical bond;

$G_{1a}$, $G_{1b}$, $G_{2a}$, $G_{2b}$, $G_{3a}$, $G_{3b}$, $G_{4a}$ and $G_{4b}$ are independently a chemical bond or $C_{1-7}$ alkylene, which is optionally substituted with 1, 2, 3, 4 or 5 $R^s$;

$G_{1a}$, $G_{1b}$, $G_{2a}$ and $G_{2b}$ have a total length of 1, 2, 3, 4, 5, 6 or 7 carbon atoms;

$G_{3a}$, $G_{3b}$, $G_{4a}$ and $G_{4b}$ have a total length of 1, 2, 3, 4, 5, 6 or 7 carbon atoms;

$R^{s'}$ is independently H, $C_{1-14}$ alkyl, $-L_d-OR_d$ or $-L_d-NR_dR'_d$;

alternatively, one of $L_3$ and $L_5$, or one of $L_4$ and $L_6$ is $-(CHR^s)_2-$, $-CH{=}CH-$ or $-C{\equiv}C-$, and the other is a chemical bond;

$G_{1a}$ and $G_{3a}$ are independently a chemical bond or $C_{1-7}$ alkylene;

$G_{1b}$ and $G_{3b}$ are independently a chemical bond or $C_{1-3}$ alkylene;

$G_{2a}$ and $G_{4a}$ are independently a chemical bond or $C_{1-3}$ alkylene;

$G_{2b}$ and $G_{4b}$ are independently a chemical bond or $C_{1-4}$ alkylene;

$G_{1a}$, $G_{1b}$, $G_{2a}$ and $G_{2b}$ have a total length of 1, 2, 3, 4, 5, 6 or 7 carbon atoms;

$G_{3a}$, $G_{3b}$, $G_{4a}$ and $G_{4b}$ have a total length of 1, 2, 3, 4, 5, 6 or 7 carbon atoms.

Alternatively, one of $L_3$ and $L_5$, or one of $L_4$ and $L_6$ is $-(CH_2)_2-$, $-CH{=}CH-$ or $-C{\equiv}C-$, and the other is a chemical bond;

$G_{1a}$ and $G_{3a}$ are independently a chemical bond, $-CH_2-$, $-(CH_2)_2-$, $-(CH_2)_3-$, $-(CH_2)_4-$, $-(CH_2)_5-$ or $-(CH_2)_6-$;

$G_{1b}$ and $G_{3b}$ is a chemical bond;

$G_{2a}$ and $G_{4a}$ is a chemical bond;

$G_{2b}$ and $G_{4b}$ are independently a chemical bond, $-CH_2-$, $-(CH_2)_2-$ or $-(CH_2)_3-$;

$G_{1a}$, $G_{1b}$, $G_{2a}$ and $G_{2b}$ have a total length of 1, 2, 3, 4, 5 or 6 carbon atoms;

$G_{3a}$, $G_{3b}$, $G_{4a}$ and $G_{4b}$ have a total length of 1, 2, 3, 4, 5 or 6 carbon atoms.

Alternatively, $R^s$ and $R^{s'}$ are independently H, $C_{1-10}$ alkyl, $-L_d-OR_d$ or $-L_d-NR_dR'_d$; alternatively H or $C_{1-6}$ alkyl; more alternatively H;

alternatively, $-G_{1a}-L_3-G_{1b}-$ or $-G_{3a}-L_4-G_{3b}-$ is independently selected from the following groups:

$-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_3-CH{=}CH-$, $-(CH_2)_3-C{\equiv}C-$, $-(CH_2)_2-CH{=}CH-$ and $-(CH_2)_2-C{\equiv}C-$;

$-G_{2a}-L_5-G_{2b}-$ or $-G_{4a}-L_6-G_{4b}-$ is independently selected from the following groups:

a chemical bond, $-CH_2-$, $-(CH_2)_2-$, $-(CH_2)_3-$, $-CH{=}CH-CH_2-$, $-C{\equiv}C-$ and $-C{\equiv}C-CH_2-$;

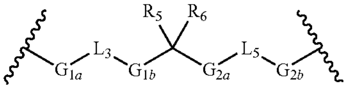 or

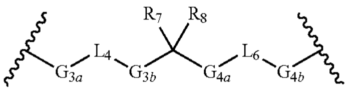

have a total length of 4, 5, 6, 7, 8 or 9 carbon atoms.

Alternatively,

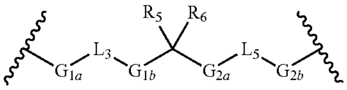 or

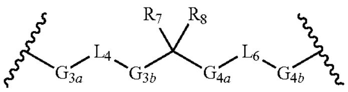

is independently selected from the following groups:

$-(CH_2)_3-C(CH_3)_2-$, $-(CH_2)_4-C(CH_3)_2-$, $-(CH_2)_5-C(CH_3)_2-$, $-(CH_2)_6-C(CH_3)_2-$, $-(CH_2)_7-C(CH_3)_2-$, $-(CH_2)_8-C(CH_3)_2-$, $-(CH_2)_3-CH{=}CH-C(CH_3)_2-$, $-(CH_2)_3-C{\equiv}C-C(CH_3)_2-$, $-(CH_2)_4-C(CH_3)_2-CH_2-$, $-(CH_2)_3-C(CH_3)_2-(CH_2)_2-$, $-(CH_2)_2-C$ $(CH_3)_2—(CH_2)_3—$, $—(CH_2)_2—CH{=}CH—C(CH_3)_2—CH_2—$, $—(CH_2)_2—C(CH_3)_2—C{\equiv}C—CH_2—$, $—(CH_2)_2—C(CH_3)_2—CH{=}CH—CH_2—$, $—(CH_2)_2—C{\equiv}C—C(CH_3)_2—CH_2—$ and $—(CH_2)_3—C(CH_3)_2—C{\equiv}C—$, alternatively $—(CH_2)_4—C(CH_3)_2—$, $—(CH_2)_5—C(CH_3)_2—$ and $—(CH_2)_6—C(CH_3)_2—$, more alternatively $—(CH_2)_5—C(CH_3)_2—$.

Technical solution 9: In a more specific embodiment, the present disclosure provides a nanoparticle composition as described above, wherein in the compound of formula (IV), $R_3$ and $R_4$ are independently H, $C_{1-6}$ alkyl, $C_{1-6}$ haloalkyl, 3- to 10-membered cycloalkyl or 3- to 10-membered heterocyclyl, which is optionally substituted with 1, 2, 3, 4 or 5 R*;

or, $R_3$ and $R_4$ are taken together with the N atom to which they are attached to form 3- to 10-membered heterocyclyl, which is optionally substituted with 1, 2, 3, 4 or 5 R*;

or, $R_4$ and $R_9$ are taken together with the atoms to which they are attached to form 3- to 10-membered heterocyclyl, which is optionally substituted with 1, 2, 3 or 4 R*.

Alternatively, $R_3$ and $R_4$ are independently H, $C_{1-6}$ alkyl, $C_{1-6}$ haloalkyl, 3- to 7-membered cycloalkyl or 3- to 7-membered heterocyclyl, which is optionally substituted with 1, 2, 3, 4 or 5 R*;

or, $R_3$ and $R_4$ are taken together with the N atom to which they are attached to form 3- to 7-membered heterocyclyl, which is optionally substituted with 1, 2, 3, 4 or 5 R*;

or, $R_4$ and $R_9$ are taken together with the atoms to which they are attached to form 3- to 7-membered heterocyclyl, which is optionally substituted with 1, 2, 3, 4 or 5 R*.

Alternatively, $R_3$ and $R_4$ are independently $C_{1-6}$ alkyl, alternatively $C_{1-3}$ alkyl, which is optionally substituted with 1, 2, 3, 4 or 5 R*;

or, $R_3$ and $R_4$ are taken together with the N atom to which they are attached to form 5- to 7-membered heterocyclyl, alternatively 4- to 6-membered heterocyclyl, more alternatively 5-membered heterocyclyl, which is optionally substituted with 1, 2, 3, 4 or 5 R*;

or, $R_4$ and $R_9$ are taken together with the atoms to which they are attached to form 6-membered heterocyclyl, which is optionally substituted with 1, 2, 3, 4 or 5 R*.

Alternatively, R* is independently H, halogen, cyano, $C_{1-6}$ alkyl, $C_{1-6}$ haloalkyl, $-L_b-OR_b$ or $-L_b-NR_bR'_b$; alternatively H, $C_{1-6}$ alkyl, $C_{1-6}$ haloalkyl or $—OR_b$; alternatively H, halogen, $C_{1-6}$ alkyl or $C_{1-6}$ haloalkyl; alternatively H, $C_{1-6}$ alkyl or $C_{1-6}$ haloalkyl; alternatively independently H, Me or OH; more alternatively H or Me.

Alternatively, $R_3$ is Me, $—CH_2CH_3$, $—CH_2CH_2OH$ or $—CH(CH_3)_2$, alternatively Me, $—CH_2CH_3$ or $—CH(CH_3)_2$, more alternatively Me or $—CH_2CH_3$;

$R_4$ is Me;

or, $R_3$ and $R_4$ are taken together with the N atom to which they are attached to form

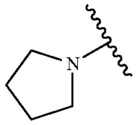,
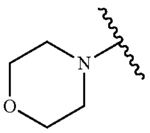,
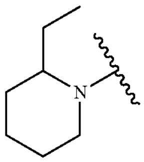
or

-continued

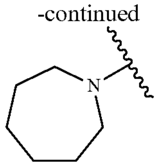, alternatively

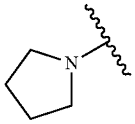
or
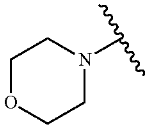, more alternatively

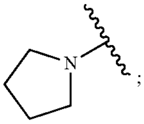 [SMILES: *N1CCCC1];

or, $R_4$ and $R_9$ are taken together with the atoms to which they are attached to form

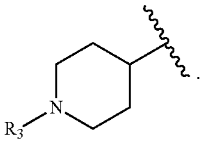.

Technical solution 10: In a more specific embodiment, the present disclosure provides a nanoparticle composition as described above, in the compound of formula (IV), $R_5$, $R_6$, $R_7$ and $R_8$ are independently $C_{1-6}$ alkyl; alternatively $C_{1-3}$ alkyl; more alternatively Me.

Alternatively, $R_5$, $R_6$, $R_7$ and $R_8$ is optionally substituted with 1, 2, 3, 4 or 5 R*.

Technical solution 11: In a more specific embodiment, the present disclosure provides a nanoparticle composition as described above, wherein in the compound of formula (IV), $R_1$ is $-G_7-L_1-G_8-H$, $R_2$ is $-G_9-L_2-G_{10}-H$, wherein, $L_1$ and $L_2$ are independently $—(CRR')_2—$, $—CH{=}CH—$, $—C{\equiv}C—$ or $—NR''—$;

$G_7$, $G_8$, $G_9$ and $G_{10}$ are independently a chemical bond or $C_{1-12}$ alkylene, which is optionally substituted with 1, 2, 3, 4, 5 or 6 R;

$G_7$ and $G_8$ have a total length of 4, 5, 6, 7, 8, 9, 10, 11 or 12 carbon atoms;

$G_9$ and $G_{10}$ have a total length of 4, 5, 6, 7, 8, 9, 10, 11 or 12 carbon atoms;

1, 2 or 3 methylenes in $G_7$, $G_8$, $G_9$ or $G_{10}$ are optionally and independently substituted with 1 R;

R' is independently H, $C_{1-20}$ alkyl, $-L_a-OR_a$ or $-L_a-NR_aR'_a$.

Alternatively, $L_1$ and $L_2$ are independently $—(CHR)_2—$, $—CH{=}CH—$, $—C{\equiv}C—$ or $—NR''—$;

$G_7$ and $G_9$ are independently a chemical bond or $C_{1-6}$ alkylene;

$G_8$ and $G_{10}$ are independently $C_{1-10}$ alkylene;

$G_7$ and $G_8$ have a total length of 4, 5, 6, 7, 8, 9 or 10 carbon atoms;

$G_9$ and $G_{10}$ have a total length of 4, 5, 6, 7, 8, 9 or 10 carbon atoms;

1, 2 or 3 methylenes in $G_7$, $G_8$, $G_9$ or $G_{10}$ are optionally and independently substituted with 1 R.

Alternatively, $L_1$ and $L_2$ are independently —$(CHR)_2$—, —CH═CH—, —C≡C— or —NR"—;

$G_7$ and $G_9$ are independently a chemical bond or $C_{1-5}$ alkylene, alternatively a chemical bond or $C_{1-5}$ linear alkylene;

$G_8$ and $G_{10}$ are independently $C_{1-8}$ alkylene, alternatively $C_{1-8}$ linear alkylene;

$G_7$ and $G_8$ have a total length of 4, 5, 6, 7, 8, 9, 10 carbon atoms, alternatively 6, 7, 8, 9, 10 carbon atoms;

$G_9$ and $G_{10}$ have a total length of 4, 5, 6, 7, 8, 9, 10 carbon atoms, alternatively 6, 7, 8, 9, 10 carbon atoms;

1 or 2 methylenes in $G_7$, $G_8$, $G_9$ or $G_{10}$ are optionally and independently substituted with 1 R.

Alternatively, $L_1$ and $L_2$ are independently —$(CHR)_2$—, —CH═CH—, —C≡C— or —NR"—;

$G_7$ and $G_9$ are independently a chemical bond, —$CH_2$—, —$(CH_2)_2$—, —$(CH_2)_4$— or —$(CH_2)_5$—;

$G_8$ and $G_{10}$ are independently —$(CH_2)_2$—, —$(CH_2)_4$—, —$(CH_2)_6$—, —$(CH_2)_7$— or —$(CH_2)_8$—;

$G_7$ and $G_8$ have a total length of 4, 5, 6, 7, 8, 9, 10 carbon atoms, alternatively 6, 7, 8, 9, 10 carbon atoms;

$G_9$ and $G_{10}$ have a total length of 4, 5, 6, 7, 8, 9, 10 carbon atoms, alternatively 6, 7, 8, 9, 10 carbon atoms;

1 or 2 methylenes in $G_7$, $G_8$, $G_9$ or $G_{10}$ are optionally and independently substituted with 1 R.

Alternatively, R and R' are independently H, $C_{1-14}$ alkyl, $-L_a-OR_a$ or $-L_a-NR_aR'_a$; alternatively H or $C_{1-10}$ alkyl; alternatively H or $C_{1-8}$ alkyl; alternatively H or $C_{1-7}$ alkyl; alternatively H or $C_{1-6}$ alkyl; alternatively H or $C_{1-8}$ linear alkyl; alternatively H or $C_{1-7}$ linear alkyl; alternatively H or $C_{1-6}$ linear alkyl; alternatively H, Me, —$(CH_2)_3CH_3$, —$(CH_2)_4CH_3$, —$(CH_2)_5CH_3$, —$(CH_2)_6CH_3$ or —$(CH_2)_7CH_3$; alternatively H, Me, —$(CH_2)_3CH_3$, —$(CH_2)_4CH_3$, —$(CH_2)_5CH_3$ or —$(CH_2)_6CH_3$; more alternatively H, Me, —$(CH_2)_3CH_3$, —$(CH_2)_4CH_3$ or —$(CH_2)_5CH_3$.

Alternatively, R" is H or $C_{1-14}$ alkyl; alternatively H or $C_{1-10}$ alkyl; alternatively H or $C_{7-9}$ alkyl; alternatively H or $C_{7-9}$ linear alkyl; more alternatively —$(CH_2)_7CH_3$.

Alternatively, $-G_7-L_1-G_8-H$ or $-G_9-L_2-G_{10}-H$ is independently selected from the following groups:

$(CH_2)_5CH_3$, —$(CH_2)_6CH_3$, —$(CH_2)_7CH_3$, —$(CH_2)_8CH_3$, —$(CH_2)_9CH_3$, —$(CH_2)_{10}CH_3$, —$(CH_2)_{11}CH_3$, —$CH_2$—C≡C—$(CH_2)_5CH_3$, —$CH_2$—C≡C—$(CH_2)_6CH_3$, —$(CH_2)_2$—C≡C—$(CH_2)_5CH_3$, —$(CH_2)_4$—C≡C—$(CH_2)_3CH_3$, —$CH_2$—CH═CH—$(CH_2)_5CH_3$, —$CH_2$—CH═CH—$(CH_2)_6CH_3$, —$(CH_2)_2$—CH═CH—$(CH_2)_5CH_3$, —$(CH_2)_4$—CH═CH—$(CH_2)_3CH_3$, —$(CH_2)_5$—CH═CH—$CH_2CH_3$,

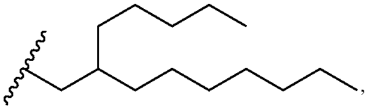,

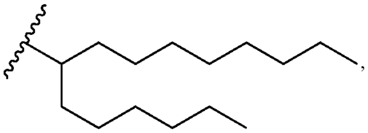,

-continued

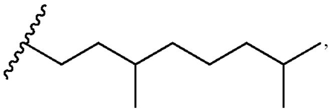,

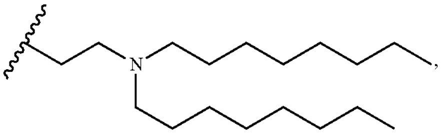,

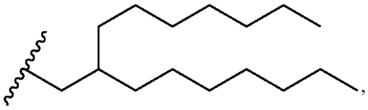,

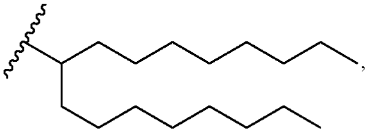,

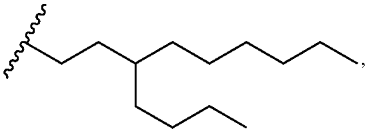,

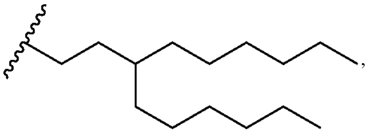,

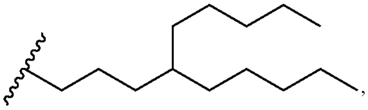,

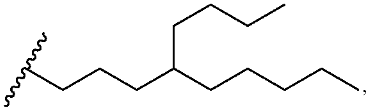,

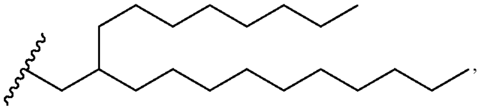,

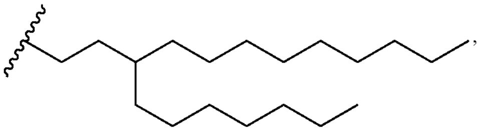,

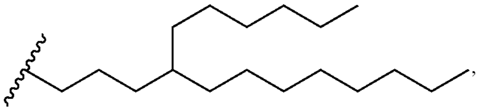,

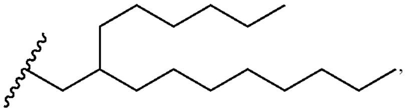,

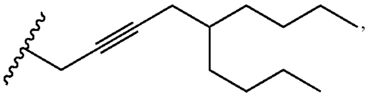,

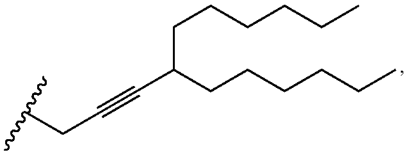,

-continued

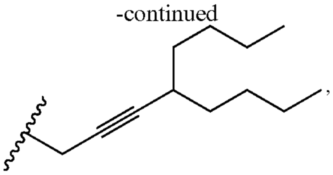
,

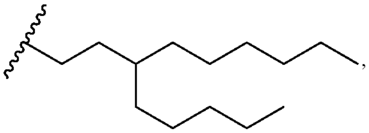
, and

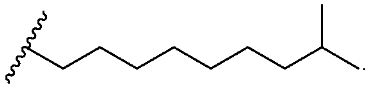
.

Technical solution 12: In a more specific embodiment, the present disclosure provides a nanoparticle composition as described above, wherein the compound of formula (IV) has the following structural formula:

(V)

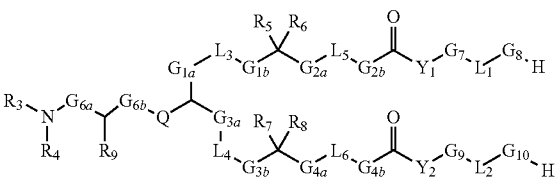

(VI)

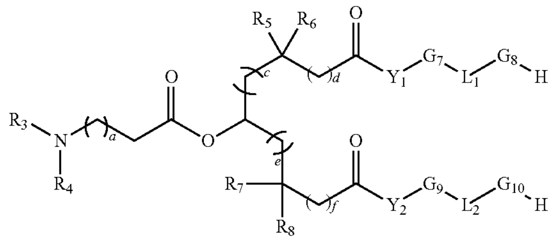

(VII)

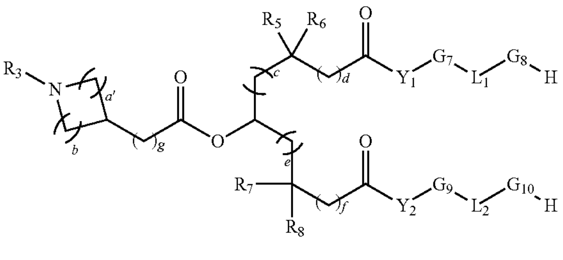

wherein, a, a', b and g are independently 0, 1, 2, 3, 4 or 5, a' and b are not 0 at the same time;

a'+g=0, 1, 2, 3, 4 or 5;

c and e are independently 3, 4, 5, 6, 7, 8 or 9;

d and f are independently 0, 1, 2, 3 or 4;

c+d=3, 4, 5, 6, 7, 8 or 9, e+f=3, 4, 5, 6, 7, 8 or 9;

methylenes in

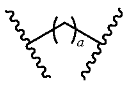
or
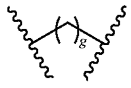

are optionally and independently substituted with 1, 2, 3, 4 or 5 $C_{1-6}$ alkyl.

The remaining groups are defined in any one of the above.

Technical solution 13: In a more specific embodiment, the present disclosure provides a nanoparticle composition as described above, wherein in the compound of formula (V), Q is selected from —C(O)O—, —O—, —SC(O)O—, —OC(O)$NR_b$—, —$NR_b$C(O)$NR_b$—, —OC(O)S—, —OC(O)O—, —$NR_b$C(O)O—, —OC(O)—, —SC(O)—, —C(O)S—, —$NR_b$—, —C(O)$NR_b$—, —$NR_b$C(O)—, —$NR_b$C(O)S—, —SC(O)$NR_b$—, —C(O)—, —OC(S)—, —C(S)O—, —OC(S)$NR_b$—, —$NR_b$C(S)O—, —S—S—, and —$S(O)_{0-2}$—;

$G_{6a}$ and $G_{6b}$ are independently a chemical bond or $C_{1-5}$ alkylene, which is optionally substituted with 1, 2, 3 or 4 R**;

$G_{6a}$ and $G_{6b}$ have a total length of 0, 1, 2, 3, 4 or 5 carbon atoms;

$R_9$ and R** are independently H, $C_{1-6}$ alkyl, -$L_c$-$OR_c$ or -$L_c$-$NR_cR'_c$;

one of $L_3$ and $L_5$, or one of $L_4$ and $L_6$ is —$(CR^sR^{s'})_2$—, —CH═CH—, or —C≡C—, and the other is a chemical bond;

$G_{1a}$, $G_{1b}$, $G_{2a}$, $G_{2b}$, $G_{3a}$, $G_{3b}$, $G_{4a}$ and $G_{4b}$ are independently a chemical bond or $C_{1-7}$ alkylene, which is optionally substituted with 1, 2, 3, 4 or 5 $R^s$;

$G_{1a}$, $G_{1b}$, $G_{2a}$ and $G_{2b}$ have a total length of 1, 2, 3, 4, 5, 6 or 7 carbon atoms;

$G_{3a}$, $G_{3b}$, $G_{4a}$ and $G_{4b}$ have a total length of 1, 2, 3, 4, 5, 6 or 7 carbon atoms;

$R_3$ and $R_4$ are independently H, $C_{1-6}$ alkyl, $C_{1-6}$ haloalkyl, 3- to 10-membered cycloalkyl or 3- to 10-membered heterocyclyl, which is optionally substituted with 1, 2, 3, 4 or 5 R*;

or, $R_3$ and $R_4$ are taken together with the N atom to which they are attached to form 3- to 10-membered heterocyclyl, which is optionally substituted with 1, 2, 3, 4 or 5 R*;

or, $R_4$ and $R_9$ are taken together with the atoms to which they are attached to form 3- to 10-membered heterocyclyl, which is optionally substituted with 1, 2, 3 or 4 R*;

R* is independently H, halogen, cyano, $C_{1-6}$ alkyl, $C_{1-6}$ haloalkyl, -$L_b$-$OR_b$ or -$L_b$-$NR_bR'_b$;

$R_5$, $R_6$, $R_7$ and $R_8$ are independently $C_{1-6}$ alkyl, which is optionally substituted with 1, 2, 3, 4 or 5 R*;

$Y_1$ and $Y_2$ are independently O, S or $NR_a$;

$L_1$ and $L_2$ are independently —$(CRR')_2$—, —CH═CH—, —C≡C— or —NR"—;

$G_7$, $G_8$, $G_9$ and $G_{10}$ are independently a chemical bond or $C_{1-12}$ alkylene, which is optionally substituted with 1, 2, 3, 4, 5 or 6 R;

$G_7$ and $G_8$ have a total length of 4, 5, 6, 7, 8, 9, 10, 11 or 12 carbon atoms;

$G_9$ and $G_{10}$ have a total length of 4, 5, 6, 7, 8, 9, 10, 11 or 12 carbon atoms;

1, 2 or 3 methylenes in $G_7$, $G_8$, $G_9$ or $G_{10}$ are optionally and independently substituted with 1 R;

$R^s$ and $R^{s'}$ are independently H, $C_{1-10}$ alkyl, $-L_d-OR_d$ or $-L_d-NR_dR'_d$;

R and R' are independently H, $C_{1-14}$ alkyl, $-L_a-OR_a$ or $-L_a-NR_aR'_a$;

R" is independently H or $C_{1-14}$ alkyl;

$L_a$ is independently a chemical bond or $C_{1-14}$ alkylene;

$L_b$ is independently a chemical bond or $C_{1-6}$ alkylene;

$L_c$ is independently a chemical bond or $C_{1-6}$ alkylene;

$L_d$ is independently a chemical bond or $C_{1-10}$ alkylene;

$R_a$ and $R'_a$ are independently H, $C_{1-14}$ alkyl, 3- to 10-membered cycloalkyl or 3- to 10-membered heterocyclyl;

$R_b$ and $R'_b$ are independently H, $C_{1-6}$ alkyl, 3- to 10-membered cycloalkyl or 3- to 10-membered heterocyclyl;

$R_c$ and $R'_d$ are independently H or $C_{1-6}$ alkyl;

$R_d$ and $R'_d$ are independently H or $C_{1-10}$ alkyl.

Technical solution 14: In a more specific embodiment, the present disclosure provides a nanoparticle composition as described above, wherein in the compound of formula (V), Q is selected from —C(O)O—, —O—, —SC(O)O—, —OC(O)NH—, —NHC(O)NH—, —OC(O)S—, —OC(O)O—, —NHC(O)O—, —OC(O)—, —SC(O)—, —C(O)S—, —NH—, —C(O)NH—, —NHC(O)—, —NHC(O)S—, —SC(O)NH—, —C(O)—, —OC(S)—, —C(S)O—, —OC(S)NH— and —NHC(S)O—;

$G_{6a}$ is a chemical bond or $C_{1-4}$ alkylene, which is optionally substituted with 1, 2, 3 or 4 R**;

$G_{6b}$ is a chemical bond or $C_{1-2}$ alkylene, which is optionally substituted with 1 or 2 R**;

$G_{6a}$ and $G_{6b}$ have a total length of 0, 1, 2, 3 or 4 carbon atoms;

$R_9$ and R** are independently H or $C_{1-6}$ alkyl;

one of $L_3$ and $L_5$, or one of $L_4$ and $L_6$ is $—(CHR^s)_2—$, —CH═CH— or —C≡C—, and the other is a chemical bond;

$G_{1a}$ and $G_{3a}$ are independently a chemical bond or $C_{1-7}$ alkylene;

$G_{1b}$ and $G_{3b}$ are independently a chemical bond or $C_{1-3}$ alkylene;

$G_{2a}$ and $G_{4a}$ are independently a chemical bond or $C_{1-3}$ alkylene;

$G_{2b}$ and $G_4O$ are independently a chemical bond or $C_{1-4}$ alkylene;

$G_{1a}$, $G_{1b}$, $G_{2a}$ and $G_{2b}$ have a total length of 1, 2, 3, 4, 5, 6 or 7 carbon atoms;

$G_{3a}$, $G_{3b}$, $G_{4a}$ and $G_{4b}$ have a total length of 1, 2, 3, 4, 5, 6 or 7 carbon atoms;

$R_3$ and $R_4$ are independently H, $C_{1-6}$ alkyl, $C_{1-6}$ haloalkyl, 3- to 7-membered cycloalkyl or 3- to 7-membered heterocyclyl, which is optionally substituted with 1, 2, 3, 4 or 5 R*;

or, $R_3$ and $R_4$ are taken together with the N atom to which they are attached to form 3- to 7-membered heterocyclyl, which is optionally substituted with 1, 2, 3, 4 or 5 R*;

or, $R_4$ and $R_9$ are taken together with the atoms to which they are attached to form 3- to 7-membered heterocyclyl, which is optionally substituted with 1, 2, 3, 4 or 5 R*;

R* is independently H, halogen, cyano, $C_{1-6}$ alkyl, $C_{1-6}$ haloalkyl, $-L_b-OR_b$ or $-L_b-NR_bR'_b$;

$R_5$, $R_6$, $R_7$ and $R_8$ are independently $C_{1-6}$ alkyl;

$Y_1$ and $Y_2$ are independently O, S or $NR_a$;

$L_1$ and $L_2$ are independently $—(CHR)_2—$, —CH═CH—, —C≡C— or —NR"—;

$G_7$ and $G_9$ are independently a chemical bond or $C_{1-6}$ alkylene;

$G_8$ and $G_{10}$ are independently $C_{1-10}$ alkylene;

$G_7$ and $G_8$ have a total length of 4, 5, 6, 7, 8, 9 or 10 carbon atoms;

$G_9$ and $G_{10}$ have a total length of 4, 5, 6, 7, 8, 9 or 10 carbon atoms;

1, 2 or 3 methylenes in $G_7$, $G_8$, $G_9$ or $G_{10}$ are optionally and independently substituted with 1 R;

$R^s$ is independently H or $C_{1-6}$ alkyl;

R is independently H or $C_{1-10}$ alkyl;

R" is independently H or $C_{1-10}$ alkyl;

$L_b$ is independently a chemical bond or $C_{1-6}$ alkylene;

$R_a$ is independently H or $C_{1-10}$ alkyl;

$R_b$ and $R'_b$ are independently H or $C_{1-6}$ alkyl.

Technical solution 15: In a more specific embodiment, the present disclosure provides a nanoparticle composition as described above, wherein in the compound of formula (V), Q is —C(O)O—, —O—, —SC(O)O—, —OC(O)NH—, —NHC(O)NH—, —OC(O)S—, —OC(O)O— or —NHC(O)O—;

$G_{6a}$ is a chemical bond or $C_{1-4}$ alkylene, alternatively a chemical bond or $C_{1-4}$ linear alkylene;

$G_{6b}$ is a chemical bond or methylene;

$G_{6a}$ and $G_{6b}$ have a total length of 0, 1, 2, 3 or 4 carbon atoms;

$R_9$ is H;

one of $L_3$ and $L_5$, or one of $L_4$ and $L_6$ is $—(CH_2)_2—$, —CH═CH—, or —C≡C—, and the other is a chemical bond;

$G_{1a}$ and $G_{3a}$ are independently a chemical bond, $—CH_2—$, $—(CH_2)_2—$, $—(CH_2)_3—$, $—(CH_2)_4—$, $—(CH_2)_5—$ or $—(CH_2)_6—$;

$G_{1b}$ and $G_{3b}$ are a chemical bond;

$G_{2a}$ and $G_{4a}$ are a chemical bond;

$G_{2b}$ and $G_{4b}$ are independently a chemical bond, $—CH_2—$, $—(CH_2)_2—$ or $—(CH_2)_3—$;

$G_{1a}$, $G_{1b}$, $G_{2a}$ and $G_{2b}$ have a total length of 1, 2, 3, 4, 5 or 6 carbon atoms;

$G_{3a}$, $G_{3b}$, $G_{4a}$ and $G_{4b}$ have a total length of 1, 2, 3, 4, 5 or 6 carbon atoms;

$R_3$ and $R_4$ are independently $C_{1-6}$ alkyl, which is optionally substituted with 1, 2 or 3 R*;

or, $R_3$ and $R_4$ are taken together with the N atom to which they are attached to form 5- to 7-membered heterocyclyl, which is optionally substituted with 1, 2, 3, 4 or 5 R*;

or, $R_4$ and $R_9$ are taken together with the atoms to which they are attached to form 6-membered heterocyclyl, which is optionally substituted with 1, 2, 3, 4 or 5 R*;

R* is independently H, $C_{1-6}$ alkyl, $C_{1-6}$ haloalkyl or $—OR_b$;

$R_5$, $R_6$, $R_7$ and $R_8$ are independently $C_{1-3}$ alkyl;

$Y_1$ and $Y_2$ are independently O, S or $NR_a$, alternatively O or S;

$L_1$ and $L_2$ are independently $—(CHR)_2—$, —CH═CH—, —C≡C— or —NR"—;

$G_7$ and $G_9$ are independently a chemical bond or $C_{1-5}$ alkylene, alternatively a chemical bond or $C_{1-5}$ linear alkylene;

$G_8$ and $G_{10}$ are independently $C_{1-8}$ alkylene, alternatively $C_{1-8}$ linear alkylene;

$G_7$ and $G_8$ have a total length of 4, 5, 6, 7, 8, 9, 10 carbon atoms;

$G_9$ and $G_{10}$ have a total length of 4, 5, 6, 7, 8, 9, 10 carbon atoms;

1 or 2 methylenes in $G_7$, $G_8$, $G_9$ or $G_{10}$ are optionally and independently substituted with 1 R;

R is independently H or $C_{1-8}$ alkyl, alternatively H or $C_{1-8}$ linear alkyl;

R" is independently H or $C_{7-9}$ alkyl, alternatively H or $C_{7-9}$ linear alkyl;

$R_a$ is independently H or $C_{8-10}$ alkyl, alternatively H or $C_{8-10}$ linear alkyl;

$R_b$ is independently H or $C_{1-6}$ alkyl, alternatively H.

Technical solution 16: In a more specific embodiment, the present disclosure provides a nanoparticle composition as described above, wherein in the compound of formula (V), Q is —C(O)O—, —O—, —SC(O)O—, —OC(O)NH—, —NHC(O)NH—, —OC(O)S—, —OC(O)O— or —NHC(O)O—;

$G_{6a}$ is a chemical bond, —$CH_2$—, —$(CH_2)_2$—, —$(CH_2)_3$— or —$(CH_2)_4$—;

$G_{6b}$ is a chemical bond or methylene;

$G_{6a}$ and $G_{6b}$ have a total length of 0, 1, 2, 3 or 4 carbon atoms;

$R_9$ is H;

-$G_{1a}$-$L_3$-$G_{1b}$- or -$G_{3a}$-$L_4$-$G_{3b}$- is independently selected from the following groups:

—$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_3$—CH═CH—, —$(CH_2)_3$—C≡C—, —$(CH_2)_2$—CH═CH— and —$(CH_2)_2$—C≡C—;

-$G_{2a}$-$L_5$-$G_{2b}$- or -$G_{4a}$-$L_6$-$G_{4b}$- is independently selected from the following groups:

a chemical bond, —$CH_2$—, —$(CH_2)_2$—, —$(CH_2)_3$—, —CH═CH—$CH_2$—, —C≡C— and —C≡C—$CH_2$—;

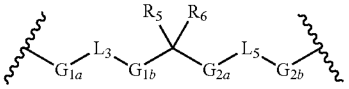

or

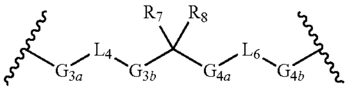

have a total length of 4, 5, 6, 7, 8 or 9 carbon atoms;

$R_3$ is Me, —$CH_2CH_3$, —$CH_2CH_2OH$ or —$CH(CH_3)_2$;

$R_4$ is Me;

or, $R_3$ and $R_4$ are taken together with the N atom to which they are attached to form

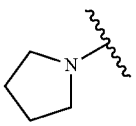,

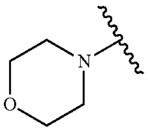,

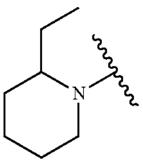

or

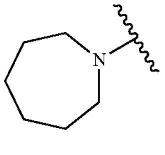;

or, $R_4$ and $R_9$ are taken together with the atoms to which they are attached to form

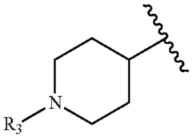;

$R_5$, $R_6$, $R_7$ and $R_8$ are Me;

$Y_1$ and $Y_2$ are independently O, S or $NR_a$;

$L_1$ and $L_2$ are independently —$(CHR)_2$—, —CH═CH—, —C≡C— or —NR"—;

$G_7$ and $G_9$ are independently a chemical bond, —$CH_2$—, —$(CH_2)_2$—, —$(CH_2)_4$— or —$(CH_2)_5$—;

$G_8$ and $G_{10}$ are independently —$(CH_2)_2$—, —$(CH_2)_4$—, —$(CH_2)_6$—, —$(CH_2)_7$— or —$(CH_2)_8$—;

$G_7$ and $G_8$ have a total length of 4, 5, 6, 7, 8, 9, 10 carbon atoms;

$G_9$ and $G_{10}$ have a total length of 4, 5, 6, 7, 8, 9, 10 carbon atoms;

1 or 2 methylenes in $G_7$, $G_8$, $G_9$ or $G_{10}$ are optionally and independently substituted with 1 R;

R is independently H, Me, —$(CH_2)_3CH_3$, —$(CH_2)_4CH_3$, —$(CH_2)_5CH_3$, —$(CH_2)_6CH_3$ or —$(CH_2)_7CH_3$;

R" is —$(CH_2)_7CH_3$;

$R_a$ is independently H or —$(CH_2)_8CH_3$.

Alternatively,

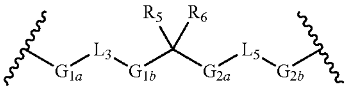

or

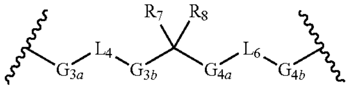

is independently selected from the following groups:

—$(CH_2)_3$—$C(CH_3)_2$—, —$(CH_2)_4$—$C(CH_3)_2$—, —$(CH_2)_5$—$C(CH_3)_2$—, —$(CH_2)_6$—$C(CH_3)_2$—, —$(CH_2)_7$—$C(CH_3)_2$—, —$(CH_2)_8$—$C(CH_3)_2$—, —$(CH_2)_3$—CH═CH—$C(CH_3)_2$—, —$(CH_2)_3$—C≡C—$C(CH_3)_2$—, —$(CH_2)_4$—$C(CH_3)_2$—$CH_2$—, —$(CH_2)_3$—$C(CH_3)_2$—$(CH_2)_2$—, —$(CH_2)_2$—$C(CH_3)_2$—$(CH_2)_3$—, —$(CH_2)_2$—CH═CH—$C(CH_3)_2$—$CH_2$—, —$(CH_2)_2$—$C(CH_3)_2$—C≡C—$CH_2$—, —$(CH_2)_2$—$C(CH_3)_2$—CH═CH—$CH_2$—, —$(CH_2)_2$—C≡C—$C(CH_3)_2$—$CH_2$— and —$(CH_2)_3$—$C(CH_3)_2$—C≡C—;

-$G_7$-$L_1$-$G_8$-H or -$G_9$-$L_2$-$G_{10}$-H is independently selected from the following groups:

—$(CH_2)_5CH_3$, —$(CH_2)_6CH_3$, —$(CH_2)_7CH_3$, —$(CH_2)_8CH_3$, —$(CH_2)_9CH_3$, —$(CH_2)_{10}CH_3$, —$(CH_2)_{11}CH_3$, —$CH_2$—C≡C—$(CH_2)_5CH_3$, —$CH_2$—C≡C—$(CH_2)_6CH_3$, —$(CH_2)_2$—C≡C—$(CH_2)_5CH_3$, —$(CH_2)_4$—C≡C—$(CH_2)_3CH_3$, —$CH_2$—CH═CH—$(CH_2)_5CH_3$, —$CH_2$—CH═CH—$(CH_2)_6CH_3$, —$(CH_2)_2$—CH═CH—$(CH_2)_5CH_3$, —$(CH_2)_4$—CH═CH—$(CH_2)_3$ $CH_3$, —$(CH_2)_5$—CH═CH—$CH_2CH_3$,

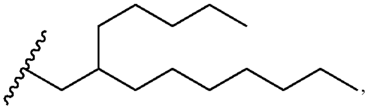,

-continued

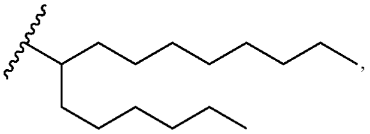

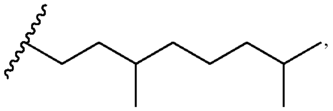

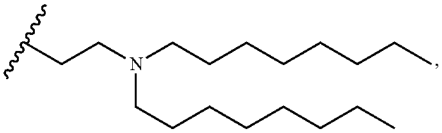

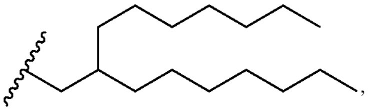

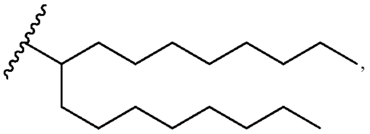

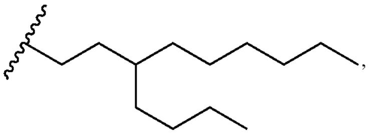

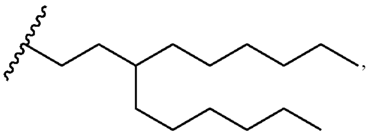

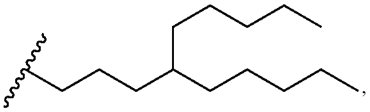

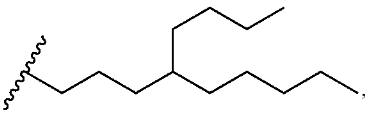

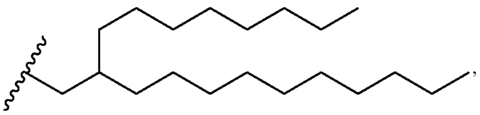

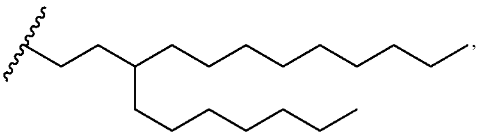

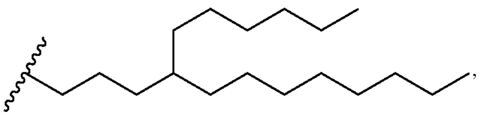

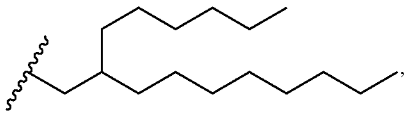

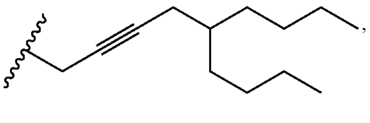

-continued

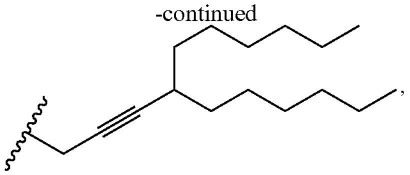

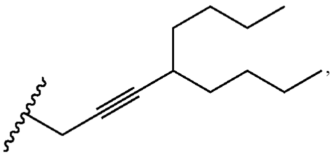

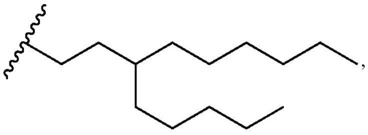

and

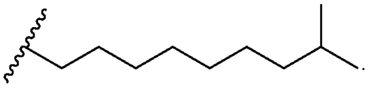

Technical solution 17: In a more specific embodiment, the present disclosure provides a nanoparticle composition as described above, wherein in the compound of formula (VI) or formula (VII), a, a', b and g are independently 0, 1, 2, 3, 4 or 5, a' and b are not 0 at the same time;

a'+g=0, 1, 2, 3, 4 or 5;

c and e are independently 3, 4, 5, 6, 7, 8 or 9;

d and f are independently 0, 1, 2, 3 or 4;

c+d=3, 4, 5, 6, 7, 8 or 9, e+f=3, 4, 5, 6, 7, 8 or 9;

methylenes in

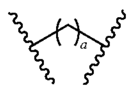

or

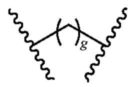

are optionally and independently substituted with 1, 2, 3, 4 or 5 $C_{1-6}$ alkyl;

$R_3$ and $R_4$ are independently H, $C_{1-6}$ alkyl, $C_{1-6}$ haloalkyl, 3- to 10-membered cycloalkyl or 3- to 10-membered heterocyclyl, which is optionally substituted with 1, 2, 3, 4 or 5 R*;

or, $R_3$ and $R_4$ are taken together with the N atom to which they are attached to form 3- to 10-membered heterocyclyl, which is optionally substituted with 1, 2, 3, 4 or 5 R*;

R* is independently H, halogen, cyano, $C_{1-6}$ alkyl, $C_{1-6}$ haloalkyl, $-L_b-OR_b$ or $-L_b-NR_bR'_b$;

$R_5$, $R_6$, $R_7$ and $R_8$ are independently $C_{1-6}$ alkyl, which is optionally substituted with 1, 2, 3, 4 or 5 R*;

$Y_1$ and $Y_2$ are independently O, S or $NR_a$;

$L_1$ and $L_2$ are independently —$(CRR')_2$—, —CH═CH—, —C≡C— or —NR"—;

$G_7$, $G_8$, $G_9$ and $G_{10}$ are independently a chemical bond or $C_{1-12}$ alkylene, which is optionally substituted with 1, 2, 3, 4, 5 or 6 R;

$G_7$ and $G_8$ have a total length of 6, 7, 8, 9, 10, 11 or 12 carbon atoms;

$G_9$ and $G_{10}$ have a total length of 6, 7, 8, 9, 10, 11 or 12 carbon atoms;

1, 2 or 3 methylenes in $G_7$, $G_8$, $G_9$ or $G_{10}$ are optionally and independently substituted with 1 R;

R and R' are independently H, $C_{1-14}$ alkyl, $-L_a-OR_a$ or $-L_a-NR_aR'_a$;

$L_a$ is independently a chemical bond or $C_{1-14}$ alkylene;

$L_b$ is independently a chemical bond or $C_{1-6}$ alkylene;

$R_a$ and $R'_a$ are independently H, $C_{1-14}$ alkyl, 3- to 10-membered cycloalkyl or 3- to 10-membered heterocyclyl;

$R_b$ and $R'_b$ are independently H, $C_{1-6}$ alkyl, 3- to 10-membered cycloalkyl or 3- to 10-membered heterocyclyl;

R" is independently H or $C_{1-14}$ alkyl.

Technical solution 18: In a more specific embodiment, the present disclosure provides a nanoparticle composition as described above, wherein in the compound of formula (VI) or formula (VII), a is 0, 1, 2, 3 or 4, alternatively 1, 2, 3 or 4, alternatively 2, 3 or 4;

a' and b are independently 0, 1, 2, 3 or 4, alternatively 2;

g is 0, 1 or 2, alternatively 0 or 1;

a'+g=0, 1, 2, 3, 4 or 5, alternatively a'+g=2 or 3;

c and e are independently 3, 4, 5 or 6;

d and f are independently 0, 1 or 2;

c+d=4, 5 or 6, e+f=4, 5 or 6;

methylenes in

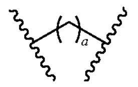

are optionally and independently substituted with 1, 2, 3, 4 or 5 $C_{1-6}$ alkyl;

methylenes in

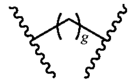

are optionally and independently substituted with 1 or 2 $C_{1-6}$ alkyl;

$R_3$ and $R_4$ are independently $C_{1-6}$ alkyl, which is optionally substituted with 1, 2 or 3 R*;

R* is independently H, $C_{1-6}$ alkyl, $C_{1-6}$ haloalkyl or $—OR_b$;

or, $R_3$ and $R_4$ are taken together with the N atom to which they are attached to form 3- to 7-membered heterocyclyl, alternatively 5-membered heterocyclyl, which is optionally substituted with 1, 2 or 3 R*;

$R_5$, $R_6$, $R_7$ and $R_8$ are independently $C_{1-6}$ alkyl, which is optionally substituted with 1, 2, 3, 4 or 5 R*;

$Y_1$ and $Y_2$ are independently O, S or $NR_a$, alternatively O or S;

$L_1$ and $L_2$ are independently $—(CHR)_2—$, —CH═CH—, —C≡C— or —NR"—, alternatively $—(CHR)_2—$, —CH═CH— or —C≡C—;

$G_7$ and $G_9$ are independently a chemical bond or $C_{1-6}$ alkylene;

$G_8$ and $G_{10}$ are independently $C_{1-10}$ alkylene;

$G_7$ and $G_8$ have a total length of 6, 7, 8, 9 or 10 carbon atoms;

$G_9$ and $G_{10}$ have a total length of 6, 7, 8, 9 or 10 carbon atoms;

1, 2 or 3 methylenes in $G_7$, $G_8$, $G_9$ or $G_{10}$ are optionally and independently substituted with 1 R, alternatively the methylene collected to $Y_1$ and $Y_2$ is not substituted with R;

R is independently H or $C_{1-8}$ alkyl;

R" is independently H or $C_{1-10}$ alkyl;

$R_a$ is independently H or $C_{1-10}$ alkyl;

$R_b$ is independently H or $C_{1-6}$ alkyl, alternatively H.

Technical solution 19: In a more specific embodiment, the present disclosure provides a nanoparticle composition as described above, wherein in the compound of formula (VI), a is 0, 1, 2, 3 or 4, alternatively 1, 2, 3 or 4, alternatively 2, 3 or 4;

c and e are independently 3, 4, 5 or 6;

d and f are independently 0, 1 or 2;

c+d=4, 5 or 6, e+f=4, 5 or 6;

$R_3$ and $R_4$ are independently $C_{1-6}$ alkyl;

or, $R_3$ and $R_4$ are taken together with the N atom to which they are attached to form 4- to 6-membered heterocyclyl, alternatively 5-membered heterocyclyl, which is optionally substituted with 1, 2 or 3 R*;

R* is independently H, $C_{1-6}$ alkyl or $C_{1-6}$ haloalkyl;

$R_5$, $R_6$, $R_7$ and $R_8$ are independently $C_{1-6}$ alkyl, which is optionally substituted with 1, 2, 3, 4 or 5 R*, alternatively $C_{1-3}$ alkyl;

$Y_1$ and $Y_2$ are independently O, S or $NR_a$, alternatively O or S;

$L_1$ and $L_2$ are independently $—(CHR)_2—$, —CH═CH—, —C≡C— or —NR"—, alternatively $—(CHR)_2—$, —CH═CH— or —C≡C—;

$G_7$ and $G_9$ are independently a chemical bond or $C_{1-5}$ alkylene, alternatively a chemical bond or $C_{1-5}$ linear alkylene;

$G_8$ and $G_{10}$ are independently $C_{1-8}$ alkylene, alternatively $C_{1-8}$ linear alkylene;

$G_7$ and $G_8$ have a total length of 6, 7, 8, 9 or 10 carbon atoms;

$G_9$ and $G_{10}$ have a total length of 6, 7, 8, 9 or 10 carbon atoms;

1, 2 or 3 methylenes in $G_7$, $G_8$, $G_9$ or $G_{10}$ are optionally and independently substituted with 1 R, alternatively the methylene collected to $Y_1$ and $Y_2$ is not substituted with R;

R is independently H or $C_{1-8}$ alkyl, alternatively H or $C_{1-7}$ alkyl, alternatively H or $C_{1-6}$ alkyl;

R" is independently H or $C_{7-9}$ alkyl;

$R_a$ is independently H or $C_{8-10}$ alkyl.

Alternatively, R is independently H or $C_{1-8}$ linear alkyl, alternatively H or $C_{1-7}$ linear alkyl, alternatively H or $C_{1-6}$ linear alkyl.

Alternatively, R" is independently H or $C_{7-9}$ linear alkyl.

Alternatively, $R_a$ is independently H or $C_{8-10}$ linear alkyl.

Technical solution 20: In a more specific embodiment, the present disclosure provides a nanoparticle composition as described above, wherein in the compound of formula (VI), a is 0, 1, 2, 3 or 4, alternatively 1, 2, 3 or 4, alternatively 2, 3 or 4;

c and e are independently 3, 4, 5 or 6;

d and f are independently 0, 1 or 2;

c+d=4, 5 or 6, e+f=4, 5 or 6; alternatively,

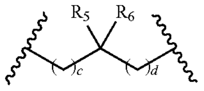 and 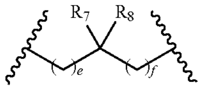

are independently $—(CH_2)_4—C(CH_3)_2—$, $—(CH_2)_5—C(CH_3)_2—$, $—(CH_2)_6—C(CH_3)_2—$, $—(CH_2)_4—C(CH_3)_2—CH_2—$ or $—(CH_2)_3—C(CH_3)_2—(CH_2)_2—$;

$R_3$ and $R_4$ are independently $C_{1-6}$ alkyl, alternatively Me; or, $R_3$ and $R_4$ are taken together with the N atom to which they are attached to form

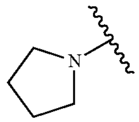 or 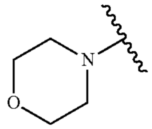, alternatively

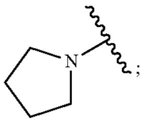 [SMILES: *N1CCCC1];

$R_5$, $R_6$, $R_7$ and $R_8$ are Me;

$Y_1$ and $Y_2$ are independently O, S or $NR_a$, alternatively O or S;

$L_1$ and $L_2$ are independently —$(CHR)_2$—, —CH═CH—, —C≡C— or —NR"—, alternatively —$(CHR)_2$—, —CH═CH— or —C≡C—;

$G_7$ and $G_9$ are independently a chemical bond, —$CH_2$—, —$(CH_2)_2$—, —$(CH_2)_4$— or —$(CH_2)_5$—;

$G_8$ and $G_{10}$ are independently —$(CH_2)_2$—, —$(CH_2)_4$—, —$(CH_2)_6$—, —$(CH_2)_7$— or —$(CH_2)_8$—;

$G_7$ and $G_8$ have a total length of 6, 7, 8, 9, 10 carbon atoms;

$G_9$ and $G_{10}$ have a total length of 6, 7, 8, 9, 10 carbon atoms;

1, 2 or 3 methylenes in $G_7$, $G_8$, $G_9$ or $G_{10}$ are optionally and independently substituted with 1 R, alternatively the methylene collected to $Y_1$ and $Y_2$ is not substituted with R;

R is independently H, Me, —$(CH_2)_3CH_3$, —$(CH_2)_4CH_3$, —$(CH_2)_5CH_3$, —$(CH_2)_6CH_3$ or —$(CH_2)_7CH_3$, alternatively H, Me, —$(CH_2)_3CH_3$, —$(CH_2)_4CH_3$, —$(CH_2)_5CH_3$ or —$(CH_2)_6CH_3$, alternatively H, Me, —$(CH_2)_3CH_3$, —$(CH_2)_4CH_3$ or —$(CH_2)_5CH_3$;

$R_a$ is independently H or —$(CH_2)_8CH_3$;

R" is —$(CH_2)_7CH_3$.

Alternatively, -$G_7$-$L_1$-$G_8$-H or -$G_9$-$L_2$-$G_{10}$-H is independently selected from the following groups:

—$(CH_2)_7CH_3$, —$(CH_2)_8CH_3$, —$(CH_2)_9CH_3$, —$(CH_2)_{10}CH_3$, —$CH_2$—C≡C—$(CH_2)_5CH_3$, —$CH_2$—C≡C—$(CH_2)_6CH_3$, —$(CH_2)_2$—C≡C—$(CH_2)_5CH_3$, —$(CH_2)_4$—C≡C—$(CH_2)_3CH_3$, —$CH_2$—CH═CH—$(CH_2)_6CH_3$, —$(CH_2)_2$—CH═CH—$(CH_2)_5CH_3$, —$(CH_2)_4$—CH═CH—$(CH_2)_3CH_3$, —$(CH_2)_5$—CH═CH—$CH_2CH_3$,

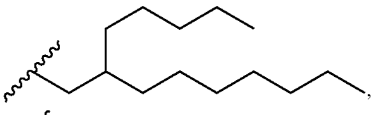,

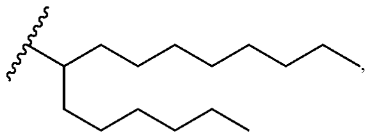,

-continued

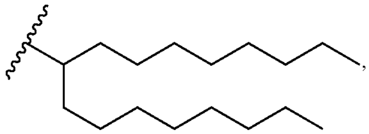,

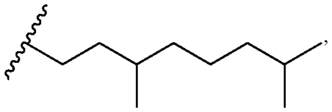,

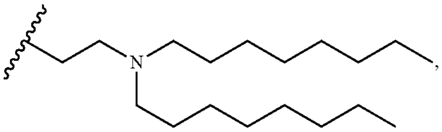,

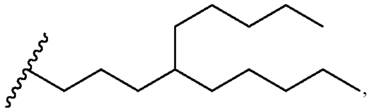,

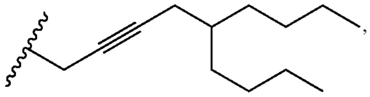,

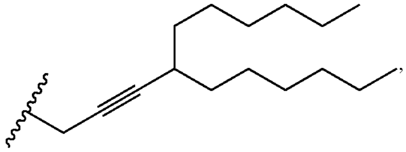,

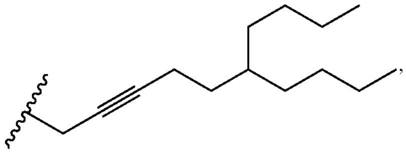,

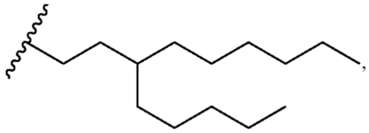,

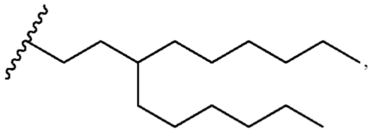,

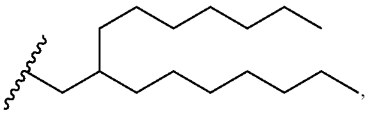, and

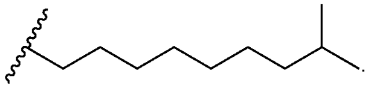.

alternatively is not

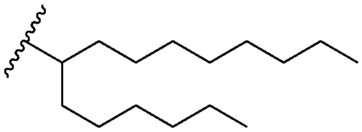 and

-continued

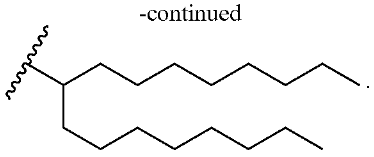

Technical solution 21: In a more specific embodiment, the present disclosure provides a nanoparticle composition as described above, wherein in the compound of formula (VI), a is 2, 3 or 4;

c and e are independently 3, 4, 5 or 6;

d and f are independently 0, 1 or 2;

c+d=4, 5 or 6, e+f=4, 5 or 6;

$R_3$ and $R_4$ are independently $C_{1-6}$ alkyl, alternatively $C_{1-3}$ alkyl;

$R_5$, $R_6$, $R_7$ and $R_8$ are independently $C_{1-6}$ alkyl, alternatively $C_{1-3}$ alkyl;

$Y_1$ and $Y_2$ are independently O or S;

$L_1$ and $L_2$ are independently $-(CHR)_2-$, $-CH{=}CH-$ or $-C{\equiv}C-$;

$G_7$ and $G_9$ are independently $C_{1-4}$ alkylene, alternatively $C_{1-4}$ linear alkylene;

$G_8$ and $G_{10}$ are independently $C_{2-7}$ alkylene, alternatively $C_{2-7}$ linear alkylene;

$G_7$ and $G_8$ have a total length of 6, 7 or 8 carbon atoms;

$G_9$ and $G_{10}$ have a total length of 6, 7 or 8 carbon atoms;

1, 2 or 3 methylenes in $G_7$, $G_8$, $G_9$ or $G_{10}$ are optionally and independently substituted with 1 R;

R is independently H or $C_{1-7}$ alkyl, alternatively H or $C_{1-7}$ linear alkyl;

provided that, when $L_1$ is $-C{\equiv}C-$, then $G_7$ is $C_{1-2}$ alkylene, alternatively $C_{1-2}$ linear alkylene; and when $L_2$ is $-C{\equiv}C-$, then $G_9$ is $C_{1-2}$ alkylene, alternatively $C_{1-2}$ linear alkylene.

Alternatively, the methylene collected to $Y_1$ and $Y_2$ is not substituted with R.

Technical solution 22: In a more specific embodiment, the present disclosure provides a nanoparticle composition as described above, in the compound of formula (VI), a is 2, 3 or 4;

c and e are independently 3, 4, 5 or 6;

d and f are independently 0, 1 or 2;

c+d=4, 5 or 6, e+f=4, 5 or 6; alternatively,

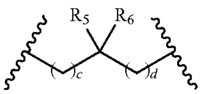

and

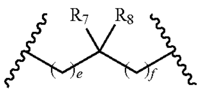

are independently $-(CH_2)_4-C(CH_3)_2-$, $-(CH_2)_5-C(CH_3)_2-$, $-(CH_2)_6-C(CH_3)_2-$, $-(CH_2)_4-C(CH_3)_2-CH_2-$ or $-(CH_2)_3-C(CH_3)_2-(CH_2)_2-$;

$R_3$ and $R_4$ are independently $C_{1-6}$ alkyl, alternatively Me;

$R_5$, $R_6$, $R_7$ and $R_8$ are independently $C_{1-6}$ alkyl, alternatively Me;

$Y_1$ and $Y_2$ are independently O or S;

$L_1$ and $L_2$ are independently $-(CHR)_2-$, $-CH{=}CH-$ or $-C{\equiv}C-$;

$G_7$ and $G_9$ are independently $-CH_2-$, $-(CH_2)_2-$ or $-(CH_2)_4-$;

$G_8$ and $G_{10}$ are independently $-(CH_2)_4-$, $-(CH_2)_6-$ or $-(CH_2)_7-$;

$G_7$ and $G_8$ have a total length of 6, 7 or 8 carbon atoms;

$G_9$ and $G_{10}$ have a total length of 6, 7 or 8 carbon atoms;

1, 2 or 3 methylenes in $G_7$, $G_8$, $G_9$ or $G_{10}$ are optionally and independently substituted with 1 R;

R is independently H, Me, $-(CH_2)_3CH_3$, $-(CH_2)_4CH_3$, $-(CH_2)_5CH_3$ or $-(CH_2)_6CH_3$;

provided that, when $L_1$ is $-C{\equiv}C-$, then $G_7$ is $-CH_2-$ or $-(CH_2)_2-$, and when $L_2$ is $-C{\equiv}C-$, then $G_9$ is $-CH_2-$ or $-(CH_2)_2-$;

alternatively, $-G_7-L_1-G_8-H$ or $-G_9-L_2-G_{10}-H$ is independently selected from the following groups:

$-(CH_2)_7CH_3$, $-(CH_2)_8CH_3$, $-(CH_2)_9CH_3$, $-CH_2-C{\equiv}C-(CH_2)_5CH_3$, $-CH_2-C{\equiv}C-(CH_2)_6CH_3$, $-(CH_2)_2-C{\equiv}C-(CH_2)_5CH_3$, $-CH_2-CH{=}CH-(CH_2)_6CH_3$, $-(CH_2)_2-CH{=}CH-(CH_2)_5CH_3$, $-(CH_2)_4-CH{=}CH-(CH_2)_3CH_3$,

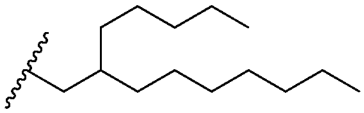,

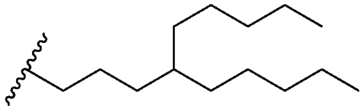,

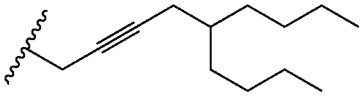,

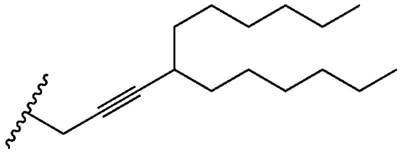,

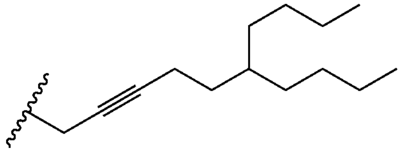,

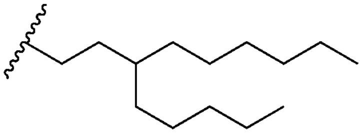,

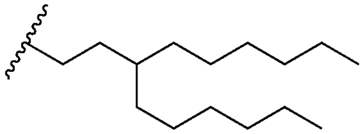,

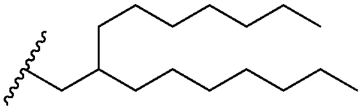

and

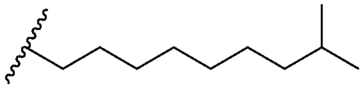.

Technical solution 23: In a more specific embodiment, the present disclosure provides a nanoparticle composition as described above, wherein in the compound of formula (VI), a is 2, 3 or 4, alternatively 2 or 3;

c and e are independently 4, 5 or 6;

d and f are 0;

$R_3$ and $R_4$ are independently $C_{1-6}$ alkyl, alternatively $C_{1-3}$ alkyl;

$R_5$, $R_6$, $R_7$ and $R_8$ are independently $C_{1-6}$ alkyl, alternatively $C_{1-3}$ alkyl;

$Y_1$ and $Y_2$ are O;

$L_1$ and $L_2$ are independently —$(CHR)_2$— or —CH═CH—;

$G_7$ and $G_9$ are independently —$CH_2$— or —$CH_2CHR$—;

$G_8$ and $G_{10}$ are independently —$(CH_2)_6$— or —$(CH_2)_7$—;

$G_7$ and $G_8$ have a total length of 7 or 8 carbon atoms;

$G_9$ and $G_{10}$ have a total length of 7 or 8 carbon atoms;

1, 2 or 3 methylenes in $G_8$ or $G_{10}$ are optionally and independently substituted with 1 R;

R is independently H or $C_{4-6}$ alkyl, alternatively H or $C_5$ alkyl;

alternatively -$G_7$-$L_1$-$G_8$-H and -$G_9$-$L_2$-$G_{10}$-H are not —$(CH_2)_9CH_3$ at the same time.

Alternatively, R is independently H or $C_{4-6}$ linear alkyl, alternatively H or $C_5$ linear alkyl.

Technical solution 24: In a more specific embodiment, the present disclosure provides a nanoparticle composition as described above, in the compound of formula (VI), a is 2, 3 or 4, alternatively 2 or 3;

c and e are independently 4, 5 or 6;

d and f are 0;

$R_3$ and $R_4$ are Me;

$R_5$, $R_6$, $R_7$ and $R_8$ are Me;

$Y_1$ and $Y_2$ are O;

-$G_7$-$L_1$-$G_8$-H and -$G_9$-$L_2$-$G_{10}$-H are independently selected from the following groups:

—$(CH_2)_8CH_3$, —$(CH_2)_9CH_3$, —$CH_2$—CH═CH—$(CH_2)_6CH_3$, —$(CH_2)_2$—CH═CH—$(CH_2)_5CH_3$,

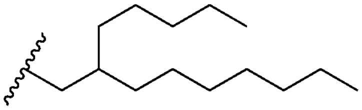

,

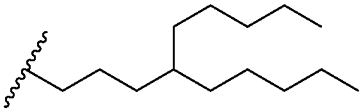

and

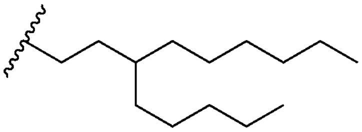

;

alternatively —$(CH_2)_8CH_3$, —$(CH_2)_9CH_3$, —$CH_2$—CH═CH—$(CH_2)_6CH_3$, —$(CH_2)_2$—CH═CH—$(CH_2)_5CH_3$ and

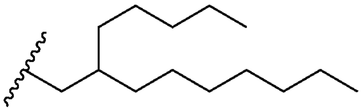

;

alternatively -$G_7$-$L_1$-$G_8$-H and -$G_9$-$L_2$-$G_{10}$-H are not —$(CH_2)_9CH_3$ at the same time.

Technical solution 25: In a more specific embodiment, the present disclosure provides a nanoparticle composition as described above, wherein in the compound of formula (VI), a is 3;

c and e are independently 5 or 6, alternatively 6;

d and f are 0;

$R_3$ and $R_4$ are independently $C_{1-3}$ alkyl;

$R_5$, $R_6$, $R_7$ and $R_8$ are independently $C_{1-3}$ alkyl;

$Y_1$ and $Y_2$ are O;

$L_1$ and $L_2$ are independently —$(CHR)_2$— or —CH═CH, alternatively —$(CHR)_2$—;

$G_7$ and $G_9$ are independently —$CH_2$— or —$CH_2CHR$—;

$G_8$ and $G_{10}$ are independently —$(CH_2)_6$— or —$(CH_2)_7$—;

$G_7$ and $G_8$ have a total length of 7 or 8 carbon atoms, alternatively 7 carbon atoms;

$G_9$ and $G_{10}$ have a total length of 7 or 8 carbon atoms, alternatively 7 carbon atoms;

1, 2 or 3 methylenes in $G_8$ or $G_{10}$ are optionally and independently substituted with 1 R;

R is independently H or $C_{4-6}$ alkyl, alternatively H or $C_5$ alkyl.

Alternatively, R is independently H or $C_{4-6}$ linear alkyl, alternatively H or $C_5$ linear alkyl.

Technical solution 26: In a more specific embodiment, the present disclosure provides a nanoparticle composition as described above, wherein in the compound of formula (VI), a is 3;

c and e are 6;

d and f are 0;

$R_3$ and $R_4$ are Me;

$R_5$, $R_6$, $R_7$ and $R_8$ are Me;

$Y_1$ and $Y_2$ are O;

-$G_7$-$L_1$-$G_8$-H and -$G_9$-$L_2$-$G_{10}$-H are independently selected from the following groups:

—$(CH_2)_8CH_3$,

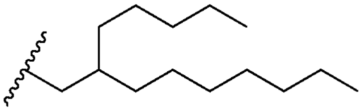

,

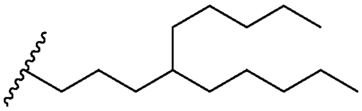

and

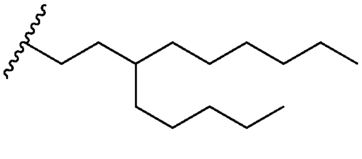

;

alternatively —$(CH_2)_8CH_3$ and

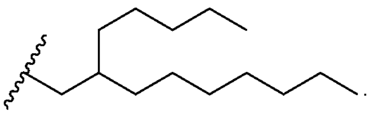 [SMILES: *CC(CCCCC)CCCCCCC]

.

Technical solution 27: In a more specific embodiment, the present disclosure provides a nanoparticle composition as described above, wherein in the compound of formula (VI), a is 2 or 3, alternatively 2;

c and e are independently 4, 5 or 6, alternatively 5;

d and f are 0;

$R_3$ and $R_4$ are independently $C_{1-3}$ alkyl;

$R_5$, $R_6$, $R_7$ and $R_8$ are independently $C_{1-3}$ alkyl;

one of $Y_1$ and $Y_2$ is O, and the other is S;

$L_1$ and $L_2$ are independently —$(CHR)_2$— or —CH═CH, alternatively —$(CHR)_2$—;

$G_7$ and $G_9$ are independently —$CH_2$— or —$CH_2CHR$—;

$G_8$ and $G_{10}$ are independently —$(CH_2)_5$— or —$(CH_2)_6$—;

$G_7$ and $G_8$ have a total length of 7 carbon atoms;

$G_9$ and $G_{10}$ have a total length of 7 carbon atoms;

1, 2 or 3 methylenes in $G_8$ or $G_{10}$ are optionally and independently substituted with 1 R;

R is independently H or $C_{4-6}$ alkyl, alternatively H or $C_5$ alkyl.

Alternatively, R is independently H or $C_{4-6}$ linear alkyl, alternatively H or $C_5$ linear alkyl.

Technical solution 28: In a more specific embodiment, the present disclosure provides a nanoparticle composition as described above, wherein in the compound of formula (VI), a is 2;

c and e are 5;

d and f are 0;

$R_3$ and $R_4$ are Me;

$R_5$, $R_6$, $R_7$ and $R_8$ are Me;

one of $Y_1$ and $Y_2$ is O, and the other is S;

-$G_7$-$L_1$-$G_8$-H and -$G_9$-$L_2$-$G_{10}$-H are independently selected from the following groups:

—$(CH_2)_8CH_3$,

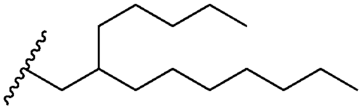

,

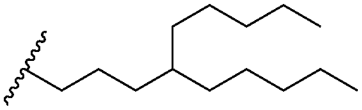

and

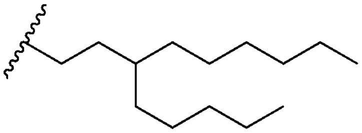

;

alternatively —$(CH_2)_8CH_3$.

Technical solution 29: In a more specific embodiment, the present disclosure provides a nanoparticle composition as described above, wherein in the compound of formula (VI), a are 2;

c and e are independently 4, 5 or 6, alternatively 5;

d and f are 0;

$R_3$ and $R_4$ are independently $C_{1-6}$ alkyl, alternatively $C_{1-3}$ alkyl;

$R_5$, $R_6$, $R_7$ and $R_8$ are independently $C_{1-6}$ alkyl, alternatively $C_{1-3}$ alkyl;

$Y_1$ and $Y_2$ are independently O or S;

one of $L_1$ and $L_2$ is —C≡C—, the other is —$(CHR)_2$—, or both of $L_1$ and $L_2$ are —C≡C—; alternatively one of $L_1$ and $L_2$ is —C≡C—, the other is —$(CHR)_2$—;

$G_7$ and $G_9$ are —$CH_2$—;

$G_8$ and $G_{10}$ are independently —$(CH_2)_6$— or —$(CH_2)_7$—;

1 methylene in $G_8$ or $G_{10}$ optionally and independently substituted with 1 R, alternatively $G_8$ and $G_{10}$ are independently —CHR—$(CH_2)_5$—, —CHR—$(CH_2)_6$—, —$CH_2$—CHR—$(CH_2)_4$— or —$(CH_2)_2$—CHR—$(CH_2)_4$—;

R is independently H or $C_{4-6}$ alkyl, alternatively H or $C_5$ alkyl;

provided that, only one of the -$G_7$-$L_1$-$G_8$-H and -$G_9$-$L_2$-$G_{10}$-H is substituted with one non-hydrogen R substituent and the other is unsubstituted.

Alternatively, R is independently H or $C_{4-6}$ linear alkyl, alternatively H or $C_5$ linear alkyl.

Technical solution 30: In a more specific embodiment, the present disclosure provides a nanoparticle composition as described above, wherein in the compound of formula (VI), a is 2;

c and e are 5;

d and f are 0;

$R_3$ and $R_4$ are Me;

$R_5$, $R_6$, $R_7$ and $R_8$ are Me;

$Y_1$ and $Y_2$ are independently O or S;

-$G_7$-$L_1$-$G_8$-H and -$G_9$-$L_2$-$G_{10}$-H are independently selected from the following groups:

—$(CH_2)_8CH_3$, —$(CH_2)_9CH_3$, —$CH_2$—C≡C—$(CH_2)_6CH_3$,

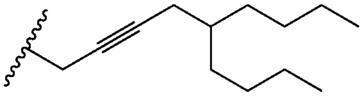

,

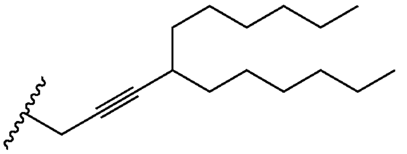

,

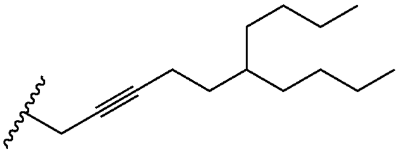

,

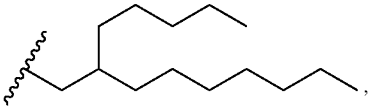 [SMILES: *CC(CCCCC)CCCCCCC]

,

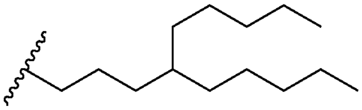

and

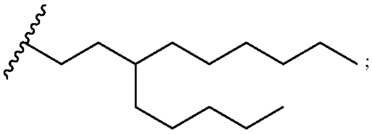

;

provided that, at least one of -$G_7$-$L_1$-$G_8$-H and -$G_9$-$L_2$-$G_{10}$-H comprises alkynyl, and one of the two has a substituent while the other one has no substituent.

Technical solution 31: In a more specific embodiment, the present disclosure provides a nanoparticle composition as described above, wherein in the compound of formula (VI), a is 2;

c and e are independently 4, 5 or 6, alternatively 5;

d and f are 0;

$R_3$ and $R_4$ are independently $C_{1-3}$ alkyl, alternatively Me;

$R_5$, $R_6$, $R_7$ and $R_8$ are independently $C_{1-3}$ alkyl, alternatively Me;

$Y_1$ and $Y_2$ are independently O or S, alternatively O;

both of $L_1$ and $L_2$ are —C≡C—;

$G_7$ and $G_9$ are —$CH_2$—;

$G_8$ and $G_{10}$ are independently —$(CH_2)_6$— or —$(CH_2)_7$—, alternatively —$(CH_2)_7$—.

Technical solution 32: In a more specific embodiment, the present disclosure provides a nanoparticle composition as described above, wherein in the compound of formula (VI), a is 2;

c and e are 3;

d and f are 2;

$R_3$ and $R_4$ are independently $C_{1-3}$ alkyl, alternatively Me;

$R_5$, $R_6$, $R_7$ and $R_8$ are independently $C_{1-3}$ alkyl;

$Y_1$ and $Y_2$ are independently O or S, alternatively O;

$L_1$ and $L_2$ are $—(CHR)_2—$;

$G_7$ and $G_9$ are independently $—CH_2—$ or $—CH_2CHR—$;

$G_8$ and $G_{10}$ are independently $—(CH_2)_5—$, $—(CH_2)_6—$ or $—(CH_2)_7—$;

$G_7$ and $G_8$ have a total length of 6, 7 or 8 carbon atoms, alternatively 7 carbon atoms;

$G_9$ and $G_{10}$ have a total length of 6, 7 or 8 carbon atoms, alternatively 7 carbon atoms;

1, 2 or 3 methylenes in $G_8$ or $G_{10}$ are optionally and independently substituted with 1 R;

R is independently H or $C_{1-7}$ alkyl, alternatively H or $C_{1-6}$ alkyl, alternatively Me.

Alternatively, R is independently H or $C_{1-7}$ linear alkyl, alternatively H or $C_{1-6}$ linear alkyl, alternatively Me.

Technical solution 33: In a more specific embodiment, the present disclosure provides a nanoparticle composition as described above, wherein in the compound of formula (VI), a is 2;

c and e are 3;

d and f are 2;

$R_3$ and $R_4$ are Me;

$R_5$, $R_6$, $R_7$ and $R_8$ are Me;

$Y_1$ and $Y_2$ are independently O or S, alternatively O;

$-G_7-L_1-G_8-H$ and $-G_9-L_2-G_{10}-H$ are independently selected from the following groups:

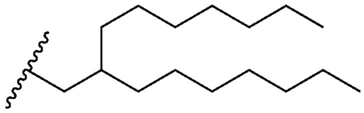

,

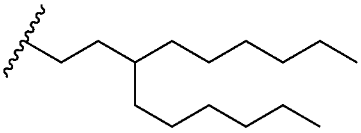

and

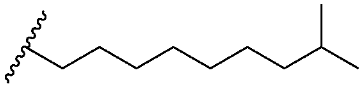

, alternatively

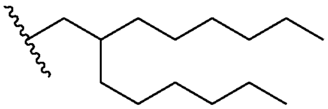

and

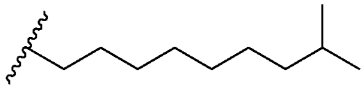

, alternatively

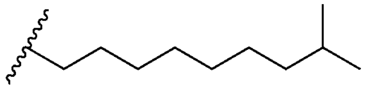

.

Technical solution 34: In a more specific embodiment, the present disclosure provides a nanoparticle composition as described above, wherein in the compound of formula (VI), a is 2;

c and e are 4, 5, or 6, alternatively 5;

d and f are 0;

$R_3$ and $R_4$ are independently $C_{1-6}$ alkyl, alternatively $C_{1-3}$ alkyl;

$R_5$, $R_6$, $R_7$ and $R_8$ are independently $C_{1-6}$ alkyl, alternatively $C_{1-3}$ alkyl;

$Y_1$ and $Y_2$ are S;

$L_1$ and $L_2$ are $—(CHR)_2—$;

$G_7$ and $G_9$ are independently $—CH_2—$ or $—CH_2CHR—$;

$G_8$ and $G_{10}$ are independently $—(CH_2)_5—$, $—(CH_2)_6—$ or $—(CH_2)_7—$;

$G_7$ and $G_8$ have a total length of 7 or 8 carbon atoms, alternatively 8 carbon atoms;

$G_9$ and $G_{10}$ have a total length of 7 or 8 carbon atoms, alternatively 8 carbon atoms;

1, 2 or 3 methylenes in $G_8$ or $G_{10}$ are optionally and independently substituted with 1 R;

R is independently H or $C_{4-6}$ alkyl, alternatively H or $C_5$ alkyl.

Alternatively, R is independently H or $C_{4-6}$ linear alkyl, alternatively H or $C_5$ linear alkyl.

Technical solution 35: In a more specific embodiment, the present disclosure provides a nanoparticle composition as described above, wherein in the compound of formula (VI), a is 2;

c and e are 5;

d and f are 0;

$R_3$ and $R_4$ are independently Me;

$R_5$, $R_6$, $R_7$ and $R_8$ are independently Me;

$Y_1$ and $Y_2$ are S;

$-G_7-L_1-G_8-H$ and $-G_9-L_2-G_{10}-H$ are independently selected from the following:

$—(CH_2)_8CH_3$, $—(CH_2)_9CH_3$,

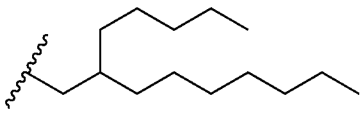

,

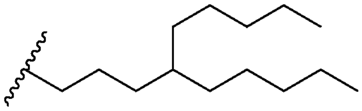

and

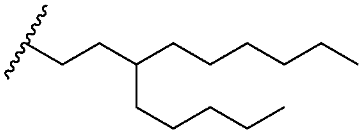

, alternatively $—(CH_2)_8CH_3$ or $—(CH_2)_9CH_3$, alternatively $—(CH_2)_9CH_3$.

Technical solution 36: In a more specific embodiment, the present disclosure provides a nanoparticle composition as described above, wherein in the compound of formula (VII), a' and bare 2;

g is 0 or 1;

c and e are 5;

d and f are 0;

$R_3$ is $C_{1-6}$ alkyl, which is optionally substituted with 1, 2 or 3 R*;

R* is independently H, $C_{1-6}$ alkyl, $C_{1-6}$ haloalkyl or $—OR_b$, alternatively H, $C_{1-6}$ alkyl or $C_{1-6}$ haloalkyl;

$R_5$, $R_6$, $R_7$ and $R_8$ are independently $C_{1-3}$ alkyl;

$Y_1$ and $Y_2$ are independently O or S;

$L_1$ and $L_2$ are $—(CHR)_2—$;

$G_7$ and $G_9$ are independently $—CH_2—$ or $—CH_2CHR—$;

$G_8$ and $G_{10}$ are independently $—(CH_2)_5—$, $—(CH_2)_6—$ or $—(CH_2)_7—$;

$G_7$ and $G_8$ have a total length of 6, 7 or 8 carbon atoms;

$G_9$ and $G_{10}$ have a total length of 6, 7 or 8 carbon atoms;

1, 2 or 3 methylenes in $G_8$ or $G_{10}$ are optionally and independently substituted with 1 R;

R is independently H or $C_{4-6}$ alkyl;

$R_b$ is independently H or $C_{1-6}$ alkyl, alternatively H.

Alternatively, R is independently H or $C_{4-6}$ linear alkyl.

Technical solution 37: In a more specific embodiment, the present disclosure provides a nanoparticle composition as described above, wherein in the compound of formula (VII), a' and b are 2;

g is 0 or 1;

c and e are 5;

d and f are 0;

$R_3$ is Me, $—CH_2CH_3$, $—CH_2CH_2OH$ or $—CH(CH_3)_2$, alternatively Me, $—CH_2CH_3$ or $—CH(CH_3)_2$;

$R_5$, $R_6$, $R_7$ and $R_8$ are independently Me;

$Y_1$ and $Y_2$ are independently O or S;

$-G_7-L_1-G_8-H$ or $-G_9-L_2-G_{10}-H$ is independently selected from the following groups:

$—(CH_2)_7CH_3$, $—(CH_2)_8CH_3$, $—(CH_2)_9CH_3$,

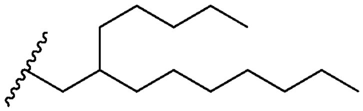
,

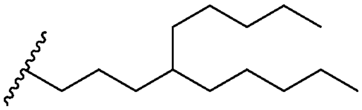
and

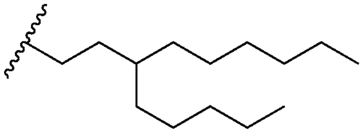
;

alternatively $—(CH_2)_7CH_3$, $—(CH_2)_8CH_3$, $—(CH_2)_9CH_3$ and

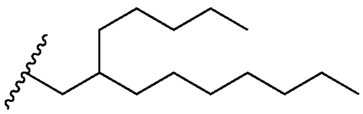
.

Technical solution 38: In a more specific embodiment, the present disclosure provides a nanoparticle composition as described above, wherein in the compound of formula (VII), $R_3$ is Me or $—CH_2CH_3$, alternatively Me;

Both of $Y_1$ and $Y_2$ are O;

$G_7$ and $G_8$ have a total length of 6 or 7 carbon atoms, alternatively 7 carbon atoms;

$G_9$ and $G_{10}$ have a total length of 6 or 7 carbon atoms, alternatively 7 carbon atoms.

Technical solution 39: In a more specific embodiment, the present disclosure provides a nanoparticle composition as described above, wherein in the compound of formula (VII), a' and bare 2;

g is 0 or 1;

c and e are 5;

d and f are 0;

$R_3$ is Me or $—CH_2CH_3$, alternatively Me;

$R_5$, $R_6$, $R_7$ and $R_8$ are independently Me;

both of $Y_1$ and $Y_2$ are O;

$-G_7-L_1-G_8-H$ or $-G_9-L_2-G_{10}-H$ is independently selected from the following groups:

$—(CH_2)_7CH_3$, $—(CH_2)_8CH_3$,

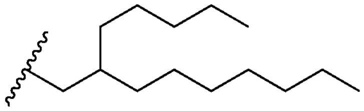
,

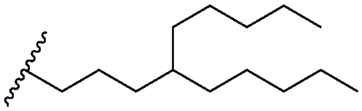
and

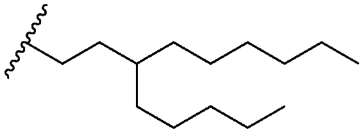
;

alternatively $—(CH_2)_7CH_3$, $—(CH_2)_8CH_3$ and

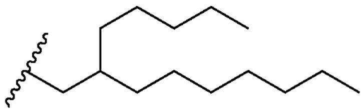
;

alternatively is not $—(CH_2)_7CH_3$.

Technical solution 40: In a more specific embodiment, the present disclosure provides a nanoparticle composition as described above, wherein in the compound of formula (VII), $R_3$ is Me or $—CH_2CH_3$;

$Y_1$ and $Y_2$ are independently O or S, where $Y_1$ and $Y_2$ are not O at the same time;

$G_7$ and $G_8$ have a total length of 6, 7 or 8 carbon atoms;

$G_9$ and $G_{10}$ have a total length of 6, 7 or 8 carbon atoms.

Technical solution 41: In a more specific embodiment, the present disclosure provides a nanoparticle composition as described above, wherein in the compound of formula (VII), g is 0 or 1, alternatively 1;

$R_3$ is Me or $—CH_2CH_3$, alternatively Me;

one of $Y_1$ and $Y_2$ is O, and the other is S;

$G_7$ and $G_8$ have a total length of 7 carbon atoms;

$G_9$ and $G_{10}$ have a total length of 7 carbon atoms.

Technical solution 42: In a more specific embodiment, the present disclosure provides a nanoparticle composition as described above, wherein in the above compound of formula (VII), a' and b are 2;

g is 0 or 1, alternatively 1;

c and e are 5;

d and f are 0;

$R_3$ is Me or $—CH_2CH_3$, alternatively Me;

$R_5$, $R_6$, $R_7$ and $R_8$ are independently Me;

one of $Y_1$ and $Y_2$ is O, and the other is S;

$-G_7-L_1-G_8-H$ or $-G_9-L_2-G_{10}-H$ is independently selected from the following groups:

$—(CH_2)_8CH_3$,

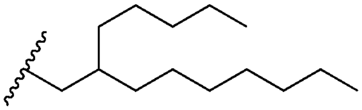
,
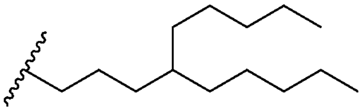
and
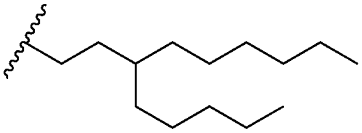
;

alternatively $-(CH_2)_8CH_3$ and

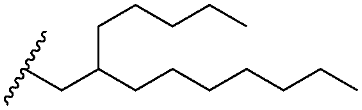
.

Technical solution 43: In a more specific embodiment, the present disclosure provides a nanoparticle composition as described above, wherein in the above compound of formula (VII), g is 0 or 1, alternatively 0;

$R_3$ is Me or $-CH_2CH_3$;

both of $Y_1$ and $Y_2$ are S;

$G_7$ and $G_8$ have a total length of 7 or 8 carbon atoms;

$G_9$ and $G_{10}$ have a total length of 7 or 8 carbon atoms.

Technical solution 44: In a more specific embodiment, the present disclosure provides a nanoparticle composition as described above, wherein in the above compound of formula (VII), a' and b are 2;

g is 0 or 1, alternatively 0;

c and e are 5;

d and f are 0;

$R_3$ is Me or $-CH_2CH_3$;

$R_5$, $R_6$, $R_7$ and $R_8$ are independently Me;

both of $Y_1$ and $Y_2$ are S;

$-G_7-L_1-G_8-H$ or $-G_9-L_2-G_{10}-H$ is independently selected from the following groups:

$-(CH_2)_8CH_3$, $-(CH_2)_9CH_3$,

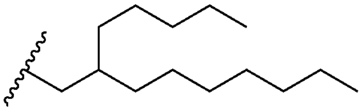
,
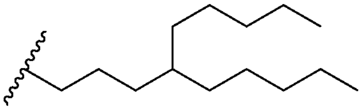
and
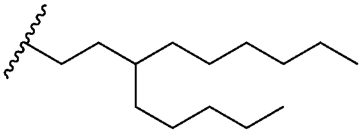
;

alternatively $-(CH_2)_8CH_3$, $-(CH_2)_9CH_3$ and

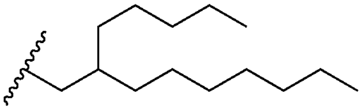
.

Technical solution 45: In a more specific embodiment, the present disclosure provides a nanoparticle composition as described above, wherein the compound of formula (IV) is selected from the following:

1

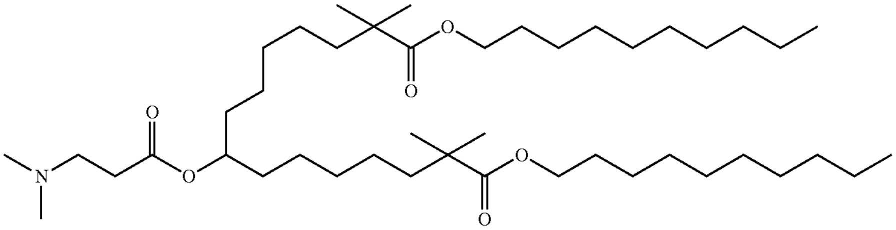

2

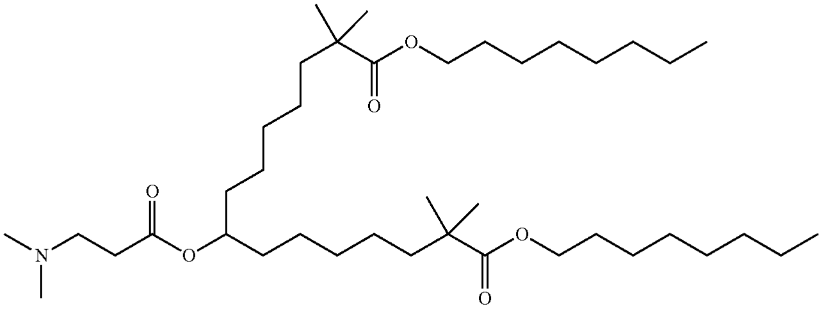

-continued
3
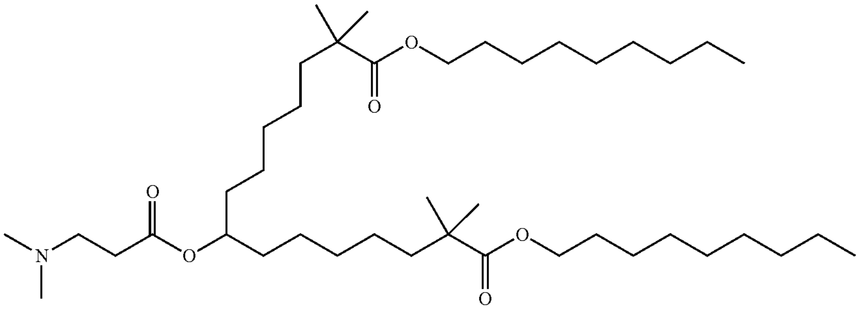
4
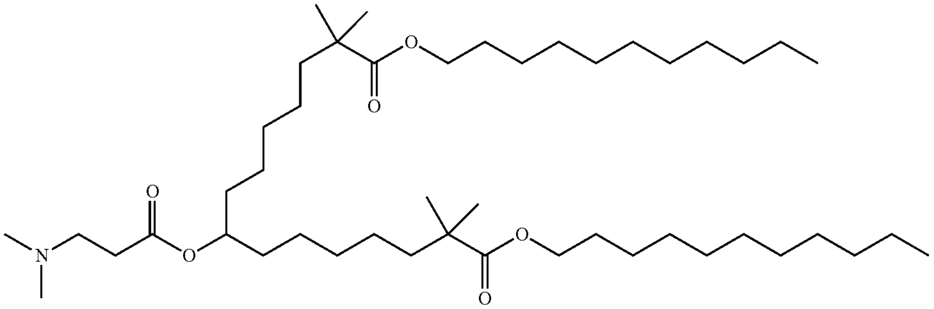
5
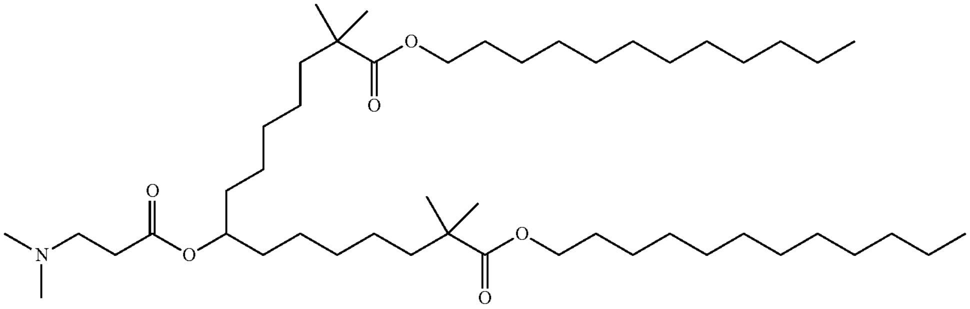
6
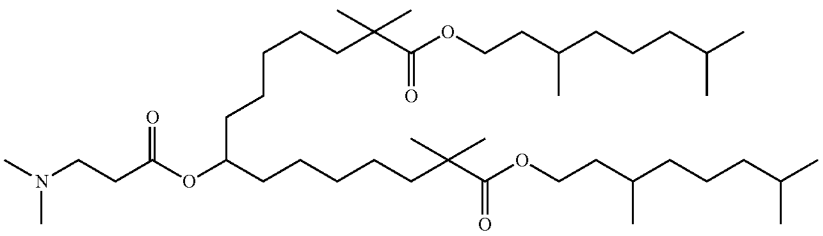
7
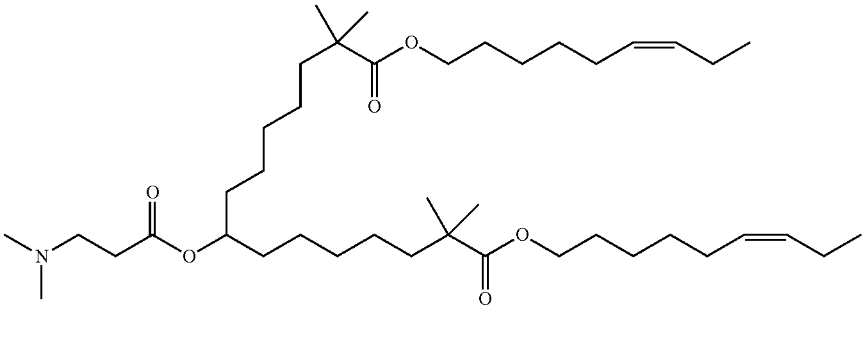

-continued
8
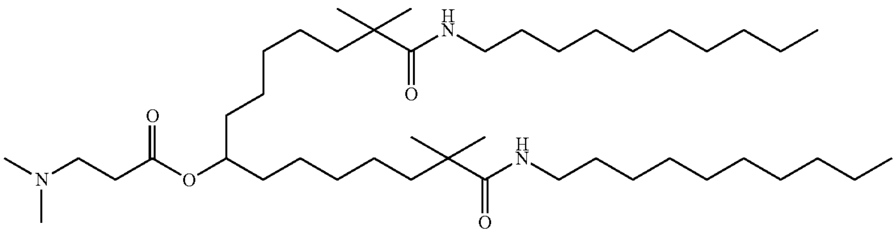
9
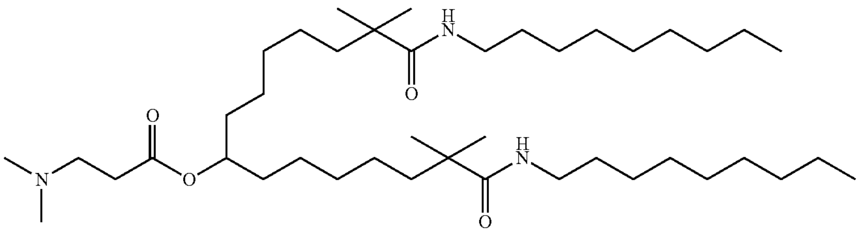
10
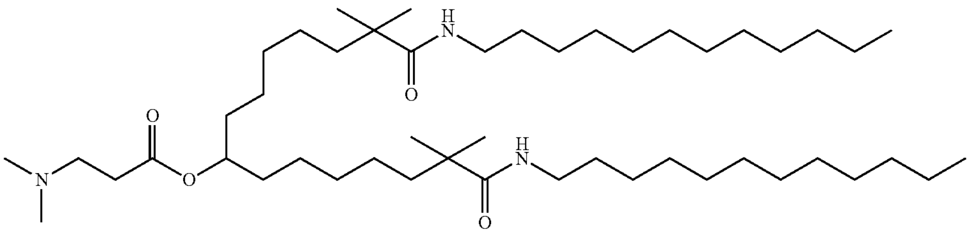
11
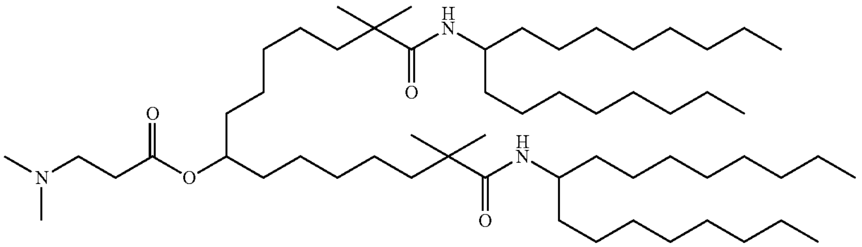
12
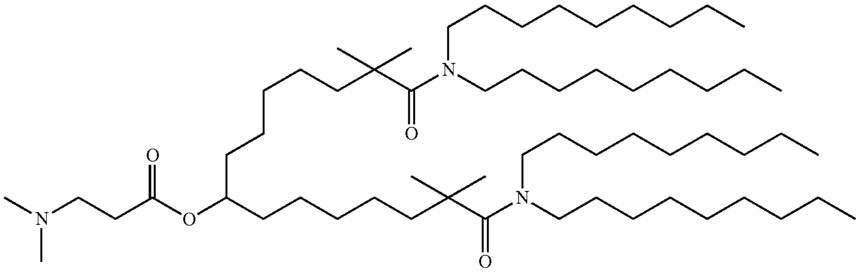
13
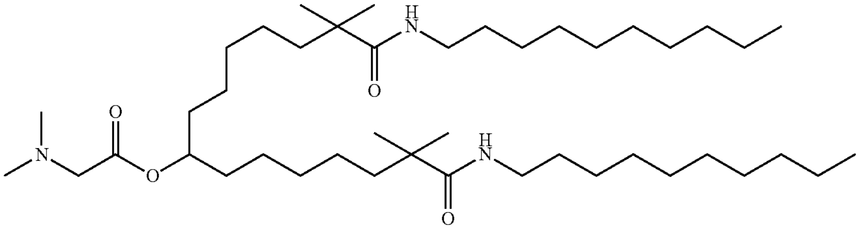

-continued
14
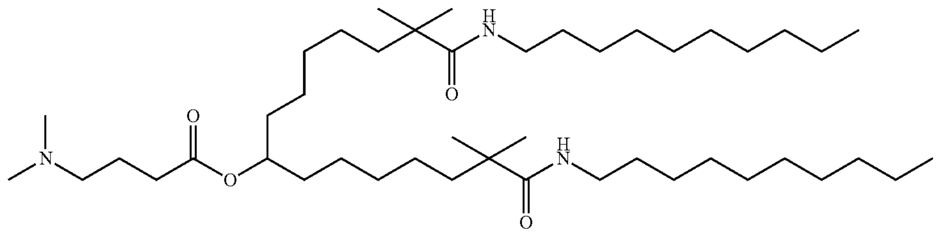
15
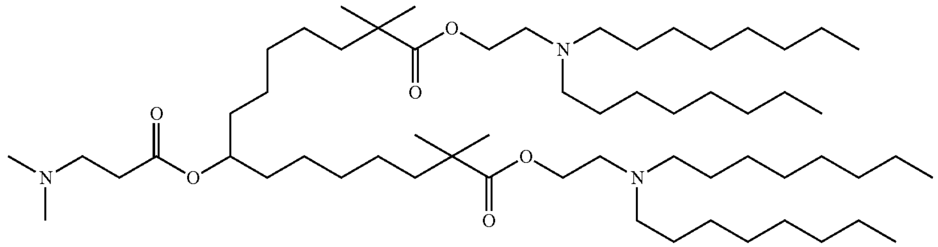
16
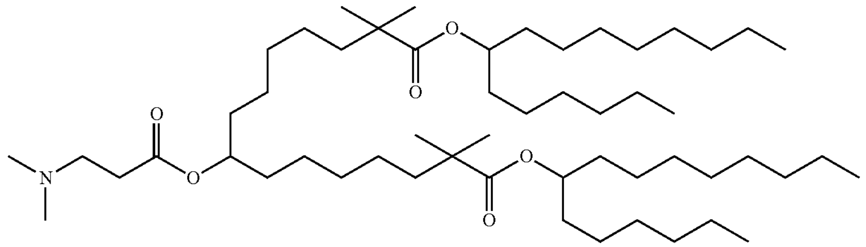
17
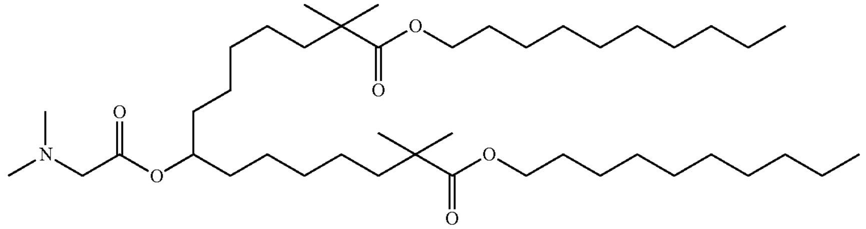
18
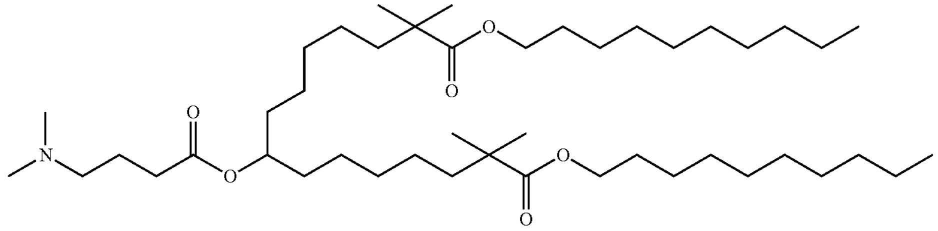
19
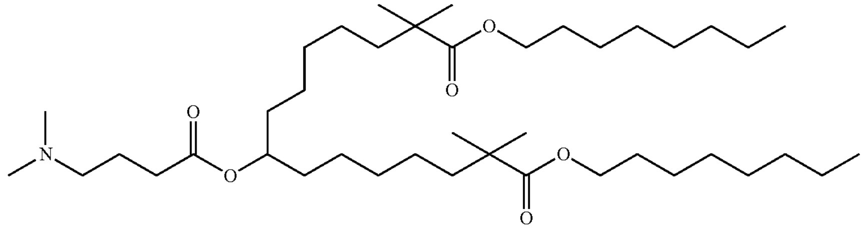

-continued
20
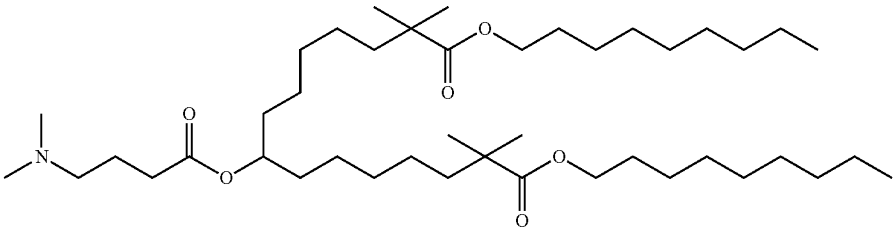
21
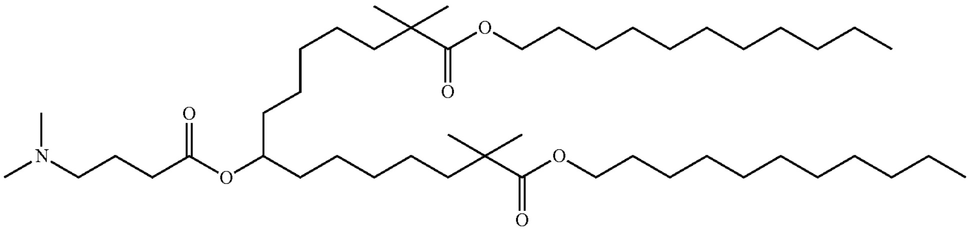
22
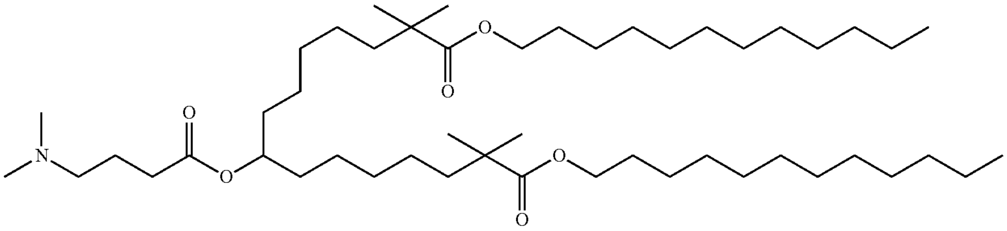
23
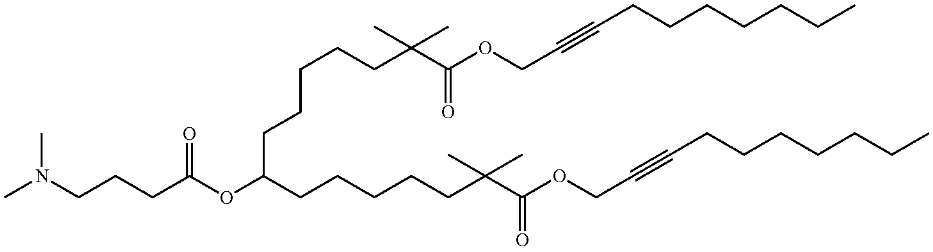
24
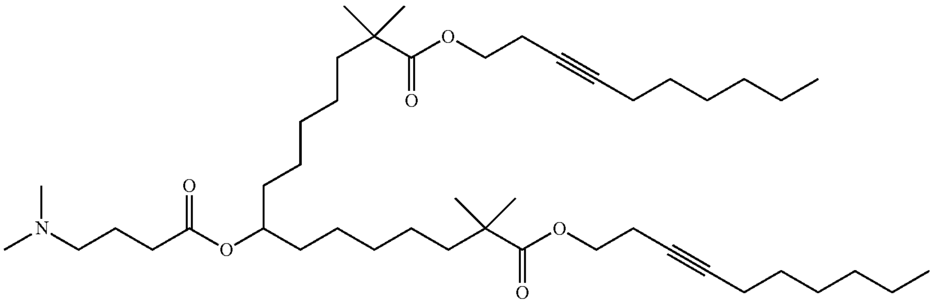
25
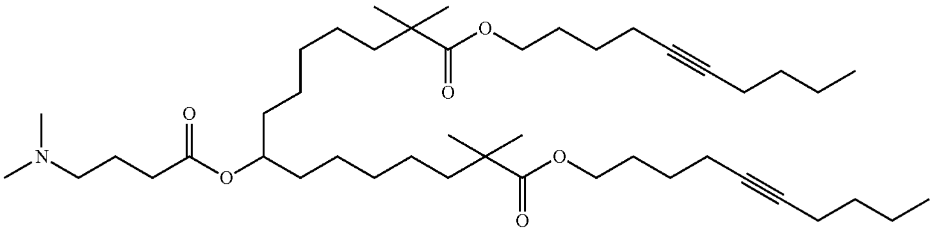

-continued
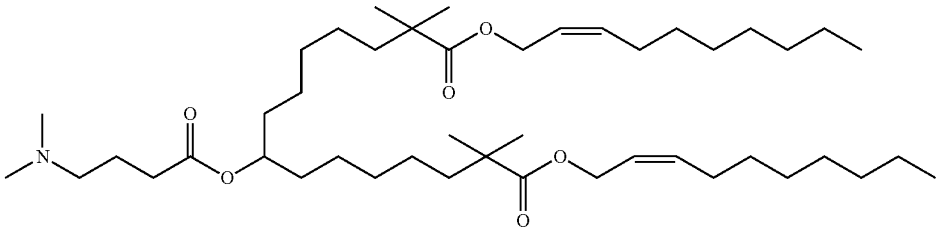
26
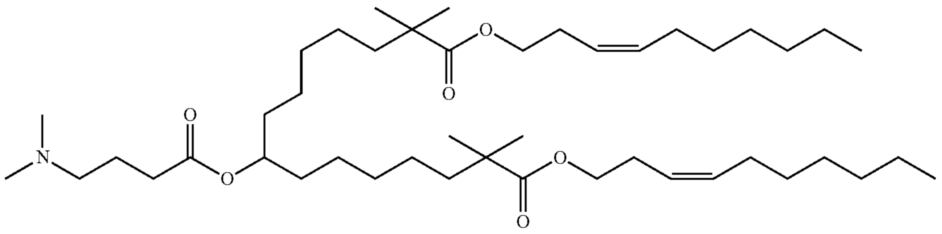
27
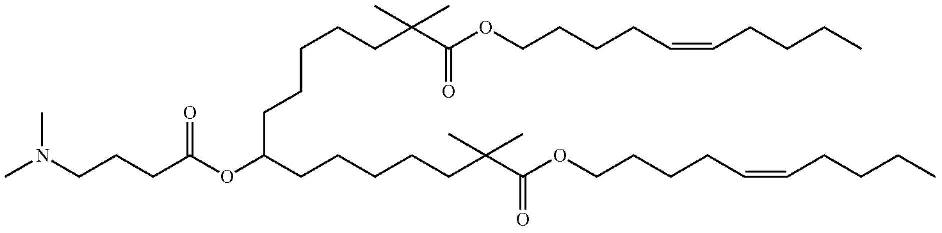
28
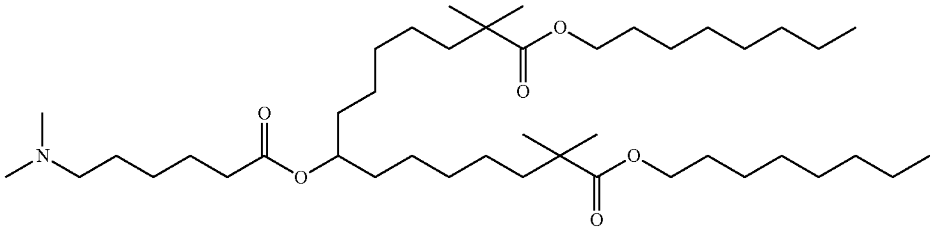
30
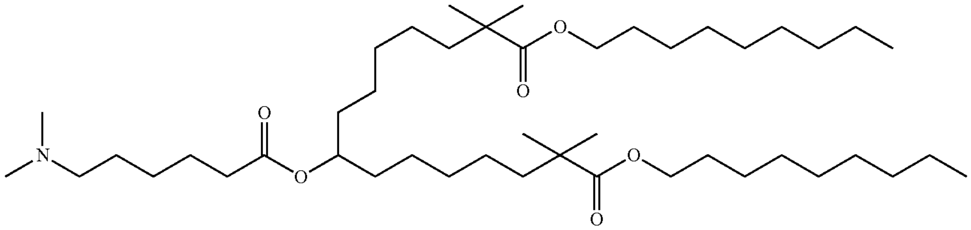
32
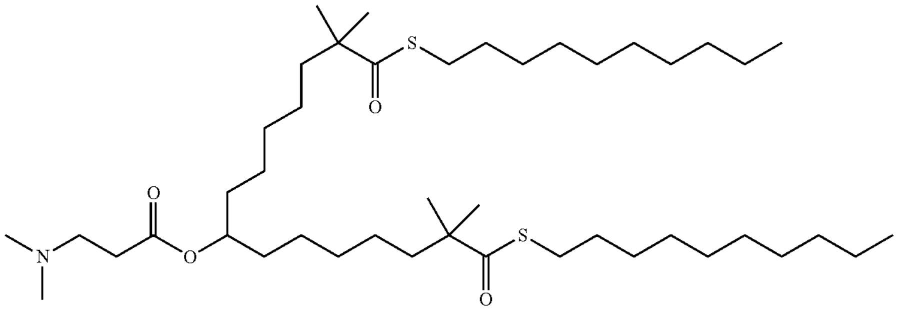
33

-continued
34
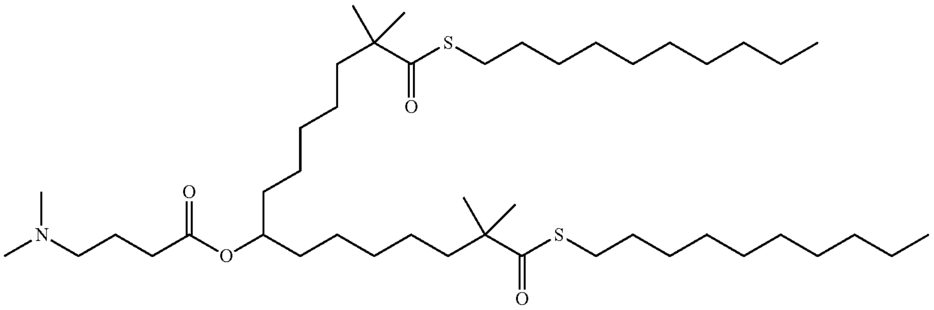
36
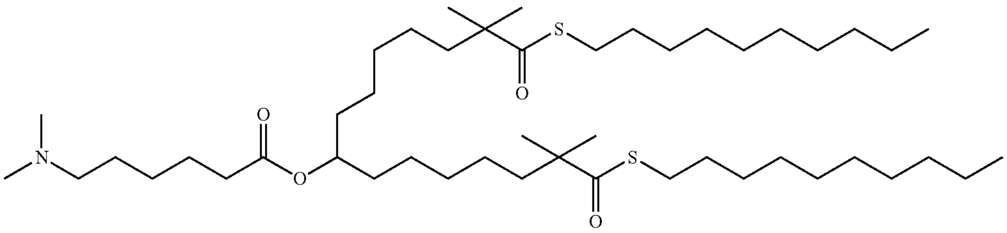
37
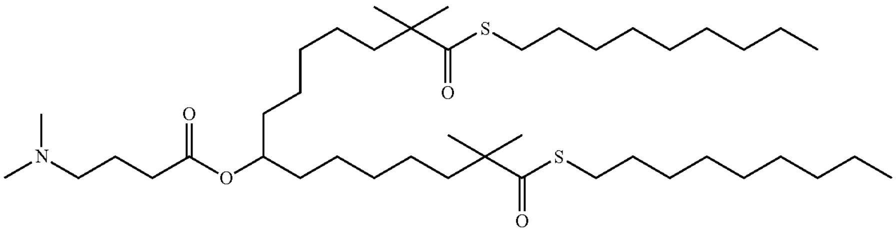
39
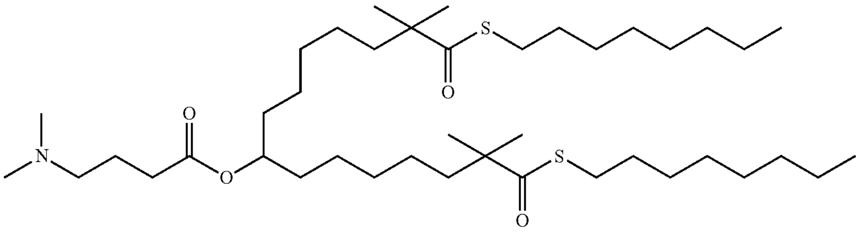
40
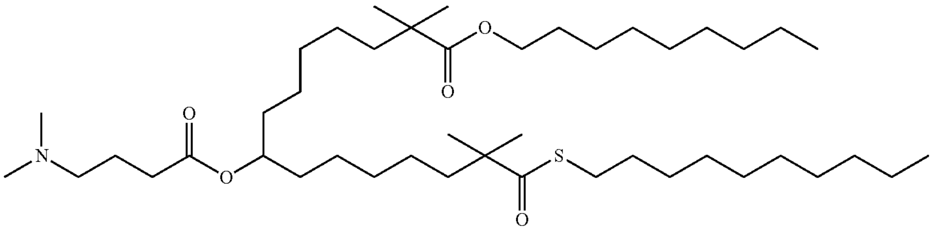
41
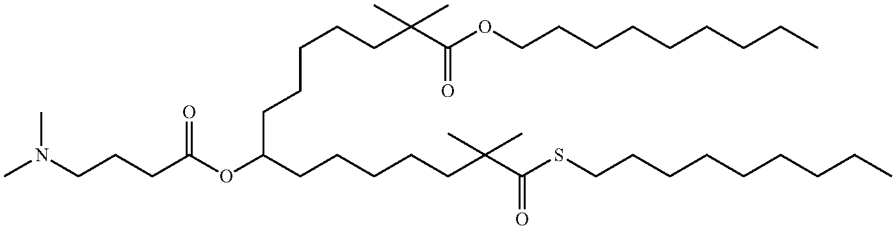

-continued
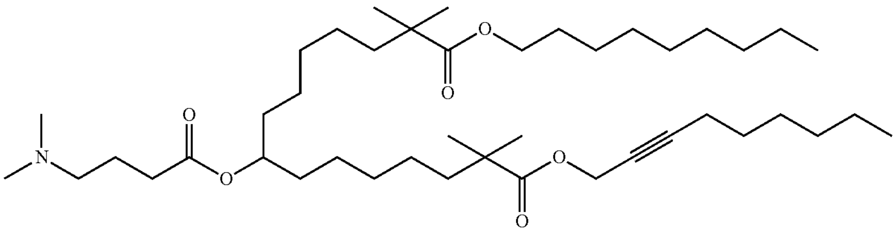
42
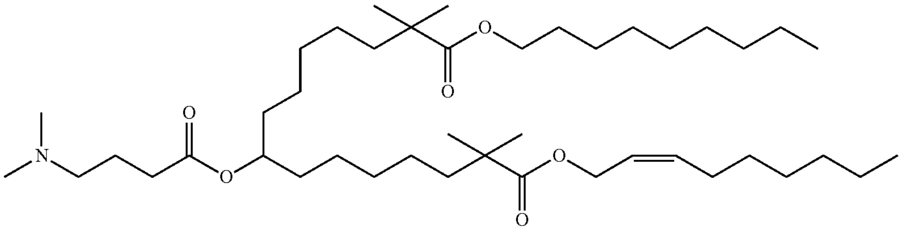
43
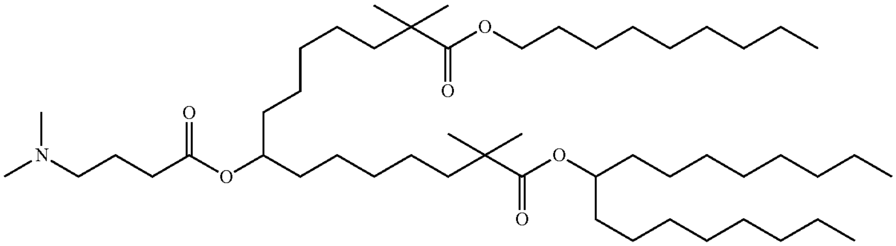
44
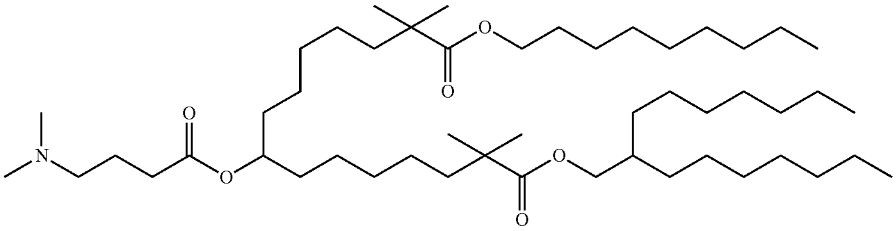
45
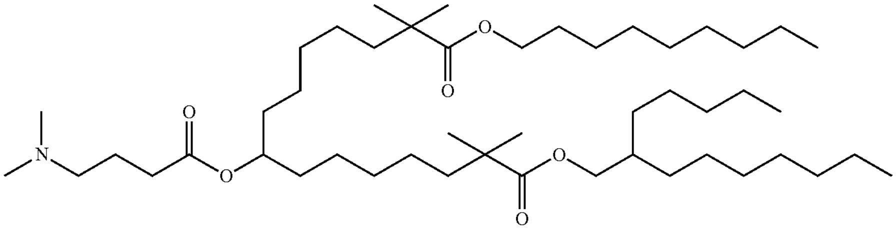
46
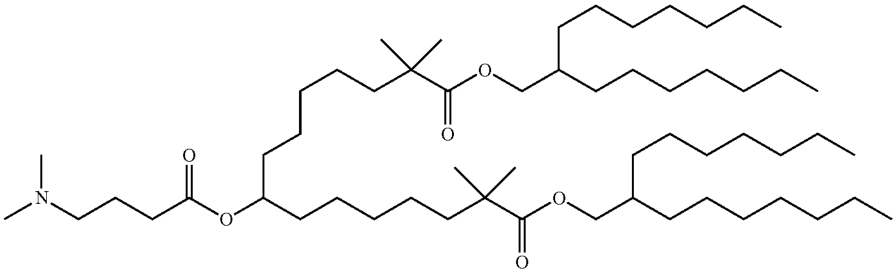
47

-continued
48
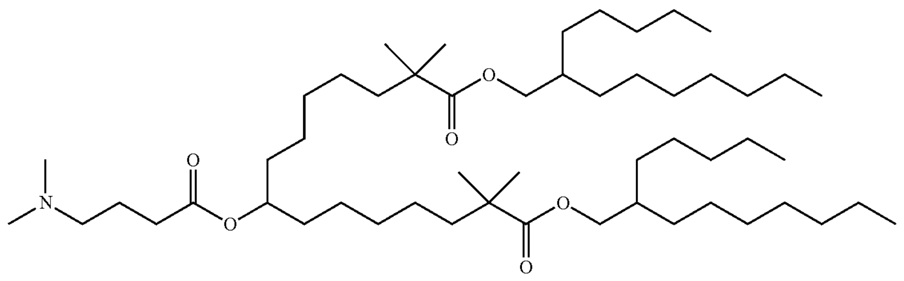
49
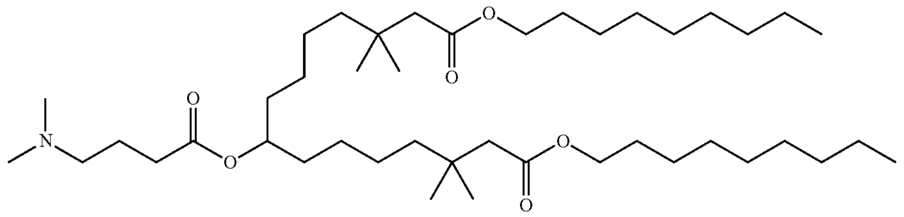
50
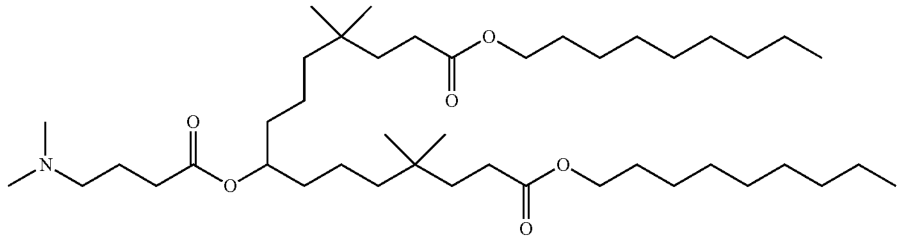
51
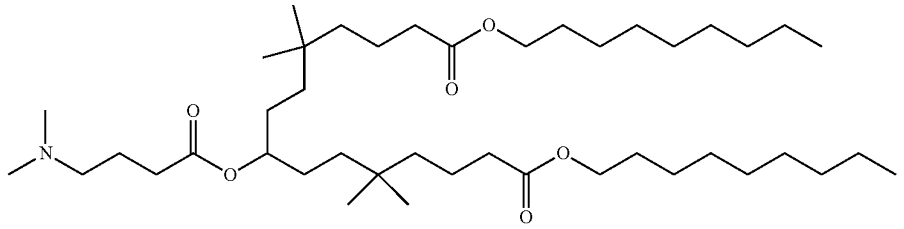
52
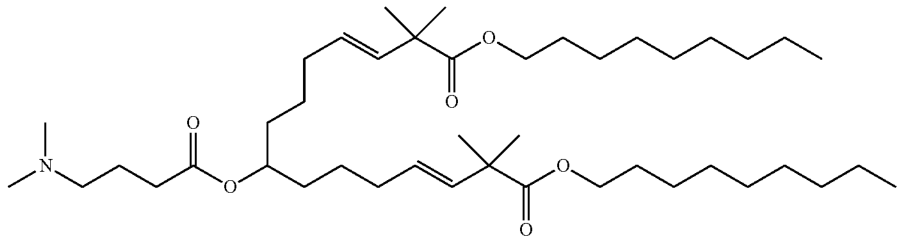
53
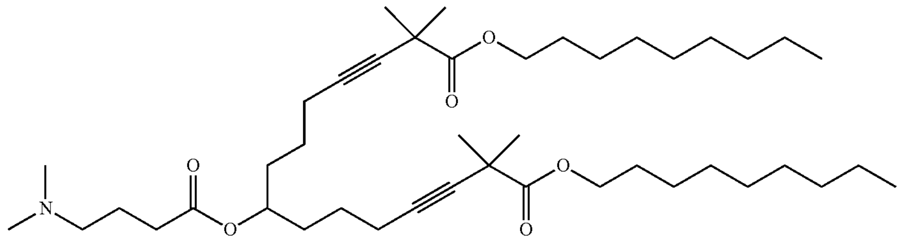

-continued
54
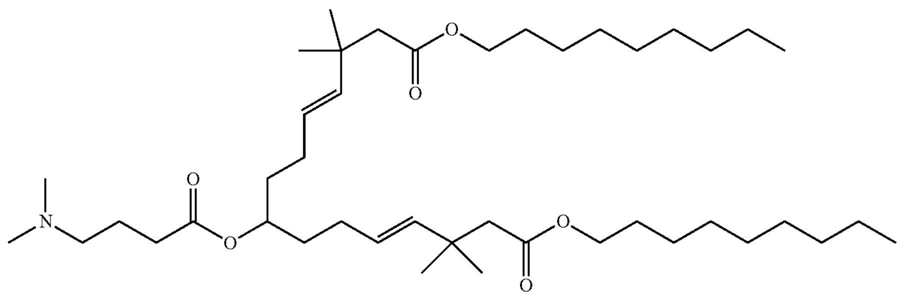
55
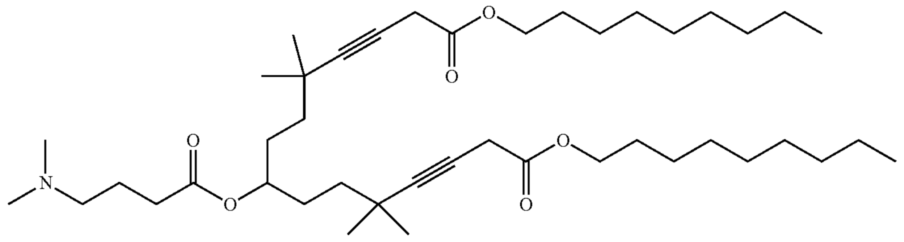
56
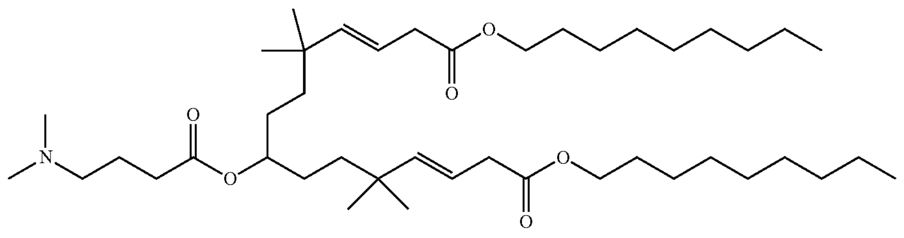
57
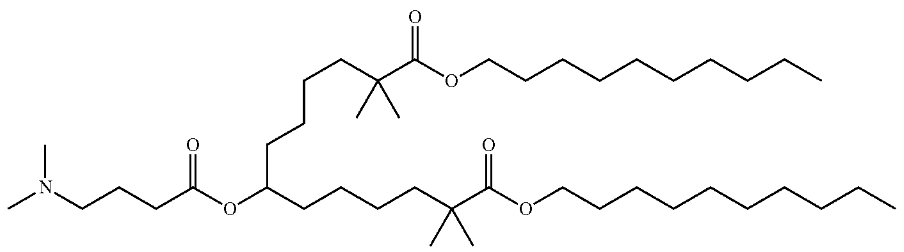
58
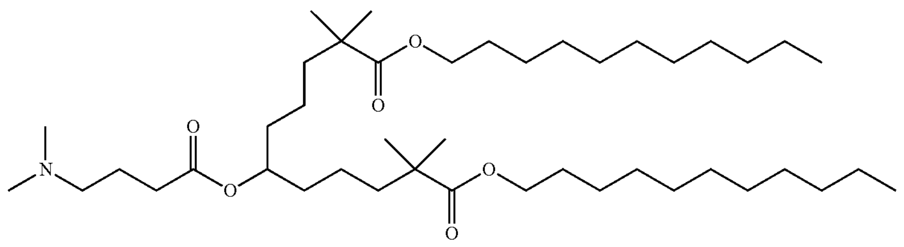
59
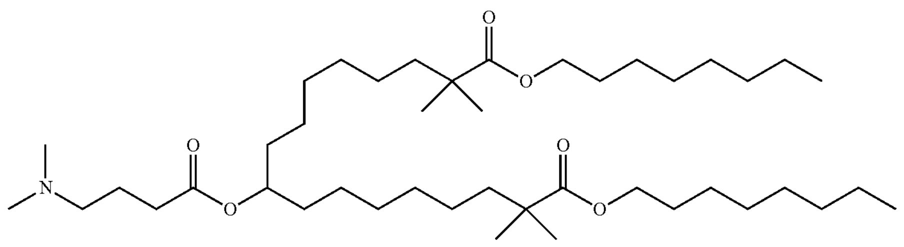

-continued
60
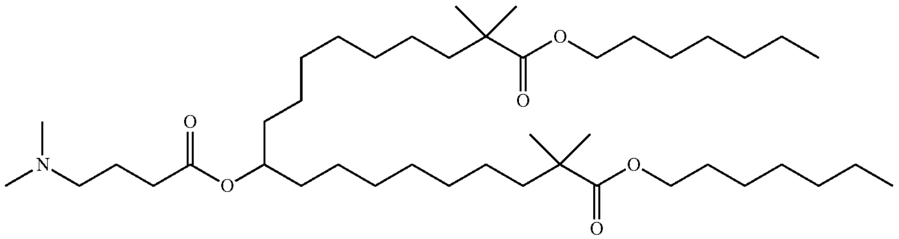
61
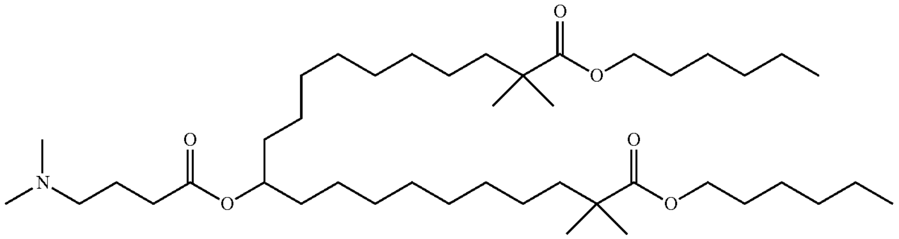
62
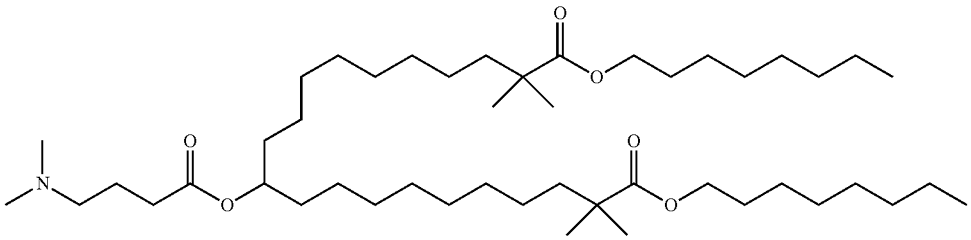
63
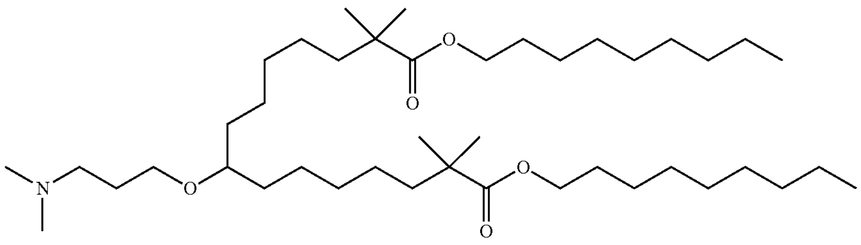
64
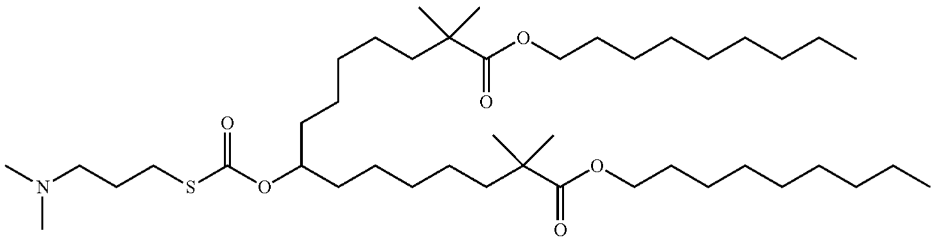
65
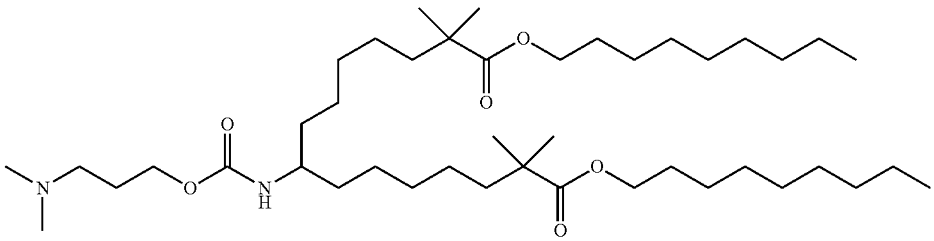

-continued
66
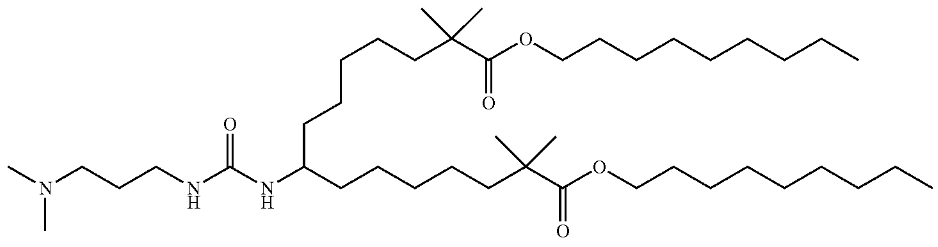
67
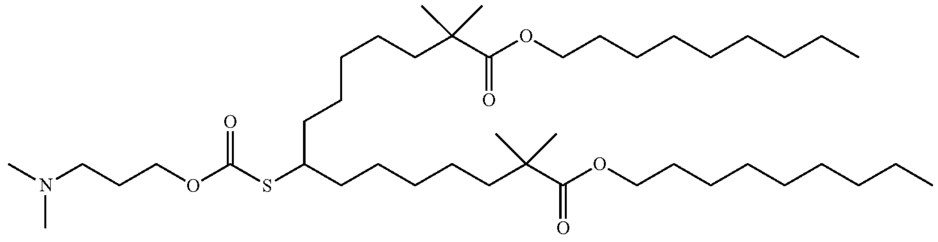
68
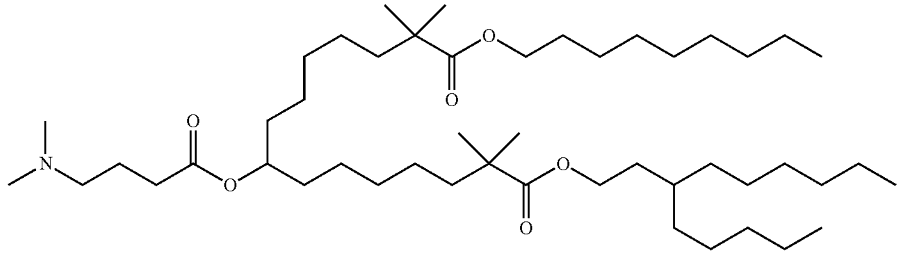
69
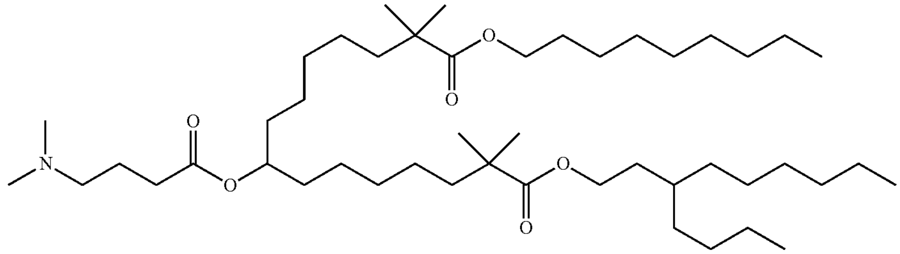
70
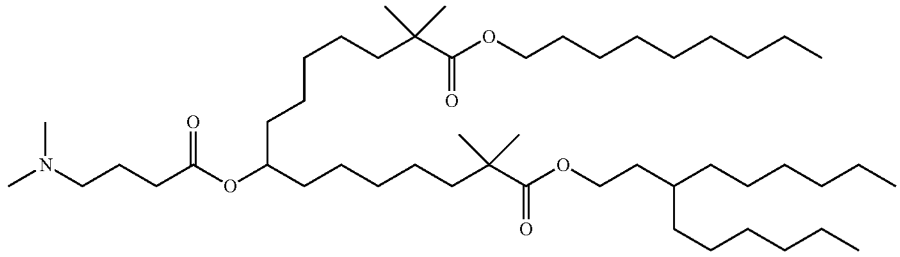
71
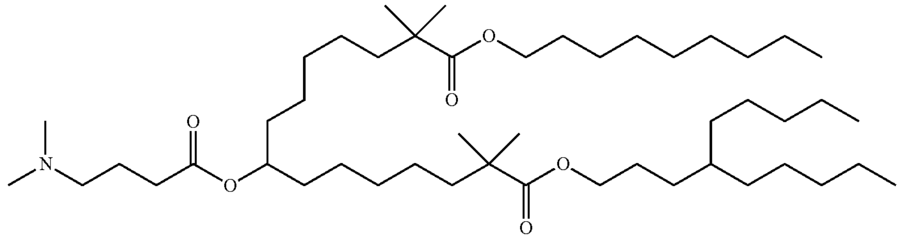

-continued
72
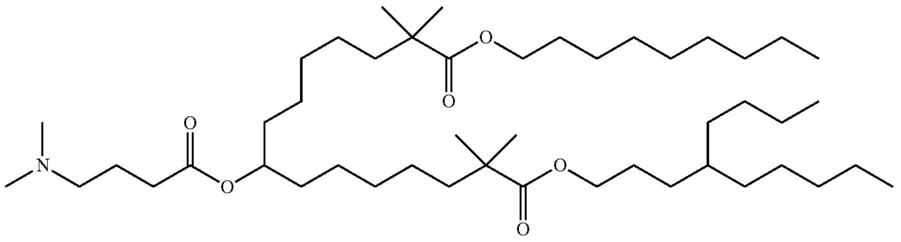
73
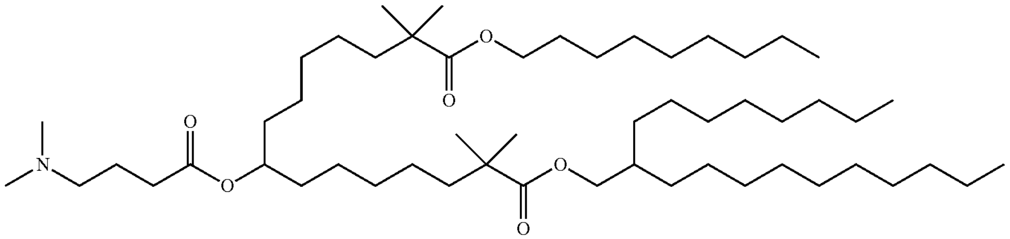
74
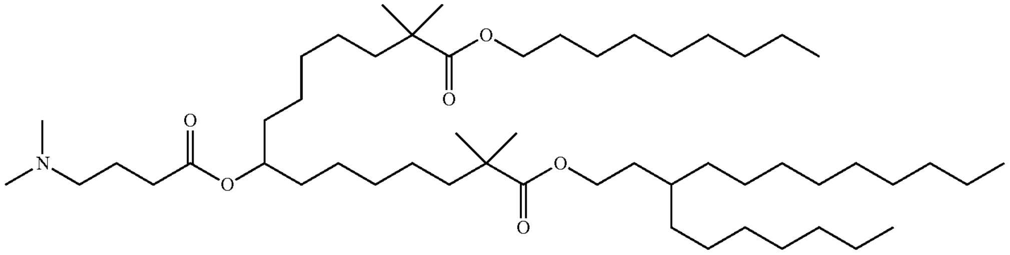
75
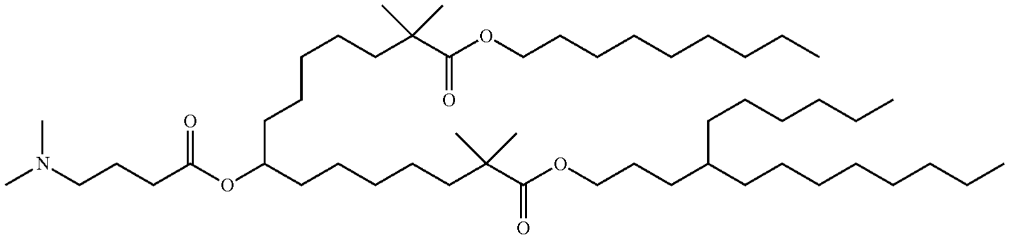
77
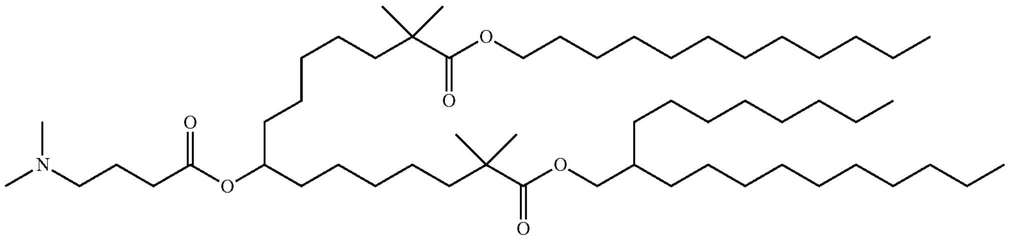
78
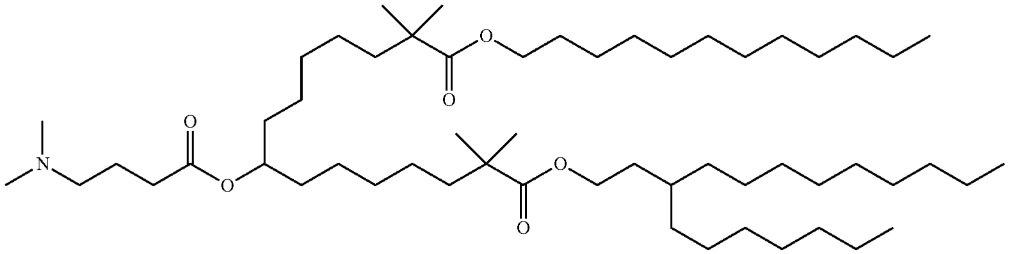

-continued
79
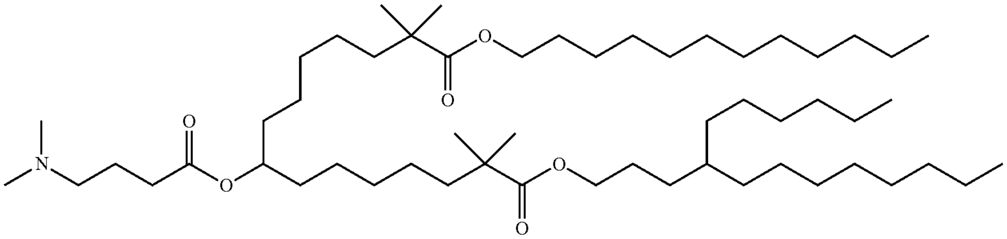
80
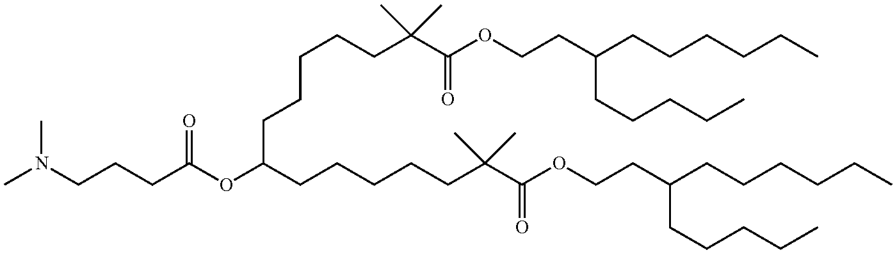
81
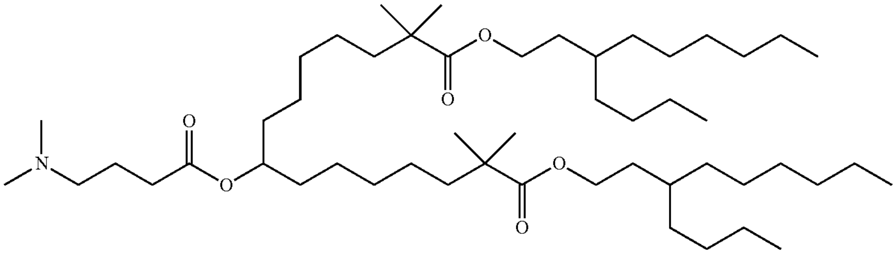
82
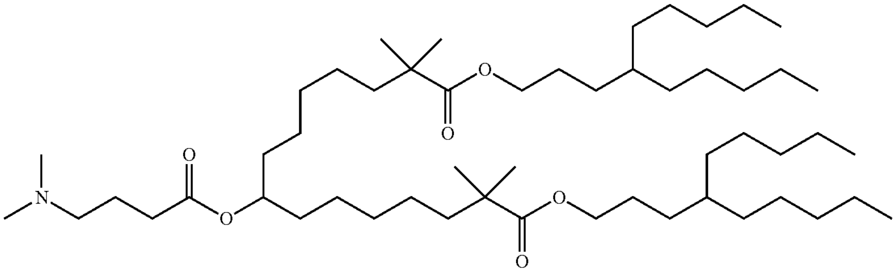
83
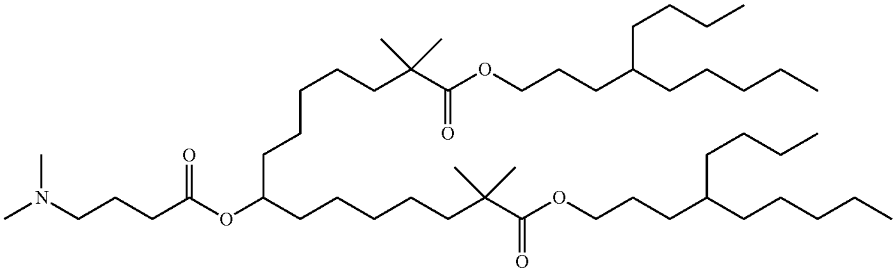
84
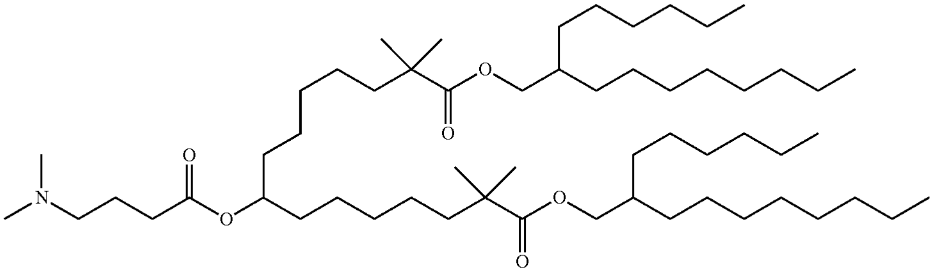

-continued
85
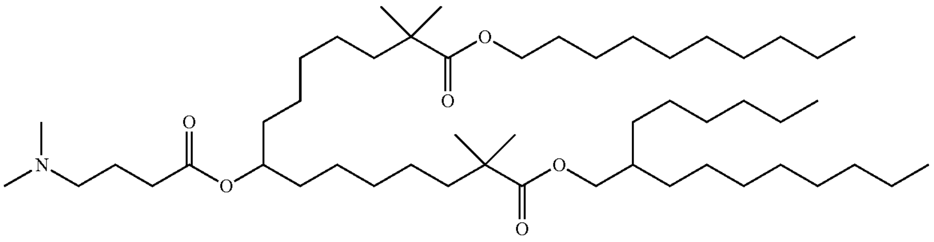
86
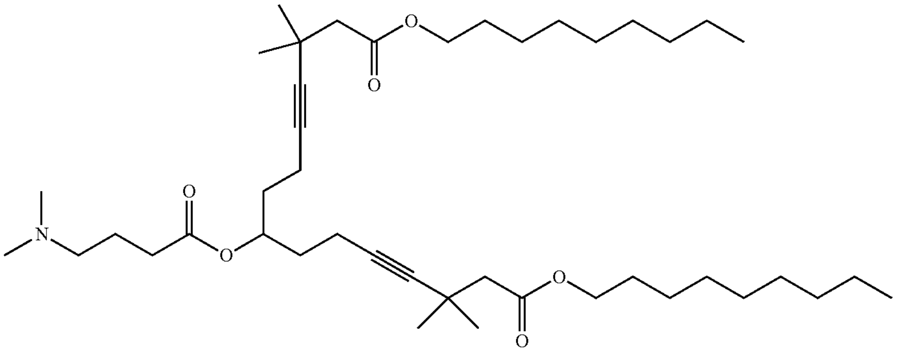
87
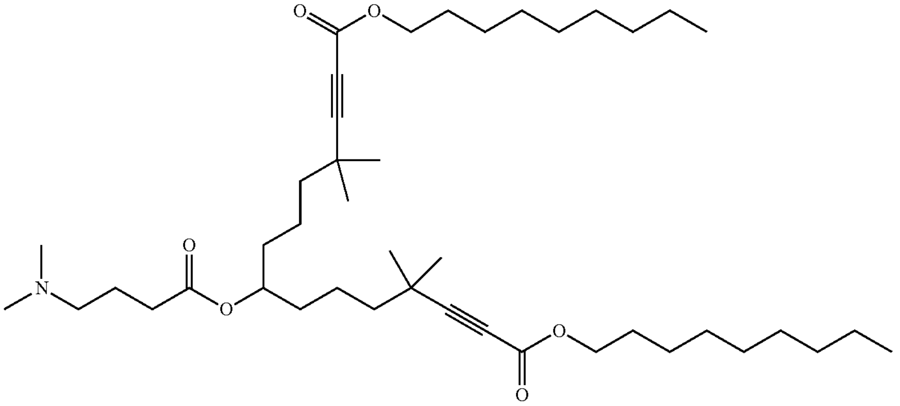
88
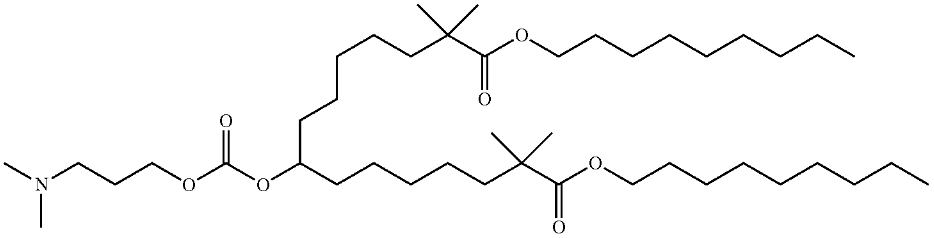
89
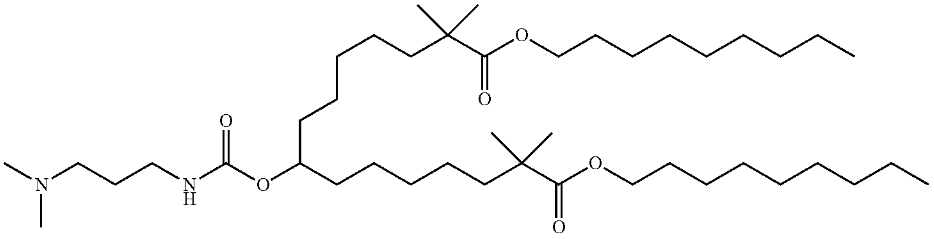

-continued
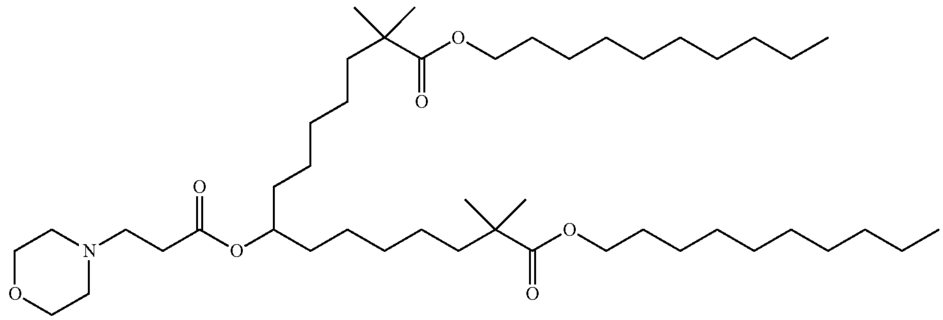
90
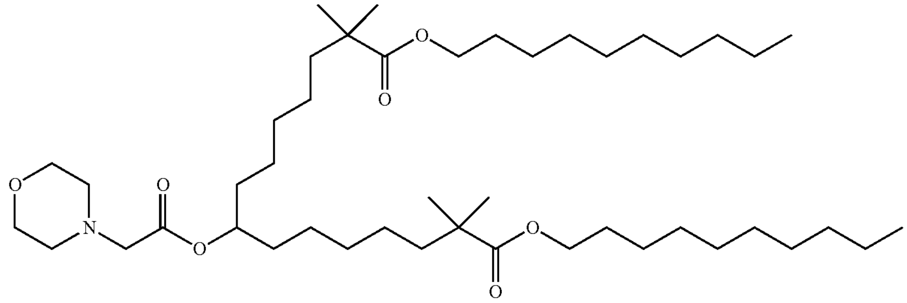
91
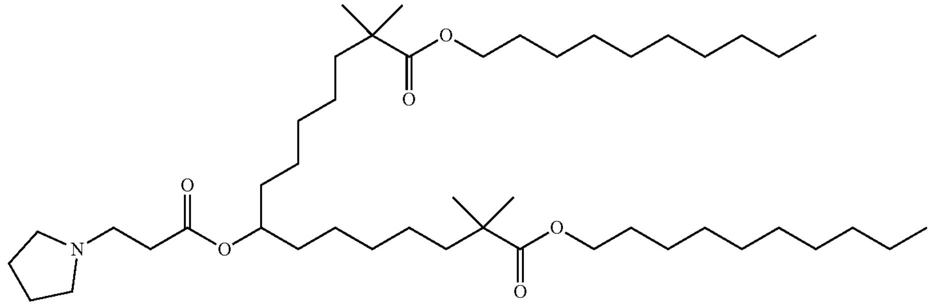
92
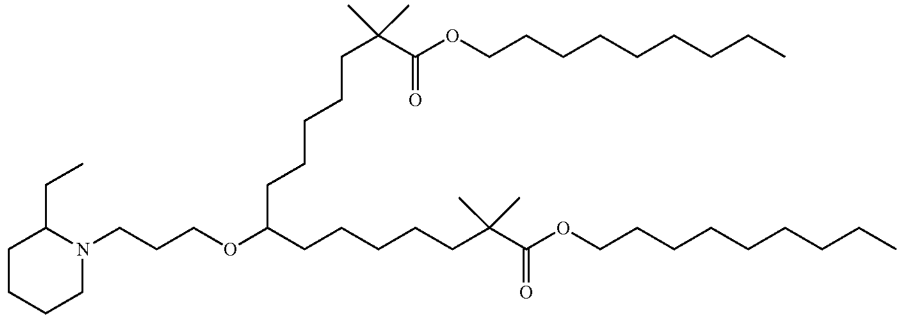
93
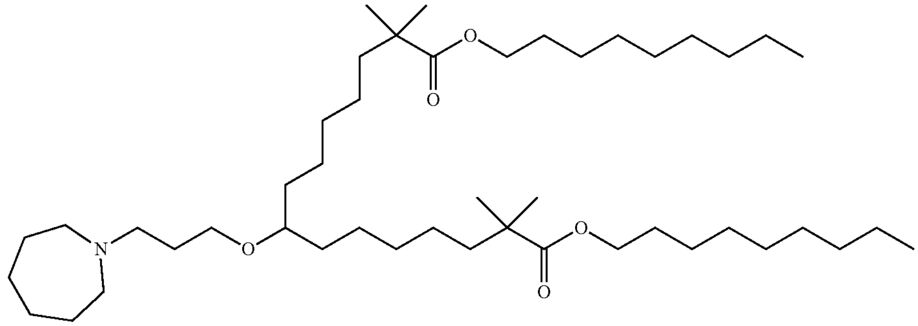
94

-continued
95
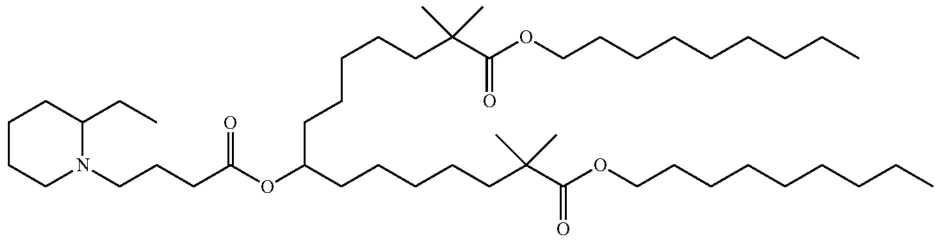
96
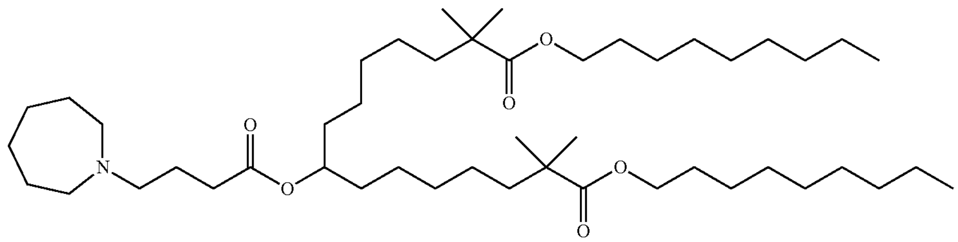
97
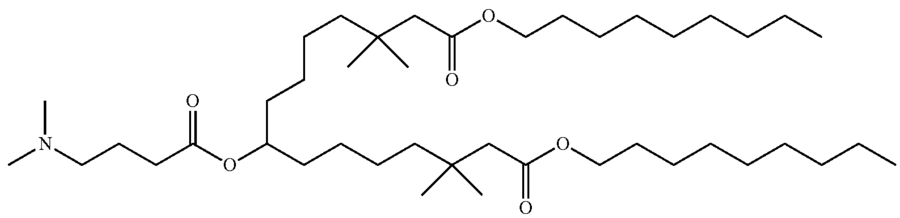
98
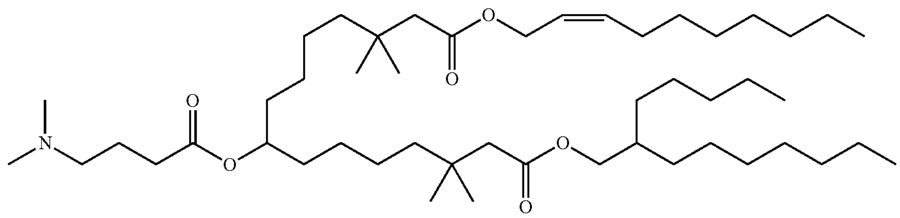
99
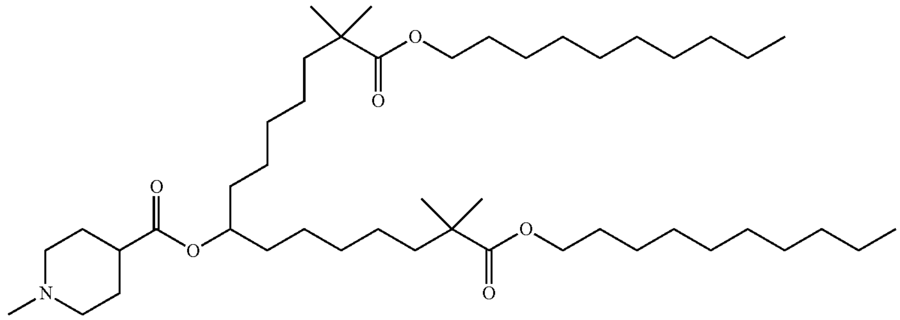
100
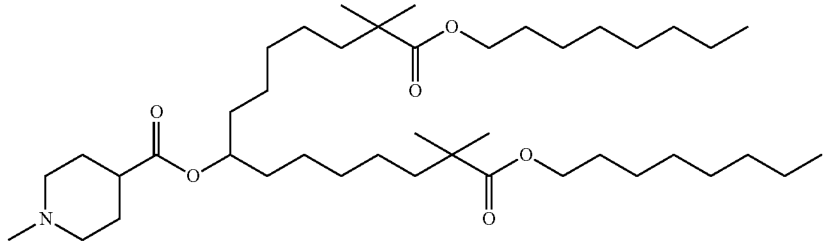

-continued
101
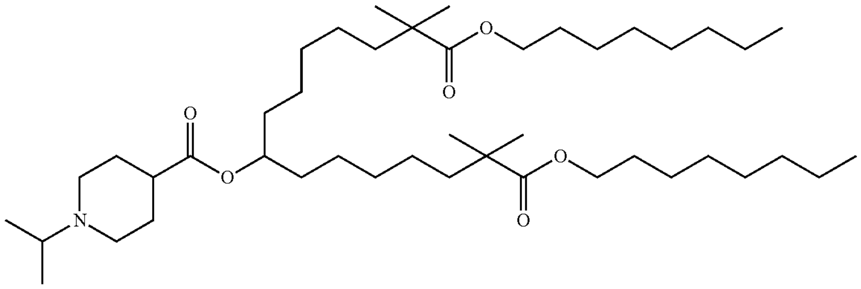
102
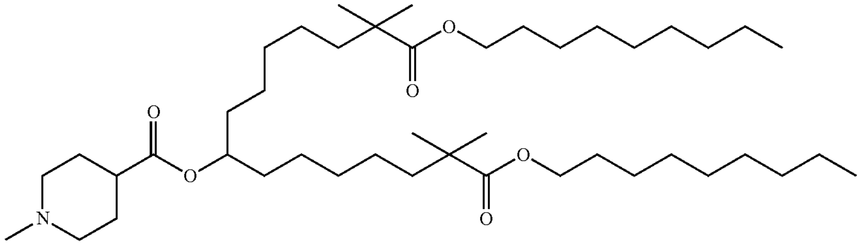
103
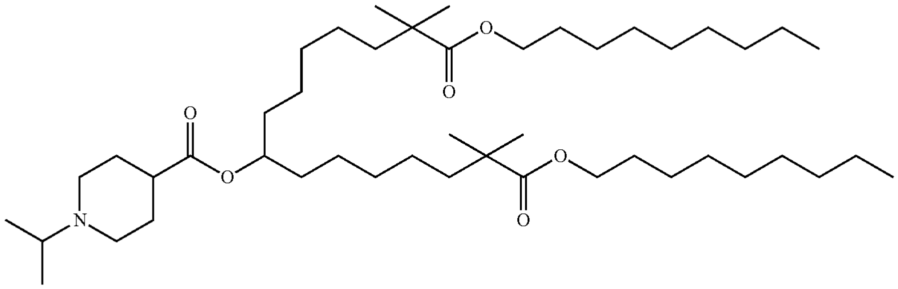
104
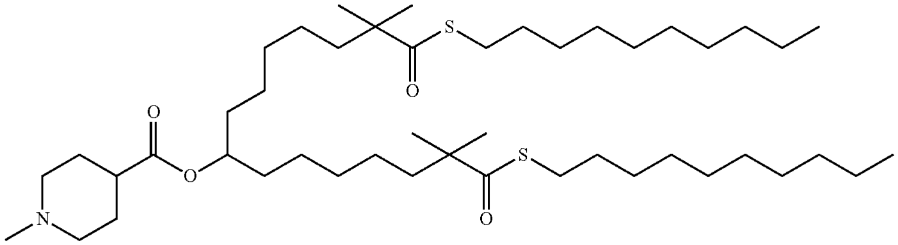
105
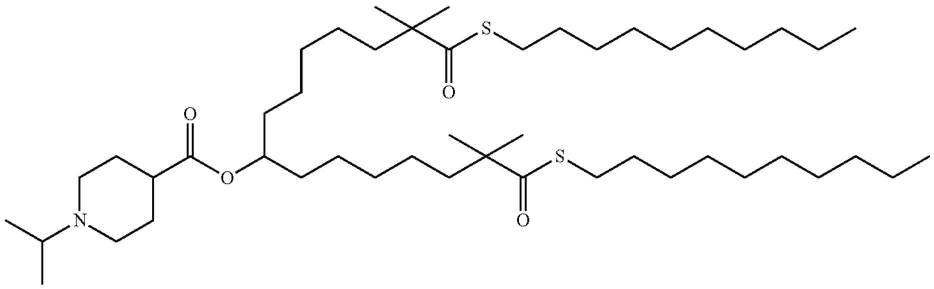
106
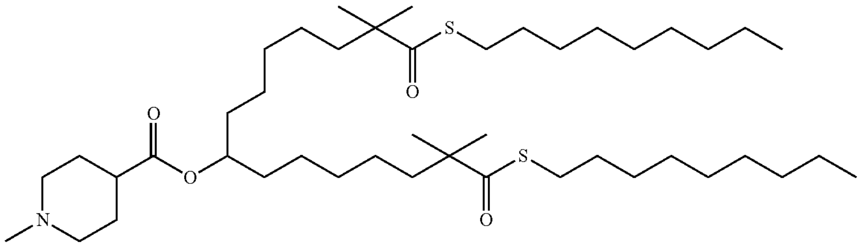

-continued
107
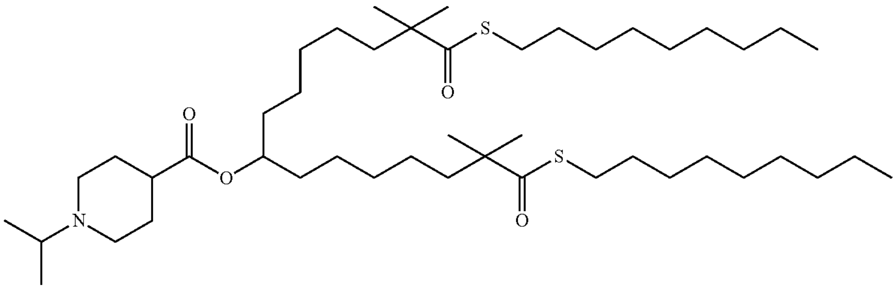
108
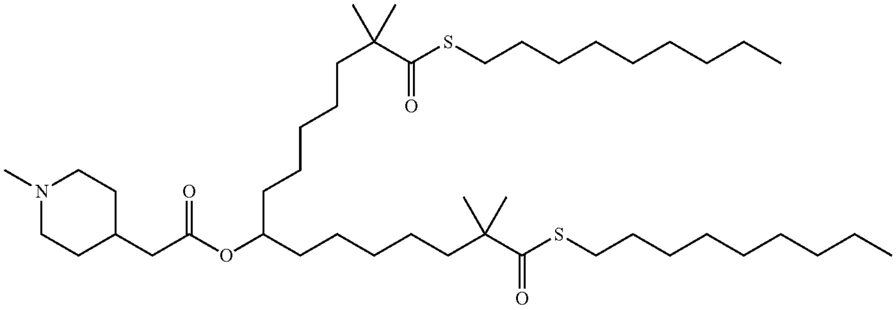
109
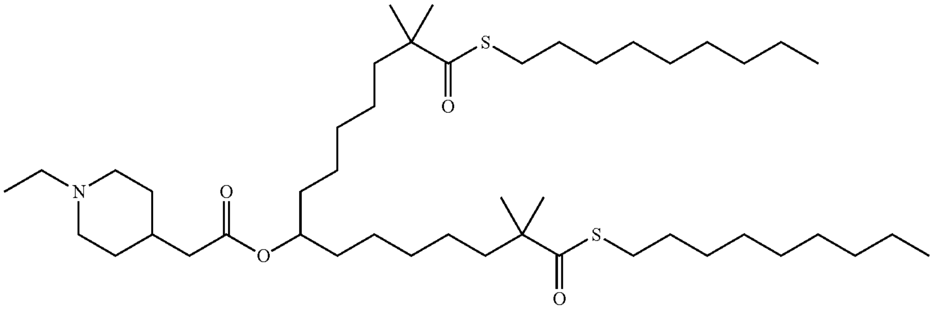
110
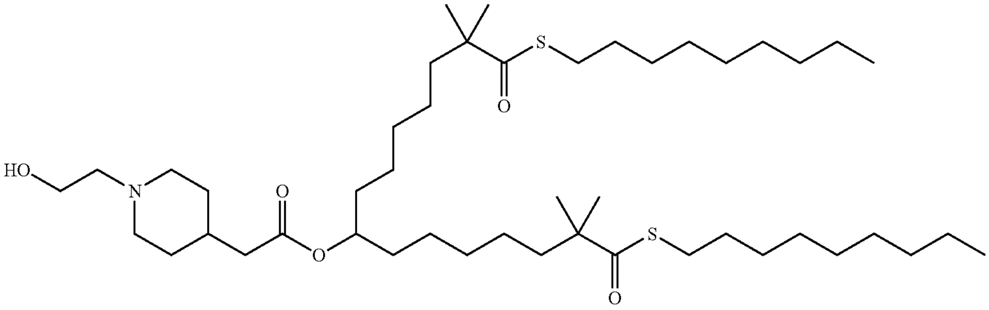
111
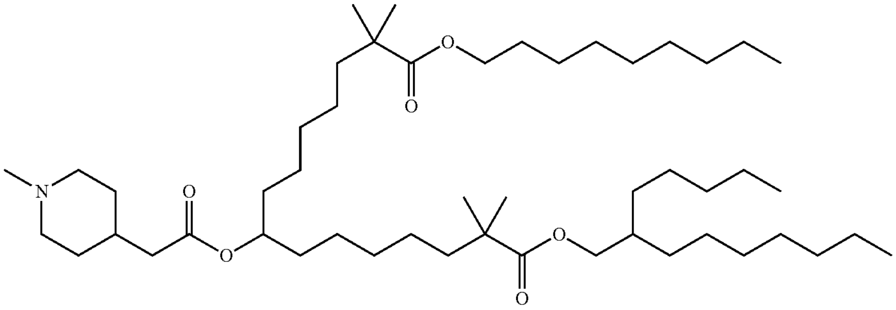

-continued
112
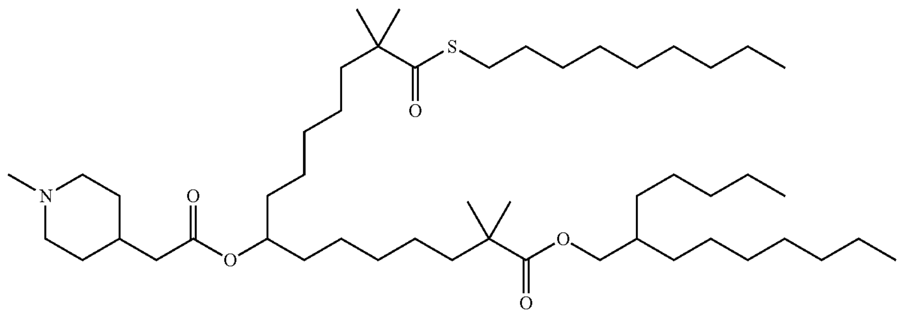
113
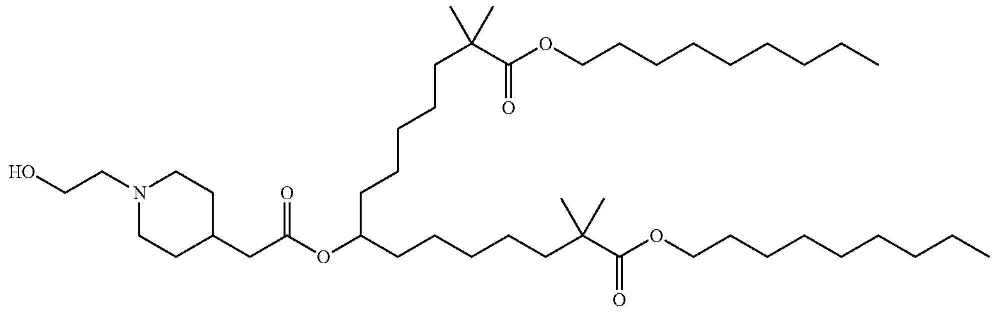
114
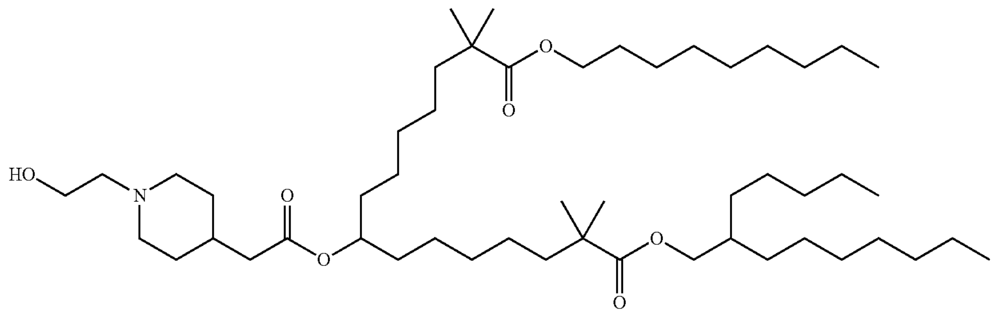
115
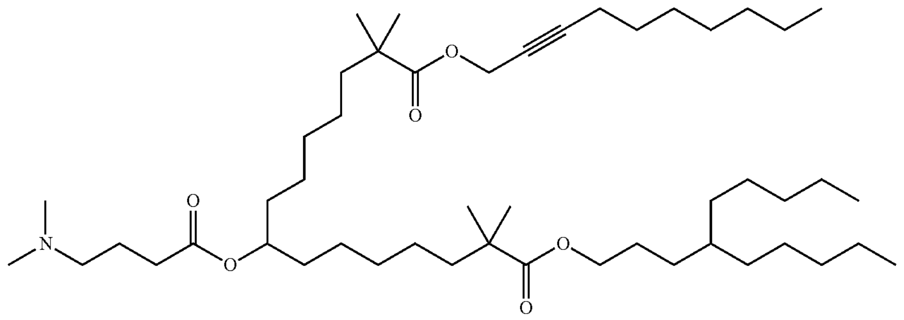
116
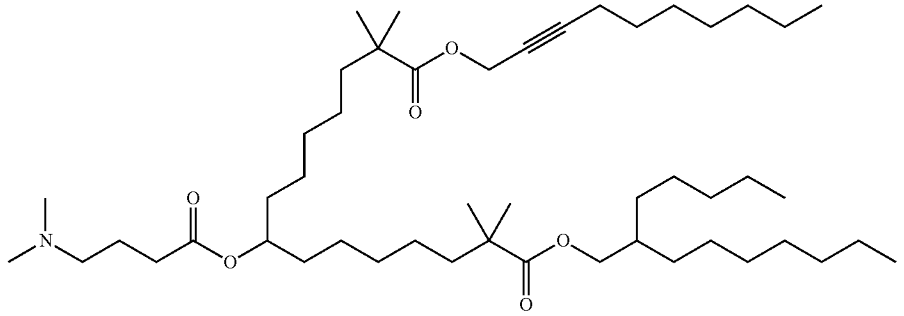

-continued
117
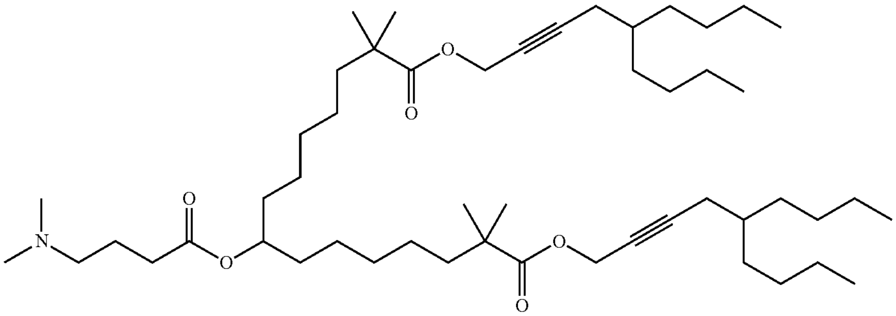
118
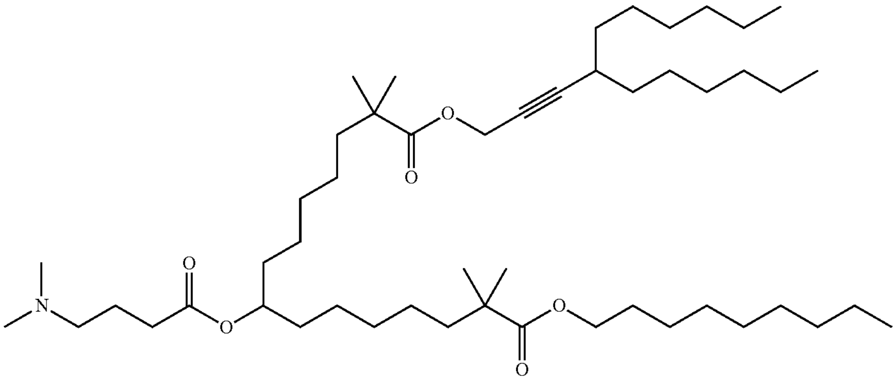
119
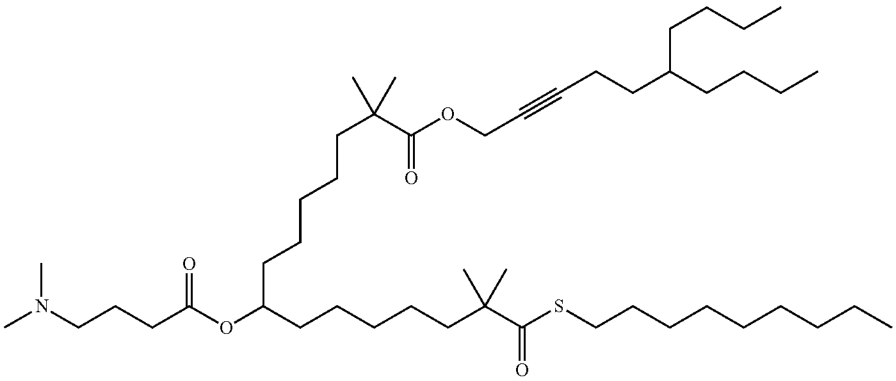
120
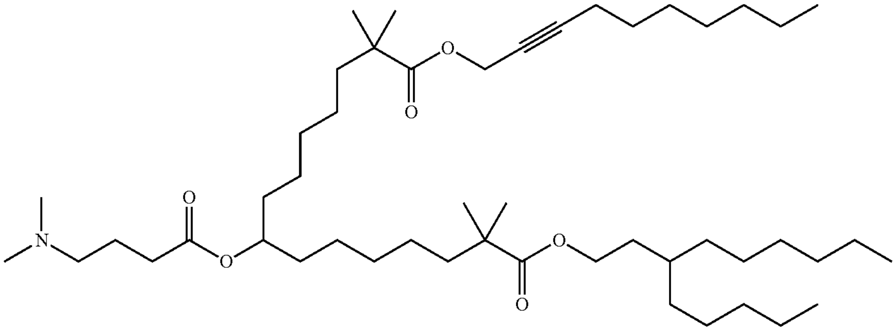

-continued
121
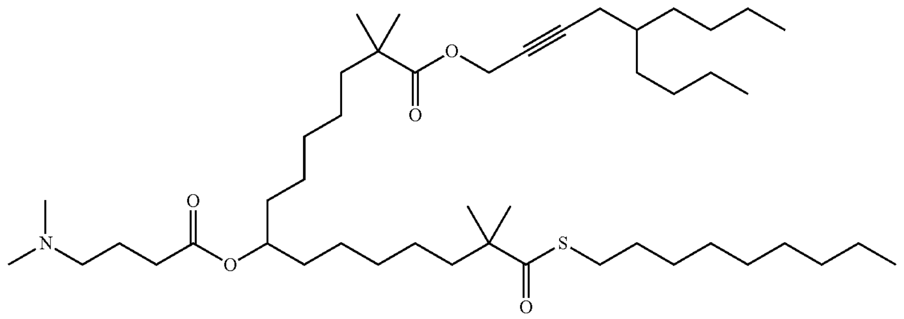
122
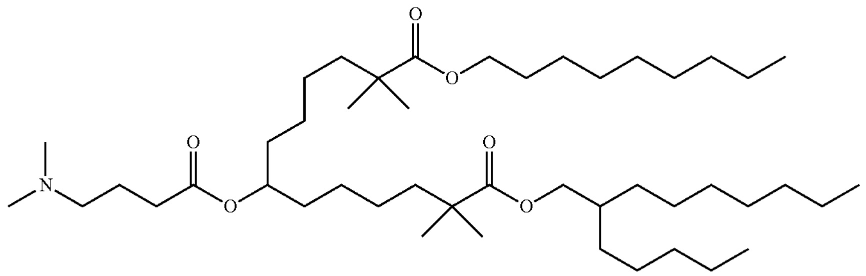
123
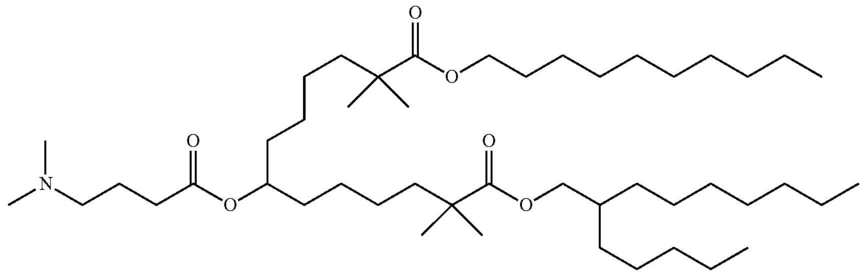
124
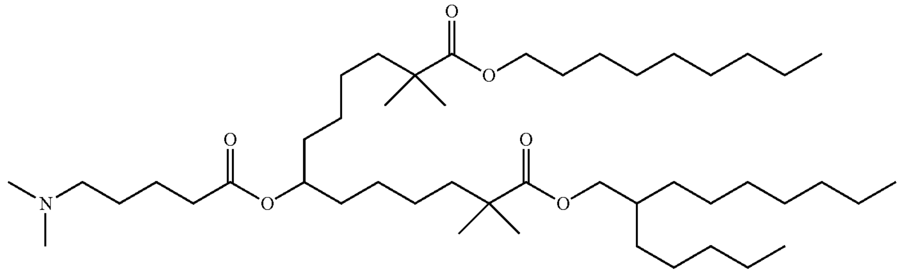
125
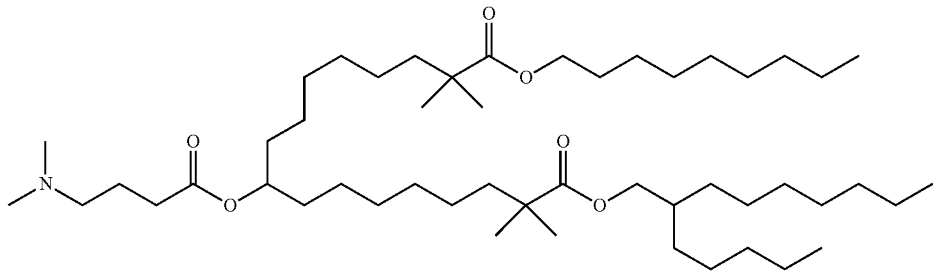

-continued

126

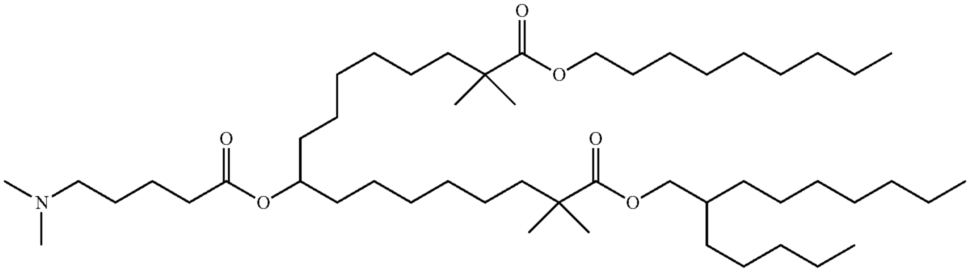

127

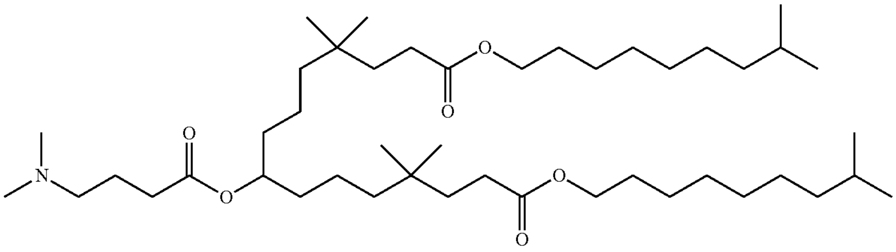

128

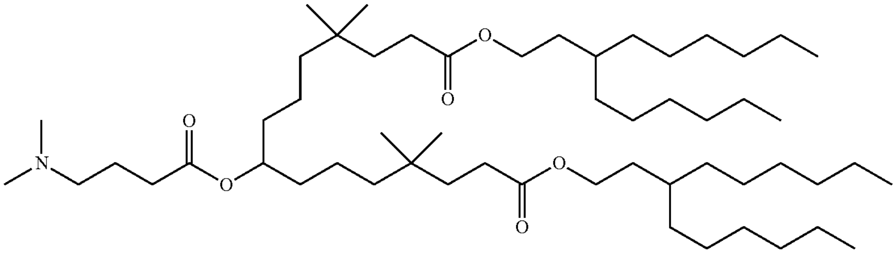

129

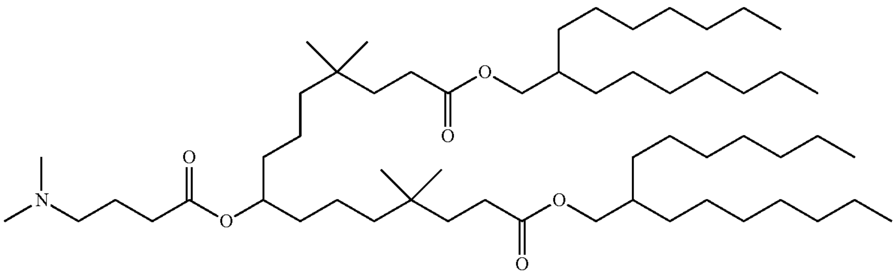

.

Technical solution 46: In a more specific embodiment, the present disclosure provides a nanoparticle composition as described above, wherein, the N:P molar ratio of N atoms in the ionizable cationic lipids to P atoms in the load molecules is 1-15:1, alternatively 3-12:1, alternatively 3-7:1, alternatively 6-12:1, more alternatively 3-6:1.

In some specific embodiments, the N:P molar ratio of N atoms in the ionizable cationic lipids to P atoms in the load molecules is 1-10:1, alternatively 3-6:1, more alternatively 3-5:1.

In some specific embodiments, the N:P molar ratio of N atoms in the ionizable cationic lipids to P atoms in the load molecules is 1-15:1, alternatively 3-12:1, more alternatively 6-12:1.

In some specific embodiments, the N:P molar ratio of N atoms in the ionizable cationic lipids to P atoms in the load molecules is 1-10:1, alternatively 3-7:1, more alternatively 5:1.

Technical solution 47: In a more specific embodiment, the present disclosure provides a nanoparticle composition as described above, wherein, the particle size of the particles is 65-200 nm, alternatively 65-180 nm, alternatively 70-170 nm, more alternatively 70-130 nm.

In some specific embodiments, the particle size of the particles is 70-180 nm, alternatively 80-180 nm, alternatively 90-180 nm, more alternatively 100-135 nm.

In some specific embodiments, the particle size of the particles is 65-160 nm, alternatively 65-150 nm, alternatively 70-150 nm, alternatively 90-130 nm, more alternatively 90-115 nm.

In some specific embodiments, the particle size of the particles is 65-140 nm, alternatively 65-130 nm, alternatively 70-130 nm, more alternatively 65-75 nm.

Technical solution 48: In a more specific embodiment, the present disclosure provides a nanoparticle composition as described above, wherein the lipid ingredient comprises the following components in the molar percentages:

Ionizable cationic lipids 30 mol %-55 mol %, alternatively 32.5 mol %-50 mol %;

Structure lipids 28 mol %-64 mol %, alternatively 30.6 mol %-61 mol %;

Neutral lipids 5 mol %-20 mol %;

Polymer lipids 1 mol %-3 mol %, alternatively 1 mol %-2 mol %;
the ionizable cationic lipid is as described in any one of technical solutions 12-45, alternatively is as described in technical solution 23, alternatively is:
46
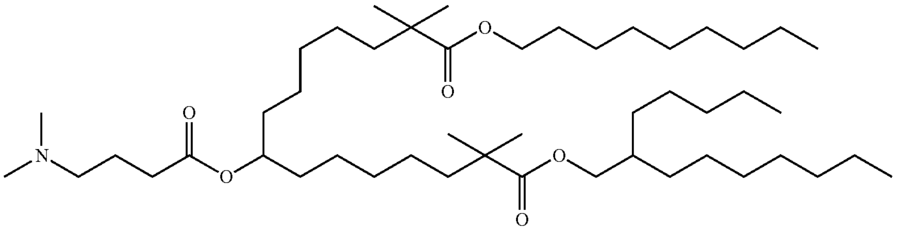
,
122
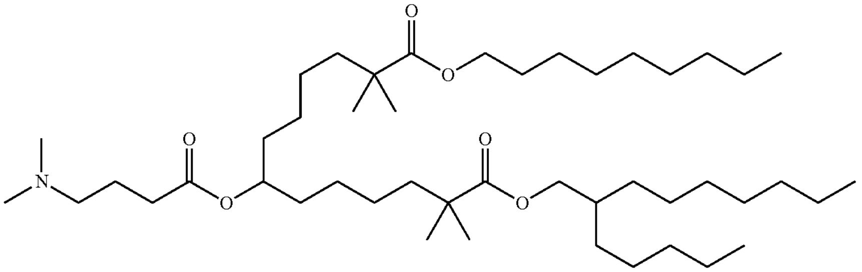
,
123
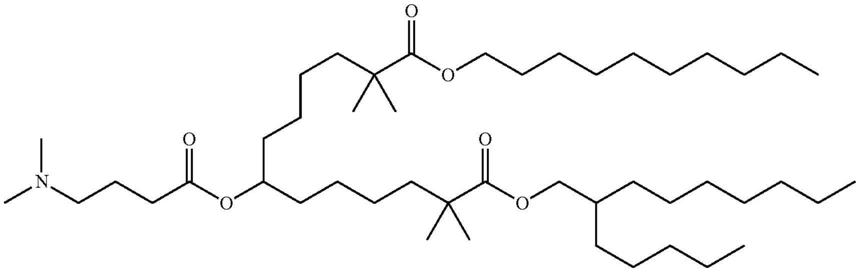
or
126
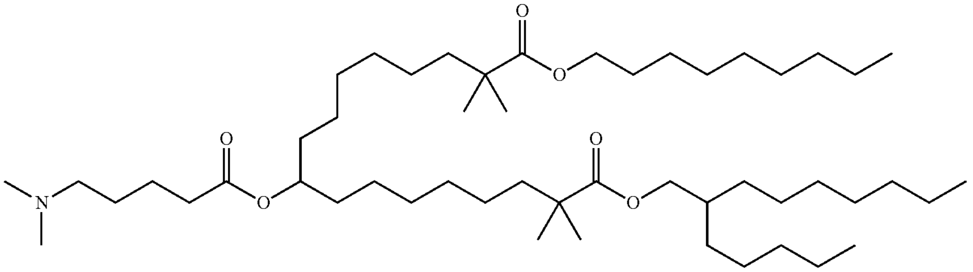
,
most alternatively is:
46
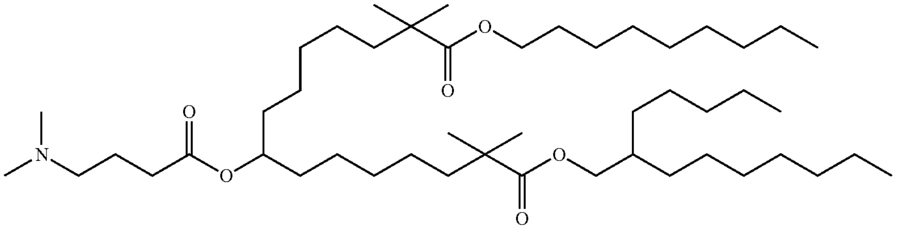
.

Alternatively, the lipid ingredient comprises the following components in the molar percentages:

Ionizable cationic lipids 40 mol %-52.5 mol %, alternatively 42.5 mol %-50 mol %;

Structure lipids 28 mol %-54 mol %, alternatively 30.6 mol %-51 mol %;

Neutral lipids 5 mol %-20 mol %;

Polymer lipids 1 mol %-3 mol %, alternatively 1 mol %-2 mol %;

the ionizable cationic lipid is as described in any one of technical solutions 12-45, alternatively is as described in technical solution 23, alternatively is:

46

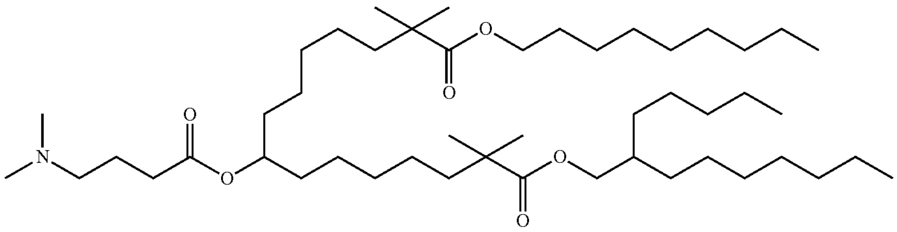

,

122

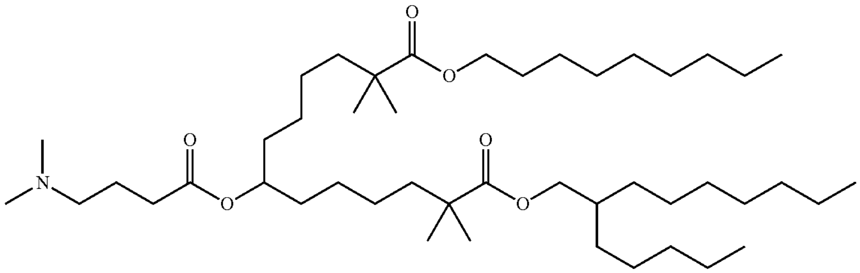

,

123

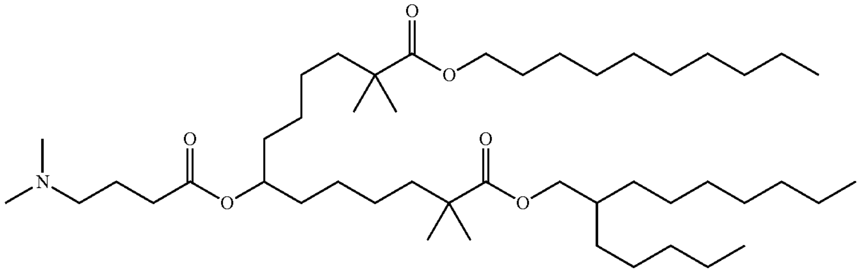

or

126

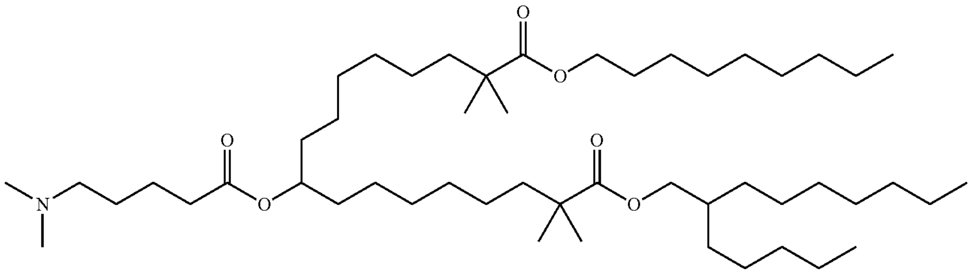

, most alternatively is:

46

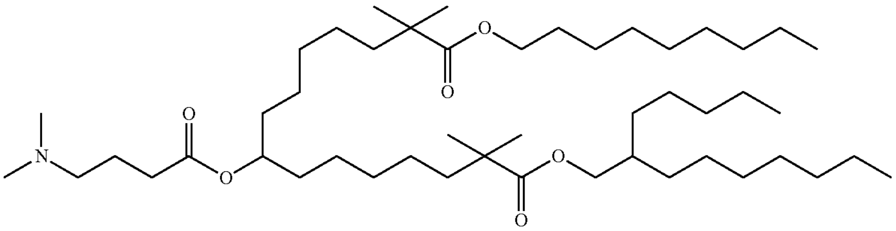

.

Alternatively, the lipid ingredient comprises the following components in the molar percentages:

Ionizable cationic lipids 45 mol %-52.5 mol %, alternatively 47.5 mol %-50 mol %;

Structure lipids 28 mol %-43 mol %, alternatively 30.6 mol %-40.5 mol %;

Neutral lipids 10 mol %-20 mol %;

Polymer lipids 1.4 mol %-2 mol %;

the ionizable cationic lipid is as described in any one of technical solutions 12-45, alternatively is as described in technical solution 23, alternatively is:

46

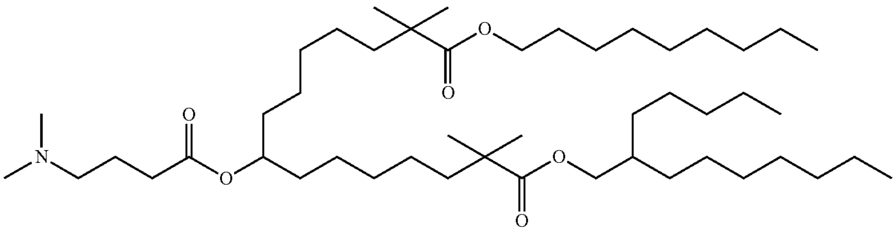

,

122

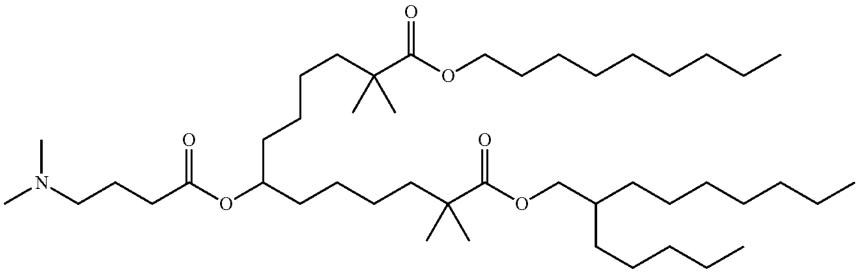

,

123

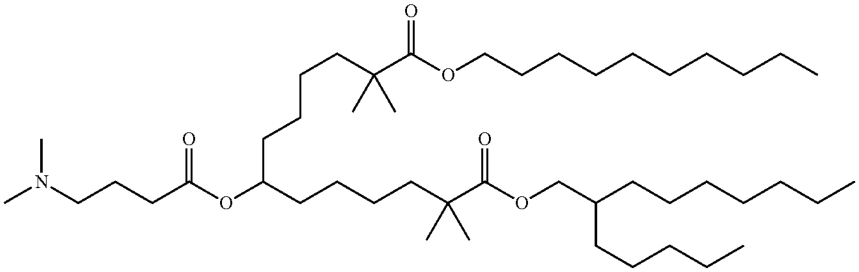

or

126

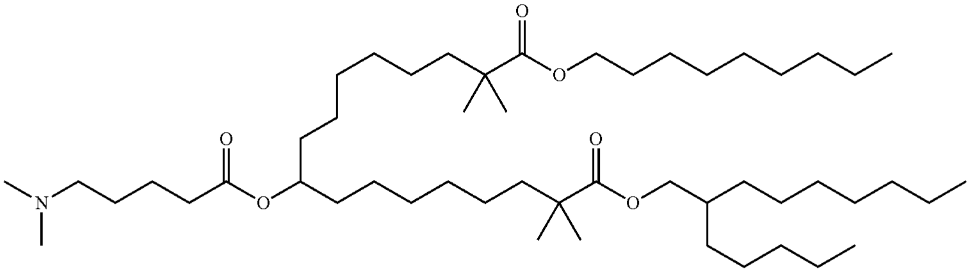

, most alternatively is:

46

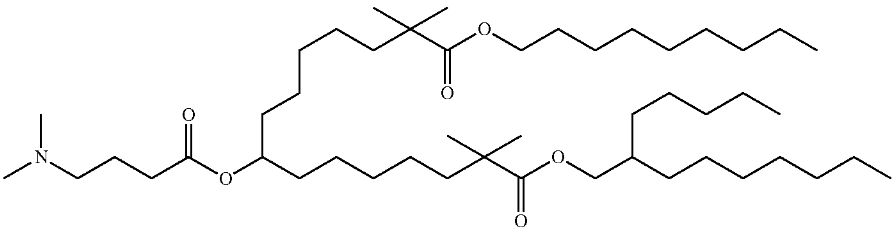

.

Alternatively, the lipid ingredient comprises the following components in the molar percentages:

Ionizable cationic lipids 45 mol %-50 mol %, alternatively 47 mol %-48 mol %, alternatively 47.6 mol %;

Structure lipids 28 mol %-40.5 mol %, alternatively 30.6 mol %-38.1 mol %;

Neutral lipids 12.5 mol %-20 mol %;

Polymer lipids 1.8 mol %-2 mol %;

the ionizable cationic lipid is as described in any one of technical solutions 12-45, alternatively is as described in technical solution 23, alternatively is:

46

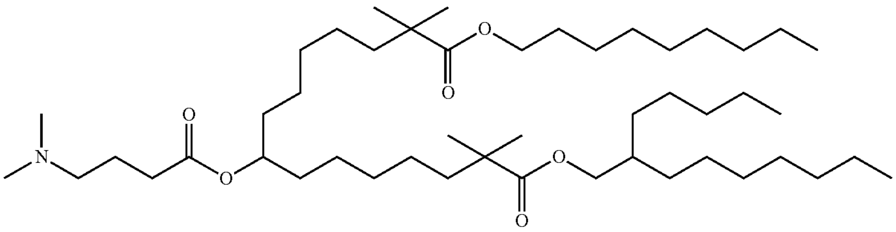

,

122

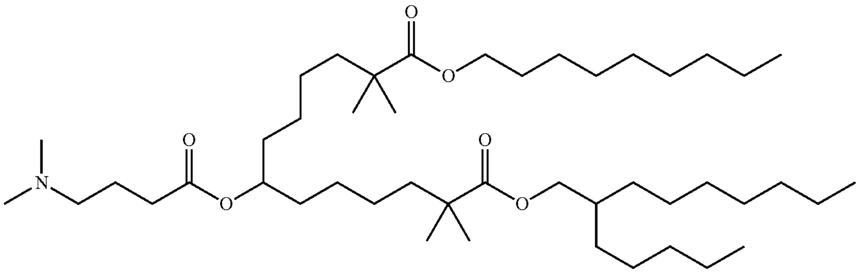

,

123

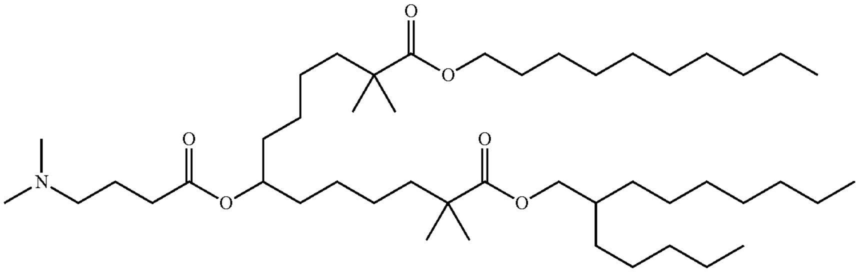

or

126

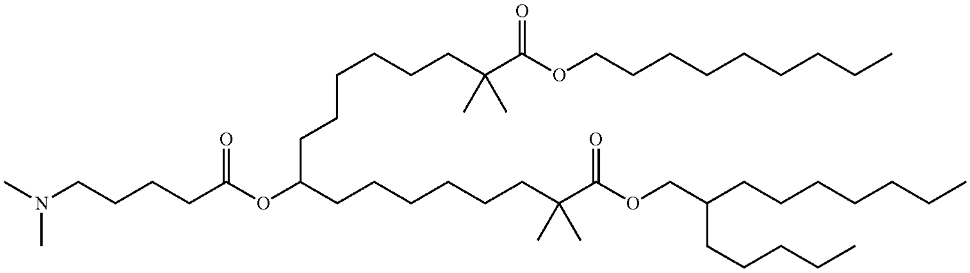

, most alternatively is:

46

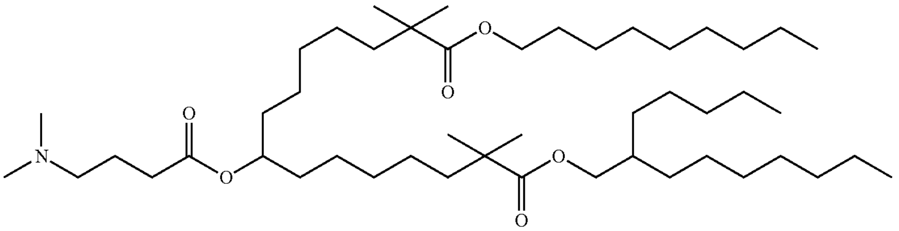

.

Technical solution 49: In a more specific embodiment, the present disclosure provides a nanoparticle composition as described above, wherein, the molar ratio of ionizable cationic lipids:structure lipids:neutral lipids:polymer lipids is: 32.5:61:5:1.5, 32.5:51.5:15:1, 42.5:49:7.5:1, 42.5:51:5:1.5, 47.6:38.1:12.5:1.8, 47.6:30.6:20:1.8, 47.5:40.5:10:2, 47.6:32.9:17.5:2, 47.6:36:15:1.4 or 50:38.5:10:1.5; alternatively: 42.5:49:7.5:1, 42.5:51:5:1.5, 47.6:38.1:12.5:1.8, 47.6:30.6:20:1.8, 47.5:40.5:10:2, 47.6:32.9:17.5:2, 47.6:36:15:1.4 or 50:38.5:10:1.5; alternatively: 47.6:38.1:12.5:1.8, 47.6:30.6:20:1.8, 47.5:40.5:10:2, 47.6:32.9:17.5:2, 47.6:36:15:1.4 or 50:38.5:10:1.5; more alternatively: 47.6:38.1:12.5:1.8, 47.6:30.6:20:1.8 or 47.6:32.9:17.5:2.

Technical solution 50: In a more specific embodiment, the present disclosure provides a nanoparticle composition as described above, wherein, the N:P molar ratio of N atoms in the ionizable cationic lipids to P atoms in the load molecules is 1-10:1, alternatively 3-6:1, more alternatively 3-5:1.

Technical solution 51: In a more specific embodiment, the present disclosure provides a nanoparticle composition as described above, wherein, the particle size of the particles is 70-180 nm, alternatively 80-180 nm, alternatively 90-180 nm, more alternatively 100-135 nm.

Technical solution 52: In a more specific embodiment, the present disclosure provides a nanoparticle composition as described above, wherein the lipid ingredient comprises the following components in the molar percentages:

Ionizable cationic lipids 30 mol %-60 mol %;

Structure lipids 27.5 mol %-66 mol %;

Neutral lipids 1.5 mol %-20 mol %;

Polymer lipids 1.5 mol %-5 mol %;

the ionizable cationic lipid is as described in any one of technical solutions 12-45, or

34

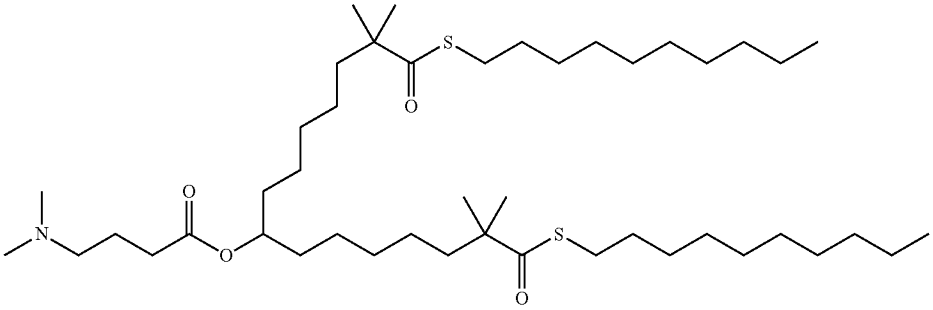

or

41

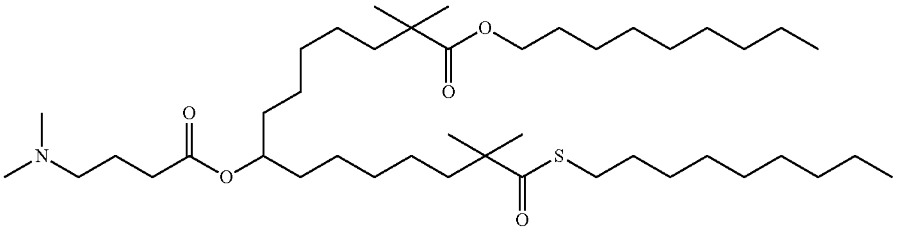

;

alternatively is as described in technical solution 23, alternatively is:

18

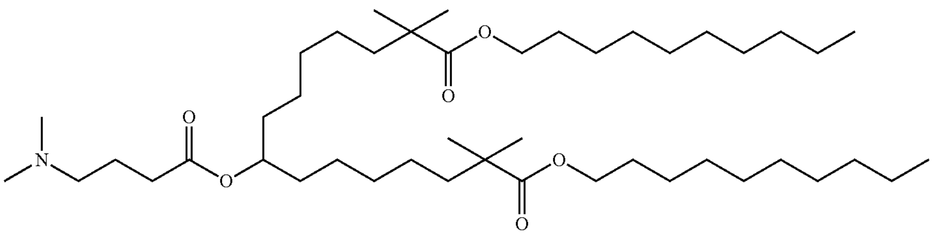

or

20

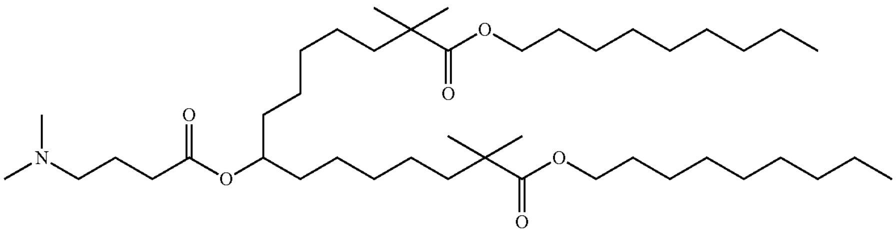

, most alternatively is:

20

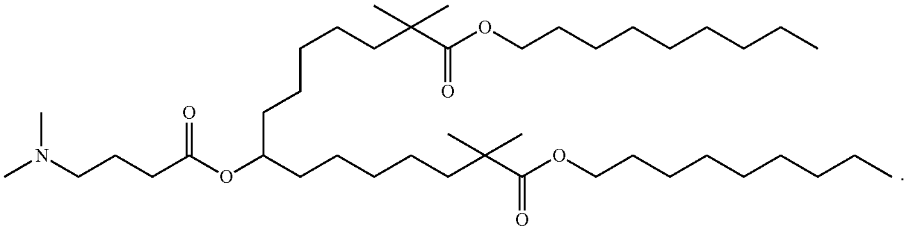

Alternatively, the lipid ingredient comprises the following components in the molar percentages:

Ionizable cationic lipids 30 mol %-50 mol %;

Structure lipids 35 mol %-66 mol %;

Neutral lipids 1.5 mol %-20 mol %;

Polymer lipids 1.5 mol %-5 mol %;

the ionizable cationic lipid is as described in any one of technical solutions 12-45, or is

34

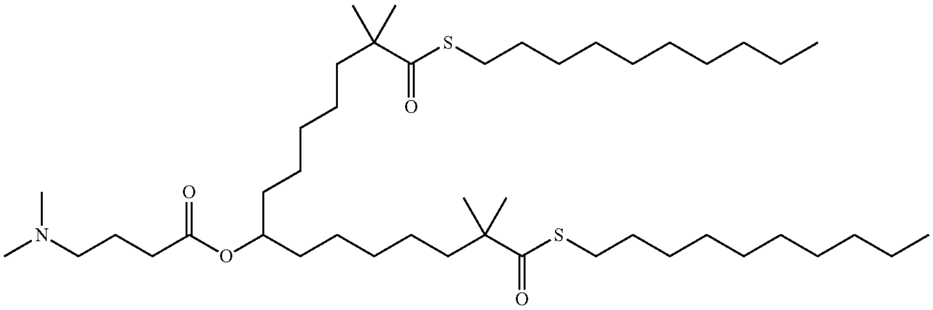

or

41

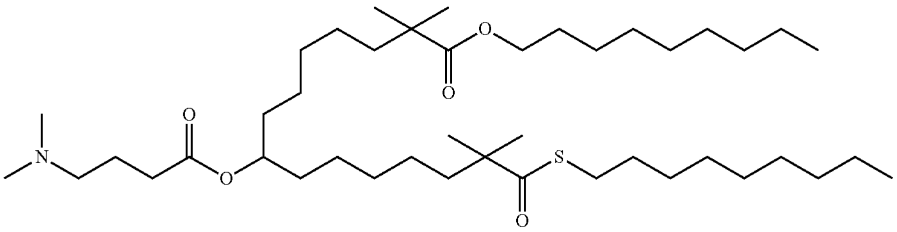

;

- alternatively is as described in technical solution 23, alternatively is:

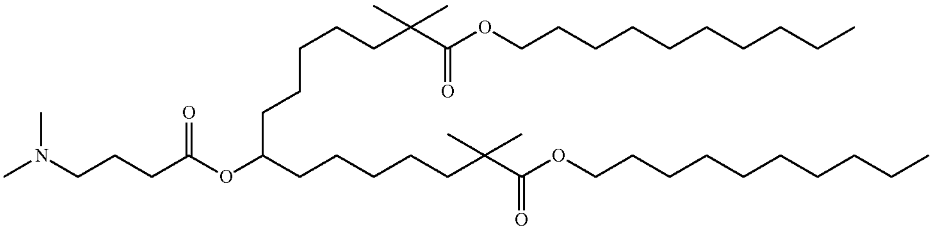

or

18

-continued

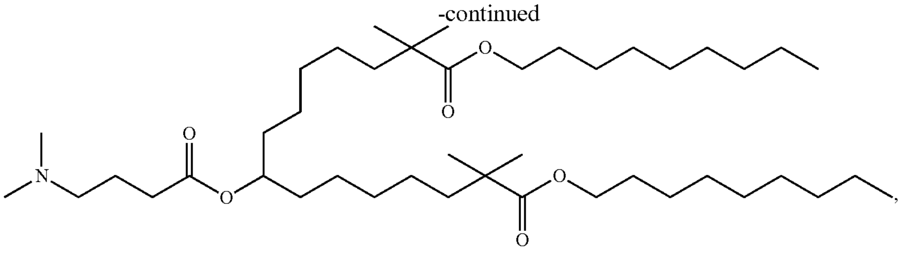,

20 most alternatively is:

20

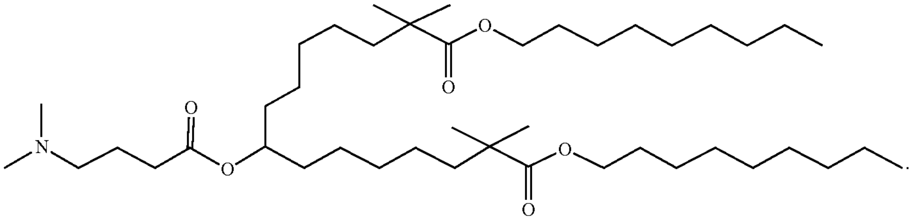.

Alternatively, the lipid ingredient comprises the following components in the molar percentages:

Ionizable cationic lipids 30 mol %-50 mol %;

Structure lipids 38.5 mol %-63.5 mol %;

Neutral lipids 1.5 mol %-10 mol %;

Polymer lipids 1.5 mol %-4 mol %, alternatively 1.5 mol %-3.5 mol %;

the ionizable cationic lipid is as described in any one of technical solutions 12-45, or is

34

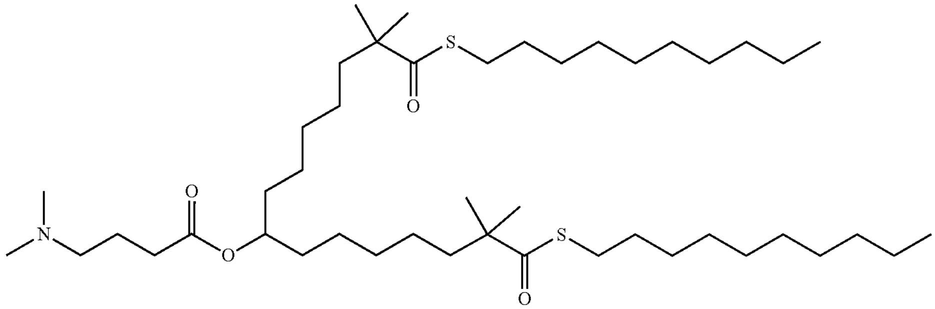

or

41

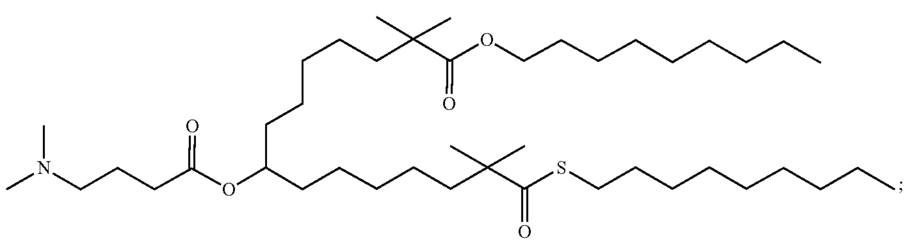;

alternatively is as described in technical solution 23, alternatively is:

18

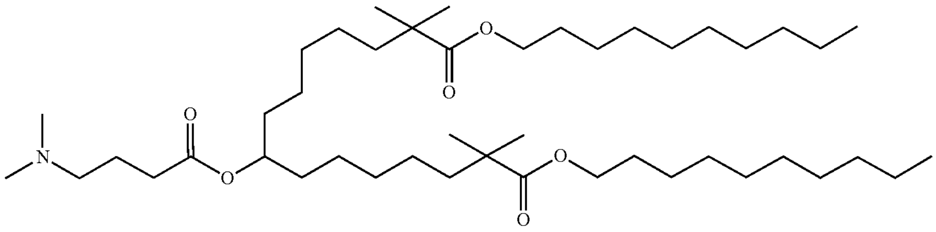

or

20

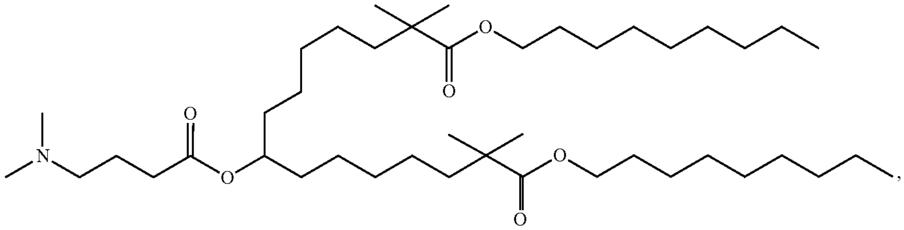

, most alternatively is:

20

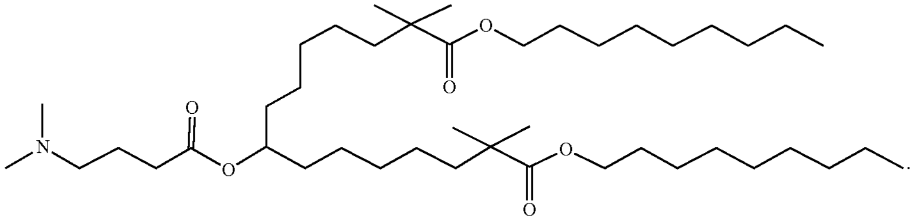

.

Alternatively, the lipid ingredient comprises the following components in the molar percentages:

Ionizable cationic lipids 30 mol %-50 mol %, alternatively 30 mol %-48.5 mol %;

Structure lipids 43 mol %-60 mol %, alternatively 45.5 mol %-57.5 mol %;

Neutral lipids 1.5 mol %-10 mol %;

Polymer lipids 1.5 mol %-4 mol %, alternatively 1.5 mol %-3.5 mol %;

the ionizable cationic lipid is as described in any one of technical solutions 12-45, or is

34

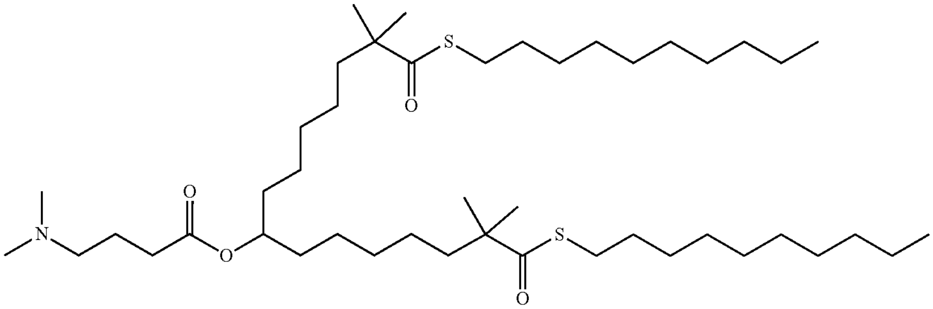

or

-continued

41

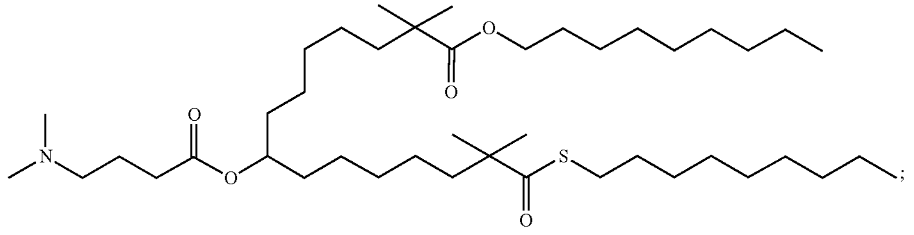

alternatively is as described in technical solution 23, alternatively is:

18

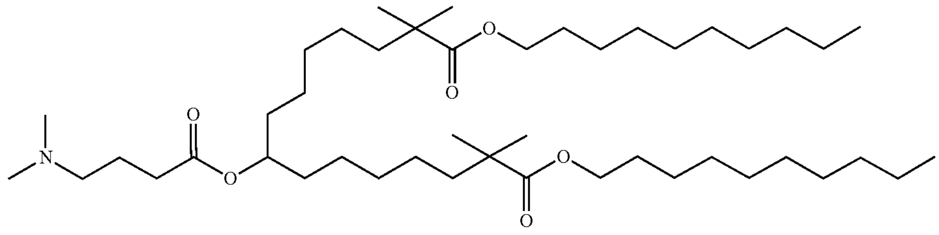

or

20

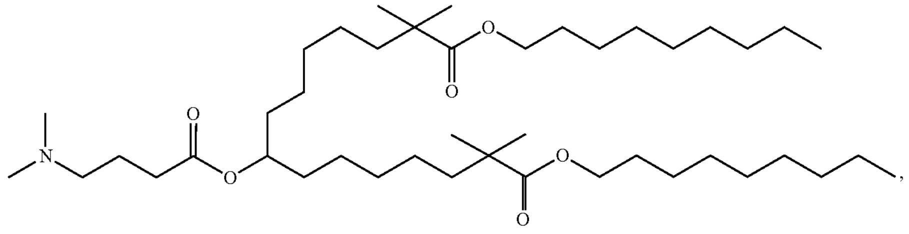

most alternatively is:

20

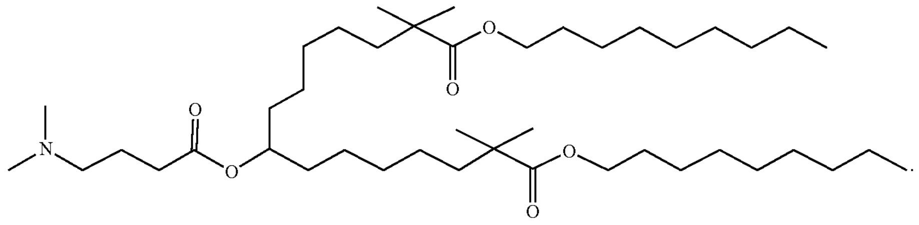

Alternatively, the lipid ingredient comprises the following components in the molar percentages:

Ionizable cationic lipids 46 mol %-50 mol %, alternatively 48 mol %-49 mol %, alternatively 48.5 mol %;

Structure lipids 43 mol %-50 mol %, alternatively 45.5 mol %-47.5 mol %;

Neutral lipids 1.5 mol %-3.5 mol %, alternatively 1.5 mol %-2.5 mol %;

Polymer lipids 2 mol %-4 mol %, alternatively 2.5 mol %-3.5 mol %;

the ionizable cationic lipid is as described in any one of technical solutions 12-45, or is 34
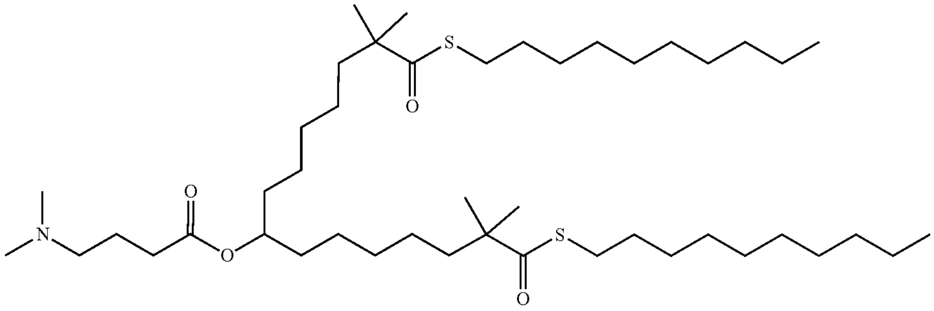
or
41
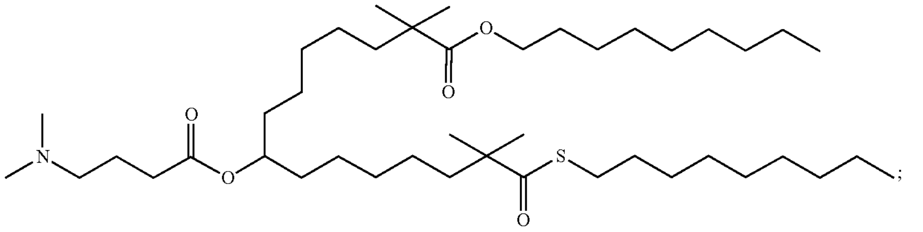
alternatively is as described in technical solution 23, alternatively is:
18
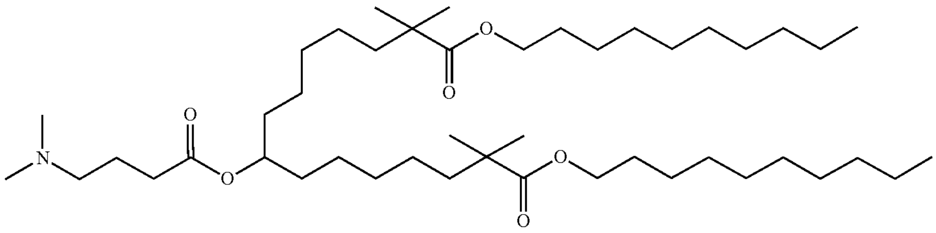
or
20
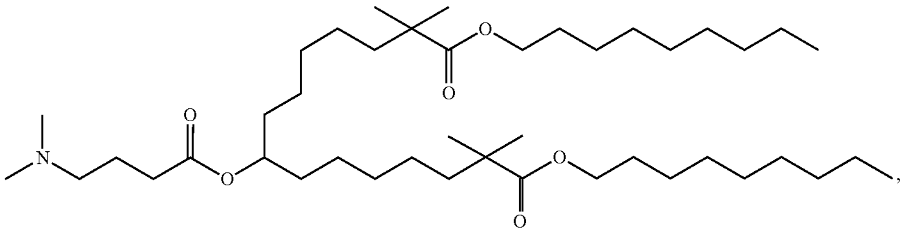
most alternatively is:
20
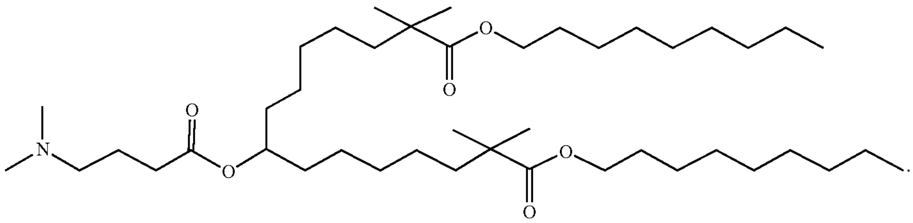
Alternatively, the lipid ingredient comprises the following components in the molar percentages:
Ionizable cationic lipids 46 mol %-50 mol %, alternatively 48 mol %-49 mol %, alternatively 48.5 mol %;

Structure lipids 43 mol %-49 mol %, alternatively 45.5 mol %-46.5 mol %;
Neutral lipids 1.5 mol %-3.5 mol %, alternatively 1.5 mol %-2.5 mol %;
Polymer lipids 3 mol %-4 mol %, alternatively 3.5 mol %;
the ionizable cationic lipid is as described in an one of technical solutions 12-45, or is
34
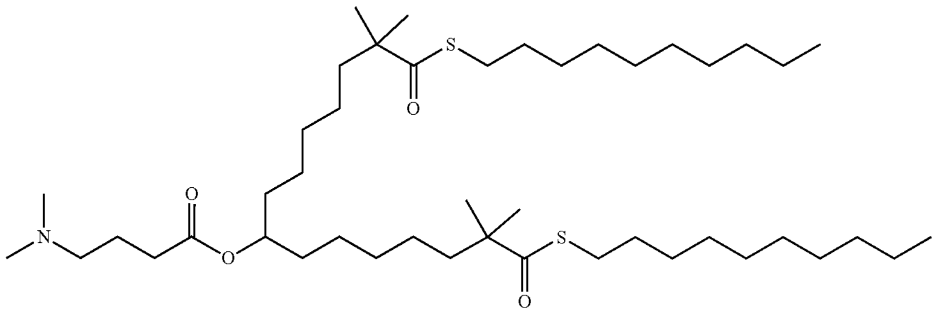
or
41
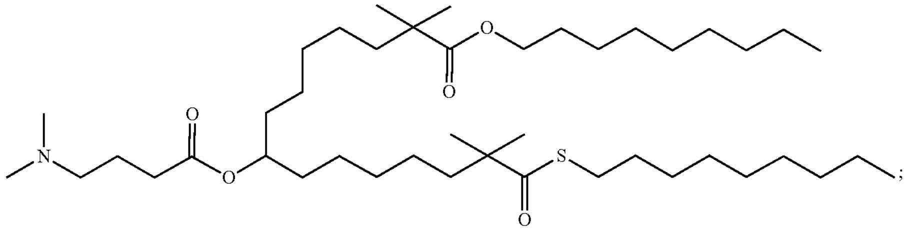
;
as is described in technical solution 9, alternatively is:
18
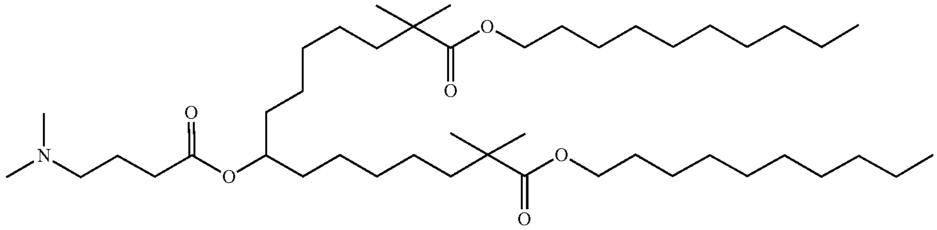
or
20
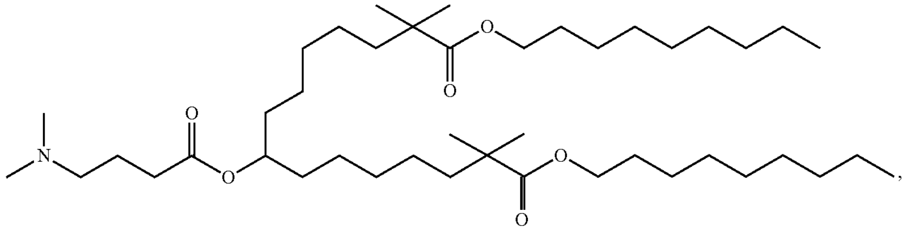
,
most alternatively is:
20
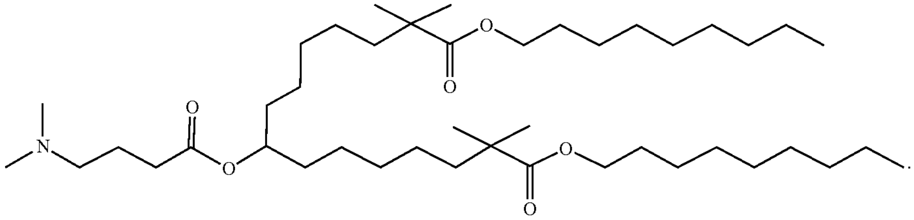
.

Technical solution 53: In a more specific embodiment, the present disclosure provides a nanoparticle composition as described above, wherein, the molar ratio of ionizable cationic lipids:structure lipids:neutral lipids:polymer lipids is: 40:35:20:5, 40:48.5:10:1.5, 30:66:2.5:1.5, 40:53.5:5:1.5, 30:63.5:5:1.5, 40:55:2.5:2.5, 30:62.5:5:2.5, 30:57.5:10:2.5, 48.5:47.5:1.5:2.5, 48.5:46.5:2.5:2.5, 48.5:45.5:2.5:3.5, 48.5:46.5:1.5:3.5, 50:42.5:5:2.5, 60:27.5:10:2.5 or 50:38.5:10:1.5;

alternatively: 40:35:20:5, 40:48.5:10:1.5, 30:66:2.5:1.5, 40:53.5:5:1.5, 30:63.5:5:1.5, 40:55:2.5:2.5, 30:62.5:5:2.5, 30:57.5:10:2.5, 48.5:47.5:1.5:2.5, 48.5:46.5:2.5:2.5, 48.5:45.5:2.5:3.5, 48.5:46.5:1.5:3.5, 50:42.5:5:2.5 or 50:38.5:10:1.5;

alternatively: 40:48.5:10:1.5, 40:53.5:5:1.5, 30:63.5:5:1.5, 40:55:2.5:2.5, 30:62.5:5:2.5, 30:57.5:10:2.5, 48.5:47.5:1.5:2.5, 48.5:46.5:2.5:2.5, 48.5:45.5:2.5:3.5, 48.5:46.5:1.5:3.5, 50:42.5:5:2.5 or 50:38.5:10:1.5;

alternatively: 40:48.5:10:1.5, 40:53.5:5:1.5, 40:55:2.5:2.5, 30:57.5:10:2.5, 48.5:47.5:1.5:2.5, 48.5:46.5:2.5:2.5, 48.5:45.5:2.5:3.5 or 48.5:46.5:1.5:3.5;

alternatively: 48.5:47.5:1.5:2.5, 48.5:46.5:2.5:2.5, 48.5:45.5:2.5:3.5 or 48.5:46.5:1.5:3.5; alternatively: 48.5:45.5:2.5:3.5 or 48.5:46.5:1.5:3.5.

Technical solution 54: In a more specific embodiment, the present disclosure provides a nanoparticle composition as described above, wherein, the N:P molar ratio of N atoms in the ionizable cationic lipids to P atoms in the load molecules is 1-15:1, alternatively 3-12:1, more alternatively 6-12:1.

Technical solution 55: In a more specific embodiment, the present disclosure provides a nanoparticle composition as described above, wherein, the particle size of the particles is 65-160 nm, alternatively 65-150 nm, alternatively 70-150 nm, alternatively 90-130 nm, more alternatively 90-115 nm.

Technical solution 56: In a more specific embodiment, the present disclosure provides a nanoparticle composition as described above, wherein the lipid ingredient comprises the following components in the molar percentages:

Ionizable cationic lipids 27.5 mol %-55 mol %, alternatively 30 mol %-50 mol %;

Structure lipids 35 mol %-68.5 mol %, alternatively 38.5 mol %-66 mol %;

Neutral lipids 1.5 mol %-20 mol %, alternatively 2.5 mol %-15 mol %;

Polymer lipids 1 mol %-5 mol %, alternatively 1.5 mol %-3.5 mol %;

the ionizable cationic lipid is as described in technical solution 23, alternatively is:

26

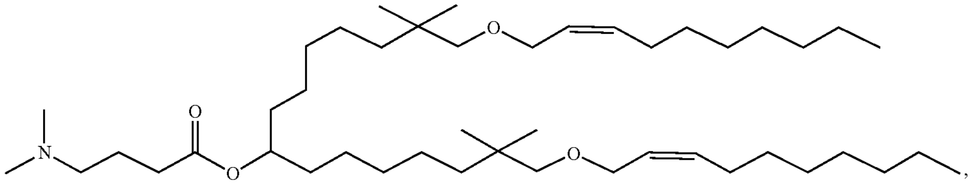

,

27

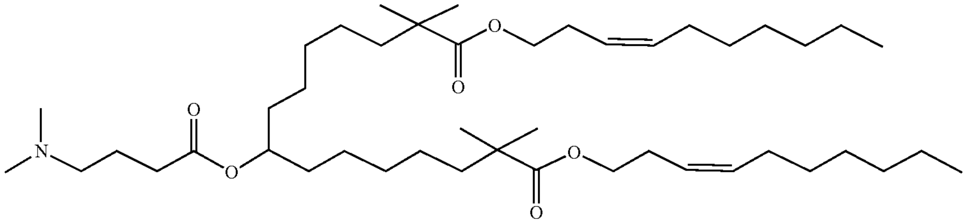

or

98

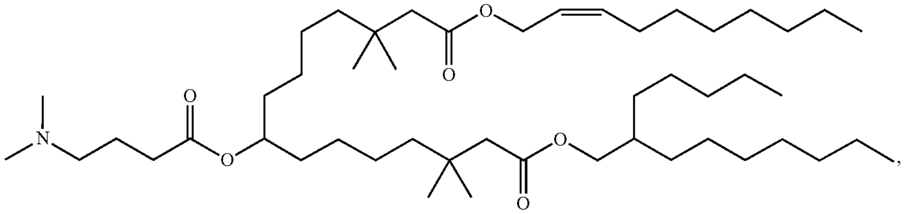

, most alternatively is:

26

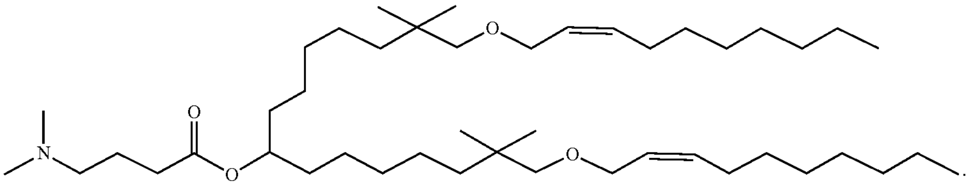

.

Alternatively, the lipid ingredient comprises the following components in the molar percentages:

Ionizable cationic lipids 27.5 mol %-42.5 mol %, alternatively 30 mol %-40 mol %;

Structure lipids 41 mol %-68.5 mol %, alternatively 43.5 mol %-66 mol %;

Neutral lipids 2 mol %-18 mol %, alternatively 2.5 mol %-15 mol %;

Polymer lipids 1 mol %-4 mol %, alternatively 1.5 mol %-3.5 mol %;

the ionizable cationic lipid is as described in technical solution 23, alternatively is:

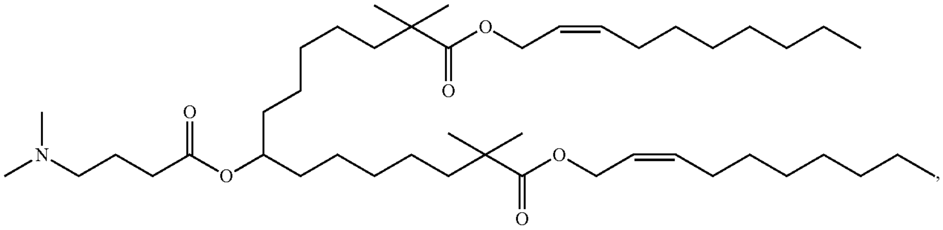

26 or

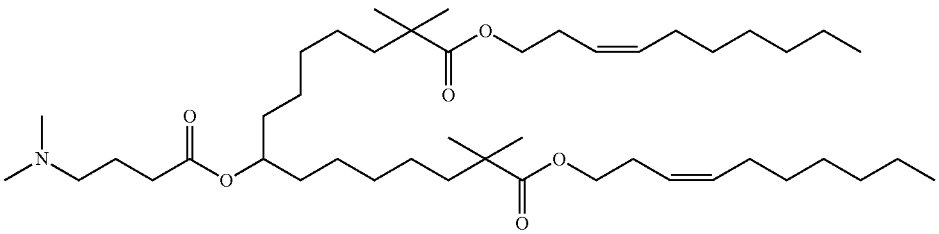

27

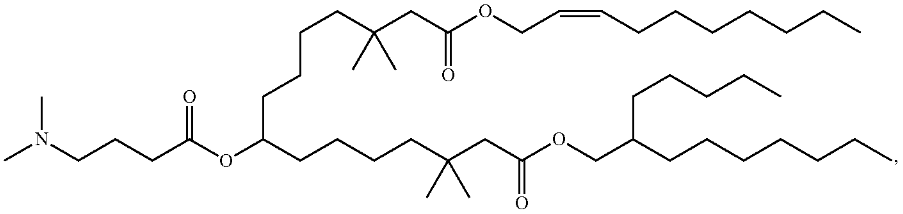

98 most alternatively is:

26

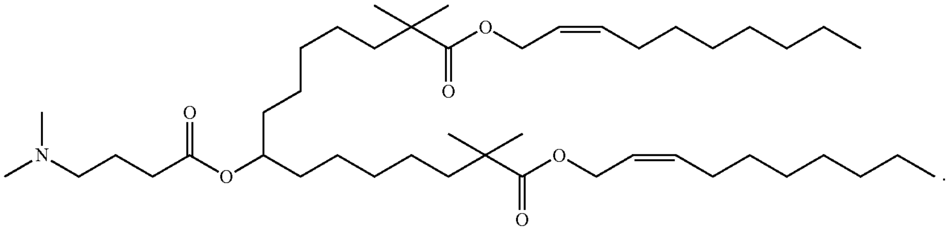

Alternatively, the lipid ingredient comprises the following components in the molar percentages:

Ionizable cationic lipids 37.5 mol %-42.5 mol %, alternatively 40 mol %;

Structure lipids 41 mol %-58.5 mol %, alternatively 43.5 mol %-56 mol %;

Neutral lipids 2 mol %-18 mol %, alternatively 2.5 mol %-15 mol %;

Polymer lipids 1 mol %-4 mol %, alternatively 1.5 mol %-3.5 mol %;

the ionizable cationic lipid is as described in technical solution 23, alternatively is:

26

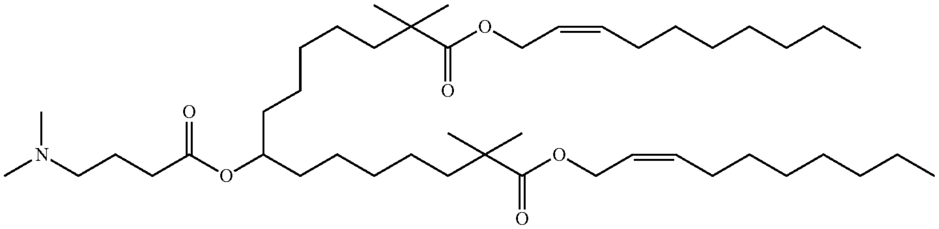
,

27

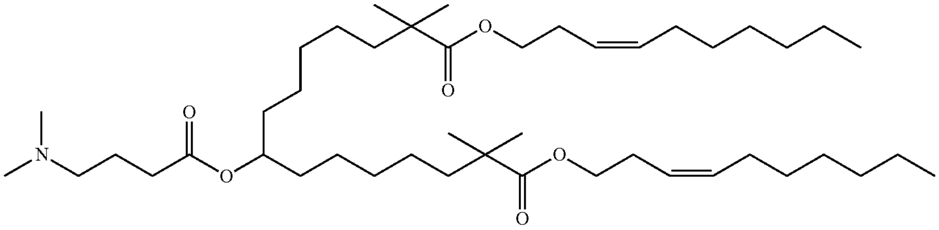
or

98

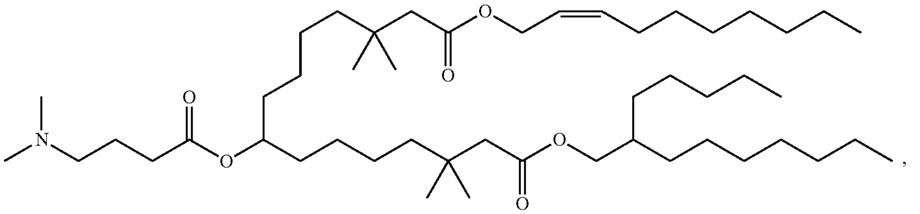
, most alternatively is:

26

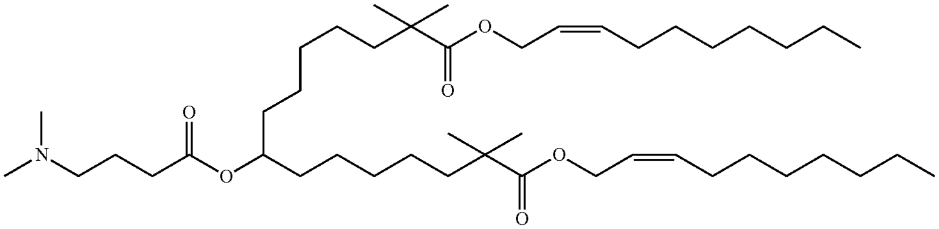
.

Alternatively, the lipid ingredient comprises the following components in the molar percentages:

Ionizable cationic lipids 27.5 mol %-32.5 mol %, alternatively 30 mol %;

Structure lipids 63.5 mol %-68.5 mol %, alternatively 66 mol %;

Neutral lipids 2 mol %-3 mol %, alternatively 2.5 mol %;

Polymer lipids 1 mol %-2 mol %, alternatively 1.5 mol %;

the ionizable cationic lipid is as described in technical solution 23, alternatively is:

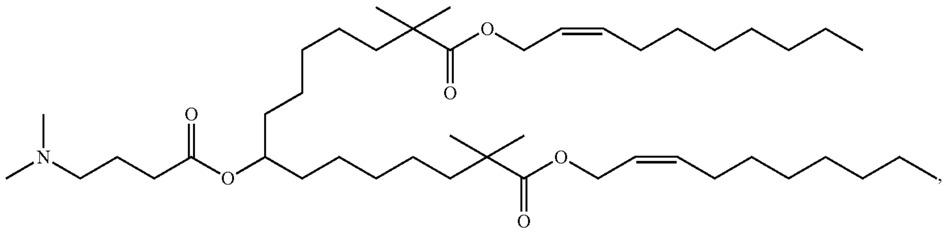
,

26

-continued

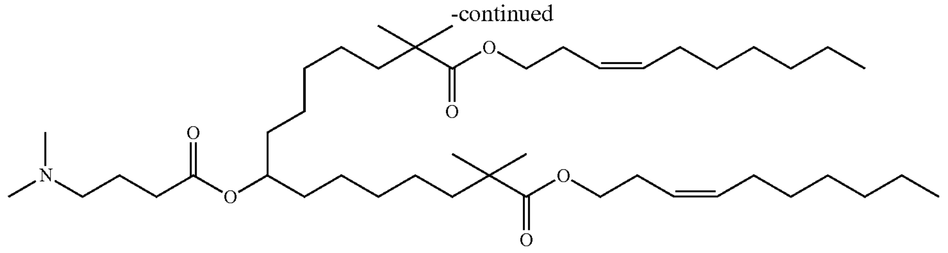

or

27

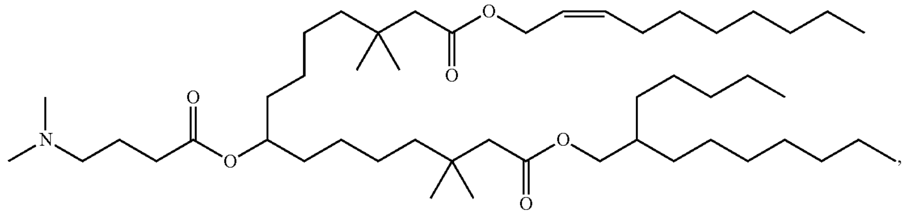

98 most alternatively is:

26

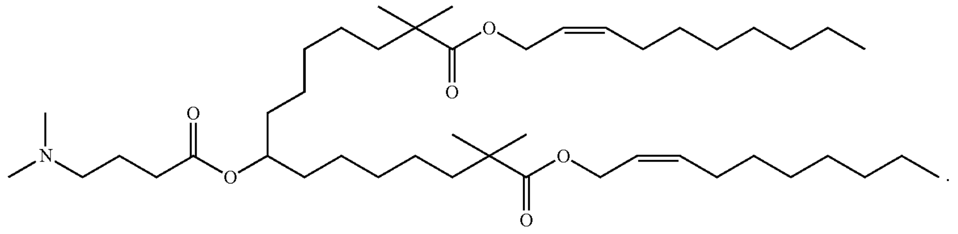

Technical solution 57: In a more specific embodiment, the present disclosure provides a nanoparticle composition as described above, the molar ratio of ionizable cationic lipids: structure lipids:neutral lipids:polymer lipids is: 40:44:12.5:3.5, 40:53.5:5:1.5, 40:43.5:15:1.5, 30:66:2.5:1.5, 40:56:2.5:1.5, 40:51:7.5:1.5 or 50:38.5:10:1.5; alternatively: 40:44:12.5:3.5, 40:53.5:5:1.5, 40:43.5:15:1.5, 30:66:2.5:1.5, 40:56:2.5:1.5 or 40:51:7.5:1.5; alternatively: 30:66:2.5:1.5.

Technical solution 58: In a more specific embodiment, the present disclosure provides a nanoparticle composition as described above, wherein, the N:P molar ratio of N atoms in the ionizable cationic lipids to P atoms in the load molecules is 1-10:1, alternatively 3-7:1, more alternatively 5:1.

Technical solution 59: In a more specific embodiment, the present disclosure provides a nanoparticle composition as described above, wherein, the particle size of the particles is 65-140 nm, alternatively 65-130 nm, alternatively 70-130 nm, more alternatively 65-75 nm.

Technical solution 60: In a more specific embodiment, the present disclosure provides the nanoparticle composition described above, wherein, the neutral lipids are selected from one or more of DSPC, DMPC, DOPC, DPPC, POPC, DOPE, DMPE, POPE and DPPE, alternatively DSPC and/or DOPE.

Technical solution 61: In a more specific embodiment, the present disclosure provides the nanoparticle composition described above, wherein, the structure lipids are selected from one or more of cholesterol, sitosterol, coprosterol, fucosterol, brassicasterol, ergosterol, tomatine, ursolic acid, α-tocopherol, stigmasterol, avenasterol, ergocalciferol and campestero, alternatively cholesterol and/or β-sitosterol, more alternatively cholesterol.

Technical solution 62: In a more specific embodiment, the present disclosure provides the nanoparticle composition described above, wherein, the polymer lipids are polyethylene glycolated lipids.

Optionally, the polyethylene glycolated lipids are selected from one or more of: PEG modified phosphatidylethanolamine, PEG modified phosphatidic acid, PEG modified ceramide, PEG modified dialkyl amine, PEG modified diacylglycerol, and PEG modified dialkylglycerol.

Alternatively, the polyethylene glycolated lipids contain a PEG moiety of about 1000 Da to about 20 kDa, alternatively a PEG moiety of about 1000 Da to about 5000 Da.

Alternatively, the polyethylene glycolated lipids are selected from one or more of DMPE-PEG1000, DPPE-PEG1000, DSPE-PEG1000, DOPE-PEG1000, DMG-PEG2000, Ceramide-PEG2000, DMPE-PEG2000, DPPE-PEG2000, DSPE-PEG2000, Azido-PEG2000, DSPE-PEG2000-Mannose, Ceramide-PEG5000, and DSPE-PEG5000, alternatively DMG-PEG2000.

Technical solution 63: In a more specific embodiment, the present disclosure provides the nanoparticle composition described above, wherein, the load is selected from one or more of therapeutic, prophylactic and diagnostic agents;

alternatively, the therapeutic, prophylactic or diagnostic agent is a nucleic acid;

alternatively, the nucleic acid is selected from one or more of ASO, RNA and DNA;

alternatively, the RNA is selected from one or more of interfering RNA (RNAi), small interfering RNA (siRNA), short hairpin RNA (shRNA), antisense RNA (aRNA), messenger RNA (mRNA), modified messenger RNA (mmRNA), long non-coding RNA (lncRNA), microRNA (miRNA), small activating RNA (saRNA), multimeric coding nucleic acid (MCNA), polymeric coding nucleic acid (PCNA), guide RNA (gRNA), CRISPRRNA (crRNA) and nucleases, alternatively mRNA, more alternatively, modified mRNA.

Technical solution 64: In a more specific embodiment, the present disclosure provides a method for preparing the nanoparticle composition as described above, comprising: mixing the components of the lipid ingredient, and then with a load;

alternatively, mixing each component of the lipid ingredient with a solvent, and then with a solution of the load;

alternatively, the solvent is an organic solvent, alternatively alcohol solvent, alternatively ethanol;

alternatively, the load is a nucleic acid, which is dissolved with a sodium acetate solution, alternatively with a 20-30 mmol/L sodium acetate solution.

Technical solution 65: In a more specific embodiment, the present disclosure provides a method of preparing the nanoparticle composition as described above, further comprising a step of removing impurities; alternatively removing impurities by ultrafiltration; alternatively using a 30 kDa ultrafiltration tube for ultrafiltration.

Technical solution 66: In a more specific embodiment, the present disclosure provides a method of preparing the nanoparticle composition as described above, further comprising a sterilization step; alternatively, using a sterile filter membrane for filtration and sterilization; alternatively, the sterile filter membrane has a pore size of 0.2 μm.

Technical solution 67: In a more specific embodiment, the present disclosure also provides a lipid compound, a pharmaceutically acceptable salt or stereoisomer thereof, the lipid compound having the structure of general formula (I):

(I)

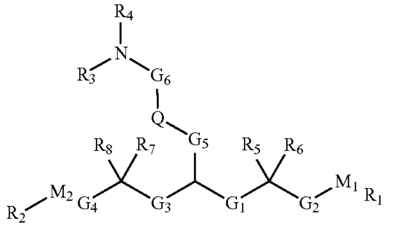

wherein, $G_1$, $G_2$, $G_3$ or $G_4$ is each independently a bond, $C_{1-20}$ alkylene, $C_{2-20}$ alkenylene or $C_{2-20}$ alkynylene;

$G_5$ or $G_6$ is each independently a bond or $C_{1-8}$ alkylene;

$M_1$ or $M_2$ is each independently biodegradable groups;

Q is a bond or biodegradable groups;

$R_1$ or $R_2$ is each independently $C_{4-28}$ alkyl, $C_{4-28}$ alkenyl or $C_{4-28}$ alkynyl;

$R_3$ or $R_4$ is each independently H, alkyl, alkenyl, alkynyl, cycloalkyl, heterocyclyl, aryl or heteroaryl;

or, $R_3$ and $R_4$ are taken together with the N atom to which they are attached to form 3- to 14-membered heterocyclyl;

$R_5$, $R_6$, $R_7$ or $R_8$ is each independently $C_{1-8}$ alkyl;

each of the alkyl, alkenyl, alkynyl, alkylene, alkenylene, alkynylene, cycloalkyl, heterocyclyl, aryl or heteroaryl is each independently and optionally further substituted.

Further, the lipid compound has the structure of general formula (I).

(I)

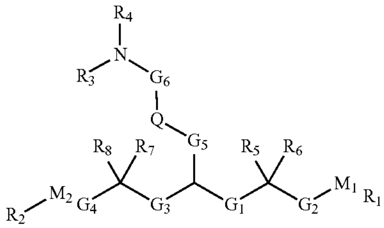

wherein, $G_1$, $G_2$, $G_3$ or $G_4$ is each independently a bond, $C_{1-20}$ alkylene, $C_{2-20}$ alkenylene or $C_{2-20}$ alkynylene; the $C_{1-20}$ alkylene, $C_{2-20}$ alkenylene or $C_{2-20}$ alkynylene is optionally substituted with one or more substituents selected from H, OH, alkyl, hydroxyalkyl, alkoxy, amino, alkylamino, and dialkylamino;

$G_5$ or $G_6$ is each independently a bond or $C_{1-6}$ alkylene; the $C_{1-6}$ alkylene is optionally substituted with one or more substituents selected from H, OH, alkyl, hydroxyalkyl, alkoxy, amino, alkylamino, and dialkylamino;

$M_1$ or $M_2$ is each independently selected from —OC(O)—, —C(O)O—, —SC(O)—, —C(O)S—, —O—, —OC(O)O—, —SC(O)O—, —OC(O)S—, —$NR_a$—, —C(O)$NR_a$—, —$NR_a$C(O)—, —$NR_a$C(O)O—, —OC(O)$NR_a$—, —$NR_a$C(O)S—, —SC(O)$NR_a$—, —$NR_a$C(O)$NR_a$—, —C(O)—, —OC(S)—, —C(S)O—, —OC(S)$NR_a$—, —$NR_a$C(S)O—, —S—S— and —$S(O)_m$—;

Q is selected from a bond, —OC(O)—, —C(O)O—, —SC(O)—, —C(O)S—, —O—, —OC(O)O—, —SC(O)O—, —OC(O)S—, —$NR_b$—, —C(O)$NR_b$—, —$NR_b$C(O)—, —$NR_b$C(O)O—, —OC(O)$NR_b$—, —$NR_b$C(O)S—, —SC(O)$NR_b$—, —$NR_b$C(O)$NR_b$—, —C(O)—, —OC(S)—, —C(S)O—, —OC(S)$NR_b$—, —$NR_a$C(S)O—, —S—S—, —$S(O)_n$—, phenylene and pyridylidene; the phenylene or pyridylidene group is optionally substituted with one or more substituents selected from H, hydroxy, halogen, cyano, alkyl, hydroxyalkyl, haloalkyl and alkoxy;

$R_1$ or $R_2$ is each independently $C_{4-28}$ alkyl, $C_{4-28}$ alkenyl or $C_{4-28}$ alkynyl; the $C_{4-28}$ alkyl, $C_{4-28}$ alkenyl or $C_{4-28}$ alkynyl is optionally substituted with one or more substituents selected from H, OH, alkyl, hydroxyalkyl, alkoxy, amino, alkylamino, and dialkylamino;

$R_3$ or $R_4$ is each independently H or $C_{1-20}$ alkyl; the $C_{1-20}$ alkyl is optionally substituted with one or more substituents selected from H, OH, alkyl, hydroxyalkyl, alkoxy, amino, alkylamino, and dialkylamino;

or, $R_3$ and $R_4$ are taken together with the N atom to which they are attached to form 3- to 14-membered heterocyclyl; the 3- to 14-membered heterocyclyl is optionally further substituted with a substituent selected from halogen, cyano, OH, alkyl, hydroxyalkyl, haloalkyl, alkoxy, amino, alkylamino, and dialkylamino;

$R_5$, $R_6$, $R_7$ or $R_8$ is each independently $C_{1-8}$ alkyl;

each of $R_a$ or $R_b$ is each independently H, $C_{1-28}$ alkyl or $C_{3-14}$ cycloalkyl; the $C_{1-28}$ alkyl or $C_{3-14}$ cycloalkyl is optionally substituted with one or more substituents selected from H, OH, alkyl, hydroxyalkyl, alkoxy, amino, alkylamino, and dialkylamino;

m or n is each independently 0, 1 or 2.

Further, the $G_1$ and $G_3$ are both $C_{2-8}$ alkylene, and $G_2$ and $G_4$ are both a bond; alternatively $G_1$ and $G_3$ are both $C_5$ alkylene, and $G_2$ and $G_4$ are both a bond.

Further, the $G_5$ is a bond.

Further, the $G_6$ is a bond or $C_{1-6}$ alkylene.

Further, the $M_1$ or $M_2$ is each independently —C(O)O—, —OC(O)—, —C(O)S—, —SC(O)—, —$NR_a$C(O)— or —C(O)$NR_a$—, the $R_a$ is H or $C_{4-24}$ alkyl; alternatively $M_1$ or $M_2$ is each independently —C(O)O— or —C(O)S—.

Further, the Q is a bond, —O—, —OC(O)—, —C(O)O—, —OC(O)O— or —OC(O)NH—, —NHC(O)O—, —NHC(O)NH—, —OC(O)S—, or —SC(O)O—; alternatively Q is —C(O)O—.

Further, the $R_1$ or $R_2$ is each independently $C_{4-28}$ alkyl, $C_{4-28}$ alkenyl or $C_{4-28}$ alkynyl, the $C_{4-28}$ alkyl, $C_{4-28}$ alkenyl or $C_{4-28}$ alkynyl is optionally substituted with one or more substituents H, hydroxyl or $C_{2-14}$ alkyl; alternatively $R_1$ or $R_2$ is each independently $C_{4-28}$ alkyl, $C_{4-28}$ alkenyl or $C_{4-28}$ alkynyl.

Further, the $R_3$ or $R_4$ is each independently $C_{1-6}$ alkyl or hydroxyethyl; alternatively $R_3$ or $R_4$ are both methyl.

Further, the $R_5$, $R_6$, $R_7$ or $R_8$ is each independently $C_{1-3}$ alkyl; alternatively $R_5$, $R_6$, $R_7$ or $R_8$ are both methyl.

Further, the lipid compound is the compounds of general formula (II) or general formula (III):

(II)

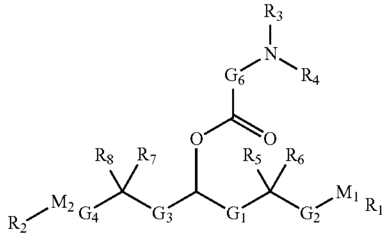

(III)

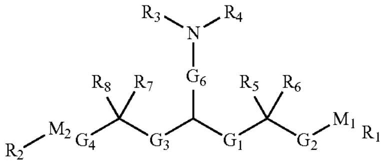

wherein the substituents are defined as described in general formula (I). PGP

Technical solution 68: The present disclosure provides a lipid compound, a pharmaceutically acceptable salt or stereoisomer thereof, wherein the lipid compound is selected from the following compounds:

1

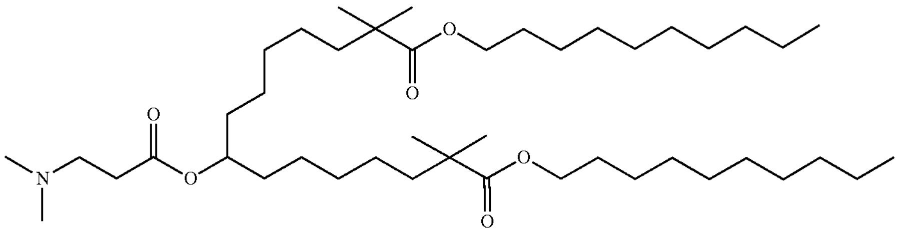

2

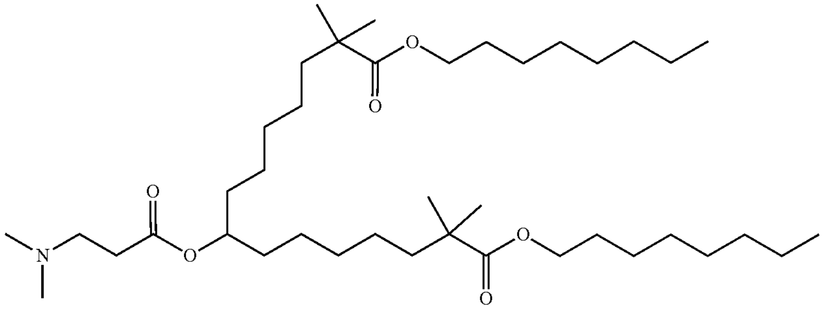

3

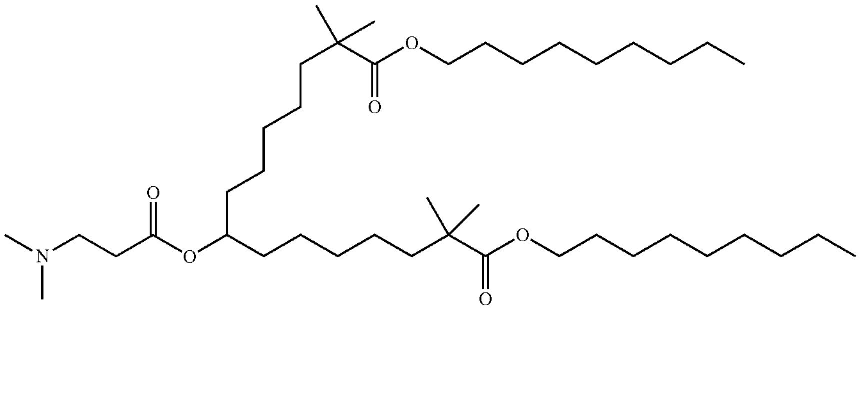

-continued
4
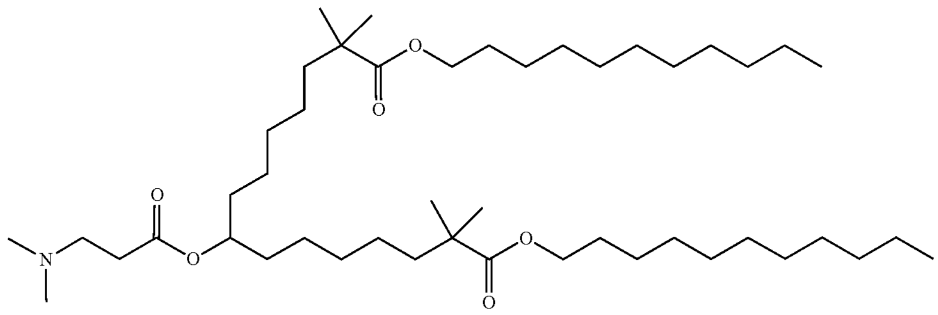
5
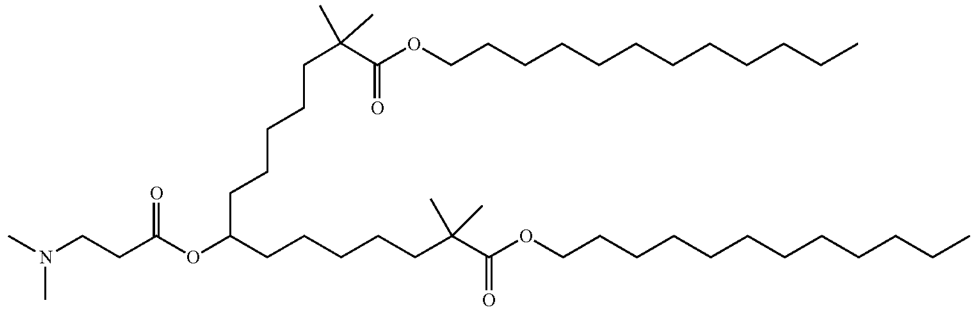
6
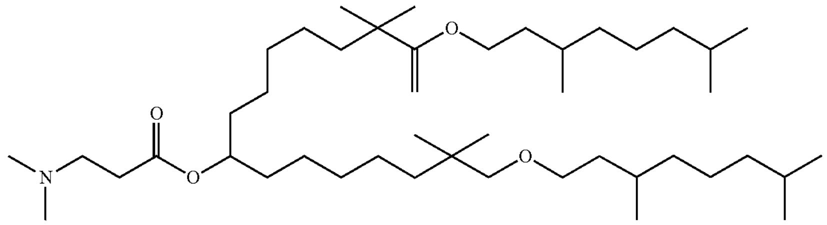
7
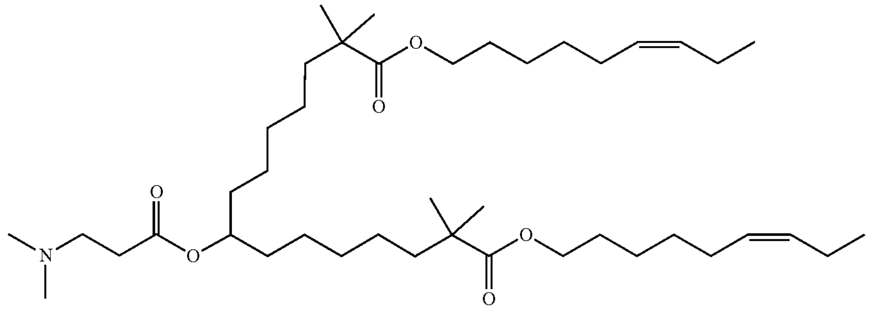
8
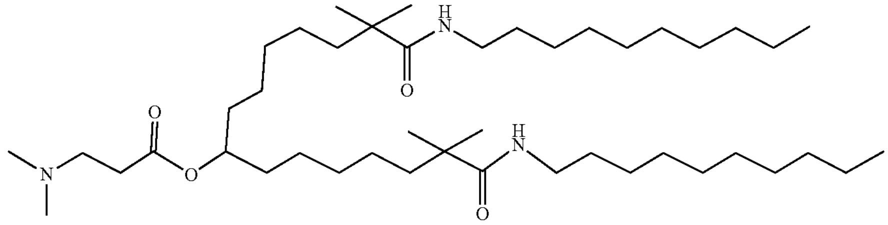

-continued
9
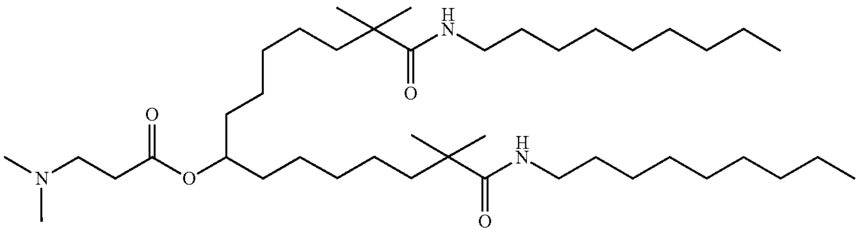
10
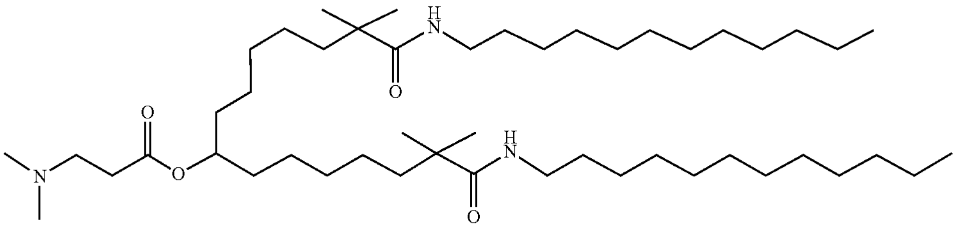
11
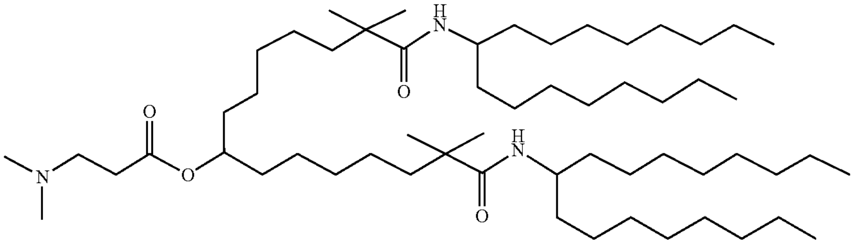
12
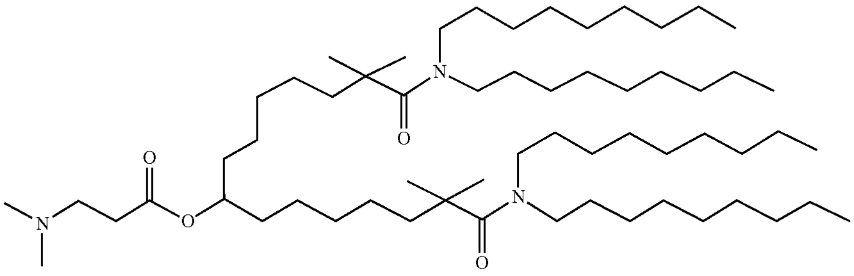
13
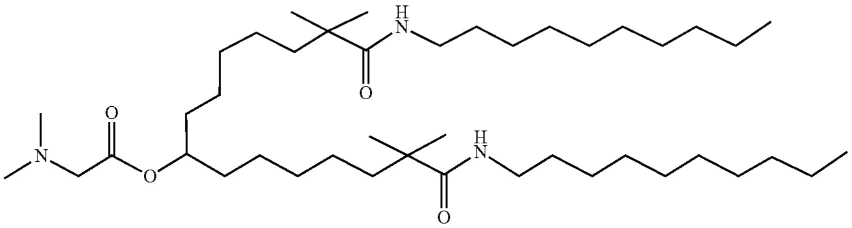
14
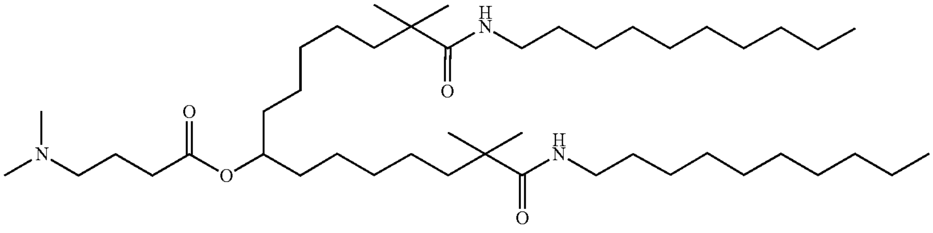

-continued
15
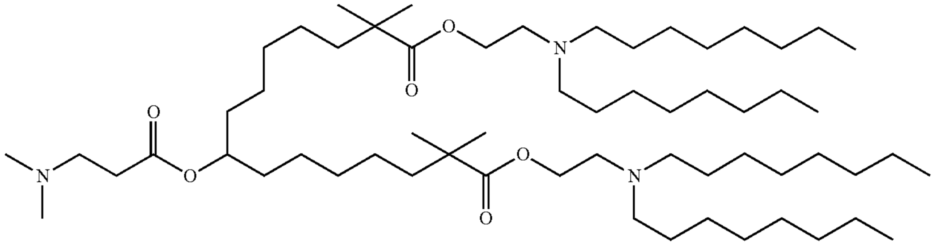
16
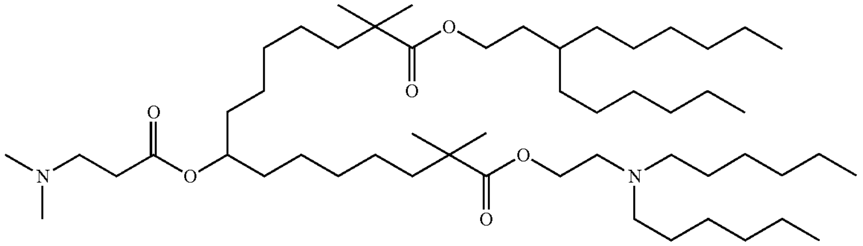
17
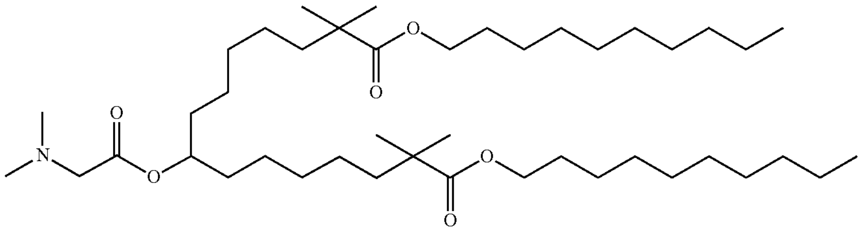
18
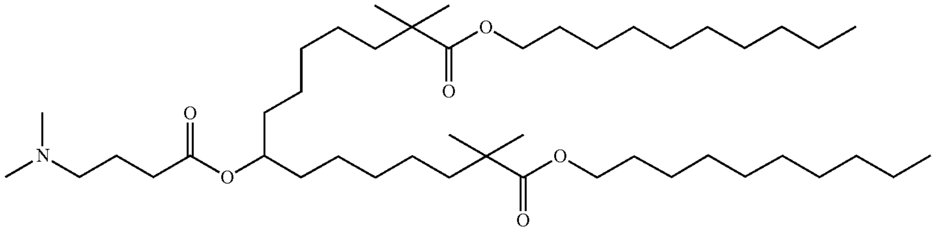
19
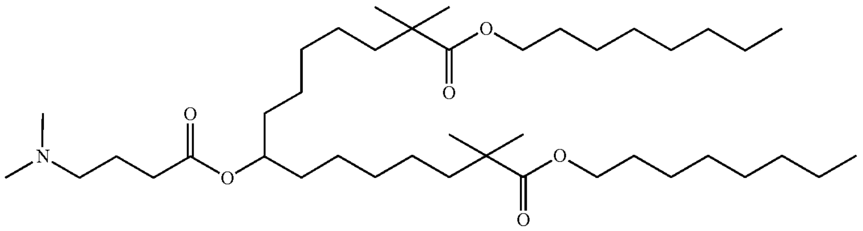
20
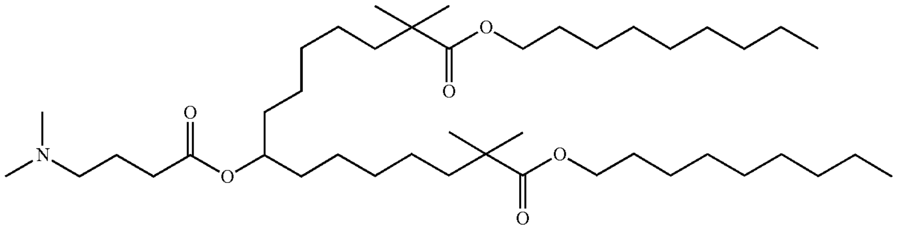

-continued
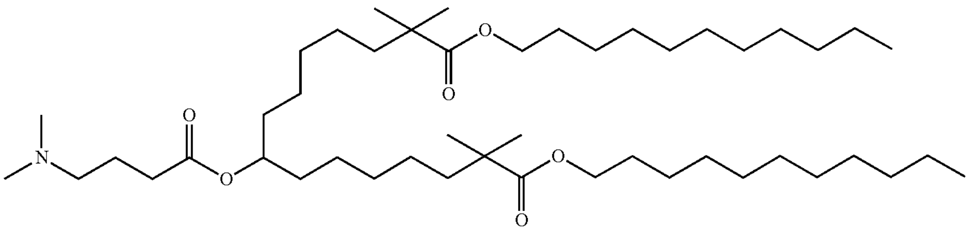
21
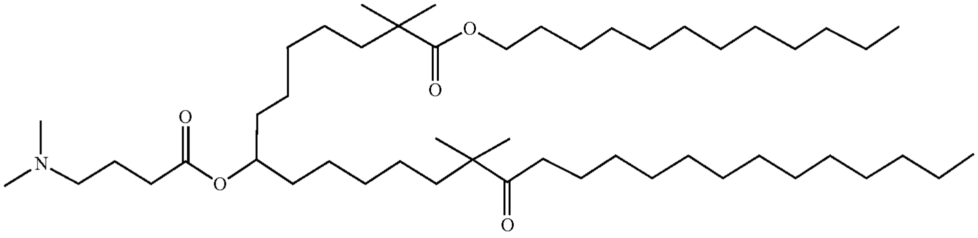
22
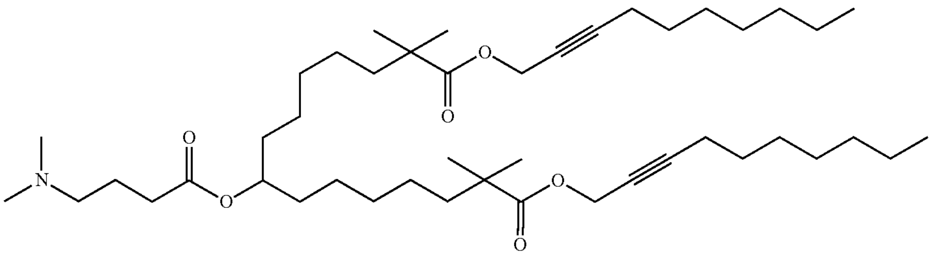
23
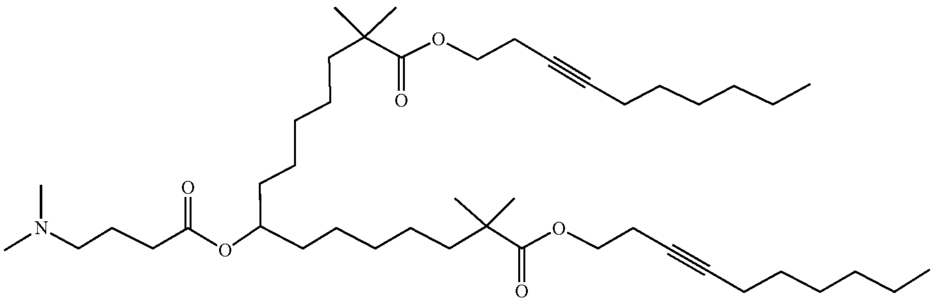
24
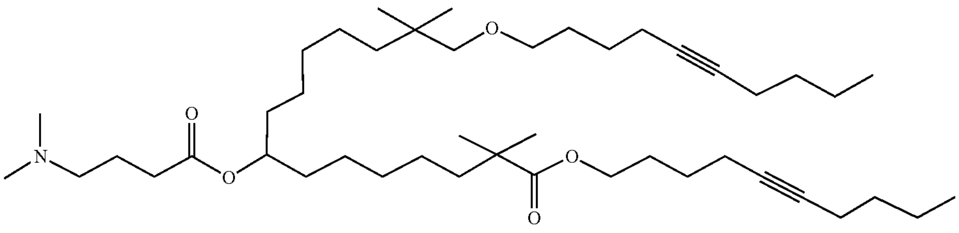
25
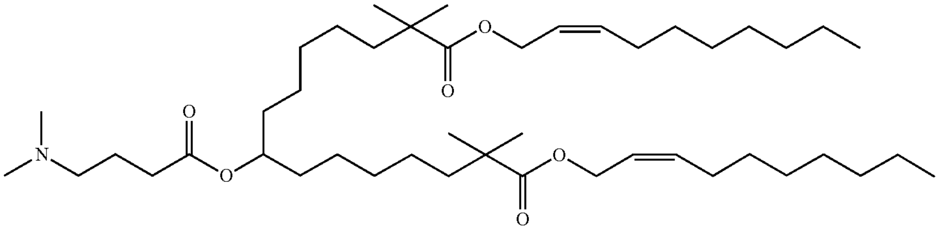
26

-continued
27
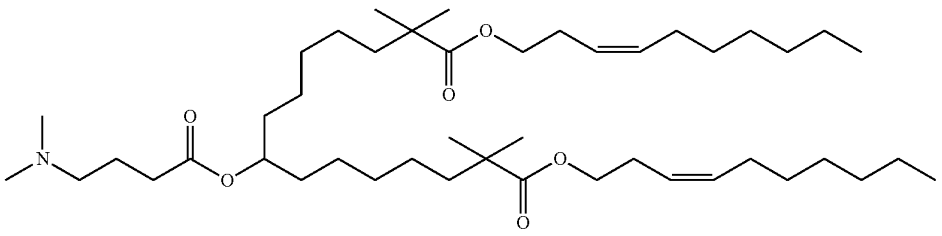
28
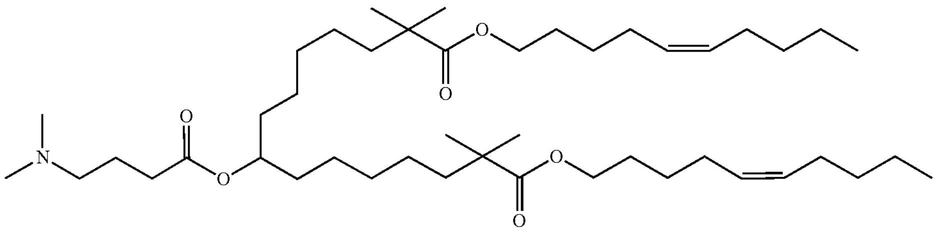
30
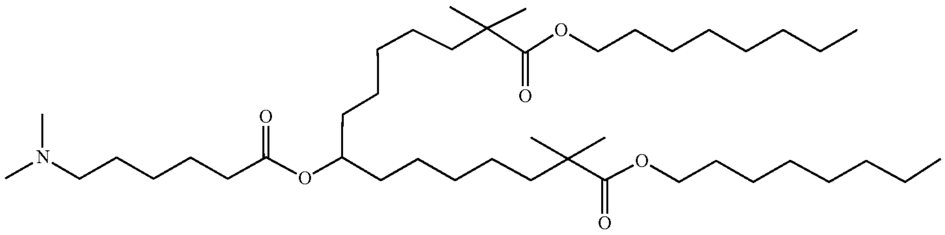
32
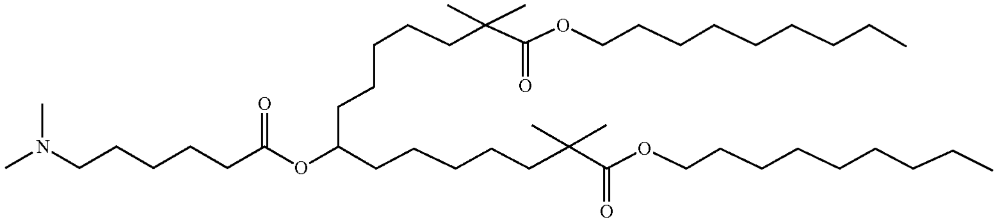
33
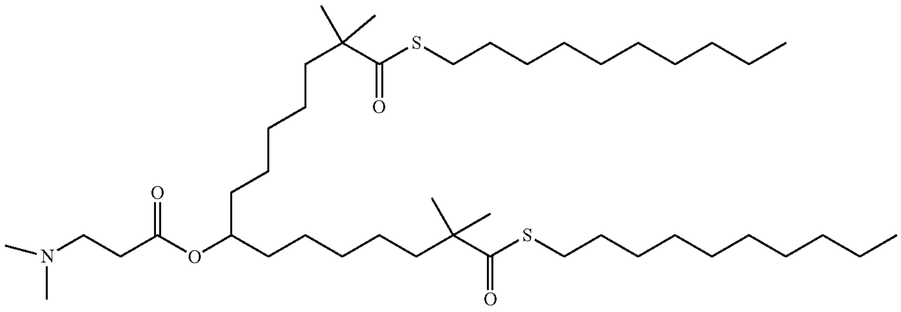
34
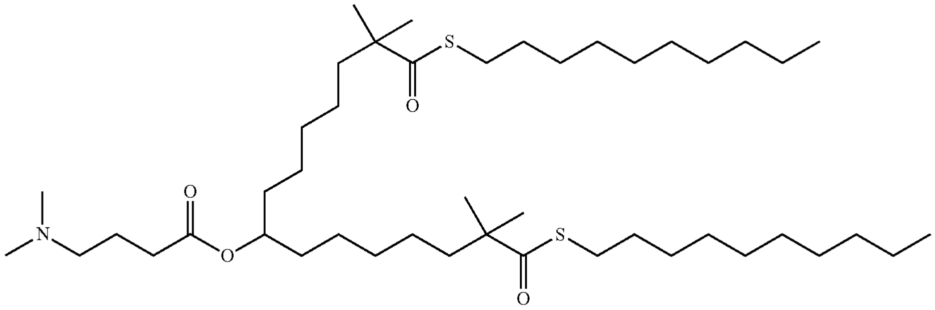

-continued
35
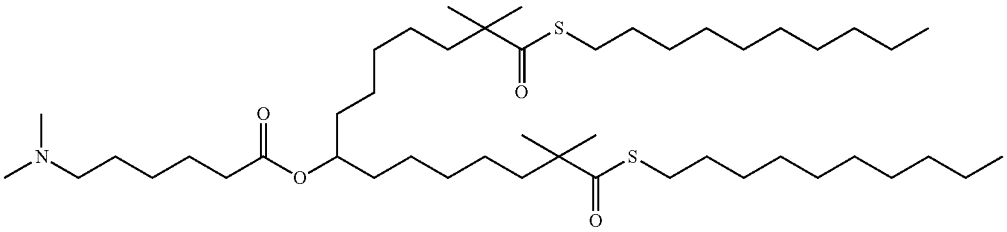
37
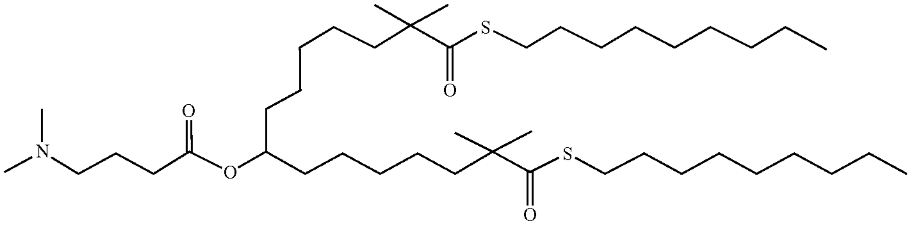
39
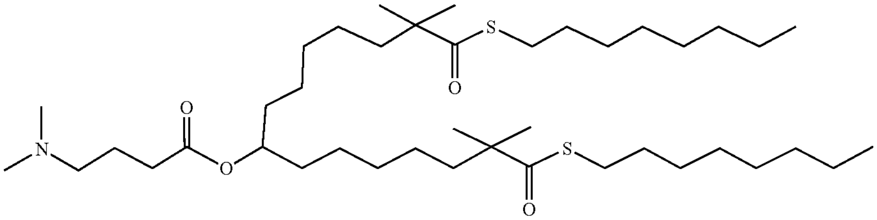
40
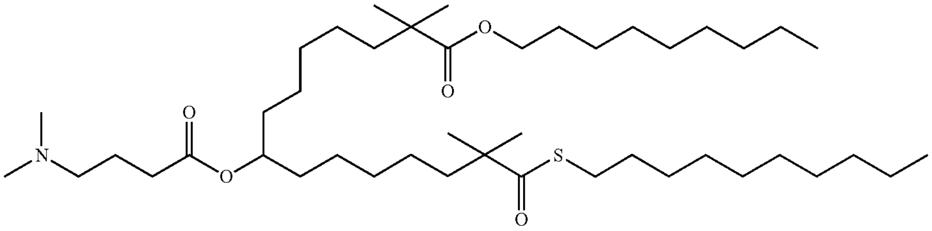
41
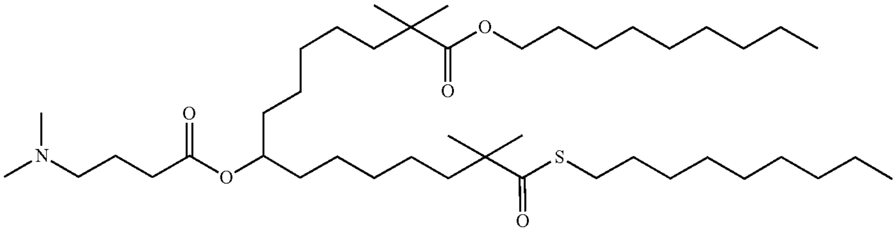
42
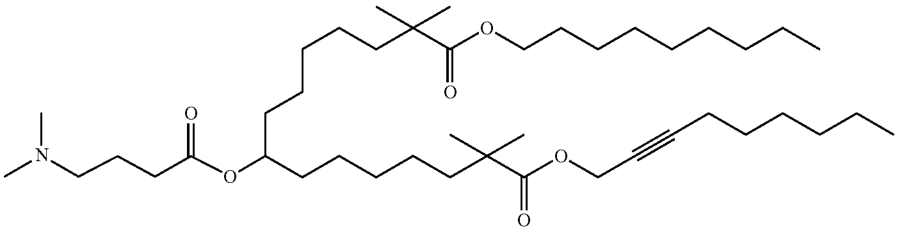

-continued
43
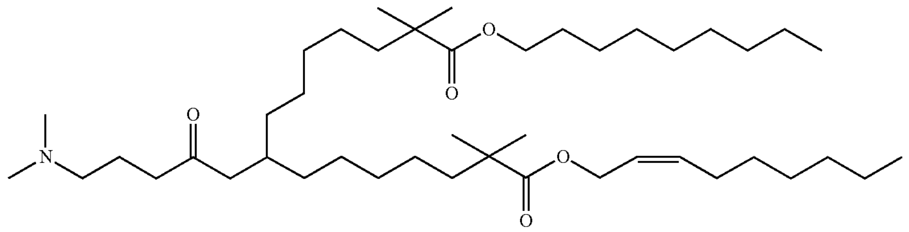
44
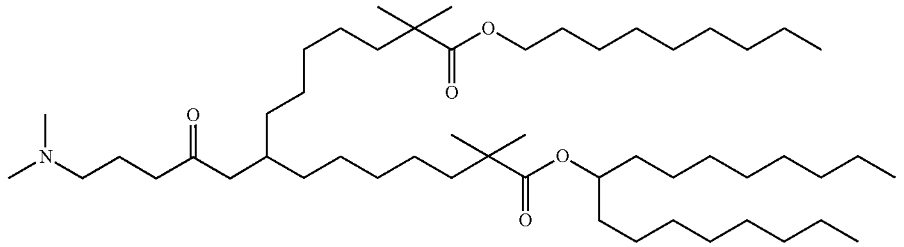
45
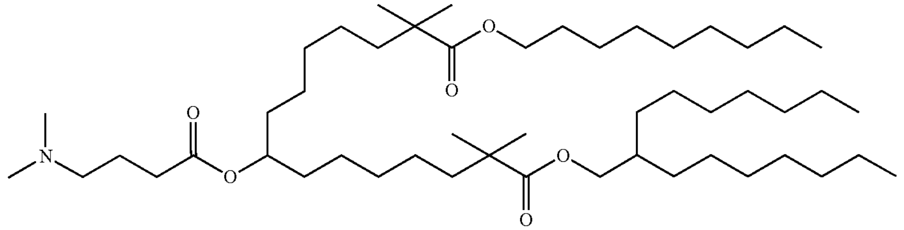
46
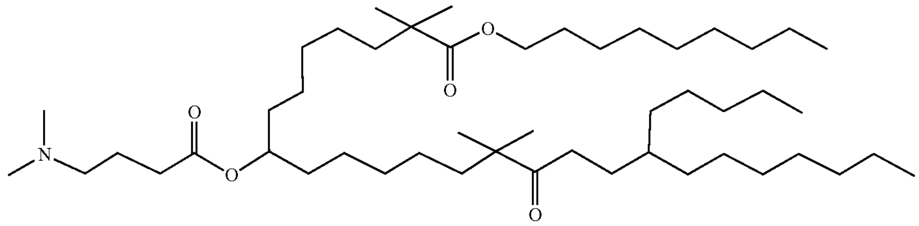
47
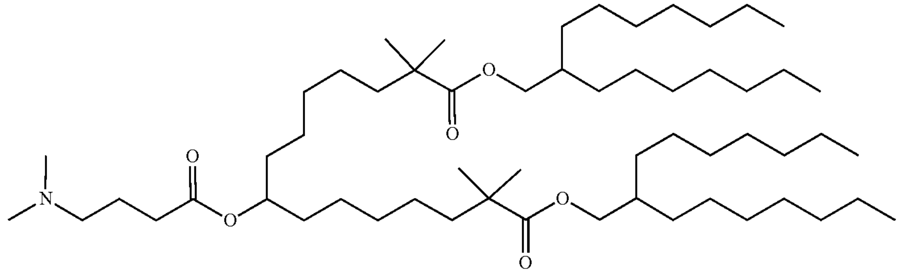
48
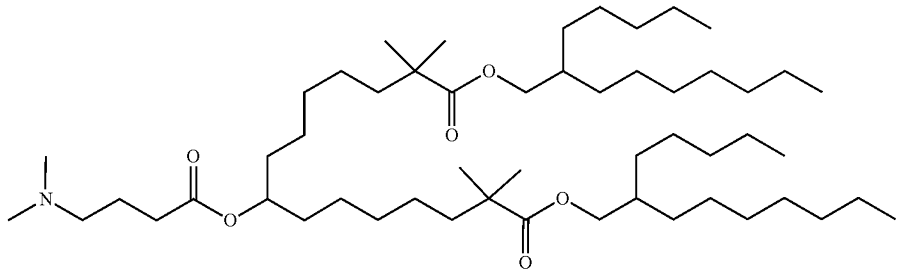

-continued
49
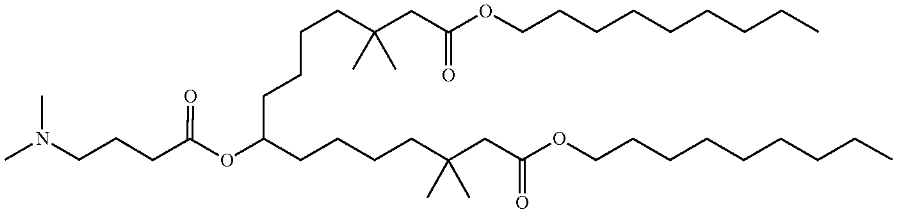
50
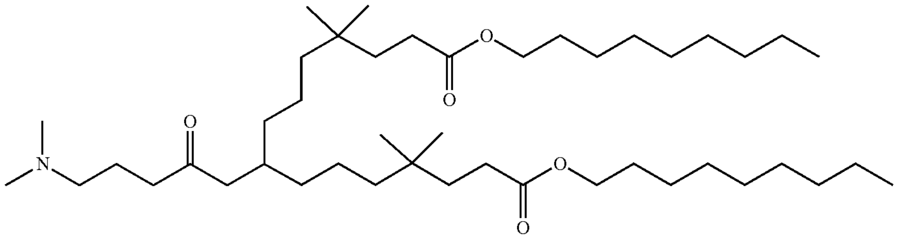
51
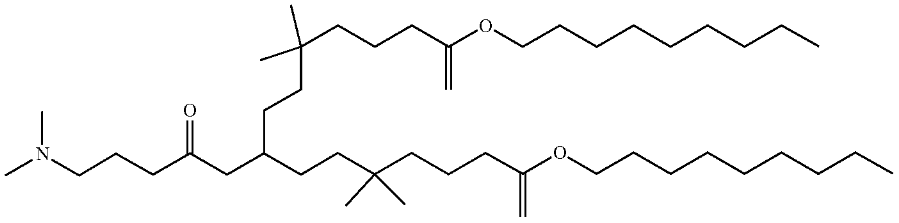
52
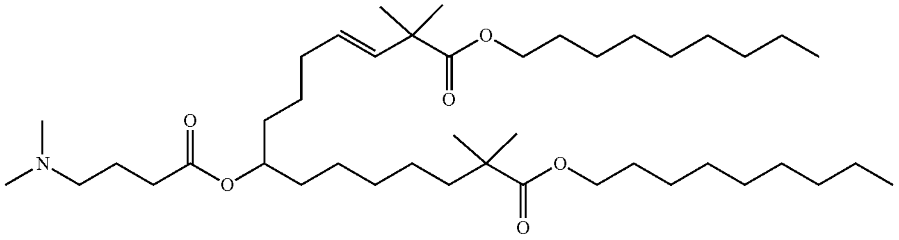
53
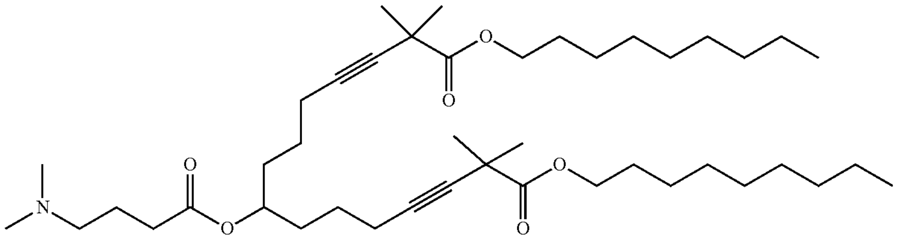
54
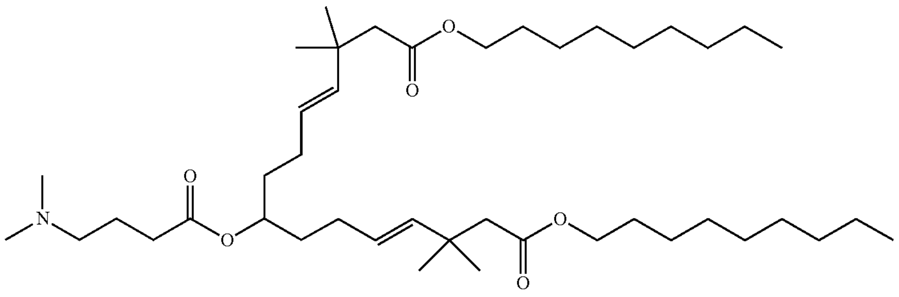

-continued
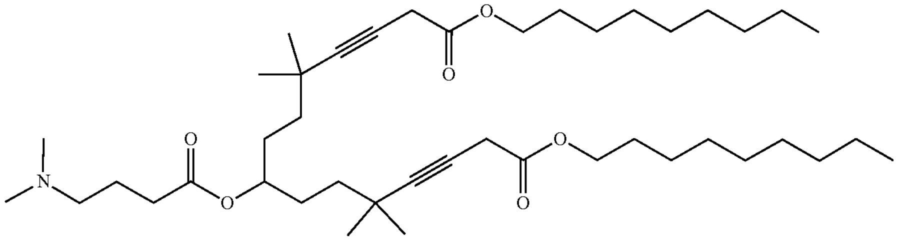
55
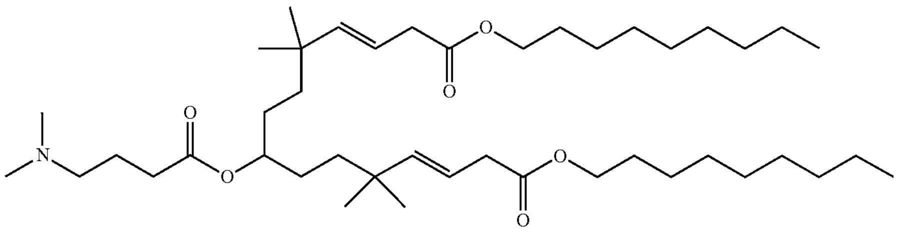
56
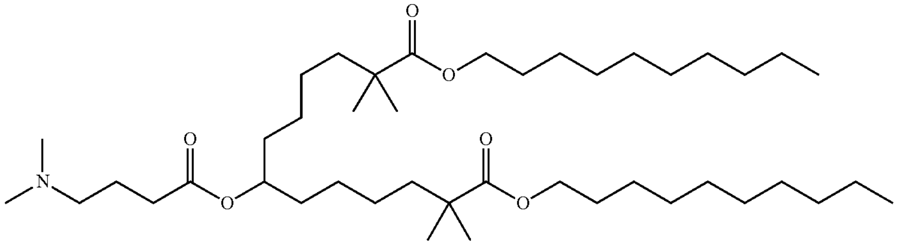
57
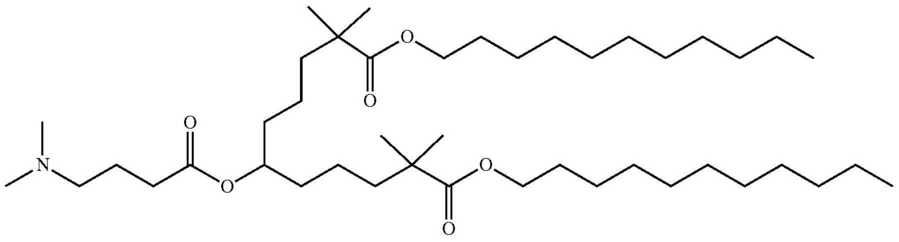
58
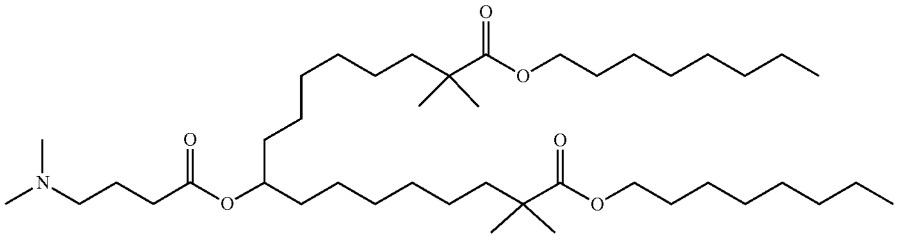
59
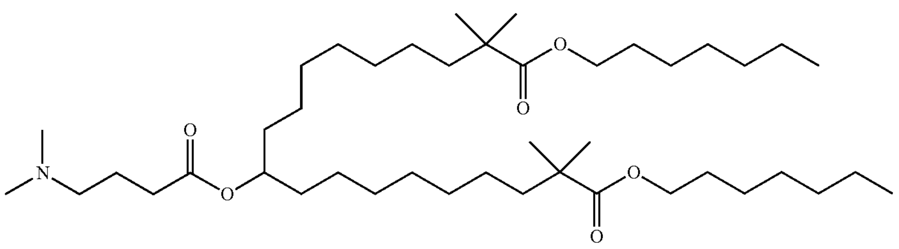
60

-continued
61
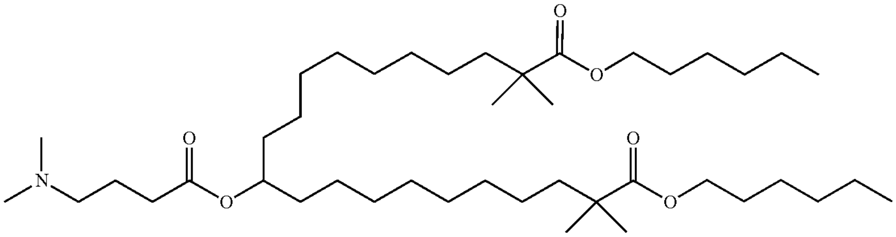
62
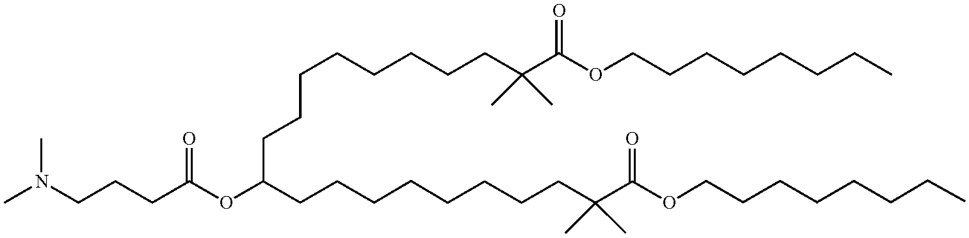
63
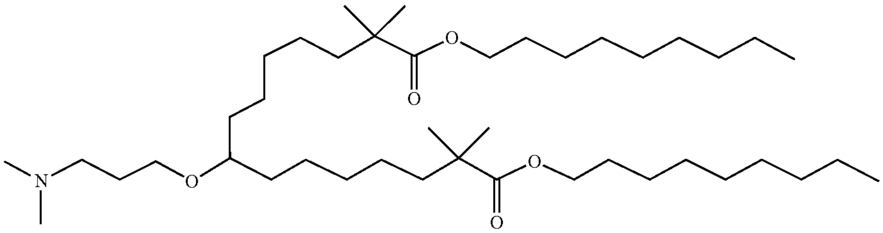
64
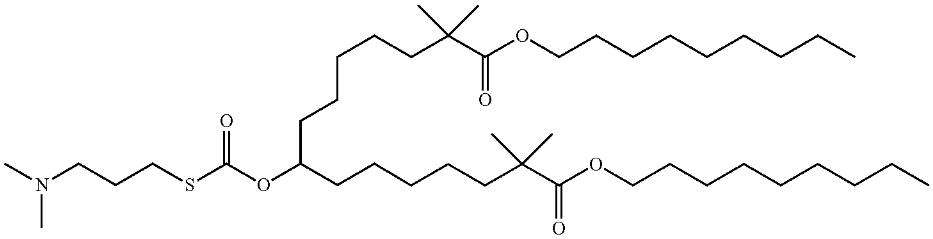
65
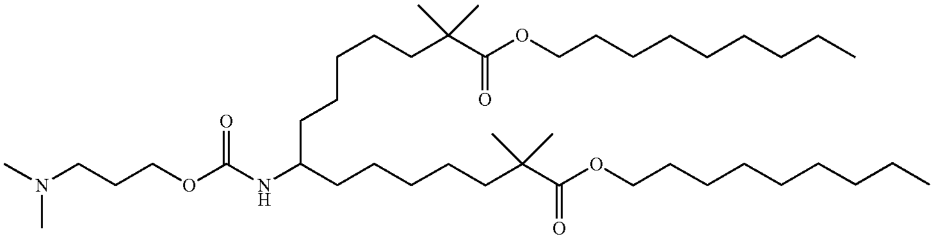
66
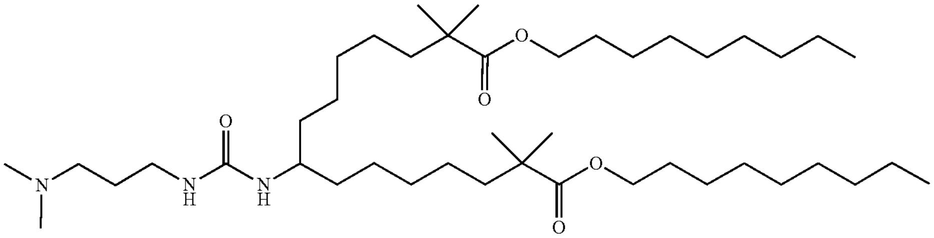

-continued
67
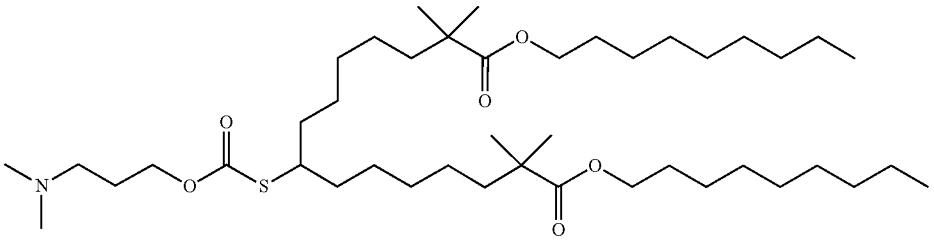
68
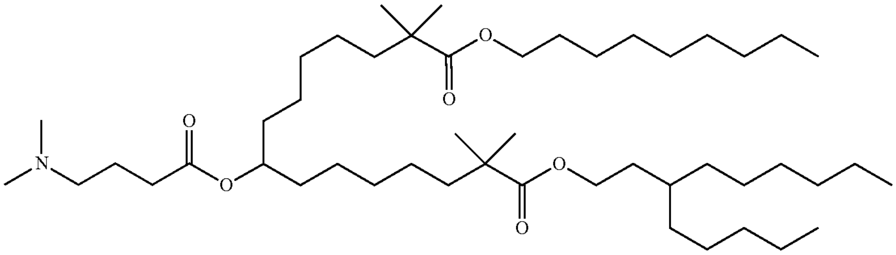
69
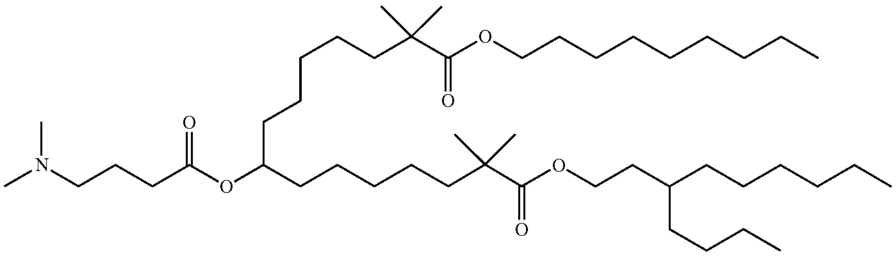
70
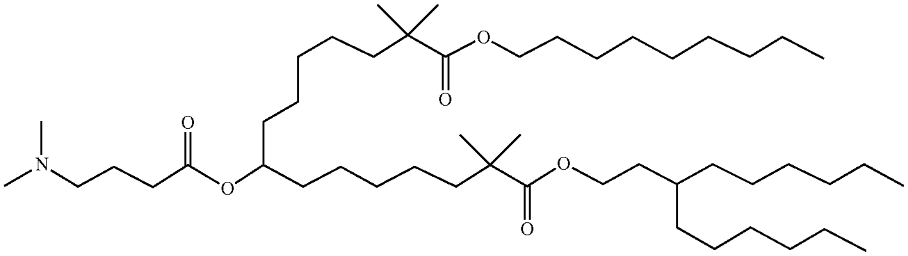
71
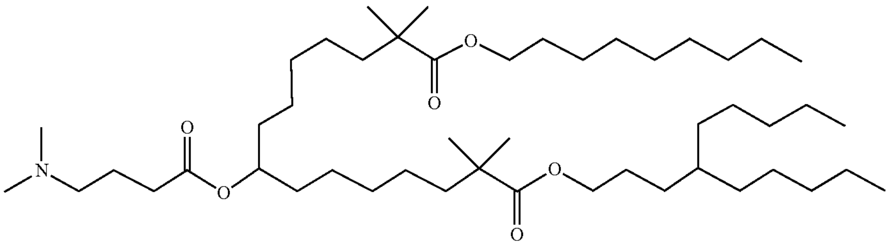
72
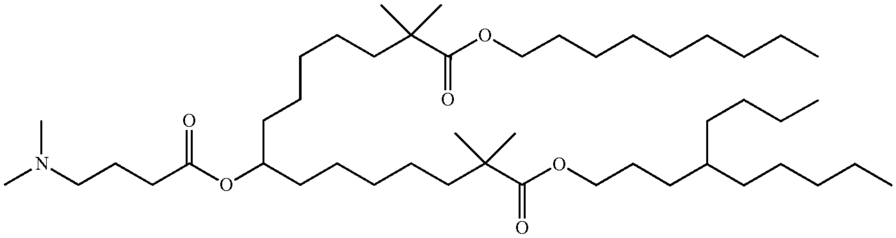

-continued
73
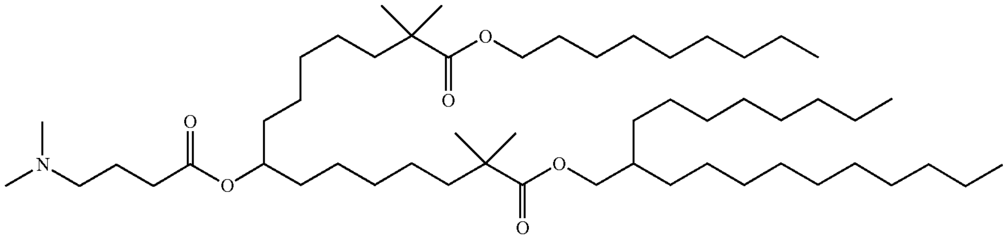
74
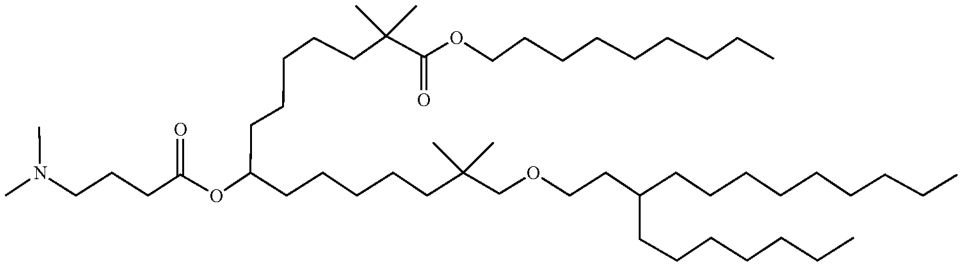
75
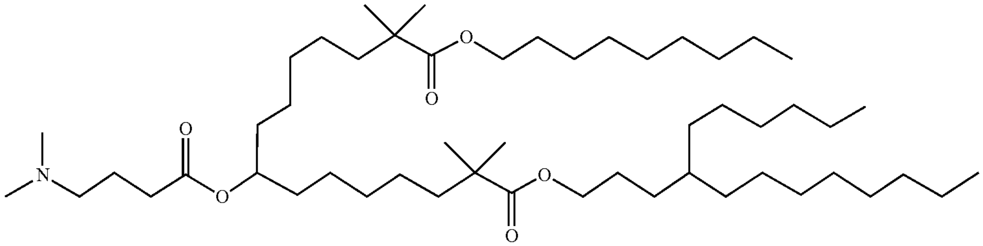
77
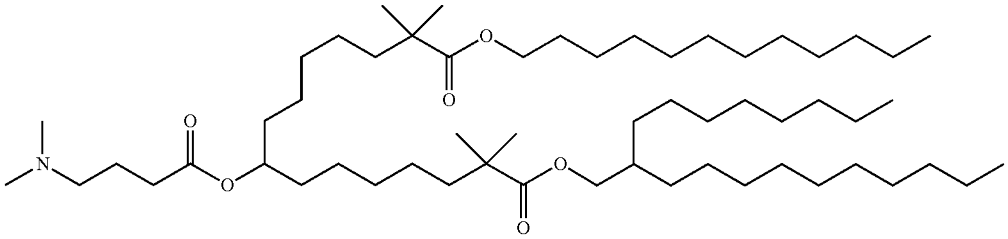
78
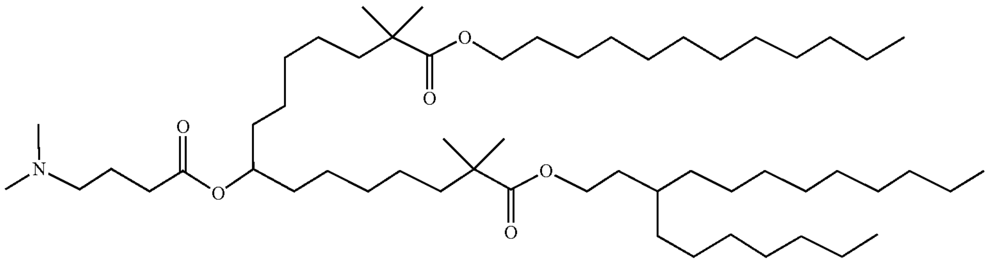
79
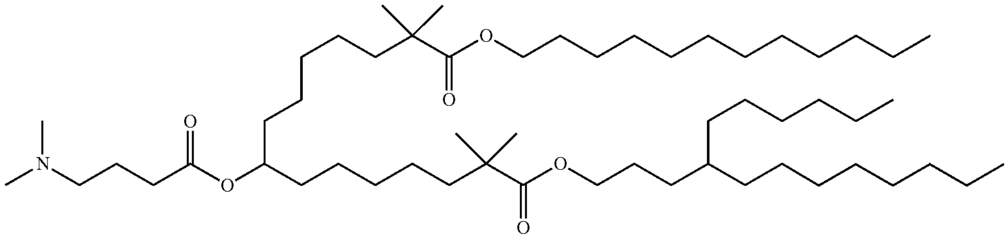

-continued
80
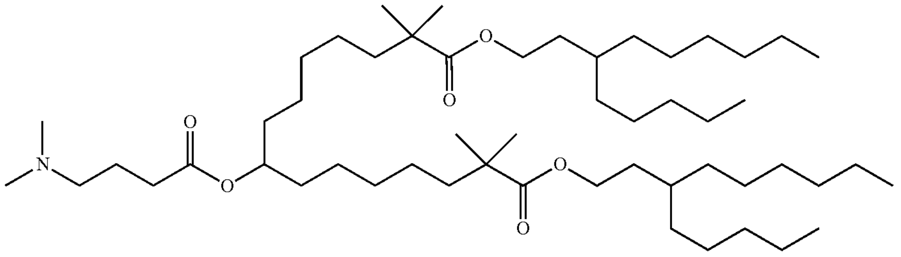
81
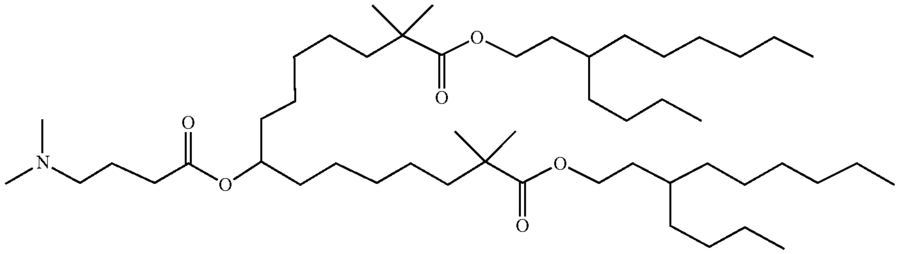
82
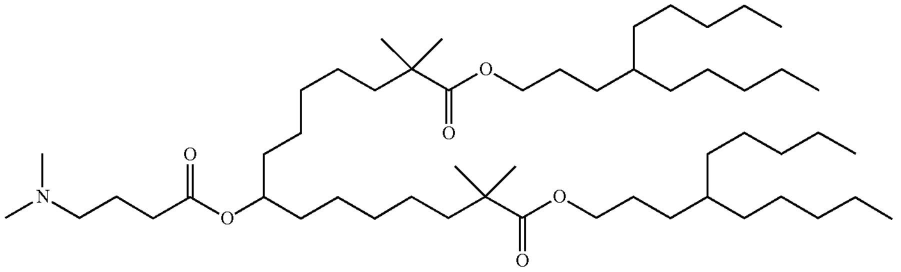
83
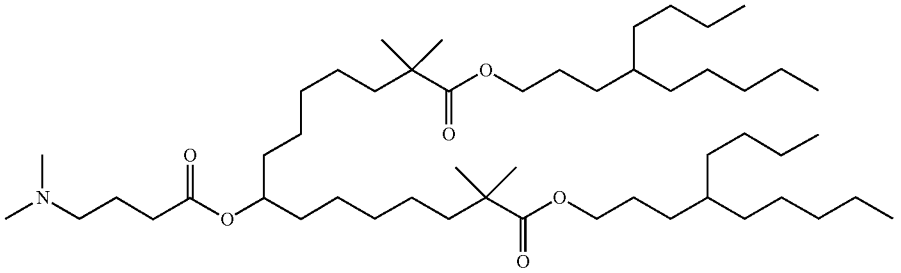
84
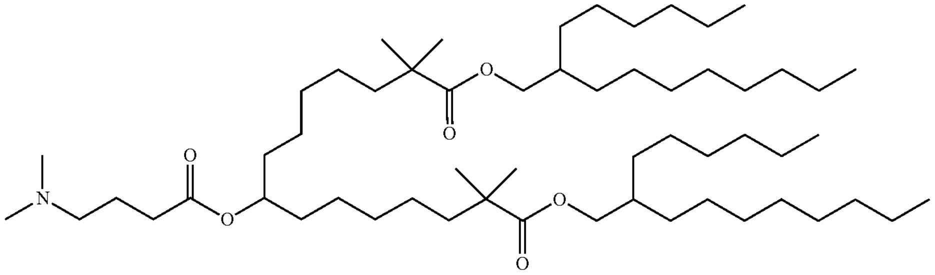
85
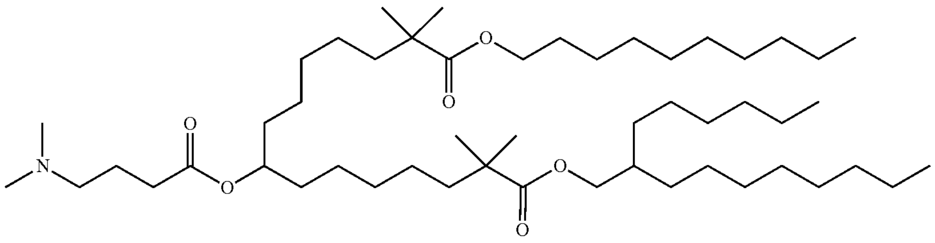

-continued
86
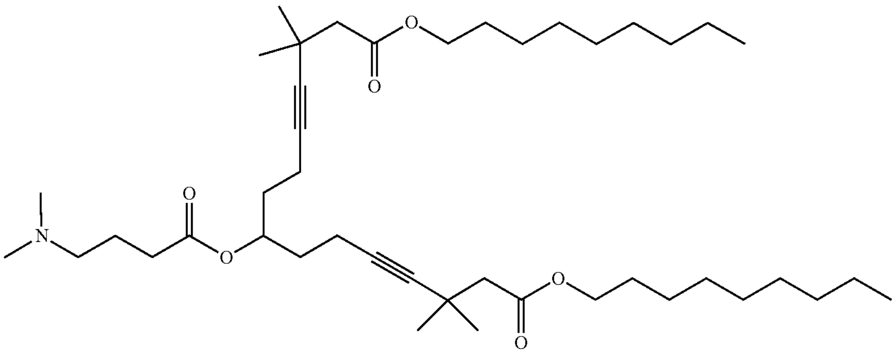
87
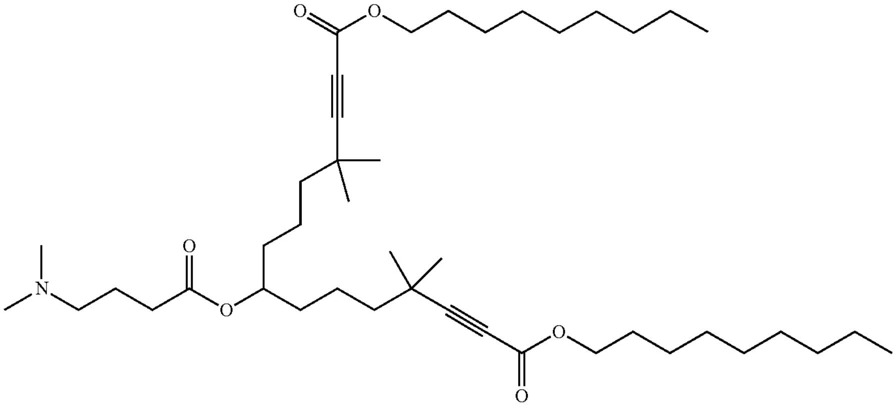
88
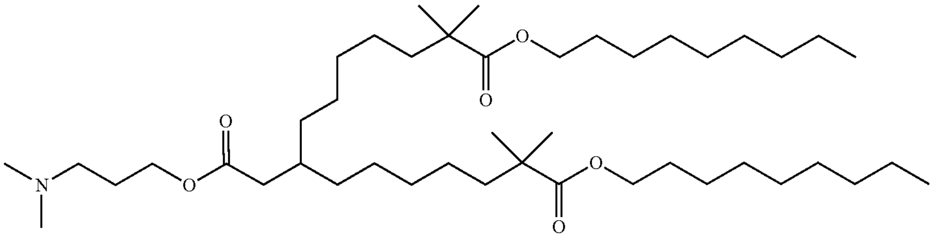
89
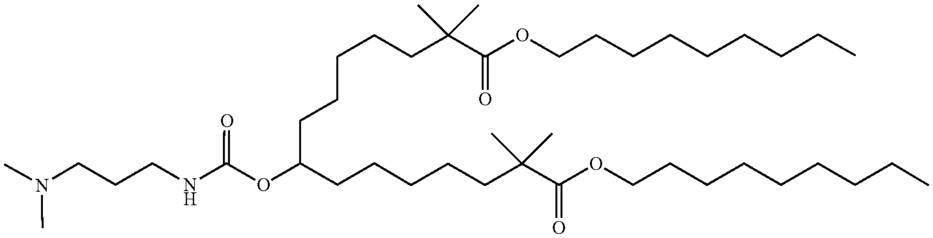
90
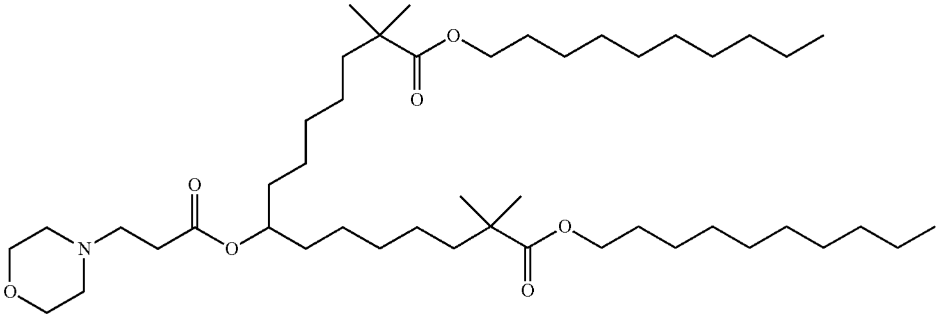

-continued
91
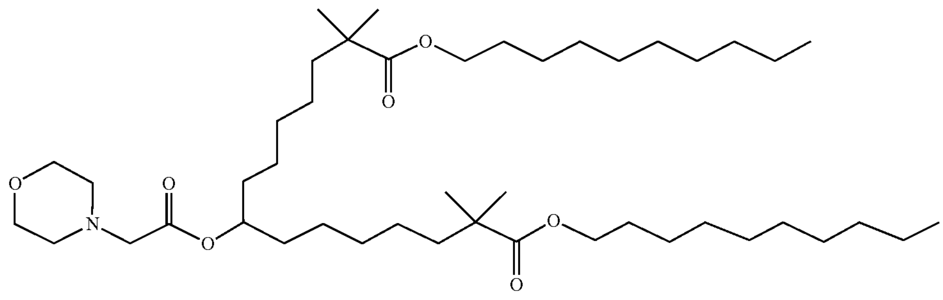
92
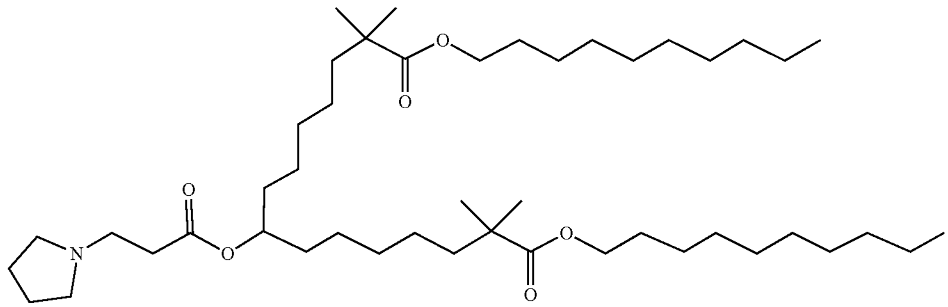
93
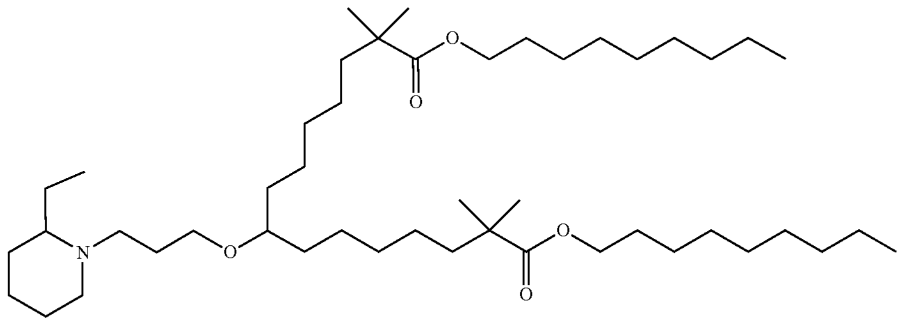
94
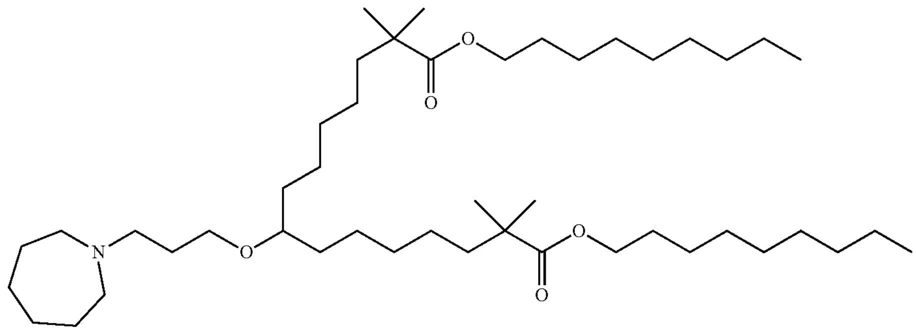
95
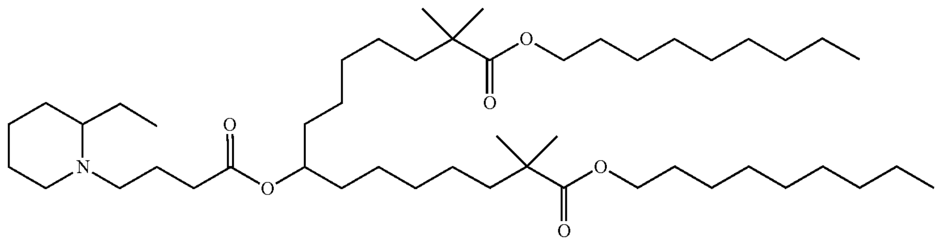

-continued

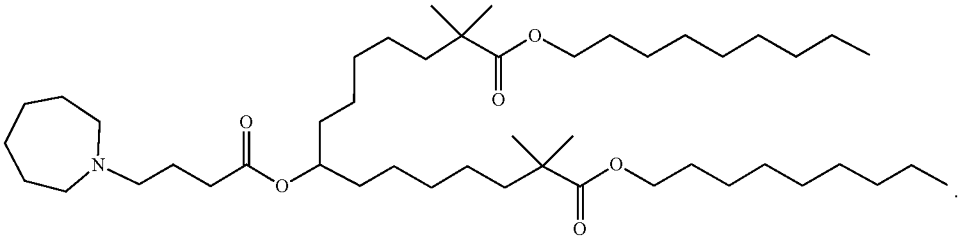

96

Technical solution 69: The present disclosure provides a composition, the composition comprises a biologically active substance and lipid compounds of the present disclosure.

Further, the biologically active substance is DNA or RNA.

Further, the composition further comprises neutral lipids, structure lipids and polymeric lipids.

Further, the neutral lipids are DSPC, DMPC, DOPC, DPPC, POPC, DOPE, DMPE, POPE or DPPE.

Further, the structure lipids are selected from one of, or a combination of cholesterol, sitosterol, coprosterol, fucosterol, brassicasterol, ergosterol, tomatine, ursolic acid, α-tocopherol, stigmasterol, avenasterol, ergocalciferol and campesterol.

Further, the polymeric lipids are selected from one of, or a combination of DMPE-PEG1000, DPPE-PEG1000, DSPE-PEG1000, DOPE-PEG1000, DMG-PEG2000, Ceramide-PEG2000, DMPE-PEG2000, DPPE-PEG2000, DSPE-PEG2000, Azido-PEG2000, DSPE-PEG2000-Mannose, Ceramide-PEG5000, and DSPE-PEG5000.

Technical solution 70: The present disclosure provides a lipid nanoparticle comprising the lipid compound of the present disclosure or the composition of the present disclosure.

Technical solution 71: The present disclosure provides a pharmaceutical composition comprising the lipid compound of the present disclosure, the composition of the present disclosure or the lipid nanoparticle of the present disclosure, and pharmaceutically acceptable excipient(s).

Technical solution 72: The present disclosure provides the use of the lipid compound of the present disclosure, the composition of the present disclosure, the lipid nanoparticle of the present disclosure or the pharmaceutical composition of the present disclosure in the manufacture of a medicament for treating or preventing a disease.

Technical solution 73: The present disclosure provides a method for preparing the compound of general formula (II), comprising:

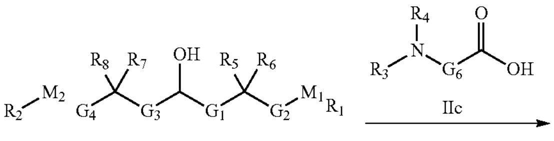

IIb IIc

-continued

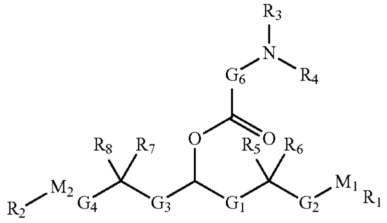

II reacting the compound of general formula (IIb) with the compound of general formula (IIc), to give the compound of general formula (II);

wherein the substituents are defined as described in general formula (I).

Technical solution 74: The present disclosure provides a compound, a pharmaceutically acceptable salt thereof or a stereoisomer thereof, the compound having the structure of general formula (IIa) or general formula (IIb):

IIa

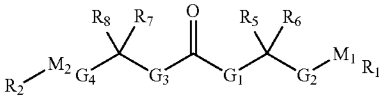

IIb

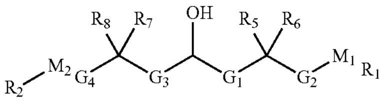

wherein the substituents are defined as described in general formula (I).

When the degradable group in the compound is changed, the compound of the corresponding structure can be prepared by the conventional methods in the field such as esterification and amide condensation.

Technical solution 75: The present disclosure provides the use of the compounds having the structure of general formula (IIa) or general formula (IIb), pharmaceutically acceptable salts or stereoisomers thereof in the preparation of cationic lipids.

Technical solution 76: The present disclosure also provides a lipid compound, a pharmaceutically acceptable salt, or a stereoisomer thereof, the lipid compound having the structure of general formula (I'):

(I')

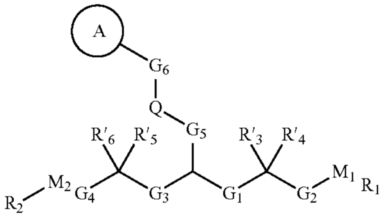

wherein, ring A is $C_{3-14}$ cycloalkyl, 3- to 14-membered heterocyclyl, $C_{6-14}$ aryl or 5- to 14-membered heteroaryl; the ring A is connected to the parent structure by a C atom on the ring; the ring A is optionally further substituted;

$G_1$, $G_2$, $G_3$ or $G_4$ is each independently a bond, $C_{1-20}$ alkylene, $C_{2-20}$ alkenylene or $C_{2-20}$ alkynylene;

$G_5$ or $G_6$ is each independently a bond or $C_{1-8}$ alkylene;

$M_1$ or $M_2$ is each independently biodegradable groups;

Q is a bond or biodegradable groups;

$R_1$ or $R_2$ is each independently $C_{4-28}$ alkyl, $C_{4-28}$ alkenyl or $C_{4-28}$ alkynyl;

$R'_3$, $R'_4$, $R'_5$ or $R'_6$ is each independently $C_{1-8}$ alkyl;

each of the alkyl, alkenyl, alkynyl, alkylene, alkenylene, alkynylene, cycloalkyl, heterocyclyl, aryl or heteroaryl is each independently and optionally further substituted.

Further, the lipid compound has the structure of general formula (I').

(I')

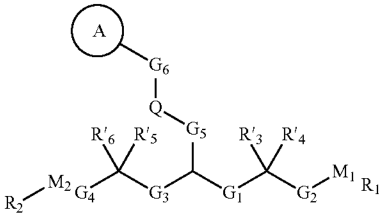

wherein, ring A is $C_{3-14}$ cycloalkyl, 3- to 14-membered heterocyclyl, $C_{6-14}$ aryl or 5- to 14-membered heteroaryl; the ring A is connected to the parent structure by a C atom on the ring; the ring A is optionally further substituted;

$G_1$, $G_2$, $G_3$ or $G_4$ is each independently a bond, $C_{1-20}$ alkylene, $C_{2-20}$ alkenylene or $C_{2-20}$ alkynylene; the $C_{1-20}$ alkylene, $C_{2-20}$ alkenylene or $C_{2-20}$ alkynylene is optionally substituted with one or more substituents selected from H, OH, alkyl, hydroxyalkyl, alkoxy, amino, alkylamino, and dialkylamino;

$G_5$ or $G_6$ is each independently a bond or $C_{1-6}$ alkylene; the $C_{1-6}$ alkylene is optionally substituted with one or more substituents selected from H, OH, alkyl, hydroxyalkyl, alkoxy, amino, alkylamino, and dialkylamino;

$M_1$ or $M_2$ is each independently selected from —OC(O)—, —C(O)O—, —SC(O)—, —C(O)S—, —O—, —OC(O)O—, —SC(O)O—, —OC(O)S—, —$NR_a$—, —C(O)$NR_a$—, —$NR_a$C(O)—, —$NR_a$C(O)O—, —OC(O)$NR_a$—, —$NR_a$C(O)S—, —SC(O)$NR_a$—, —$NR_a$C(O)$NR_a$—, —C(O)—, —OC(S)—, —C(S)O—, —OC(S)$NR_a$—, —$NR_a$C(S)O—, —S—S— and —$S(O)_m$—;

Q is selected from a bond, —OC(O)—, —C(O)O—, —SC(O)—, —C(O)S—, —O—, —OC(O)O—, —SC(O)O—, —OC(O)S—, —$NR_b$—, —C(O)$NR_b$—, —$NR_b$C(O)—, —$NR_b$C(O)O—, —OC(O)$NR_b$—, —$NR_b$C(O)S—, —SC(O)$NR_b$—, —$NR_b$C(O)$NR_b$—, —C(O)—, —OC(S)—, —C(S)O—, —OC(S)$NR_b$—, —$NR_a$C(S)O—, —S—S—, —$S(O)_n$—, phenylene and pyridylidene; the phenylene or pyridylidene group is optionally substituted with one or more substituents selected from H, hydroxy, halogen, cyano, alkyl, hydroxyalkyl, haloalkyl and alkoxy;

$R_1$ or $R_2$ is each independently $C_{4-28}$ alkyl, $C_{4-28}$ alkenyl or $C_{4-28}$ alkynyl; the $C_{4-28}$ alkyl, $C_{4-28}$ alkenyl or $C_{4-28}$ alkynyl is optionally substituted with one or more substituents selected from H, OH, alkyl, hydroxyalkyl, alkoxy, amino, alkylamino, and dialkylamino;

$R'_3$, $R'_4$, $R'_5$ or $R'_6$ is each independently $C_{1-8}$ alkyl;

each of $R_a$ or $R_b$ is each independently H, $C_{1-28}$ alkyl or $C_{3-14}$ cycloalkyl; the $C_{1-28}$ alkyl or $C_{3-14}$ cycloalkyl is optionally substituted with one or more substituents selected from H, OH, alkyl, hydroxyalkyl, alkoxy, amino, alkylamino, and dialkylamino;

m or n is each independently 0, 1 or 2.

Further, the $G_1$ and $G_3$ are both $C_2$-s alkylene, and $G_2$ and $G_4$ are both a bond; alternatively $G_1$ and $G_3$ are both $C_5$ alkylene, and $G_2$ and $G_4$ are both a bond.

Further, the $G_5$ is a bond.

Further, the $G_6$ is a bond or $C_{1-6}$ alkylene.

Further, the $M_1$ or $M_2$ is each independently —C(O)O—, —OC(O)—, —C(O)S—, —SC(O)—, —$NR_a$C(O)— or —C(O)$NR_a$—, the $R_a$ is H or $C_{4-24}$ alkyl; alternatively $M_1$ or $M_2$ is each independently —C(O)O— or —C(O)S—.

Further, the Q is a bond, —O—, —OC(O)—, —C(O)O—, —OC(O)O— or —OC(O)NH—, —NHC(O)—O—, —NHC(O)NH—, —OC(O)S—, —SC(O)O—; alternatively Q is —C(O)O—.

Further, the ring A is 3- to 8-membered heterocyclyl, the ring A is optionally substituted with one or more of $R_7$; alternatively the ring A is

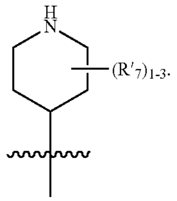

Further, the $R_1$ or $R_2$ is each independently $C_{4-28}$ alkyl, $C_{4-28}$ alkenyl or $C_{4-28}$ alkynyl, the $C_{4-28}$ alkyl, $C_{4-28}$ alkenyl or $C_{4-28}$ alkynyl is optionally substituted with one or more substituents H, hydroxyl or $C_{2-14}$ alkyl; alternatively $R_1$ or $R_2$ is each independently $C_{4-28}$ alkyl, $C_{4-28}$ alkenyl or $C_{4-28}$ alkynyl.

Further, the $R'_3$, $R'_4$, $R'_5$ or $R'_6$ is each independently $C_{1-3}$ alkyl; alternatively $R'_3$, $R'_4$, $R'_5$ or $R'_6$ are both methyl.

Further, each of the $R'_7$ is each independently H, halogen, cyano, OH, oxo, $C_{1-6}$ alkyl, $C_{1-6}$ alkoxy, —$NH_2$, —$NHC_{1-6}$ alkyl, or —N($C_{1-6}$ alkyl)$_2$; the $C_{1-6}$ alkyl is optionally further substituted with a substituent selected from halogen, cyano, OH, oxo, —$NH_2$, —$NHC_{1-6}$ alkyl, and —N($C_{1-6}$ alkyl)$_2$; alternatively $R'_7$ is $C_{1-3}$ alkyl.

Technical solution 77: Further, the lipid compound is the compound of general formula (II'):

(II')
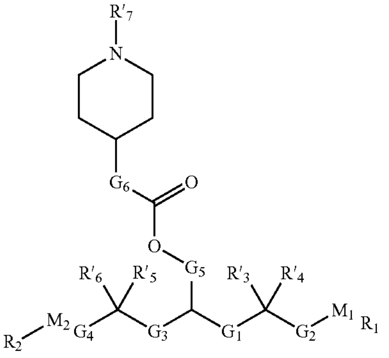
wherein the substituents are defined as described in general formula (I').
Technical solution 78: The present disclosure provides a lipid compound, a pharmaceutically acceptable salt or a stereoisomer thereof, wherein the lipid compound is selected from:
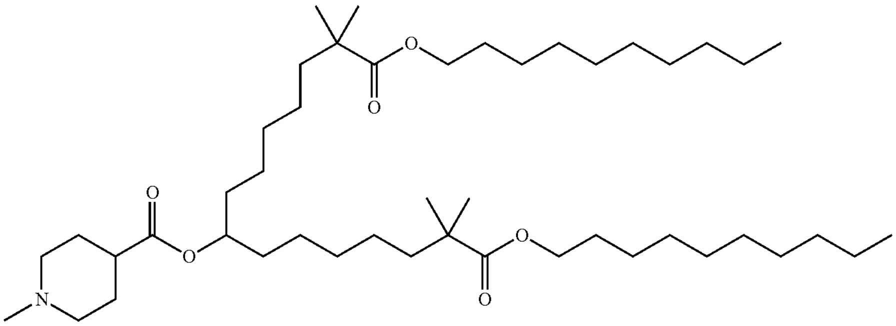
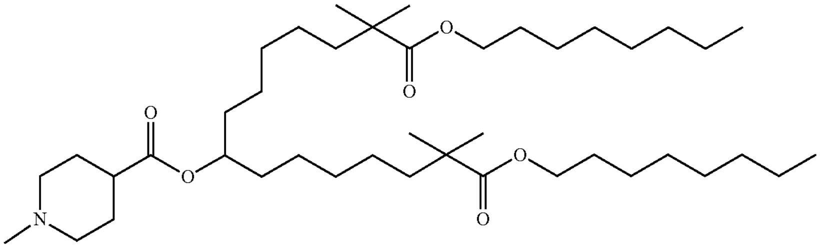
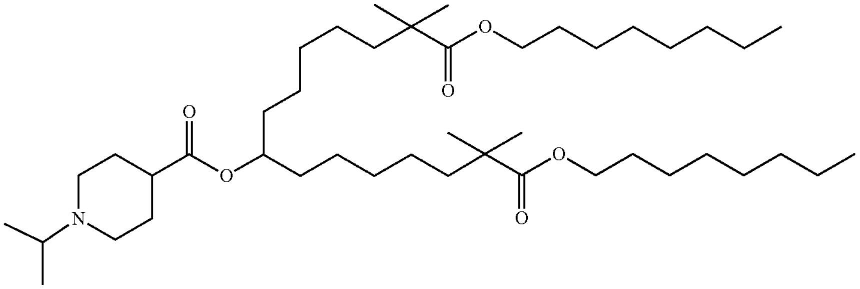
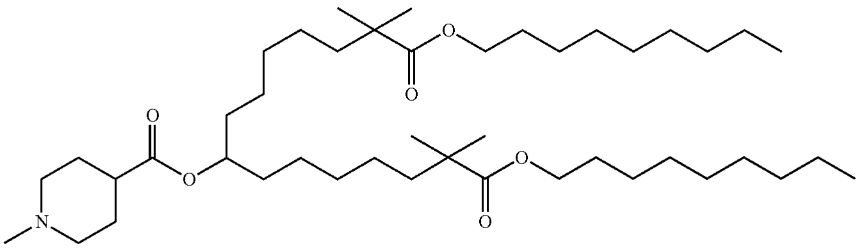

-continued

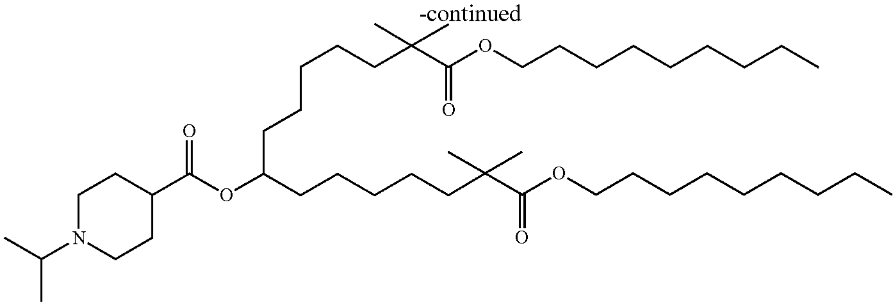

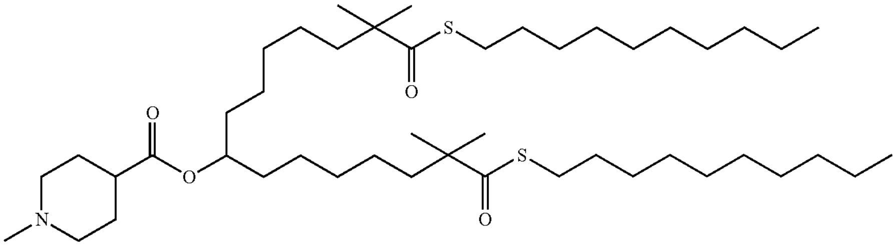

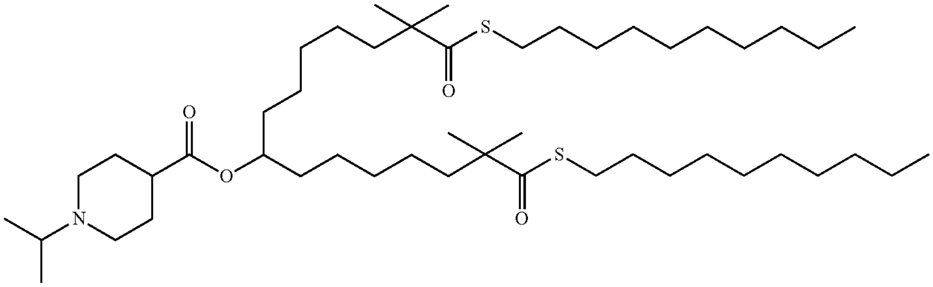

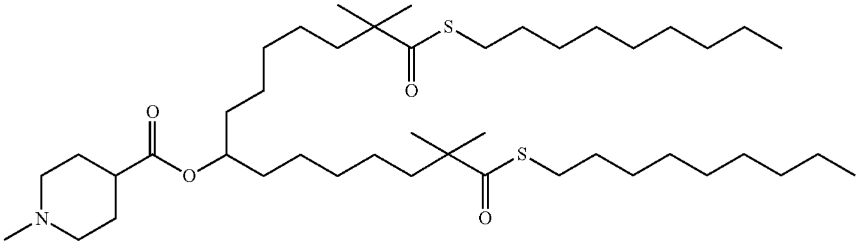

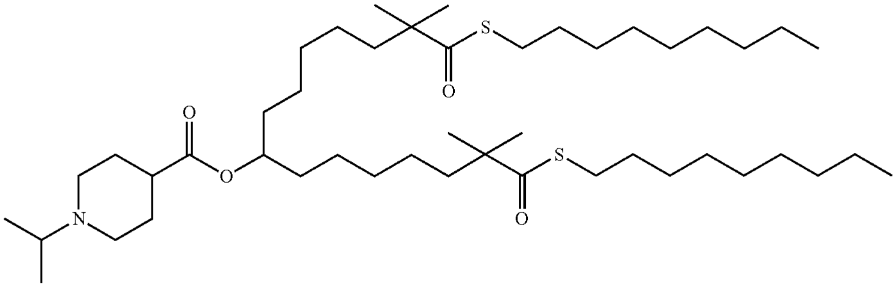

.

Technical solution 79: The present disclosure provides a composition, the composition comprises a biologically active substance and lipid compounds of the present disclosure.

Further, the biologically active substance is DNA or RNA.

Further, the composition further comprises neutral lipids, structure lipids and polymeric lipids.

Further, the neutral lipids are DSPC, DMPC, DOPC, DPPC, POPC, DOPE, DMPE, POPE or DPPE.

Further, the structure lipids are selected from one of, or a combination of cholesterol, sitosterol, coprosterol, fucosterol, brassicasterol, ergosterol, tomatine, ursolic acid, α-tocopherol, stigmasterol, avenasterol, ergocalciferol and campesterol.

Further, the polymeric lipids are selected from one of, or a combination of DMPE-PEG1000, DPPE-PEG1000, DSPE-PEG1000, DOPE-PEG1000, DMG-PEG2000, Ceramide-PEG2000, DMPE-PEG2000, DPPE-PEG2000, DSPE-PEG2000, Azido-PEG2000, DSPE-PEG2000-Mannose, Ceramide-PEG5000, and DSPE-PEG5000.

Technical solution 80: The present disclosure provides a lipid nanoparticle comprising the lipid compound of the present disclosure or the composition of the present disclosure.

Technical solution 81: The present disclosure provides a pharmaceutical composition comprising the lipid compound of the present disclosure, the composition of the present disclosure or the lipid nanoparticle of the present disclosure, and pharmaceutically acceptable excipient(s).

Technical solution 82: The present disclosure provides the use of the lipid compound of the present disclosure, the composition of the present disclosure, the lipid nanoparticle of the present disclosure or the pharmaceutical composition of the present disclosure in the manufacture of a medicament for treating or preventing a disease.

Technical solution 83: The present disclosure provides a method for preparing the compound of general formula (II'), comprising:

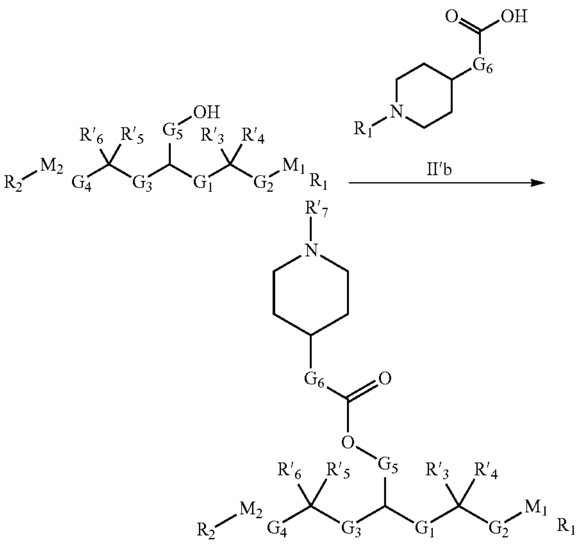

II' reacting the compound of general formula (II'a) with the compound of general formula (II'b), to give the compound of general formula (II');

wherein the substituents are defined as described in general formula (I').

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

The compounds of the present disclosure may exist in tautomer forms. The tautomer is a functional group isomer resulting from the rapid shift of an atom between two positions in a molecule. The tautomer is a special functional group isomer, wherein a pair of tautomers can convert between each other, but usually exist in a relatively stable isomer as its main form. The most important examples are the enol and keto tautomers.

The present disclosure also comprises compounds that are labeled with isotopes (isotope variants), which are equivalent to those described in formula (IV), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}H$ and $^{14}C$), can be used for the measurement of the distribution of drug and/or substrate in tissue. Tritium, which is $^{3}H$ and carbon-14, which is $^{14}C$ isotope, are yet alternative, because they are easy to prepare and detect. Furthermore, replaced by heavier isotopes, such as deuterium, which is $^{2}H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

The present disclosure also provides a pharmaceutical formulation comprising a therapeutically effective amount of a compound of formula (VI), or therapeutically acceptable salts thereof, and pharmaceutically acceptable carriers, diluents or excipients thereof. All of these forms belong to the present disclosure.

Pharmaceutical Compositions and Kits

In another aspect, the present disclosure provides a pharmaceutical composition comprising nanoparticle compositions of the present disclosure and pharmaceutically acceptable excipient(s), the nanoparticle composition comprises the compounds of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a nanoparticle composition of the present disclosure and other therapeutic, or diagnostic, or prophylactic agents, and a first and a second containers (e.g., vials, ampoules, bottles, syringes, and/or dispersible packages or other materials) containing the nanoparticle composition of the present disclosure or other therapeutic, or diagnostic, or prophylactic agents. In some embodiments, kits provided can also optionally include a third container containing a pharmaceutically acceptable excipient for diluting or suspending the nanoparticle composition of the present disclosure and/or other therapeutic, or diagnostic, or prophylactic agent. In some embodiments, the nanoparticle composition of the present disclosure provided in the first container and the other therapeutic, or diagnostic, or prophylactic agents provided in the second container is combined to form a unit dosage form.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the pharmaceutical compositions provided herein are administered in an effective amount. The amount of the pharmaceutical composition actually administered will typically be determined by a physician, in the light of the relevant circumstances, including the condition to be treated or prevented, the chosen route of administration, the actual pharmaceutical composition administered, the age, weight, and response of the individual patient, the severity of the patient's symptoms, and the like.

When used to prevent the disorder of the present disclosure, the pharmaceutical compositions provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the active substance is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.001 mg/kg to about 10 mg/kg of the therapeutic, or diagnostic, or prophylactic agents, with alternative doses each providing from about 0.1 mg/kg to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and still alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient (s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The nanoparticle compositions of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

EXAMPLE

In order to make the technical solutions of the present disclosure clearer and more explicit, the present disclosure is further elaborated through the following examples. The following examples are used only to illustrate specific embodiments of the present disclosure so that a person skilled in the art can understand the present disclosure, but are not intended to limit the scope of protection of the present disclosure. The technical means or methods, etc. not specifically described in the specific embodiments of the present disclosure are conventional technical means or methods, etc. in the art. The materials, reagents, etc. used in examples are commercially available if not otherwise specified.

TABLE 1

| Abbreviation | Full name |
|---|---|
| THF | Tetrahydrofuran |
| DCM | dichloromethane |
| MeOH | methanol |
| DMF | N,N-Dimethylformamide |
| DMSO | Dimethyl sulfoxide |
| DCE | 1,2-Dichloroethane |
| $CDCl_3$ | Deuterated chloroform |
| TBAI | Tetrabutylammonium iodide |
| $TsCH_2CN$ | 4-Toluenesulfonylacetonitrile |
| TMSOK | Potassium trimethylsiloxide |
| TBDMSCl | tert-Butyldimethylsilyl chloride |
| LDA | Lithium diisopropylamide |
| DMAP | 4-Dimethylaminopyridine |
| $(COCl)_2$ | Oxalyl chloride |
| $SOCl_2$ | Thionyl dichloride |
| $NaBH_4$ | Sodium borohydride |
| NaH | Sodium hydride |
| $K_2CO_3$ | Potassium carbonate |
| EDCI | 1-(3-Dimethylaminopropyl)-3-ethylcarbodiimide |
| DIPEA | N,N-Diisopropylethylamine |
| $Et_3N$ | Triethylamine |
| AcOH | Acetic acid |
| $NaBH_3CN$ | Sodium cyanoborohydride |
| Imidazole | Imidazole |
| NMO | 4-Methylmorpholine N-oxide |
| BDMEP | 2,6-di-tert-Butylpyridine |

Example 1: Synthesis of Compound 1

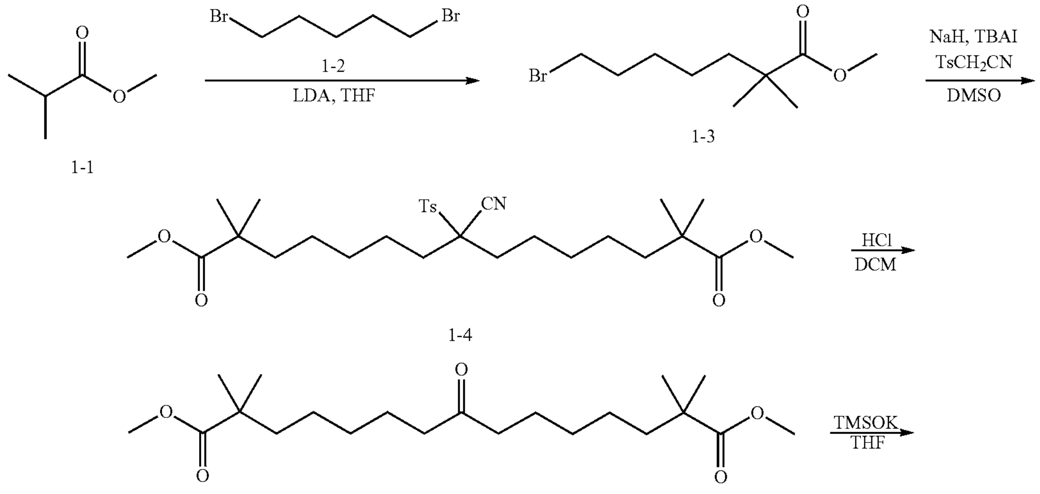

1-1 1-3 1-4 1-5

-continued

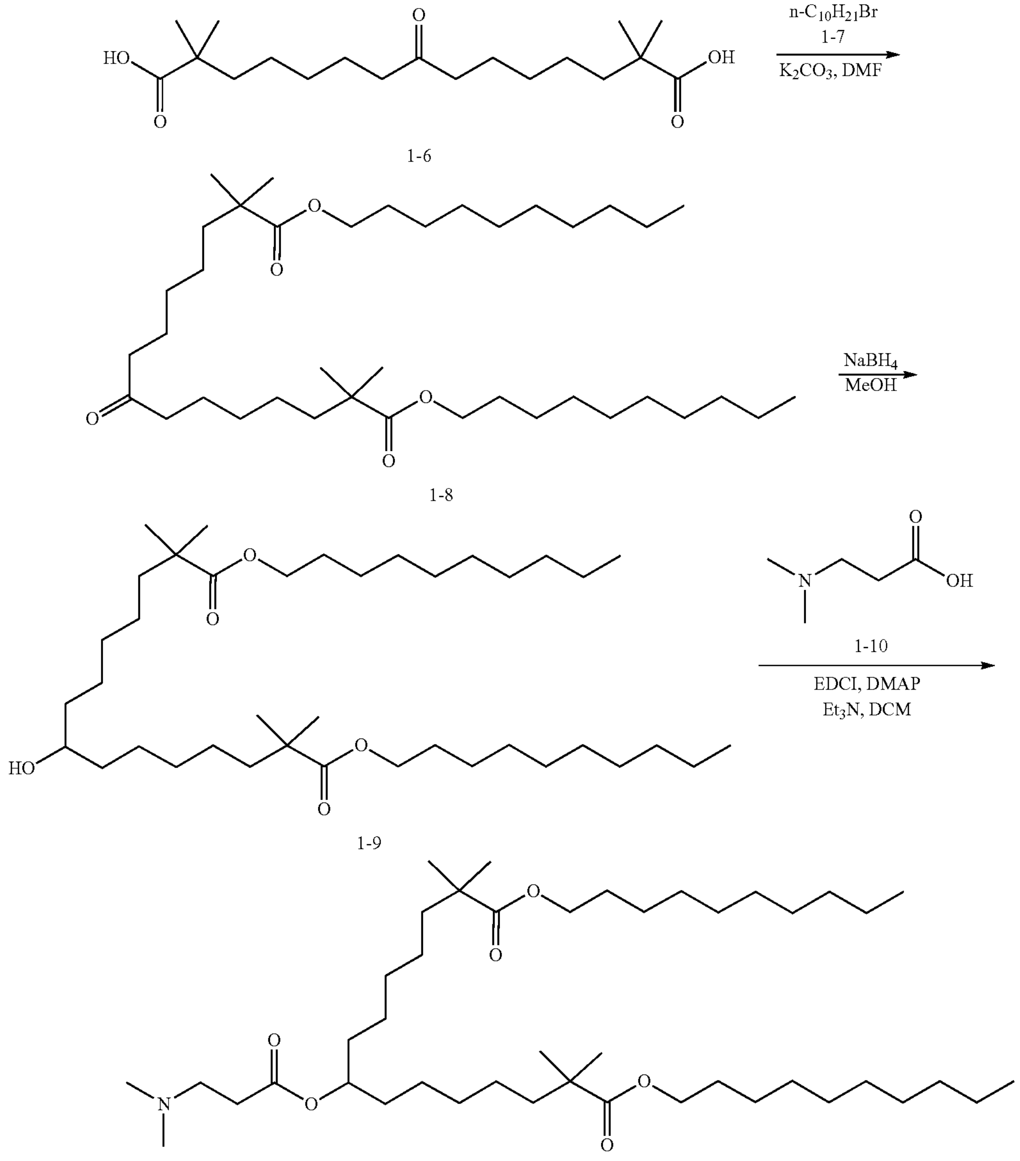

1-6

1-8

1-9

1

A solution of compound 1-1 (100 g, 979 mmol) in tetrahydrofuran (800 mL) was cooled to −40° C. LDA (2 M, 490 mL) was added slowly dropwise to the solution and the mixture was stirred for another 1 h after completion of the dropwise addition. A solution of 1-2 (315 g, 1.37 mol) in tetrahydrofuran (100 mL) was added dropwise to the reaction system at the same temperature and the reaction system was stirred overnight. The reaction system was quenched with saturated aqueous ammonium chloride, and extracted with ethyl acetate. The organic phases were combined, dried over anhydrous sodium sulfate, and filtered. The filtrate was concentrated to dryness to give the crude product. The crude product was purified by silica gel column to give compound 1-3 (115 g). $^1H$ NMR (400 MHz, $CDCl_3$): δ ppm 1.06-1.11 (m, 6H), 1.13-1.22 (m, 2H), 1.29-1.39 (m, 2H), 1.42-1.49 (m, 2H), 1.73-1.82 (m, 2H), 3.28-3.40 (m, 2H), 3.55-3.66 (m, 3H).

A solution of compound 1-3 (100 g, 398 mmol), $TsCH_2CN$ (38.9 g, 199 mmol) and TBAI (14.7 g, 39.8 mmol) in dimethyl sulfoxide (800 mL) was cooled to 0° C., and sodium hydride (20.7 g, 517 mmol) was added slowly in batches. The mixture was reacted at room temperature overnight. The reaction system was quenched with saturated aqueous sodium chloride solution and extracted with ethyl acetate. The organic phases were combined, dried over anhydrous sodium sulfate, and filtered. The filtrate was concentrated to dryness to give 115 g of crude compound 1-4, which was used directly in the next reaction without isolation and purification.

To a solution of compound 1-4 crude (110 g, 205 mmol) in dichloromethane (880 mL) was added 330 mL of concentrated hydrochloric acid, and the mixture was reacted at room temperature for 2 h. The complete reaction of the substrate was monitored by TLC. The reaction system was quenched with saturated aqueous ammonium chloride solution and extracted with ethyl acetate. The organic phases were combined, dried over anhydrous sodium sulfate, and filtered. The filtrate was concentrated to dryness to give the crude product. The crude product was purified by silica gel column to give compound 1-5 (30.0 g, 80.9 mmol, yield 39.4%).

TMSOK (11.0 g, 86.4 mmol) was added to a solution of compound 1-5 (8.0 g, 21.6 mmol) in tetrahydrofuran (35.0 mL) at room temperature, and the reaction system was heated to 70° C. with stirring. The complete consumption of reaction materials was monitored by TLC. The reaction solution was cooled to room temperature, and the organic solvent was removed by rotary evaporation. The crude product was added to 20 mL of water and extracted with dichloromethane. The aqueous layer was collected, and the solution was adjusted to a pH of <5 with 1 M hydrochloric acid. The solution was extracted with dichloromethane. The organic phases were combined, dried over anhydrous sodium sulfate, and filtered. The filtrate was collected and concentrated to give compound 1-6 (7.0 g). $^1$H NMR (400 MHz, $CDCl_3$): δ ppm 1.03 (s, 12H), 1.08-1.17 (m, 8H), 1.34-1.45 (m, 8H), 2.21 (t, J=7.2 Hz, 4H).

Potassium carbonate (482 mg, 3.48 mmol) was added to a solution of compound 1-6 (294 mg, 0.87 mmol) and 1-7 (771 mg, 3.48 mmol) in DMF, then the reaction was warmed up to 60° C. for 6 h. The complete disappearance of reactant 1-6 was monitored. The mixture was cooled to room temperature. The reaction system was quenched with saturated aqueous sodium chloride solution and extracted with ethyl acetate. The organic phases were combined, dried over anhydrous sodium sulfate, and filtered. The filtrate was concentrated to dryness to give the crude product. The crude was purified by silica gel column to give compound 1-8 (325 mg).

Compound 1-8 (325 mg) was dissolved in 4.0 mL of methanol and sodium borohydride (30 mg, 0.84 mmol) was added to the reaction system. The mixture was reacted at room temperature. The complete disappearance of the reactants was monitored by TLC. The reaction system was quenched with saturated aqueous sodium chloride solution and extracted with dichloromethane. The organic phases were combined, dried over anhydrous sodium sulfate, and filtered. The filtrate was concentrated to dryness to give crude compound 1-9 (260 mg), which was used directly in the next reaction without purification.

Crude compound 1-9 (260 mg, 0.42 mmol), 1-10 (73.1 mg, 0.63 mmol), EDCI (238 mg, 1.26 mmol), triethylamine (0.17 mL, 1.26 mmol) and DMAP (51 mg, 0.42 mmol) were dissolved in 5.0 mL of dichloromethane, and the reaction solution was stirred to react at room temperature for 12 h. The reaction solution was quenched with saturated aqueous sodium chloride and extracted with dichloromethane. The organic phases were combined, dried over anhydrous sodium sulfate, and filtered. The organic phase was collected and the organic solvent was removed using a rotary-evaporator to give the crude product, which was purified by preparative high performance liquid chromatography to give compound 1 (130 mg).

$^1$H NMR (400 MHz, $CDCl_3$): δ ppm 0.89 (t, J=7.2 Hz, 6H), 1.15 (s, 12H), 1.27 (m, 40H), 1.49 (m, 8H), 1.61 (m, 4H), 2.26 (s, 6H), 2.44-2.52 (t, J=7.2 Hz, 2H), 2.63 (t, J=7.2 Hz, 2H), 4.04 (t, J=6.8 Hz, 4H), 4.86 (m, 1H); ESI-MS m/z: 724.7 $[M+H]^+$.

Example 2: Synthesis of Compound 2

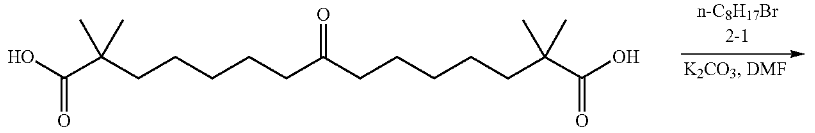

1-6

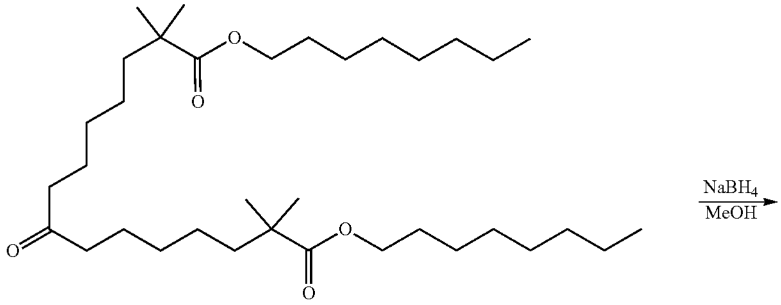

2-2

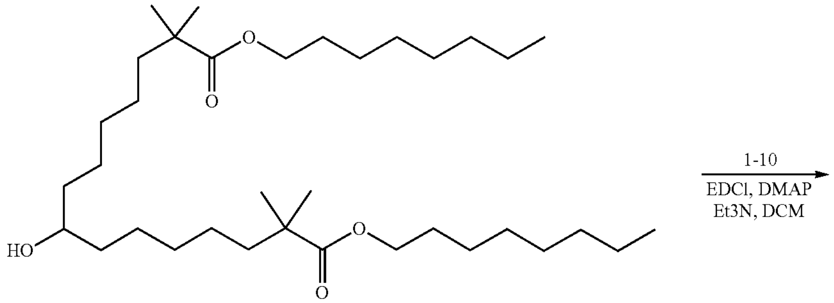

2-3

-continued
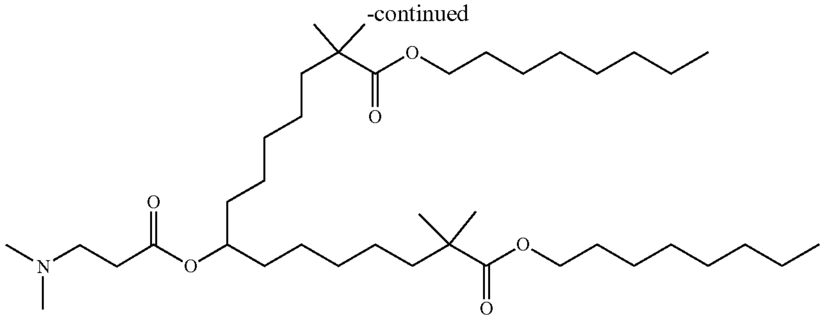
2
Referring to the method of Example 1, compound 2 was prepared as an oily product: 25.7 mg.
$^1$H NMR (400 MHz, $CDCl_3$): δ ppm 0.89 (t, J=6.8 Hz, 6H), 1.15 (s, 12H), 1.29 (m, 32H), 1.49 (m, 8H), 1.60 (m, 4H), 2.24 (s, 6H), 2.46 (t, J=7.2 Hz, 2H), 2.61 (t, J=7.2 Hz, 2H), 4.04 (t, J=6.8 Hz, 4H), 4.86 (m, 1H); ESI-MS m/z: 668.6 $[M+H]^+$.
Example 3: Synthesis of Compound 3
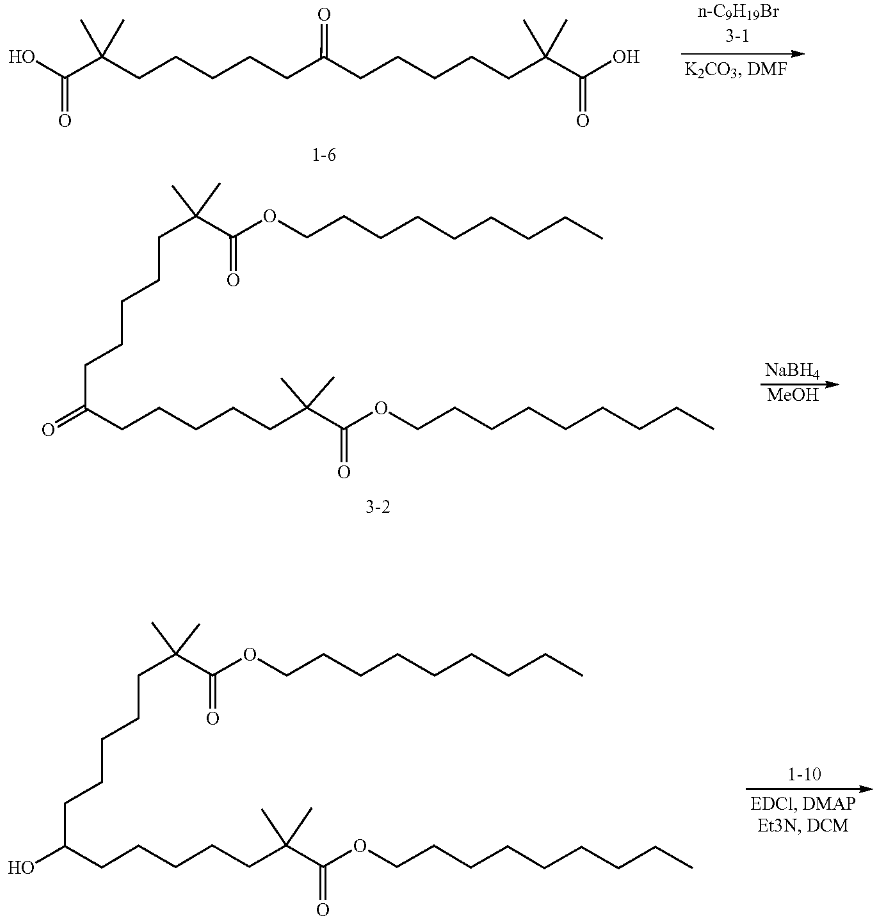
1-6
3-2
3-3

-continued
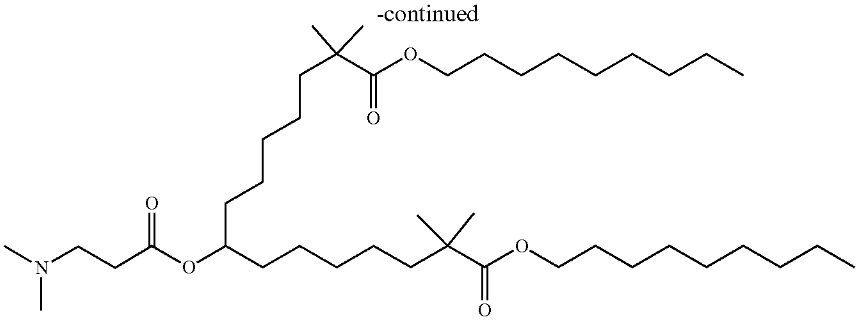
3
Referring to the method of Example 1, compound 3 was prepared as an oily product: 31.2 mg.
$^{1}H$ NMR (400 MHz, $CDCl_3$): δ ppm 0.89 (t, J=6.8 Hz, 6H), 1.16 (s, 12H), 1.28 (m, 36H), 1.49 (m, 8H), 1.62 (m, 4H), 2.25 (s, 6H), 2.47 (t, J=7.2 Hz, 2H), 2.62 (t, J=7.2 Hz, 2H), 4.05 (t, J=6.8 Hz, 4H), 4.88 (m, 1H); ESI-MS m/z: 696.6 $[M+H]^+$.
Example 4: Synthesis of Compound 4
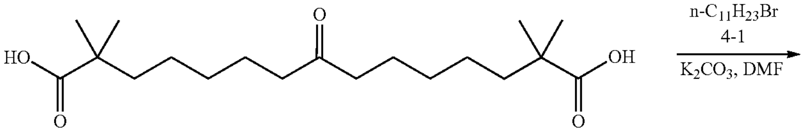
1-6
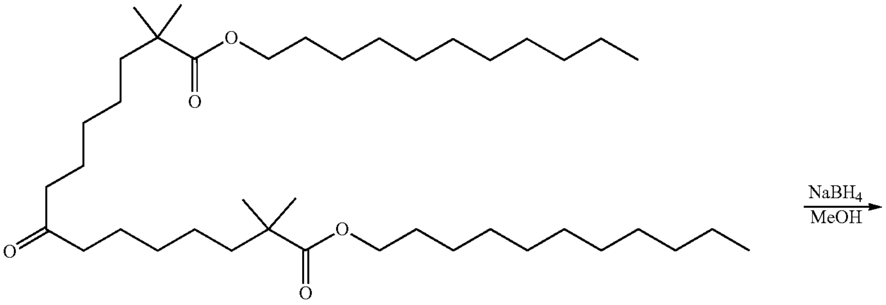
4-2
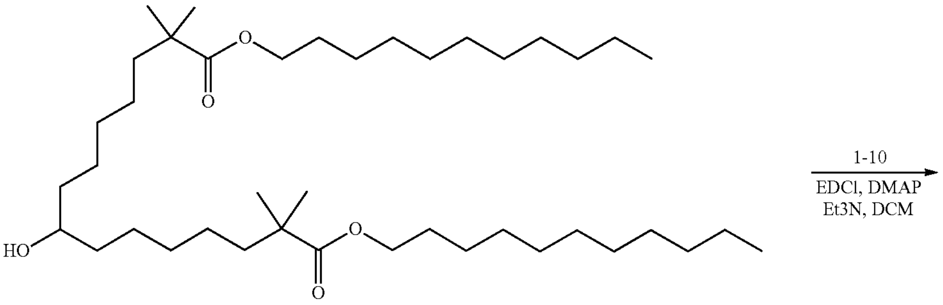
4-3

-continued
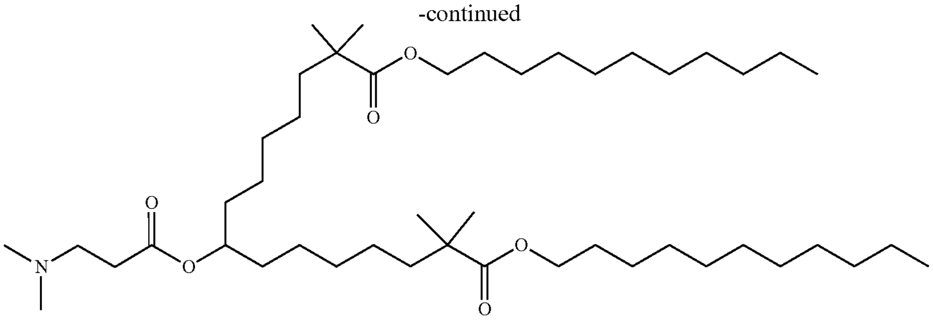
4
Referring to the method of Example 1, compound 4 was prepared as an oily product: 32 mg.
$^{1}$H NMR (400 MHz, $CDCl_3$): δ ppm 0.89 (t, J=6.8 Hz, 6H), 1.16 (s, 12H), 1.28 (m, 44H), 1.49 (m, 8H), 1.52 (m, 4H), 2.51 (s, 6H), 2.53 (t, J=7.2 Hz, 2H), 3.12 (t, J=7.2 Hz, 2H), 3.91 (t, J=6.8 Hz, 4H), 4.82 (m, 1H); ESI-MS m/z: 752.7 $[M+H]^+$.
Example 5: Synthesis of Compound 5
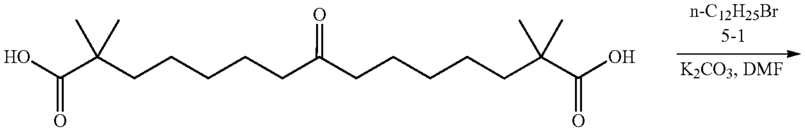
1-6
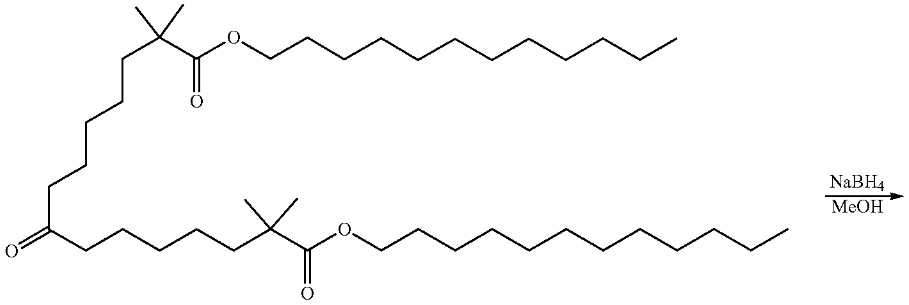
5-2
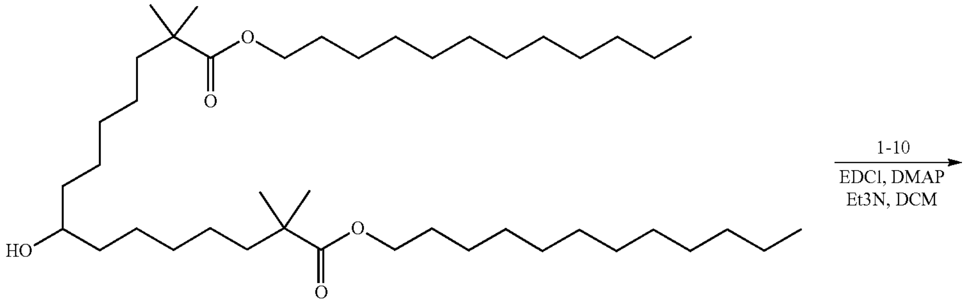
5-3

-continued
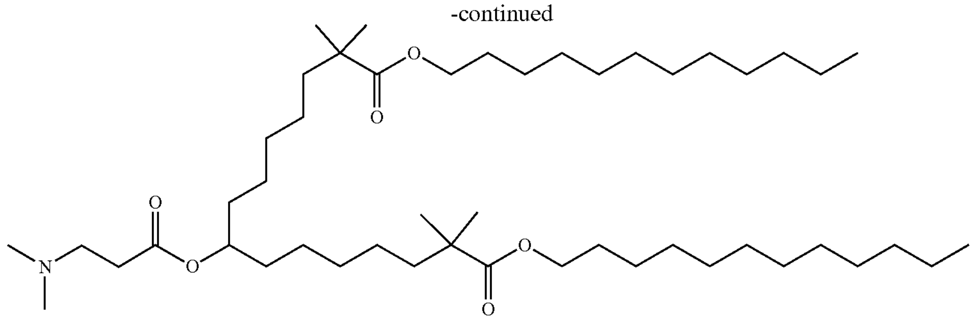
5
Referring to the method of Example 1, compound 5 was prepared as an oily product: 31.4 mg.
$^1$H NMR (400 MHz, $CDCl_3$): δ ppm 0.88 (t, J=6.8 Hz, 6H), 1.15 (s, 12H), 1.25 (m, 48H), 1.49 (m, 8H), 1.52 (m, 4H), 2.46 (s, 6H), 2.63 (m, 2H), 2.86 (m, 2H), 4.03 (t, J=6.8 Hz, 4H), 4.84 (m, 1H); ESI-MS m/z: 780.7 $[M+H]^+$.
Example 6: Synthesis of Compound 6
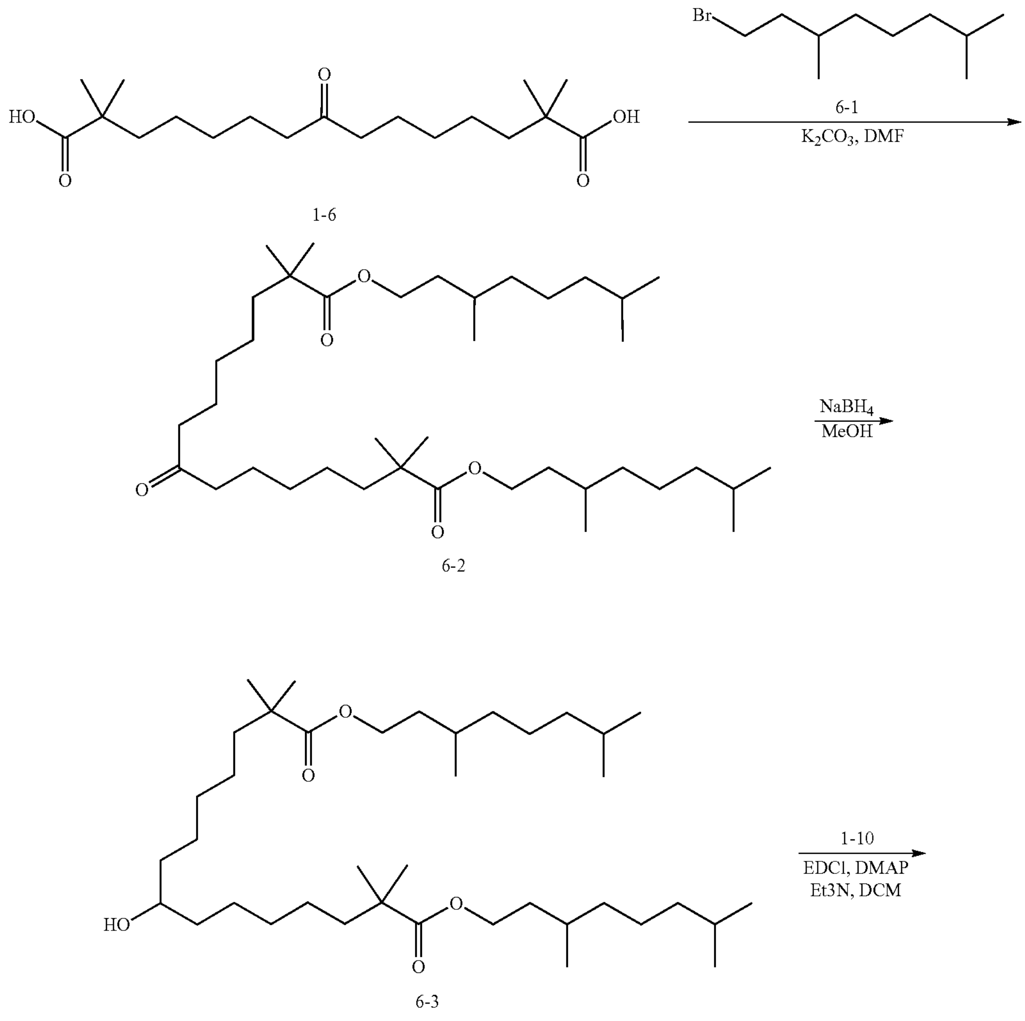

-continued
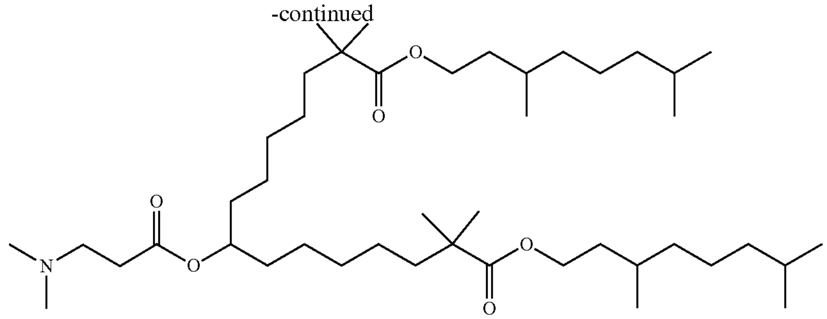
6
Referring to the method of Example 1, compound 6 was prepared as an oily product: 30.7 mg.
$^1$H NMR (400 MHz, $CDCl_3$): δ ppm 0.83 (t, J=6.8 Hz, 18H), 1.00-1.28 (m, 34H), 1.31-1.62 (m, 18H), 2.21 (s, 6H), 2.36-2.46 (m, 2H), 2.51-2.62 (m, 2H), 4.02 (t, J=6.8 Hz, 4H), 4.71-4.85 (m, 1H); ESI-MS m/z: 724.6 $[M+H]^+$.
Example 7: Synthesis of Compound 7
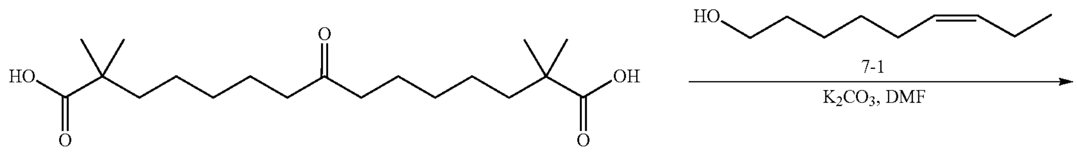
1-6
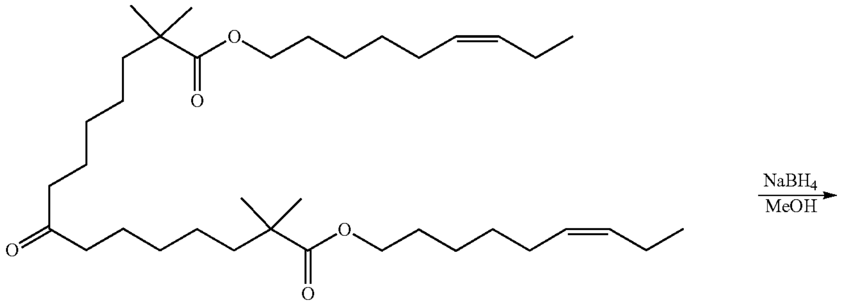
7-2
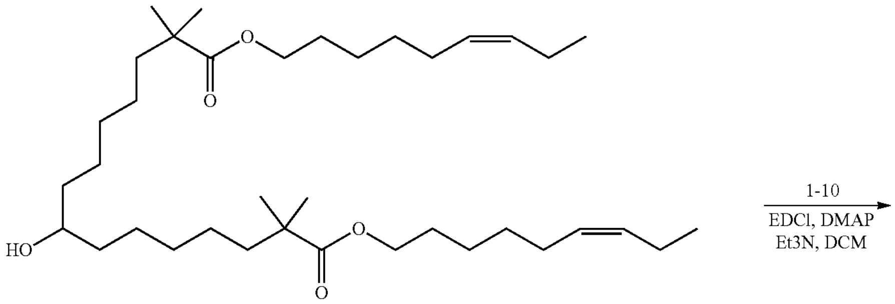
7-3

-continued

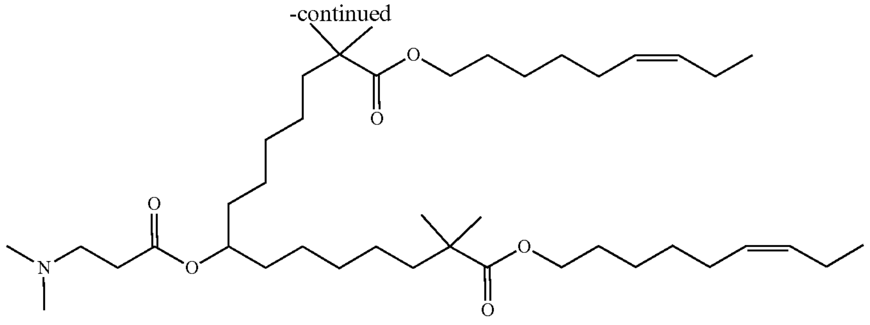

7

Compound 1-6 (548 mg, 1.5 mmol) was dissolved in 5.0 mL of dichloromethane, and the reaction system was cooled to 0° C. in an ice bath. DMF (12 μL, 0.15 mmol) was added and oxalyl chloride (0.47 mL, 6.0 mmol) was added drop-wise to the reaction solution. The ice bath was removed and the mixture was stirred for 1 h at room temperature. The solvent was removed using a rotary-evaporator to give acyl chloride crude product (458 mg) as an oil, which was used directly in the next reaction step.

The above obtained acyl chloride crude product (458 mg) was dissolved in 3.0 mL of 1,2-dichloroethane, and then compound 7-1 (429 mg, 3.0 mmol) was added to the reaction solution. The mixture was stirred at room temperature until the substrate was reacted completely. The solvent was removed using a rotary-evaporator to give the crude product, which was purified by silica gel column to give compound 7-2 (540 mg).

Then referring to the method of Example 1, compound 7 was prepared as an oily product: 33.2 mg.

$^1$H NMR (400 MHz, $CDCl_3$): δ ppm 0.89 (t, J=6.8 Hz, 6H), 1.23 (s, 12H), 1.29-1.51 (m, 32H), 1.95 (m, 8H), 2.18 (s, 6H), 2.41 (m, 2H), 2.53 (m, 2H), 3.91 (t, J=6.8 Hz, 4H), 4.78 (m, 1H), 5.25 (m, 4H); ESI-MS m/z: 692.6 [M+H]$^+$.

Example 8: Synthesis of Compound 8

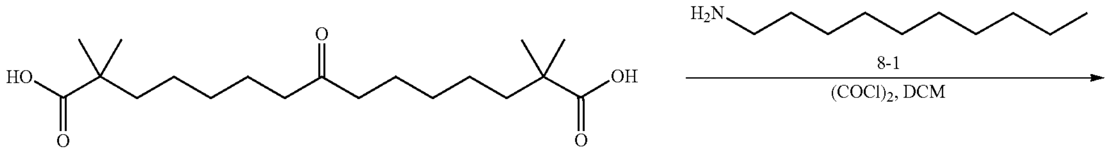

1-6

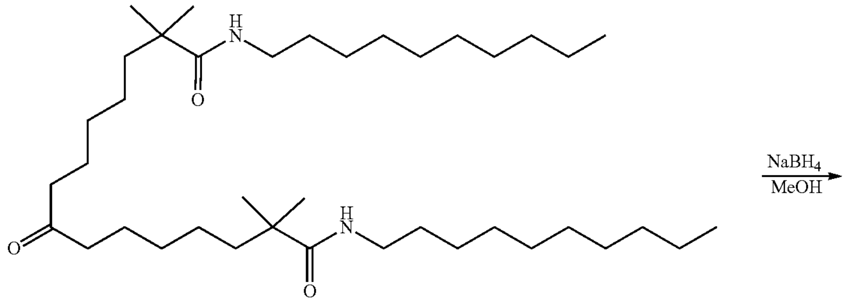

8-2

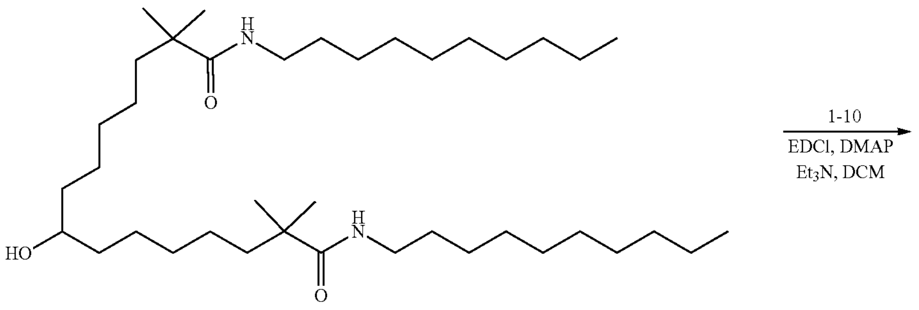

8-3

-continued

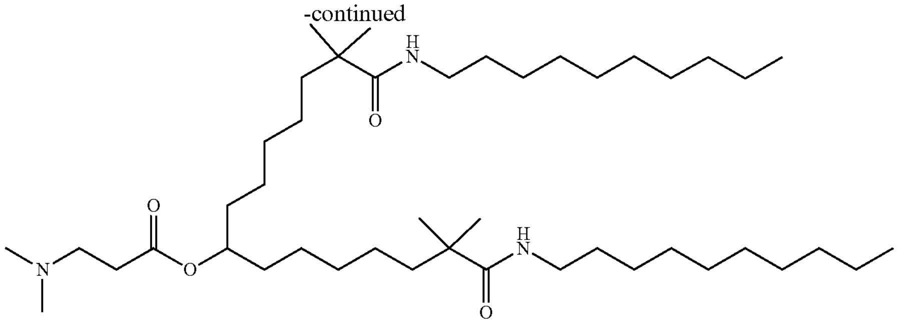

8

Compound 1-6 (548 mg, 1.5 mmol) was dissolved in 5.0 mL of dichloromethane, and the reaction system was cooled in an ice bath. DMF (12 μL, 0.15 mmol) was added and oxalyl chloride (0.47 mL, 6.0 mmol) was added dropwise to the reaction solution. The ice bath was removed and the mixture was stirred for 1 h at room temperature. The solvent was removed using a rotary-evaporator to give acyl chloride crude product (458 mg) as an oil, which was used directly in the next reaction step.

The above obtained 458 mg of acyl chloride crude product was dissolved in 3.0 mL of 1,2-dichloroethane, and then compound 8-1 (472 mg, 3.0 mmol) was added to the reaction solution. The mixture was stirred at room temperature until the substrate was reacted completely. The solvent was removed using a rotary-evaporator to give crude product, which was purified by silica gel column to give compound 8-2 (518 mg).

518 mg of compound 8-2 was dissolved in 5.0 mL of methanol, and sodium borohydride (48 mg, 1.25 mmol) was added to the reaction system. The mixture was reacted at room temperature. The complete disappearance of the reactants was monitored by TLC. The reaction system was quenched with saturated aqueous sodium chloride solution and extracted with dichloromethane. The organic phases were combined, dried over anhydrous sodium sulfate, and filtered. The filtrate was concentrated to dryness to give 473 mg of crude compound 8-3, which was used directly in the next reaction without purification.

Crude compound 8-3 (270 mg, 0.43 mmol), 1-10 (76.1 mg, 0.65 mmol), EDCI (248 mg, 1.3 mmol), triethylamine (0.18 mL, 1.3 mmol) and DMAP (53 mg, 0.43 mmol) were dissolved in 5.0 mL of dichloromethane, and the reaction solution was stirred to react at room temperature for 12 h. The reaction system was quenched with saturated aqueous sodium chloride and extracted with dichloromethane. The organic phases were combined, dried over anhydrous sodium sulfate, and filtered. The organic phase was collected and the organic solvent was removed using a rotary-evaporator to give the crude product, which was purified by preparative high performance liquid chromatography to give compound 8 (39 mg).

$^1$H NMR (400 MHz, $CDCl_3$): δ ppm 0.89 (t, J=6.8 Hz, 6H), 1.14 (s, 12H), 1.15-1.31 (m, 40H), 1.40-1.52 (m, 12H), 2.25 (s, 6H), 2.45 (m, 2H), 2.60 (m, 2H), 3.15 (t, J=6.8 Hz, 4H), 4.77-4.89 (m, 1H), 5.51-5.67 (m, 2H); ESI-MS m/z: 722.7 $[M+H]^+$.

Example 9: Synthesis of Compound 9

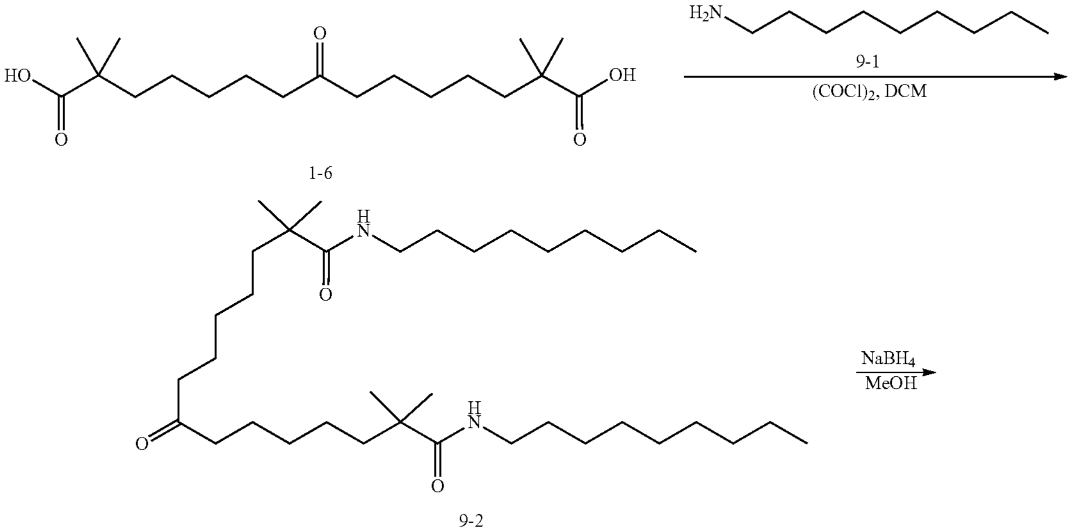

1-6

9-2

-continued
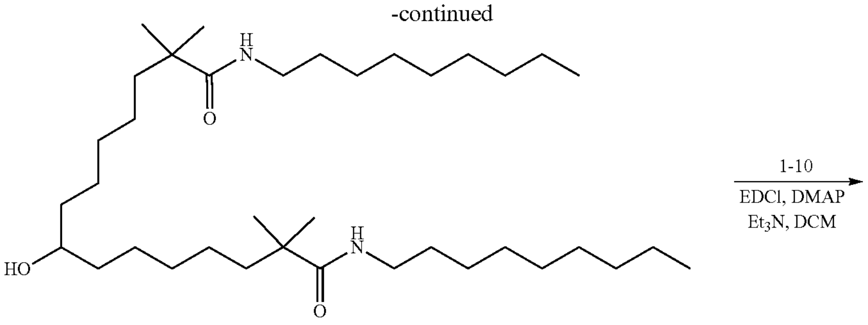
9-3
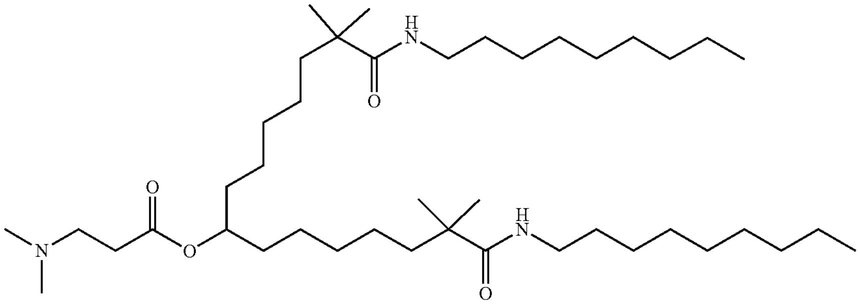
9
Referring to the method of Example 8, compound 9 (73 mg) was prepared.
$^1$H NMR (400 MHz, $CDCl_3$): δ ppm 0.89 (t, J=6.8 Hz, 6H), 1.15 (s, 12H), 1.27-1.49 (m, 48H), 2.25 (s, 6H), 2.46 (t, J=7.2 Hz, 2H), 2.62 (t, J=7.2 Hz, 2H), 3.24 (m, 4H), 4.85 (m, 1H), 5.58 (m, 2H); ESI-MS m/z: 694.6 $[M+H]^+$.
Example 10: Synthesis of Compound 10
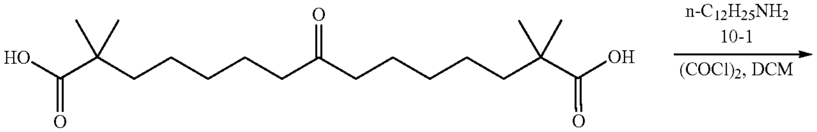
1-6
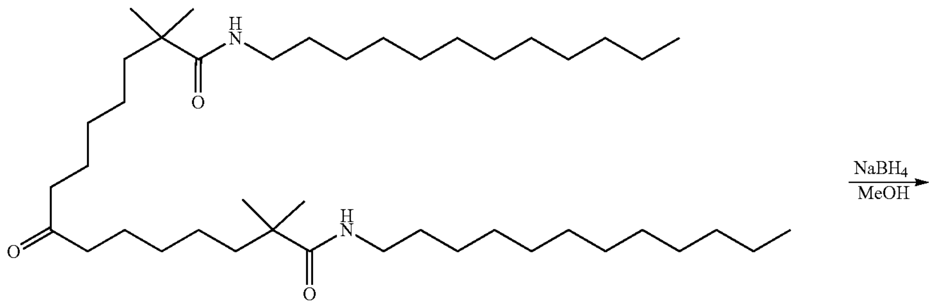
10-2

-continued
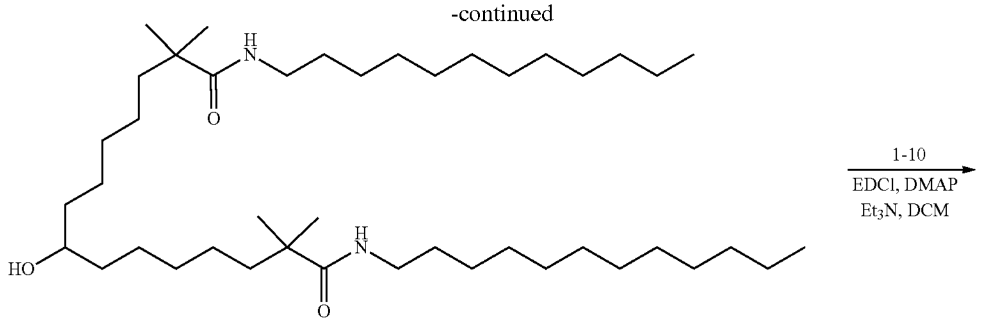
10-3
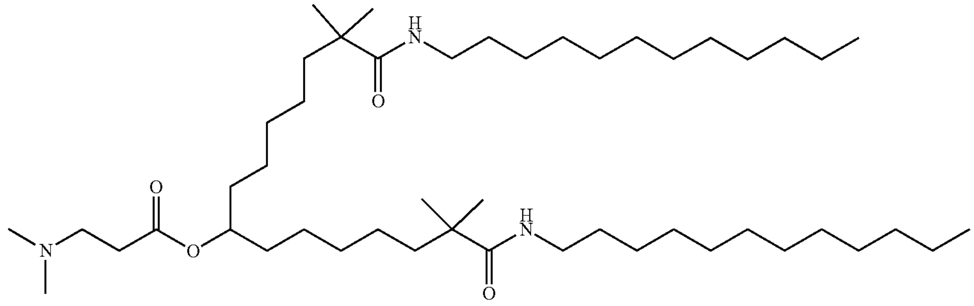
10
Referring to the method of Example 8, compound 10 (31.2 mg) was prepared.
$^1H$ NMR (400 MHz, $CDCl_3$): δ ppm 0.79 (t, J=7.2 Hz, 6H), 1.07 (s, 12H), 1.27-1.49 (m, 48H), 1.41 (m, 12H), 2.18 (s, 6H), 2.41 (t, J=7.2 Hz, 2H), 2.55 (t, J=7.2 Hz, 2H), 3.16 (m, 4H), 4.78 (m, 1H), 5.51 (m, 2H); ESI-MS m/z: 778.8 $[M+H]^+$.
Example 11: Synthesis of Compound 11
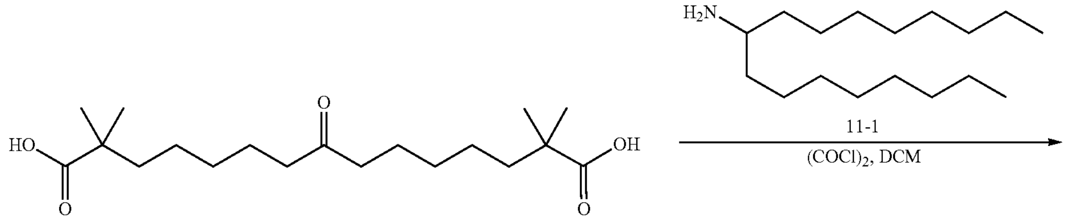
1-6
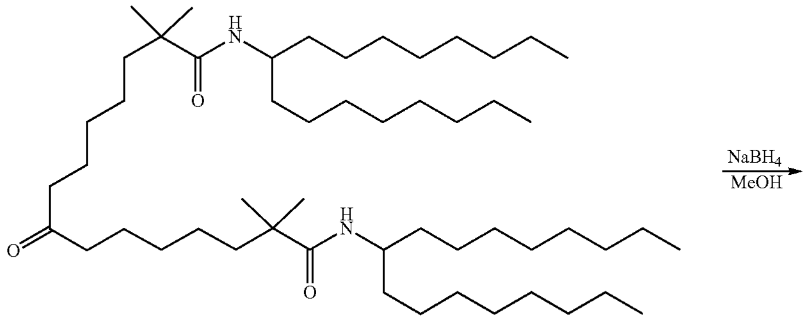
11-2

-continued
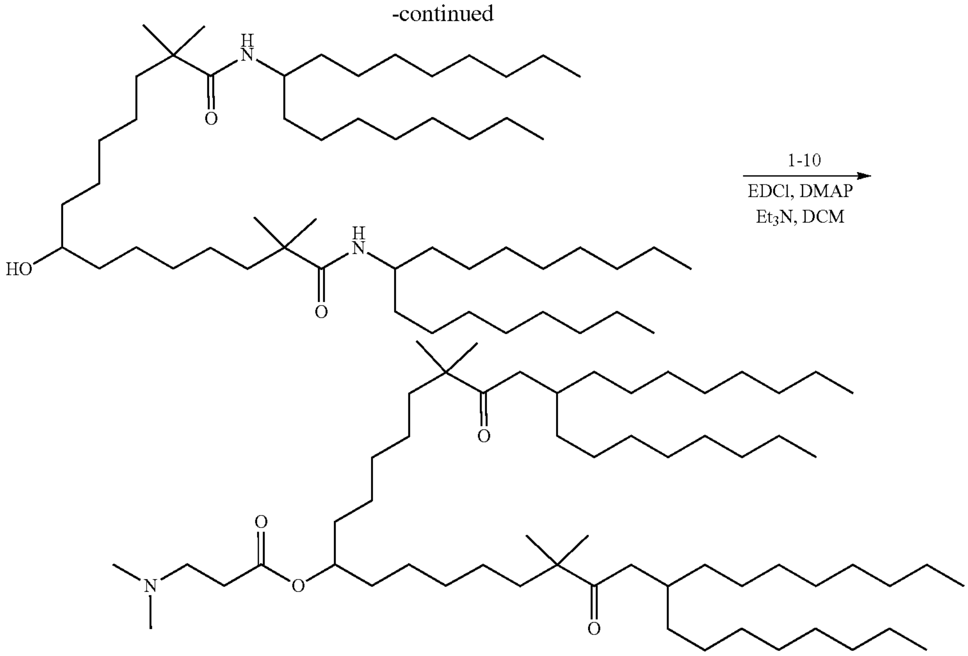
11
Referring to the method of Example 8, compound 11 (48.1 mg) was prepared.
$^1H$ NMR (400 MHz, $CDCl_3$): δ ppm 0.78 (t, J=7.2 Hz, 12H), 1.07 (s, 12H), 1.14-1.19 (m, 60H), 1.40 (m, 16H), 2.18 (s, 6H), 2.36-2.47 (m, 2H), 2.49-2.68 (m, 2H), 3.76-3.88 (m, 2H), 4.74-4.83 (m, 1H), 5.10-5.19 (m, 2H); ESI-MS m/z: 918.9 $[M+H]^+$.
Example 12: Synthesis of Compound 12
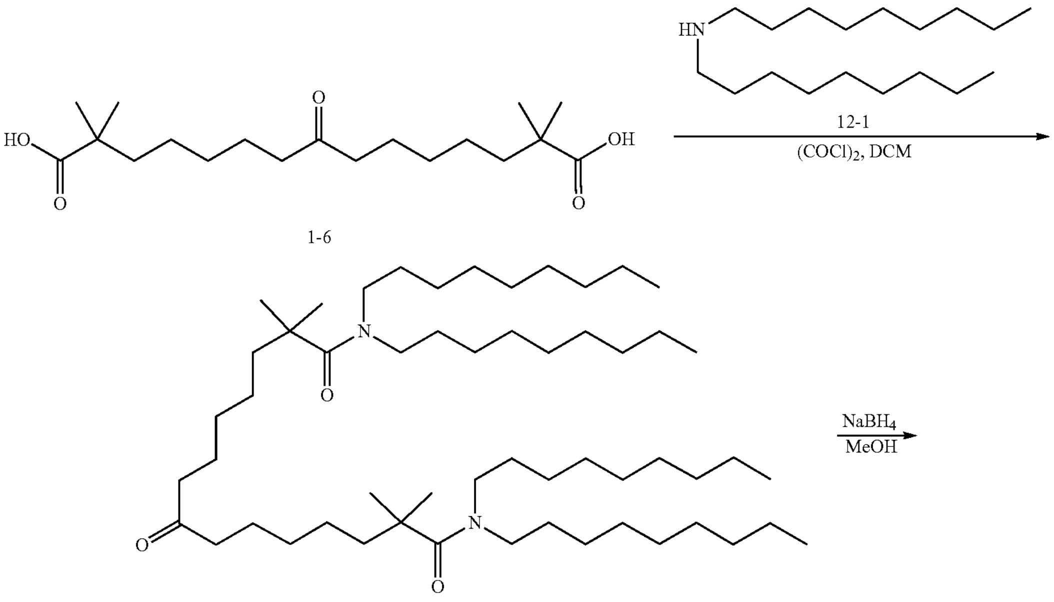
1-6
12-2

-continued
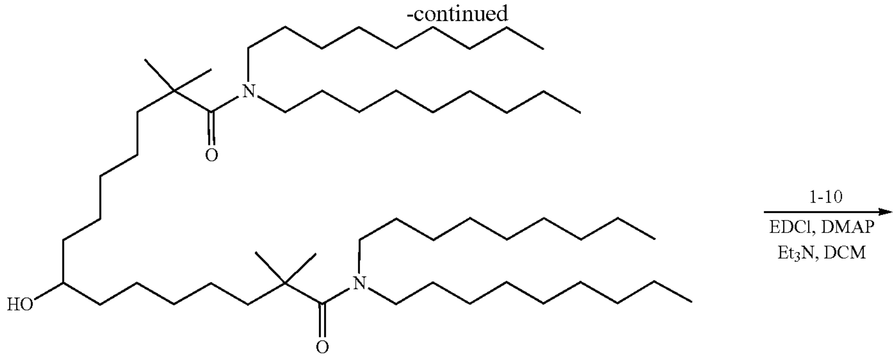
12-3
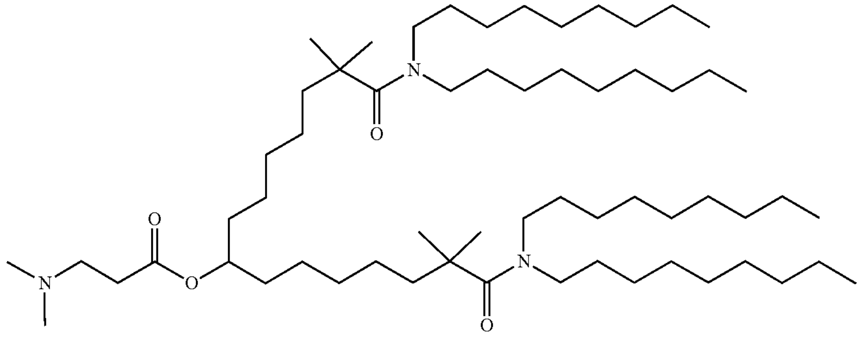
12
Referring to the method of Example 8, compound 12 (52 mg) was prepared.
$^{1}$H NMR (400 MHz, $CDCl_3$): δ ppm 0.82 (t, J=6.8 Hz, 12H), 1.15-1.32 (m, 72H), 1.54 (m, 16H), 2.31 (s, 6H), 2.51 (t, J=7.2 Hz, 2H), 2.60 (t, J=7.2 Hz, 2H), 3.14-3.33 (m, 8H), 4.75-4.83 (m, 1H); ESI-MS m/z: 946.9 $[M+H]^+$.
Example 13: Synthesis of Compound 13
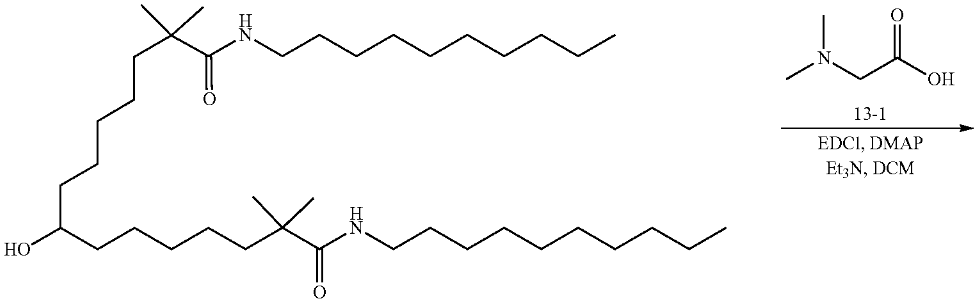
8-3
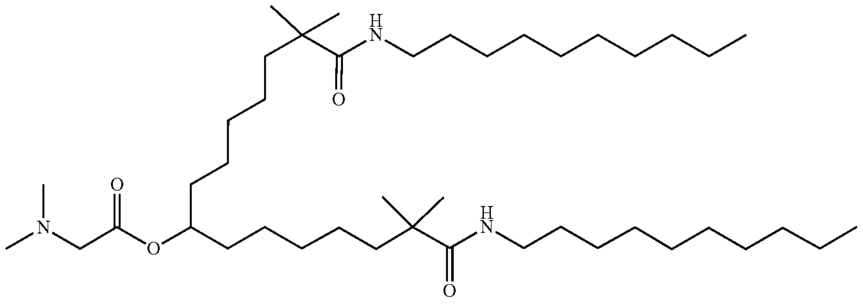
13

Referring to the method of Example 8, compound 13 (32 mg) was prepared.
$^1$H NMR (400 MHz, $CDCl_3$): δ ppm 0.81 (t, J=7.2 Hz, 6H), 1.19 (m, 52H), 1.41 (m, 12H), 2.26 (s, 6H), 3.05 (s, 2H), 3.16 (m, 4H), 4.83 (m, 1H), 5.51 (m, 2H); ESI-MS m/z: 708.7 $[M+H]^+$.
Example 14: Synthesis of Compound 14
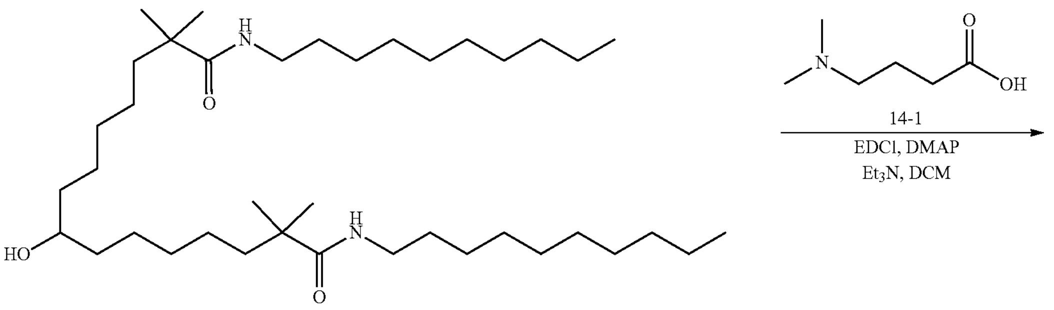
8-3
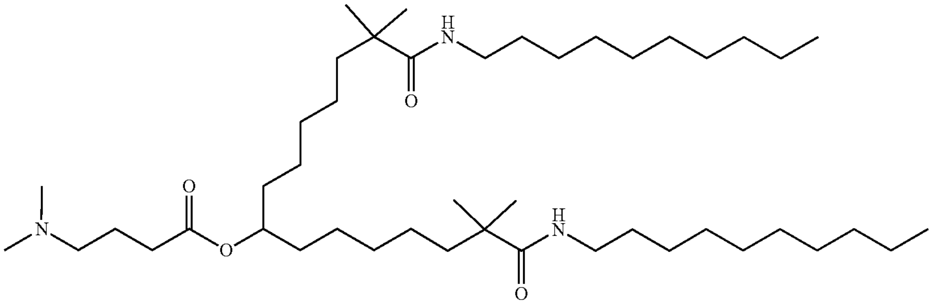
14
Referring to the method of Example 8, compound 14 (18 mg) was prepared.
$^1$H NMR (400 MHz, $CDCl_3$): δ ppm 0.81 (t, J=7.2 Hz, 6H), 1.07 (s, 12H), 1.08-1.31 (m, 44H), 1.35-1.47 (m, 8H), 1.71-1.84 (m, 2H), 2.09-2.38 (m, 10H), 3.12-3.27 (m, 4H), 4.70-4.82 (m, 1H), 5.49-5.63 (m, 2H); ESI-MS m/z: 736.7 $[M+H]^+$.
Example 15: Synthesis of Compound 15
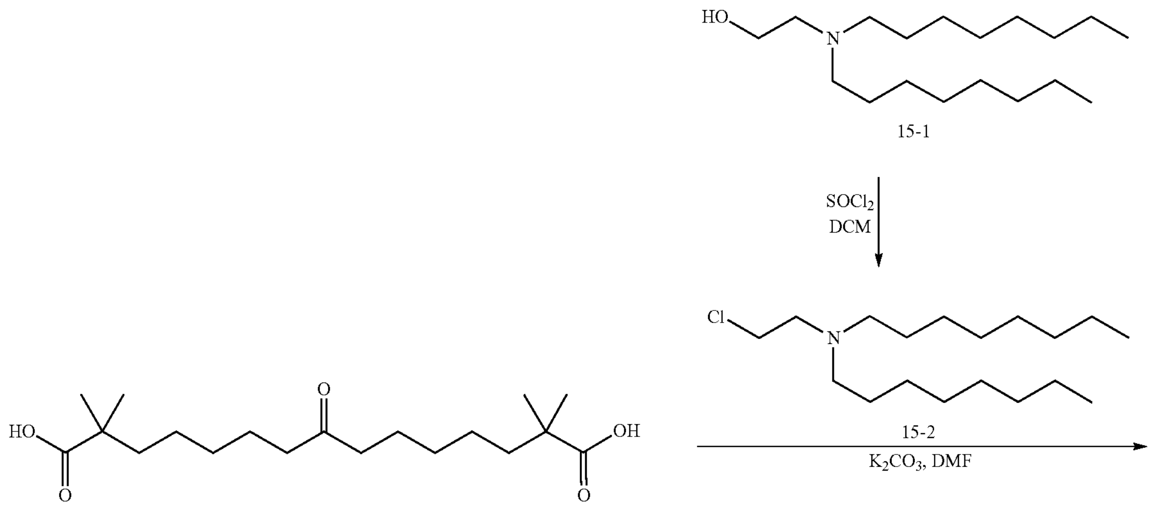
1-6

-continued

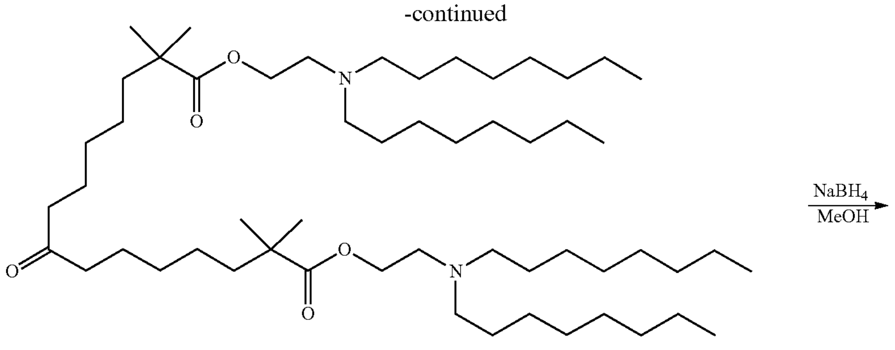

15-3

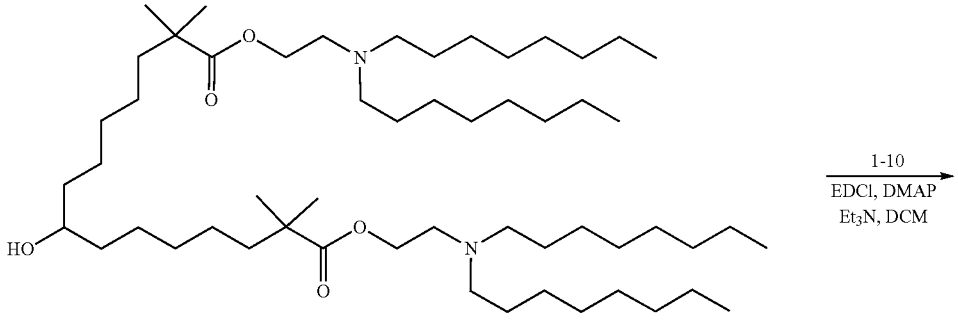

15-4

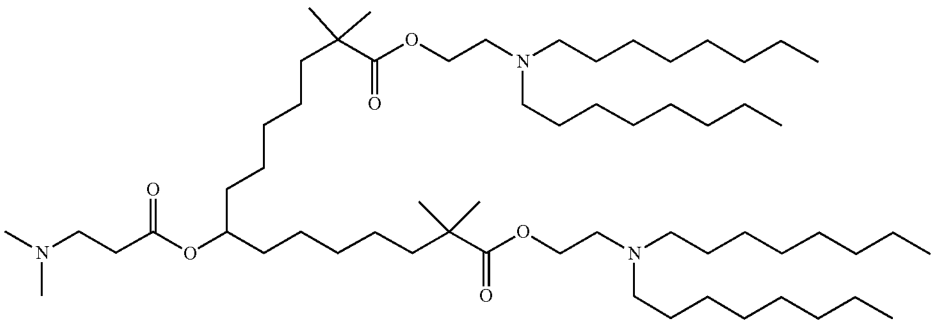

15

A solution of compound 15-1 (400 mg, 1.4 mmol) in dichloromethane (3.0 mL) was cooled to 0° C., then a solution of $SOCl_2$ (0.12 mL, 1.68 mmol) in dichloromethane (2.0 mL) was added dropwise. After the dropwise addition was completed, the mixture was stirred at 0° C. for another 1 h. After the reaction was completed, the reaction was quenched by adding saturated sodium bicarbonate solution to the reaction system, and the reaction system was extracted with dichloromethane. The organic phases were combined and the organic solvent was removed to give crude compound 15-2, which was used directly in the next reaction without purification.

Compound 1-6 (223, 0.65 mmol), 15-2 (496 mg, 1.63 mmol) and potassium carbonate (361 mg, 2.6 mmol) were dissolved in 5.0 mL of DMF and the reaction solution was heated to 70° C. to react for 6 hours. The reaction solution was cooled to room temperature, then the reaction was quenched by adding saturated sodium chloride solution to the reaction system, and the reaction system was extracted with dichloromethane. The organic phases were combined and the organic solvent was removed to give the crude product. The crude was purified by silica gel column to give compound 15-3.

Then referring to the method of Example 1, compound 15 (40 mg) was prepared.

$^1H$ NMR (400 MHz, $CDCl_3$): δ ppm 0.89 (t, J=7.2 Hz, 12H), 1.08 (s, 12H), 1.12-1.35 (m, 46H), 1.38-1.58 (m, 22H), 2.35 (s, 6H), 2.41-2.52 (m, 10H), 2.57-2.65 (m, 2H), 2.62 (m, 4H), 4.10 (t, J=6.4 Hz, 4H), 4.86 (m, 1H); ESI-MS m/z: 978.9 $[M+H]^+$.

Example 16: Synthesis of Compound 16

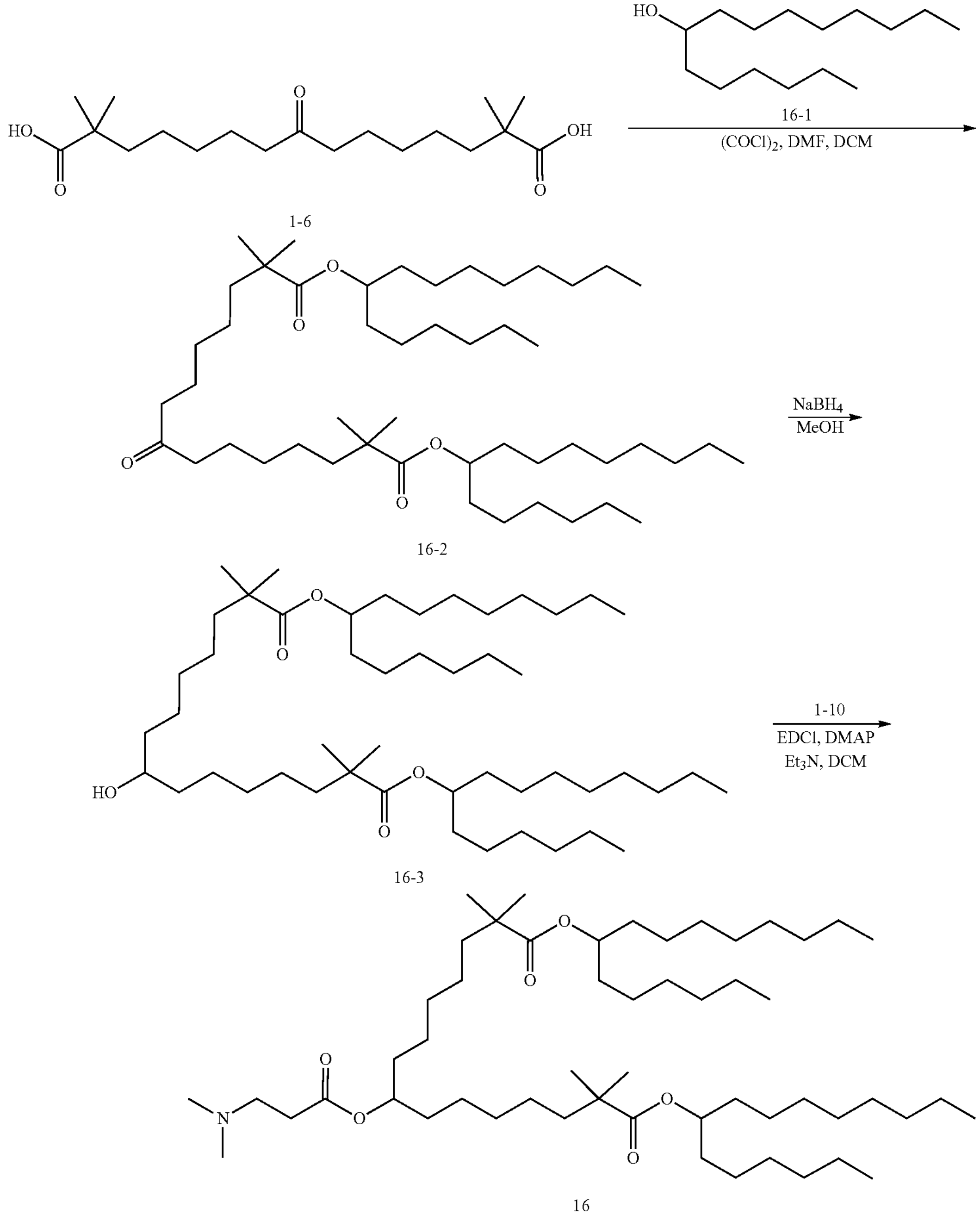

DMF (11 μL, 0.14 mmol) was added to a solution of compound 1-6 (460 mg, 1.34 mmol) in dichloromethane (5.0 mL) under ice bath conditions, and oxalyl chloride (0.47 mL, 5.37 mmol) was then added dropwise to the reaction solution. The ice bath was removed, and the mixture was stirred for 1 h at room temperature. The solvent was removed using a rotary-evaporator to give 255 mg of acyl chloride crude product as an oil, which was used directly in the next reaction step.

The above obtained acyl chloride crude product (255 mg, 0.67 mmol) was dissolved in 3.0 mL of 1,2-dichloroethane, and then compound 16-1 (384 mg, 1.68 mmol) was added to the reaction solution. The mixture was stirred at room temperature until the substrate was reacted completely. The solvent was removed using a rotary-evaporator to give the crude product, which was purified by silica gel column to give 300 mg of compound 16-2. $^1$H NMR (400 MHz, $CDCl_3$): δ ppm 0.78-0.83 (m, 12H), 1.07 (s, 12H), 1.13-1.22 (m, 48H), 1.49 (br s, 16H), 2.29 (t, J=7.50 Hz, 4H), 4.76 (m, 2H).

Compound 16-2 (300 mg, 0.39 mmol) was dissolved in 4.0 mL of methanol. Then $NaBH_4$ (45 mg, 1.17 mmol) was slowly added to the reaction solution and the mixture was stirred at room temperature for 2 h. The reaction solution was quenched with saturated ammonium chloride solution, extracted with ethyl acetate. The organic phases were combined and the organic solvent was removed to give 300 mg of crude compound 16-3, which was used directly in the next reaction without purification.

Crude compound 16-3 (300 mg, 0.39 mmol) was dissolved in 2.0 mL DMF, and then 1-10 (69 mg, 0.59 mmol), EDCI (225 mg, 1.17 mmol), triethylamine (119 mg, 1.17 mmol) and DMAP (48 mg, 0.39 mmol) were added. The mixture was stirred at room temperature until the reactants was reacted completely. The reaction solution was quenched with saturated sodium chloride solution and extracted with ethyl acetate. The organic phases were combined, dried over anhydrous sodium sulfate, and filtered. The filtrate was concentrated to dryness to give the crude product. The crude product was purified by preparative high performance liquid chromatography to give compound 16 (32.5 mg).

$^1$H NMR (400 MHz, $CDCl_3$): δ ppm 0.79 (t, J=7.2 Hz, 12H), 1.07 (s, 12H), 1.19 (m, 52H), 1.40-1.46 (m, 16H), 2.15 (s, 6H), 2.34-2.58 (m, 4H), 4.74-4.81 (m, 3H); ESI-MS m/z: 864.8 $[M+H]^+$.

Example 17: Synthesis of Compound 17

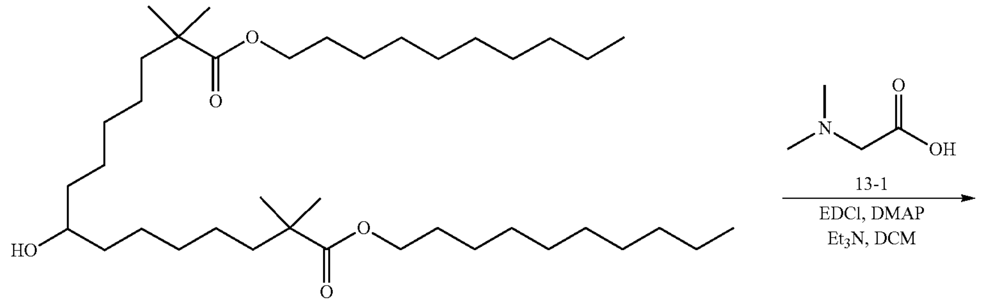

1-9

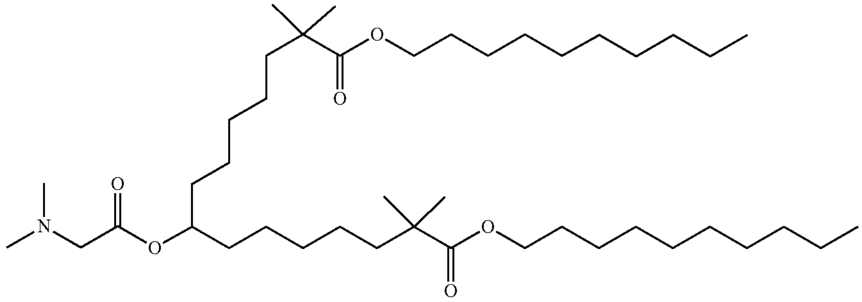

17

Referring to the method of Example 1, compound 17 was prepared as an oily product: 41.3 mg.

$^1$H NMR (400 MHz, $CDCl_3$): δ ppm 0.82 (t, J=7.2 Hz, 6H), 1.08 (s, 12H), 1.14-1.20 (m, 36H), 1.40-1.64 (m, 16H), 2.32 (s, 6H), 3.08-3.21 (m, 2H), 3.97 (t, J=7.2 Hz, 4H), 4.83-4.92 (m, 1H); ESI-MS m/z: 710.6 $[M+H]^+$.

Example 18: Synthesis of Compound 18

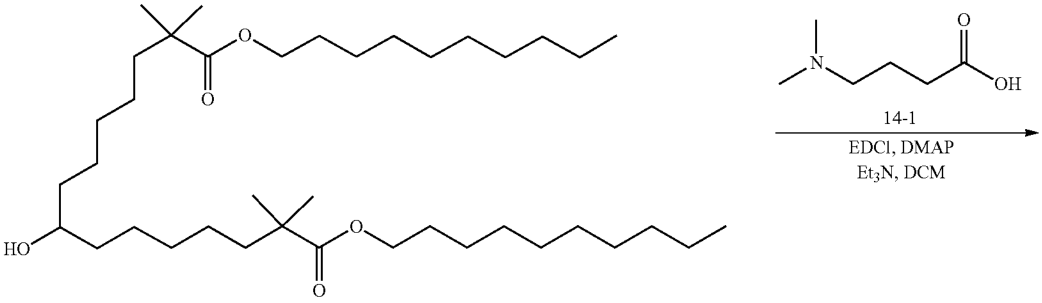

1-9

-continued
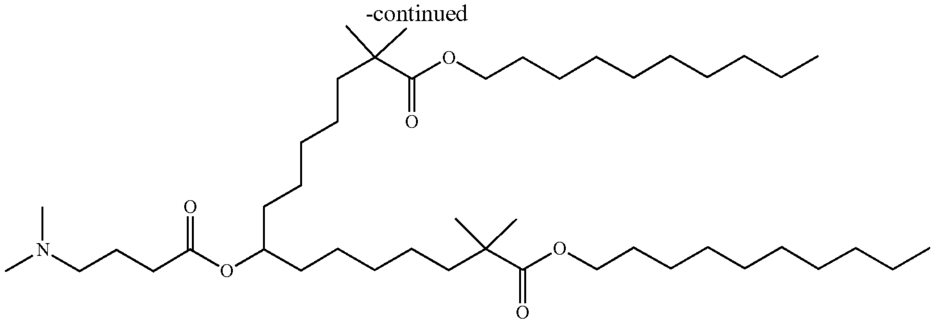
18
Referring to the method of Example 1, compound 18 was prepared as an oily product: 35.4 mg.
$^1$H NMR (400 MHz, $CDCl_3$): δ ppm 0.79 (t, J=7.2 Hz, 6H), 1.08 (s, 12H), 1.13-1.25 (m, 36H), 1.28-1.47 (m, 10H), 1.47-1.62 (m, 6H), 1.68-1.79 (m, 2H), 2.15 (s, 6H), 2.21-2.31 (m, 4H), 3.97 (t, J=7.2 Hz, 4H), 4.73-4.82 (m, 1H); ESI-MS m/z: 738.7 $[M+H]^+$.
Example 19: Synthesis of Compound 19
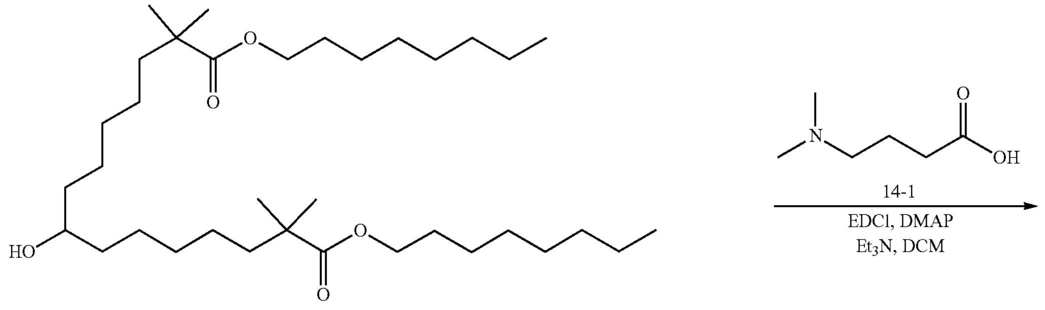
2-3
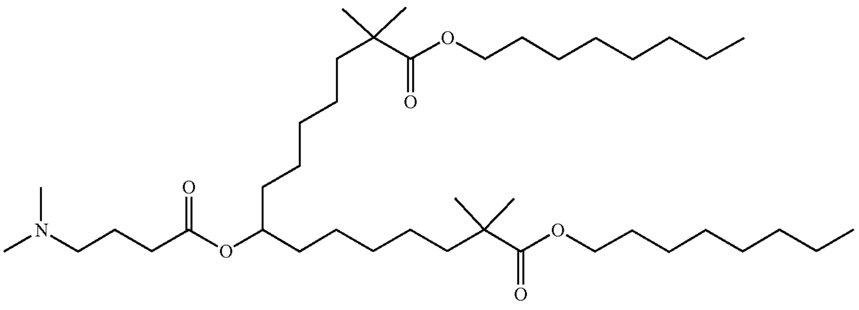
19
Referring to the method of Example 1, compound 19 was prepared as an oily product: 33.1 mg.
$^1$H NMR (400 MHz, $CDCl_3$): δ ppm 0.89 (t, J=7.2 Hz, 6H), 1.15 (s, 12H), 1.29 (m, 30H), 1.50 (m, 8H), 1.60 (m, 6H), 1.64 (m, 2H), 2.23 (s, 6H), 2.33 (m, 4H), 4.05 (t, J=6.8 Hz, 4H), 4.86 (m, 1H); ESI-MS m/z: 682.6 $[M+H]^+$.

Example 20: Synthesis of Compound 20
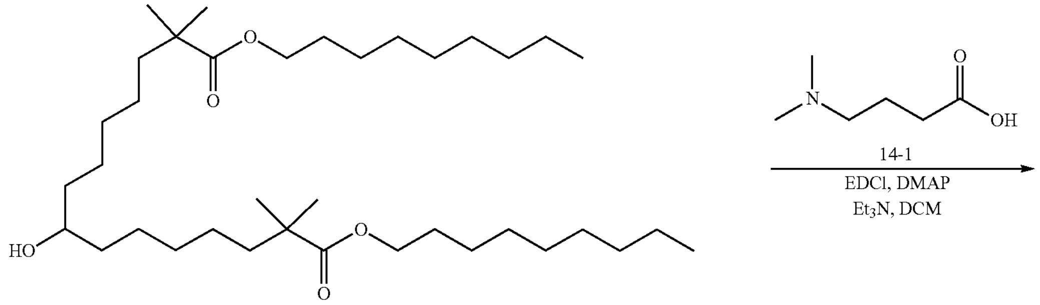
3-3
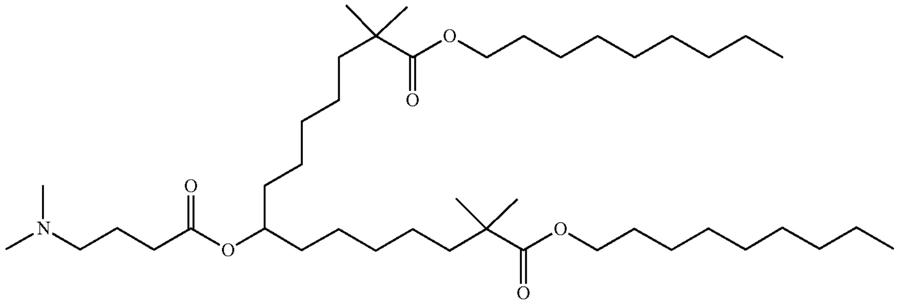
20
Referring to the method of Example 1, compound 20 was prepared as an oily product: 302 mg.
$^1$H NMR (400 MHz, $CDCl_3$): δ ppm 0.89 (t, J=7.2 Hz, 6H), 1.15 (s, 12H), 1.27 (m, 34H), 1.47 (m, 8H), 1.51 (m, 6H), 1.79 (m, 2H), 2.23 (s, 6H), 2.33 (m, 4H), 4.04 (t, J=6.8 Hz, 4H), 4.85 (m, 1H); ESI-MS m/z: 710.7 $[M+H]^+$.
Example 21: Synthesis of Compound 21
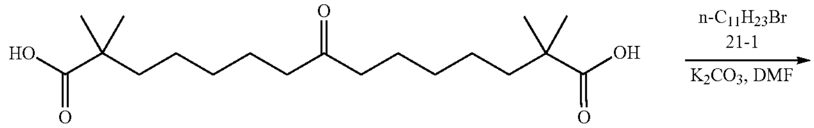
1-6
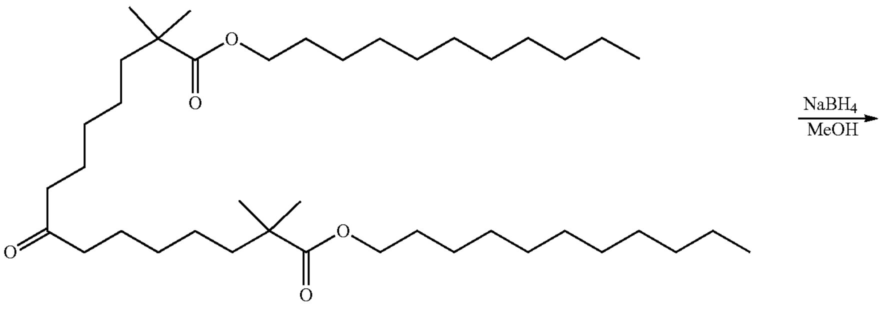
21-2

-continued
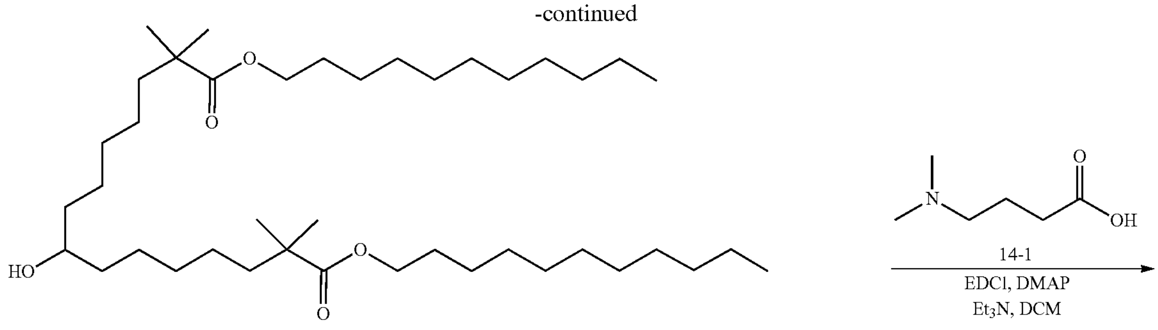
21-3
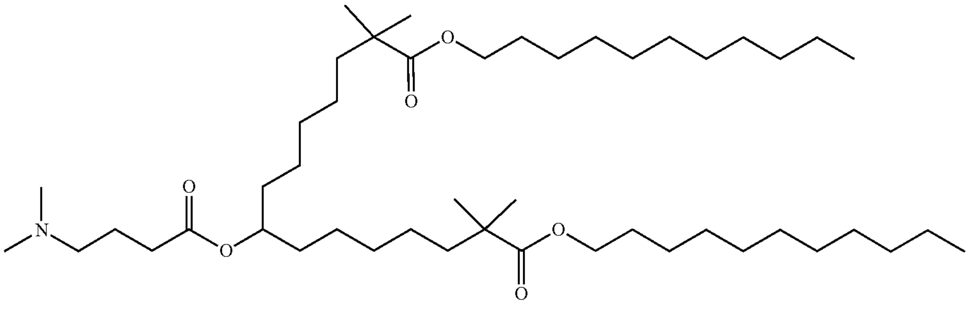
21
Referring to the method of Example 1, compound 21 was prepared as an oily product: 31.2 mg.
$^1$H NMR (400 MHz, $CDCl_3$): δ ppm 0.79 (t, J=7.2 Hz, 6H), 1.08 (s, 12H), 1.25 (m, 44H), 1.39 (m, 8H), 1.51 (m, 4H), 1.82 (m, 2H), 2.25 (t, J=7.2 Hz, 2H), 2.32 (s, 6H), 2.41 (m, 2H), 3.96 (t, J=6.8 Hz, 4H), 4.75 (m, 1H); ESI-MS m/z: 766.7 $[M+H]^+$.
Example 22: Synthesis of Compound 22
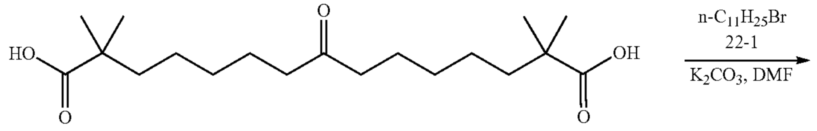
1-6
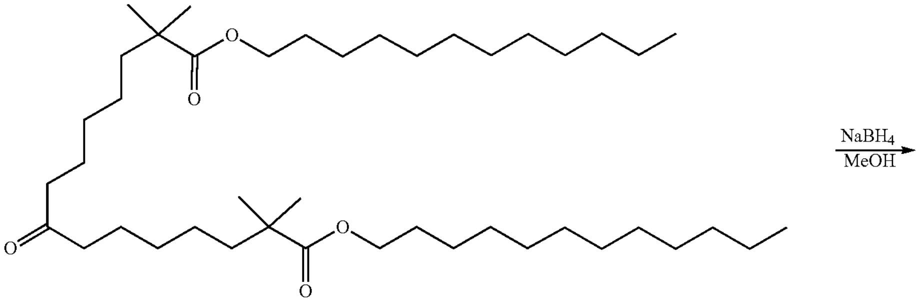
22-2

-continued
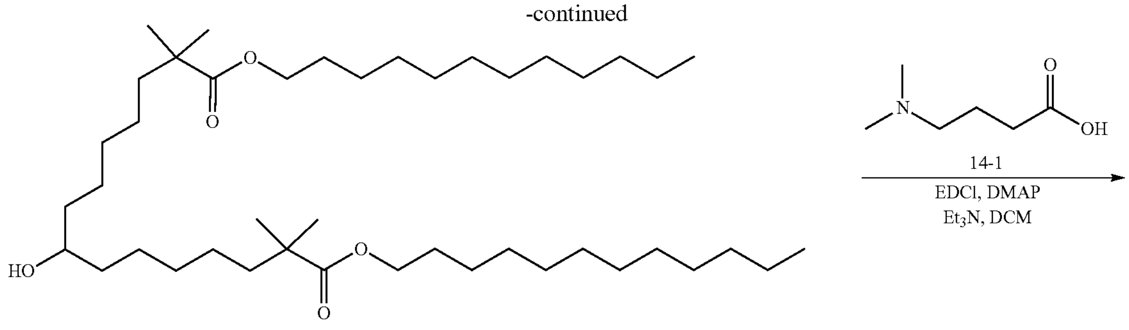
22-3
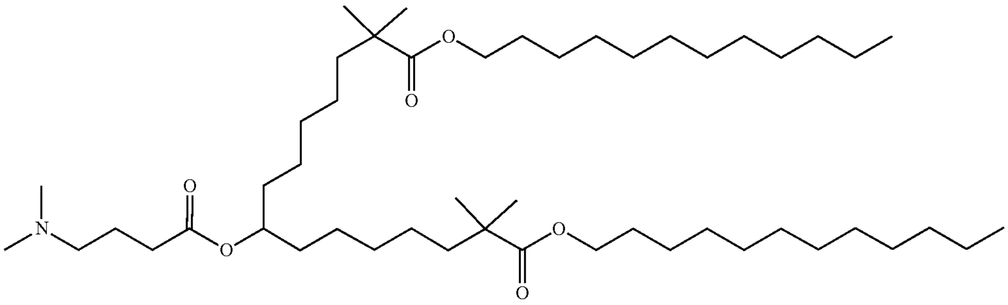
22
Referring to the method of Example 1, compound 22 was prepared as an oily product: 31.8 mg.
$^1$H NMR (400 MHz, $CDCl_3$): δ ppm 0.79 (t, J=7.2 Hz, 6H), 1.07 (s, 12H), 1.28 (m, 48H), 1.40 (m, 8H), 1.53 (m, 4H), 1.84 (m, 2H), 2.26 (t, J=7.2 Hz, 2H), 2.35 (s, 6H), 2.48 (m, 2H), 3.98 (t, J=6.8 Hz, 4H), 4.75 (m, 1H); ESI-MS m/z: 794.7 $[M+H]^+$.
Example 23: Synthesis of Compound 23
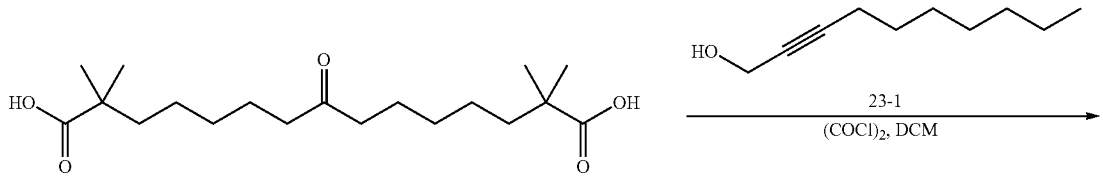
1-6
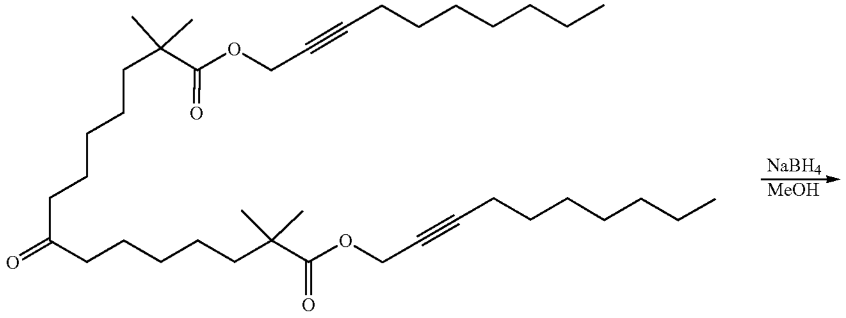
23-2

-continued
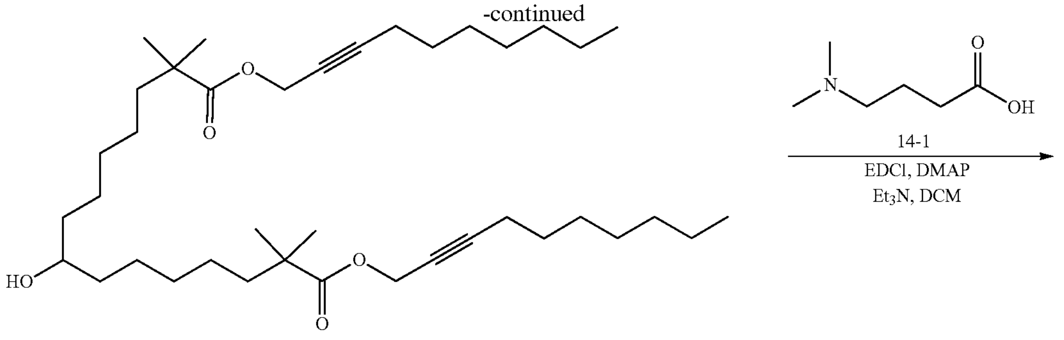
23-3
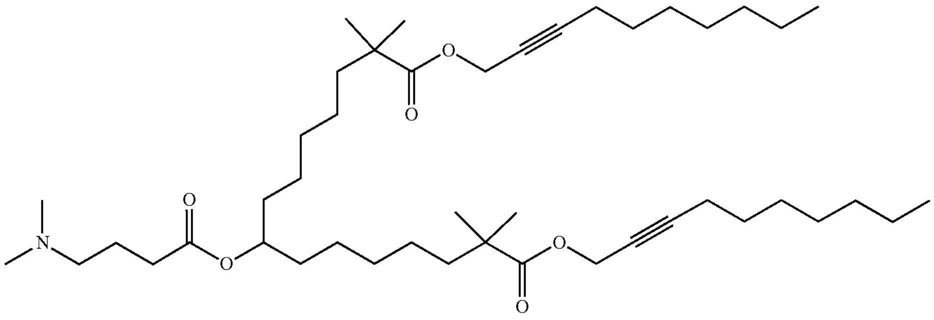
23
Referring to the method of Example 7, compound 23 was prepared as an oily product: 31.0 mg.
$^1$H NMR (400 MHz, $CDCl_3$): δ ppm 0.87 (t, J=7.2 Hz, 6H), 1.16 (s, 12H), 1.20-1.39 (m, 28H), 1.45-1.54 (m, 12H), 1.74-1.82 (m, 2H), 2.12-2.35 (m, 14), 4.63 (t, J=2.4 Hz, 4H), 4.79-4.88 (m, 1H); ESI-MS m/z: 730.6 $[M+H]^+$.
Example 24: Synthesis of Compound 24
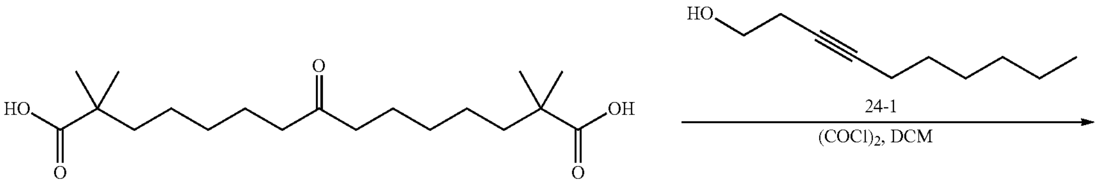
1-6
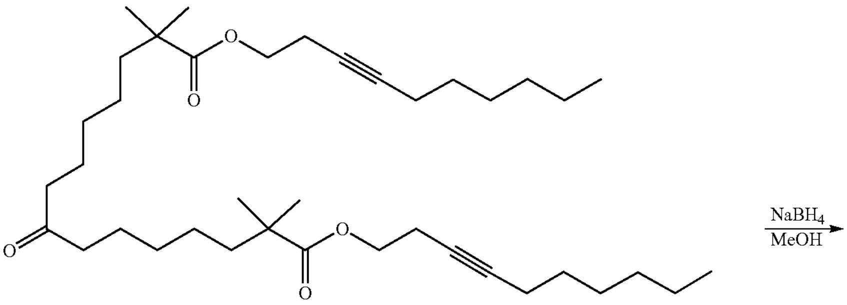
24-2

-continued
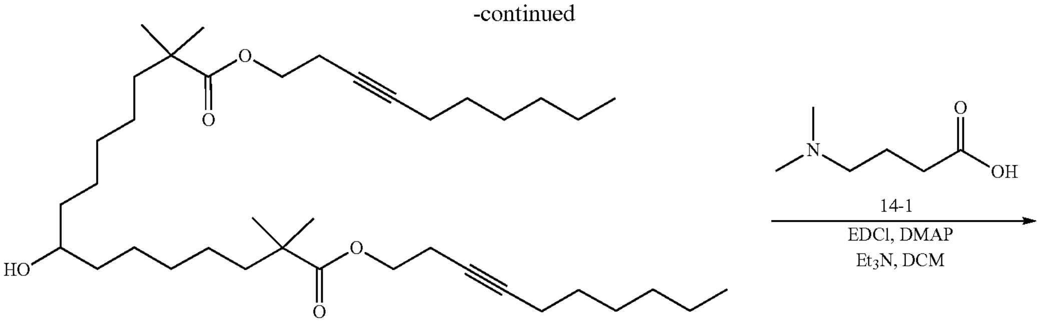
24-3
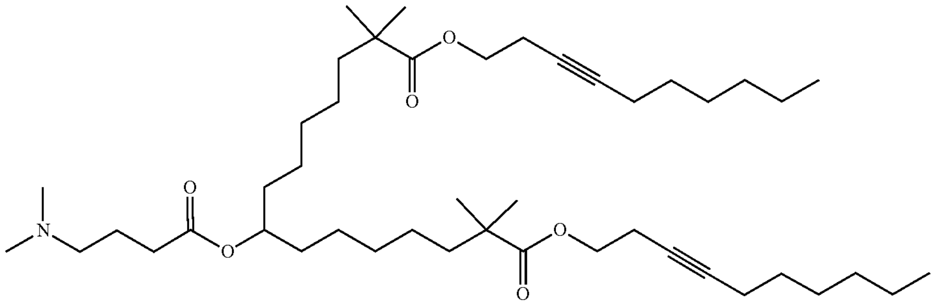
24
Referring to the method of Example 7, compound 24 was prepared as an oily product: 31.0 mg.
$^{1}$H NMR (400 MHz, $CDCl_3$): δ ppm 0.88 (t, J=7.2 Hz, 6H), 1.15 (s, 12H), 1.20-1.38 (m, 24H), 1.43-1.52 (m, 12H), 1.76-1.84 (m, 2H), 2.09-2.14 (m, 4H), 2.23 (s, 6H), 2.28-2.36 (m, 4H), 2.43-2.49 (m, 4H), 4.10 (t, J=7.2 Hz, 4H), 4.80-4.88 (m, 1H); ESI-MS m/z: 730.6 $[M+H]^+$.
Example 25: Synthesis of Compound 25
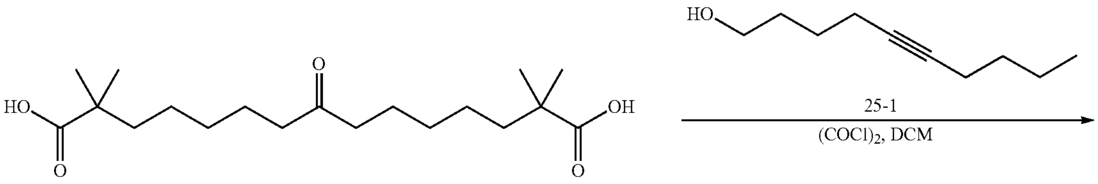
1-6
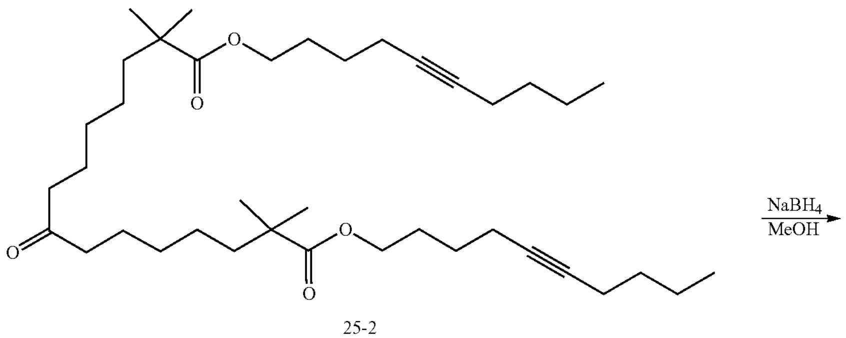
25-2

-continued
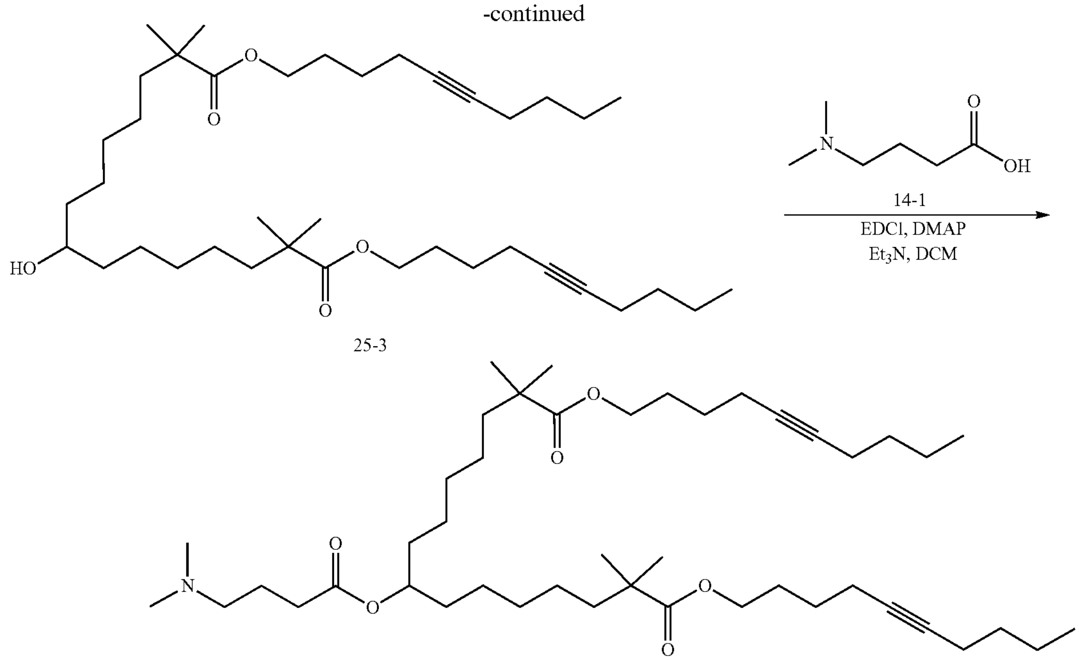
25-3
25
Referring to the method of Example 7, compound 25 was prepared as an oily product: 32.1 mg.
$^1$H NMR (400 MHz, $CDCl_3$): δ ppm 0.84 (t, J=7.2 Hz, 6H), 1.08 (s, 12H), 1.02-1.21 (m, 12H), 1.38-1.47 (m, 22H), 1.59-1.78 (m, 6H), 2.02-2.17 (m, 14H), 2.19-2.30 (m, 4H), 4.01 (t, J=6.8 Hz, 4H), 4.71-4.83 (m, 1H); ESI-MS m/z: 730.6 $[M+H]^+$.
Example 26: Synthesis of Compound 26
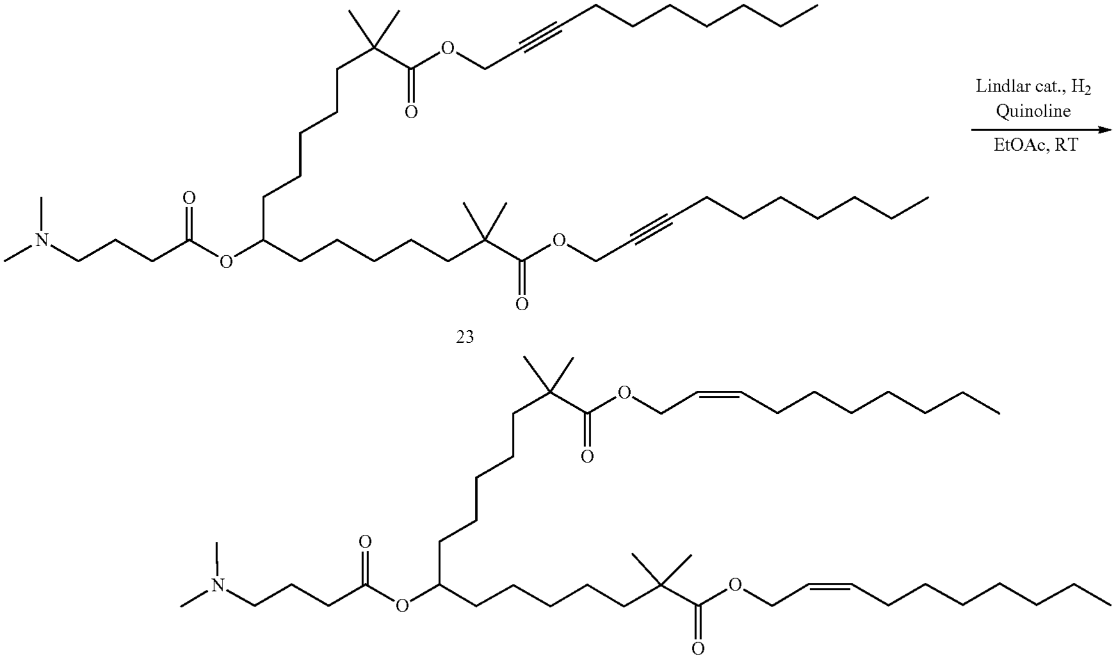
23
26

Compound 23 (300 mg, 0.41 mmol) and quinoline (106 mg, 0.82 mmol) were dissolved in 3.0 mL of ethyl acetate, and the air in the reaction system was replaced with nitrogen for 2-3 min at room temperature, then lindlar catalyst (16.9 mg) was added. Hydrogen gas was introduced to the reaction solution and the air was replaced with hydrogen for 2~3 min. The reaction system was kept under hydrogen atmosphere (15 psi) at room temperature for 30 min. The complete disappearance of the reactants was monitored by LC-MS. The reaction solution was filtered, and the filter cake was rinsed with ethyl acetate 3-4 times. The combined ethyl acetate was collected and the organic solvent was removed using a rotary-evaporator to give the crude product, which was purified by preparative high performance liquid chromatography to give compound 26 (31.3 mg).

$^1H$ NMR (400 MHz, $CDCl_3$): δ ppm 0.81 (t, J=7.2 Hz, 6H), 1.08 (s, 12H), 1.15-1.28 (m, 32H), 1.38-1.44 (m, 8H), 1.70-1.79 (m, 2H), 2.01 (m, 4H), 2.15 (s, 6H), 2.16-2.28 (m, 4H), 4.54 (d, J=12.0 Hz, 4H), 4.75 (m, 1H), 5.39-5.59 (m, 4H); ESI-MS m/z: 734.6 $[M+H]^+$.

Example 27: Synthesis of Compound 27

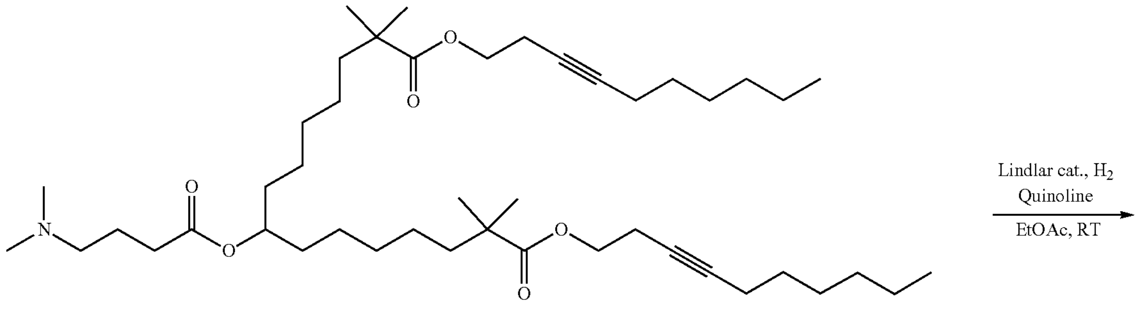

24

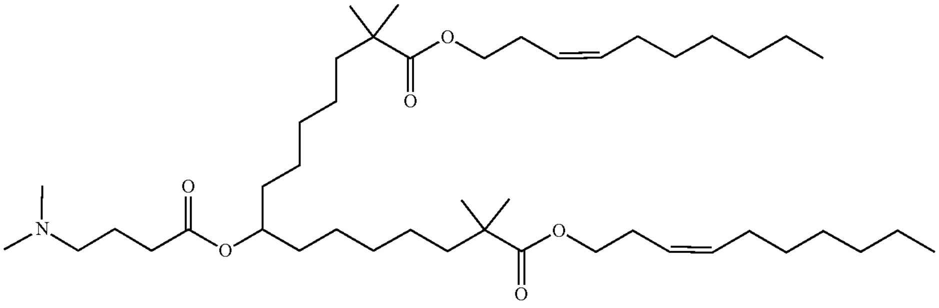

27

Referring to the method of Example 26, compound 27 was prepared as an oily product: 35.0 mg.

$^1H$ NMR (400 MHz, $CDCl_3$): δ ppm 0.82 (m, 6H), 1.08 (s, 12H), 1.14-1.31 (m, 28H), 1.37-1.45 (m, 8H), 1.70-1.79 (m, 2H), 1.96 (m, 4H), 2.06-2.36 (m, 14H), 3.98 (t, J=7.2 Hz, 4H), 4.74-4.82 (m, 1H), 5.22-5.31 (m, 2H), 5.37-5.48 (m, 2H); ESI-MS m/z: 734.7 $[M+H]^+$.

Example 28: Synthesis of Compound 28

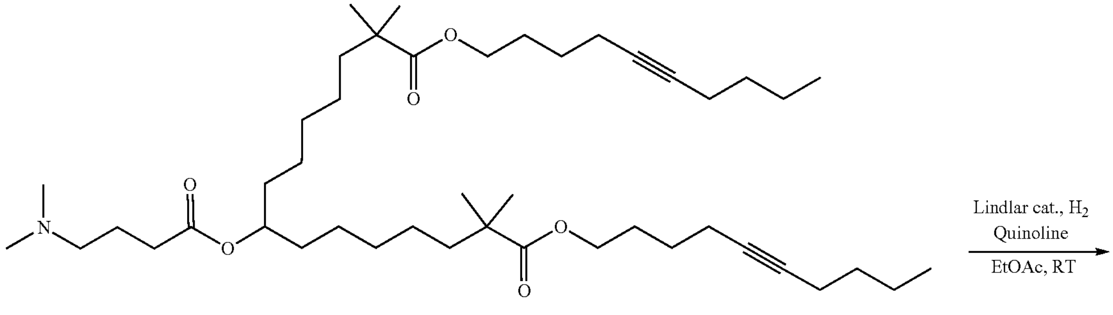

25

-continued
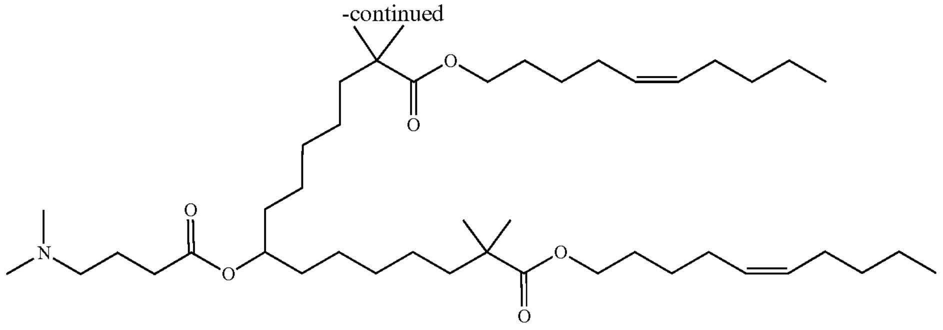
28
Referring to the method of Example 26, compound 28 was prepared as an oily product: 31.8 mg.
$^1$H NMR (400 MHz, $CDCl_3$): δ ppm 0.92 (t, J=6.8 Hz, 6H), 1.18 (s, 12H), 1.21-1.39 (m, 22H), 1.40-1.59 (m, 12H), 1.60-1.72 (m, 4H), 1.89-2.01 (m, 2H), 2.02-2.15 (m, 8H), 2.34-2.69 (m, 8H), 4.08 (t, J=6.4 Hz, 4H), 4.82-4.92 (m, 1H), 5.30-5.48 (m, 4H); ESI-MS m/z: 734.6 $[M+H]^+$.
Example 30: Synthesis of Compound 30
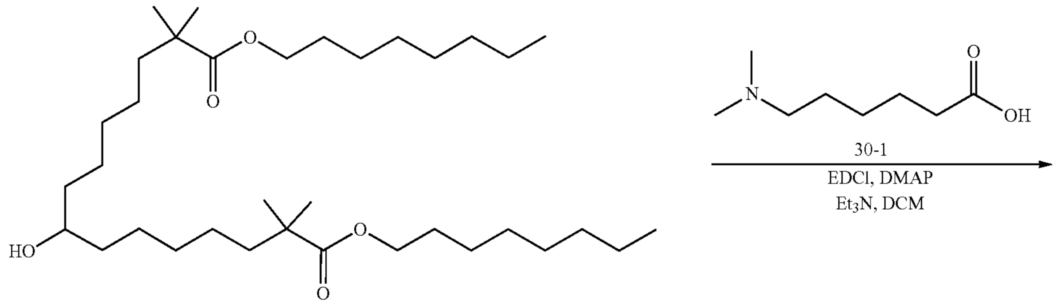
2-3
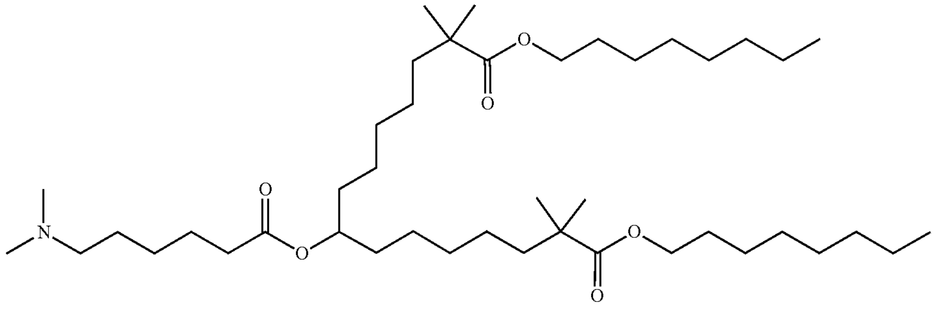
30
Referring to the method of Example 1, compound 30 was prepared as an oily product: 33.0 mg.
$^1$H NMR (400 MHz, $CDCl_3$): δ ppm 0.92 (t, J=6.8 Hz, 6H), 1.18 (s, 12H), 1.19-1.37 (m, 36H), 1.45-1.57 (m, 8H), 1.58-1.74 (m, 8H), 2.27-2.50 (m, 8H), 4.07 (t, J=6.8 Hz, 4H), 4.83-4.90 (m, 1H); ESI-MS m/z: 710.6 $[M+H]^+$.

Example 32: Synthesis of Compound 32
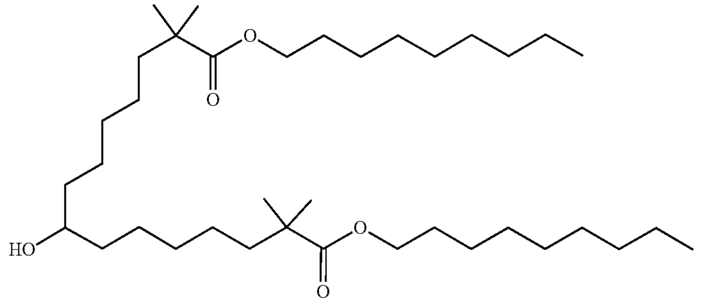
3-3
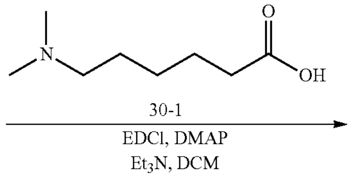
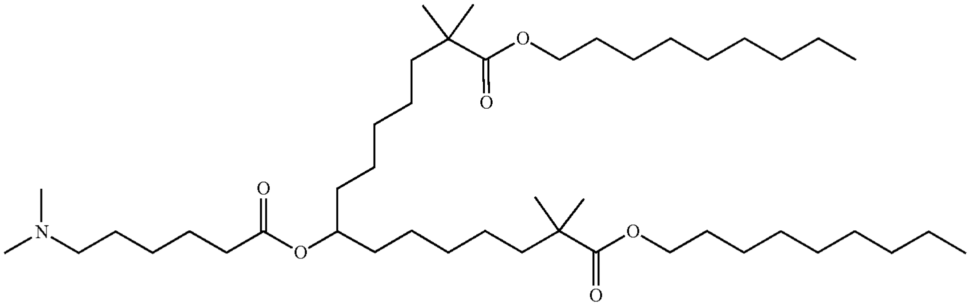
32
Referring to the method of Example 1, compound 32 was prepared as an oily product: 31.1 mg.
$^1$H NMR (400 MHz, $CDCl_3$): δ ppm 0.80 (t, J=6.8 Hz, 6H), 1.08 (s, 12H), 1.20-1.27 (m, 34H), 1.34-1.47 (m, 12H), 1.48-1.62 (m, 8H), 2.15 (s, 6H), 2.19-2.24 (m, 4H), 3.97 (t, J=6.8 Hz, 4H), 4.74-4.80 (m, 1H); ESI-MS m/z: 738.6 $[M+H]^+$.
Example 33: Synthesis of Compound 33
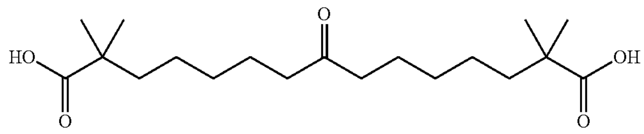
1-6
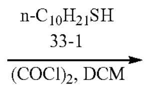
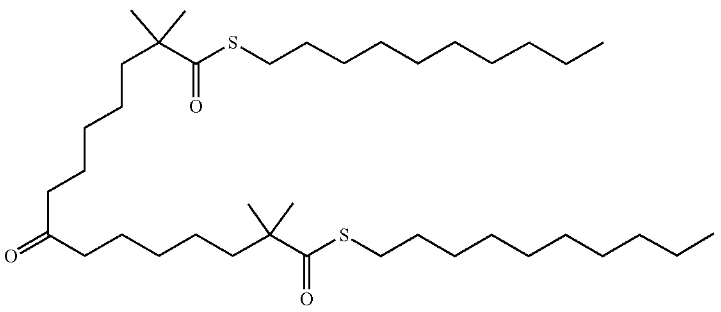
33-2
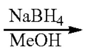

-continued

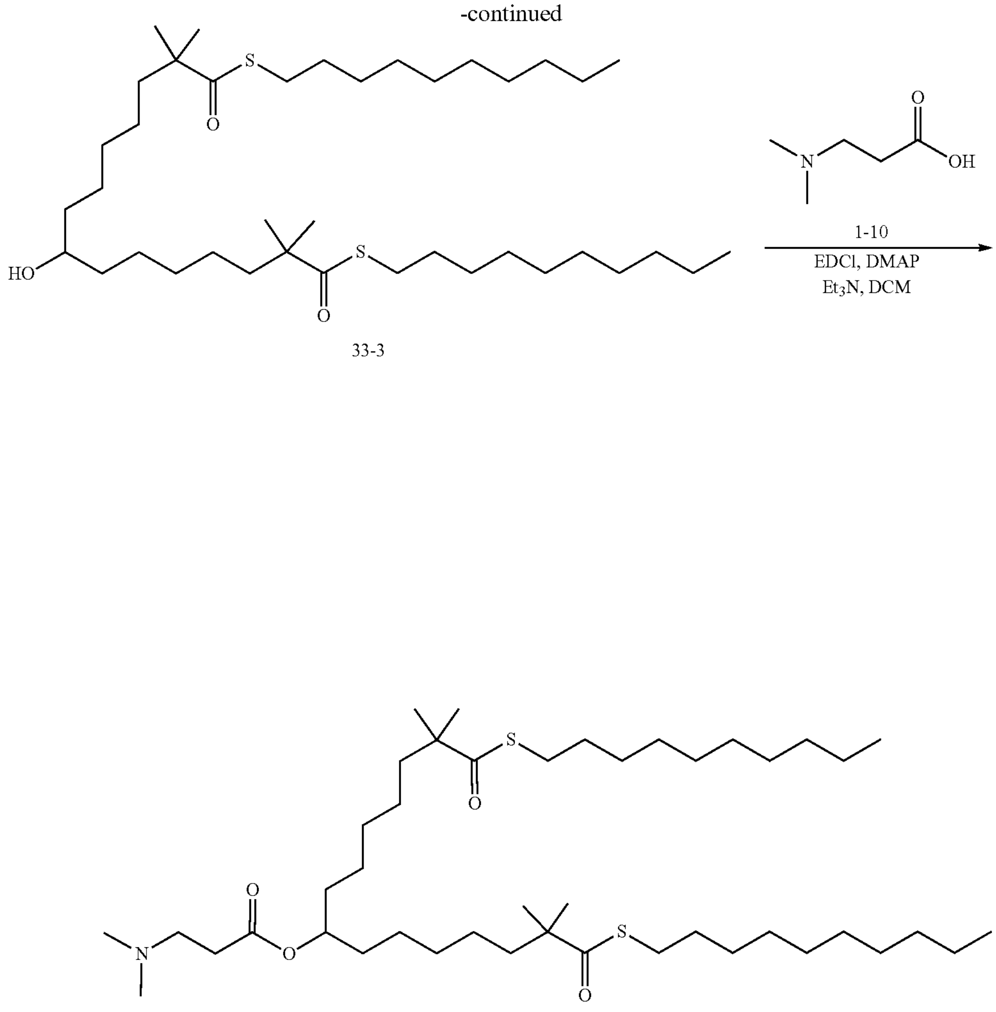

33-3

33

Compound 1-6 (448 mg, 1.3 mmol) was dissolved in 5.0 mL of dichloromethane, and the reaction system was cooled to 0° C. in an ice bath. DMF (10 μL, 0.13 mmol) was added, and oxalyl chloride (0.44 mL, 5.2 mmol) was then added dropwise to the reaction solution. The ice bath was removed after the dropwise addition was completed and the mixture was stirred for 1 h at room temperature. The solvent was removed using a rotary-evaporator to give acyl chloride crude product (330 mg) as an oil, which was used directly in the next reaction step.

1-Decanethiol 33-1 (455 mg, 2.61 mmol) was added to a solution of crude acyl chloride (330 mg, 0.87 mmol) in DCE (3.0 mL), and the reaction was heated to 70° C. to react overnight. The reaction solution was cooled to room temperature and the solvent was removed using a rotary-evaporator to give the crude product, which was purified by silica gel column to give compound 33-2 (400 mg). $^1$H NMR (400 MHz, $CDCl_3$): δ ppm 0.84-0.87 (m, 6H), 1.14-1.18 (m, 12H), 1.20-1.28 (m, 36H), 1.48-1.55 (m, 12H), 2.33 (t, J=7.2 Hz, 4H), 2.79 (t, J=7.2 Hz, 4H).

Compound 33-2 (300 mg, 0.46 mmol) was dissolved in 3.0 mL of methanol and $NaBH_4$ (52.5 mg, 1.38 mmol) was added in batches. The reaction solution was stirred under nitrogen atmosphere at room temperature for 2 h. The complete disappearance of the reaction material was monitored by TLC. The reaction solution was quenched by adding saturated ammonium chloride solution, and extracted with ethyl acetate. The organic phases were combined, dried over anhydrous sodium sulfate, and filtered. The filtrate was collected and concentrated to give 300 mg of crude compound 33-3, which was directly used in the next reaction step without further purification.

Crude compound 33-3 (150 mg, 0.23 mmol) was dissolved in 3.0 mL of dichloromethane, and 1-10 (80.2 mg, 0.69 mmol), EDCI (131 mg, 0.69 mmol), triethylamine (0.1 mL, 0.69 mmol) and DMAP (28 mg, 0.23 mmol) were added to the reaction system. The reaction solution was stirred at room temperature for 12 h. The reaction solution was then quenched by adding saturated ammonium chloride solution, and extracted with dichloromethane. The organic phases were combined, dried over anhydrous sodium sulfate, and filtered. The filtrate was collected and concentrated to give the crude product, which was passed through preparative high performance liquid chromatography to give compound 33 (28.6 mg).

$^1$H NMR (400 MHz, $CDCl_3$): δ ppm 0.81 (t, J=7.2 Hz, 6H), 1.15 (s, 12H), 1.31 (m, 40H), 1.48 (m, 12H), 2.23 (s, 6H), 2.42 (m, 4H), 2.80 (t, J=7.2 Hz, 4H), 4.82 (m, 1H); ESI-MS m/z: 756.6 $[M+H]^+$.

Example 34: Synthesis of Compound 34
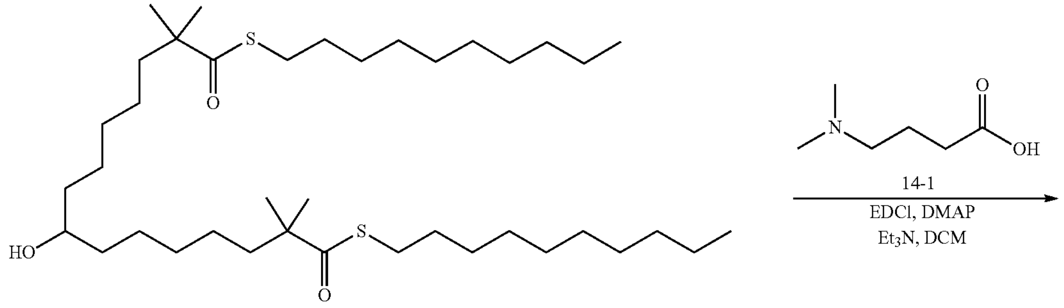
33-3
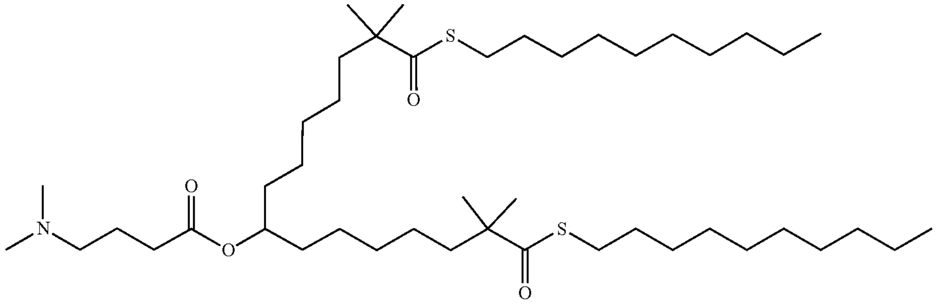
34
Referring to the method of Example 33, compound 34 was prepared as an oily product: 105.2 mg.
$^1$H NMR (400 MHz, $CDCl_3$): δ ppm 0.85 (t, J=7.2 Hz, 6H), 1.15 (s, 12H), 1.6-1.32 (m, 40H), 1.37-1.53 (m, 14H), 1.75 (m, 2H), 2.24-2.34 (m, 8H), 2.80 (t, J=7.2 Hz, 4H), 4.72-4.82 (m, 1H); ESI-MS m/z: 770.6 $[M+H]^+$.
Example 36: Synthesis of Compound 36
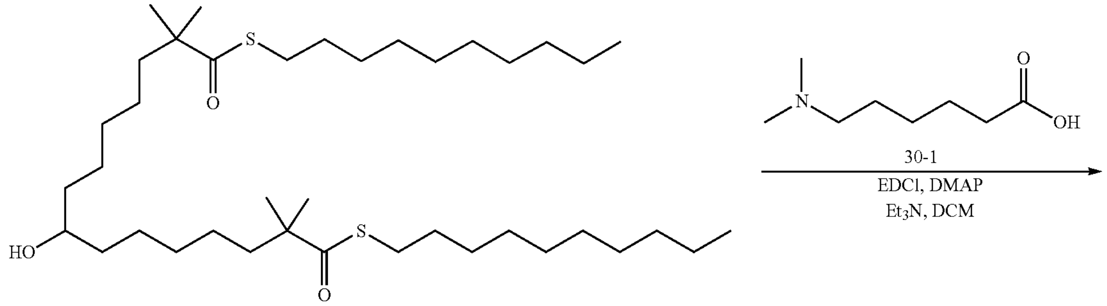
33-3
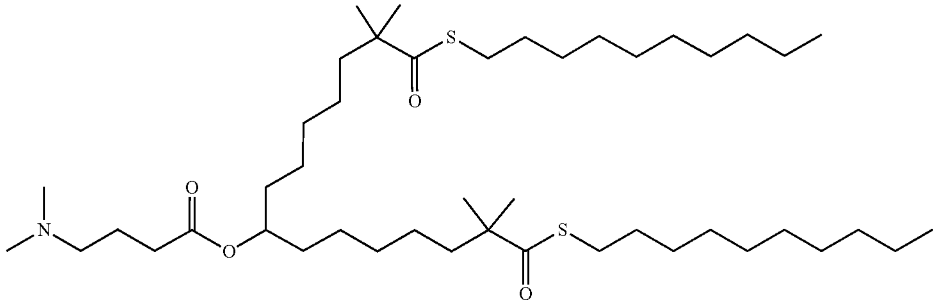
36

Referring to the method of Example 33, compound 36 was prepared as an oily product: 33.4 mg.
$^1$H NMR (400 MHz, $CDCl_3$): δ ppm 0.86 (t, J=6.8 Hz, 6H), 1.16 (s, 12H), 1.18-1.38 (m, 40H), 1.41-1.59 (m, 16H), 1.61-1.67 (m, 2H), 2.19-2.33 (m, 10H), 2.82 (t, J=7.2 Hz, 4H), 4.83 (m, H); ESI-MS m/z: 798.6 $[M+H]^+$.
Example 37: Synthesis of Compound 37
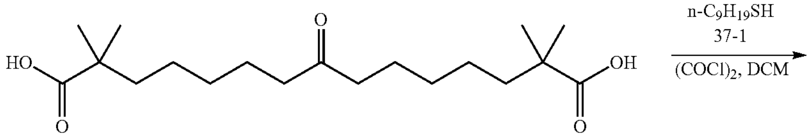
1-6
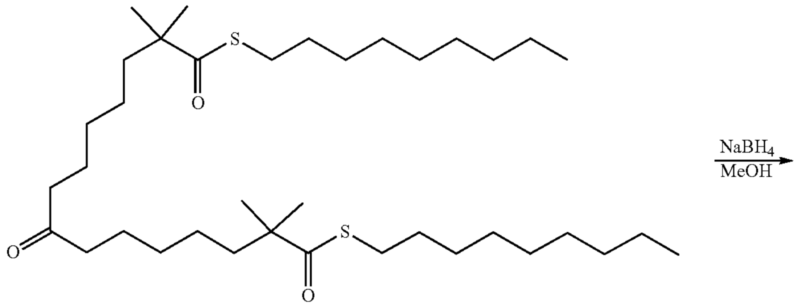
37-2
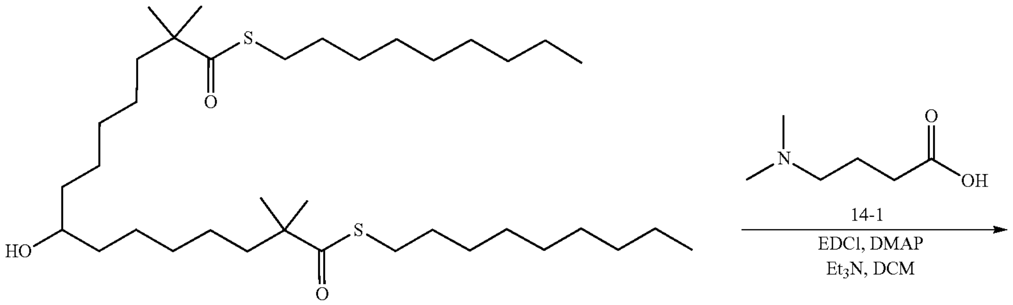
37-3
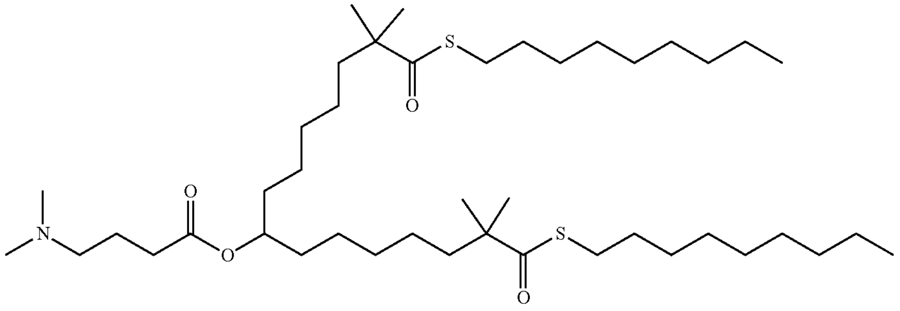
37
Referring to the method of Example 33, compound 37 was prepared as an oily product: 33.2 mg.
$^1$H NMR (400 MHz, $CDCl_3$): δ ppm 0.87 (t, J=6.8 Hz, 6H), 1.20 (s, 12H), 1.19-1.37 (m, 36H), 1.39-1.56 (m, 12H), 1.75-1.84 (m, 2H), 2.24 (s, 6H), 2.28-2.34 (m, 4H), 2.81 (t, J=7.2 Hz, 4H), 4.79-4.87 (m, 1H); ESI-MS m/z: 742.6 $[M+H]^+$.

Example 39: Synthesis of Compound 39
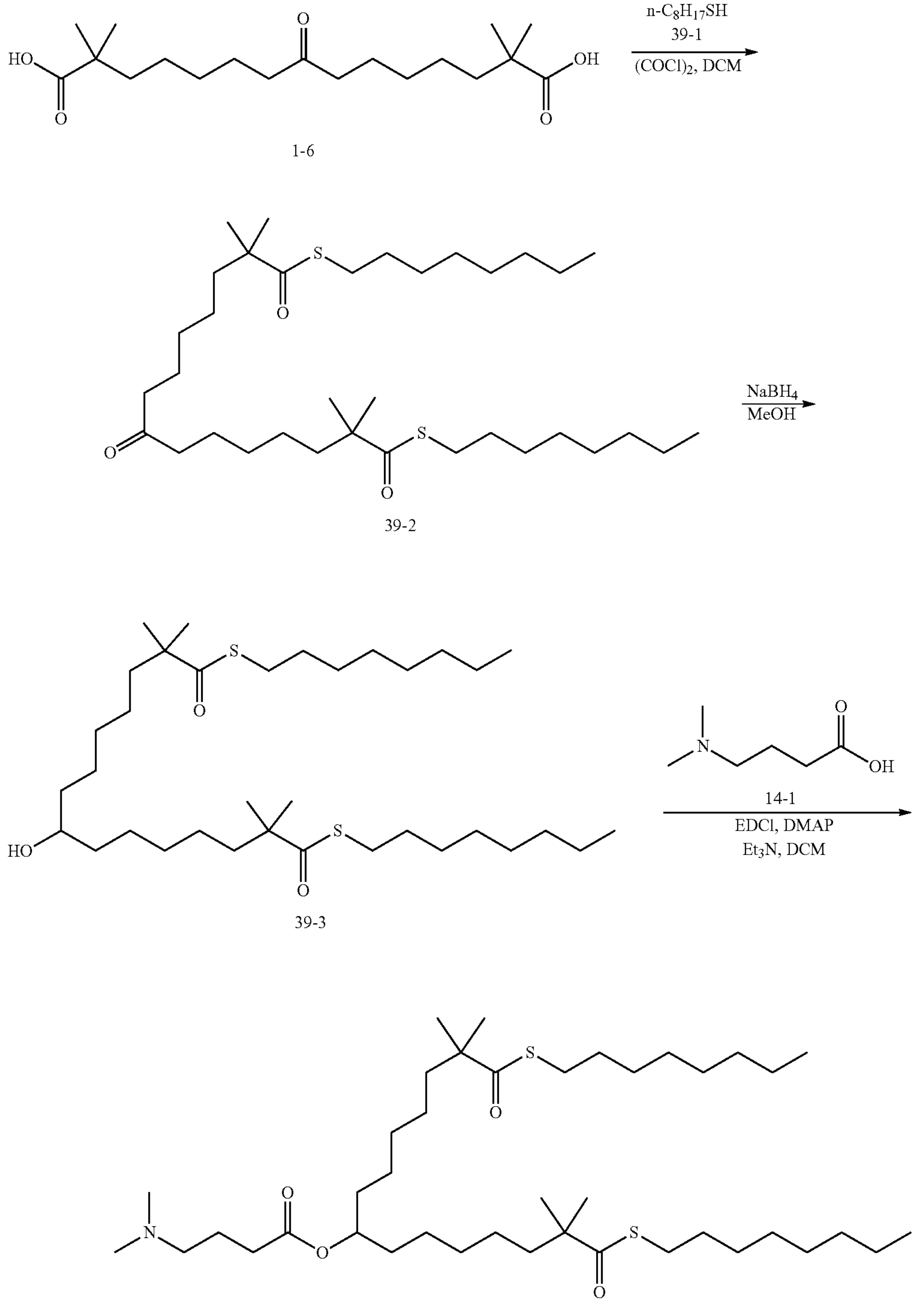
39
Referring to the method of Example 33, compound 39 was prepared as an oily product: 30.7 mg.
$^1H$ NMR (400 MHz, $CDCl_3$): δ ppm 0.91 (t, J=7.2 Hz, 6H), 1.22 (s, 12H), 1.17-1.38 (m, 32H), 1.47-1.58 (m, 12H), 1.78-1.87 (m, 2H), 2.28 (s, 6H), 2.34-2.37 (m, 4H), 2.85 (t, J=7.2 Hz, 4H), 4.81-4.90 (m, 1H); ESI-MS m/z: 714.6 $[M+H]^+$.

Example 40: Synthesis of Compound 40

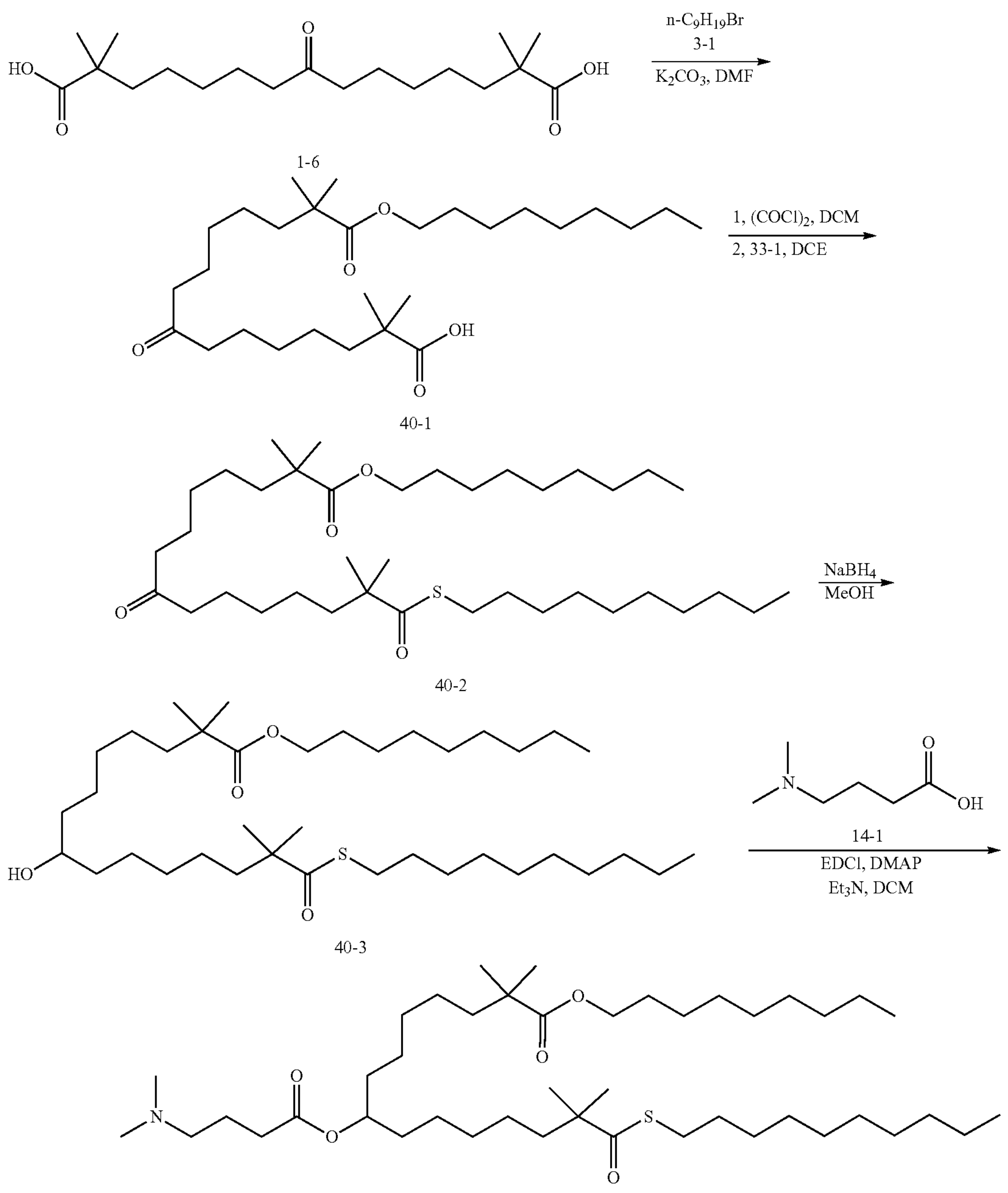

1-6

40-1

40-2

40-3

40

Potassium carbonate (1.55 g, 11.2 mmol, 4.0 eq.) was added to a solution of compound 1-6 (959 mg, 2.8 mmol, 1.0 eq.) and 3-1 (638 mg, 3.08 mmol, 1.1 eq.) in DMF. Then the reaction was warmed up to 60° C. for 4 h. The reaction was cooled to room temperature. The reaction system was quenched with saturated aqueous sodium chloride solution and extracted with ethyl acetate. The organic phases were combined, dried over anhydrous sodium sulfate, and filtered. The filtrate was concentrated to dryness to give the crude product, which was purified by silica gel column to give compound 40-1 (682 mg).

Compound 40-1 (324 mg, 0.69 mmol, 1.0 eq.) was dissolved in 5.0 mL of dichloromethane, and the reaction system was cooled to 0° C. in an ice bath. 2 drops of DMF were added and oxalyl chloride (0.24 mL, 2.8 mmol, 4.0 eq.) was then added dropwise to the reaction solution. The ice bath was removed after the dropwise addition was completed and the mixture was stirred for 1 h at room temperature. The solvent was removed using a rotary-evaporator to give acyl chloride crude product (309 mg) as an oil, which was used directly in the next reaction step.

1-Decanethiol 33-1 (331 mg, 1.9 mmol, 3.0 eq) was added to a solution of crude acyl chloride (309 mg) in DCE (3.0 mL), and the reaction was heated to 70° C. to react overnight. The reaction solution was cooled to room temperature and the solvent was removed using a rotary-evaporator to give the crude product, which was purified by silica gel column to give compound 40-2 (274 mg).

Then referring to the method of Example 1, compound 40 was prepared as an oily product: 34.2 mg.

$^1$H NMR (400 MHz, $CDCl_3$): δ ppm 0.81 (t, J=7.2 Hz, 6H), 1.05 (s, 6H), 1.12 (s, 6H), 1.08-1.28 (m, 36H), 1.37-1.57 (m, 14H), 1.71-1.76 (m, 2H), 2.22 (s, 6H), 2.25-2.31 (m, 4H), 2.75 (t, J=7.2 Hz, 2H), 3.97 (t, J=7.2 Hz, 2H), 4.75-4.84 (m, 1H); ESI-MS m/z: 740.6 $[M+H]^+$.

Example 41: Synthesis of Compound 41

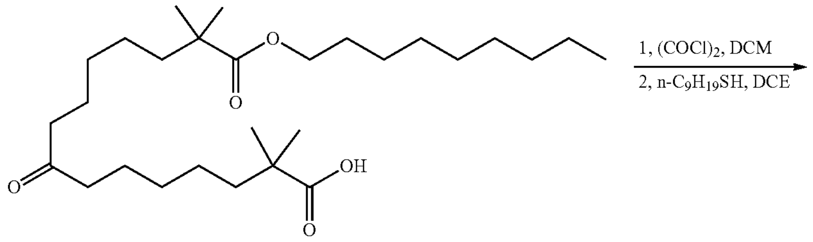

40-1

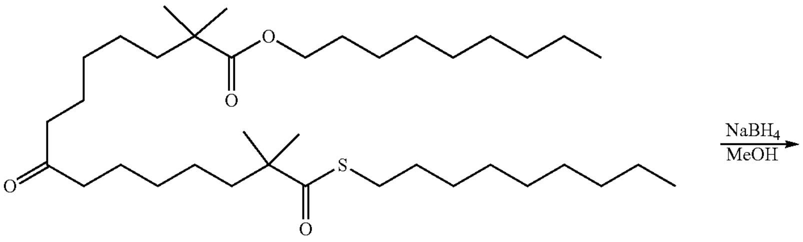

41-1

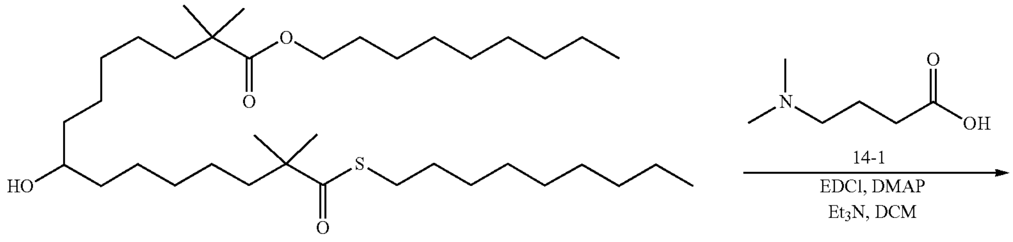

41-2

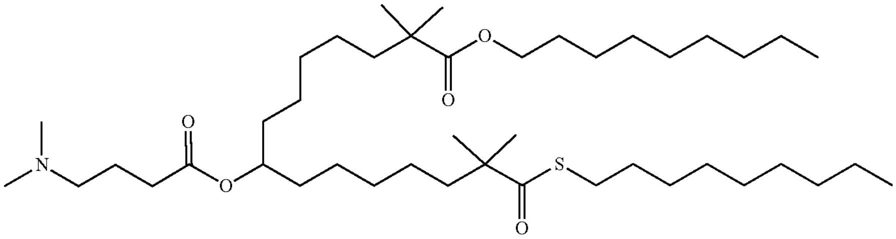

41

Referring to the method of Example 40, compound 41 was prepared as an oily product: 31.1 mg.

$^1$H NMR (400 MHz, $CDCl_3$): δ ppm 0.86-0.89 (m, 6H), 1.10 (s, 6H), 1.15 (s, 6H), 1.08-1.31 (m, 34H), 1.41-1.61 (m, 14H), 1.74-1.82 (m, 2H), 2.17-2.35 (m, 10H), 2.85 (t, J=7.2 Hz, 2H), 4.03 (t, J=7.2 Hz, 2H), 4.82-4.87 (m, 1H); ESI-MS m/z: 726.6 $[M+H]^+$.

Example 42: Synthesis of Compound 42
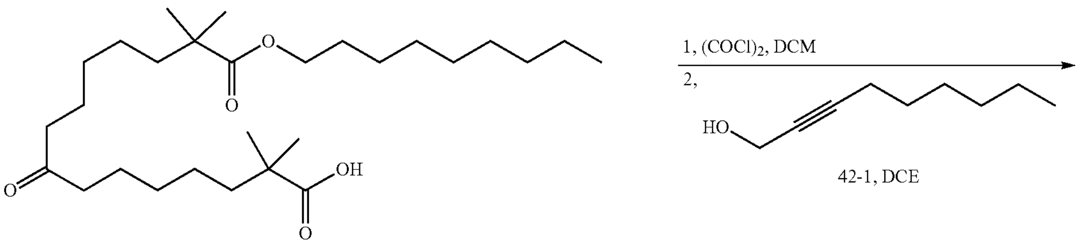
40-1
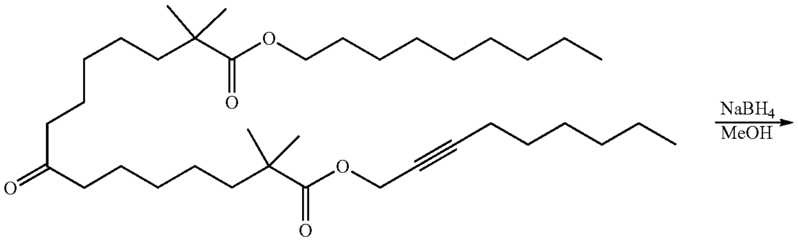
42-2
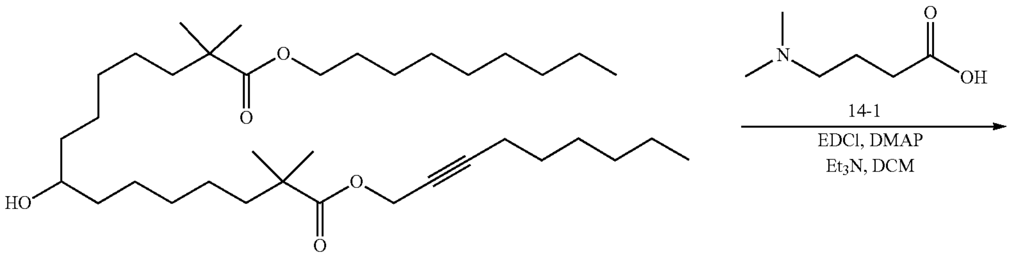
42-3
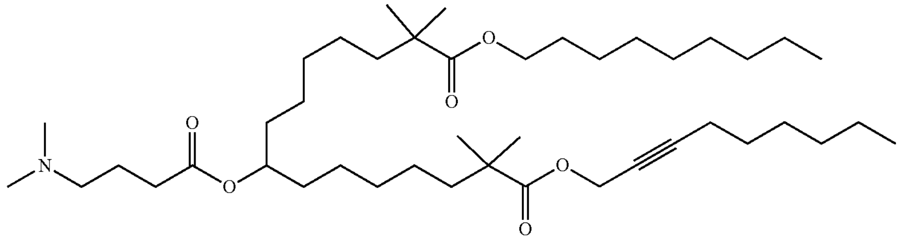
42
Referring to the method of Example 40, compound 42 was prepared as an oily product: 30.9 mg.
$^1$H NMR (400 MHz, $CDCl_3$): δ ppm 0.77-0.82 (m, 6H), 1.05 (s, 6H), 1.10 (s, 6H), 1.11-1.28 (m, 31H), 1.33-1.42 (m, 9H), 1.47-1.59 (m, 2H), 1.73-1.81 (m, 2H), 2.08-2.14 (m, 2H), 2.21-2.33 (m, 10H), 3.97 (t, J=7.2 Hz, 2H), 4.55 (m, 2H), 4.72-4.81 (m, 1H); ESI-MS m/z: 706.6 $[M+H]^+$.
Example 43: Synthesis of Compound 43
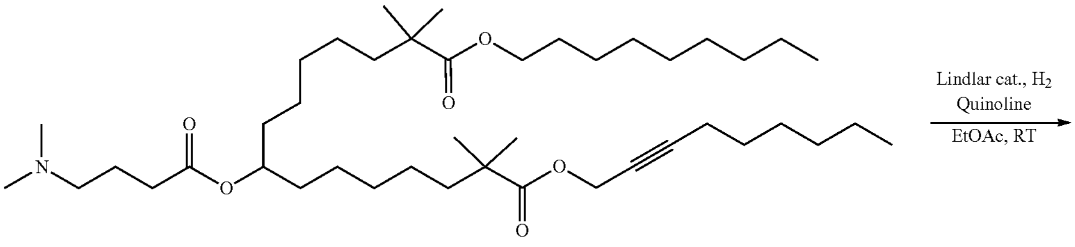
42

-continued
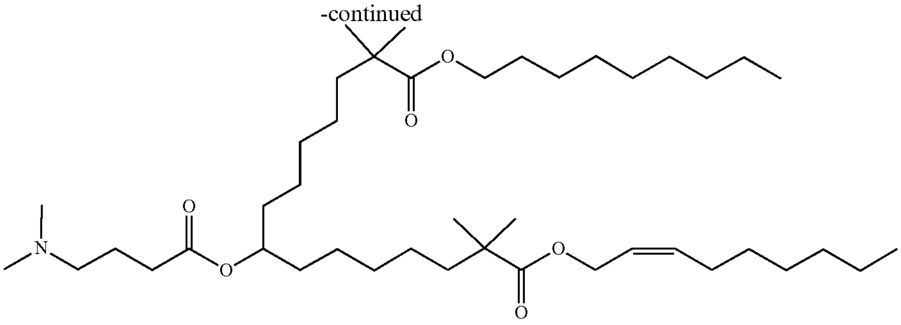
43
Referring to the method of Example 26, compound 43 was prepared as an oily product: 31.3 mg.
$^1$H NMR (400 MHz, $CDCl_3$): δ ppm 0.80 (m, 6H), 1.05 (s, 12H), 1.08-1.28 (m, 34H), 1.36-1.47 (m, 8H), 1.49-1.58 (m, 2H), 1.73-1.82 (m, 2H), 1.98-2.07 (m, 2H), 2.21-2.38 (m, 8H), 3.97 (t, J=7.2 Hz, 2H), 4.53 (d, J=7.2 Hz, 2H), 4.72-4.78 (m, 1H), 5.41-5.59 (m, 2H); ESI-MS m/z: 708.6 $[M+H]^+$.
Example 44: Synthesis of Compound 44
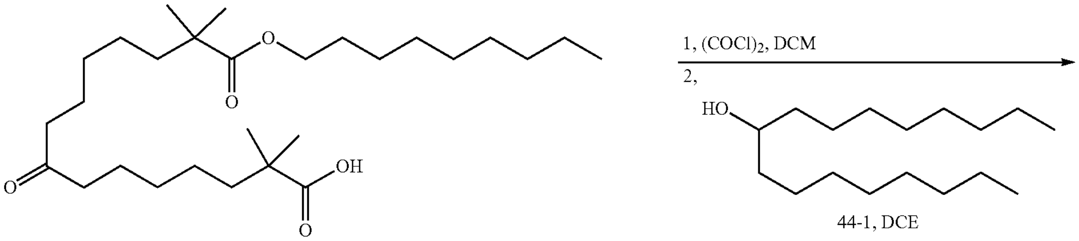
40-1
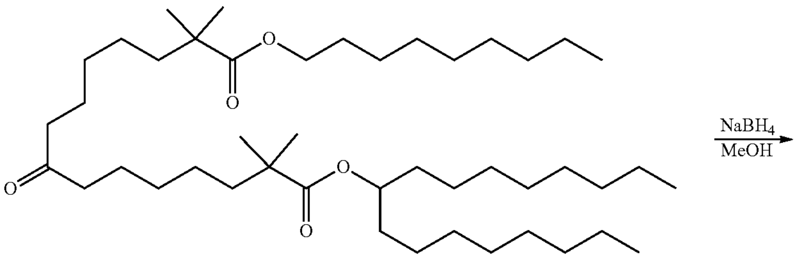
44-2
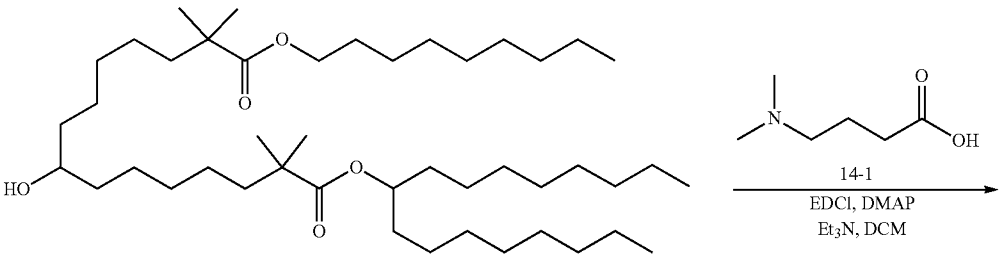
44-3

-continued
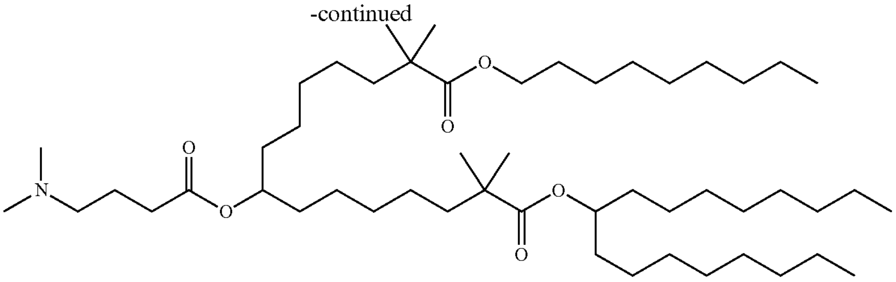
44
Referring to the method of Example 40, compound 44 was prepared as an oily product: 33.1 mg.
$^{1}$H NMR (400 MHz, $CDCl_3$): δ ppm 0.85 (m, 9H), 1.13 (s, 12H), 1.14-1.33 (m, 46H), 1.37-1.59 (m, 16H), 1.78-1.87 (m, 2H), 2.17-2.35 (m, 10H), 4.03 (t, J=6.8 Hz, 2H), 4.79-4.88 (m, 2H); ESI-MS m/z: 822.8 $[M+H]^+$.
Example 45: Synthesis of Compound 45
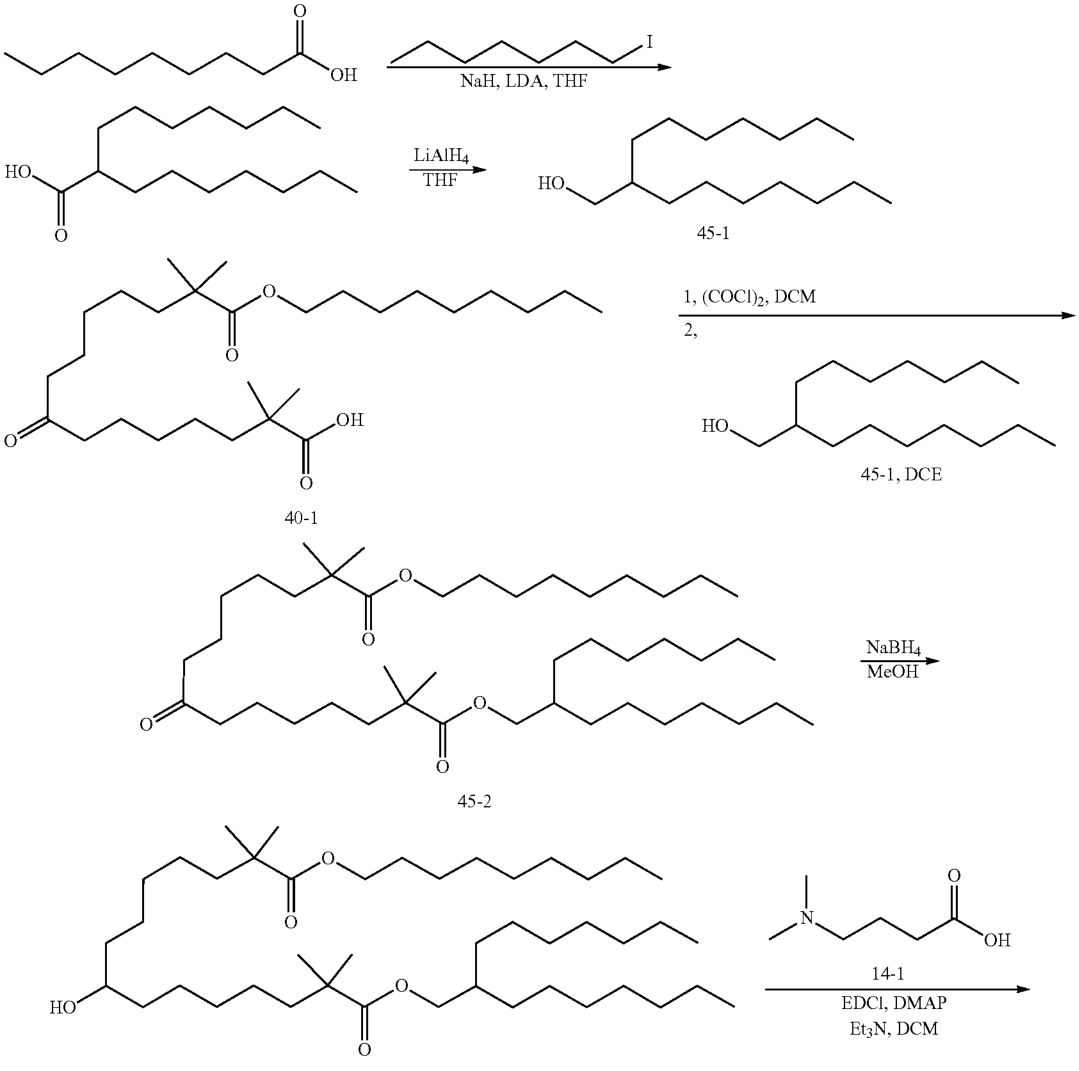
45-3

-continued

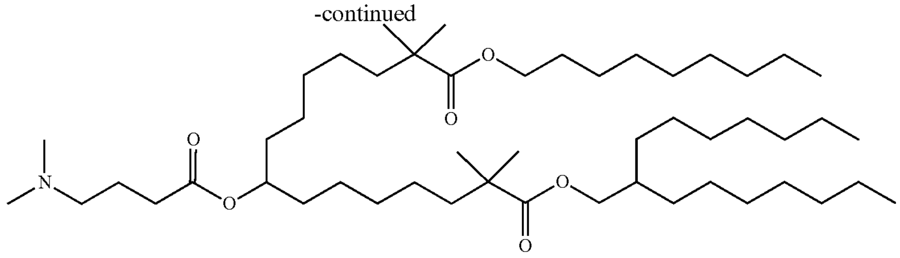

45 n-Nonanoic acid (3.0 g, 19 mmol) was added to 50 mL of anhydrous tetrahydrofuran and the reaction solution was cooled to 0° C. in an ice bath. Sodium hydride (836 mg, 20.9 mmol) and LDA (49.4 mL, 24.7 mmol) were added to the reaction solution, and the reaction solution was stirred at 0° C. for 1 hour. Then 1-iodoheptane was added dropwise to the reaction system. The ice bath was removed, then the mixture was reacted at room temperature for 12 h. The reaction solution was quenched by pouring the reaction solution into saturated ammonium chloride solution, and extracted with ethyl acetate. The organic phase was collected, dried over anhydrous sodium sulfate, and filtered. The filtrate was collected, and concentrated to remove the solvent to give the crude product, which was purified by silica gel column to give 2.0 g of compound 2-heptylnonanoic acid.

The 2-heptylnonanoic acid (2.0 g, 7.8 mmo) obtained in the previous step was dissolved in 30 mL of anhydrous tetrahydrofuran, and lithium tetrahydroaluminum (593 mg, 15.6 mmol) was added to the reaction solution. The reaction system was heated to 80° C. to react for 2 hours. The reaction solution was cooled to room temperature, quenched by pouring the reaction solution into saturated ammonium chloride solution, and extracted with ethyl acetate. The organic phase was collected, dried over anhydrous sodium sulfate, and filtered. The filtrate was collected, and concentrated to remove the solvent to give the crude product, which was purified by silica gel column to give 1.3 g of compound 45-1.

Then referring to the method of Example 40, compound 45 was prepared as an oily product: 31.6 mg.

$^1$H NMR (400 MHz, $CDCl_3$): δ ppm 0.88 (t, J=6.8 Hz, 9H), 1.14 (s, 12H), 1.15-1.26 (m, 47H), 1.47-1.50 (m, 8H), 1.57-1.62 (m, 4H), 1.79-1.81 (m, 2H), 2.25 (s, 6H), 2.32 (t, J=7.2 Hz, 4H), 3.93 (d, J=5.6 Hz, 2H), 4.03 (t, J=7.2 Hz, 2H), 4.81-4.87 (m, 1H); ESI-MS m/z: 808.7 $[M+H]^+$.

Example 46: Synthesis of Compound 46

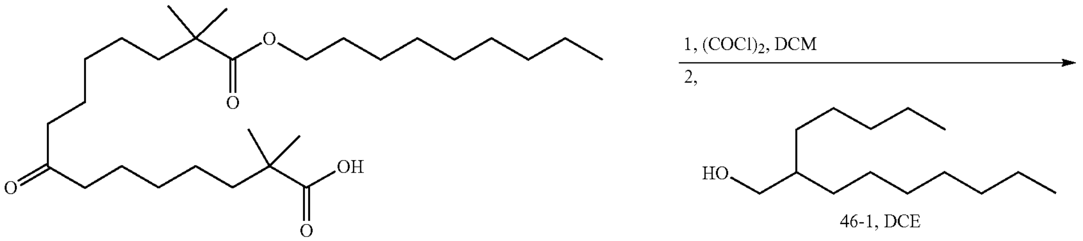

40-1

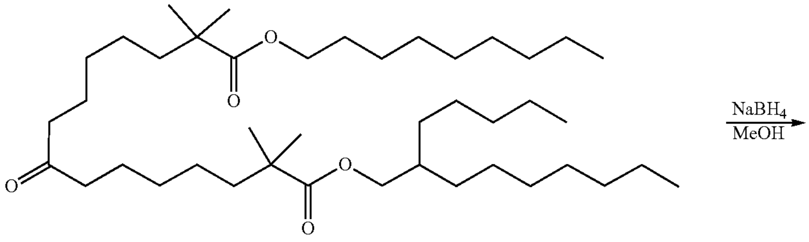

46-2

-continued
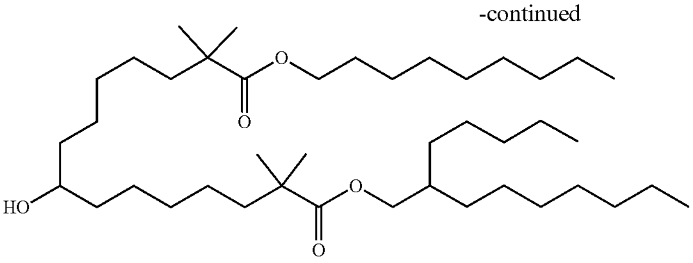
46-3
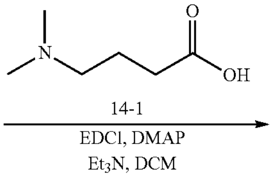
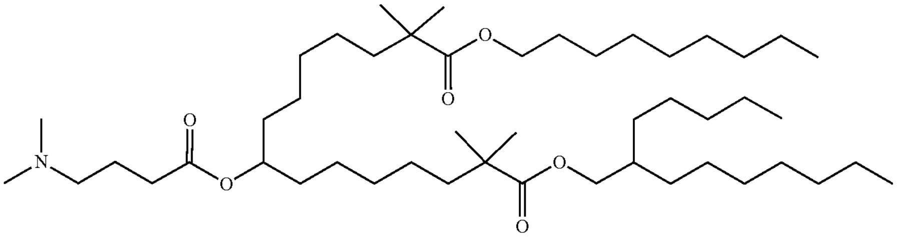
46
Referring to the method of Example 40, compound 46 was prepared as an oily product: 32.6 mg.
$^1$H NMR (400 MHz, $CDCl_3$): δ ppm 0.88 (t, J=7.2 Hz, 9H), 1.14 (s, 12H), 1.15-1.28 (m, 37H), 1.47-1.59 (m, 18H), 1.75-1.84 (m, 2H), 2.24-2.35 (m, 10H), 3.95 (d, J=5.6 Hz, 2H), 4.03 (t, J=6.8 Hz, 2H), 4.80-4.87 (m, 1H); ESI-MS m/z: 780.7 $[M+H]^+$.
Example 47: Synthesis of Compound 47
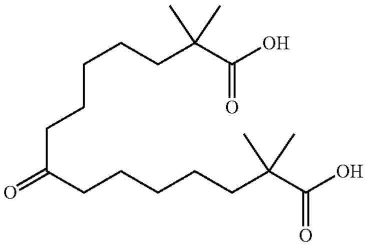
1-6
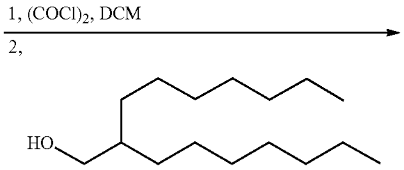
45-1, DCE
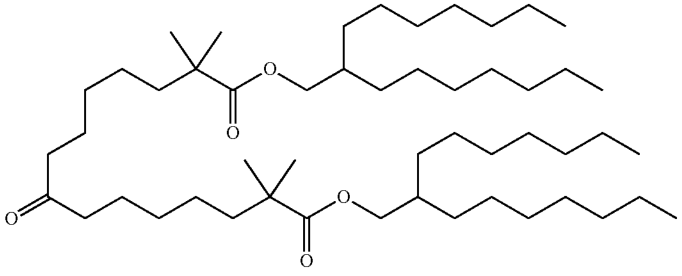
47-1
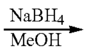

-continued
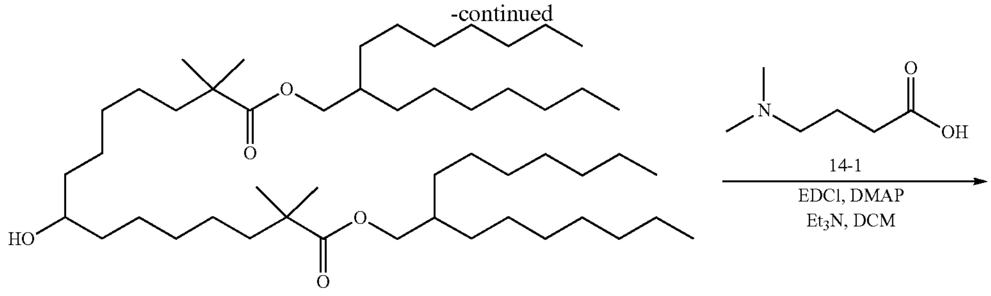
47-2
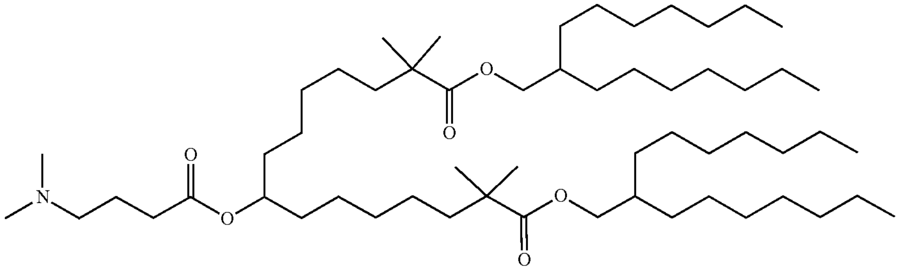
47
Referring to the method of Example 7, compound 47 was prepared as an oily product: 33.1 mg.
$^{1}$H NMR (400 MHz, $CDCl_3$): δ ppm 0.81 (t, J=6.8 Hz, 12H), 1.08 (s, 12H), 1.09-1.24 (m, 56H), 1.40-1.61 (m, 14H), 1.67-1.72 (m, 2H), 2.17 (s, 6H), 2.19-2.28 (m, 4H), 3.88 (d, J=5.6 Hz, 4H), 4.74-4.80 (m, 1H); ESI-MS m/z: 906.8 $[M+H]^+$.
Example 48: Synthesis of Compound 48
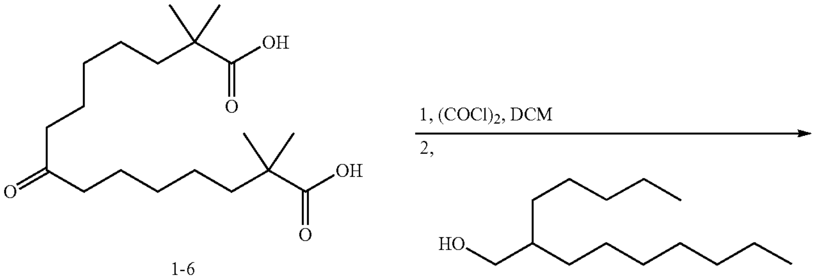
1-6
46-1, DCE
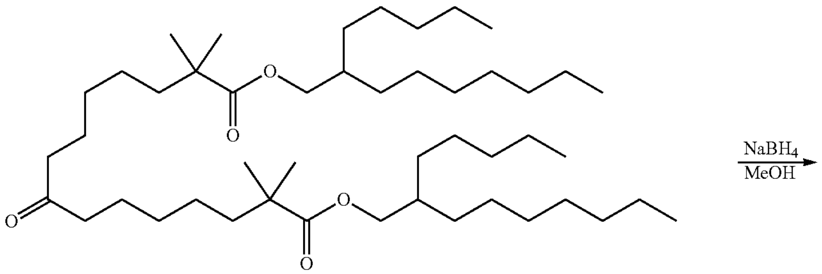
48-1

-continued
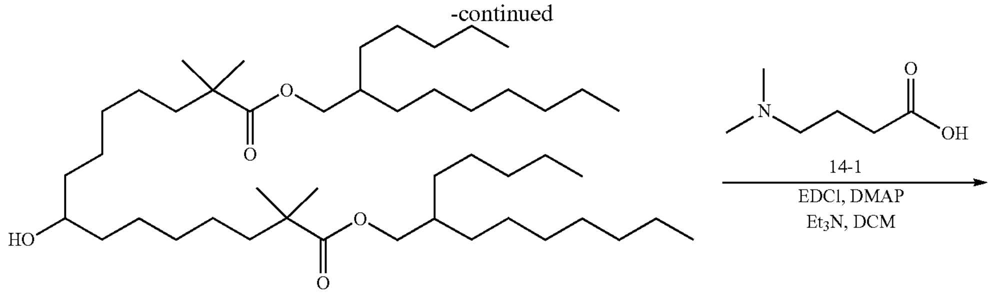
48-2
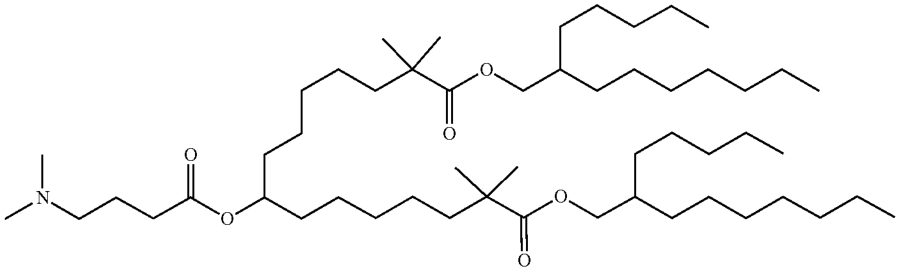
48
Referring to the method of Example 7, compound 48 was prepared as an oily product: 34.8 mg.
$^1$H NMR (400 MHz, $CDCl_3$): δ ppm 0.81 (t, J=7.2 Hz, 12H), 1.08 (s, 12H), 1.09-1.23 (m, 48H), 1.37-1.64 (m, 14H), 1.67-1.73 (m, 2H), 2.15 (s, 6H), 2.20-2.37 (m, 4H), 3.88 (d, J=5.6 Hz, 4H), 4.74-4.89 (m, 1H); ESI-MS m/z: 850.8 $[M+H]^+$.
The compounds of Table 2 were synthesized using the methods of the above examples, or similar methods using the corresponding intermediates.
TABLE 2
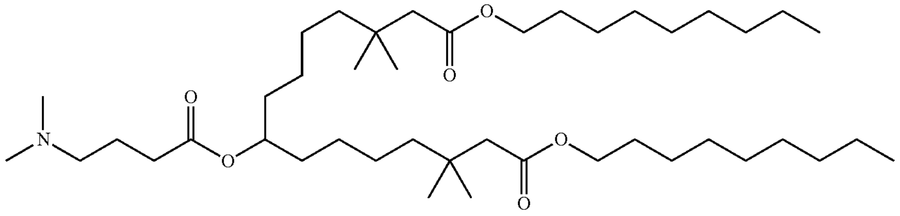 [SMILES: CCCCCCCCCOC(=O)CC(C)(C)CCCCC(CCCCC(C)(C)CC(=O)OCCCCCCCCC)OC(=O)CCCN(C)C]
Example 49: compound 49
$[M + H]^+$: 710.6
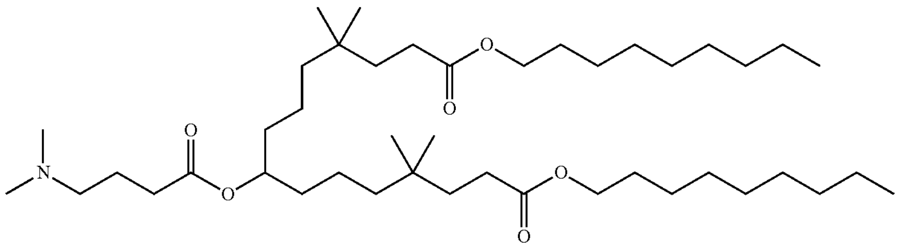 [SMILES: CCCCCCCCCOC(=O)CCC(C)(C)CCCC(CCCC(C)(C)CCC(=O)OCCCCCCCCC)OC(=O)CCCN(C)C]
Example 50: compound 50
$[M + H]^+$: 710.6

TABLE 2-continued
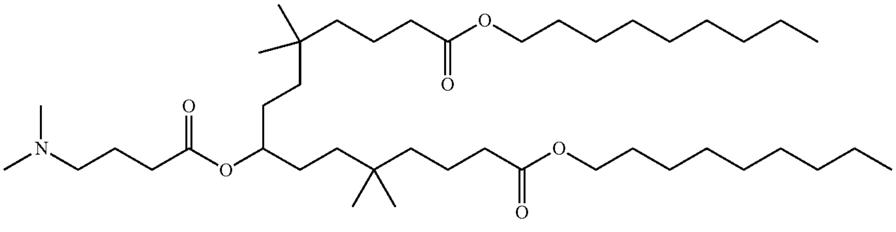 [SMILES: CCCCCCCCCOC(=O)CCCC(C)(C)CCC(CCC(C)(C)CCCC(=O)OCCCCCCCCC)OC(=O)CCCN(C)C]
Example 51: compound 51
[M + H]$^+$: 710.6
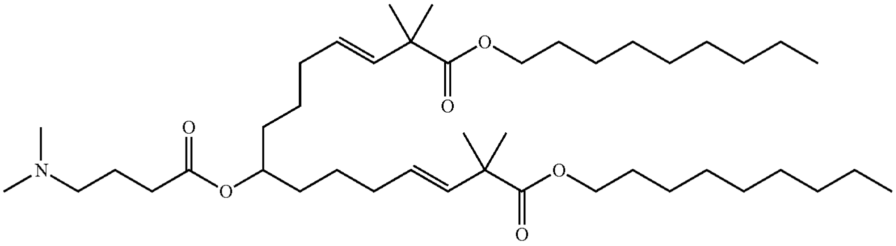 [SMILES: CCCCCCCCCOC(=O)C(C)(C)/C=C/CCCC(CCC/C=C/C(C)(C)C(=O)OCCCCCCCCC)OC(=O)CCCN(C)C]
Example 52: compound 52
[M + H]$^+$: 706.6
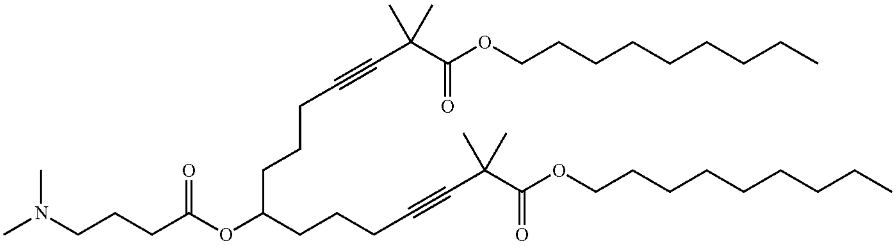 [SMILES: CCCCCCCCCOC(=O)C(C)(C)C#CCCCC(CCCC#CC(C)(C)C(=O)OCCCCCCCCC)OC(=O)CCCN(C)C]
Example 53: compound 53
[M + H]$^+$: 702.6
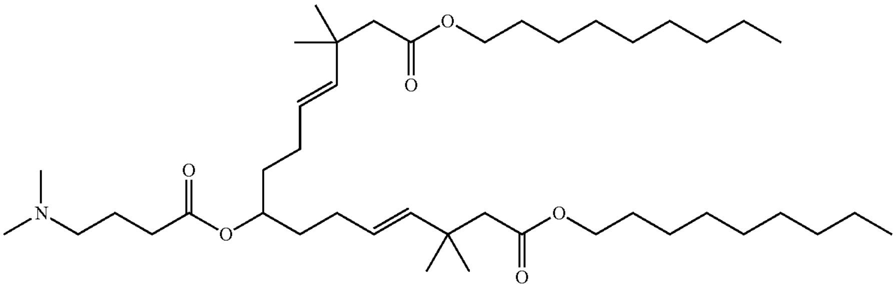 [SMILES: CCCCCCCCCOC(=O)CC(C)(C)/C=C/CCC(CC/C=C/C(C)(C)CC(=O)OCCCCCCCCC)OC(=O)CCCN(C)C]
Example 54: compound 54
[M + H]$^+$: 706.6
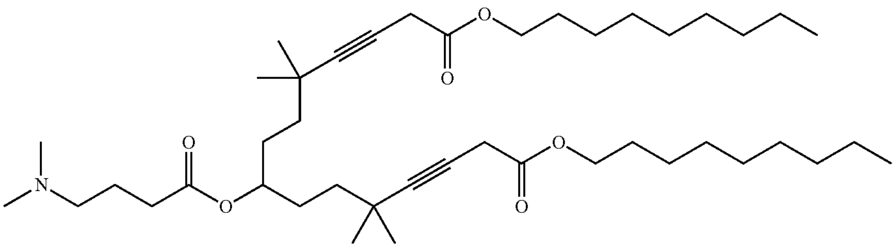 [SMILES: CCCCCCCCCOC(=O)CC#CC(C)(C)CCC(CCC(C)(C)C#CCC(=O)OCCCCCCCCC)OC(=O)CCCN(C)C]
Example 55: compound 55
[M + H]$^+$: 702.6

TABLE 2-continued
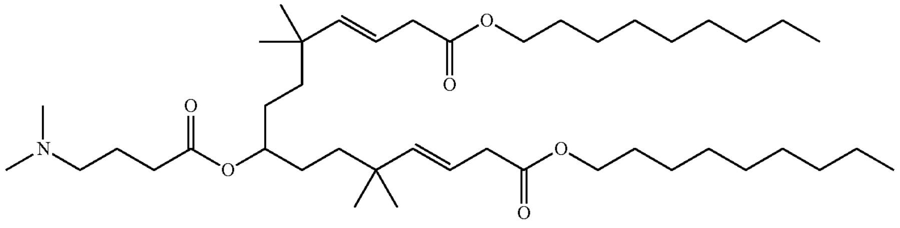 [SMILES: CCCCCCCCCOC(=O)C/C=C/C(C)(C)CCC(CCC(C)(C)/C=C/CC(=O)OCCCCCCCCC)OC(=O)CCCN(C)C]
Example 56: compound 56
[M + H]+: 706.6
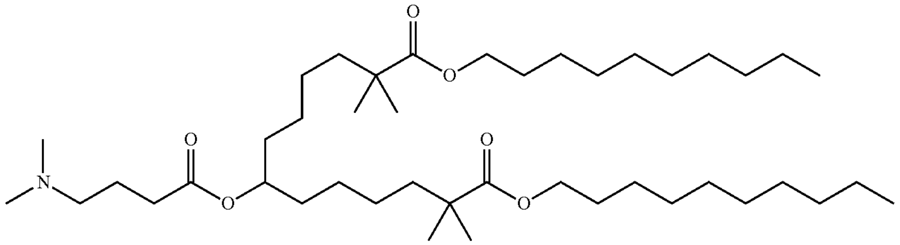 [SMILES: CCCCCCCCCCOC(=O)C(C)(C)CCCCC(CCCCC(C)(C)C(=O)OCCCCCCCCCC)OC(=O)CCCN(C)C]
Example 57: compound 57
[M + H]+: 710.6
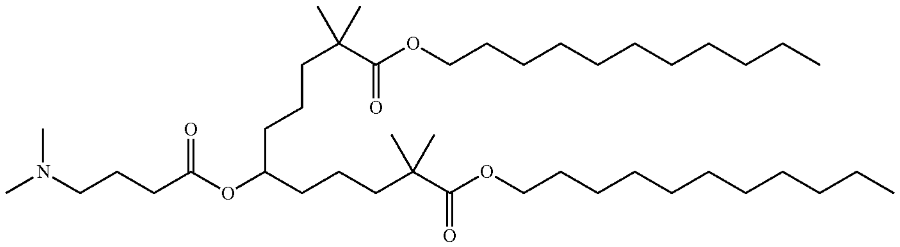 [SMILES: CCCCCCCCCCCOC(=O)C(C)(C)CCCC(CCCC(C)(C)C(=O)OCCCCCCCCCCC)OC(=O)CCCN(C)C]
Example 58: compound 58
[M + H]+: 710.6
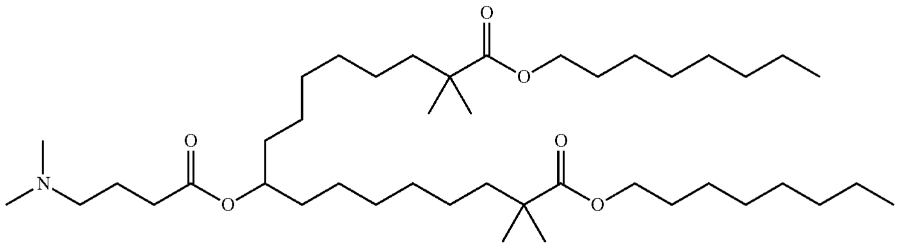 [SMILES: CCCCCCCCOC(=O)C(C)(C)CCCCCCC(CCCCCCC(C)(C)C(=O)OCCCCCCCC)OC(=O)CCCN(C)C]
Example 59: compound 59
[M + H]+: 710.6
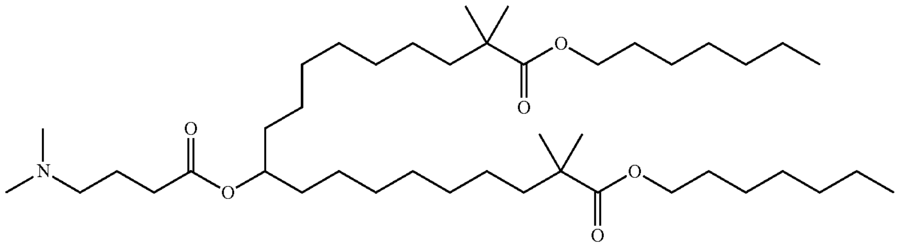 [SMILES: CCCCCCCOC(=O)C(C)(C)CCCCCCCC(CCCCCCCC(C)(C)C(=O)OCCCCCCC)OC(=O)CCCN(C)C]
Example 60: compound 60
[M + H]+: 710.6

TABLE 2-continued
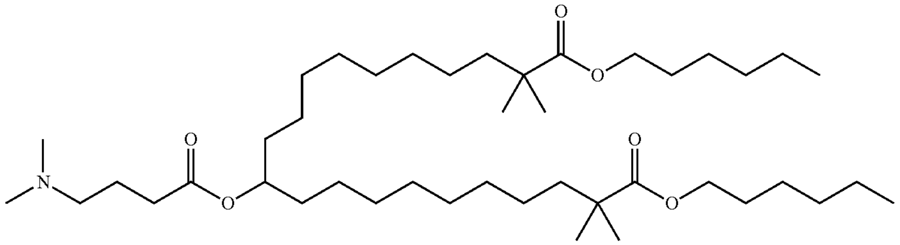 [SMILES: CCCCCCOC(=O)C(C)(C)CCCCCCCCC(CCCCCCCCC(C)(C)C(=O)OCCCCCC)OC(=O)CCCN(C)C]
Example 61: compound 61
[M + H]$^+$: 710.6
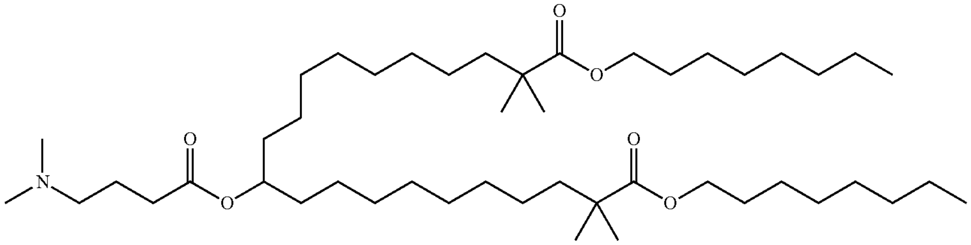 [SMILES: CCCCCCCCOC(=O)C(C)(C)CCCCCCCCC(CCCCCCCCC(C)(C)C(=O)OCCCCCCCC)OC(=O)CCCN(C)C]
Example 62: compound 62
[M + H]$^+$: 766.7
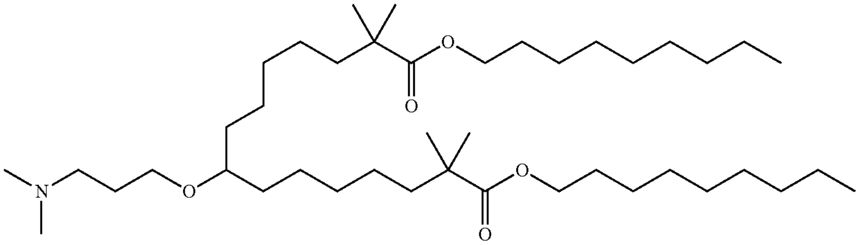 [SMILES: CCCCCCCCCOC(=O)C(C)(C)CCCCCC(CCCCCC(C)(C)C(=O)OCCCCCCCCC)OCCCN(C)C]
Example 63: compound 63
[M + H]$^+$: 682.6
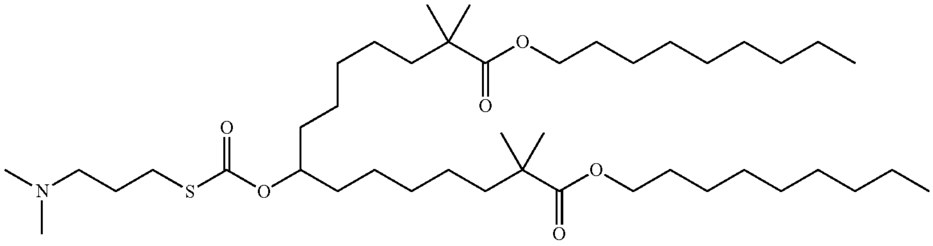 [SMILES: CCCCCCCCCOC(=O)C(C)(C)CCCCCC(CCCCCC(C)(C)C(=O)OCCCCCCCCC)OC(=O)SCCCN(C)C]
Example 64: compound 64
[M + H]$^+$: 742.6
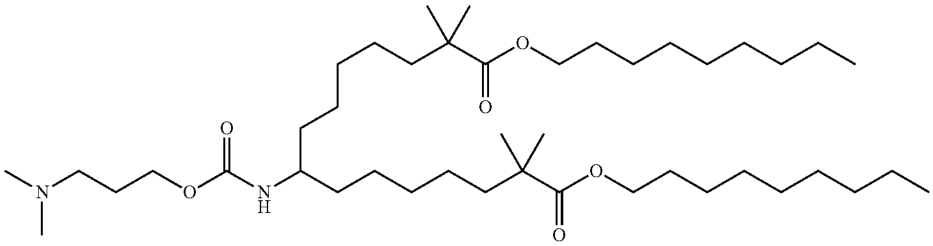
Example 65: compound 65
[M + H]$^+$: 725.6

TABLE 2-continued
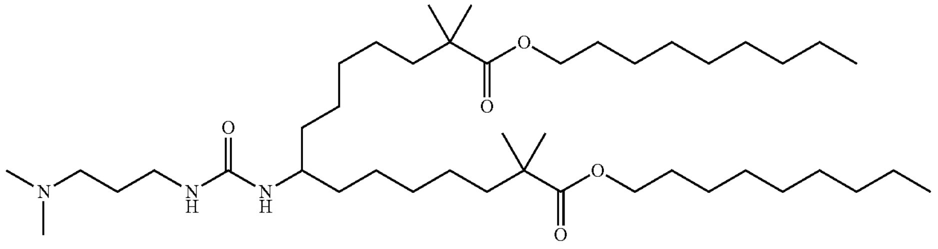 [SMILES: CCCCCCCCCOC(=O)C(C)(C)CCCCCC(CCCCCC(C)(C)C(=O)OCCCCCCCCC)NC(=O)NCCCN(C)C]
Example 66: compound 66
[M + H]+: 724.6
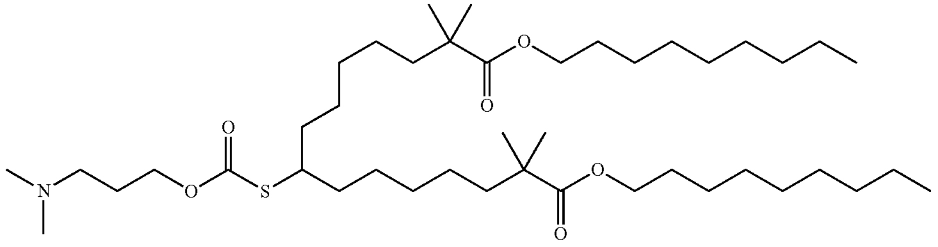 [SMILES: CCCCCCCCCOC(=O)C(C)(C)CCCCCC(CCCCCC(C)(C)C(=O)OCCCCCCCCC)SC(=O)OCCCN(C)C]
Example 67: compound 67
[M + H]+: 742.6
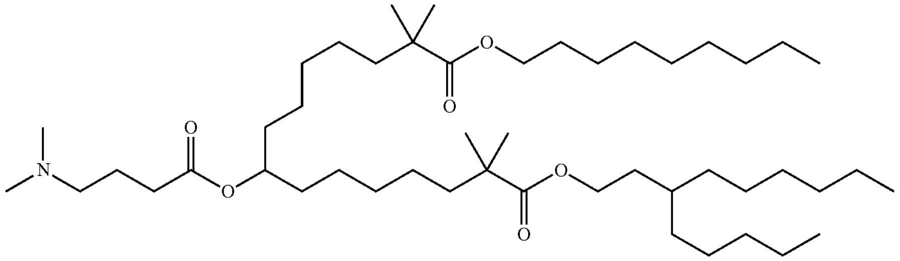 [SMILES: CCCCCCCCCOC(=O)C(C)(C)CCCCCC(CCCCCC(C)(C)C(=O)OCCC(CCCCC)CCCCCC)OC(=O)CCCN(C)C]
Example 68: compound 68
[M + H]+: 780.7
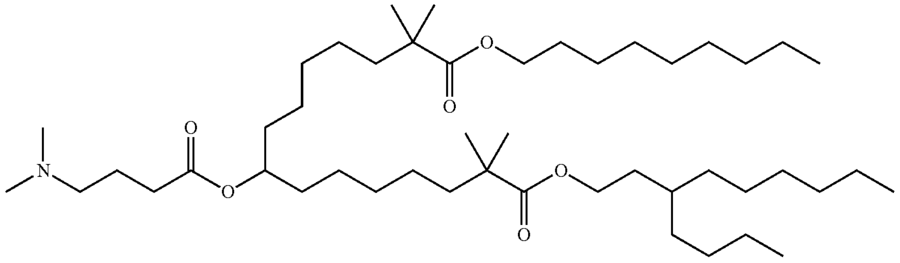 [SMILES: CCCCCCCCCOC(=O)C(C)(C)CCCCCC(CCCCCC(C)(C)C(=O)OCCC(CCCC)CCCCCC)OC(=O)CCCN(C)C]
Example 69: compound 69
[M + H]+: 766.7
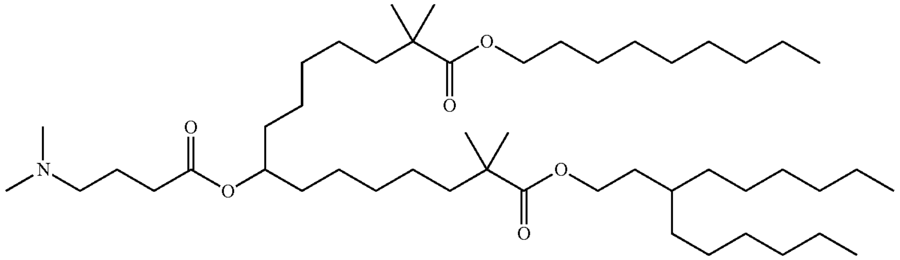 [SMILES: CCCCCCCCCOC(=O)C(C)(C)CCCCCC(CCCCCC(C)(C)C(=O)OCCC(CCCCCC)CCCCCC)OC(=O)CCCN(C)C]
Example 70: compound 70
[M + H]+: 794.7

TABLE 2-continued
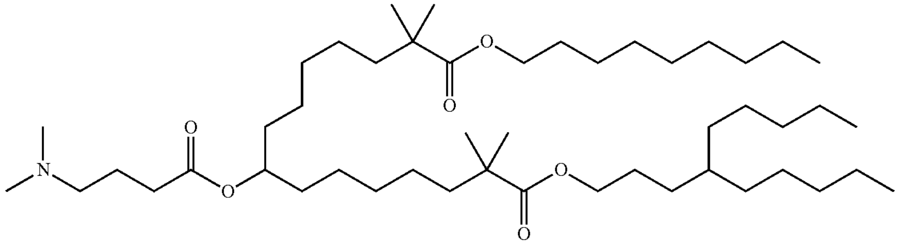 [SMILES: CCCCCCCCCOC(=O)C(C)(C)CCCCCC(CCCCCC(C)(C)C(=O)OCCCC(CCCCC)CCCCC)OC(=O)CCCN(C)C]
Example 71: compound 71
[M + H]$^+$: 780.7
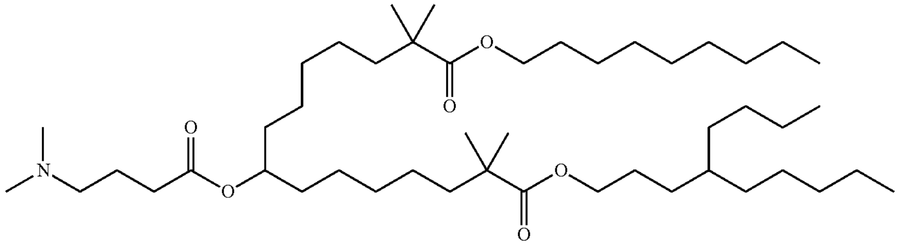 [SMILES: CCCCCCCCCOC(=O)C(C)(C)CCCCCC(CCCCCC(C)(C)C(=O)OCCCC(CCCC)CCCCC)OC(=O)CCCN(C)C]
Example 72: compound 72
[M + H]$^+$: 766.7
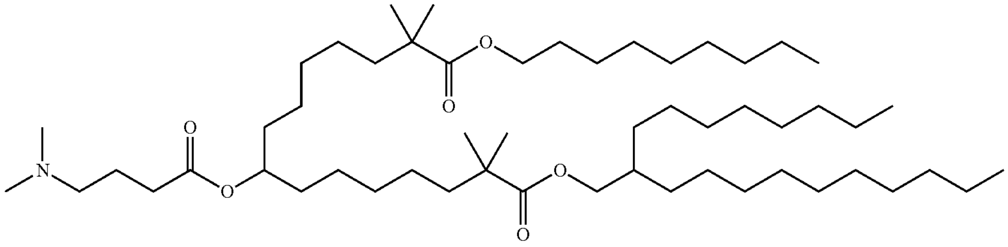 [SMILES: CCCCCCCCCCC(CCCCCCCC)COC(=O)C(C)(C)CCCCCC(CCCCCC(C)(C)C(=O)OCCCCCCCCC)OC(=O)CCCN(C)C]
Example 73: compound 73
[M + H]$^+$: 864.8
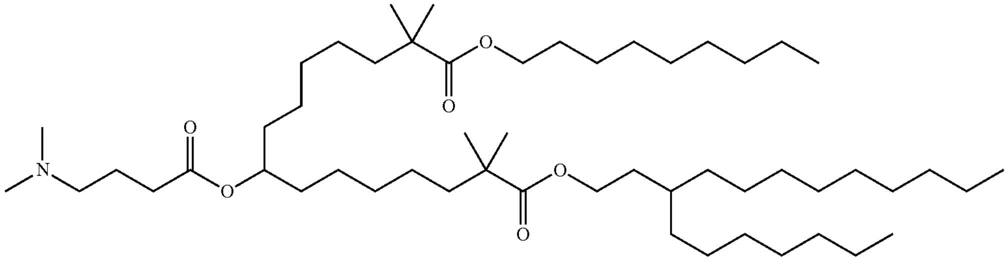 [SMILES: CCCCCCCCCOC(=O)C(C)(C)CCCCCC(CCCCCC(C)(C)C(=O)OCCC(CCCCCCC)CCCCCCCCC)OC(=O)CCCN(C)C]
Example 74: compound 74
[M + H]$^+$: 850.8
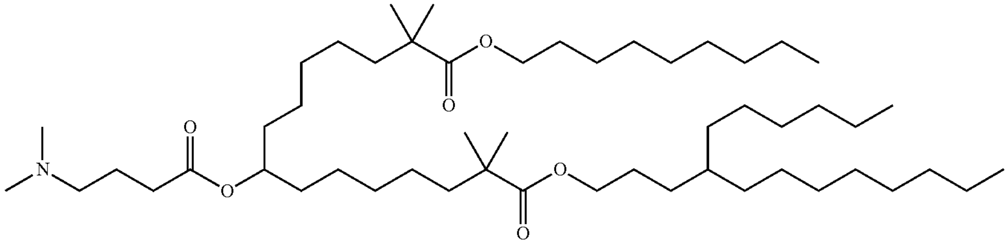 [SMILES: CCCCCCCCCOC(=O)C(C)(C)CCCCCC(CCCCCC(C)(C)C(=O)OCCCC(CCCCCC)CCCCCCCC)OC(=O)CCCN(C)C]
Example 75: compound 75
[M + H]$^+$: 836.8

TABLE 2-continued
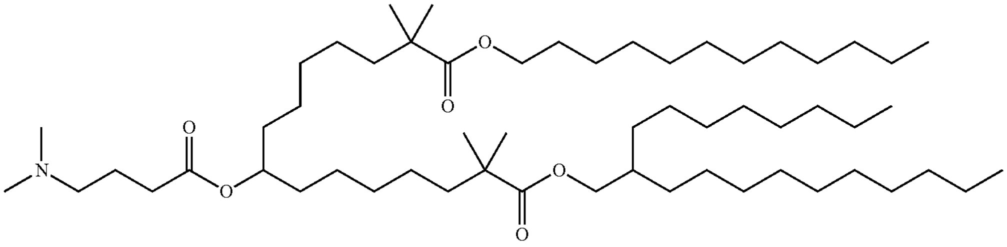 [SMILES: CCCCCCCCCCCCOC(=O)C(C)(C)CCCCCC(CCCCCC(C)(C)C(=O)OCC(CCCCCCCC)CCCCCCCCCC)OC(=O)CCCN(C)C]
Example 77: compound 77
$[M + H]^+$: 906.8
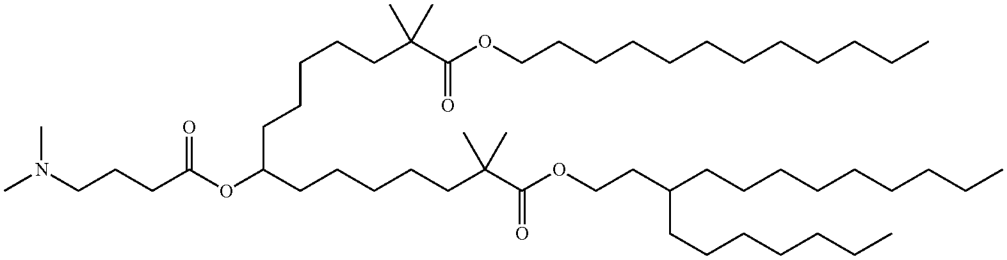 [SMILES: CCCCCCCCCCCCOC(=O)C(C)(C)CCCCCC(CCCCCC(C)(C)C(=O)OCCC(CCCCCCC)CCCCCCCCC)OC(=O)CCCN(C)C]
Example 78: compound 78
$[M + H]^+$: 892.8
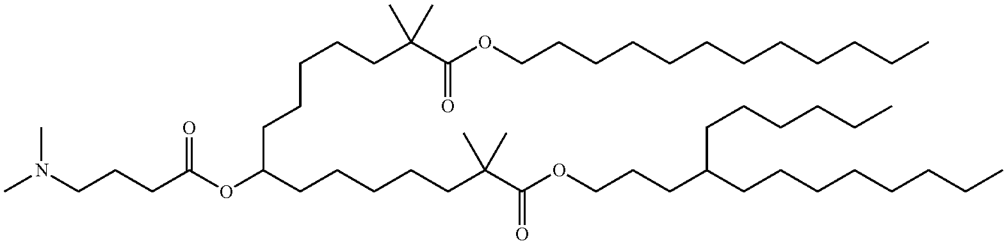 [SMILES: CCCCCCCCCCCCOC(=O)C(C)(C)CCCCCC(CCCCCC(C)(C)C(=O)OCCCC(CCCCCC)CCCCCCCC)OC(=O)CCCN(C)C]
Example 79: compound 79
$[M + H]^+$: 878.8
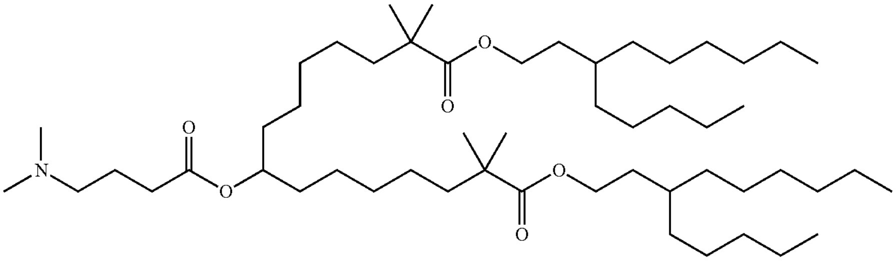 [SMILES: CCCCCCC(CCCCC)CCOC(=O)C(C)(C)CCCCCC(CCCCCC(C)(C)C(=O)OCCC(CCCCC)CCCCCC)OC(=O)CCCN(C)C]
Example 80: compound 80
$[M + H]^+$: 850.8
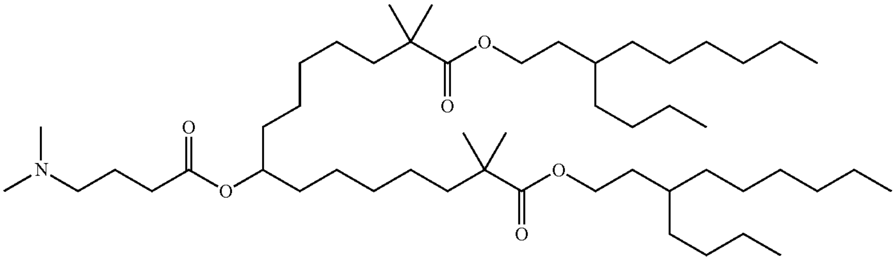 [SMILES: CCCCCCC(CCCC)CCOC(=O)C(C)(C)CCCCCC(CCCCCC(C)(C)C(=O)OCCC(CCCC)CCCCCC)OC(=O)CCCN(C)C]
Example 81: compound 81
$[M + H]^+$: 822.8

TABLE 2-continued
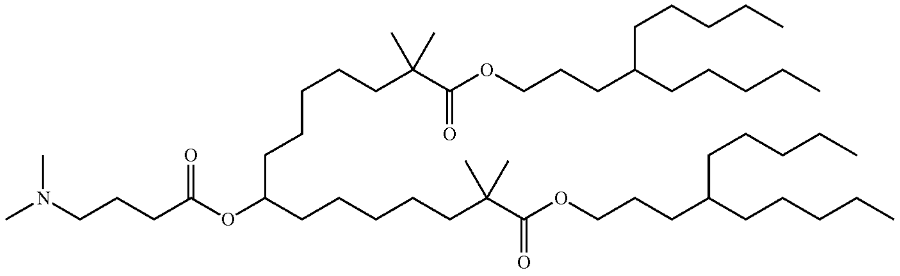 [SMILES: CCCCCC(CCCCC)CCCOC(=O)C(C)(C)CCCCCC(CCCCCC(C)(C)C(=O)OCCCC(CCCCC)CCCCC)OC(=O)CCCN(C)C]
Example 82: compound 82
$[M + H]^+$: 850.8
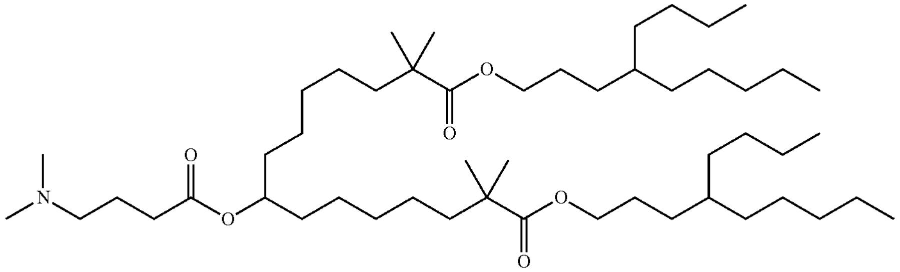 [SMILES: CCCCCC(CCCC)CCCOC(=O)C(C)(C)CCCCCC(CCCCCC(C)(C)C(=O)OCCCC(CCCC)CCCCC)OC(=O)CCCN(C)C]
Example 83: compound 83
$[M + H]^+$: 822.8
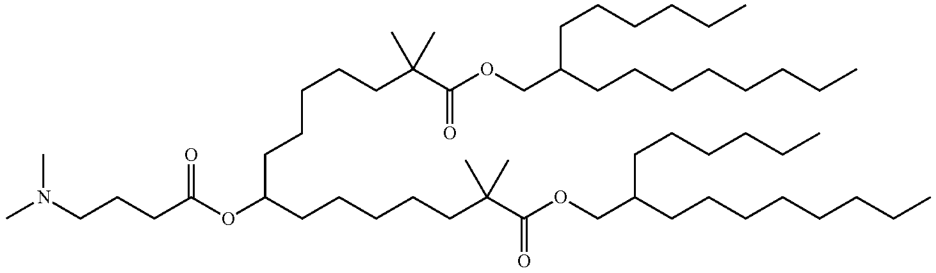 [SMILES: CCCCCCCCC(CCCCCC)COC(=O)C(C)(C)CCCCCC(CCCCCC(C)(C)C(=O)OCC(CCCCCC)CCCCCCCC)OC(=O)CCCN(C)C]
Example 84: compound 84
$[M + H]^+$: 906.8
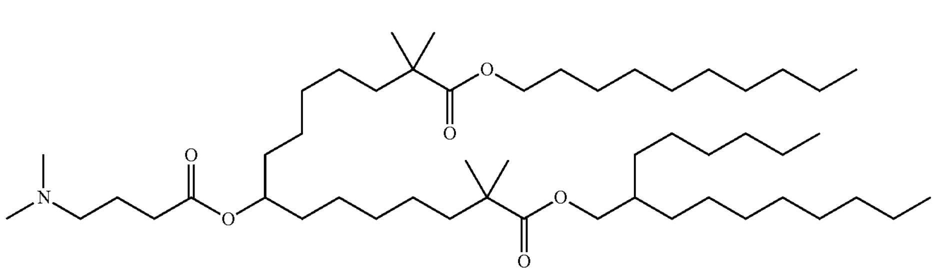 [SMILES: CCCCCCCCCCOC(=O)C(C)(C)CCCCCC(CCCCCC(C)(C)C(=O)OCC(CCCCCC)CCCCCCCC)OC(=O)CCCN(C)C]
Example 85: compound 85
$[M + H]^+$: 822.8

TABLE 2-continued
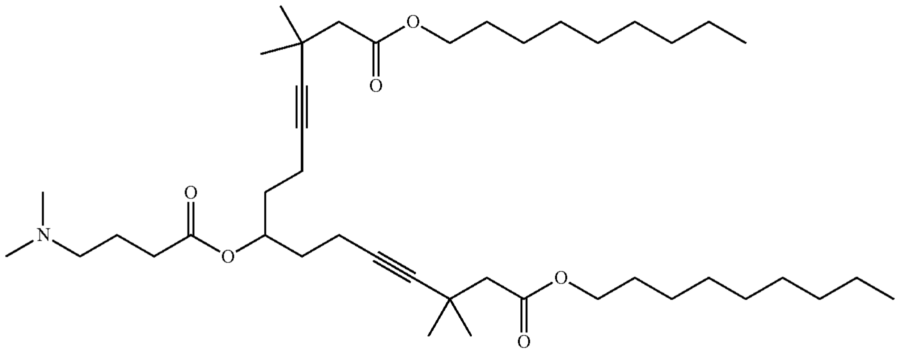 [SMILES: CCCCCCCCCOC(=O)CC(C)(C)C#CCCC(CCC#CC(C)(C)CC(=O)OCCCCCCCCC)OC(=O)CCCN(C)C]
Example 86: compound 86
[M + H]+: 702.6
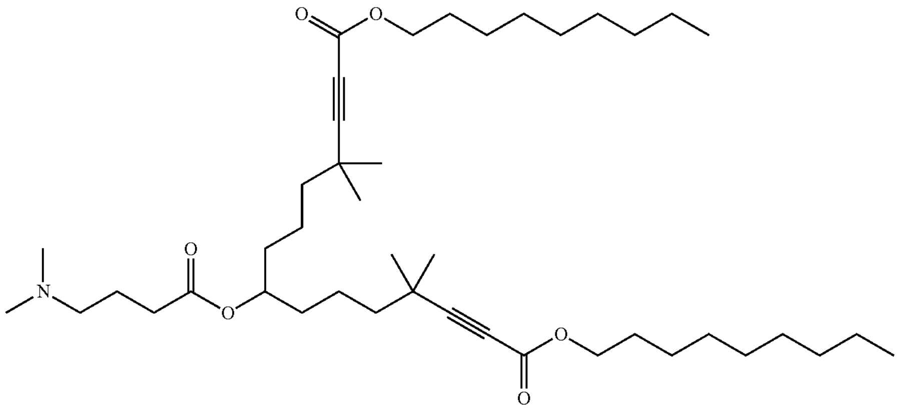 [SMILES: CCCCCCCCCOC(=O)C#CC(C)(C)CCCC(CCCC(C)(C)C#CC(=O)OCCCCCCCCC)OC(=O)CCCN(C)C]
Example 87: compound 87
[M + H]+: 702.6
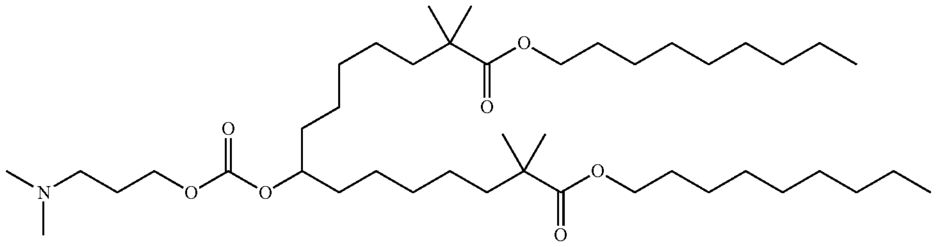
Example 88: compound 88
[M + H]+: 726.6
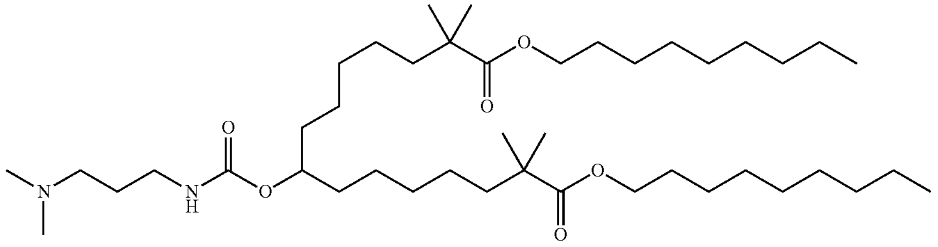 [SMILES: CCCCCCCCCOC(=O)C(C)(C)CCCCCC(CCCCCC(C)(C)C(=O)OCCCCCCCCC)OC(=O)NCCCN(C)C]
Example 89: compound 89
[M + H]+: 725.6

Example 90: Synthesis of Compound 90
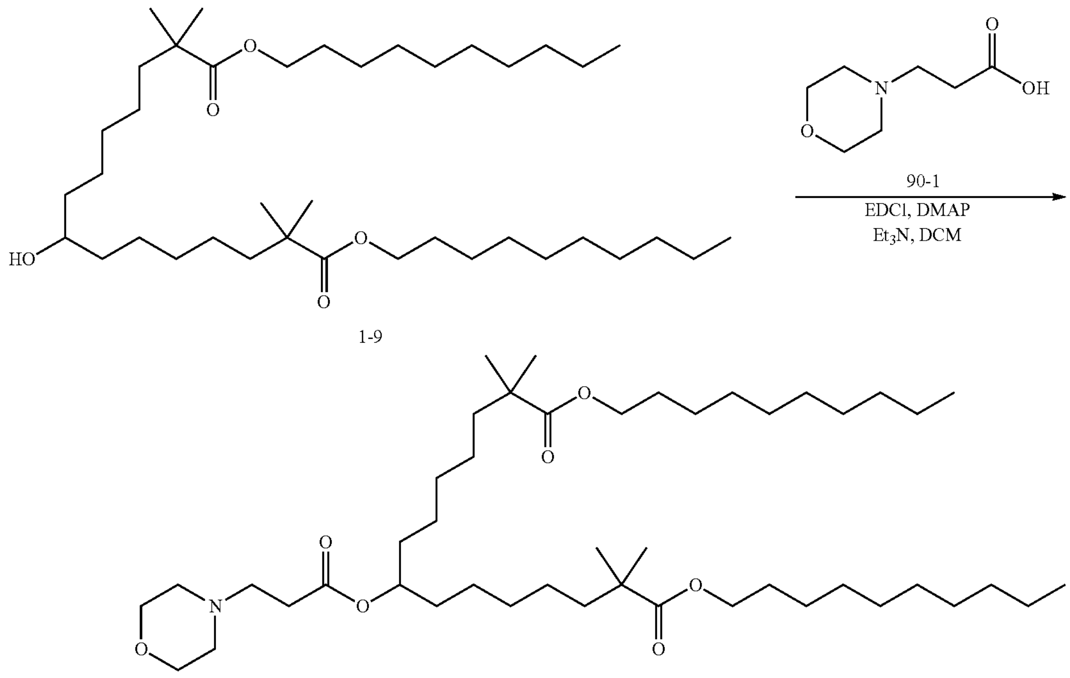
1-9
90-1
90
Referring to the method of Example 1, compound 90 was prepared as an oily product: 40.5 mg.
$^1$H NMR (400 MHz, $CDCl_3$): δ ppm 0.81 (t, J=6.8 Hz, 6H), 1.08 (s, 12H), 1.10-1.28 (m, 36H), 1.38-1.47 (m, 12H), 1.50-1.58 (m, 4H), 2.40 (m, 6H), 2.58 (t, J=6.8 Hz, 2H), 3.59-3.65 (m, 4H), 3.97 (t, J=6.8 Hz, 4H), 4.75-4.83 (m, 1H); ESI-MS m/z: 766.7 $[M+H]^+$.
Example 91: Synthesis of Compound 91
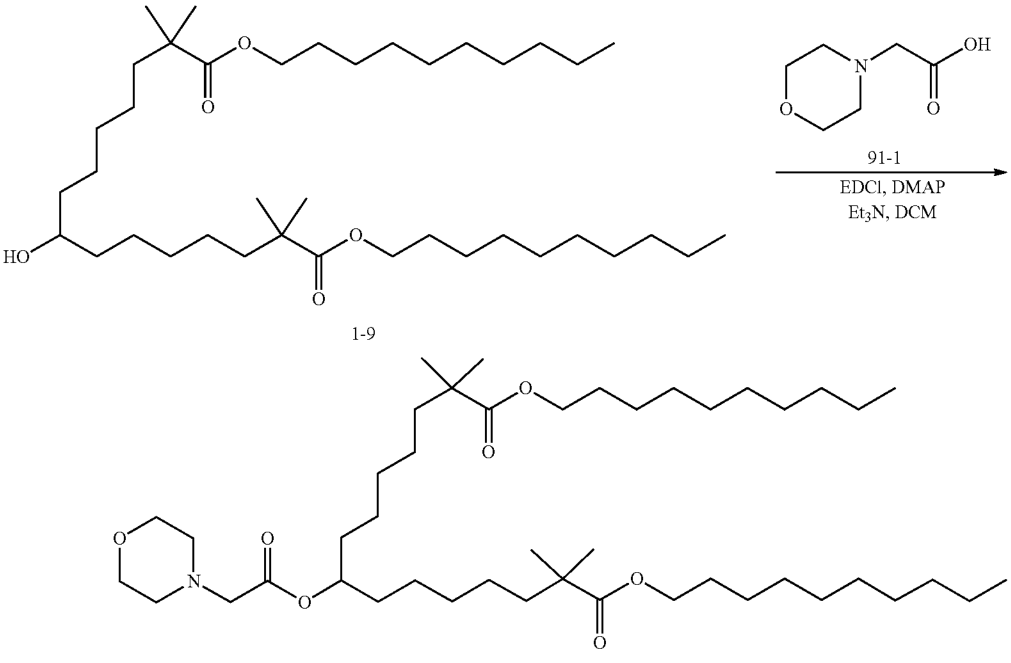
1-9
91-1
91

Referring to the method of Example 1, compound 91 was prepared as an oily product: 32.2 mg.

$^1$H NMR (400 MHz, $CDCl_3$): δ ppm 0.88 (t, J=6.8 Hz, 6H), 1.15 (s, 12H), 1.16-1.38 (m, 40H), 1.46 (m, 8H), 1.60 (m, 4H), 2.59 (m, 4H), 3.19 (s, 2H), 3.76 (t, J=4.8 Hz, 4H), 4.04 (t, J=6.8 Hz, 4H), 4.91 (m, 1H); ESI-MS m/z: 752.7 $[M+H]^+$.

Example 92: Synthesis of Compound 92

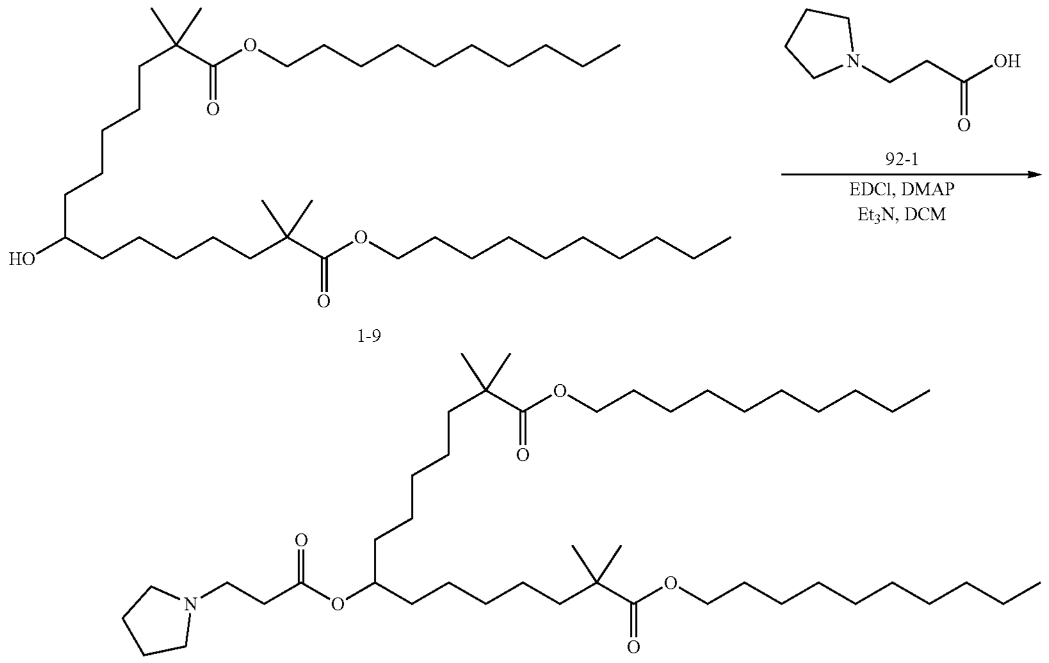

1-9

92-1

92

Referring to the method of Example 1, compound 92 was prepared as an oily product: 32 mg.

$^1$H NMR (400 MHz, $CDCl_3$): δ ppm 0.87 (t, J=6.8 Hz, 6H), 1.13 (s, 12H), 1.28 (m, 42H), 1.46 (m, 8H), 1.45 (m, 4H), 1.76 (m, 4H), 2.50 (m, 4H), 2.76 (m, 2H), 4.01 (t, J=6.8 Hz, 4H), 4.84 (m, 1H); ESI-MS m/z: 750.9 $[M+H]^+$.

Example 93: Synthesis of Compound 93

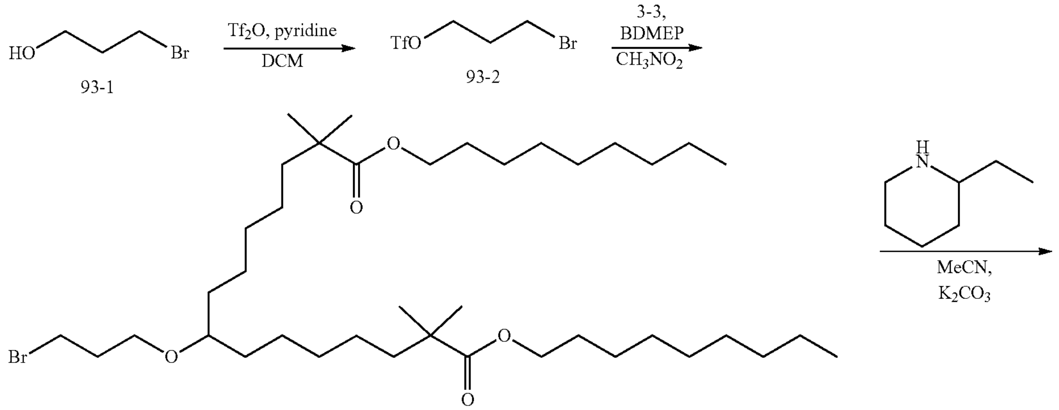

93-1

93-2

93-3

-continued

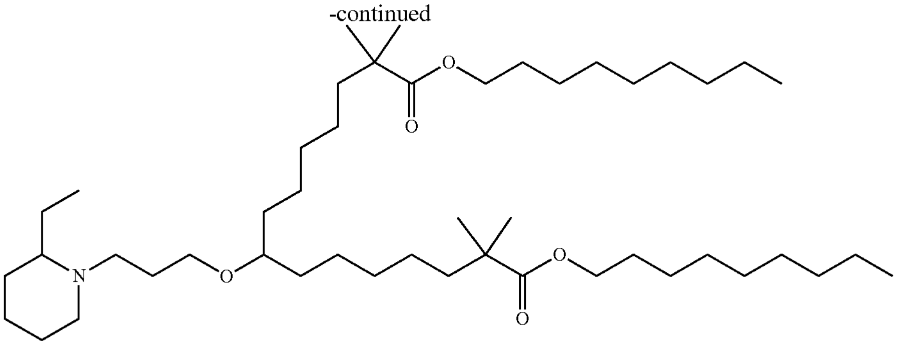

93

3-Bromopropanol (20 g, 144 mmol), trifluoromethanesulfonic anhydride (26.6 mL, 158 mmol) and pyridine (14.0 mL, 173 mmol) were added to a round bottom flask containing 500 mL of dichloromethane. The mixture was stirred at room temperature until the reaction materials were completely consumed by TLC monitoring. The reaction solution was quenched with 1 M hydrochloric acid solution, and extracted with dichloromethane. The organic phase were combined, dried over anhydrous sodium sulfate, and filtered to remove the sodium sulfate. The filtrate was collected. The solvent was removed using a rotary-evaporator to give 25 g of crude compound 93-2, which was used directly for subsequent reactions without further purification.

3-3 (6.0 g, 10 mmol) and crude compound 93-2 (3.0 g, 11 mmol) were added to a round bottom flask containing 50 mL of nitromethane, then 2,6-di-tert-butylpyridine (3.37 mL, 15 mmol) was added to the reaction solution. The reaction solution was warmed up to 95° C. to react overnight. The reaction solution was cooled to room temperature. The solvent was removed using a rotary-evaporator to give the crude product. The crude product was then dissolved in dichloromethane, extracted after adding saturated aqueous ammonium chloride. The organic phase were collected and combined, dried over anhydrous sodium sulfate, and filtered to remove the sodium sulfate. The filtrate was collected. The solvent was removed using a rotary-evaporator and then purified by silica gel column to give compound 93-3 (2.3 g).

Compound 93-3 (251 mg, 0.35 mmol) and 2-ethylpiperidine (71 μL, 0.53 mmol) were dissolved in 3.0 mL of anhydrous acetonitrile and anhydrous potassium carbonate (73 mg, 0.53 mmol) was added to the reaction solution. The mixture was warmed up to 80° C. to react for 6 hours. The reaction solution was cooled to room temperature, quenched by adding saturated aqueous ammonium chloride, and extracted with dichloromethane. The organic phase were collected and combined, dried over anhydrous sodium sulfate, and filtered to remove the sodium sulfate. The filtrate was collected. The solvent was removed using a rotary-evaporator and then purified by preparative high performance liquid chromatography to give compound 93 (82 mg).

$^1$H NMR (400 MHz, $CDCl_3$): δ ppm 0.72-0.91 (m, 9H), 1.08 (s, 12H), 1.11-1.75 (m, 60H), 1.87-2.25 (m, 3H), 2.57-2.93 (m, 4H), 3.04-3.15 (m, 2H), 3.32-3.45 (m, 2H), 3.98 (d, J=6.8 Hz, 4H); ESI-MS m/z: 750.6 $[M+H]^+$.

Example 94: Synthesis of Compound 94

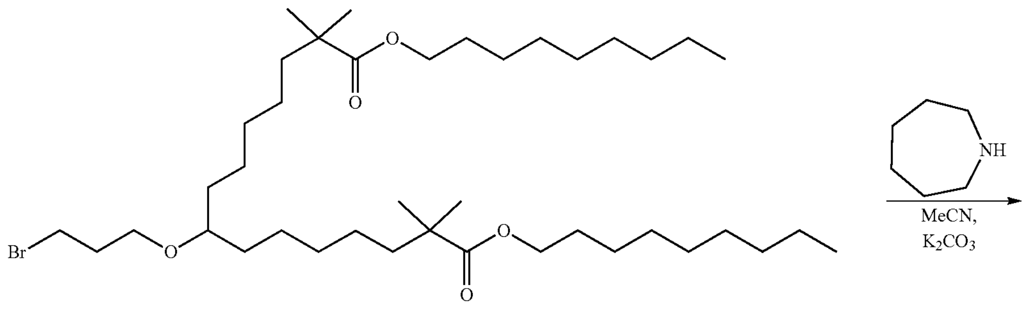

93-3

-continued

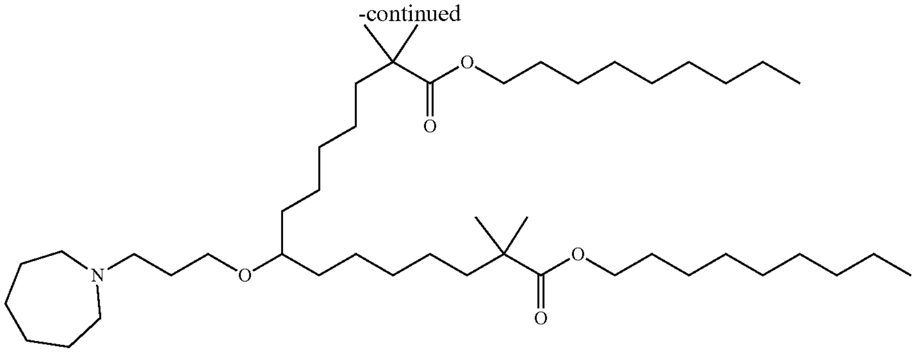

94

Referring to the method of Example 93, compound 94 was prepared as an oily product: 79.2 mg.

$^1$H NMR (400 MHz, $CDCl_3$): δ ppm 0.82 (t, J=7.2 Hz, 6H), 1.09 (s, 12H), 1.11-1.34 (m, 44H), 1.52 (m, 14H), 2.45-2.74 (m, 6H), 3.07 (m, 1H), 3.38 (m, 2H), 3.94 (t, J=6.8 Hz, 4H); ESI-MS m/z: 736.6 $[M+H]^+$.

The compounds of Table 3 were synthesized using the methods of the above examples, or similar methods using the corresponding intermediates.

TABLE 3

| |
|---|
| 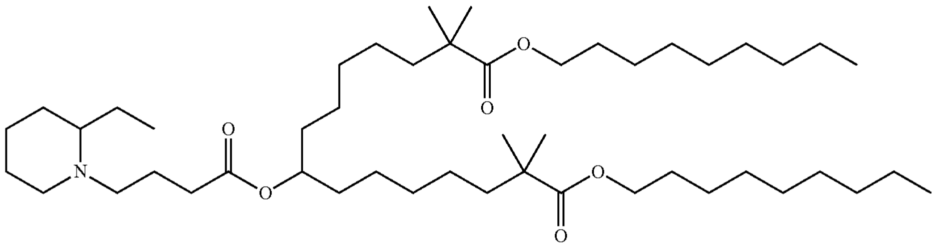 [SMILES: CCCCCCCCCOC(=O)C(C)(C)CCCCCC(CCCCCC(C)(C)C(=O)OCCCCCCCCC)OC(=O)CCCN1CCCCC1CC]<br>Example 95: compound 95<br>$[M + H]^+$: 778.7 |
| 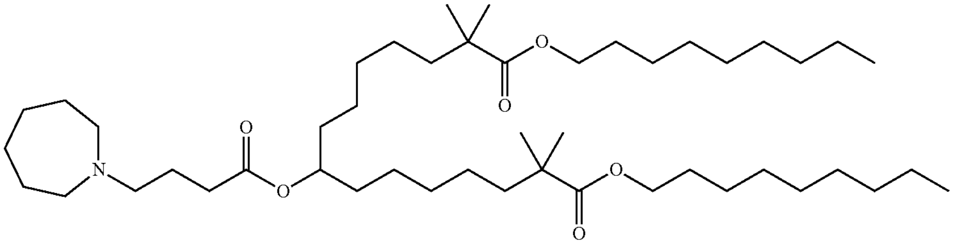 [SMILES: CCCCCCCCCOC(=O)C(C)(C)CCCCCC(CCCCCC(C)(C)C(=O)OCCCCCCCCC)OC(=O)CCCN1CCCCCC1]<br>Example 96: compound 96<br>$[M + H]^+$: 764.7 |

Example 97: Synthesis of Compound 97
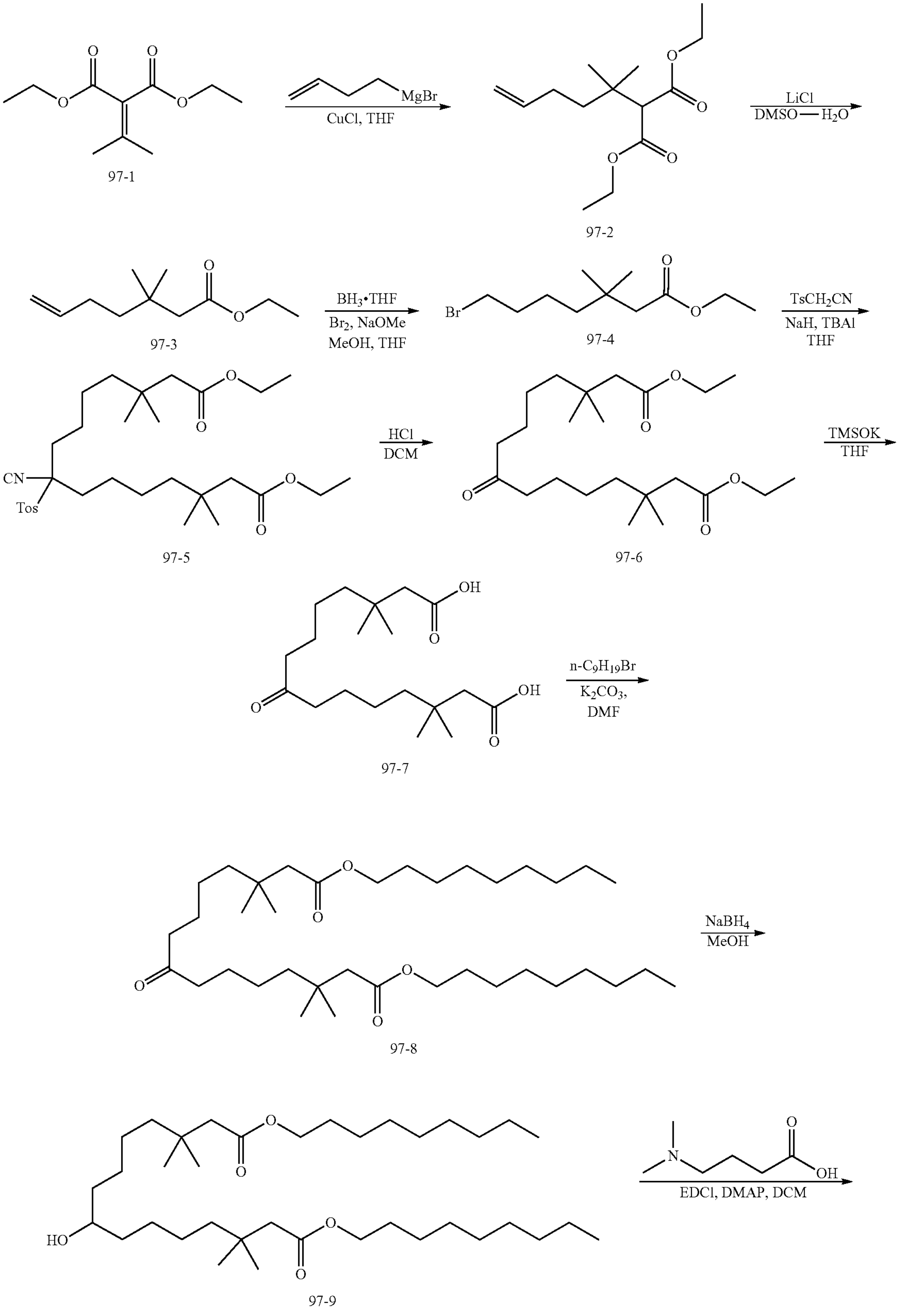

-continued

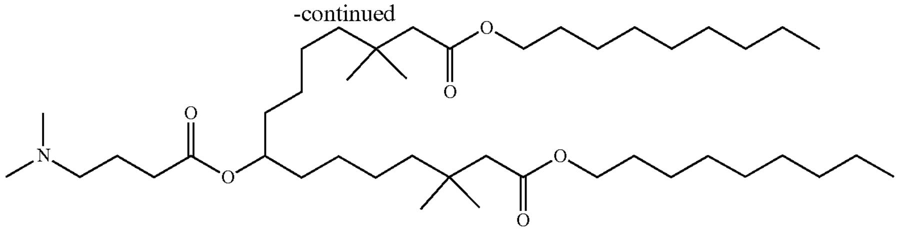

97

To a round bottom flask were added CuCl (989 mg, 9.99 mmol) and 160 mL THF, and the reaction system was cooled to −30° C. Then 3-butenylmagnesium bromide (1 M, 299 mL) was added. 160 mL of solution of compound 97-1 (40.0 g, 199 mmol) in tetrahydrofuran was slowly added to the reaction system. After the dropwise addition was completed, the reaction system was warmed up to room temperature and stirred to react for another 2 hours. After the reaction material 97-1 was reacted completely by TLC monitoring, the reaction solution was quenched with 300 mL of saturated aqueous ammonium chloride, and extracted with ethyl acetate. The organic phases were combined, dried over anhydrous sodium sulfate, and filtered. The filtrate was concentrated to dryness to give the crude product. The crude was purified by silica gel column to give compound 97-2 (45.0 g).

Compound 97-2 (42.0 g, 164 mmol) was dissolved in 400 mL of DMSO, and 4 mL of water and LiCl (27.8 g, 655 mmol) were added to the reaction solution. Then the reaction system was heated to 180° C. and stirred until the reactant 97-2 was reacted completely by TLC monitoring. The reaction system was cooled to room temperature, then poured into water and extracted with ethyl acetate. The organic phases were combined, dried over anhydrous sodium sulfate, and filtered. The filtrate was concentrated to dryness to give the crude product 97-3 (31.0 g), which was used directly in the next reaction without further purification.

Crude product 97-3 (30.0 g, 163 mmol) was dissolved in 240 mL of tetrahydrofuran and $BH_3$·THF (1 M, 244 mL) was added dropwise to the reaction solution in an ice bath. Then the mixture was warmed up to room temperature and stirred for 2 h. The reaction system was then cooled to 0° C. in an ice bath and methanol (13.2 mL, 325 mmol), $Br_2$ (8.39 mL, 163 mmol) and sodium methoxide (43.9 g, 244 mmol) were added sequentially. The mixture was warmed up to room temperature and stirred for another 1 h. The reaction solution was quenched with cold saturated aqueous ammonium chloride solution and extracted with ethyl acetate. The organic phases were combined, dried over anhydrous sodium sulfate, and filtered. The filtrate was concentrated to dryness to give the crude product, which was purified by silica gel column to give compound 97-4 (14.0 g).

Then referring to the method of Example 1, compound 97 was prepared as an oily product: 31.6 mg.

$^1$H NMR (400 MHz, $CDCl_3$): δ ppm 0.84-0.90 (m, 6H), 0.93-1.01 (m, 12H), 1.20-1.31 (m, 32H), 1.45-1.62 (m, 16H), 2.17 (s, 4H), 2.19-2.44 (m, 8H), 3.99-4.08 (m, 4H), 4.81-4.91 (m, 1H); ESI-MS m/z: 710.7 $[M+H]^+$.

Example 98: Synthesis of Compound 98

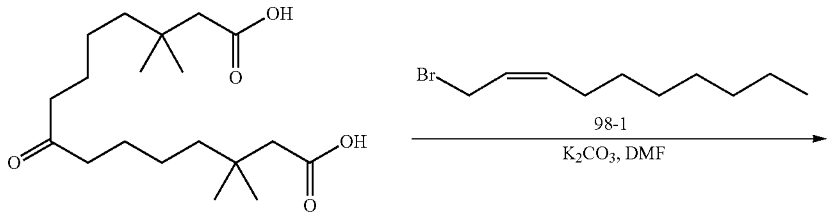

97-7

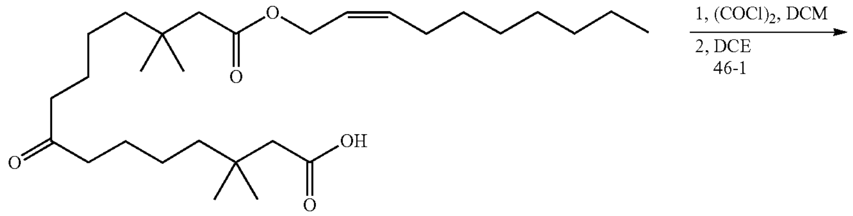

98-2

-continued
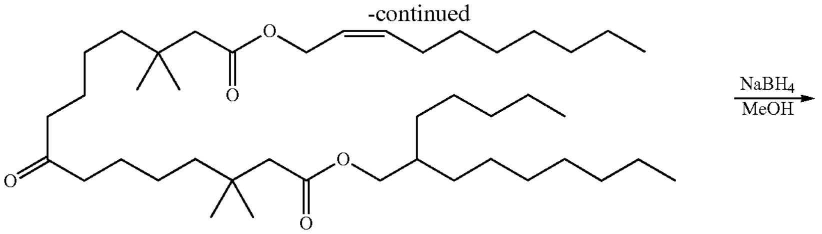
98-3
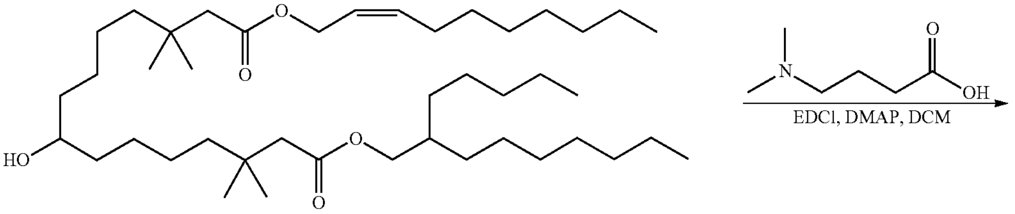
98-4
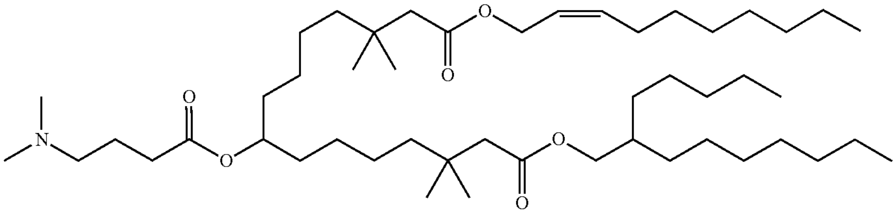
98
Referring to the method of Example 97, compound 98 was prepared as an oily product: 31.0 mg.
$^1$H NMR (400 MHz, $CDCl_3$): δ ppm 0.88 (t, J=6.8 Hz, 9H), 0.97 (s, 12H), 1.25-1.39 (m, 38H), 1.45-1.59 (m, 10H), 1.79 (m, 2H), 2.06-2.13 (m, 2H), 2.18 (m, 4H), 2.20-2.39 (m, 9H), 3.94 (d, J=5.6 Hz, 2H), 4.59 (d, J=6.8 Hz, 2H), 4.82-4.87 (m, 1H), 5.48-5.53 (m, 1H), 5.60-5.64 (m, 1H); ESI-MS m/z: 792.7 $[M+H]^+$.
Example 99: Synthesis of Compound 99
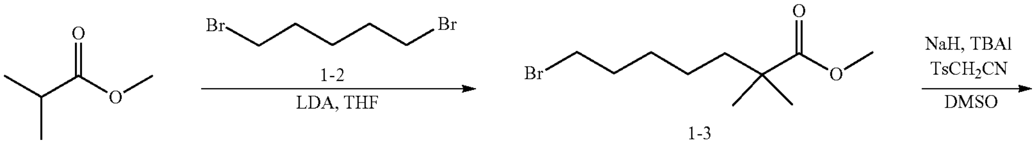
1-1
1-3
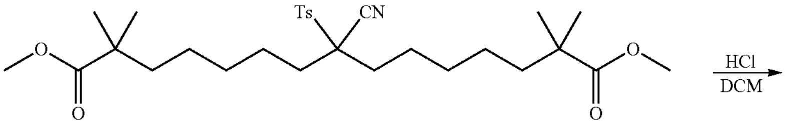
1-4
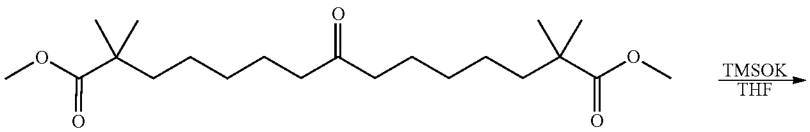
1-5

-continued

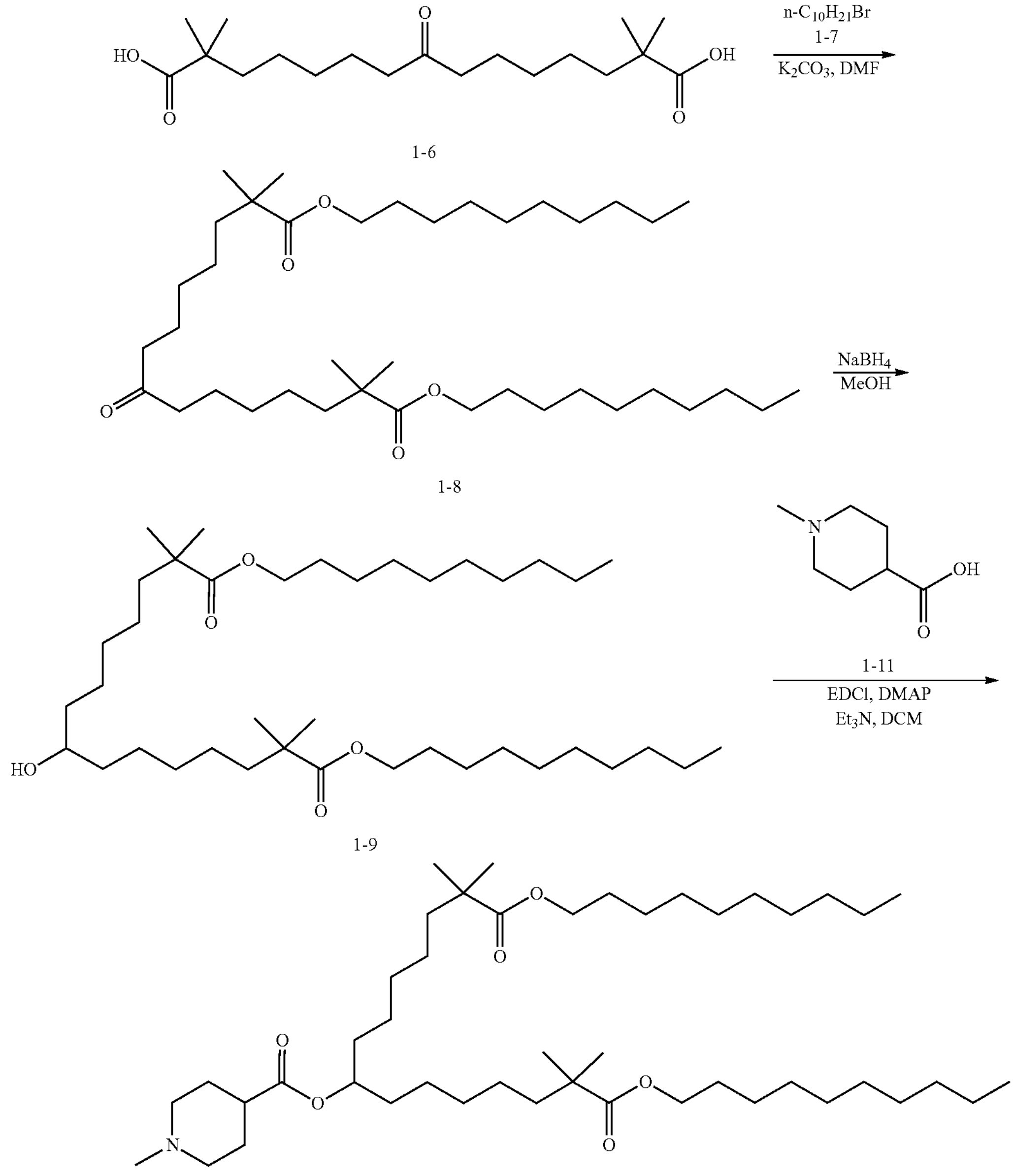

1-6

1-8

1-9

99

A solution of compound 1-1 (100 g, 979 mmol) in tetrahydrofuran (800 mL) was cooled to −40° C. LDA (2 M, 490 mL) was added slowly dropwise to the solution and the mixture was stirred for another 1 h after completion of the dropwise addition. A solution of 1-2 (315 g, 1.37 mol) in tetrahydrofuran (100 mL) was added dropwise to the reaction system at the same temperature and the reaction system was stirred overnight. The reaction system was quenched with saturated aqueous ammonium chloride, and extracted with ethyl acetate. The organic phases were combined, dried over anhydrous sodium sulfate, and filtered. The filtrate was concentrated to dryness to give the crude product. The crude product was purified by silica gel column to give compound 1-3 (115 g). $^1$H NMR (400 MHz, $CDCl_3$): δ ppm 1.06-1.11 (m, 6H), 1.13-1.22 (m, 2H), 1.29-1.39 (m, 2H), 1.42-1.49 (m, 2H), 1.73-1.82 (m, 2H), 3.28-3.40 (m, 2H), 3.55-3.66 (m, 3H).

A solution of compound 1-3 (100 g, 398 mmol), $TsCH_2CN$ (38.9 g, 199 mmol) and TBAI (14.7 g, 39.8 mmol) in dimethyl sulfoxide (800 mL) was cooled to 0° C., and sodium hydride (20.7 g, 517 mmol, 60% purity) was added slowly in batches. The mixture was reacted at room temperature overnight. The reaction system was quenched with saturated aqueous sodium chloride solution and extracted with ethyl acetate. The organic phases were combined, dried over anhydrous sodium sulfate, and filtered. The filtrate was concentrated to dryness to give 115 g of crude compound 1-4, which was used directly in the next reaction without isolation and purification.

To a solution of compound 1-4 crude (110 g, 205 mmol) in dichloromethane (880 mL) was added 330 mL of concentrated hydrochloric acid, and the mixture was reacted at room temperature for 2 h. The complete reaction of the substrate was monitored by TLC. The reaction system was quenched with saturated aqueous ammonium chloride solution and extracted with ethyl acetate. The organic phases were combined, dried over anhydrous sodium sulfate, and filtered. The filtrate was concentrated to dryness to give the crude product. The crude product was purified by silica gel column to give compound 1-5 (30.0 g, 80.9 mmol, 39.4%).

TMSOK (11.0 g, 86.4 mmol) was added to a solution of compound 1-5 (8.0 g, 21.6 mmol) in tetrahydrofuran (35.0 mL) at room temperature, and the reaction system was heated to 70° C. with stirring. The complete consumption of reaction materials was monitored by TLC. The reaction solution was cooled to room temperature, and the organic solvent was removed by rotary evaporation. The crude product was added to 20 mL of water and extracted with dichloromethane. The aqueous layer was collected, and the solution was adjusted to a pH of <5 with 1 M hydrochloric acid. The solution was extracted with dichloromethane. The organic phases were combined, dried over anhydrous sodium sulfate, and filtered. The filtrate was collected and concentrated to give compound 1-6 (7.0 g). $^{1}$H NMR (400 MHz, $CDCl_3$): δ ppm 1.03 (s, 12H), 1.08-1.17 (m, 8H), 1.34-1.45 (m, 8H), 2.21 (t, J=7.2 Hz, 4H).

Potassium carbonate (482 mg, 3.48 mmol) was added to a solution of compound 1-6 (294 mg, 0.87 mmol) and 1-7 (771 mg, 3.48 mmol) in DMF, then the reaction was warmed up to 60° C. for 6 h. The complete disappearance of reactant 1-6 was monitored. The mixture was cooled to room temperature. The reaction system was quenched with saturated aqueous sodium chloride solution and extracted with ethyl acetate. The organic phases were combined, dried over anhydrous sodium sulfate, and filtered. The filtrate was concentrated to dryness to give the crude product. The crude was purified by silica gel column to give compound 1-8 (325 mg).

Compound 1-8 (325 mg) was dissolved in 4.0 mL of methanol and sodium borohydride (30 mg, 0.84 mmol) was added to the reaction system. The mixture was reacted at room temperature. The complete disappearance of the reactants was monitored by TLC. The reaction system was quenched with saturated aqueous sodium chloride solution and extracted with dichloromethane. The organic phases were combined, dried over anhydrous sodium sulfate, and filtered. The filtrate was concentrated to dryness to give crude compound 1-9 (260 mg), which was used directly in the next reaction without purification.

Crude compound 1-9 (250 mg, 0.40 mmol), 1-11 (35.9 mg, 0.60 mmol), EDCI (230 mg, 1.20 mmol), triethylamine (0.17 mL, 1.20 mmol) and DMAP (49 mg, 0.40 mmol) were dissolved in 5.0 mL of dichloromethane, and the reaction solution was stirred to react at room temperature for 12 h. The reaction solution was quenched with saturated aqueous sodium chloride and extracted with dichloromethane. The organic phases were combined, dried over anhydrous sodium sulfate, and filtered. The organic phase was collected and the organic solvent was removed using a rotary-evaporator to give the crude product, which was purified by preparative high performance liquid chromatography to give compound 99 (31.6 mg)

$^{1}$H NMR (400 MHz, $CDCl_3$): δ ppm 0.86 (t, J=6.8 Hz, 6H), 1.13 (s, 12H), 1.25 (m, 43H), 1.46 (m, 8H), 1.57 (m, 4H), 1.84 (m, 4H), 2.33 (s, 3H), 2.86 (m, 2H), 4.01 (m, 4H), 4.81 (m, 1H); ESI-MS m/z: 751.0 [M+H]$^{+}$.

Example 100: Synthesis of Compound 100

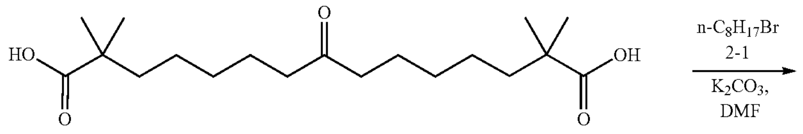

1-6

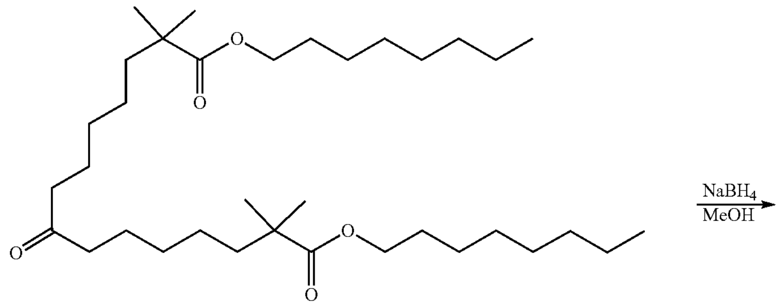

2-2

-continued
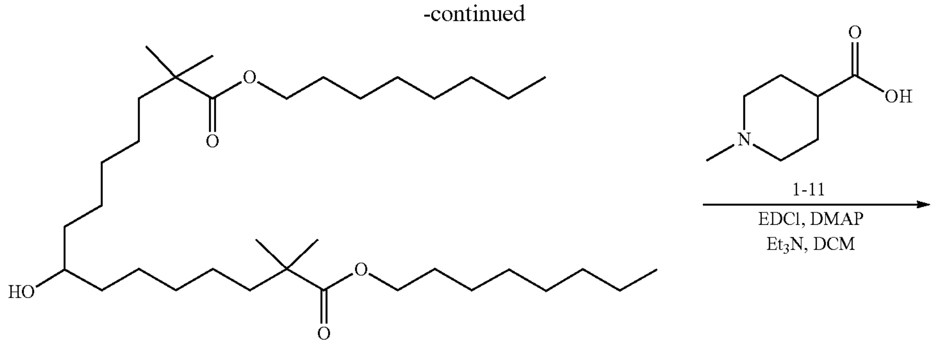
2-3
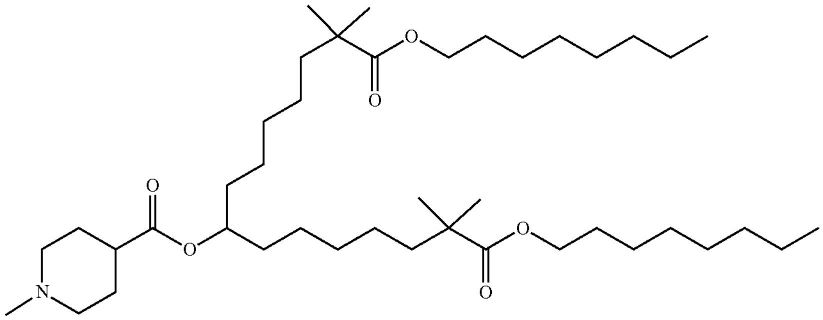
100
Referring to the method of Example 99, compound 100 was prepared as an oily product: 33.5 mg.
$^1$H NMR (400 MHz, $CDCl_3$): δ ppm 0.81 (t, J=6.8 Hz, 6H), 1.08 (s, 12H), 1.11-1.31 (m, 30H), 1.41 (m, 9H), 1.54 (m, 5H), 1.65-1.77 (m, 2H), 1.78-1.98 (m, 4H), 2.20 (m, 4H), 2.74 (m, 2H), 3.97 (t, J=6.8 Hz, 4H), 4.71-4.85 (m, 1H); ESI-MS m/z: 694.6 $[M+H]^+$.
Example 101: Synthesis of Compound 101
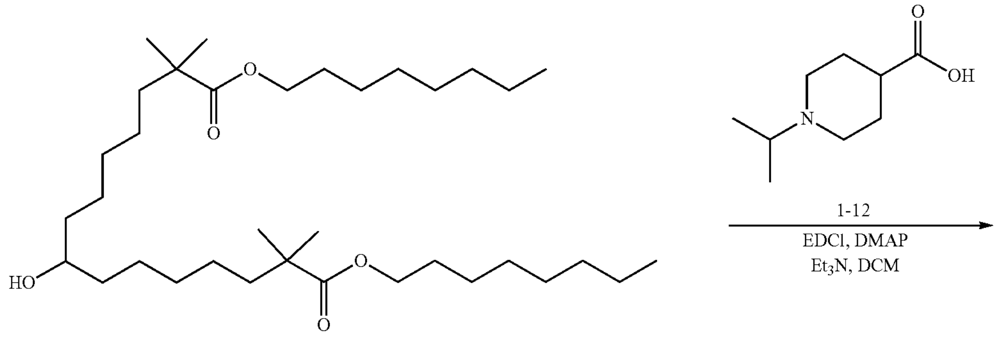
2-3

-continued
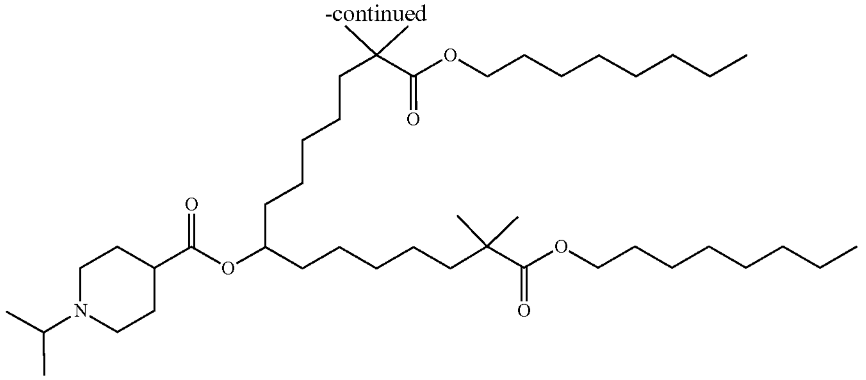
101
Referring to the method of Example 99, compound 101 was prepared as an oily product: 30.8 mg.
$^1$H NMR (400 MHz, $CDCl_3$): δ ppm 0.81 (t, J=6.8 Hz, 6H), 0.96 (d, J=6.8 Hz, 6H), 1.08 (s, 12H), 1.11-1.31 (m, 32H), 1.35-1.46 (m, 8H), 1.54 (m, 4H), 1.59-1.74 (m, 4H), 2.01-2.13 (m, 3H), 2.62 (m, 1H), 2.77 (m, 2H), 3.97 (t, J=6.8 Hz, 4H), 4.71-4.83 (m, 1H); ESI-MS m/z: 722.6 [M+H]$^+$.
Example 102: Synthesis of Compound 102
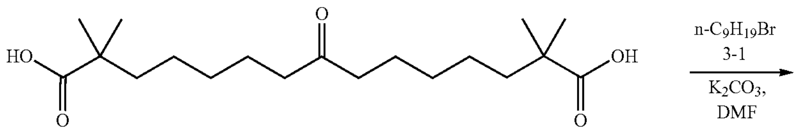
1-6
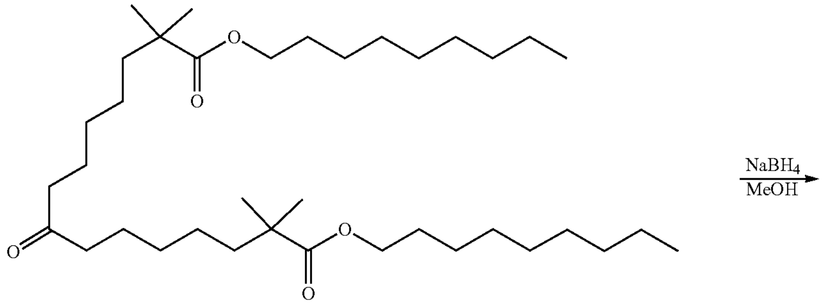
3-2
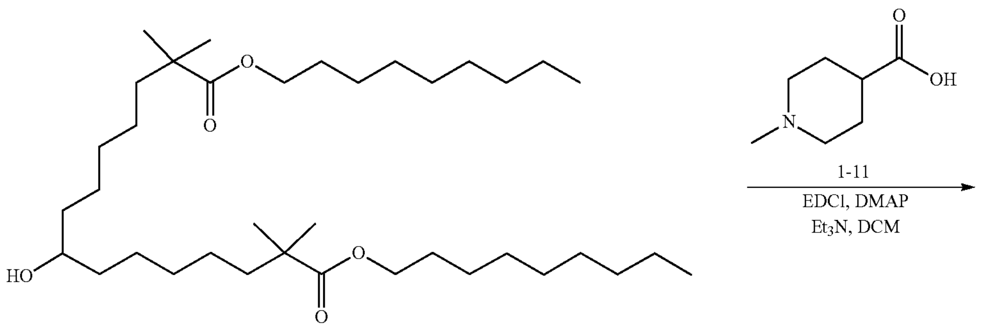
3-3

-continued

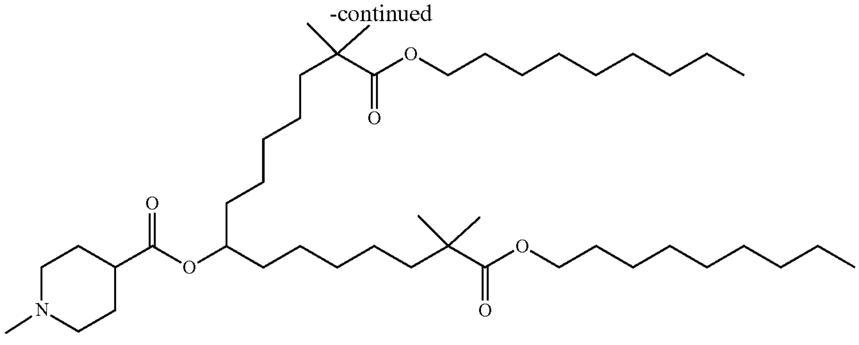

102

Referring to the method of Example 99, compound 102 was prepared as an oily product: 32.4 mg.

$^{1}H$ NMR (400 MHz, $CDCl_3$): δ ppm 0.90 (t, J=6.8 Hz, 6H), 1.17 (s, 12H), 1.20-1.41 (m, 34H), 1.44-1.55 (m, 8H), 1.57-1.69 (m, 5H), 1.73-1.86 (m, 3H), 1.92 (m, 2H), 2.02 (m, 2H), 2.21-2.33 (m, 4H), 2.82-2.85 (m, 2H), 4.06 (t, J=6.8 Hz, 4H), 4.84-4.90 (m, 1H); ESI-MS m/z: 722.6 $[M+H]^+$.

Example 103: Synthesis of Compound 103

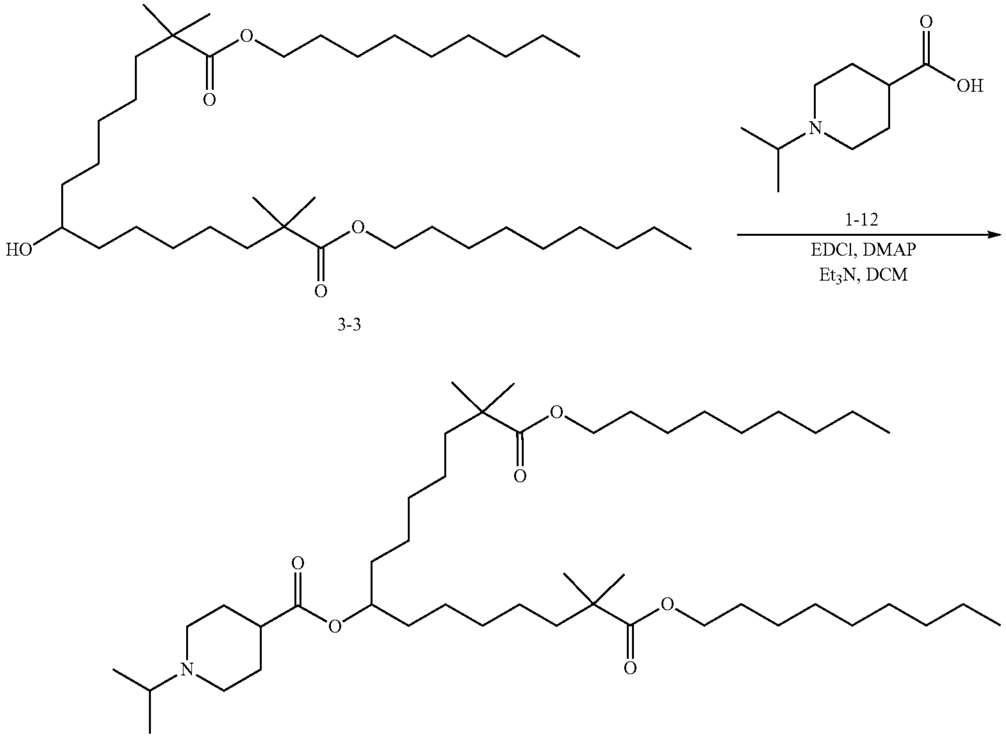

3-3

103

Referring to the method of Example 99, compound 103 was prepared as an oily product: 32.8 mg.

$^{1}H$ NMR (400 MHz, $CDCl_3$): δ ppm 0.81 (t, J=6.8 Hz, 6H), 0.96 (d, J=6.8 Hz, 6H), 1.08 (s, 12H), 1.11-1.33 (m, 34H), 1.34-1.47 (m, 8H), 1.54 (m, 5H), 1.60-1.75 (m, 3H), 1.83 (m, 2H), 2.03-2.24 (m, 3H), 2.56-2.79 (m, 3H), 3.97 (t, J=6.8 Hz, 4H), 4.74-4.81 (m, 1H); ESI-MS m/z: 750.6 $[M+H]^+$.

Example 104: Synthesis of Compound 104

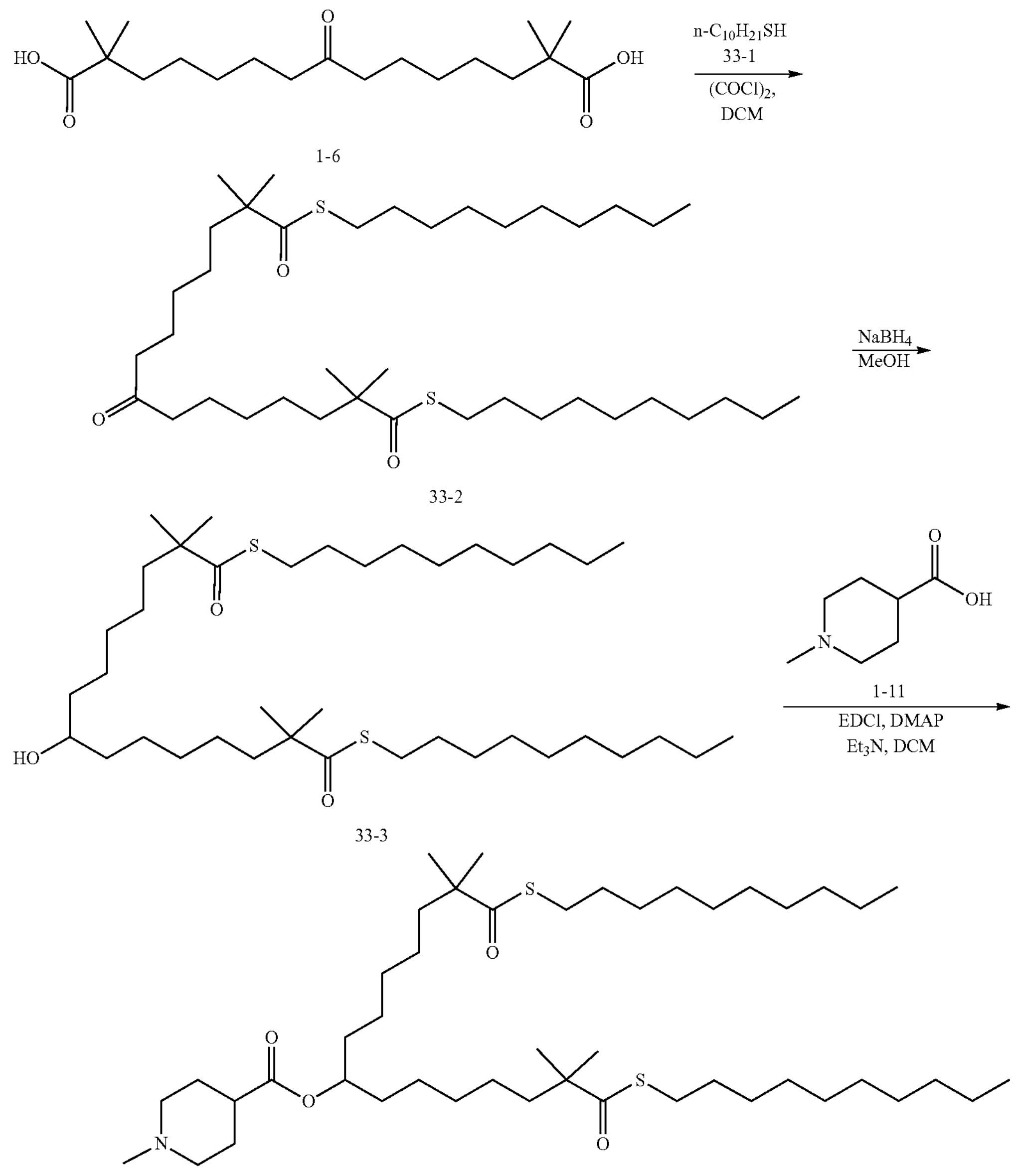

104

Compound 1-6 (448 mg, 1.3 mmol) was dissolved in 5.0 mL of dichloromethane, and the reaction system was cooled to 0° C. in an ice bath. DMF (10 μL, 0.13 mmol) was added and oxalyl chloride (0.44 mL, 5.2 mmol) was then added dropwise to the reaction solution. The ice bath was removed after the dropwise addition was completed and the mixture was stirred for 1 h at room temperature. The solvent was removed using a rotary-evaporator to give acyl chloride crude product (330 mg) as an oil, which was used directly in the next reaction step.

1-Decanethiol 33-1 (455 mg, 2.61 mmol) was added to a solution of crude acyl chloride (330 mg, 0.87 mmol) in DCE (3.0 mL), and the reaction was heated to 70° C. to react overnight. The reaction solution was cooled to room temperature and the solvent was removed using a rotary-evaporator to give the crude product, which was purified by silica gel column to give compound 33-2 (400 mg). $^1H$ NMR (400 MHz, $CDCl_3$): δ ppm 0.84-0.87 (m, 6H), 1.14-1.18 (m, 12H), 1.20-1.28 (m, 36H), 1.48-1.55 (m, 12H), 2.33 (t, J=7.2 Hz, 4H), 2.79 (t, J=7.2 Hz, 4H).

Compound 33-2 (300 mg, 0.46 mmol) was dissolved in 3.0 mL of methanol and $NaBH_4$ (52.5 mg, 1.38 mmol) was added in batches. The reaction solution was stirred under nitrogen atmosphere at room temperature for 2 h. The complete disappearance of the reaction material was monitored by TLC. The reaction solution was quenched by adding saturated ammonium chloride solution, and extracted with ethyl acetate. The organic phases were combined, dried over anhydrous sodium sulfate, and filtered. The filtrate was collected and concentrated to give 300 mg of crude compound 33-3, which was directly used in the next reaction step without further purification.

Crude compound 33-3 (300 mg, 0.46 mmol), 1-11 (98.8 mg, 0.69 mmol), EDCI (264.5 mg, 1.38 mmol), triethylamine (0.19 mL, 1.38 mmol) and DMAP (56.2 mg, 0.46 mmol) were dissolved in 8.0 mL of dichloromethane, and the reaction solution was stirred at room temperature until the reaction material 33-3 was completely consumed. The reaction solution was quenched with saturated aqueous sodium chloride and extracted with dichloromethane. The organic phases were combined, dried over anhydrous sodium sulfate, and filtered. The organic phase was collected, and the organic solvent was removed using a rotary-evaporator. The crude product was purified by preparative high performance liquid chromatography to give the compound 104 (67.3 mg).

$^1$H NMR (400 MHz, $CDCl_3$): δ ppm 0.81 (t, J=6.8 Hz, 6H), 1.08 (s, 12H), 1.09-1.31 (m, 42H), 1.35-1.51 (m, 14H), 1.61-2.25 (m, 8H), 2.73 (t, J=7.2 Hz, 4H), 4.77 (m, 1H); ESI-MS m/z: 782.7 $[M+H]^+$.

Example 105: Synthesis of Compound 105

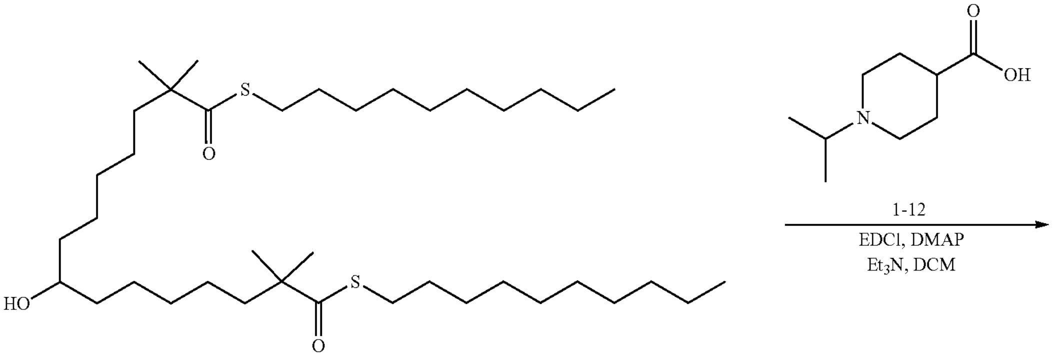

33-3

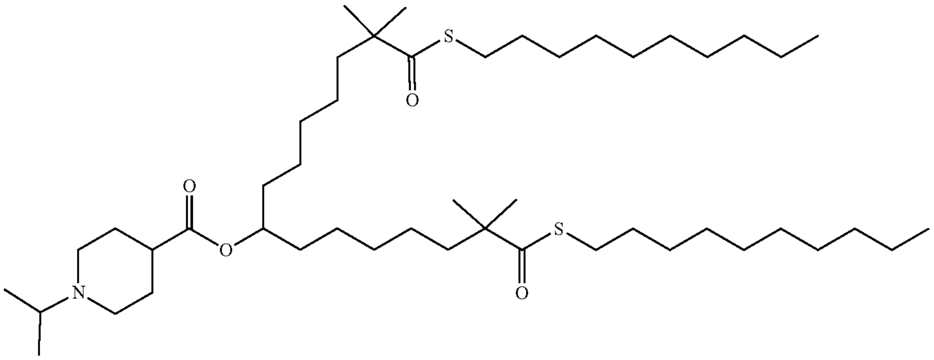

105

Referring to the method of Example 104, compound 105 was prepared as an oily product: 27.1 mg.

$^1$H NMR (400 MHz, $CDCl_3$): δ ppm 0.85-0.89 (m, 6H), 1.02 (br d, J=6.4 Hz, 6H), 1.18 (s, 12H), 1.20-1.40 (m, 40H), 1.42-1.59 (m, 12H), 1.64-1.83 (m, 3H), 1.87-1.93 (m, 2H), 2.11-2.23 (m, 3H), 2.66-2.94 (m, 6H), 4.72-4.94 (m, 1H); ESI-MS m/z: 810.6 $[M+H]^+$.

Example 106: Synthesis of Compound 106

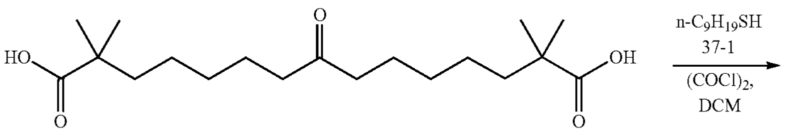

1-6

-continued
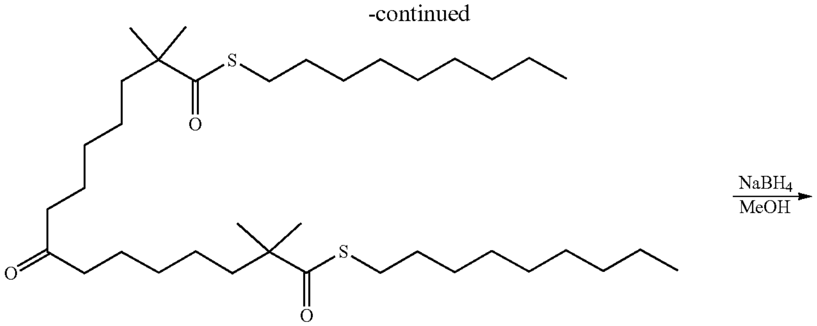
37-2
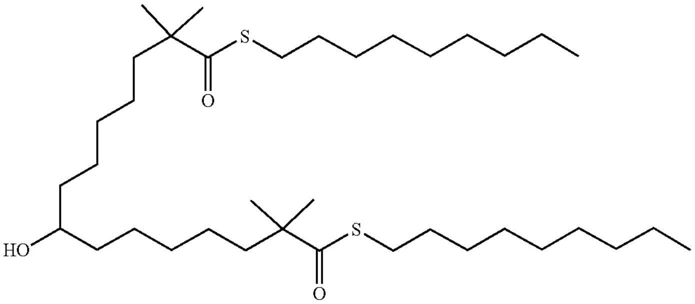
37-3
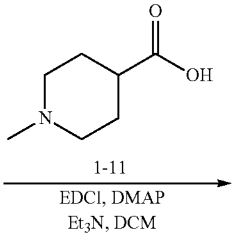
1-11
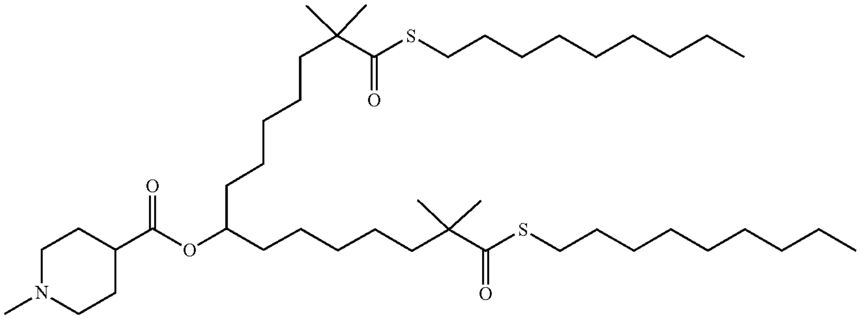
106
Referring to the method of Example 104, compound 106 was prepared as an oily product: 38.4 mg.
$^1$H NMR (400 MHz, $CDCl_3$): δ ppm 0.88 (t, J=7.2 Hz, 6H), 1.17 (s, 12H), 1.15-1.34 (m, 36H), 1.43-1.57 (m, 15H), 1.69-2.09 (m, 5H), 2.27-2.34 (m, 3H), 2.77-2.86 (m, 5H), 4.78-4.85 (m, 1H); ESI-MS m/z: 754.6 $[M+H]^+$.
Example 107: Synthesis of Compound 107
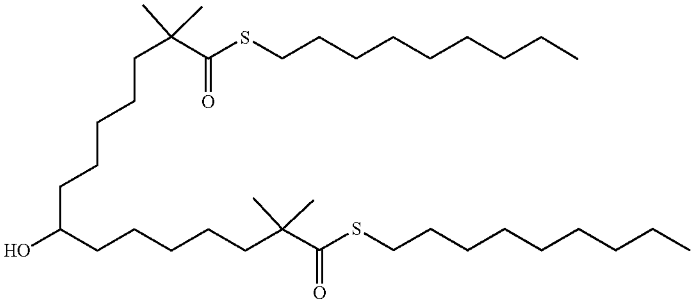
37-3
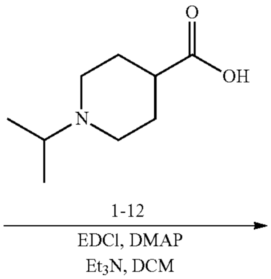
1-12

-continued
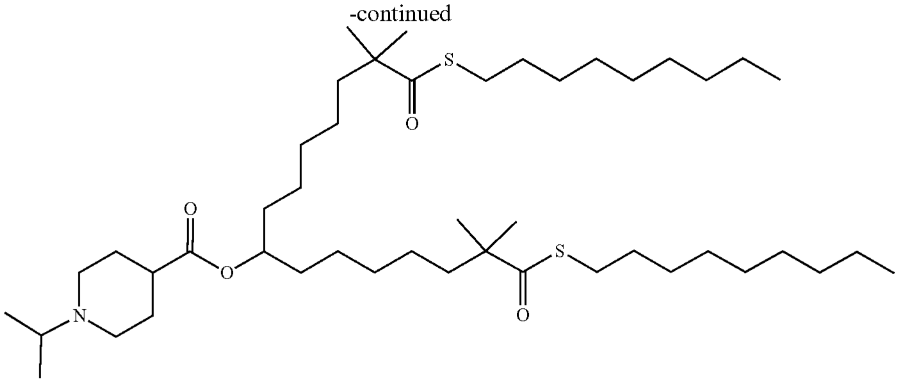
107
Referring to the method of Example 104, compound 107 was prepared as an oily product: 39 mg.
$^1$H NMR (400 MHz, $CDCl_3$): δ ppm 0.88 (t, J=6.8 Hz, 6H), 1.05 (d, J=6.8 Hz, 6H), 1.16 (s, 12H), 1.12-1.35 (m, 34H), 1.37-1.55 (m, 15H), 1.62-1.92 (m, 4H), 2.15-2.19 (m, 3H), 2.71-2.93 (m, 6H), 4.78-4.85 (m, 1H); ESI-MS m/z: 782.6 [M+H]$^+$.
Example 108: Synthesis of Compound 108
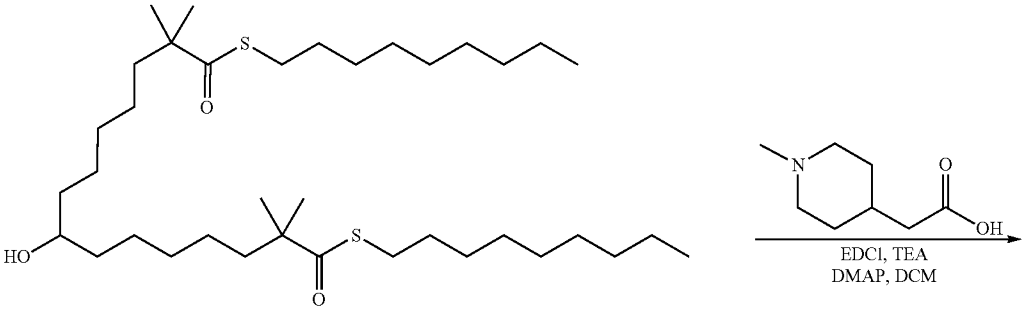
37-3
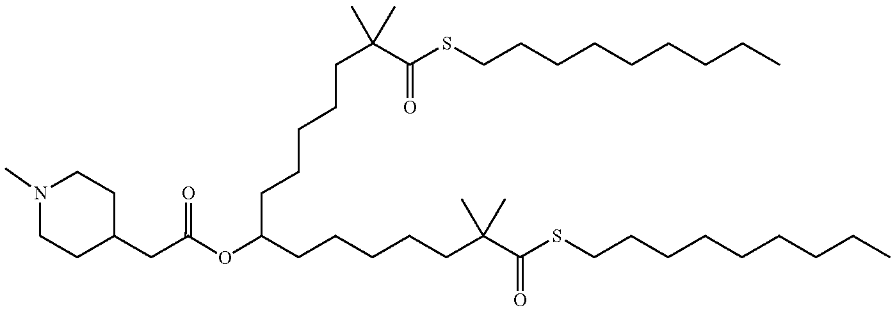
108
Referring to the method of Example 104, compound 108 was prepared as an oily product: 43.8 mg.
$^1$H NMR (400 MHz, $CDCl_3$): δ ppm 0.88 (t, J=6.80 Hz, 6H), 1.18 (s, 12H), 1.20-1.39 (m, 38H), 1.40-1.62 (m, 14H), 1.66-1.86 (m, 3H), 1.89-2.10 (m, 2H), 2.19-2.27 (m, 3H), 2.28 (br s, 2H), 2.79-2.83 (m, 4H), 4.79-4.88 (m, 1H); ESI-MS m/z: 768.5 [M+H]$^+$.

Example 109: Synthesis of Compound 109
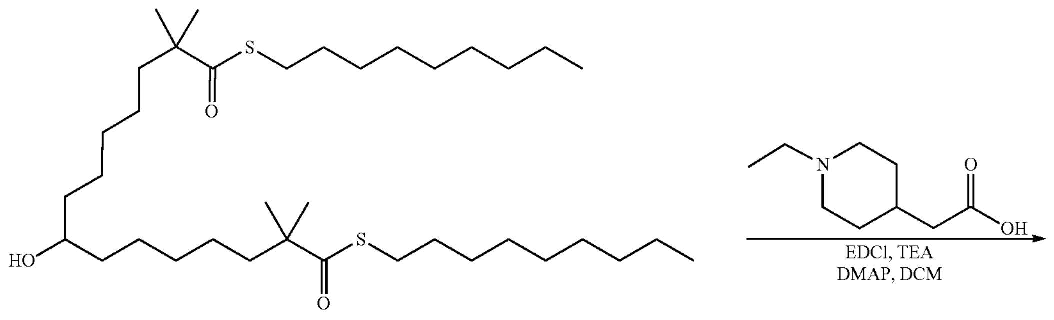
37-3
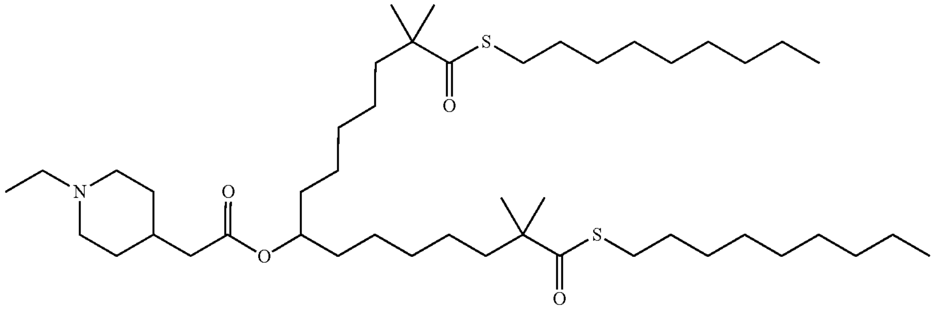
109
Referring to the method of Example 104, compound 109 was prepared as an oily product: 44.8 mg.
$^{1}$H NMR (400 MHz, $CDCl_3$): δ ppm 0.86-0.89 (m, 6H), 1.18 (s, 15H), 1.23-1.37 (m, 36H), 1.46-1.54 (m, 14H), 1.76-1.93 (m, 4H), 2.11-2.20 (m, 1H), 2.24-2.28 (m, 2H), 2.54-2.71 (m, 2H), 2.81 (d, J=7.2 Hz, 4H), 3.08-3.24 (m, 2H), 4.79-4.88 (m, 1H); ESI-MS m/z: 782.6 $[M+H]^+$.
Example 110: Synthesis of Compound 110
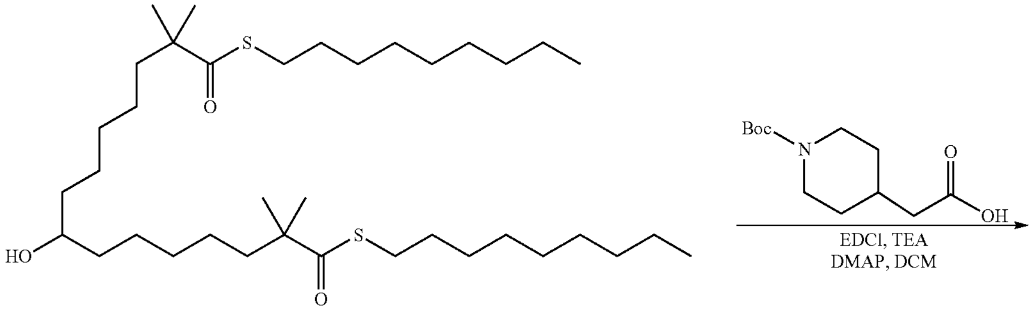
37-3
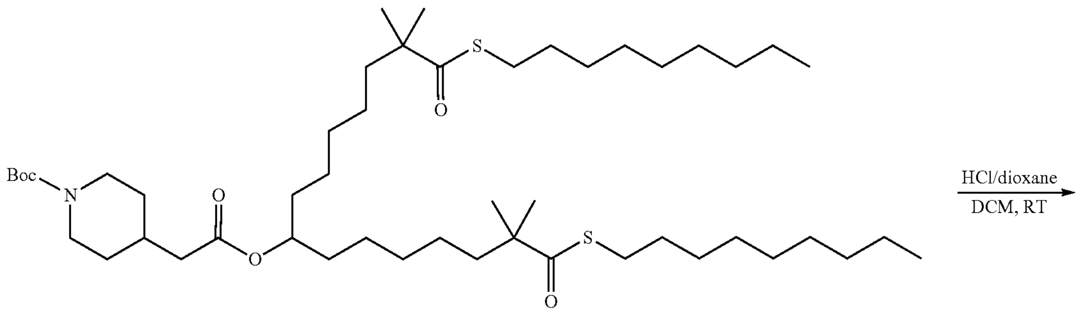

-continued
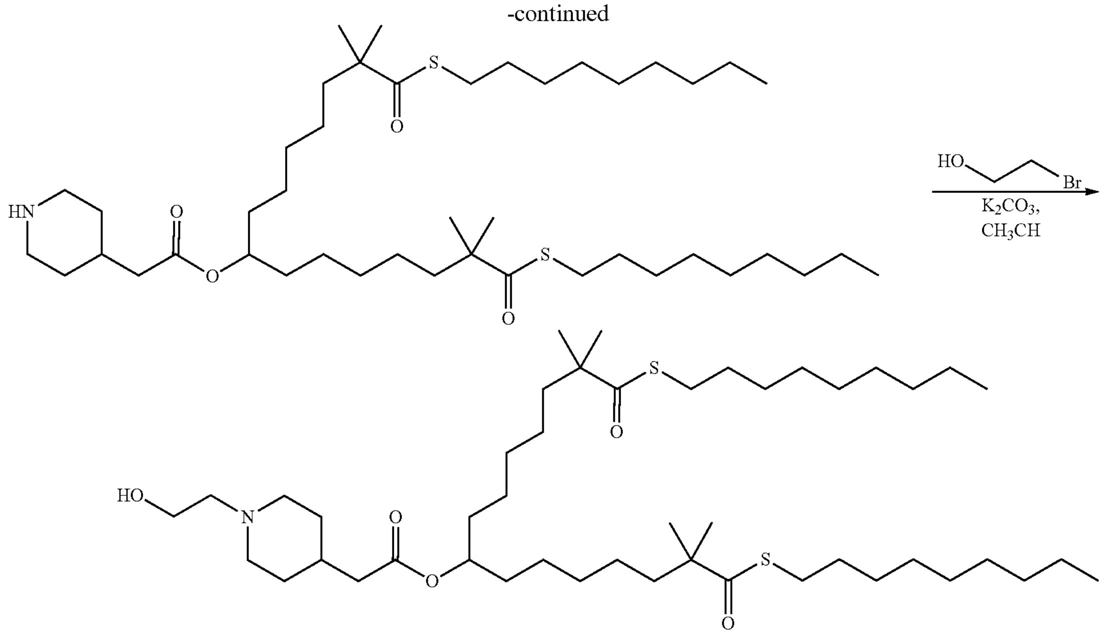
110
Referring to the method of Example 104, compound 110 was prepared as an oily product: 34.4 mg.
$^1$H NMR (400 MHz, $CDCl_3$): δ ppm 0.81 (t, J=7.2 Hz, 6H), 1.12 (s, 12H), 1.14-1.27 (m, 34H), 1.44-1.48 (m, 12H), 1.66-1.77 (m, 7H), 2.05-2.24 (m, 4H), 2.53 (m, 2H), 2.75 (t, J=7.2 Hz, 4H), 2.90-2.92 (m, 2H), 3.57 (t, J=5.2 Hz, 2H), 4.74-4.80 (m, 1H); ESI-MS m/z: 798.6 $[M+H]^+$.
Example 111: Synthesis of Compound 111
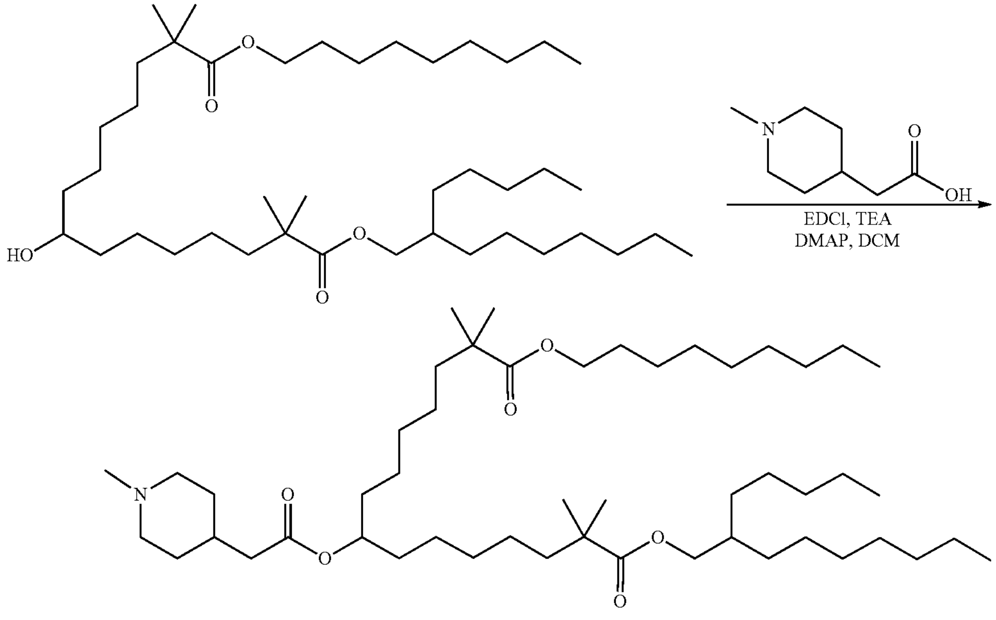
111
Referring to the method of Example 104, compound 111 was prepared as an oily product: 31.4 mg.
$^1$H NMR (400 MHz, $CDCl_3$): δ ppm 0.92 (t, J=6.8 Hz, 9H), 1.19 (s, 12H), 1.20-1.35 (m, 43H), 1.47-1.55 (m, 9H), 1.54-1.82 (m, 12H), 2.07-2.37 (m, 7H), 2.94-3.01 (m, 2H), 3.98 (d, J=6.8 Hz, 2H), 4.07 (t, J=6.8 Hz, 2H), 4.84-4.91 (m, 1H); ESI-MS m/z: 806.7 $[M+H]^+$.

Example 112: Synthesis of Compound 112
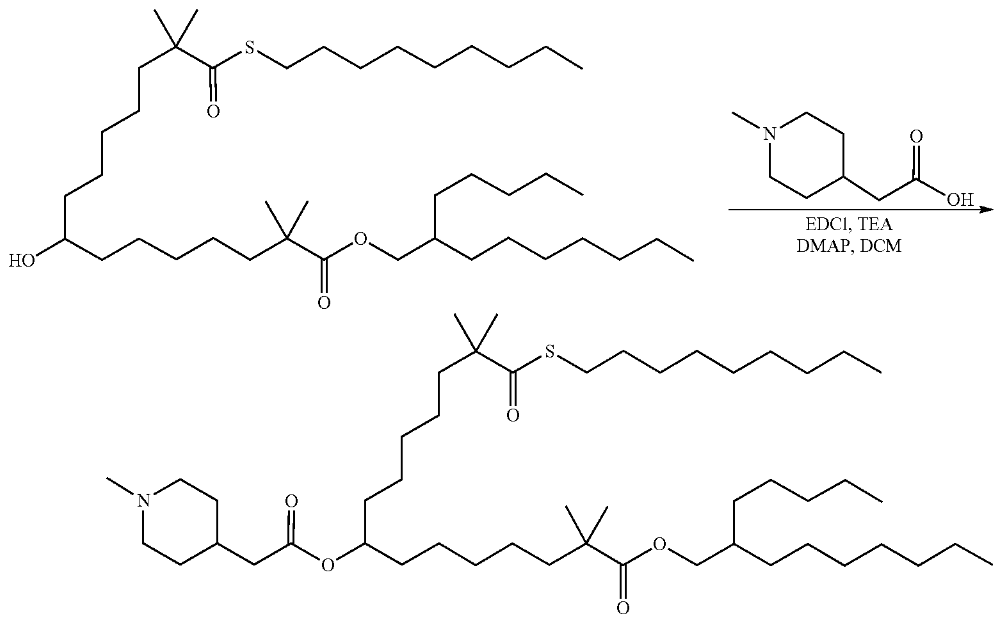
112
Referring to the method of Example 104, compound 112 was prepared as an oily product: 24.4 mg.
$^{1}$H NMR (400 MHz, $CDCl_3$): δ ppm 0.80-0.83 (m, 9H), 1.08 (s, 12H), 1.10-1.35 (m, 28H), 1.41-1.57 (m, 28H), 1.65-1.75 (m, 4H), 1.95-2.10 (m, 2H), 2.16 (d, J=6.4 Hz, 2H), 2.30 (s, 3H), 2.73-2.91 (m, 4H), 3.87 (d, J=5.6 Hz, 2H), 4.75-4.79 (m, 1H); ESI-MS m/z: 822.7 $[M+H]^+$.
Example 113: Synthesis of Compound 113
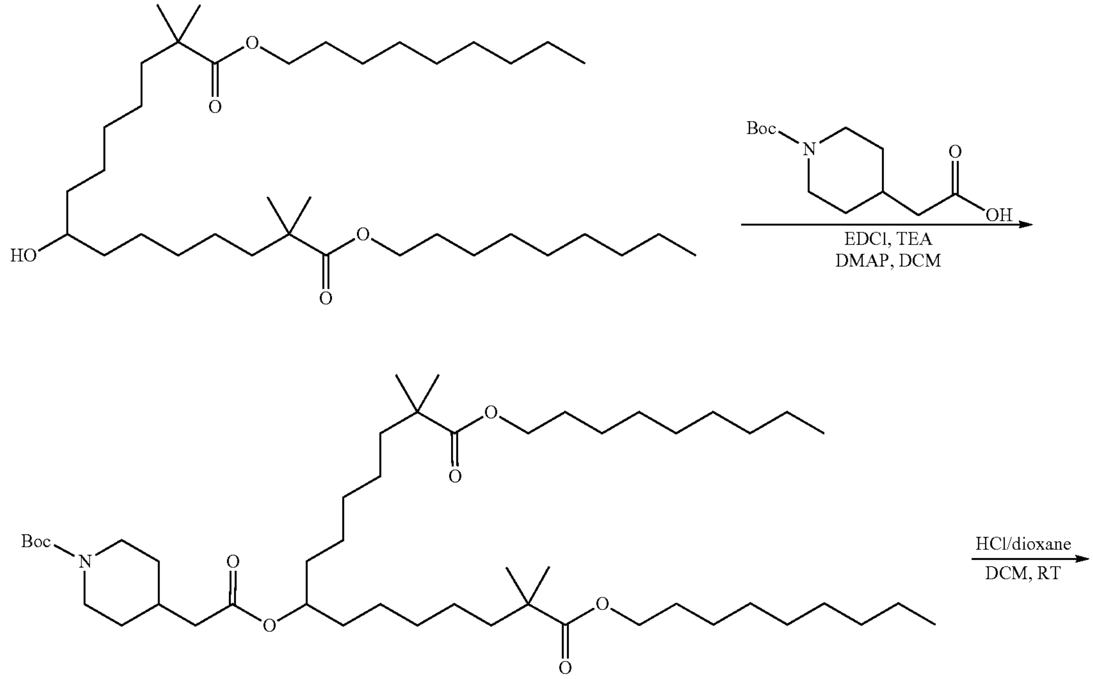

-continued
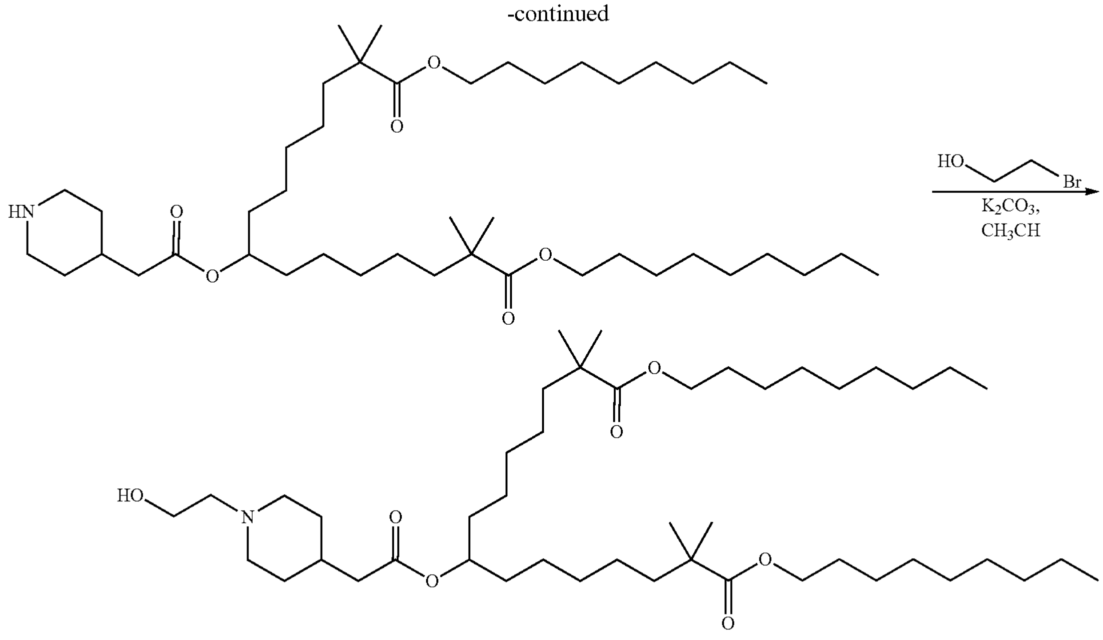
113
Referring to the method of Example 110, compound 113 was prepared as an oily product: 31.1 mg.
$^1H$ NMR (400 MHz, $CDCl_3$): δ ppm 0.81 (t, J=7.2 Hz, 6H), 1.08 (s, 12H), 1.10-1.24 (m, 36H), 1.36-1.43 (m, 8H), 1.48-1.54 (m, 6H), 1.64-1.72 (m, 6H), 2.05 (t, J=6.8 Hz, 1H), 2.15 (d, J=6.8 Hz, 2H), 2.47 (t, J=5.6 Hz, 2H), 2.82-2.89 (m, 2H), 3.54 (t, J=5.6 Hz, 2H), 3.97 (t, J=6.8 Hz, 4H), 4.73-4.79 (m, 1H); ESI-MS m/z: 766.6 $[M+H]^+$.
Example 114: Synthesis of Compound 114
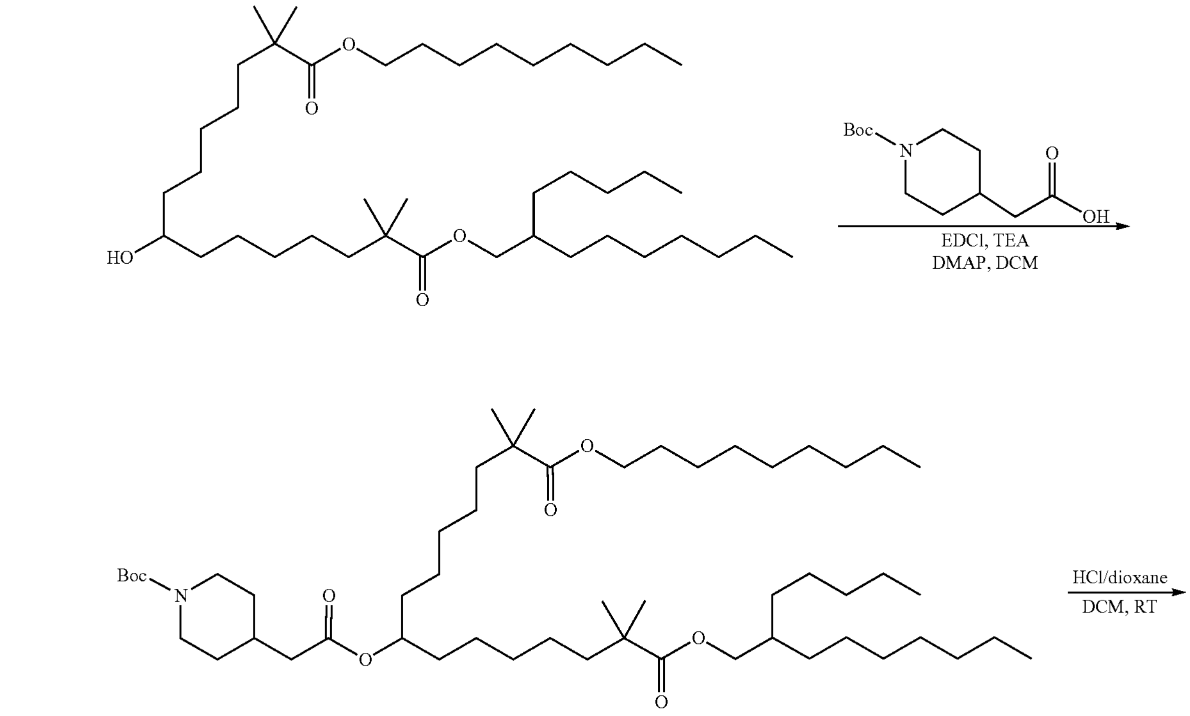

-continued
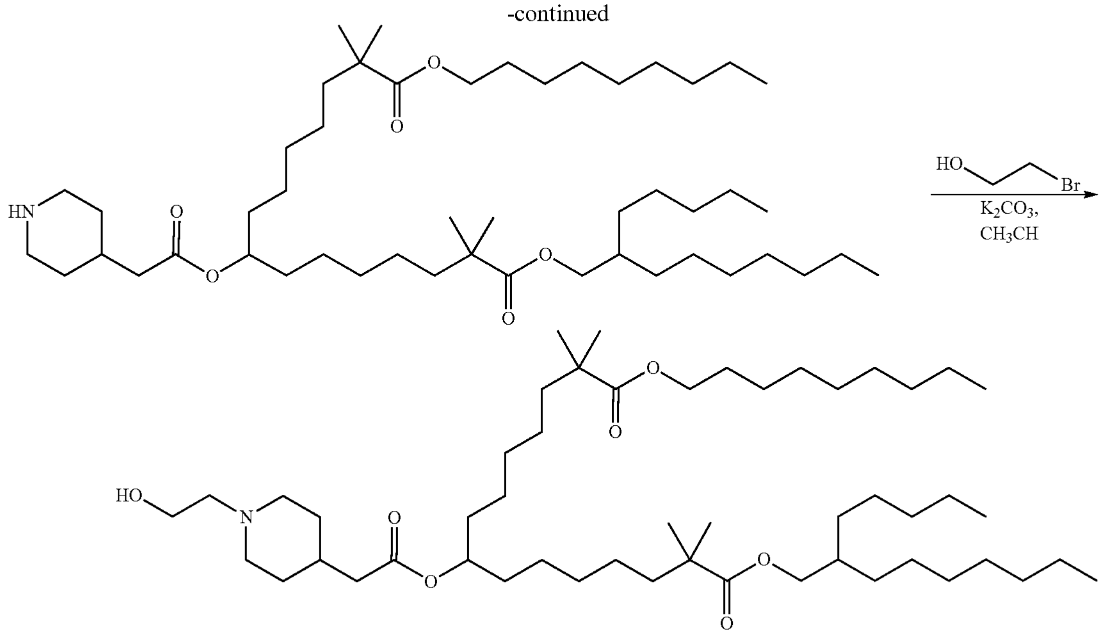
114
Referring to the method of Example 110, compound 114 was prepared as an oily product: 32.7 mg.
$^1H$ NMR (400 MHz, $CDCl_3$): δ ppm 0.85-0.88 (m, 9H), 1.07 (s, 12H), 1.09-1.35 (m, 46H), 1.41-1.58 (m, 13H), 1.97-2.25 (m, 3H), 2.32 (d, J=5.6 Hz, 2H), 2.83-2.86 (m, 2H), 3.17-3.19 (m, 2H), 3.78-3.81 (d, J=7.2 Hz, 2H), 3.92 (d, J=5.6 Hz, 2H), 4.01 (t, J=6.4 Hz, 2H), 4.10 (m, 1H), 4.81-4.86 (m, 1H); ESI-MS m/z: 836.7 $[M+H]^+$.
Example 115: Synthesis of Compound 115
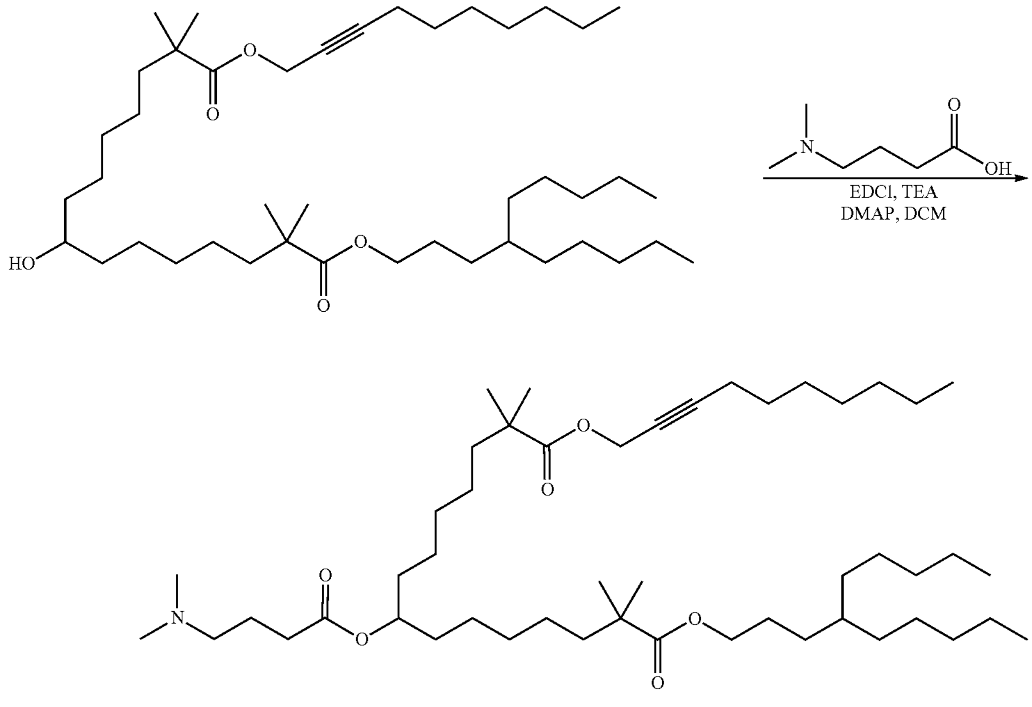
115

Referring to the method of Example 104, compound 115 was prepared as an oily product: 31.0 mg.
$^1$H NMR (400 MHz, $CDCl_3$): δ ppm 0.87-0.91 (m, 9H), 1.14-1.37 (m, 51H), 1.49-1.60 (m, 12H), 1.75-1.81 (m, 2H), 2.21-2.26 (m, 2H), 2.28 (s, 6H), 2.32-2.36 (m, 4H), 4.03 (t, J=6.4 Hz, 2H), 4.65 (s, 2H), 4.82-4.88 (m, 1H); ESI-MS m/z: 790.6 $[M+H]^+$.
Example 116: Synthesis of Compound 116
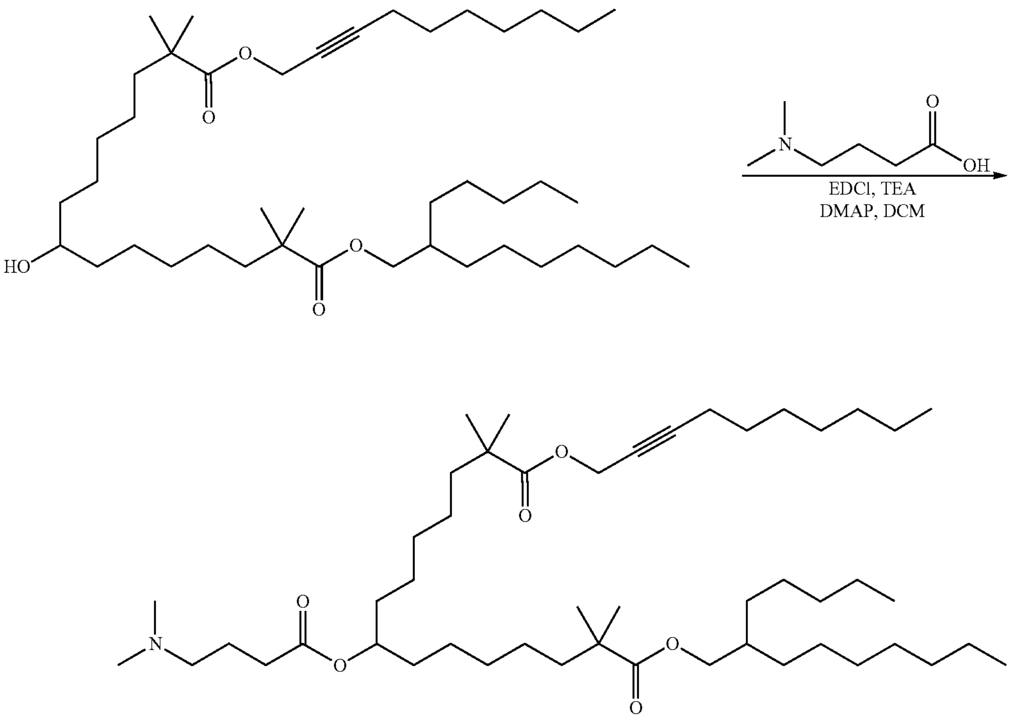
116
Referring to the method of Example 104, compound 116 was prepared as an oily product: 31.3 mg.
$^1$H NMR (400 MHz, $CDCl_3$): δ ppm 0.80-0.83 (m, 9H), 1.07-1.27 (m, 51H), 1.40-1.45 (m, 12H), 1.70-1.81 (m, 2H), 2.13-2.36 (m, 12H), 3.87 (d, J=5.6 Hz, 2H), 4.57 (s, 2H), 4.74-4.80 (m, 1H); ESI-MS m/z: 790.6 $[M+H]^+$.
Example 117: Synthesis of Compound 117
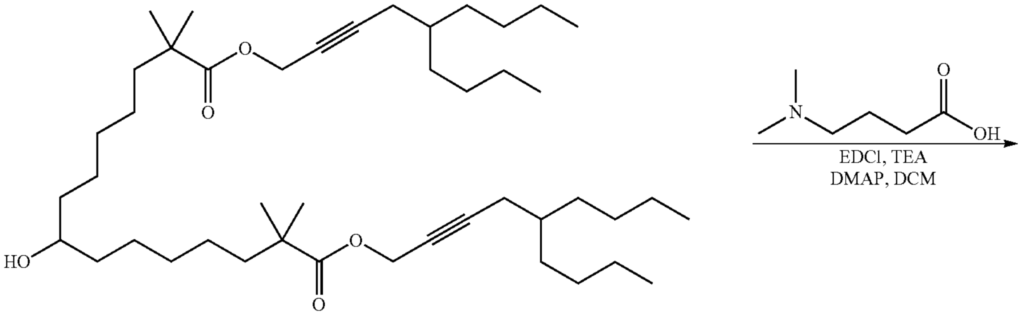

-continued
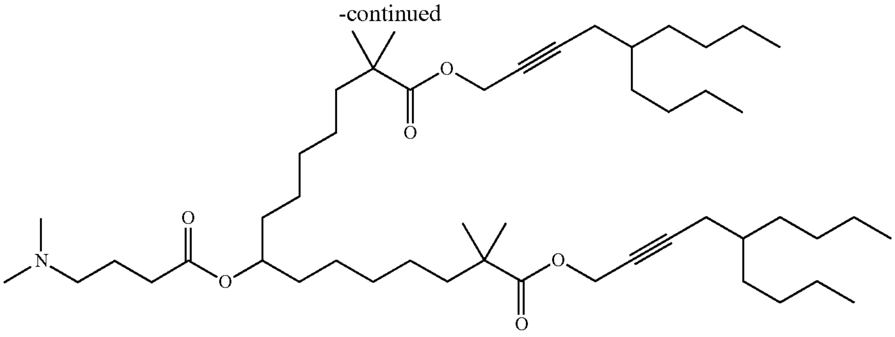
117
Referring to the method of Example 104, compound 117 was prepared as an oily product: 35.9 mg.
$^1$H NMR (400 MHz, $CDCl_3$): δ ppm 0.90 (t, J=6.8 Hz, 12H), 1.15 (s, 12H), 1.16-1.33 (m, 38H), 1.48-1.53 (m, 8H), 1.82-1.86 (m, 2H), 2.18-2.20 (m, 4H), 2.30-2.42 (m, 10H), 4.65 (m, 4H), 4.82-4.88 (m, 1H); ESI-MS m/z: 814.6 $[M+H]^+$.
Example 118: Synthesis of Compound 118
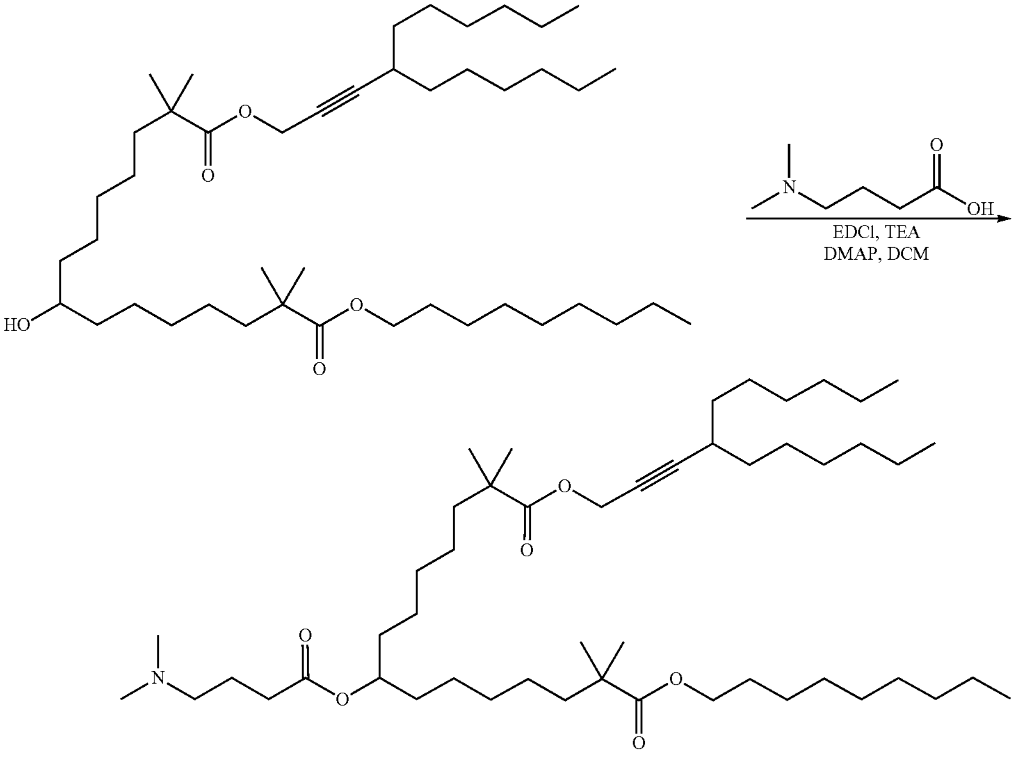
118
Referring to the method of Example 104, compound 118 was prepared as an oily product: 32.0 mg.
$^1$H NMR (400 MHz, $CDCl_3$): δ ppm 0.87-0.90 (m, 9H), 1.15-1.32 (m, 50H), 1.40-1.61 (m, 16H), 1.76-1.84 (m, 2H), 2.23 (s, 6H), 2.29-2.34 (m, 6H), 4.04 (t, J=6.8 Hz, 2H), 4.66 (d, J=2.0 Hz, 1H), 4.83-4.87 (m, 1H); ESI-MS m/z: 804.6 $[M+H]^+$.

Example 119: Synthesis of Compound 119
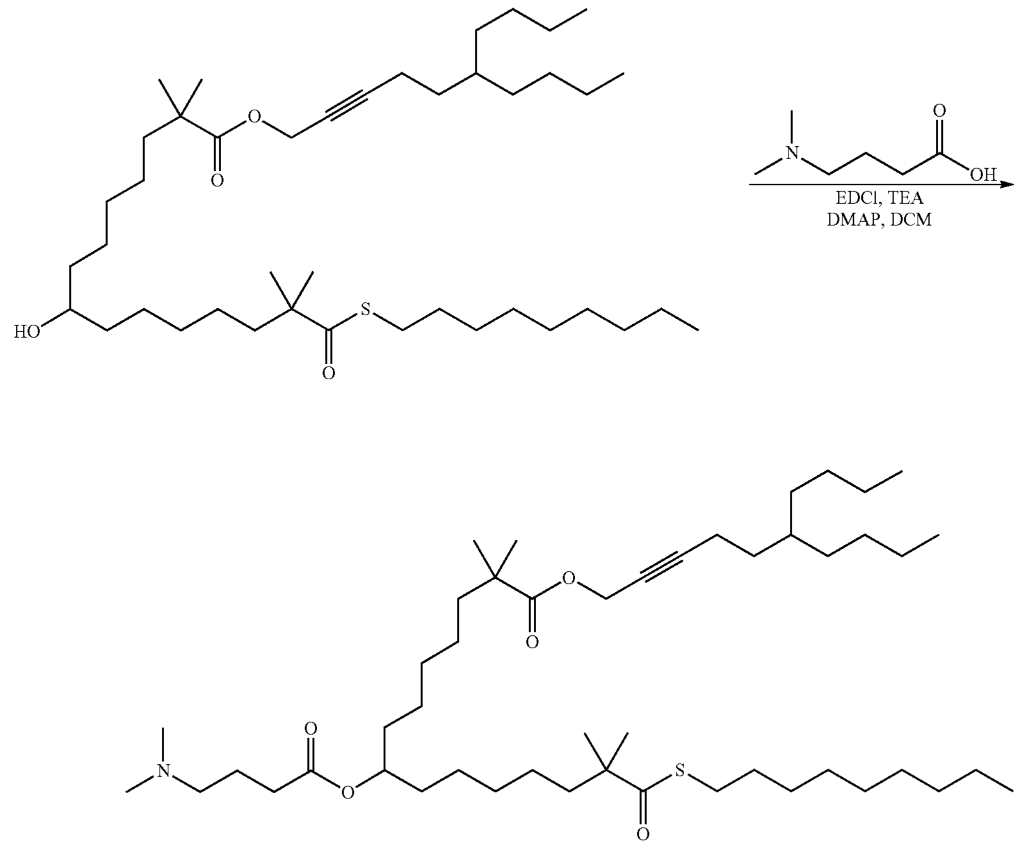
119
Referring to the method of Example 104, compound 119 was prepared as an oily product: 34.8 mg.
$^{1}$H NMR (400 MHz, $CDCl_3$): δ ppm 0.91-0.94 (m, 9H), 1.21-1.40 (m, 48H), 1.51-1.57 (m, 12H), 1.61-1.86 (m, 5H), 2.23 (m, 2H), 2.31 (s, 6H), 2.35-2.39 (m, 2H), 2.85 (t, J=7.2 Hz, 2H), 4.67 (t, J=2.0 Hz, 1H), 4.84-4.90 (m, 1H); ESI-MS m/z: 792.6 $[M+H]^+$.
Example 120: Synthesis of Compound 120
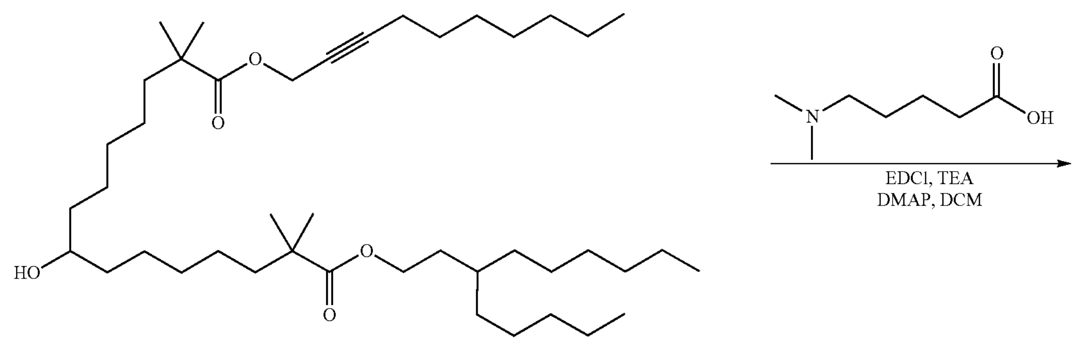

-continued
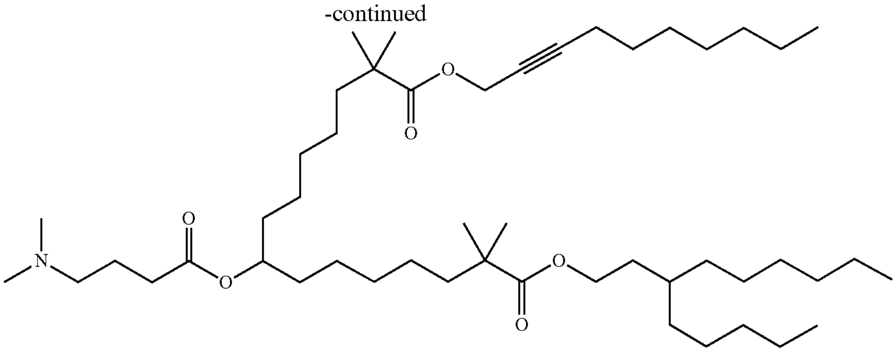
120
Referring to the method of Example 104, compound 120 was prepared as an oily product: 34.5 mg.
$^1$H NMR (400 MHz, $CDCl_3$): δ ppm 0.89 (t, J=6.8 Hz, 9H), 1.15-1.31 (m, 48H), 1.47-1.57 (m, 16H), 1.75-1.85 (m, 4H), 2.19-2.41 (m, 11H), 4.07 (t, J=6.8 Hz, 2H), 4.65 (t, J=2.0 Hz, 2H), 4.27-4.88 (m, 1H); ESI-MS m/z: 804.6 $[M+H]^+$.
Example 121: Synthesis of Compound 121
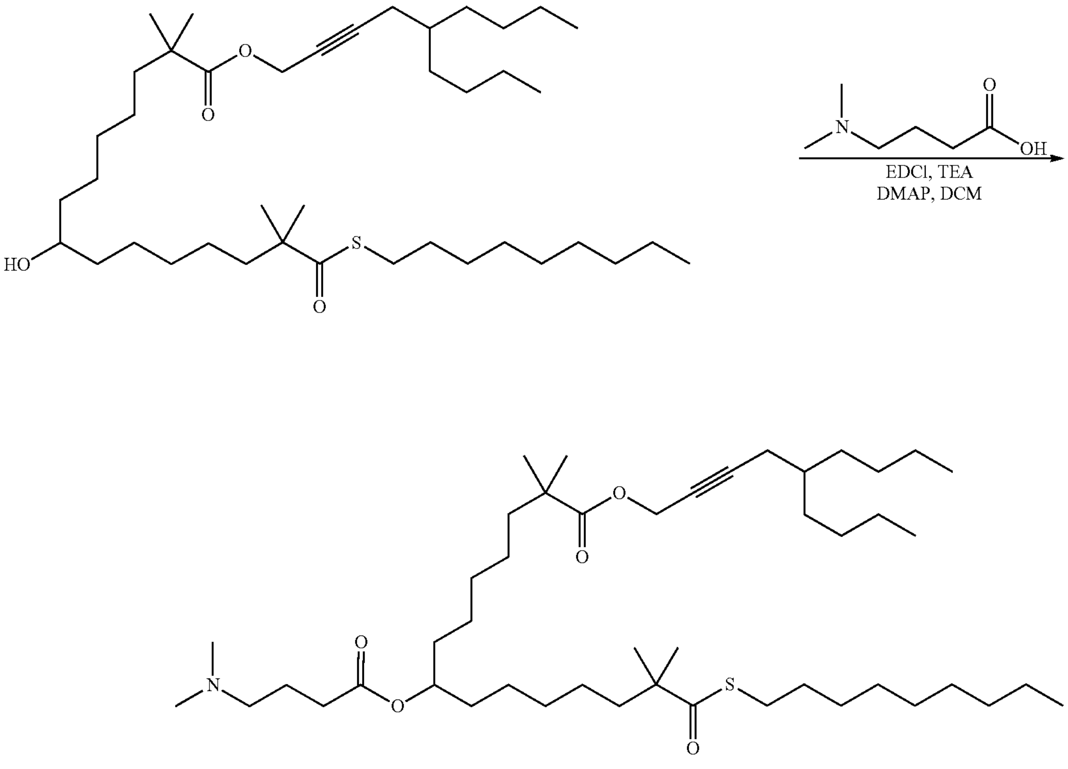
121
Referring to the method of Example 104, compound 121 was prepared as an oily product: 33.8 mg.
$^1$H NMR (400 MHz, $CDCl_3$): δ ppm 0.91-0.95 (m, 9H), 1.20-1.43 (m, 46H), 1.47-1.57 (m, 10H), 1.63-1.85 (m, 6H), 2.29-2.40 (m, 12H), 2.85 (t, J=7.2 Hz, 2H), 4.68 (s, 2H), 4.84-4.90 (m, 1H); ESI-MS m/z: 764.6 $[M+H]^+$.

Example 122: Synthesis of Compound 122

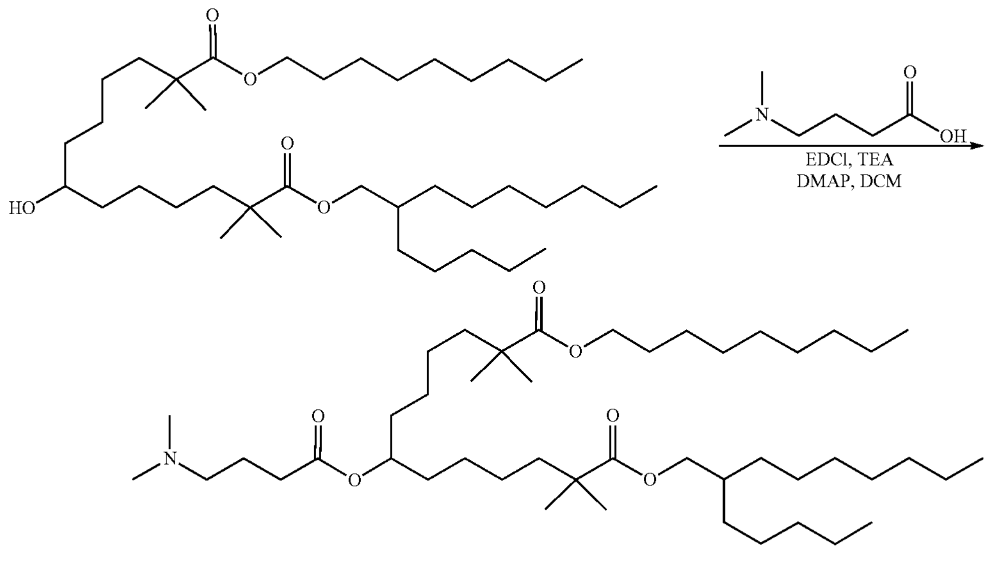

122

Referring to the method of Example 104, compound 122 was prepared as an oily product: 33.7 mg.

$^{1}$H NMR (400 MHz, $CDCl_3$): δ ppm 0.81 (t, J=6.8 Hz, 9H), 1.08-1.31 (m, 46H), 1.40-1.58 (m, 17H), 1.68-1.73 (m, 2H), 2.17 (s, 6H), 2.25 (t, J=7.2 Hz, 4H), 3.87 (d, J=5.6 Hz, 2H), 3.97 (t, J=6.8 Hz, 2H), 4.73-4.80 (m, 1H); ESI-MS m/z: 752.7 $[M+H]^+$.

Example 123: Synthesis of Compound 123

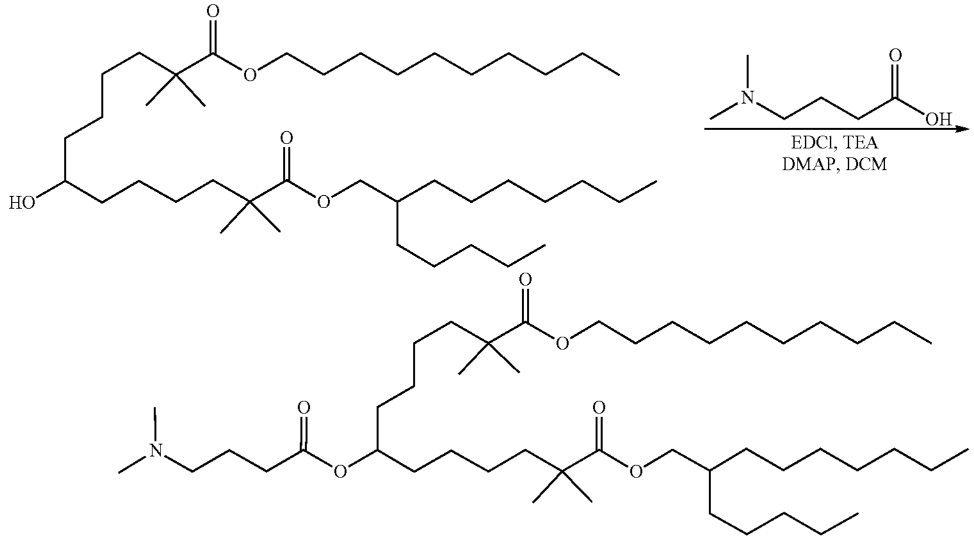

123

Referring to the method of Example 104, compound 123 was prepared as an oily product: 35.2 mg.

$^{1}$H NMR (400 MHz, $CDCl_3$): δ ppm 0.81 (t, J=6.8 Hz, 9H), 1.08 (s, 12H), 1.10-1.33 (m, 36H), 1.40-1.57 (m, 17H), 1.68-1.73 (m, 2H), 2.17 (s, 6H), 2.25 (t, J=7.2 Hz, 4H), 3.87 (d, J=5.6 Hz, 2H), 3.97 (t, J=6.8 Hz, 2H), 4.73-4.79 (m, 1H); ESI-MS m/z: 766.7 $[M+H]^+$.

Example 124: Synthesis of Compound 124

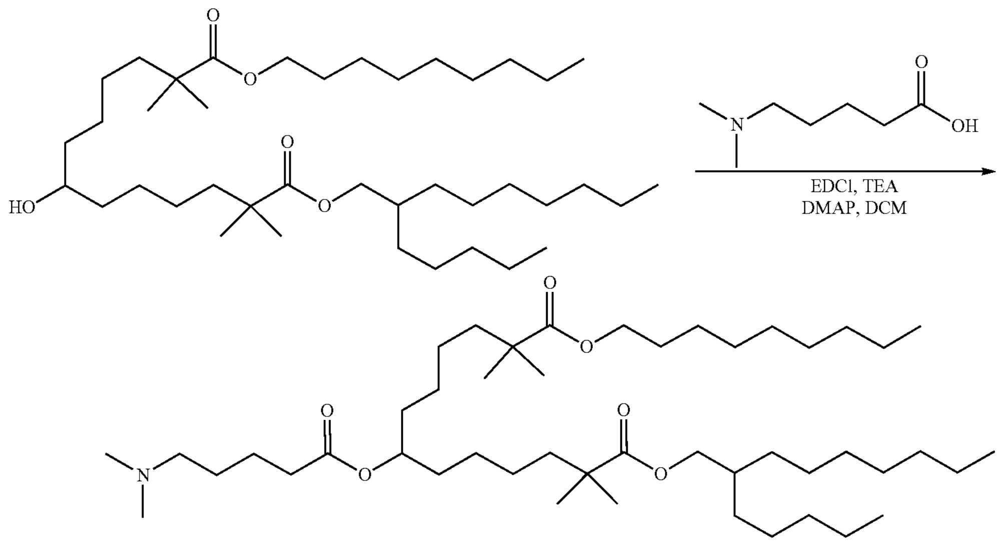

124

Referring to the method of Example 104, compound 124 was prepared as an oily product: 33.4 mg.

$^{1}H$ NMR (400 MHz, $CDCl_3$): δ ppm 0.89 (t, J=6.8 Hz, 9H), 1.15 (s, 12H), 1.18-1.37 (m, 39H), 1.47-1.65 (m, 16H), 2.28 (s, 6H), 2.29-2.35 (m, 4H), 3.95 (d, J=5.6 Hz, 2H), 4.04 (t, J=6.8 Hz, 2H), 4.79-4.86 (m, 1H); ESI-MS m/z: 766.6 $[M+H]^+$.

Example 125: Synthesis of Compound 125

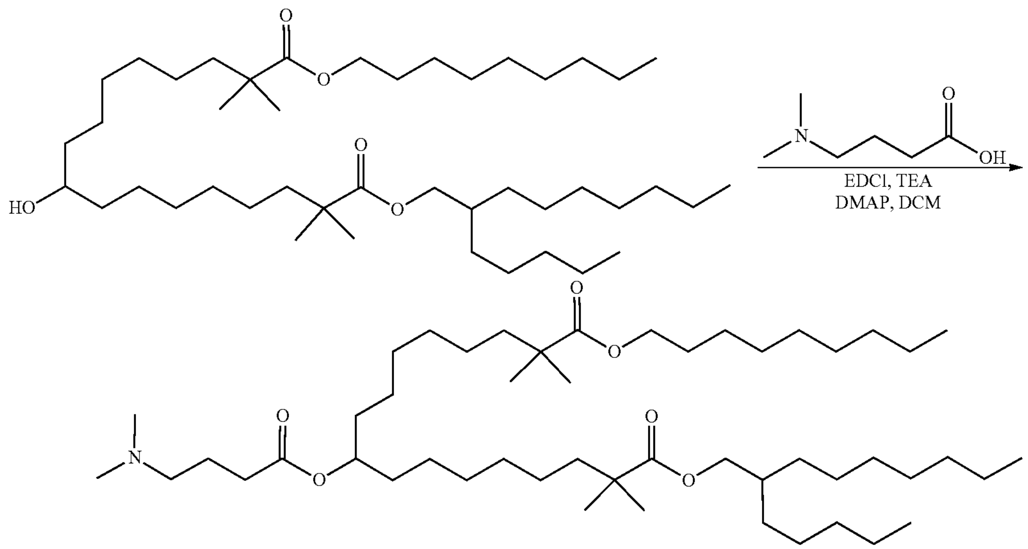

125

Referring to the method of Example 104, compound 125 was prepared as an oily product: 31.1 mg.

$^{1}H$ NMR (400 MHz, $CDCl_3$): δ ppm 0.89 (t, J=6.8 Hz, 9H), 1.15 (s, 12H), 1.18-1.37 (m, 48H), 1.48-1.51 (m, 8H), 1.60-1.63 (m, 3H), 1.80-1.88 (m, 2H), 2.32-2.41 (m, 10H), 3.95 (d, J=5.6 Hz, 2H), 4.04 (t, J=6.8 Hz, 2H), 4.81-4.88 (m, 1H); ESI-MS m/z: 808.7 $[M+H]^+$.

Example 126: Synthesis of Compound 126
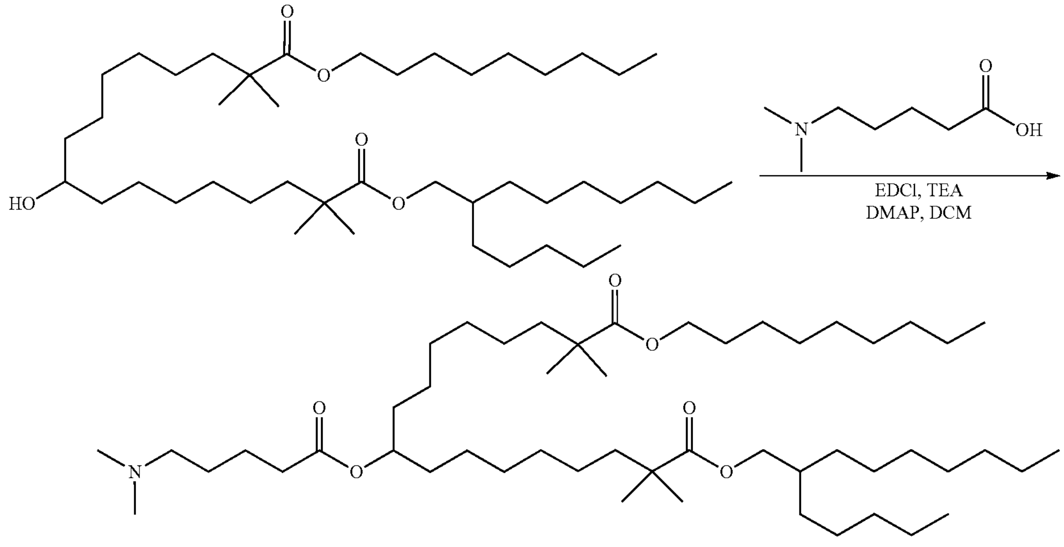
126
Referring to the method of Example 104, compound 126 was prepared as an oily product: 35.1 mg.
$^1$H NMR (400 MHz, $CDCl_3$): δ ppm 0.89 (t, J=6.8 Hz, 9H), 1.16 (s, 12H), 1.18-1.37 (m, 48H), 1.48-1.65 (m, 15H), 2.32-2.43 (m, 10H), 3.95 (d, J=5.6 Hz, 2H), 4.05 (t, J=6.8 Hz, 2H), 4.81-4.89 (m, 1H); ESI-MS m/z: 822.7 $[M+H]^+$.
Example 127: Synthesis of Compound 127
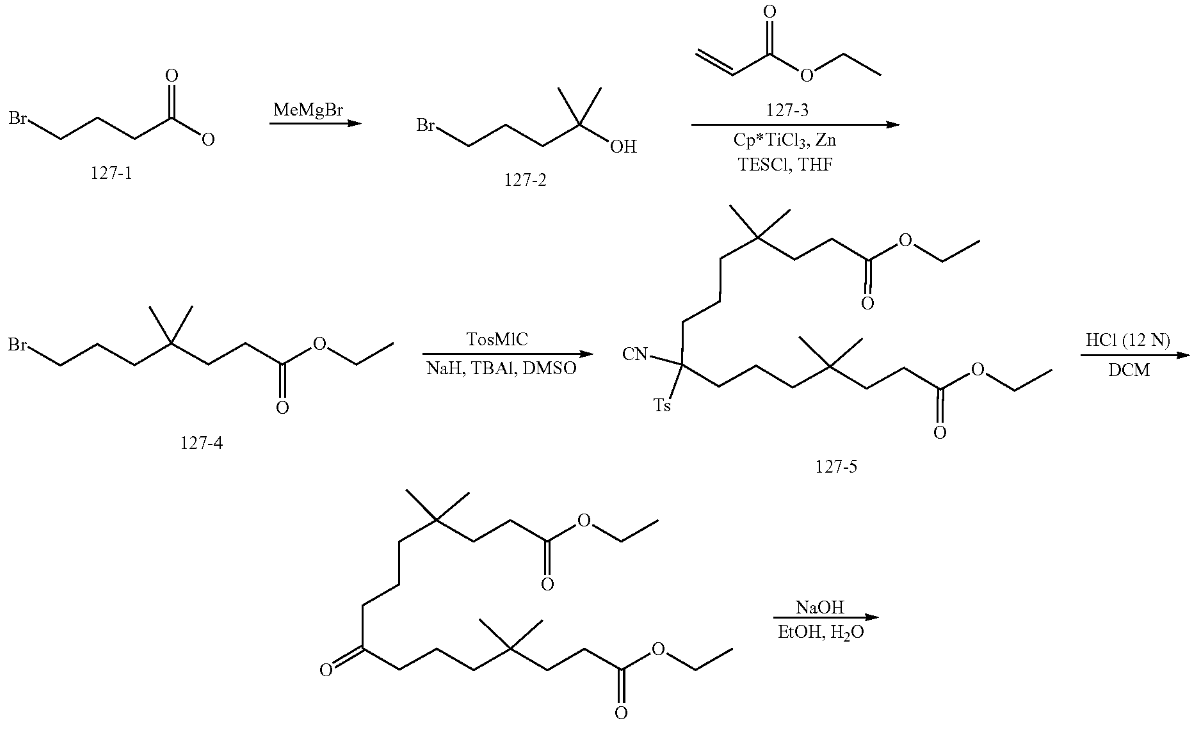
127-1 127-2 127-4 127-5 127-6

-continued

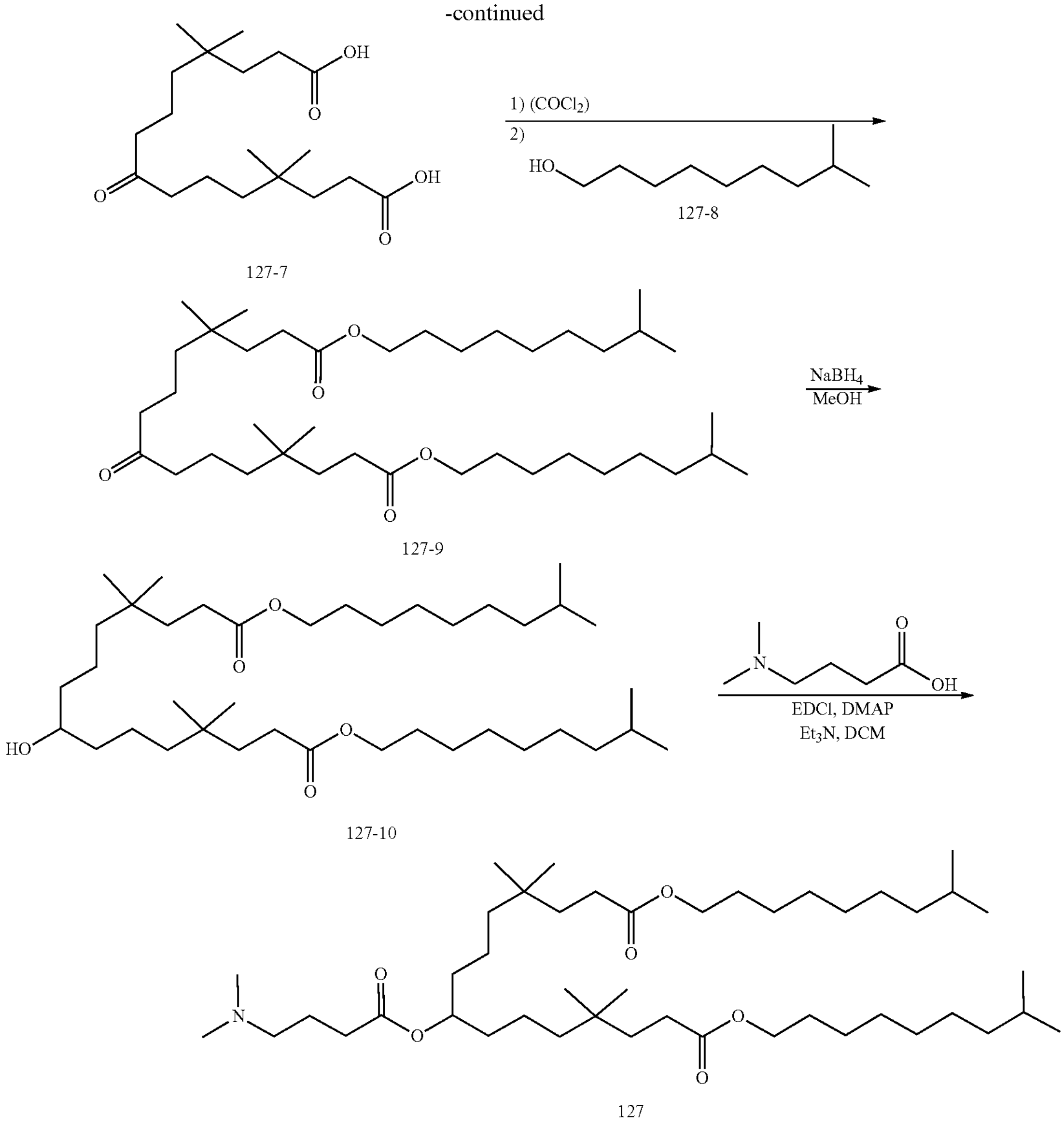

A solution of compound 127-1 (100 g, 552.4 mmol) in anhydrous ether (800 mL) was cooled to 0° C. in an ice bath, and methylmagnesium bromide (3 M in ether, 737 mL) was slowly added dropwise to the solution. After the dropwise addition was completed, the ice bath was removed and the mixture was stirred to react for 4 h at room temperature. The reaction system was quenched with saturated ammonium chloride aqueous solution, and extracted with ether. The organic phases were combined, dried over anhydrous sodium sulfate, and filtered. The filtrate was concentrated to dryness to give the crude product. The crude product was purified by silica gel column to give compound 127-2 (100 g).

Compound 127-2 (42 g, 232 mmol), compound 127-3 (30.3 mL, 278 mmol), Cp*$TiCl_3$ (5.09 g, 23.2 mmol), zinc powder (45.5 g, 696 mmol), and triethylchlorosilane (116.8 mL, 696 mmol) were added to a round bottom flask. Then anhydrous tetrahydrofuran (1200 mL) was added to the reaction system and the reaction was carried out under the protection of argon gas. The reaction system was heated to 60° C. and stirred to react for 1 hour. The reaction system was quenched with saturated aqueous sodium chloride solution and extracted with ethyl acetate. The organic phases were combined, dried over anhydrous sodium sulfate, and filtered. The filtrate was concentrated to dryness to give crude product 1-4, which was purified by silica gel column to give compound 127-4 (21 g).

Compound TosMIC (7.03 g, 36 mmol) was dissolved in DMSO (200 mL), and NaH (4.32 g, 60%, 108 mmol) was added to the reaction system in batches under ice bath conditions. After the addition was completed, the ice bath was removed and the mixture was reacted at room temperature for another 1 h. Compound 127-4 (21 g, 79 mmol) and TBAI (1.33 g, 3.6 mmol) were added to the reaction system, and the mixture was stirred at room temperature overnight. The reaction system was quenched with saturated aqueous sodium chloride solution and extracted with ethyl acetate. The organic phases were combined, dried over anhydrous sodium sulfate, and filtered. The filtrate was concentrated to dryness to give crude compound 127-5 (21.9 g), which was used directly in the next reaction step without purification.

To a solution of crude compound 127-5 (21.9 g, 38.8 mmol) in dichloromethane (350 mL) was added 200 mL of concentrated hydrochloric acid, and the mixture was reacted at room temperature for 2 h. The complete reaction of the substrate was monitored by TLC. The reaction system was quenched with saturated aqueous ammonium chloride solution and extracted with ethyl acetate. The organic phases were combined, dried over anhydrous sodium sulfate, and filtered. The filtrate was concentrated to dryness to give the crude product, which was purified by silica gel column to give compound 127-6 (12.5 g).

Compound 127-6 (12.5 g, 31.4 mmol) was dissolved in ethanol (20 mL)-water (40 mL), and NaOH (3.77 g, 94.2 mmol) was added to the mixed solution in batches under ice bath conditions. After the addition was completed, the ice bath was removed and the mixture was stirred at room temperature. The complete consumption of the reaction materials was monitored by TLC. The organic solvent was removed by rotary evaporation, and the residue was extracted with dichloromethane. The aqueous layer was collected, and the solution was adjusted to a pH of <5 with 1 M hydrochloric acid. The solution was extracted with dichloromethane. The organic phases were combined, dried over anhydrous sodium sulfate, and filtered. The filtrate was collected and concentrated to give compound 127-7 (9.7 g).

DMF (17 μL, 0.22 mmol) was added to a solution of compound 127-7 (750 mg, 2.19 mmol) in dichloromethane (10.0 mL) under ice bath conditions, and oxalyl chloride (0.77 mL, 8.76 mmol) was then added dropwise to the reaction solution. The ice bath was removed, and the mixture was stirred for 1 h at room temperature. The solvent was removed using a rotary-evaporator to give acyl chloride crude product, which was used directly in the next reaction step.

The above obtained acyl chloride crude product was dissolved in 10.0 mL of 1,2-dichloroethane, and then compound 127-8 (693 mg, 4.38 mmol) was added to the reaction solution. The mixture was stirred at room temperature until the substrate was reacted completely. The solvent was removed using a rotary-evaporator. The crude was purified by silica gel column to give compound 127-9 (800 mg).

Compound 127-9 (800 mg, 1.29 mmol) was dissolved in 5.0 mL of methanol and sodium borohydride (146 mg, 3.87 mmol) was added to the reaction system. The mixture was reacted at room temperature. The complete disappearance of the reactants was monitored by TLC. The reaction system was quenched with saturated aqueous sodium chloride solution and extracted with dichloromethane. The organic phases were combined, dried over anhydrous sodium sulfate, and filtered. The filtrate was concentrated to dryness to give crude compound 127-10 (800 mg), which was used directly in the next reaction without purification.

Crude compound 127-10 (300 mg, 0.48 mmol), 4-dimethylaminobutyric acid (94.4 mg, 0.72 mmol), EDCI (276 mg, 1.44 mmol), triethylamine (0.21 mL, 1.44 mmol) and DMAP (59 mg, 0.48 mmol) were dissolved in 5.0 mL of dichloromethane, and the reaction solution was stirred to react at room temperature for 12 h. The reaction solution was quenched with saturated aqueous sodium chloride and extracted with dichloromethane. The organic phases were combined, dried over anhydrous sodium sulfate, and filtered. The organic phase was collected, and the organic solvent was removed using a rotary-evaporator. The crude product was purified by preparative high performance liquid chromatography to give the compound 127 (43.6 mg)

$^1H$ NMR (400 MHz, $CD_3OD$): δ ppm 0.77-0.93 (m, 28H), 1.08-1.74 (m, 38H), 1.76-1.84 (m, 2H), 1.22-2.27 (m, 10H), 2.33-2.37 (m, 4H), 4.03-4.12 (m, 4H), 4.92-4.97 (m, 1H); ESI-MS m/z: 738.6 $[M+H]^+$.

Example 128: Synthesis of Compound 128

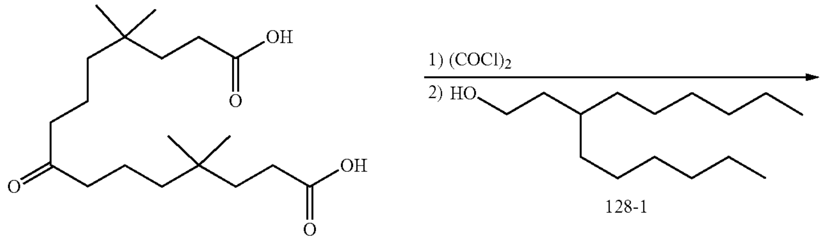

127-7

128-1

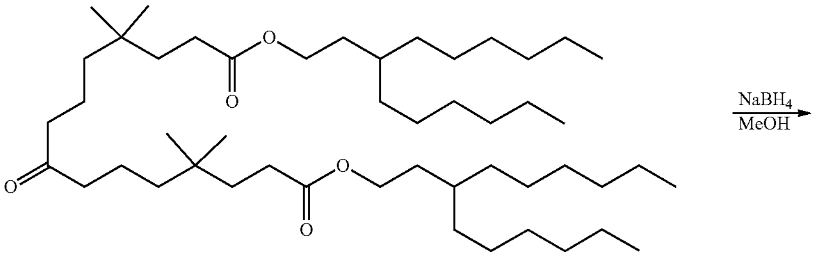

128-2

-continued
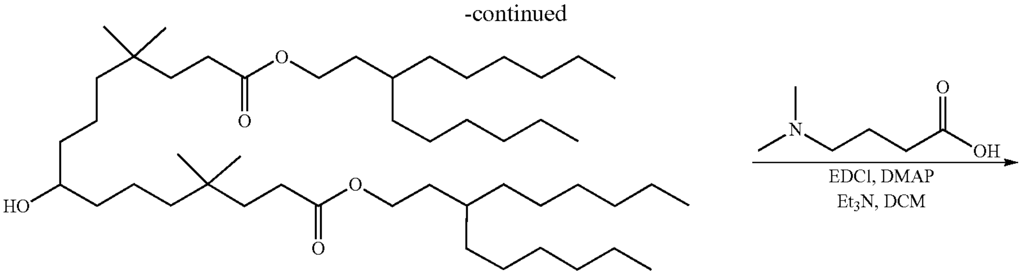
128-3
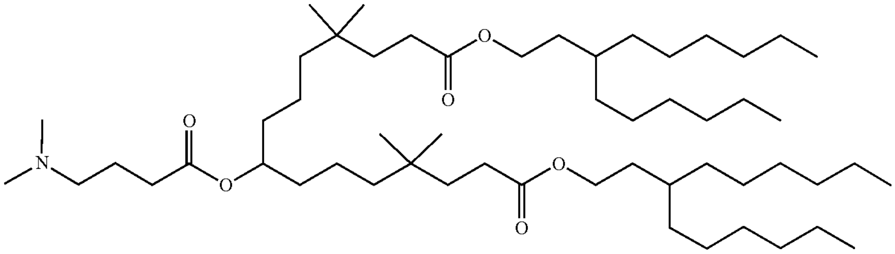
128
Referring to the method of Example 127, compound 128 was prepared as an oily product: 64.2 mg.
$^1$H NMR (400 MHz, $CD_3OD$): δ ppm 0.86 (s, 12H), 0.91 (t, J=6.8 Hz, 12H), 1.22-1.37 (m, 48H), 1.51-1.61 (m, 14H), 1.78-1.86 (m, 2H), 2.24 (t, J=8.0 Hz, 4H), 2.30 (s, 6H), 2.37 (t, J=7.2 Hz, 2H), 2.43 (t, J=8.0 Hz, 2H), 4.10 (t, J=6.8 Hz, 4H), 4.92-4.97 (m, 1H); ESI-MS m/z: 878.7 $[M+H]^+$.
Example 129: Synthesis of Compound 129
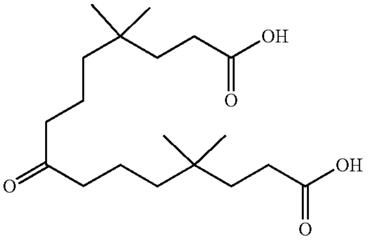
127-7
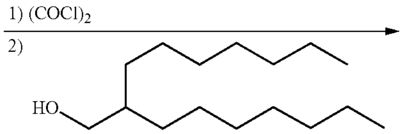
45-1
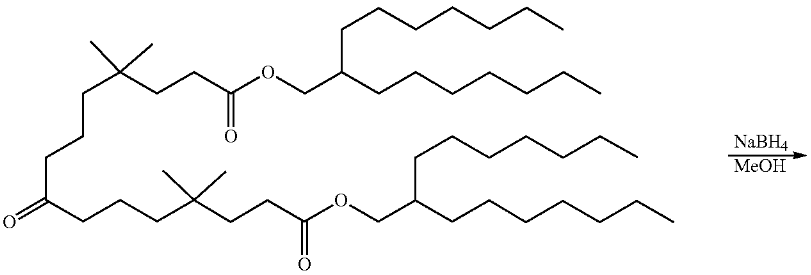
129-2
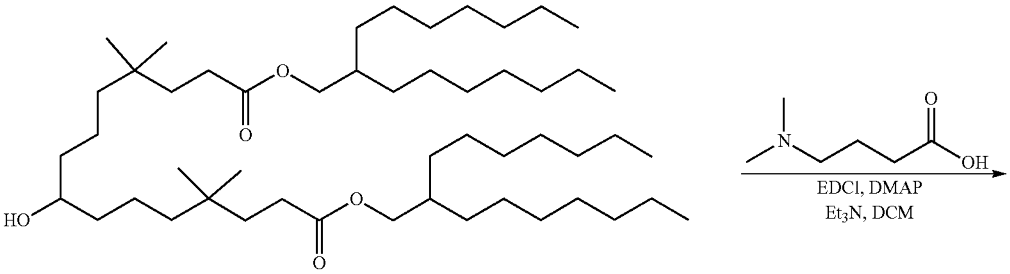
129-3

-continued

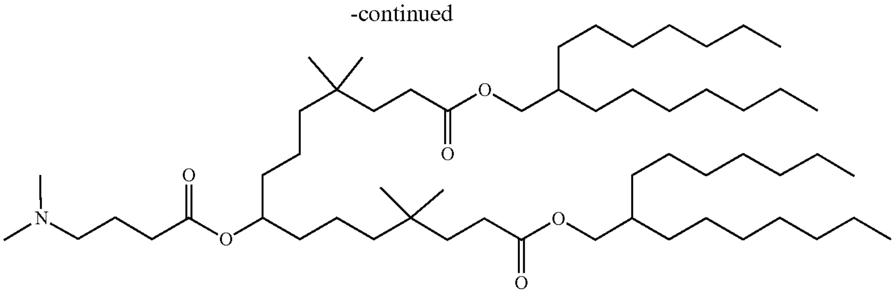

129

Referring to the method of Example 127, compound 129 was prepared as an oily product: 67.0 mg.

$^1$H NMR (400 MHz, $CD_3OD$): δ ppm 0.86 (s, 12H), 0.88-0.93 (m, 12H), 1.12-1.40 (m, 52H), 1.49-1.56 (m, 8H), 1.59-1.66 (m, 4H), 1.77-1.84 (m, 4H), 2.22-2.27 (m, 10H), 2.34-2.38 (m, 4H), 4.01 (t, J=6.8 Hz, 4H), 4.91-4.97 (m, 1H); ESI-MS m/z: 906.8 $[M+H]^+$.

Comparative Examples

Synthesis of Comparative Compound 1 (D1)

D1 was prepared according to the method of Example 20, $[M+H]^+$: 654.6. $^1$H NMR (400 MHz, $CDCl_3$): δ ppm 0.77-0.86 (t, J=7.2 Hz, 6H), 1.15-1.30 (m, 38H), 1.40-1.59 (m, 12H), 1.87-1.96 (m, 2H), 2.21 (t, J=7.2 Hz, 4H), 2.28-2.37 (m, 2H), 2.40-2.50 (m, 5H), 2.56-2.67 (m, 2H), 3.92-4.07 (m, 4H), 4.72-4.90 (m, 1H).

D1

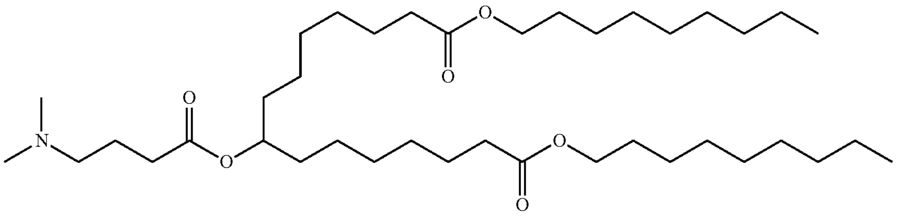

Synthesis of Comparative Compound 2 (D2)

D2

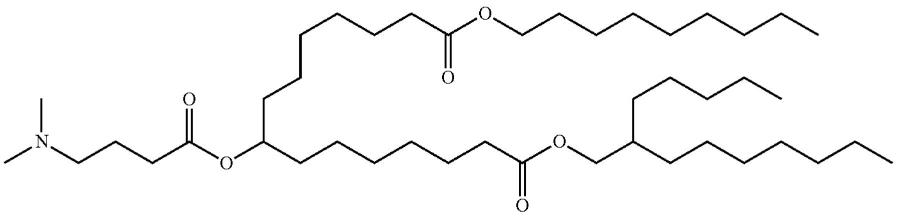

D2 was prepared according to the method of Example 46, $[M+H]^+$: 724.6. $^1$H NMR (400 MHz, $CDCl_3$): δ ppm 0.89 (t, J=7.2 Hz, 9H), 1.21-1.30 (m, 44H), 1.50-1.63 (m, 11H), 1.77-1.92 (m, 2H), 2.27-2.36 (m, 14H), 3.97 (d, J=5.6 Hz, 2H), 4.06 (t, J=6.8 Hz, 2H), 4.85-4.92 (m, 1H).

Pharmacological Assay

Assay Example 1: Preparation of Nanoparticles

Materials used for lipid nanoparticle assembly include: (1) ionizable lipid compounds: e.g., ionizable lipids designed and synthesized in the present disclosure or DLin-MC3-DMA (purchased from AVT) as a control; (2) structure lipids: e.g., Cholesterol (purchased from Sigma-Aldrich); (3) phospholipids: e.g., DSPC i.e., 1,2-distearoyl-SN-glycero-3-phosphocholine (Distearoylphosphatidylcholine, purchased from AVT); (4) polyethylene glycolated lipids: e.g. DMG-PEG2000 i.e., dimyristoylglycero-poly ethylene glycol 2000 (1,2-dimyristoyl-rac-glycero-3-methoxypoly ethylene glycol-2000, purchased from AVT); (5) active ingredients of nucleic acid fragments: e.g. Luciferase mRNA, siRNA, CRISPR Cas 9 mRNA, etc. (manufactured in-house). The names of materials of the lipid nanoparticle assembly and their structural formulae are detailed in Table 4.

Lipid nanoparticles were prepared by (1) dissolving and mixing ionizable lipid compounds, cholesterol, phospholipids and polyethylene glycolated lipids in ethanol at (molar percentages) 50%, 38.5%, 10% and 1.5%, respectively; (2) dissolving the mRNA active ingredient in 25 mM sodium acetate solution (pH=4.5); (3) using an automated high-throughput microfluidic system to mix the organic phase containing the lipid mixture and the aqueous phase containing the mRNA component in the flow ratio range of 1:1 to 1:4 at a mixing speed of 10 mL/min to 18 mL/min; (4) the prepared lipid nanoparticles (N/P ratio of 6) were diluted with phosphate buffer solution and the nanoparticle solutions were ultrafiltered to the original preparation volume using ultrafiltration tubes (purchased from Millipore) with a cut-off molecular weight of 30 kDa; and (5) the obtained nanoparticles were filtered through a sterile 0.2 μm filter membrane and then stored in a sealed glass vial at low temperature.

The preparation method of lipid nanoparticles includes microfluidic mixing systems, but is not limited to this

TABLE 4

| No. | Name | Structural formula |
|---|---|---|
| 1 | DLin-MC3-DMA | 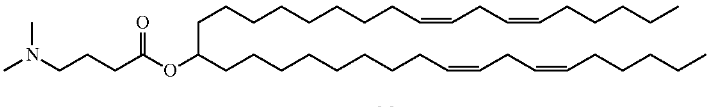 [SMILES: CCCCC/C=C\C/C=C\CCCCCCCCC(CCCCCCCC/C=C\C/C=C\CCCCC)OC(=O)CCCN(C)C] |
| 2 | Cholesterol | 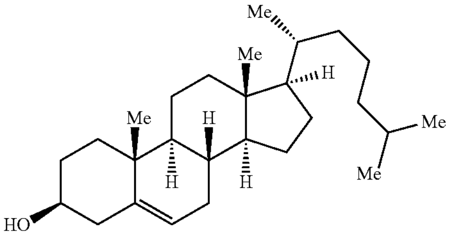 |
| 3 | DSPC | 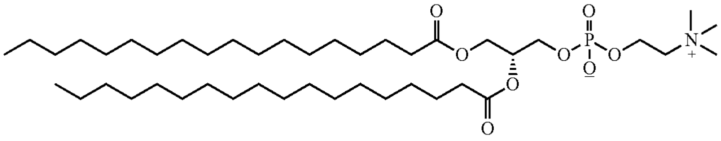 |
| 4 | DMG-PEG2000 | 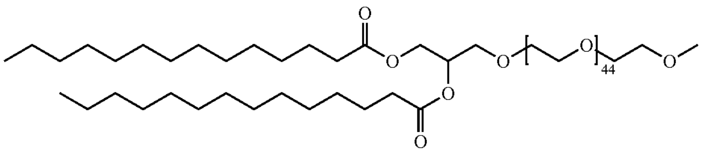 |
| 5 | SM-102 | 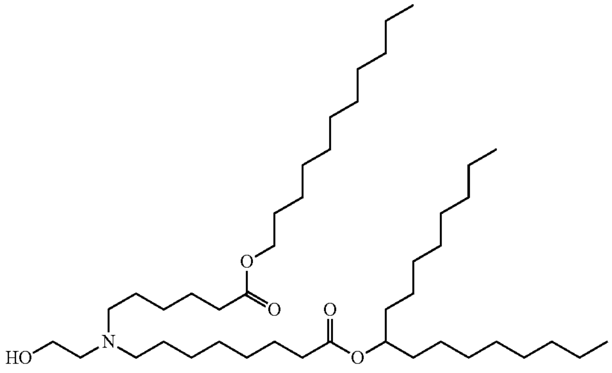 [SMILES: CCCCCCCCCCCOC(=O)CCCCCN(CCO)CCCCCCCC(=O)OC(CCCCCCCC)CCCCCCCC] |

method, which also includes T-type mixers and ethanol injection method, and the like.

Assay Example 2: Characterization of Physical Properties of Lipid Nanoparticles The particle size and particle size dispersity index (PDI) of the prepared lipid nanoparticles were measured using a Zetasizer Pro (purchased from Malvern Instruments Ltd) and a DynaPro NanoStar (purchased from Wyatt) dynamic light scattering instrument. The degree of RNA encapsulation by lipid nanoparticles was characterized by the Encapsulation Efficiency %, which reflects the degree of binding of lipid nanoparticles to RNA fragments. This parameter was measured by the method of Quant-it™ RiboGreen RNA Assay (purchased from Invitrogen). Lipid nanoparticle samples were diluted in TE buffer (10 mM Tris-HCl, 1 mM EDTA, pH=7.5). A portion of the sample solution was removed, to which 0.5% Triton (Triton X-100) was added, and then allowed to stand at 37° C. for 30 minutes. Immediately after the addition of RIBOGREEN® reaction solution, the fluorescence values were read on a Varioskan LUX multifunctional microplate reader (purchased from Thermofisher) at 485 nm for absorption and 528 nm for emission to give the encapsulation efficiency values.

Assay Example 3: Animal Experiment

The delivery effect and safety of nanoparticles encapsulated with luciferase mRNA (Trilink, L-7202) in mice were evaluated. The test mice were SPF-grade C57BL/6 mice, female, 6-8 weeks old, weighing 18-22 g, and were purchased from SPF (Beijing) Biotechnology Co., Ltd. All animals were acclimatized for more than 7 days prior to the experiment, and had free access to food and water during the experiment. The conditions include alternating light and dark for 12/12 h, the indoor temperature of 20-26° C. and the humidity of 40-70%. The mice were randomly grouped. The lipid nanoparticles encapsulated with luciferase mRNA prepared above were injected into mice by intravenous administration at a single dose of 0.5 mg/kg mRNA, and the mice were subjected to in vivo bioluminescence assay using a Small Animal In Vivo Imaging System (IVIS LUMINA III, purchased from PerkinElmer) at 6 h after administration. The assay was performed as follows: D-luciferin solution was prepared in saline at a concentration of 15 mg/mL, and each mouse was given the substrate by intraperitoneal injection. At ten minutes after administration of the substrate, the mice were anesthetized in an anesthesia chamber with isoflurane at a concentration of 2.5%. The anesthetized mice were placed in IVIS for fluorescence imaging, and data acquisition and analysis were performed on the concentrated distribution area of fluorescence.

The in vivo delivery efficiency of lipid nanoparticle carriers was expressed as the mean values of fluorescence intensity and total photon count in different animals within the same subject group, as shown in Table 5. Higher values of fluorescence intensity and total photon count indicate higher in vivo delivery efficiency of this mRNA fragment by lipid nanoparticles. The lipid nanoparticles containing the cationic lipids of the present disclosure have good in vivo delivery efficiency. Unexpectedly, compared with the molecule without tetramethyl, the corresponding lipid nanoparticles of the present disclosure have significantly increased in vivo delivery efficiency, e.g., compound 20 vs. D1, compound 46 vs. D2.

TABLE 5

| Cationic lipid compound | Particle size (nm) | Particle size dispersity (PDI) | Encapsulation efficiency (%) | Total photon count in vivo at 6 hours after administration (Total Flux) |
|---|---|---|---|---|
| 1 | 80.07 | 0.06 | 91.54 | 6.43E+08 |
| 2 | 229.35 | 0.03 | 79.14 | 4.23E+08 |
| 3 | 133.80 | 0.04 | 86.88 | 1.75E+09 |
| 6 | 106.18 | 0.05 | 90.26 | 2.25E+09 |
| 7 | 203.67 | 0.04 | 69.51 | 1.16E+08 |
| 8 | 127.82 | 0.07 | 60.36 | 3.26E+07 |
| 9 | 352.82 | 0.07 | 19.41 | 6.05E+06 |
| 10 | 118.59 | 0.07 | 53.83 | 1.26E+09 |
| 11 | 46.49 | 0.03 | 95.61 | 4.42E+06 |
| 12 | 89.34 | 0.07 | 85.02 | 1.10E+09 |
| 13 | 157.10 | 0.08 | 56.65 | 1.08E+06 |
| 14 | 306.07 | 0.08 | 45.66 | 6.34E+07 |
| 15 | 91.68 | 0.06 | 84.78 | 4.89E+08 |
| 16 | 55.39 | 0.05 | 96.52 | 3.97E+07 |
| 17 | 81.43 | 0.12 | 30.95 | 6.77E+05 |
| 18 | 161.29 | 0.05 | 87.86 | 1.14E+10 |
| 19 | 135.15 | 0.19 | 67.96 | 3.20E+09 |
| 20 | 99.61 | 0.10 | 71.93 | 2.40E+10 |
| 23 | 151.35 | 0.07 | 70.22 | 1.43E+10 |
| 24 | 133.72 | 0.04 | 60.98 | 5.56E+09 |
| 25 | 236.90 | 0.06 | 32.43 | 1.89E+08 |
| 26 | 96.69 | 0.05 | 81.29 | >4.00E+10 |
| 27 | 105.70 | 0.05 | 88.99 | 2.20E+10 |
| 28 | 138.16 | 0.06 | 80.36 | 3.21E+09 |
| 32 | 116.61 | 0.07 | 99.02 | 7.30E+09 |
| 33 | 105.84 | 0.04 | 88.67 | 2.12E+08 |
| 34 | 104.71 | 0.04 | 90.29 | 1.26E+10 |
| 36 | 88.33 | 0.07 | 97.52 | 4.84E+09 |
| 37 | 92.18 | 0.03 | 89.07 | 7.88E+09 |
| 40 | 83.90 | 0.05 | 97.06 | 4.22E+09 |
| 41 | 104.27 | 0.05 | 93.91 | 2.19E+10 |
| 42 | 152.04 | 0.07 | 71.95 | 5.32E+09 |
| 46 | 97.30 | 0.09 | 95.68 | >4.00E+10 |
| 90 | 18.17 | 0.05 | 83.21 | 1.04E+07 |
| 91 | 32.61 | 0.05 | 102.99 | 1.29E+06 |
| 92 | 107.56 | 0.05 | 91.66 | 2.13E+09 |
| 97 | 157.00 | 0.25 | 93.72 | 3.37E+09 |
| 98 | 107.87 | 0.13 | 93.28 | 2.12E+10 |
| 99 | 139.99 | 0.05 | 90.69 | 5.30E+09 |
| 100 | 118.19 | 0.07 | 83.29 | 1.18E+10 |
| 101 | 152.45 | 0.06 | 76.09 | 5.19E+09 |
| 102 | 102.18 | 0.03 | 90.03 | 2.03E+10 |
| 103 | 148.67 | 0.04 | 90.97 | 5.69E+09 |
| 104 | 71.14 | 0.06 | 85.54 | 2.61E+10 |
| 105 | 78.80 | 0.05 | 94.67 | 3.33E+09 |
| 106 | 83.09 | 0.05 | 85.65 | 1.85E+10 |
| 107 | 99.54 | 0.05 | 83.74 | 1.36E+10 |
| 108 | 121.41 | 0.05 | 92.63 | 1.21E+10 |
| 109 | 101.04 | 0.06 | 87.11 | 1.32E+10 |
| 110 | 97.59 | 0.01 | 92.65 | 2.06E+08 |
| 111 | 141.30 | 0.06 | 95.12 | 1.79E+10 |
| 112 | 121.05 | 0.08 | 94.41 | 3.53E+10 |
| 113 | 112.65 | 0.03 | 94.77 | 3.59E+08 |
| 114 | 72.32 | 0.04 | 93.41 | 1.06E+08 |
| 115 | 77.12 | 0.04 | 91.76 | 2.56E+10 |
| 116 | 88.62 | 0.05 | 89.36 | >4.00E+10 |
| 117 | 127.31 | 0.06 | 95.29 | 4.48E+09 |
| 118 | 88.33 | 0.07 | 93.87 | 3.14E+10 |
| 119 | 80.98 | 0.05 | 86.92 | 3.25E+10 |
| 120 | 98.99 | 0.07 | 95.55 | 3.15E+10 |
| 121 | 103.57 | 0.06 | 93.62 | >4.00E+10 |
| 122 | 96.72 | 0.07 | 91.76 | >4.00E+10 |
| 123 | 84.98 | 0.05 | 92.27 | >4.00E+10 |
| 125 | 95.69 | 0.07 | 89.45 | 1.99E+10 |
| 126 | 133.76 | 0.06 | 94.35 | 1.77E+10 |
| 127 | 83.01 | 0.05 | 62.35 | 3.59E+10 |
| 128 | 83.10 | 0.05 | 79.88 | 1.00E+10 |
| 129 | 112.08 | 0.06 | 57.87 | 7.82E+09 |
| DLin-MC3-DMA | 96.83 | 0.04 | 95.62 | 8.04E+09 |
| D1 | 131.2 | 0.18 | 97.08 | 4.45E+07 |
| D2 | 245.33 | 0.20 | 79.63 | 1.57E+09 |

Assay Example 4: Evaluation of Delivery Efficiency and Safety In Vitro

The delivery effect and safety of nanoparticles encapsulated with luciferase mRNA were evaluated at the cellular level in vitro. The cells used in the assay were human embryonic kidney cells 293 (HEK293T cells) cultured in DMEM (Dulbecco's Modified Eagle Medium) (purchased from Thermo Fisher) containing 10% fetal bovine serum and 5% penicillin-streptomycin double antibiotics at a indoor temperature of 37° C. and a $CO_2$ concentration of 5%. The cells were uniformly dispersed and spread in 48-well plates, and incubated in the incubator for 24 h. Then a solution of the lipid nanoparticles encapsulated with luciferase mRNA were added. After 24 h, the cells were lysed, and the intracellular expression intensity and relative light units (RLU) of luciferase in each type of lipid nanoparticles were measured with a luciferase detection reagent (purchased from Promega). The higher the intensity of expression, the higher the delivery efficiency of the lipid material at the cellular level. Meanwhile, CCK-8 reagent (purchased from DOJINDO) was used in cytotoxicity testing for the parallel lipid nanoparticle-treated cell groups after 24 hours. In the test, the group of cells to which only PBS was added was used as a negative control. The procedure was as follows: after the addition of CCK-8 solution, the cells were left to stand in an incubator at 37° C. for 4 h. The absorbance values were read on a multifunctional microplate reader at an absorbance band of 450 nm. The ratio of the absorbance value of the nanoparticle-treated cells to that of the negative control was used as a characterization parameter for cell viability.

The delivery effects and the toxicity data of nanoparticles at the cellular level in vitro are shown in Table 6.

TABLE 6

| Cationic lipids | Cell fluorescence intensity (RLU) | Cell viability (%) |
|---|---|---|
| 32 | 6.99E+06 | 96.25 |
| 37 | 1.04E+07 | 97.48 |
| 41 | 1.23E+07 | 104.91 |
| 100 | 1.98E+06 | 104.67 |
| DLin-MC3-DMA | 2.95E+06 | 97.84 |

Assay Example 5: Characterization of Physical Properties of Lipid Nanoparticles of Different Formulations Lipid nanoparticles of formulations 1-39 were prepared using the same method as used in the assay examples, wherein the ionizable cationic lipid in formulations 1-9 was compound 46, the ionizable cationic lipid in formulations 10-31 was compound 20, and the ionizable cationic lipid in formulations 32-39 was compound 26. Specific formulation information can be found in Tables 10-12. The formulations for DLin-MC3-DMA and SM-102 used as controls are as follows:

MC3 formulation:

MC3: cholesterol:DSPC:DMG-PEG=50:38.5:10:1.5, with an N/P ratio of 6;

SM102 formulation:

SM102: cholesterol:DSPC:DMG-PEG=50:38.5:10:1.5, with an N/P ratio of 6.

The particle size and particle size dispersity index (PDI) of the prepared lipid nanoparticles were measured using a Zetasizer Pro (purchased from Malvern Instruments Ltd) and a DynaPro NanoStar (purchased from Wyatt) dynamic light scattering instrument. The degree of RNA encapsulation by lipid nanoparticles was characterized by the Encapsulation Efficiency %, which reflects the degree of binding of lipid nanoparticles to RNA fragments. This parameter was measured by the method of Quant-it™ RiboGreen RNA Assay (purchased from Invitrogen). Lipid nanoparticle samples were diluted in TE buffer (10 mM Tris-HCl, 1 mM EDTA, pH=7.5). A portion of the sample solution was removed, to which 0.5% Triton (Triton X-100) was added, and then allowed to stand at 37° C. for 30 minutes. Immediately after the addition of RIBOGREEN® reaction solution, the fluorescence values were read on a Varioskan LUX multifunctional microplate reader (purchased from Thermofisher) at 485 nm for absorption and 528 nm for emission to obtain the encapsulation efficiency values.

TABLE 7

| Formulation No. | Particle size (nm) | Particle size dispersity (PDI) | Encapsulation efficiency (%) |
|---|---|---|---|
| 1 | 80 | 0.30 | 98.93 |
| 2 | 106 | 0.10 | 92.77 |
| 3 | 104 | 0.10 | 90.90 |
| 4 | 129 | 0.30 | 91.77 |
| 5 | 125 | 0.33 | 90.87 |
| 6 | 112 | 0.23 | 95.82 |
| 7 | 168 | 0.37 | 92.06 |
| 8 | 111 | 0.20 | 90.32 |
| 9 | 102 | 0.10 | 96.34 |
| MC3 | 88.9 | 0.10 | 95.62 |
| SM102 | 92.83 | 0.10 | 98.18 |

TABLE 8

| Formulation No. | Particle size (nm) | Particle size dispersity (PDI) | Encapsulation efficiency (%) |
|---|---|---|---|
| 10 | 81 | 0.37 | 71.82 |
| 11 | 129 | 0.17 | 96.34 |
| 12 | 79 | 0.10 | 87.95 |
| 13 | 93 | 0.13 | 82.10 |
| 14 | 69 | 0.10 | 90.65 |
| 15 | 115 | 0.23 | 77.97 |
| 16 | 83 | 0.13 | 77.24 |
| 17 | 141 | 0.10 | 92.25 |
| 18 | 72 | 0.07 | 83.44 |
| 19 | 77 | 0.10 | 87.68 |
| 20 | 122 | 0.23 | 94.56 |
| 21 | 106 | 0.23 | 83.93 |
| 22 | 104 | 0.17 | 86.44 |
| 23 | 117 | 0.20 | 83.48 |
| 24 | 102 | 0.17 | 84.03 |
| 25 | 121 | 0.17 | 86.10 |
| 26 | 107 | 0.27 | 83.80 |
| 27 | 120 | 0.20 | 85.83 |
| 28 | 105 | 0.23 | 83.78 |
| 29 | 116 | 0.13 | 87.34 |
| 30 | 118.53 | 0.1 | 90.32 |
| 31 | 131.66 | 0.1 | 57.37 |

TABLE 9

| Formulation No. | Particle size (nm) | Particle size dispersity (PDI) | Encapsulation efficiency (%) |
|---|---|---|---|
| 32 | 112 | 0.43 | 89.37 |
| 33 | 103 | 0.37 | 91.76 |
| 34 | 120 | 0.20 | 89.15 |
| 35 | 69 | 0.13 | 96.21 |
| 36 | 107 | 0.27 | 94.35 |

TABLE 9-continued

| Formulation No. | Particle size (nm) | Particle size dispersity (PDI) | Encapsulation efficiency (%) |
|---|---|---|---|
| 37 | 77 | 0.17 | 89.42 |
| 38 | 103 | 0.17 | 97.70 |
| 39 | 92 | 0.17 | 90.97 |

Assay Example 6: Animal Experiment with Different Formulations

The in vivo delivery effect and safety of nanoparticles encapsulated with luciferase mRNA (Trilink, L-7202) in mice were evaluated. The test mice were SPF-grade $C_{57}$BL/6 mice, female, 6-8 weeks old, weighing 18-22 g, and were purchased from SPF (Beijing) Biotechnology Co., Ltd. All animals were acclimatized for more than 7 days prior to the experiment, and had free access to food and water during the experiment. The conditions include alternating light and dark for 12/12 h, the indoor temperature of 20-26° C. and the humidity of 40-70%. The mice were randomly grouped. The lipid nanoparticles encapsulated with luciferase mRNA prepared above were injected into mice by intravenous administration at a single dose of 0.5 mg/kg mRNA, and the mice were subjected to in vivo bioluminescence assay using a Small Animal In Vivo Imaging System (IVIS LUMINA III, purchased from PerkinElmer) at 6 h after administration. The assay was performed as follows: D-luciferin solution was prepared in saline at a concentration of 15 mg/mL, and each mouse was given the substrate by intraperitoneal injection. At ten minutes after administration of the substrate, the mice were anesthetized in an anesthesia chamber with isoflurane at a concentration of 2.5%. The anesthetized mice were placed in IVIS for fluorescence imaging, and data acquisition and analysis were performed on the concentrated distribution area of fluorescence.

The in vivo delivery efficiency of lipid nanoparticle carriers was expressed as the mean values of fluorescence intensity and total photon count in different animals within the same subject group. Higher values of fluorescence intensity and total photon count indicate higher in vivo delivery efficiency of this mRNA fragment by lipid nanoparticles. The MC3 fold and SM102 fold in Tables 10-12 indicate the fold of improvement of the present disclosure LNP relative to the MC3 LNP or SM102 LNP, respectively.

The LNPs of the present disclosure have good in vivo delivery efficiency (Tables 10-12) and are more efficiently expressed in vivo than MC3 or SM102 when delivering luciferase mRNA, up to more than 35-fold.

TABLE 10

| | | LNP Formulation | | | | | |
|---|---|---|---|---|---|---|---|
| Formulation No. | N/P | Compound 46 (%) | Cholesterol (%) | DSPC (%) | DMG-PEG(%) | MC3 fold | SM102 fold |
| 1 | 4 | 32.5 | 61 | 5 | 1.5 | 2.8 | 2.7 |
| 2 | 5 | 32.5 | 51.5 | 15 | 1 | 2.6 | 2.5 |
| 3 | 5 | 42.5 | 49 | 7.5 | 1 | 8.4 | 8.3 |
| 4 | 5 | 42.5 | 51 | 5 | 1.5 | 9.1 | 8.9 |
| 5 | 3 | 47.6 | 38.1 | 12.5 | 1.8 | 21.3 | 20.9 |
| 6 | 4 | 47.6 | 30.6 | 20 | 1.8 | 20.5 | 20.1 |
| 7 | 4 | 47.5 | 40.5 | 10 | 2 | 11.2 | 11 |
| 8 | 5 | 47.6 | 32.9 | 17.5 | 2 | 19.7 | 19.3 |
| 9 | 6 | 47.6 | 36 | 15 | 1.4 | 13.7 | 13.4 |

TABLE 11

| | | LNP Formulation | | | | | |
|---|---|---|---|---|---|---|---|
| Formulation No. | N/P | Compound 20 (%) | Cholesterol (%) | DSPC (%) | DMG-PEG(%) | MC3 fold | SM102 fold |
| 10 | 9 | 40 | 35 | 20 | 5 | 2.95 | 2.89 |
| 11 | 9 | 40 | 48.5 | 10 | 1.5 | 12.18 | 11.93 |
| 12 | 3 | 30 | 66 | 2.5 | 1.5 | 3.56 | 3.49 |
| 13 | 3 | 40 | 53.5 | 5 | 1.5 | 9.13 | 8.95 |
| 14 | 6 | 30 | 66 | 2.5 | 1.5 | 4.55 | 4.46 |
| 15 | 6 | 40 | 53.5 | 5 | 1.5 | 10.52 | 10.30 |
| 16 | 9 | 30 | 63.5 | 5 | 1.5 | 8.08 | 7.92 |
| 17 | 9 | 40 | 48.5 | 10 | 1.5 | 10.51 | 10.30 |
| 18 | 3 | 40 | 55 | 2.5 | 2.5 | 11.33 | 11.10 |
| 19 | 6 | 30 | 62.5 | 5 | 2.5 | 4.93 | 4.83 |
| 20 | 9 | 30 | 57.5 | 10 | 2.5 | 12.21 | 11.96 |
| 21 | 9 | 40 | 55 | 2.5 | 2.5 | 11.15 | 10.93 |
| 22 | 6 | 48.5 | 47.5 | 1.5 | 2.5 | 17.45 | 17.10 |
| 23 | 6 | 48.5 | 46.5 | 2.5 | 2.5 | 18.04 | 17.67 |
| 24 | 6 | 48.5 | 45.5 | 2.5 | 3.5 | 30.69 | 30.07 |
| 25 | 9 | 48.5 | 47.5 | 1.5 | 2.5 | 22.87 | 22.40 |
| 26 | 9 | 48.5 | 45.5 | 2.5 | 3.5 | 26.20 | 25.67 |
| 27 | 12 | 48.5 | 47.5 | 1.5 | 2.5 | 21.21 | 20.78 |
| 28 | 12 | 48.5 | 46.5 | 1.5 | 3.5 | 35.00 | 34.29 |
| 29 | 12 | 48.5 | 46.5 | 2.5 | 2.5 | 15.56 | 15.25 |
| 30 | 6 | 50 | 42.5 | 5 | 2.5 | 6.46 | / |
| 31 | 3 | 60 | 27.5 | 10 | 2.5 | 1.07 | / |

TABLE 12

| Formulation No. | N/P | LNP Formulation Compound 26 (%) | Cholesterol (%) | Phospholipid (%) | DMG-PEG(%) | Phospholipid | MC3 fold | SM102 fold |
|---|---|---|---|---|---|---|---|---|
| 32 | 7 | 40 | 44 | 12.5 | 3.5 | DSPC | 8.19 | 8.02 |
| 33 | 5 | 40 | 53.5 | 5 | 1.5 | DOPE | 6.33 | 6.20 |
| 34 | 7 | 40 | 43.5 | 15 | 1.5 | DSPC | 8.26 | 8.09 |
| 35 | 5 | 30 | 66 | 2.5 | 1.5 | DOPE | 12.40 | 12.15 |
| 36 | 5 | 40 | 56 | 2.5 | 1.5 | DOPE | 5.92 | 5.80 |
| 37 | 5 | 40 | 51 | 7.5 | 1.5 | DOPE | 7.08 | 6.93 |
| 38 | 3 | 40 | 56 | 2.5 | 1.5 | DOPE | 7.13 | 6.99 |
| 39 | 3 | 40 | 56 | 2.5 | 1.5 | DSPC | 9.15 | 8.97 |

While the present disclosure has been fully described by way of its embodiments, it is worth noting that various variations and modifications are apparent to those skilled in the art. Such variations and modifications should all be included within the scope of the claims appended to this disclosure.

What is claimed is:

1. A nanoparticle composition, comprising a lipid ingredient, and optionally comprising a load;

wherein the lipid ingredient comprises the following components in the molar percentages:

Ionizable cationic lipids 20 mol %-85 mol %;

Structure lipids 10 mol %-75 mol %;

Neutral lipids 1.0 mol %-30 mol %;

Polymer lipids 0.25 mol %-10 mol %;

wherein the ionizable cationic lipid is a compound of formula (IV), or a pharmaceutically acceptable salt, isotopic variant, tautomer or stereoisomer thereof, (IV)

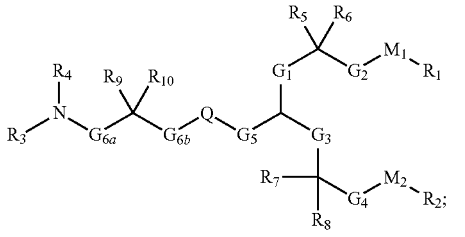

wherein;

$M_1$ and $M_2$ are independently selected from —C(O)O—, —OC(O)O—, —OC(O)—, —SC(O)—, —C(O)S—, C(O)$NR_a$—, and —$NR_a$C(O)—, alternatively —C(O)O—, —OC(O)—, —SC(O)—, and —C(O)S—, alternatively —C(O)O— and —OC(O)—;

Q is C(O)O;

$G_5$ is a chemical bond;

$G_{6a}$ and $G_{6b}$ are independently a chemical bond or $C_{1-7}$ alkylene;

$G_{6a}$ and $G_{6b}$ have a total length of 0, 1, 2, 3, 4, 5, 6 or 7 carbon atoms;

$R_9$, and $R_{10}$ are independently H, or $C_{1-8}$ alkyl;

$G_1$, $G_2$, $G_3$ and $G_4$ are independently a chemical bond, $C_{1-13}$ alkylene, $C_{2-13}$ alkenylene or $C_{2-13}$ alkynylene, which is optionally substituted with one or more $R^s$;

$G_1$ and $G_2$ have a total length of 3, 4, 5, 6, 7, 8, 9, 10, 11, 12 or 13 carbon atoms;

$G_3$ and $G_4$ have a total length of 3, 4, 5, 6, 7, 8, 9, 10, 11, 12 or 13 carbon atoms;

$R_3$ and $R_4$ are independently H, $C_{1-10}$ alkyl, $C_{1-10}$ haloalkyl, $C_{2-10}$ alkenyl, $C_{2-10}$ alkynyl, 3- to 14-membered cycloalkyl, 3- to 14-membered heterocyclyl, $C_{6-10}$ aryl or 5- to 14-membered heteroaryl, which is optionally substituted with one or more R*:

or, $R_3$ and $R_4$ are taken together with the N atom to which they are attached to form 3- to 14-membered heterocyclyl, which is optionally substituted with one or more R*;

or, $R_4$ and $R_9$ are taken together with the atoms to which they are attached to form 3- to 14-membered heterocyclyl or 5- to 14-membered heteroaryl, which is optionally substituted with one or more R*;

R* is independently H, halogen, cyano, $C_{1-10}$ alkyl, $C_{1-10}$ haloalkyl, $-L_b-OR_b$, $-L_b-SR_b$ or $-L_b-NR_bR'_b$ if present;

$R_5$, $R_6$, $R_7$ and $R_8$ are independently $C_{1-2}$ alkyl;

$R_1$ and $R_2$ are independently $C_{4-20}$ alkyl, $C_{4-20}$ alkenyl or $C_{4-20}$ alkynyl, which is optionally substituted with one or more R, and wherein one or more methylene units are optionally and independently replaced with —NR"—;

$R^s$ is independently H, $C_{1-14}$ alkyl, $-L_d-OR_d$, $-L_d-SR_d$ or $-L_d-NR_dR'_d$ if present;

R is independently H, $C_{1-20}$ alkyl, $-L_a-OR_a$, $-L_a-SR_a$ or $-L_a-NR_aR'_a$ if present;

R" is independently H or $C_{1-20}$ alkyl if present;

$L_a$ and $L_e$ are independently a chemical bond or $C_{1-20}$ alkylene if present;

$L_b$ and $L_f$ are independently a chemical bond or $C_{1-10}$ alkylene if present;

$L_d$ is independently a chemical bond or $C_{1-14}$ alkylene if present;

$R_a$ and $R'_a$ are independently H, $C_{1-20}$ alkyl, 3- to 14-membered cycloalkyl, and 3- to 14-membered heterocyclyl if present, which are optionally substituted with one or more of the following substituents: H, $C_{1-20}$ alkyl, $-L_e-OR_e$, $-L_e-SR_e$ and $-L_e-NR_eR'_e$;

$R_b$ and $R'_b$ are independently H, $C_{1-10}$ alkyl, 3- to 14-membered cycloalkyl, and 3- to 14-membered heterocyclyl if present, which are optionally substituted with one or more of the following substituents: H, $C_{1-10}$ alkyl, $-L_f-OR_f$, $-L_f-SR_f$ and $-L_f-NR_fR'_f$, $R_d$ and $R'_d$ are independently H or $C_{1-14}$ alkyl if present;

$R_e$ and $R'_e$ are independently H or $C_{1-20}$ alkyl if present;

$R_f$ and $R'_f$ are independently H or $C_{1-10}$ alkyl if present.

2. The nanoparticle composition of claim 1, wherein the lipid ingredient comprises the following components in the molar percentages:

Ionizable cationic lipids 25 mol %-65 mol %;
Structure lipids 25 mol %-70 mol %;
Neutral lipids 1 mol %-25 mol %;
Polymer lipids 0.5 mol %-8 mol %;
alternatively, the lipid ingredient comprises the following components in the molar percentages:
Ionizable cationic lipids 30 mol %-60 mol %;
Structure lipids 27.5 mol %-66 mol %;
Neutral lipids 1.5 mol %-20 mol %;
Polymer lipids 1 mol %-5 mol %;
alternatively, the lipid ingredient comprises the following components in the molar percentages:
Ionizable cationic lipids 30 mol %-50 mol %;
Structure lipids 30.5 mol %-66 mol %;
Neutral lipids 1.5 mol %-20 mol %;
Polymer lipids 1 mol %-5 mol %.

3. The nanoparticle composition of claim 1, the compound of formula (IV) has a structure of formula (V):

(V)

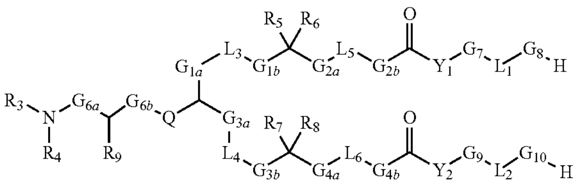

wherein:
Q is C(O)O;
$G_6a$ and $G_{6b}$ are independently a chemical bond or $C_{1-5}$ alkylene;
$G_{6a}$ and $G_{6b}$ have a total length of 0, 1, 2, 3, 4 or 5 carbon atoms;
$R_9$ is H, or $C_{1-6}$ alkyl;
one of $L_3$ and $L_5$, or one of $L_4$ and $L_6$ is selected from —$(CR^sR^{s'})_2$—, —CH═CH— and —C≡C—, and the other is a chemical bond;
$G_{1a}$, $G_{1b}$, $G_{2a}$, $G_{2b}$, $G_{3a}$, $G_{3b}$, $G_{4a}$ and $G_{4b}$ are independently a chemical bond or $C_{1-7}$ alkylene, which is optionally substituted with 1, 2, 3, 4 or 5 $R^s$;
$G_{1a}$, $G_{1b}$, $G_{2a}$ and $G_{2b}$ have a total length of 1, 2, 3, 4, 5, 6 or 7 carbon atoms;
$G_{3a}$, $G_{3b}$, $G_{4a}$ and $G_{4b}$ have a total length of 1, 2, 3, 4, 5, 6 or 7 carbon atoms;
$R_3$ and $R_4$ are independently H, $C_{1-6}$ alkyl, $C_{1-6}$ haloalkyl, 3- to 10-membered cycloalkyl or 3- to 10-membered heterocyclyl, which is optionally substituted with 1, 2, 3, 4 or 5 R*;
or, $R_3$ and $R_4$ are taken together with the N atom to which they are attached to form 3- to 10-membered heterocyclyl, which is optionally substituted with 1, 2, 3, 4 or 5 R*;
or, $R_4$ and $R_9$ are taken together with the atoms to which they are attached to form 3- to 10-membered heterocyclyl, which is optionally substituted with 1, 2, 3, 4 or 5 R*;
R* is independently H, halogen, cyano, $C_{1-6}$ alkyl, $C_{1-6}$ haloalkyl, $-L_b-OR_b$ or $-L_b-NR_bR'_b$, if present;
$R_5$, $R_6$, $R_7$ and $R_8$ are independently $C_{1-2}$ alkyl;
$Y_1$ and $Y_2$ are independently O, S or $NR_a$;
$L_1$ and $L_2$ are independently —$(CRR')_2$—, —CH═CH—, —C≡C— or —NR"—;
$G_7$, $G_8$, $G_9$ and $G_{10}$ are independently a chemical bond or $C_{1-12}$ alkylene, which is optionally substituted with 1, 2, 3, 4, 5 or 6 R;
$G_7$ and $G_8$ have a total length of 4, 5, 6, 7, 8, 9, 10, 11 or 12 carbon atoms;
$G_9$ and $G_{10}$ have a total length of 4, 5, 6, 7, 8, 9, 10, 11 or 12 carbon atoms;
1, 2 or 3 methylenes in $G_7$, $G_8$, $G_9$ or $G_{10}$ are optionally and independently substituted with 1 R;
$R^s$ and $R^{s'}$ are independently H, $C_{1-10}$ alkyl, $-L_d-OR_d$ or $-L_d-NR_dR'_d$;
$R^s$ and $R^{s'}$ are independently H, $C_{1-14}$ alkyl, $-L_a-OR_a$ or $-L_a-NR_aR'_a$;
R" is independently H or $C_{1-14}$ alkyl;
$L_a$ is independently a chemical bond or $C_{1-14}$ alkylene;
$L_b$ is independently a chemical bond or $C_{1-6}$ alkylene if present;
$L_d$ is independently a chemical bond or $C_{1-10}$ alkylene;
$R_a$ and $R'_a$ are independently H, $C_{1-14}$ alkyl, 3- to 10-membered cycloalkyl or 3- to 10-membered heterocyclyl;
$R_b$ and $R'_b$ are independently H, $C_{1-6}$ alkyl, 3- to 10-membered cycloalkyl or 3- to 10-membered heterocyclyl if present;
$R_d$ and $R'_d$ are independently H or $C_{1-10}$ alkyl if present.

4. The nanoparticle composition of claim 3, wherein in the compound of formula (V),
Q is C(O)O;
$G_6a$ is a chemical bond or $C_{1-4}$ alkylene;
$G_{6b}$ is a chemical bond or $C_{1-2}$ alkylene;
Goa and $G_{6b}$ have a total length of 0, 1, 2, 3 or 4 carbon atoms;
$R_9$ is H or $C_{1-6}$ alkyl;
one of $L_3$ and $L_5$, or one of $L_4$ and $L_6$ is selected from —$(CHR^s)_2$—, —CH═CH— and —C≡C—, and the other is a chemical bond;
$G_{1a}$ and $G_{3a}$ are independently a chemical bond or $C_{1-7}$ alkylene;
$G_{1b}$ and $G_{3b}$ are independently a chemical bond or $C_{1-3}$ alkylene;
$G_{2a}$ and $G_{4a}$ are independently a chemical bond or $C_{1-3}$ alkylene;
$G_{2b}$ and $G_{4b}$ are independently a chemical bond or $C_{1-4}$ alkylene;
$G_{1a}$, $G_{1b}$, $G_{2a}$ and $G_{2b}$ have a total length of 1, 2, 3, 4, 5, 6 or 7 carbon atoms;
$G_{3a}$, $G_{3b}$, $G_{4a}$ and $G_{4b}$ have a total length of 1, 2, 3, 4, 5, 6 or 7 carbon atoms;
$R_3$ and $R_4$ are independently H, $C_{1-6}$ alkyl, $C_{1-6}$ haloalkyl, 3- to 7-membered cycloalkyl or 3- to 7-membered heterocyclyl, which is optionally substituted with 1, 2, 3, 4 or 5 R*;
or, $R_3$ and $R_4$ are taken together with the N atom to which they are attached to form 3- to 7-membered heterocyclyl, which is optionally substituted with 1, 2, 3, 4 or 5 R*;
or, $R_4$ and $R_9$ are taken together with the atoms to which they are attached to form 3- to 7-membered heterocyclyl, which is optionally substituted with 1, 2, 3, 4 or 5 R*;
R* is independently H, halogen, cyano, $C_{1-6}$ alkyl, $C_{1-6}$ haloalkyl, $-L_b-OR_b$ or $-L_b-NR_bR'_b$ if present;
$R_5$, $R_6$, $R_7$ and $R_8$ are independently $C_{1-6}$ alkyl;
$Y_1$ and $Y_2$ are independently O, S or $NR_a$;
$L_1$ and $L_2$ are independently —$(CHR)_2$—, —CH═CH—, —C≡C— or —NR"—;

$G_7$ and $G_9$ are independently a chemical bond or $C_{1-6}$ alkylene;

$G_8$ and $G_{10}$ are independently $C_{1-10}$ alkylene;

$G_7$ and $G_8$ have a total length of 4, 5, 6, 7, 8, 9 or 10 carbon atoms;

$G_9$ and $G_{10}$ have a total length of 4, 5, 6, 7, 8, 9 or 10 carbon atoms;

1, 2 or 3 methylenes in $G_7$, $G_8$, $G_9$ or $G_{10}$ are optionally and independently substituted with 1 R;

$R^s$ is independently H or $C_{1-6}$ alkyl;

R is independently H or $C_{1-10}$ alkyl;

R" is independently H or $C_{1-10}$ alkyl;

$L_b$ is independently a chemical bond or $C_{1-6}$ alkylene;

$R_a$ is independently H or $C_{1-10}$ alkyl;

$R_b$ and $R'_b$ are independently H or $C_{1-6}$ alkyl;

alternatively,

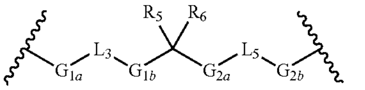

or

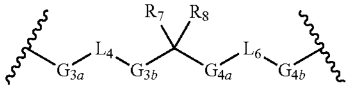

is independently selected from the following groups: $—(CH_2)_3—C(CH_3)_2—$, $—(CH_2)_4—C(CH_3)_2—$, $—(CH_2)_5—C(CH_3)_2—$, $—(CH_2)_6—C(CH_3)_2—$, $—(CH_2)_7—C(CH_3)_2—$, $—(CH_2)_8—C(CH_3)_2—$, $—(CH_2)_3—CH{=}CH—C(CH_3)_2—$, $—(CH_2)_3—C{\equiv}C—C(CH_3)_2—$, $—(CH_2)_4—C(CH_3)_2—CH_2—$, $—(CH_2)_3—C(CH_3)_2—(CH_2)_2—$, $—(CH_2)_2—C(CH_3)_2—(CH_2)_3—$, $—(CH_2)_2—CH{=}CH—C(CH_3)_2—CH_2—$, $—(CH_2)_2—C(CH_3)_2—C{\equiv}C—CH_2—$, $—(CH_2)_2—C(CH_3)_2—CH{=}CH—CH_2—$, $—(CH_2)_2—C{\equiv}C—C(CH_3)_2—CH_2—$ and $—(CH_2)_3—C(CH_3)_2—C{\equiv}C—$;

$-G_7-L_1-G_8-H$ or $-G_9-L_2-G_{10}-H$ is independently selected from the following groups: $—(CH_2)_5CH_3$, $—(CH_2)_6CH_3$, $—(CH_2)_7CH_3$, $—(CH_2)_8CH_3$, $—(CH_2)_9CH_3$, $—(CH_2)_{10}CH_3$, $—(CH_2)_{11}CH_3$, $—CH_2—C{\equiv}C—(CH_2)_5CH_3$, $—CH_2—C{\equiv}C—(CH_2)_6CH_3$, $—(CH_2)_2—C{\equiv}C—(CH_2)_5CH_3$, $—(CH_2)_4—C{\equiv}C—(CH_2)_3CH_3$, $—CH_2—CH{=}CH—(CH_2)_5CH_3$, $—CH_2—CH{=}CH—(CH_2)_6CH_3$, $—(CH_2)_2—CH{=}CH—(CH_2)_5CH_3$, $—(CH_2)_4—CH{=}CH—(CH_2)_3CH_3$, $—(CH_2)_5—CH{=}CH—CH_2CH_3$,

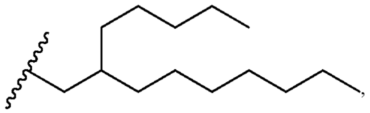

,

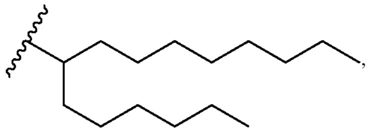

,

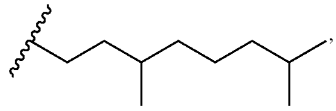

,

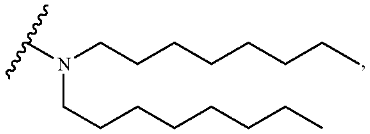

,

-continued

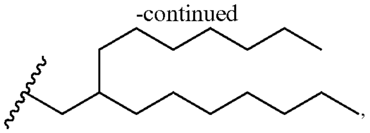

,

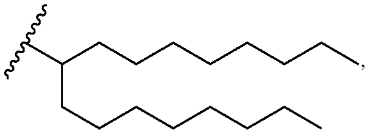

,

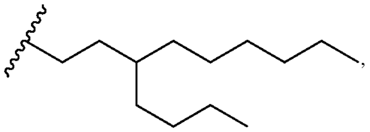

,

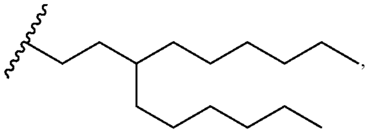

,

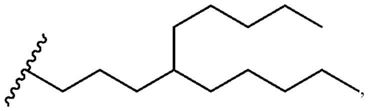

,

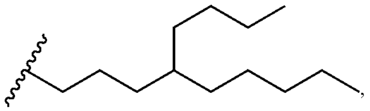

,

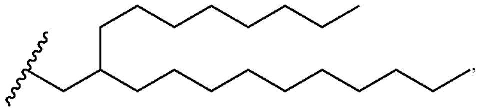

,

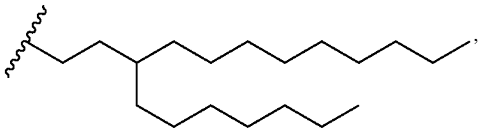

,

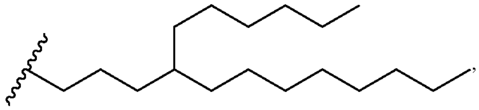

,

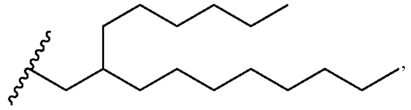

,

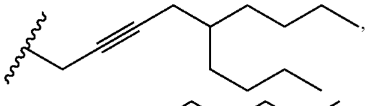

,

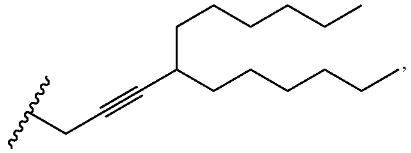

,

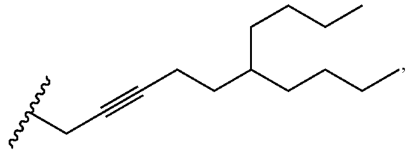

,

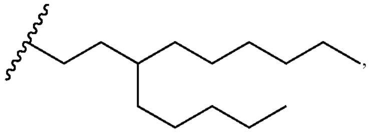

, and

-continued

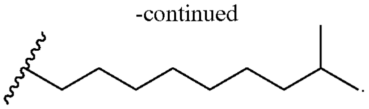

5. The nanoparticle composition of claim 1, wherein the compound of formula (IV) has a structure of formula (VI) or formula (VII):

(VI)

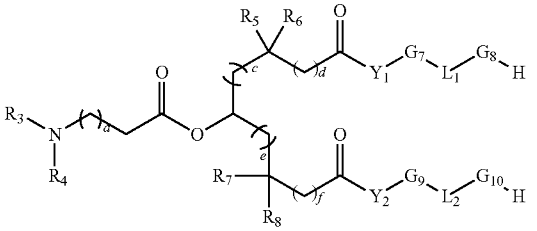

or (VII)

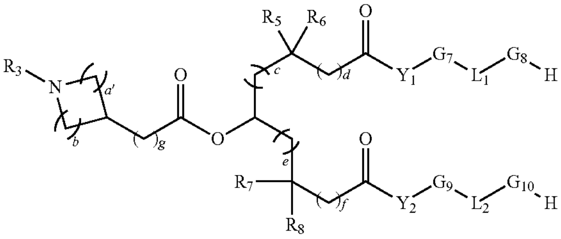

wherein:

a, a', b and g if present are independently 0, 1, 2, 3, 4 or 5, a' and b if present are not 0 at the same time;

a'+g if present=0, 1, 2, 3, 4 or 5;

c and e are independently 3, 4, 5, 6, 7, 8 or 9;

d and f are independently 0, 1, 2, 3 or 4;

c+d=3, 4, 5, 6, 7, 8 or 9, e+f=3, 4, 5, 6, 7, 8 or 9;

methylenes in

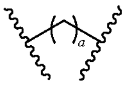

or

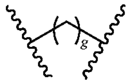

if present are optionally and independently substituted with 1, 2, 3, 4, or 5 $C_{1-6}$ alkyl;

$R_3$ and $R_4$ if present are independently H, $C_{1-6}$ alkyl, $C_{1-6}$ haloalkyl, 3- to 10-membered cycloalkyl or 3- to 10-membered heterocyclyl, which is optionally substituted with 1, 2, 3, 4 or 5 R*; or, $R_3$ and $R_4$ if present are taken together with the N atom to which they are attached to form 3- to 10-membered heterocyclyl, which is optionally substituted with 1, 2, 3, 4 or 5 R*;

R* is independently H, halogen, cyano, $C_{1-6}$ alkyl, $C_{1-6}$ haloalkyl, $-L_b-OR_b$ or $-L_b-NR_bR'_b$ if present;

$R_5$, $R_6$, $R_7$ and R& are independently C1-2 alkyl;

$Y_1$ and $Y_2$ are independently O, S or $NR_4$;

$L_1$; and $L_2$ are independently $—(CRR')_2—$, —CH═CH—, —C≡C— or —NR"—;

$G_7$, $G_8$, $G_9$ and $G_{10}$ are independently a chemical bond or $C_{1-12}$ alkylene, which is optionally substituted with 1, 2, 3, 4, 5 or 6 R;

$G_7$ and $G_8$ have a total length of 6, 7, 8, 9, 10, 11 or 12 carbon atoms;

$G_9$ and $G_{10}$ have a total length of 6, 7, 8, 9, 10, 11 or 12 carbon atoms;

1, 2 or 3 methylenes in $G_7$, $G_8$, $G_9$ or $G_{10}$ are optionally and independently substituted with 1 R;

R and R' are independently H, $C_{1-14}$ alkyl, $-L_a-OR_a$ or $-L_a-NR_aR'_a$ if present;

$L_a$ is independently a chemical bond or $C_{1-14}$ alkylene if present;

$L_b$ is independently a chemical bond or $C_{1-6}$ alkylene if present;

$R_a$ and $R'_a$ are independently H, $C_{1-14}$ alkyl, 3- to 10-membered cycloalkyl or 3- to 10-membered heterocyclyl if present;

$R_b$ and $R'_b$ are independently H, $C_{1-6}$ alkyl, 3- to 10-membered cycloalkyl or 3- to 10-membered heterocyclyl if present;

R" is independently H or $C_{1-14}$ alkyl.

6. The nanoparticle composition of claim 5, wherein in the compound of formula (VI) or formula (VII), a is 0, 1, 2, 3 or 4, alternatively 1, 2, 3 or 4, alternatively 2, 3 or 4 if present;

a' and b are independently 0, 1, 2, 3 or 4, alternatively 2 if present, provided that a' and b are not 0 at the same time;

g is 0, 1 or 2, alternatively 0 or 1 if present;

a'+q=0, 1, 2, 3, 4 or 5, alternatively a'+g=2 or 3 if present;

c and e are independently 3, 4, 5 or 6;

d and f are independently 0, 1 or 2;

c+d=4, 5 or 6, e+f=4, 5 or 6;

methylenes in

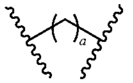

if present are optionally and independently substituted with 1, 2, 3, 4 or 5 $C_{1-6}$ alkyl;

methylenes in

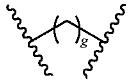

if present are optionally and independently substituted with 1 or 2 $C_{1-6}$ alkyl;

$R_3$ and $R_4$ if present are independently $C_{1-6}$ alkyl, which is optionally substituted with 1, 2 or 3 R*;

R* is independently H, $C_{1-6}$ alkyl, $C_{1-6}$ haloalkyl or $—OR_b$ if present;

or, $R_3$ and $R_4$ if present are taken together with the N atom to which they are attached to form 3- to 7-membered heterocyclyl, alternatively 5-membered heterocyclyl, which is optionally substituted with 1, 2 or 3 R*;

$R_5$, $R_6$, $R_7$ and $R_8$ are independently $C_{1-2}$ alkyl;

$Y_1$ and $Y_2$ are independently O, S or $NR_a$, alternatively O or S;

$L_1$ and $L_2$ are independently $—(CHR)_2—$, —CH═CH—, —C≡C— or —NR"—, alternatively $—(CHR)_2—$, —CH═CH— or —C≡C—;

$G_7$ and Gg are independently a chemical bond or $C_{1-6}$ alkylene;

$G_8$ and $G_{10}$ are independently $C_{1-10}$ alkylene;

$G_7$ and $G_9$ have a total length of 6, 7, 8, 9 or 10 carbon atoms;

$G_8$ and $G_{10}$ have a total length of 6, 7, 8, 9 or 10 carbon atoms;

1, 2 or 3 methylenes in $G_7$, $G_8$, $G_9$ or $G_{10}$ are optionally and independently substituted with 1 R;

R is independently H or $C_{1-8}$ alkyl if present;

R" is independently H or $C_{1-10}$ alkyl;

$R_a$ is independently H or $C_{1-10}$ alkyl;

$R_b$ is independently H or $C_{1-6}$ alkyl, alternatively H if present.

7. The nanoparticle composition of claim 6, wherein in the compound of formula (VI), a is 0, 1, 2, 3 or 4, alternatively 1, 2, 3 or 4, alternatively 2, 3 or 4;

c and e are independently 3, 4, 5 or 6;

d and f are independently 0, 1 or 2;

c+d=4, 5 or 6, e+f=4, 5 or 6;

$R_3$ and $R_4$ are independently $C_{1-6}$ alkyl;

or, $R_3$ and $R_4$ are taken together with the N atom to which they are attached to form 4- to 6-membered heterocyclyl, alternatively 5-membered heterocyclyl, which is optionally substituted with 1, 2 or 3 R*;

R* is independently H, $C_{1-6}$ alkyl or $C_{1-6}$ haloalkyl if present;

$R_5$, $R_6$, $R_7$ and $R_8$ are independently $C_{1-2}$ alkyl;

$Y_1$ and $Y_2$ are independently O, S or $NR_a$, alternatively O or S;

$L_1$ and $L_2$ are independently $-(CHR)_2-$, $-CH{=}CH-$, $-C{\equiv}C-$ or $-NR"-$, alternatively $-(CHR)_2-$, $-CH{=}CH-$ or $-C{\equiv}C-$;

$G_7$ and $G_9$ are independently a chemical bond or $C_{1-5}$ alkylene;

$G_8$ and $G_{10}$ are independently $C_{1-8}$ alkylene;

$G_7$ and $G_8$ have a total length of 6, 7, 8, 9 or 10 carbon atoms;

$G_9$ and $G_{10}$ have a total length of 6, 7, 8, 9 or 10 carbon atoms;

1, 2 or 3 methylenes in $G_7$, $G_8$, $G_9$ or $G_{10}$ are optionally and independently substituted with 1 R;

R is independently H or $C_{1-8}$ alkyl, alternatively H or $C_{1-7}$ alkyl, alternatively H or $C_{1-6}$ alkyl if present;

R" is independently H or $C_{7-9}$ alkyl;

$R_a$ is independently H or $C_{8-10}$ alkyl.

8. The nanoparticle composition of claim 7, wherein in the compound of formula (VI), a is 2, 3 or 4;

c and e are independently 3, 4, 5 or 6;

d and f are independently 0, 1 or 2;

c+d=4, 5 or 6, e+f=4, 5 or 6;

$R_3$ and $R_4$ are independently $C_{1-6}$ alkyl;

$R_5$, $R_6$, $R_7$ and $R_8$ are independently $C_{1-2}$ alkyl;

$Y_1$ and $Y_2$ are independently O or S;

$L_1$ and $L_2$ are independently $-(CHR)_2-$, $-CH{=}CH-$ or $-C{\equiv}C-$;

$G_7$ and $G_9$ are independently $C_{1-4}$ alkylene;

$G_8$ and $G_{10}$ are independently $C_{2-7}$ alkylene;

$G_7$ and $G_8$ have a total length of 6, 7 or 8 carbon atoms;

$G_9$ and $G_{10}$ have a total length of 6, 7 or 8 carbon atoms;

1, 2 or 3 methylenes in $G_7$, $G_8$, $G_9$ or $G_{10}$ are optionally and independently substituted with 1 R;

R is independently H or $C_{1-7}$ alkyl if present;

provided that, when $L_1$ is $-C{\equiv}C-$, then $G_7$ is $C_{1-2}$ alkylene, or when $L_2$ is $-C{\equiv}C-$, then $G_9$ is $C_{1-2}$ alkylene.

9. The nanoparticle composition of claim 7, wherein in the compound of formula (VI), a is 2, 3 or 4, alternatively 2 or 3;

c and e are independently 4, 5 or 6;

d and f are 0;

$R_3$ and $R_4$ are independently $C_{1-6}$ alkyl;

$R_5$, $R_6$, $R_7$ and $R_8$ are independently $C_{1-2}$ alkyl;

$Y_1$ and $Y_2$ are O;

$L_1$ and $L_2$ are independently $-(CHR)_2-$ or $-CH{=}CH-$;

$G_7$ and $G_9$ are independently $-CH_2-$ or $-CH_2CHR-$;

$G_8$ and $G_{10}$ are independently $-(CH_2)_6-$ or $-(CH_2)_7-$;

$G_7$ and $G_8$ have a total length of 7 or 8 carbon atoms;

$G_9$ and $G_{10}$ have a total length of 7 or 8 carbon atoms;

1, 2 or 3 methylenes in $G_8$ or $G_{10}$ are optionally and independently substituted with 1 R;

R is independently H or $C_{4-6}$ alkyl, alternatively H or $C_5$ alkyl if present;

alternatively $-G_7-L_1-G_8-H$ and $-G_9-L_2-G_{10}-H$ are not $-(CH_2)_9CH_3$ at the same time.

10. The nanoparticle composition of claim 7, wherein in the compound of formula (VI), a is 2;

c and e are independently 4, 5 or 6, alternatively 5;

d and f are 0;

$R_3$ and $R_4$ are independently $C_{1-6}$ alkyl;

$R_5$, $R_6$, $R_7$ and $R_8$ are independently $C_{1-2}$ alkyl;

$Y_1$ and $Y_2$ are independently O or S;

one of $L_1$ and $L_2$ is $-C{\equiv}C-$, the other is $-(CHR)_2-$, or both of $L_1$ and $L_2$ are $-C{\equiv}C-$; alternatively one of $L_1$ and $L_2$ is $-C{\equiv}C-$, the other is $-(CHR)_2-$;

$G_7$ and $G_9$ are $-CH_2-$;

$G_8$ and $G_{10}$ are independently $-(CH_2)_6-$ or $-(CH_2)_7-$;

1 methylene in $G_8$ or $G_{10}$ is optionally and independently substituted with 1 R, alternatively $G_8$ and $G_{10}$ are independently $-CHR-(CH_2)_5-$, $-CHR-(CH_2)_6-$, $-CH_2-CHR-(CH_2)_4-$ or $-(CH_2)_2-CHR-(CH_2)_4-$;

R is independently H or $C_{4-6}$ alkyl, alternatively H or $C_5$ alkyl if present;

provided that, only one of the $-G_7-L_1-G_8-H$ and $-G_9-L_2-G_{10}-H$ is substituted with one non-hydrogen R substituent and the other is unsubstituted.

11. The nanoparticle composition of claim 7, wherein in the compound of formula (VI), a is 2;

c and e are independently 4, 5 or 6, alternatively 5;

d and f are 0;

$R_3$ and $R_4$ are independently $C_{1-3}$ alkyl, alternatively Me;

$R_5$, $R_6$, $R_7$ and $R_8$ are independently $C_{1-2}$ alkyl, alternatively Me;

$Y_1$ and $Y_2$ are independently O or S, alternatively O;

both of $L_1$ and $L_2$ are $-C{\equiv}C-$;

$G_7$ and $G_9$ are $-CH_2-$;

$G_8$ and $G_{10}$ are independently $-(CH_2)_6-$ or $-(CH_2)_7-$, alternatively $-(CH_2)_7-$.

12. The nanoparticle composition of claim 7, wherein in the compound of formula (VI), a is 2;

c and e are 3;

d and f are 2;

$R_3$ and $R_4$ are independently $C_{1-3}$ alkyl, alternatively Me;

$R_5$, $R_6$, $R_7$ and $R_8$ are independently $C_{1-2}$ alkyl;

$Y_1$ and $Y_2$ are independently O or S, alternatively O;

$L_1$ and $L_2$ are $-(CHR)_2-$;

$G_7$ and $G_9$ are independently $-CH_2-$ or $-CH_2CHR-$;

$G_8$ and $G_{10}$ are independently $-(CH_2)_5-$, $-(CH_2)_6-$ or $-(CH_2)_7-$;

$G_7$ and $G_8$ have a total length of 6, 7 or 8 carbon atoms, alternatively 7 carbon atoms;

$G_9$ and $G_{10}$ have a total length of 6, 7 or 8 carbon atoms, alternatively 7 carbon atoms;

1, 2 or 3 methylenes in $G_8$ or $G_{10}$ are optionally and independently substituted with 1 R;

R is independently H or $C_{1-7}$ alkyl, alternatively H or $C_{1-6}$ alkyl, alternatively Me if present.

13. The nanoparticle composition of claim 7, wherein in the compound of formula (VI), a is 2;

c and e are 4, 5, or 6, alternatively 5;

d and f are 0;

$R_3$ and $R_4$ are independently $C_{1-6}$ alkyl;

$R_5$, $R_6$, $R_7$ and $R_8$ are independently $C_{1-2}$ alkyl;

$Y_1$ and $Y_2$ are S;

$L_1$ and $L_2$ are $-(CHR)_2-$;

$G_7$ and $G_9$ are independently $-CH_2-$ or $-CH_2CHR-$;

$G_8$ and $G_{10}$ are independently $-(CH_2)_5-$, $-(CH_2)_6-$ or $-(CH_2)_7-$;

$G_7$ and $G_8$ have a total length of 7 or 8 carbon atoms, alternatively 8 carbon atoms;

$G_9$ and $G_{10}$ have a total length of 7 or 8 carbon atoms, alternatively 8 carbon atoms;

1, 2 or 3 methylenes in $G_8$ or $G_{10}$ are optionally and independently substituted with 1 R;

R is independently H or $C_{4-6}$ alkyl, alternatively H or $C_5$ alkyl if present.

14. The nanoparticle composition of claim 6, wherein in the compound of formula (VII), a' and b are 2;

g is 0 or 1;

c and e are 5;

d and f are 0;

$R_3$ is $C_{1-6}$ alkyl, which is optionally substituted with 1, 2 or 3 R*;

R* is independently H, $C_{1-6}$ alkyl, $C_{1-6}$ haloalkyl or $-OR_b$, alternatively H, $C_{1-6}$ alkyl or $C_{1-6}$ haloalkyl if present;

$R_5$, $R_6$, $R_7$ and $R_8$ are independently $C_{1-2}$ alkyl;

$Y_1$ and $Y_2$ are independently O or S;

$L_1$ and $L_2$ are $-(CHR)_2-$;

$G_7$ and $G_9$ are independently $-CH_2-$ or $-CH_2CHR-$;

$G_8$ and $G_{10}$ are independently $-(CH_2)_5-$, $-(CH_2)_6-$ or $-(CH_2)_7-$;

$G_7$ and $G_8$ have a total length of 6, 7 or 8 carbon atoms;

$G_9$ and $G_{10}$ have a total length of 6, 7 or 8 carbon atoms;

1, 2 or 3 methylenes in $G_8$ or $G_{10}$ are optionally and independently substituted with 1 R;

R is independently H or $C_{4-6}$ alkyl if present;

$R_b$ is independently H or $C_{1-6}$ alkyl, alternatively H if present.

15. The nanoparticle composition of claim 14, wherein in the compound of formula (VII), $R_3$ is Me or $-CH_2CH_3$, alternatively Me;

both of $Y_1$ and $Y_2$ are O;

$G_7$ and $G_8$ have a total length of 6 or 7 carbon atoms, alternatively 7 carbon atoms;

$G_9$ and $G_{10}$ have a total length of 6 or 7 carbon atoms, alternatively 7 carbon atoms.

16. The nanoparticle composition of claim 14, wherein in the compound of formula (VII), $R_3$ is Me or $-CH_2CH_3$;

$Y_1$ and $Y_2$ are independently O or S, where $Y_1$ and $Y_2$ are not O at the same time;

$G_7$ and $G_8$ have a total length of 6, 7 or 8 carbon atoms;

$G_9$ and $G_{10}$ have a total length of 6, 7 or 8 carbon atoms.

17. The nanoparticle composition of claim 16, wherein in the compound of formula (VII), g is 0 or 1, alternatively 1;

$R_3$ is Me or $-CH_2CH_3$, alternatively Me;

one of $Y_1$ and $Y_2$ is O, and the other is S;

$G_7$ and $G_8$ have a total length of 7 carbon atoms;

$G_9$ and $G_{10}$ have a total length of 7 carbon atoms.

18. The nanoparticle composition of claim 16, wherein in the compound of formula (VII), g is 0 or 1, alternatively 0;

$R_3$ is Me or $-CH_2CH_3$;

both of $Y_1$ and $Y_2$ are S;

$G_7$ and $G_8$ have a total length of 7 or 8 carbon atoms;

$G_9$ and $G_{10}$ have a total length of 7 or 8 carbon atoms.

19. The nanoparticle composition of claim 1, wherein the ionizable cationic lipid is selected from the following:

1

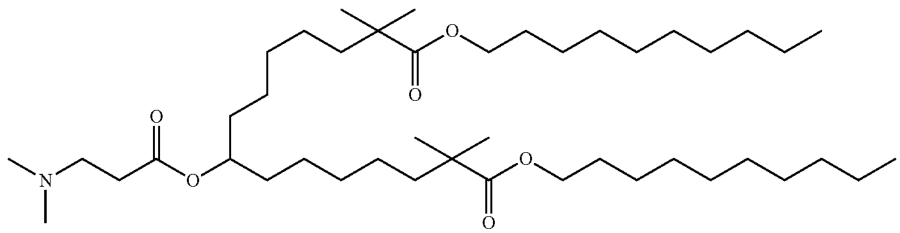

2

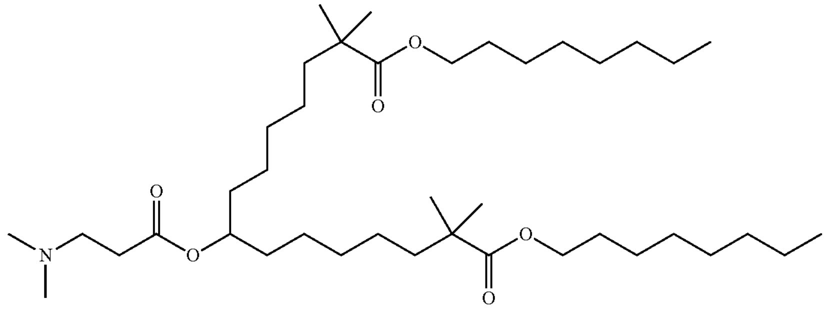

-continued
3
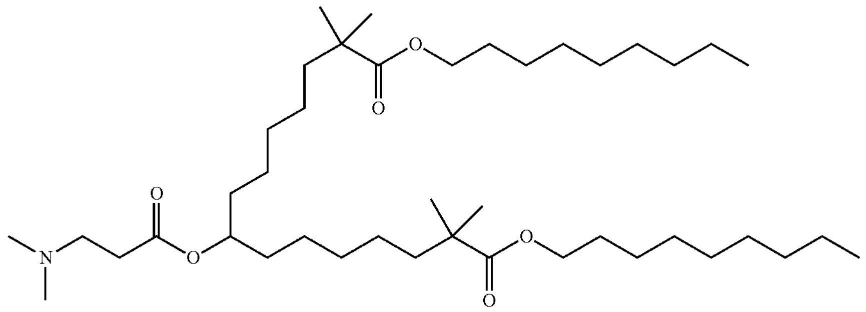
4
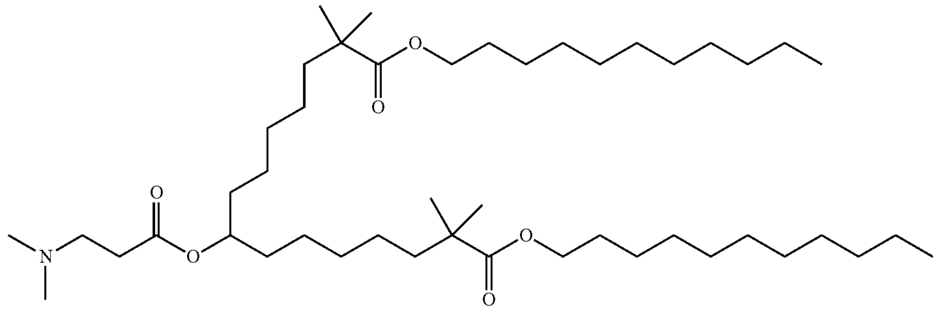
5
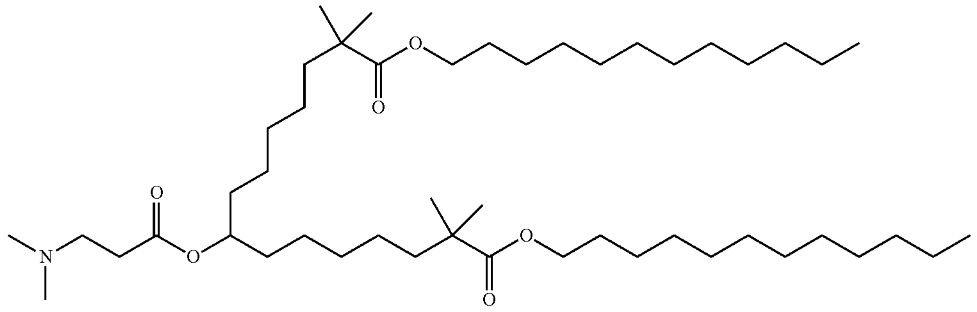
6
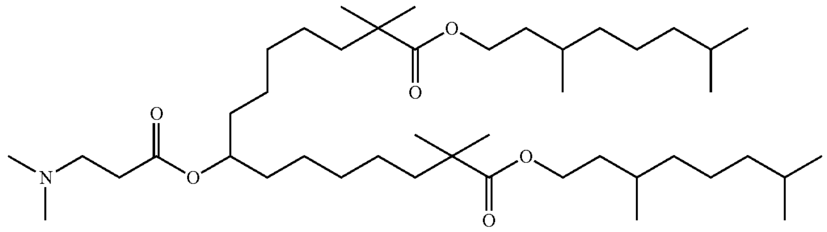
7
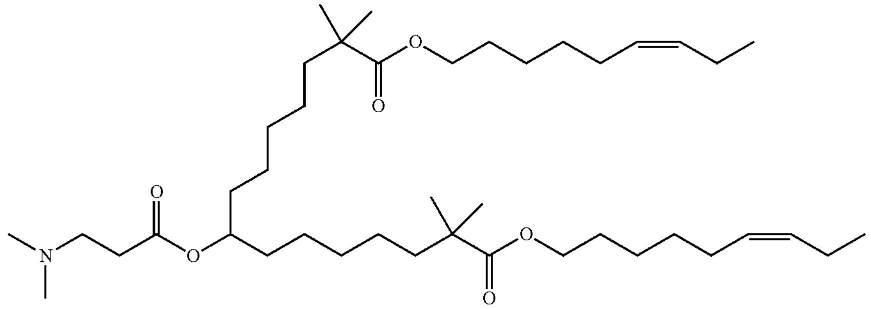

-continued
8
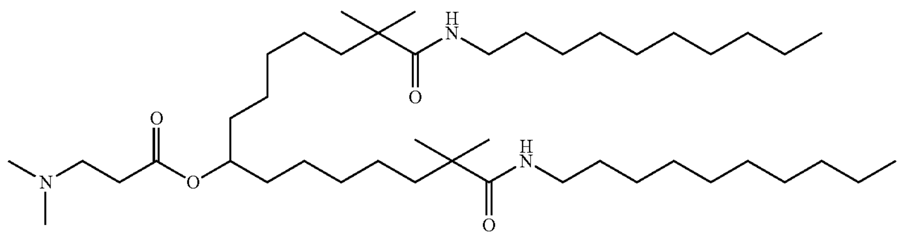
9
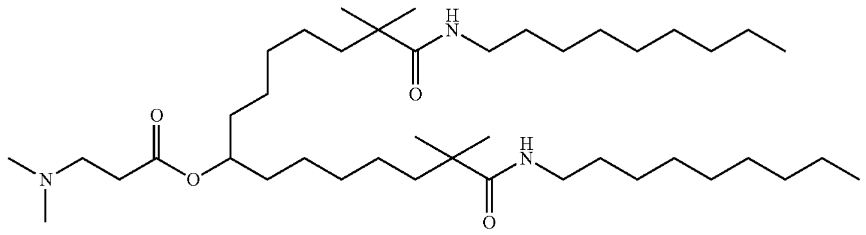
10
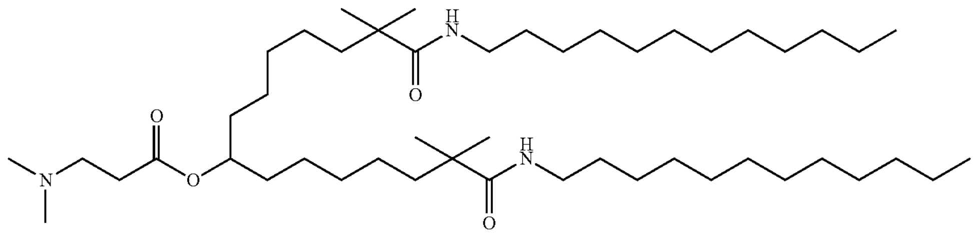
11
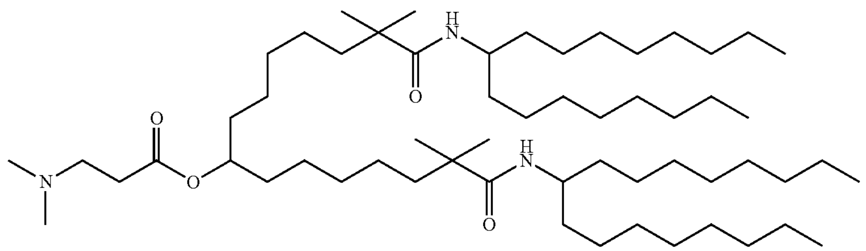
12
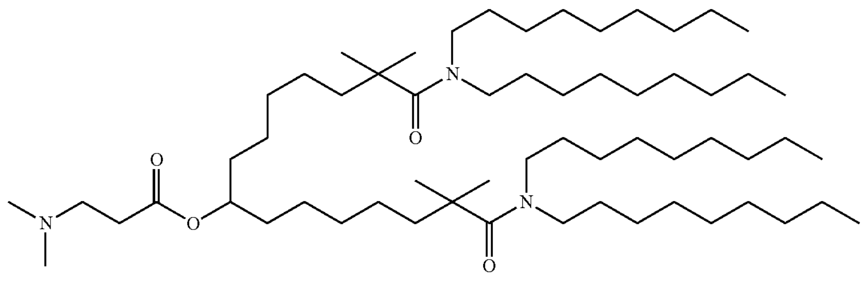
13
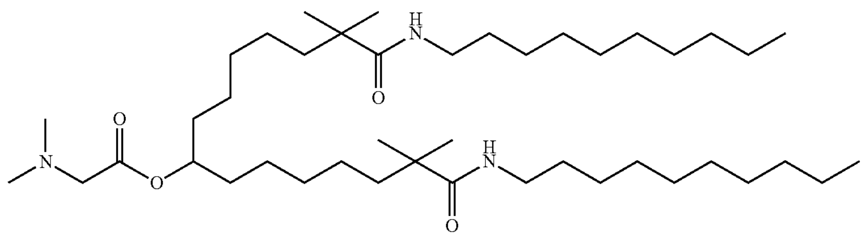

-continued
14
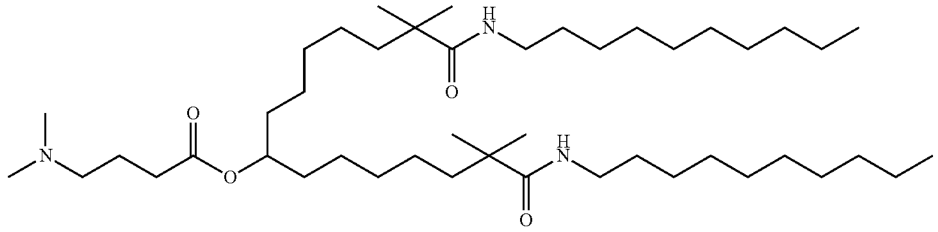
15
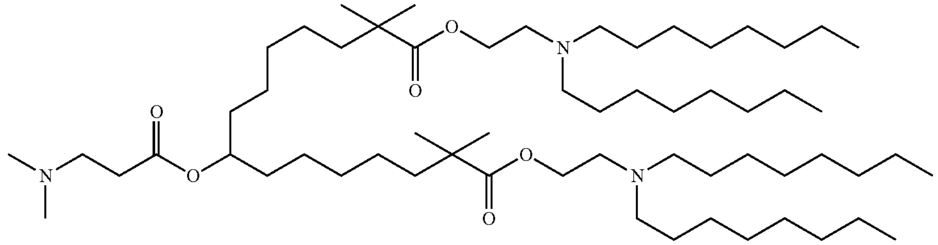
16
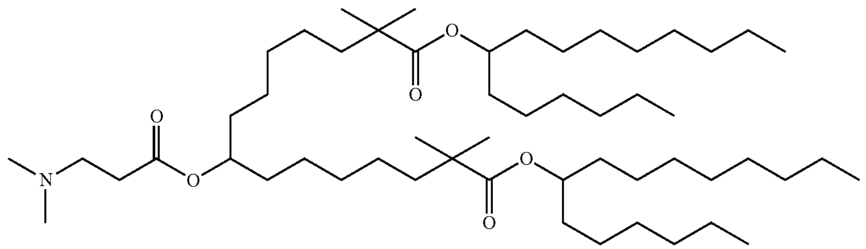
17
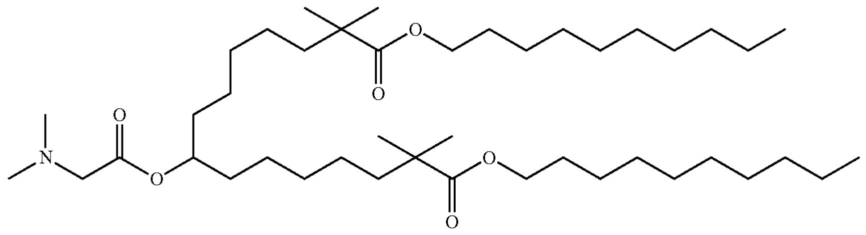
18
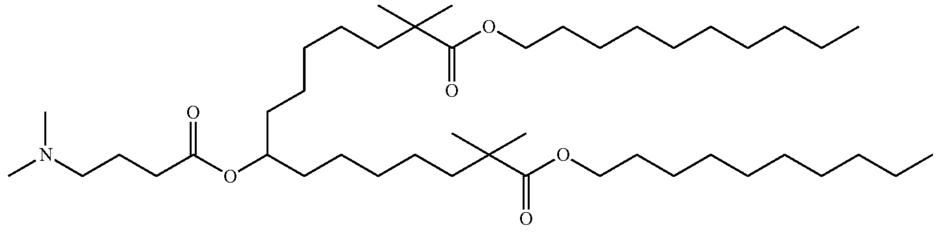
19
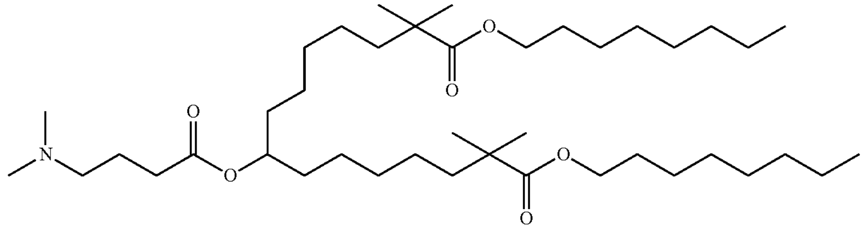

-continued
20
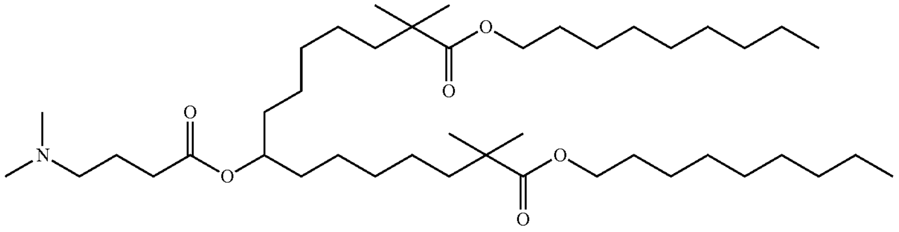
21
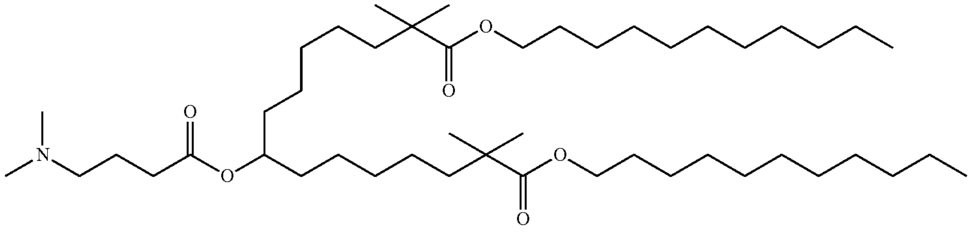
22
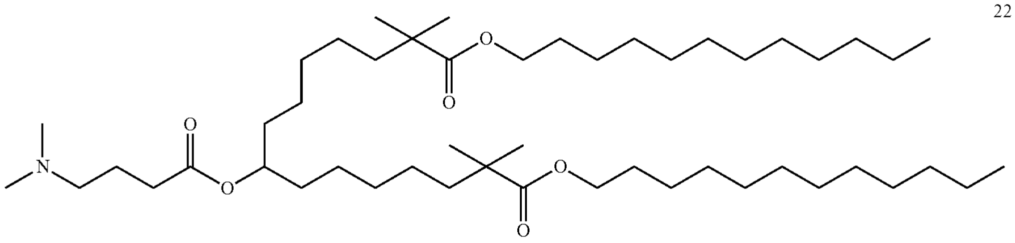
23
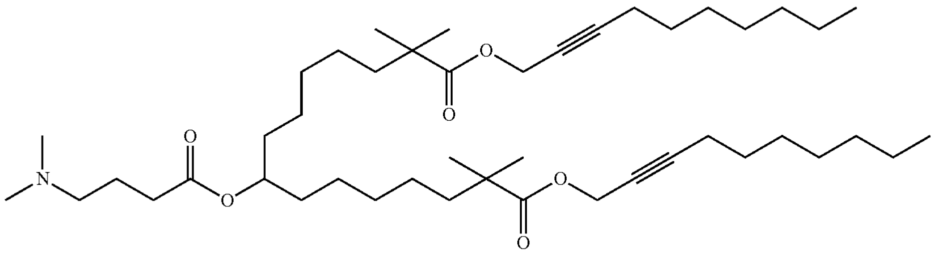
24
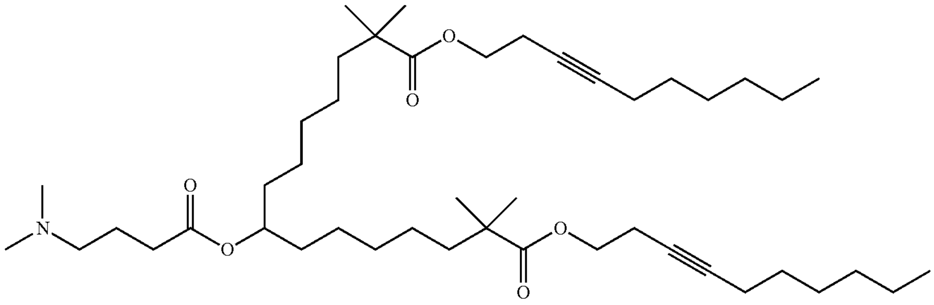
25
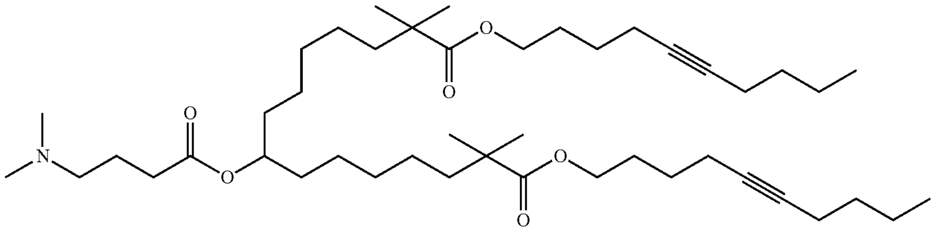

-continued
26
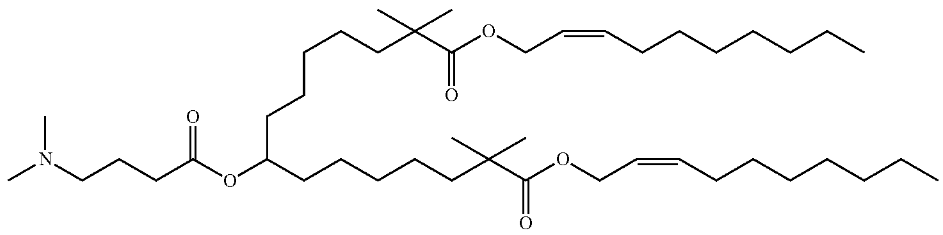
27
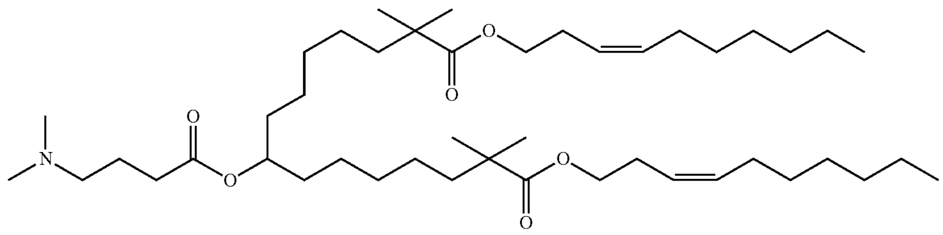
28
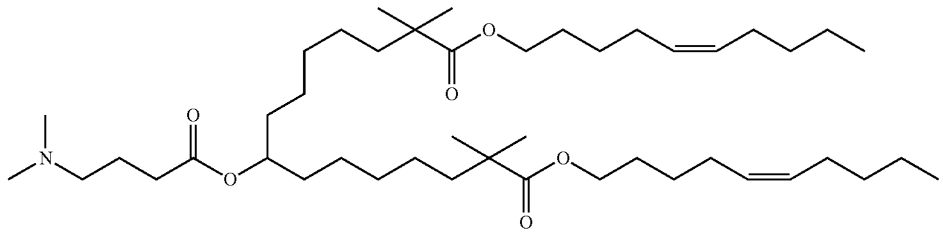
30
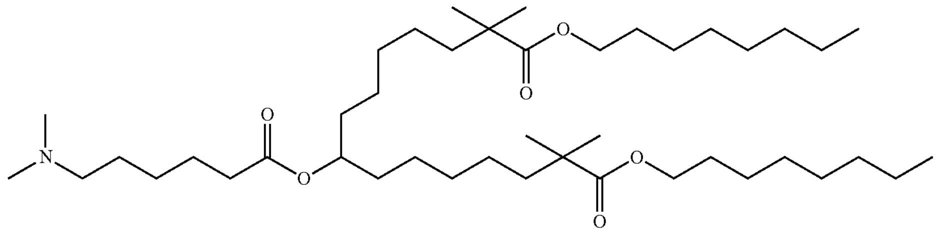
32
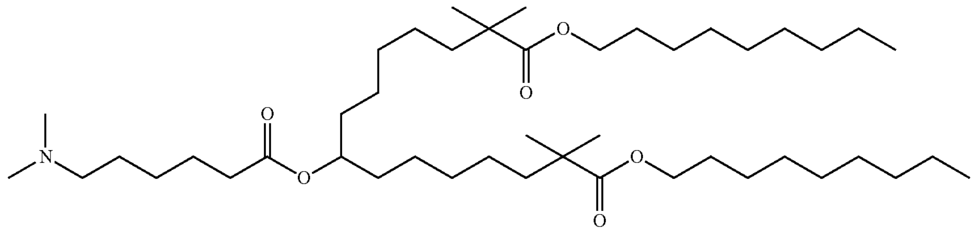
33
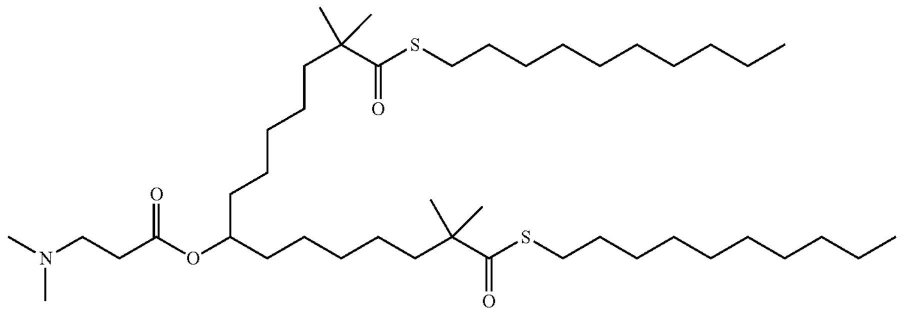

-continued
34
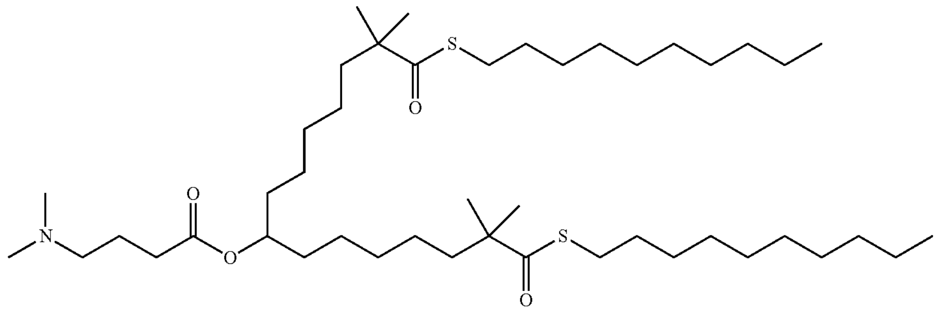
36
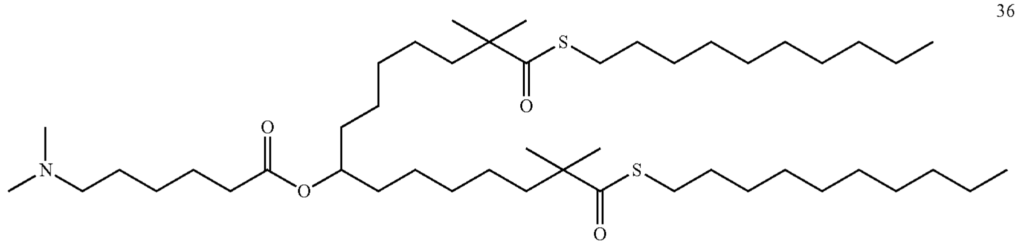
37
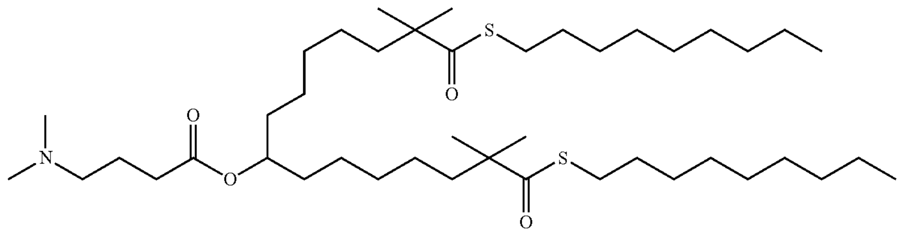
39
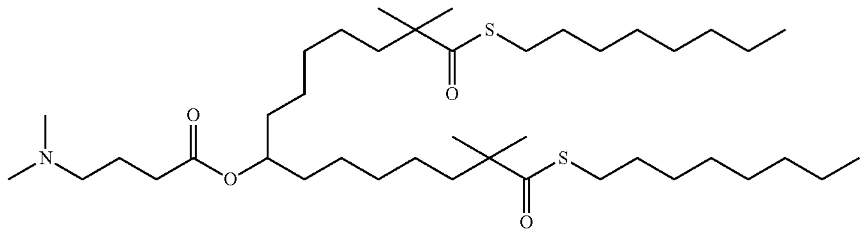
40
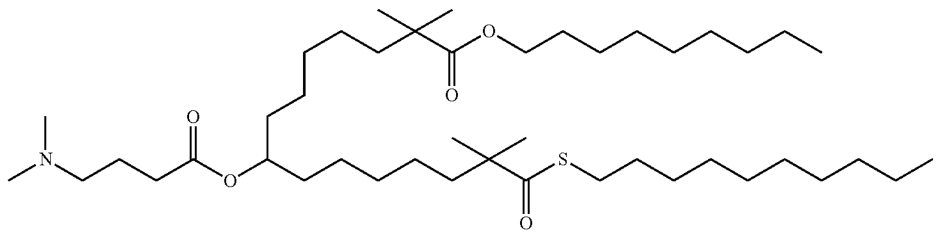
41
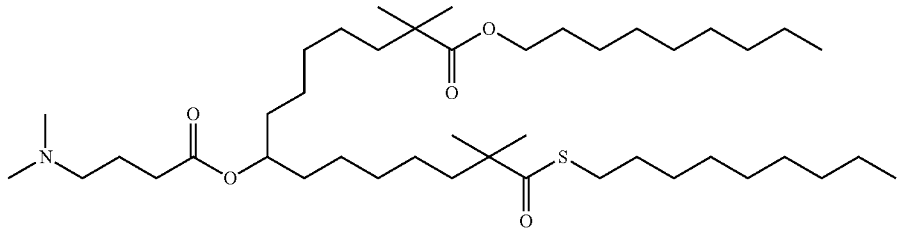

-continued
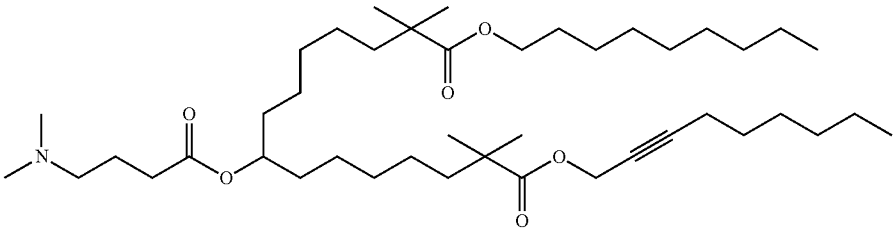
42
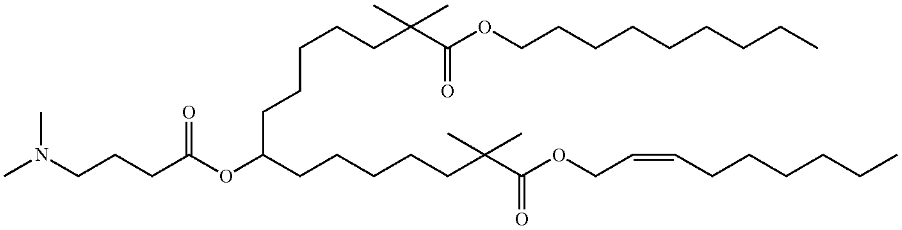
43
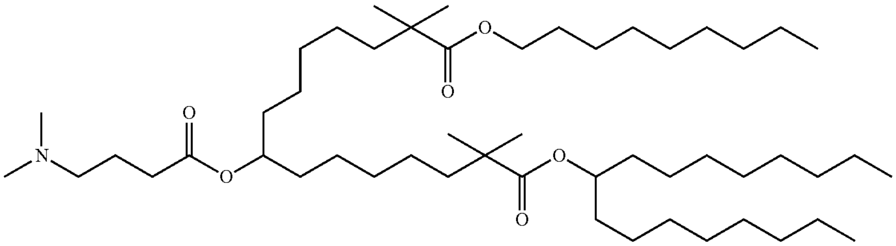
44
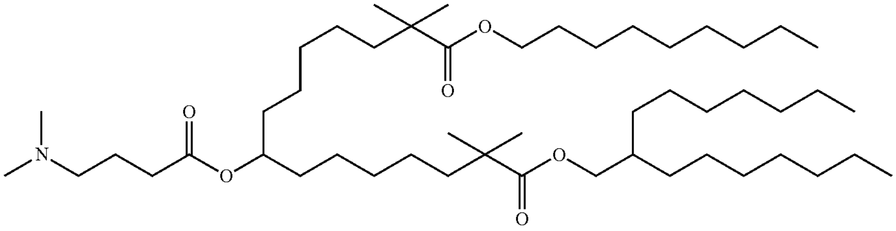
45
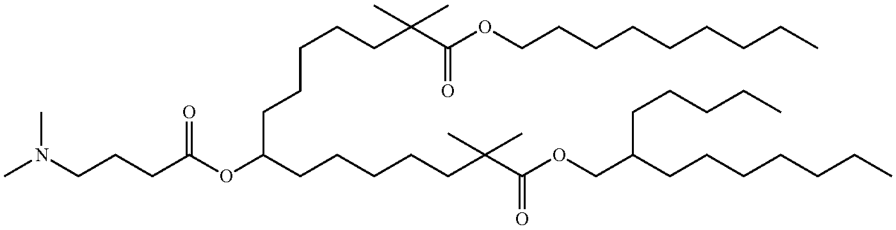
46
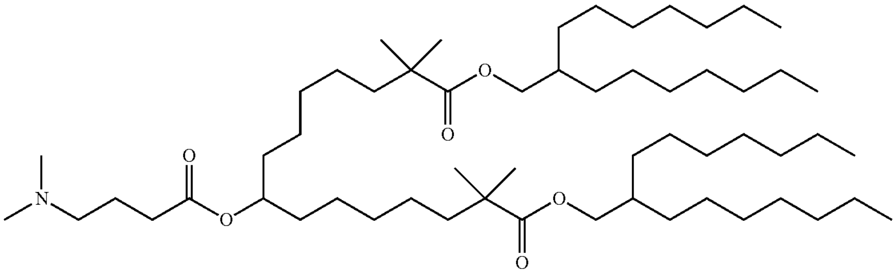
47

-continued
48
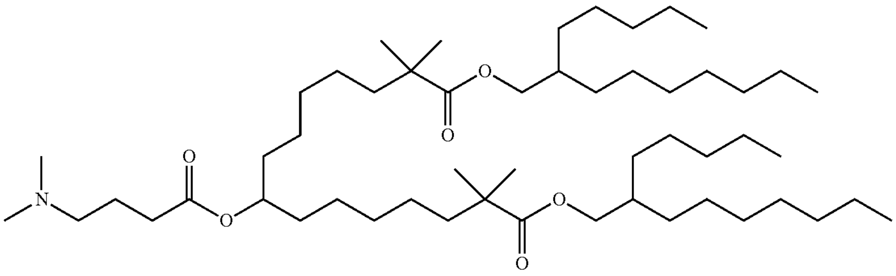
49
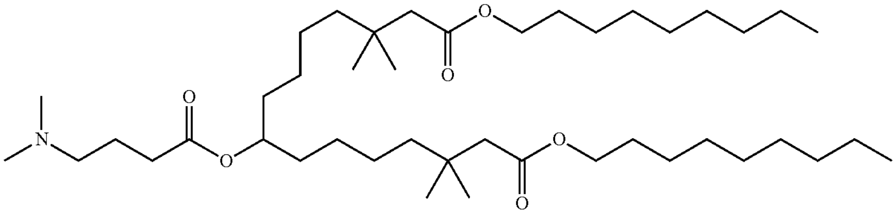
50
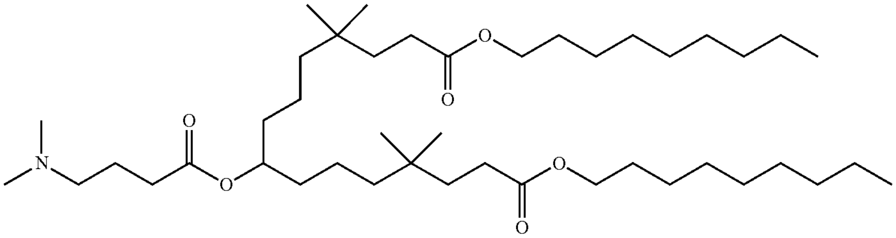
51
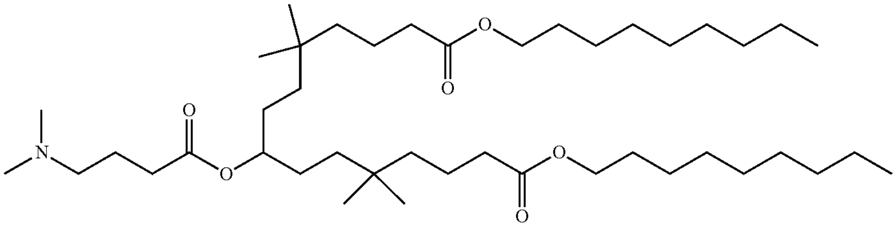
52
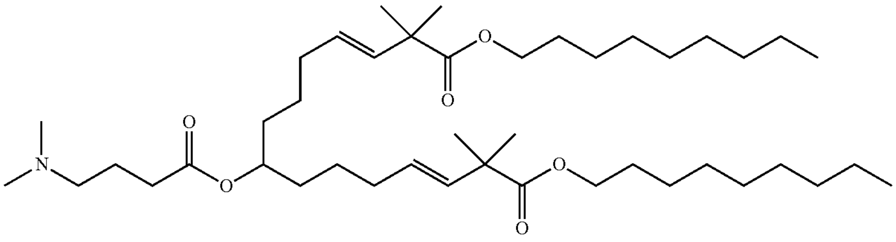
53
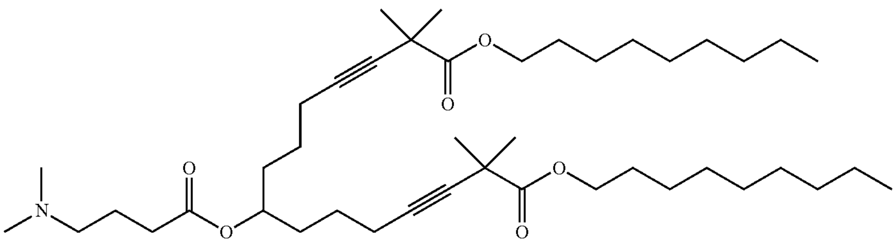

-continued
54
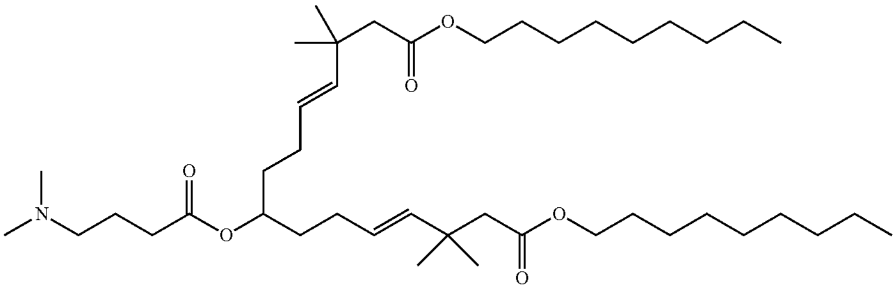
55
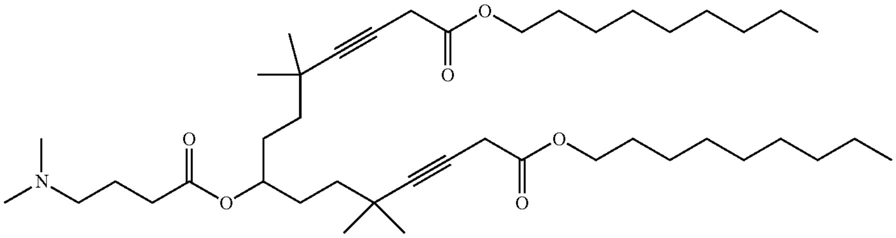
56
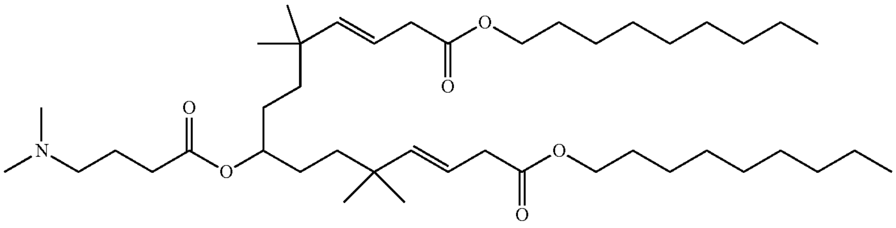
57
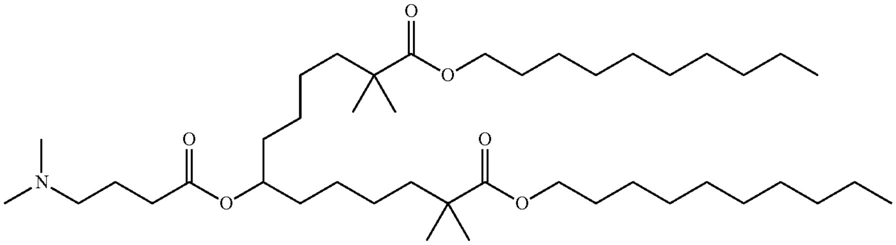
58
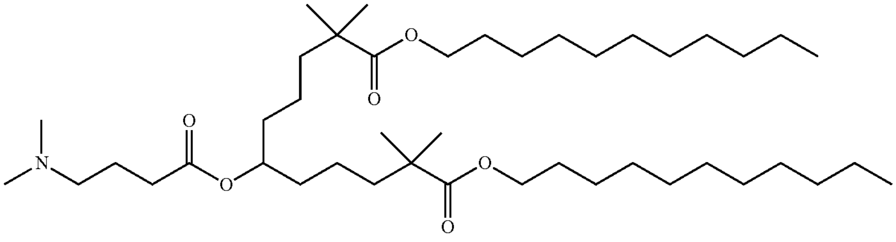
59
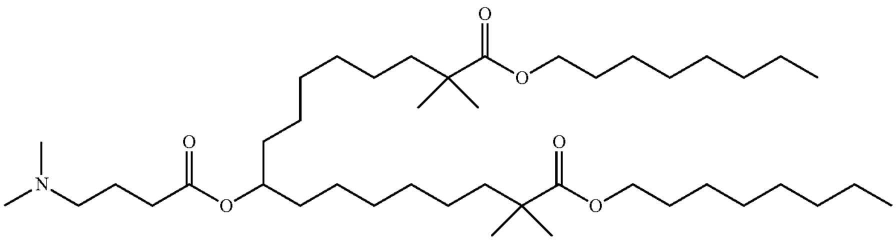

-continued
60
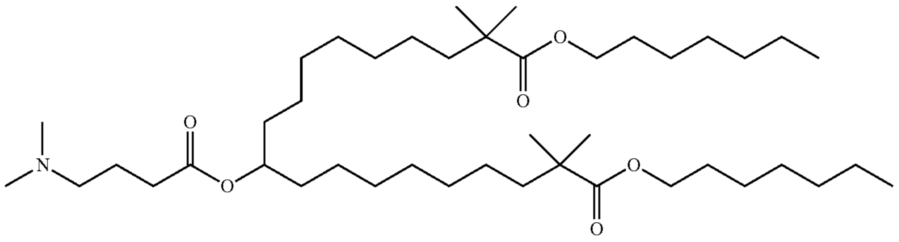
61
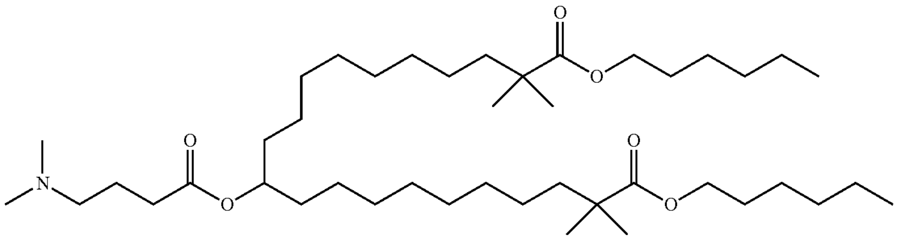
62
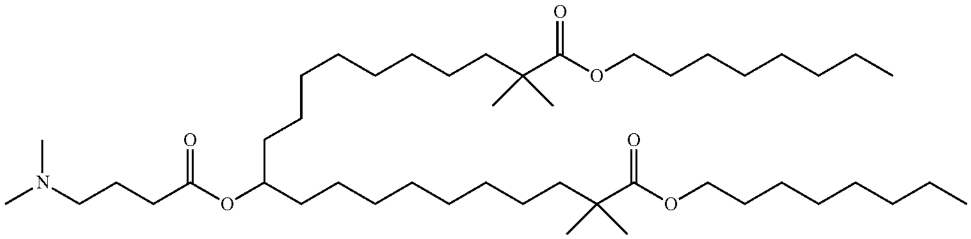
63
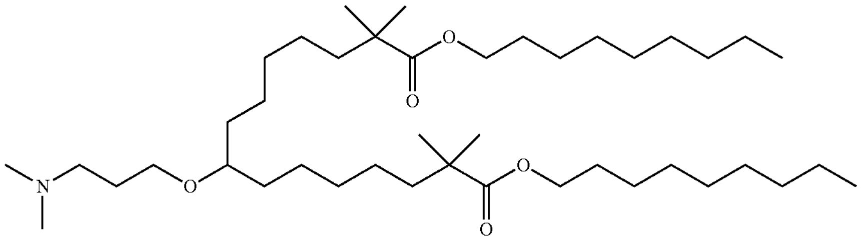
64
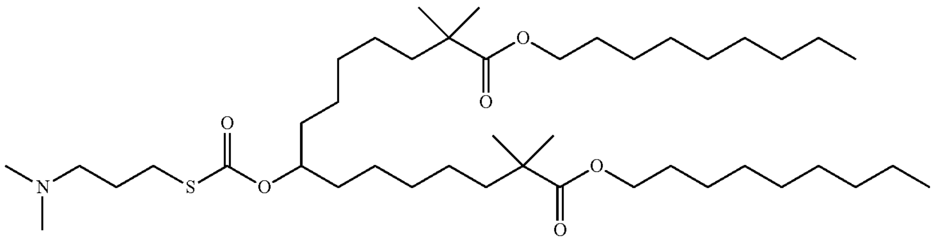
65
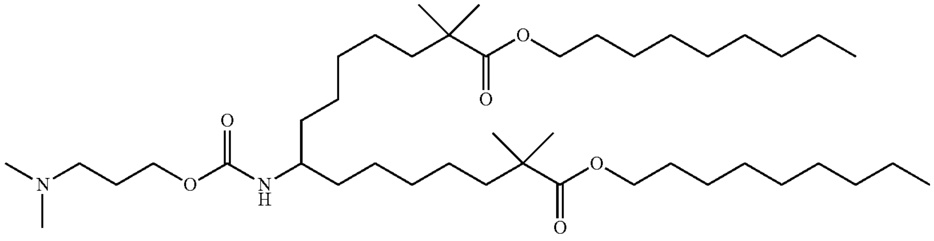

-continued
66
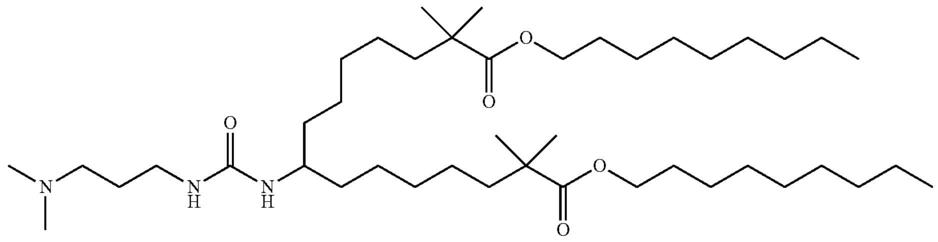
67
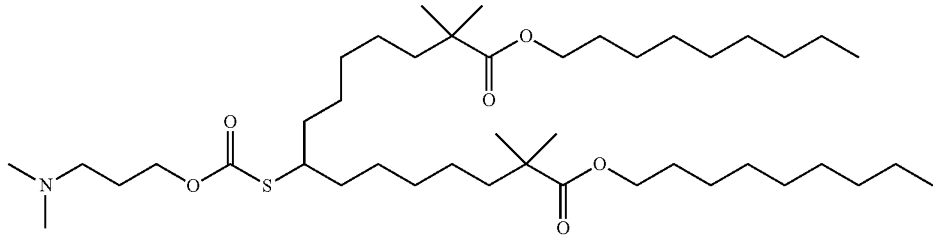
68
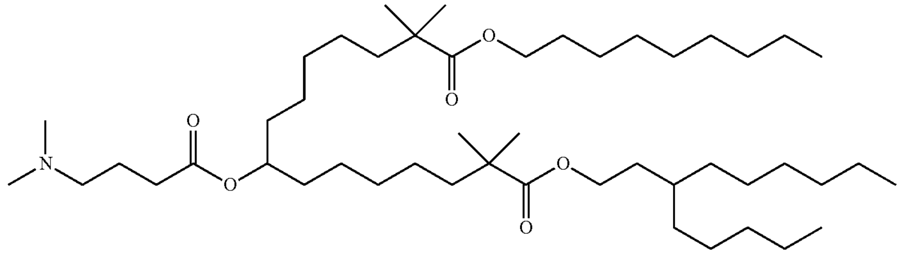
69
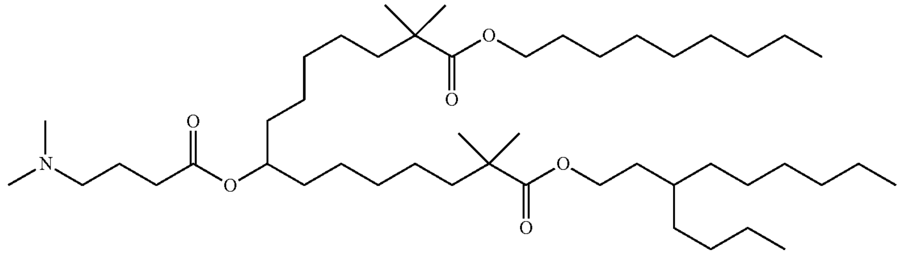
70
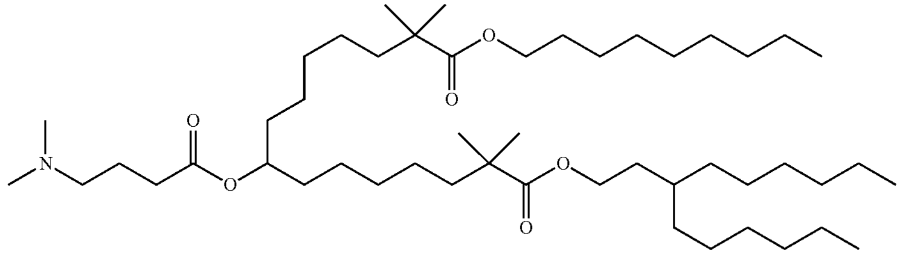
71
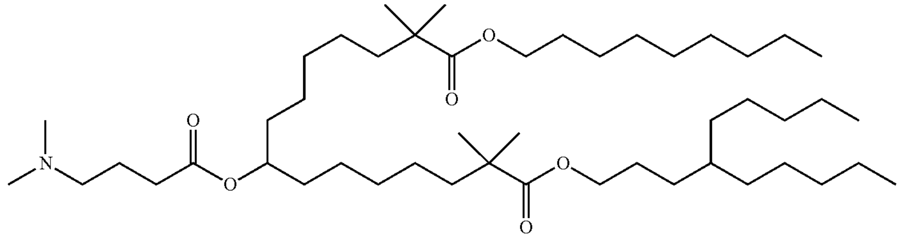

-continued
72
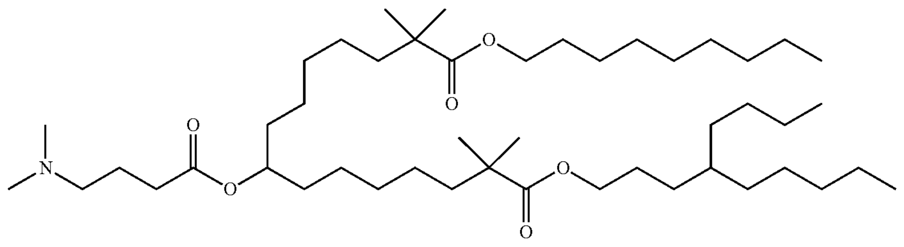
73
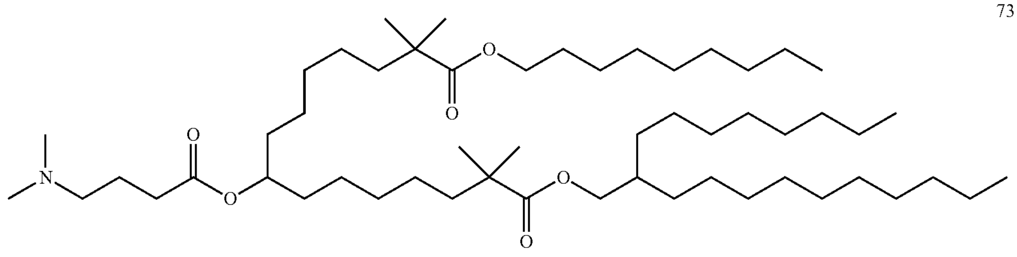
74
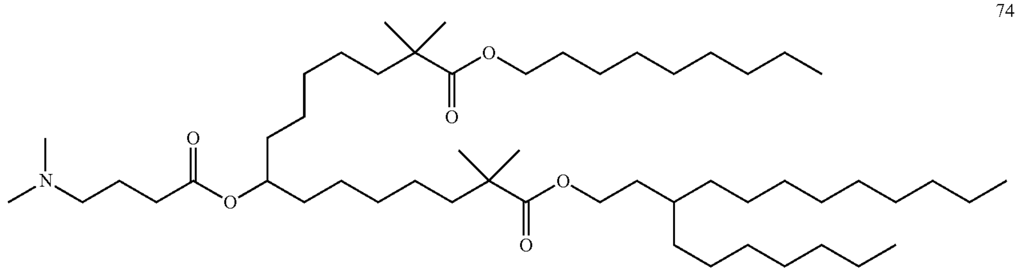
75
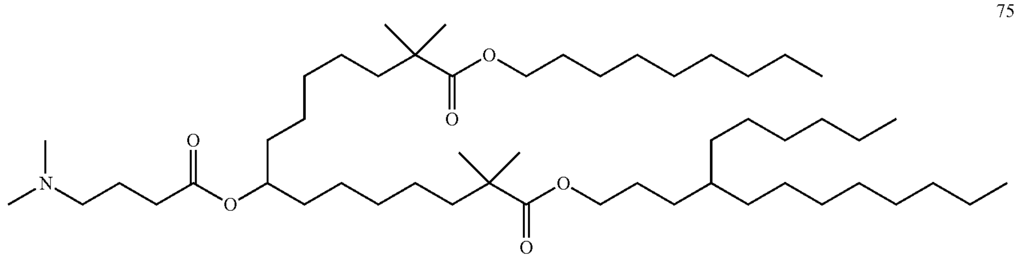
77
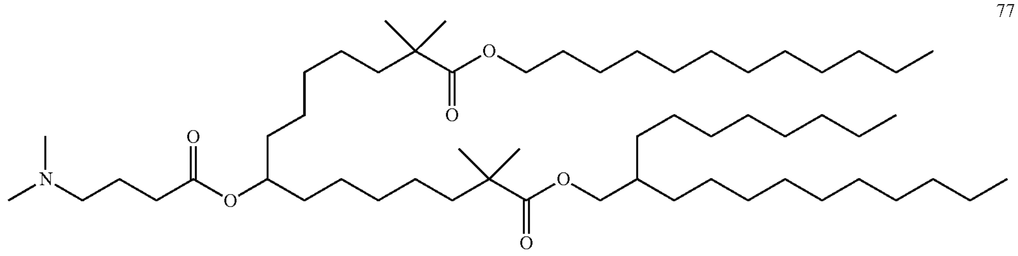
78
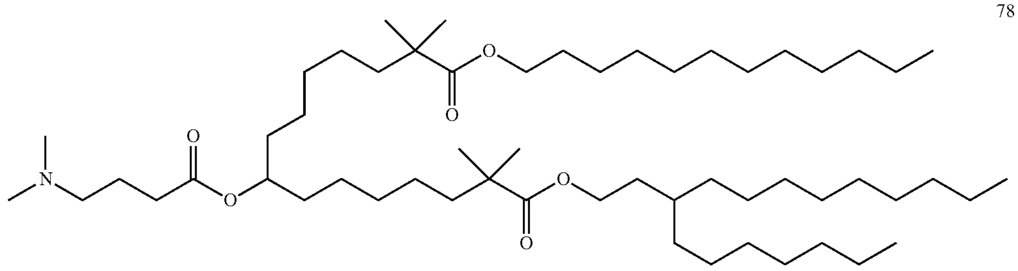

-continued
79
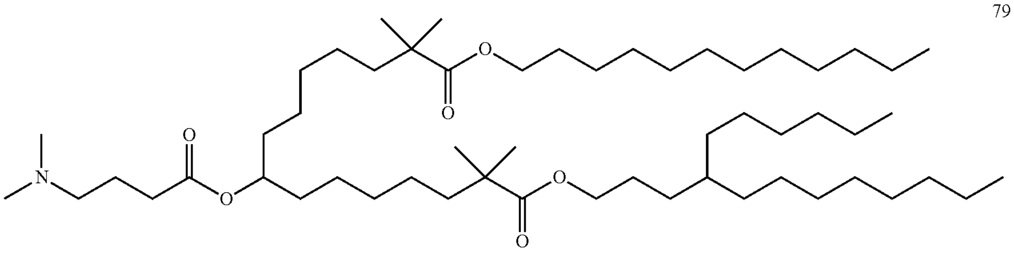
80
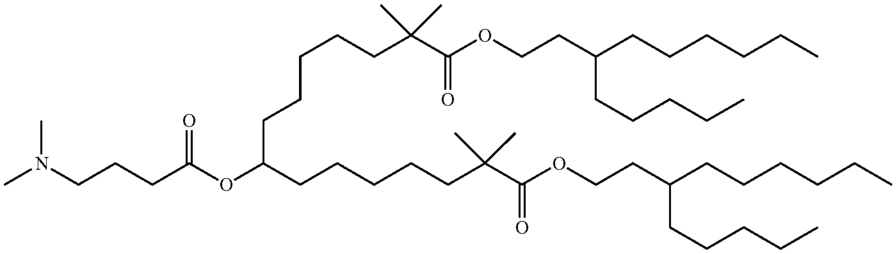
81
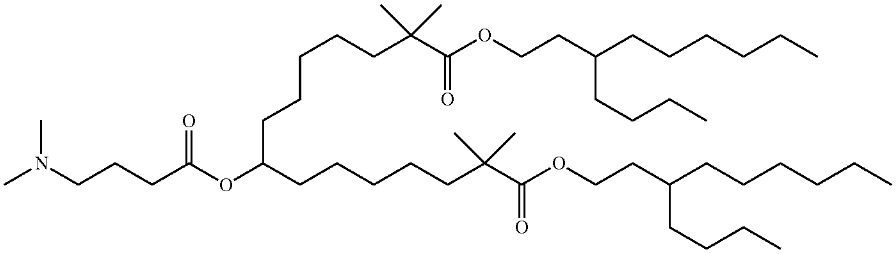
82
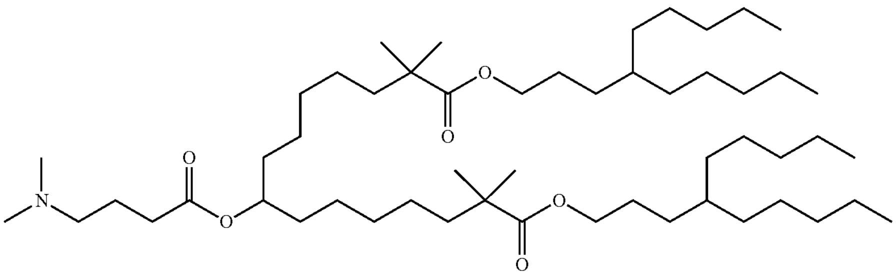
83
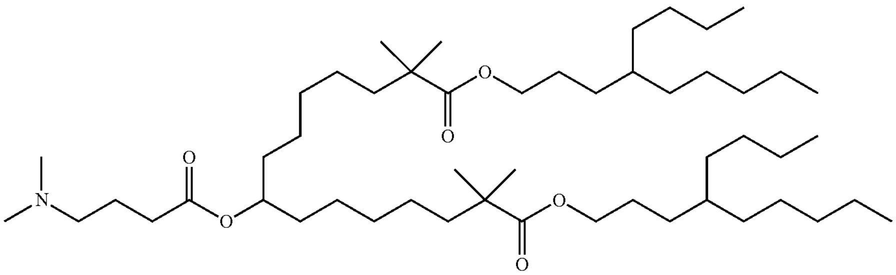
84
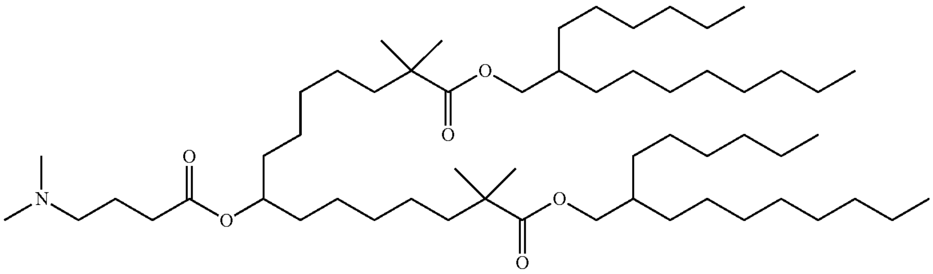

-continued
85
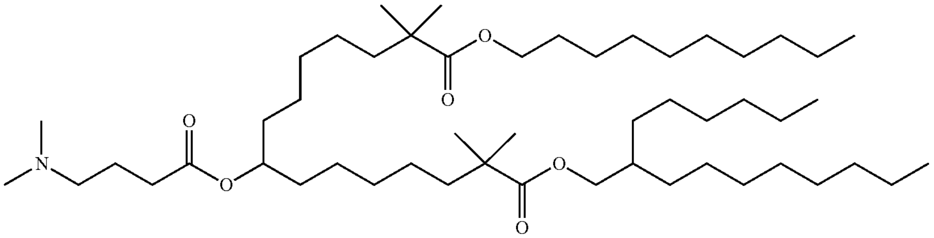
86
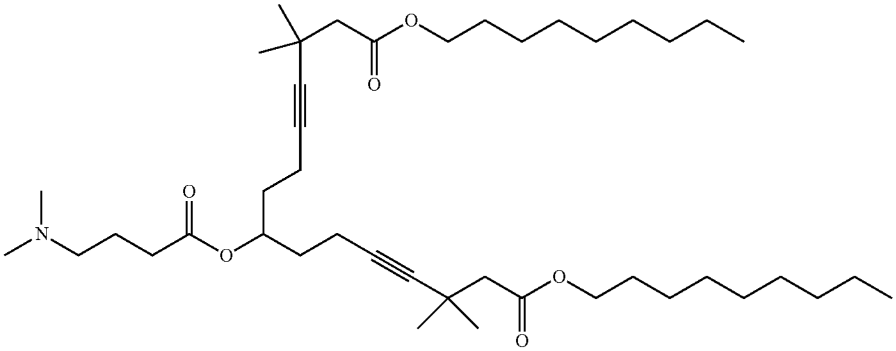
87
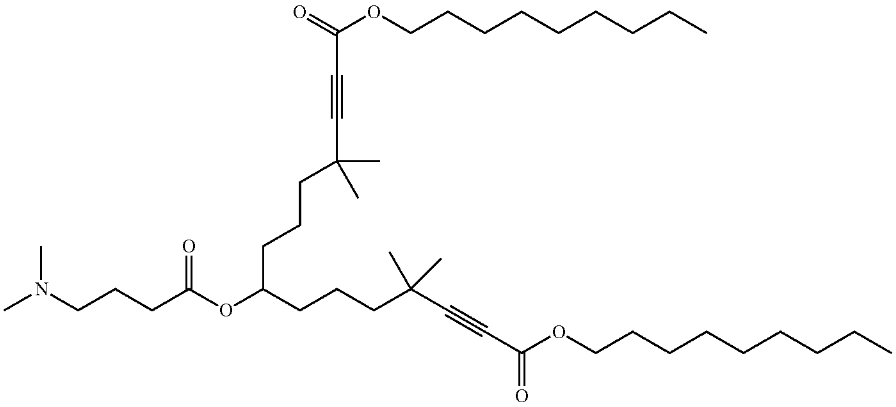
88
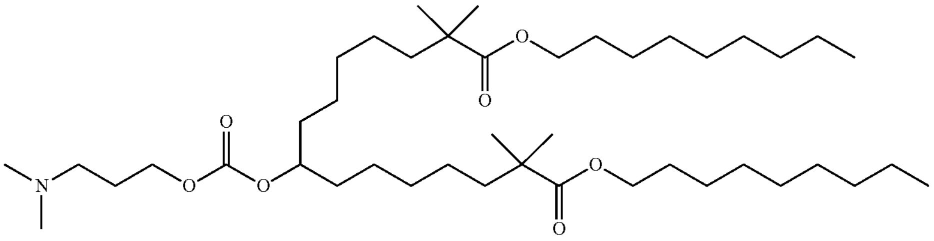
89
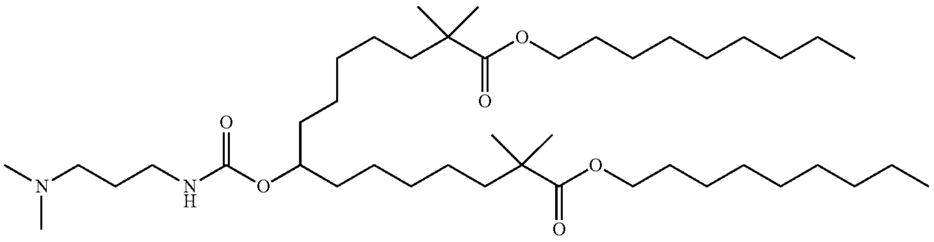

-continued
90
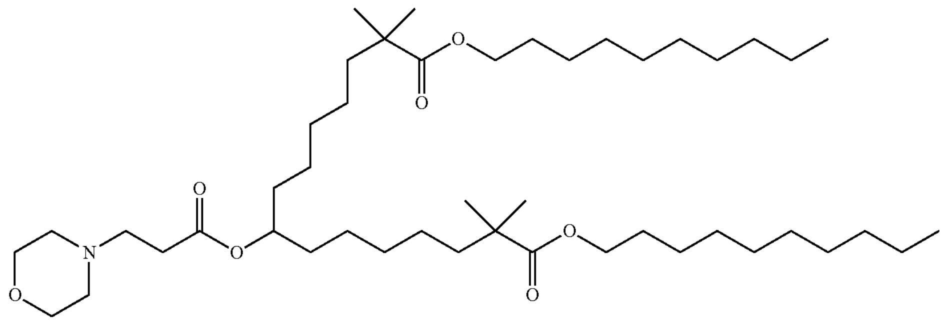
91
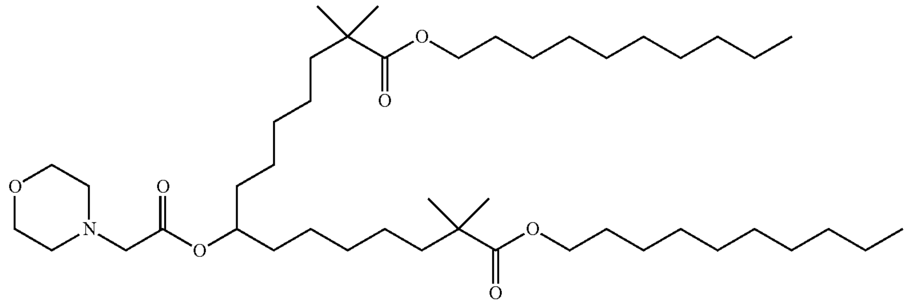
92
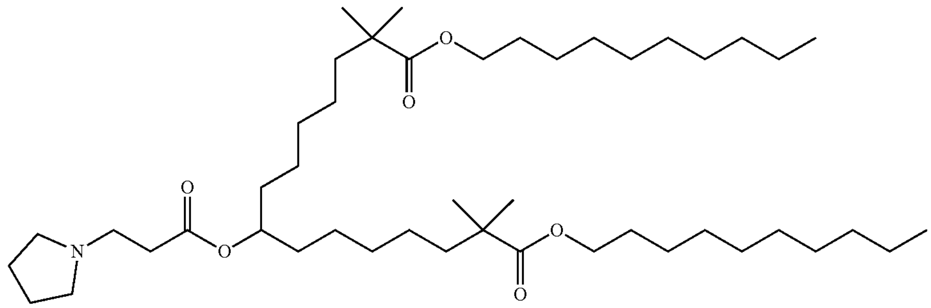
93
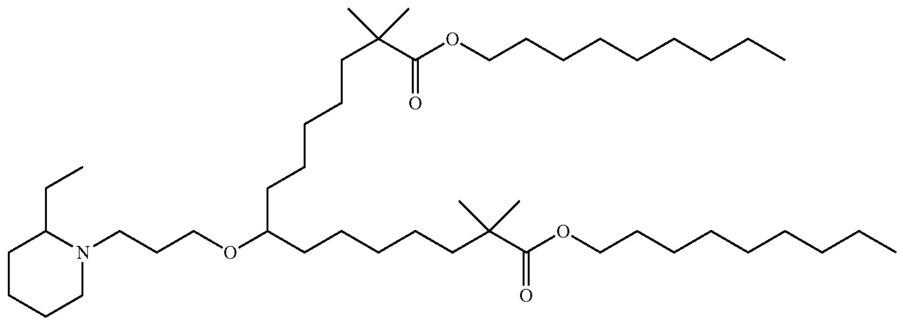
94
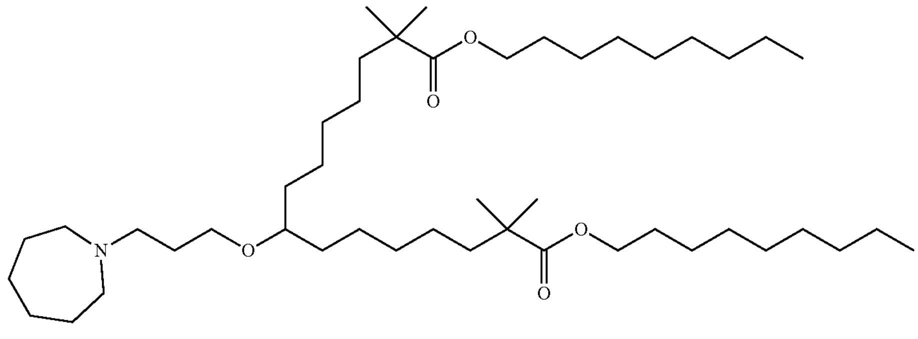

-continued
95
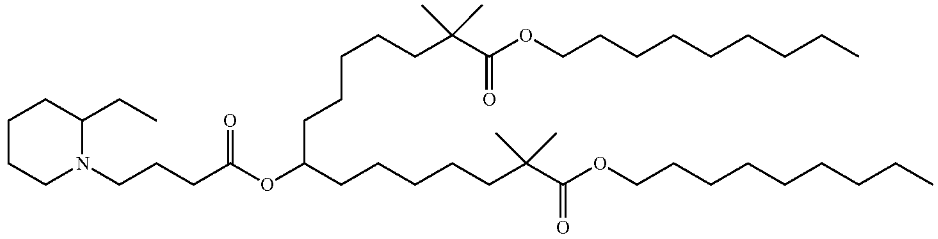
96
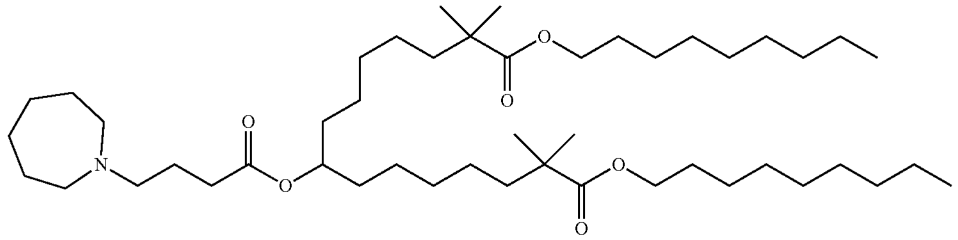
97
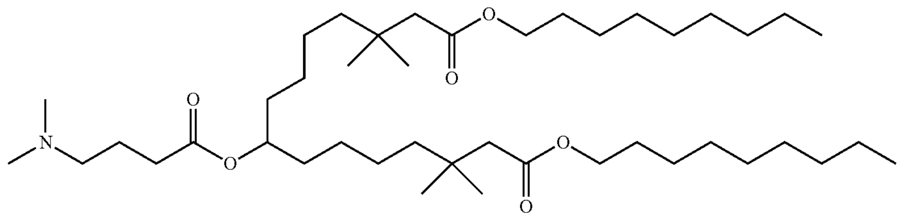
98
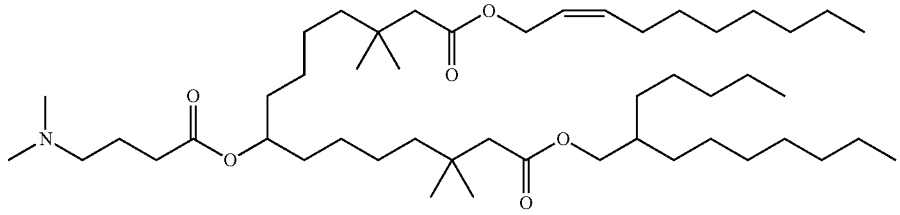
99
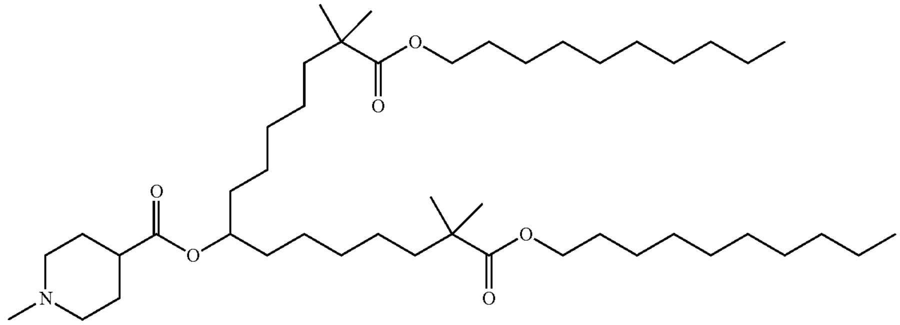
100
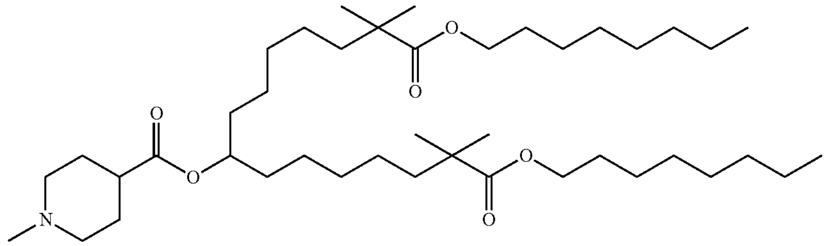

-continued
101
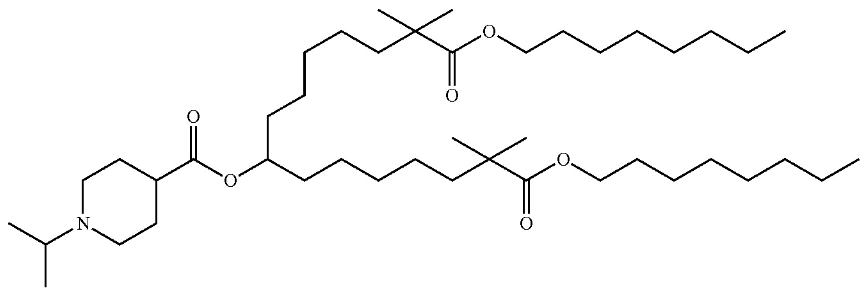
102
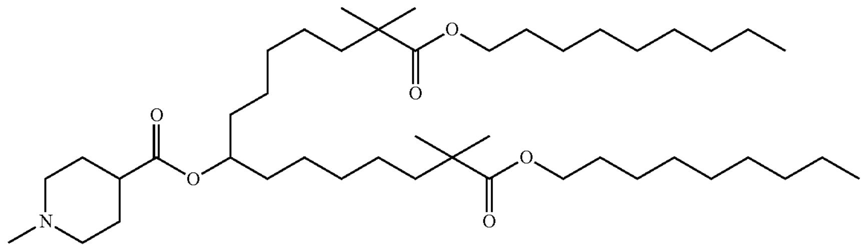
103
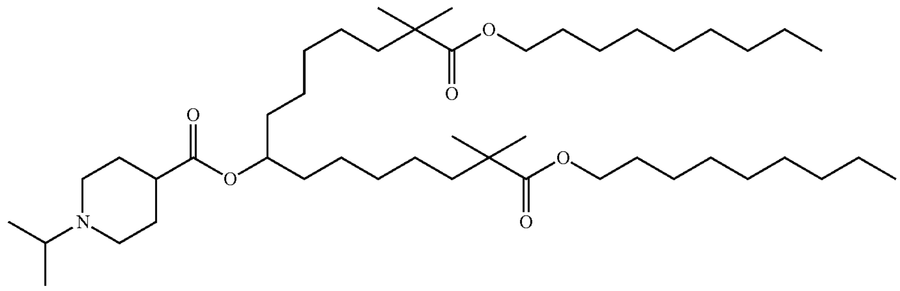
104
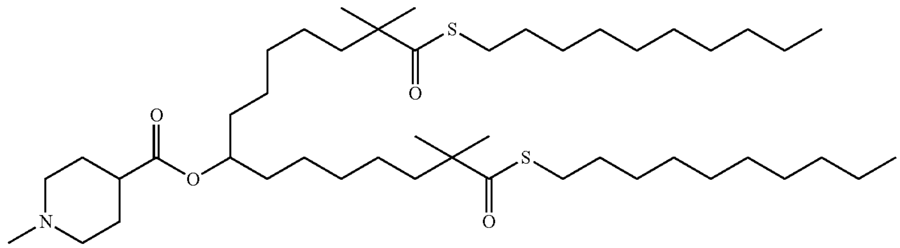
105
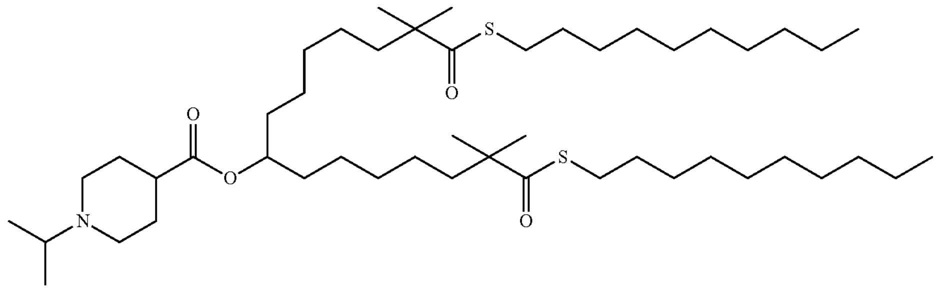
106
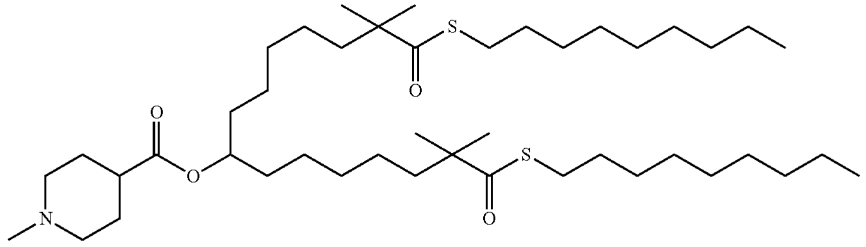

-continued
107
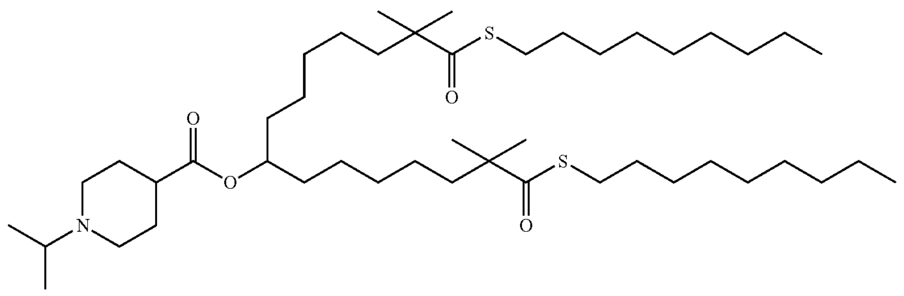
108
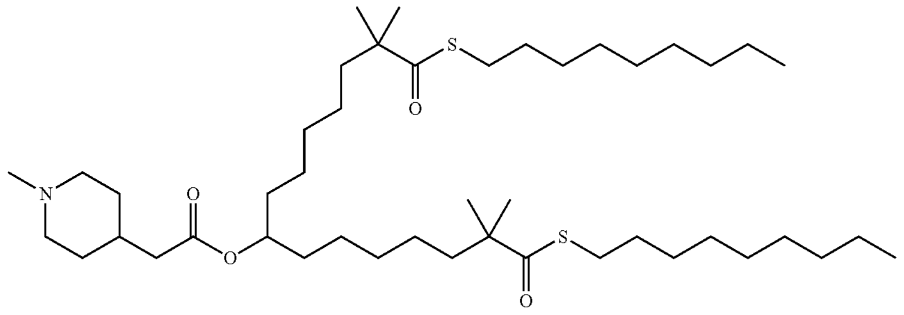
109
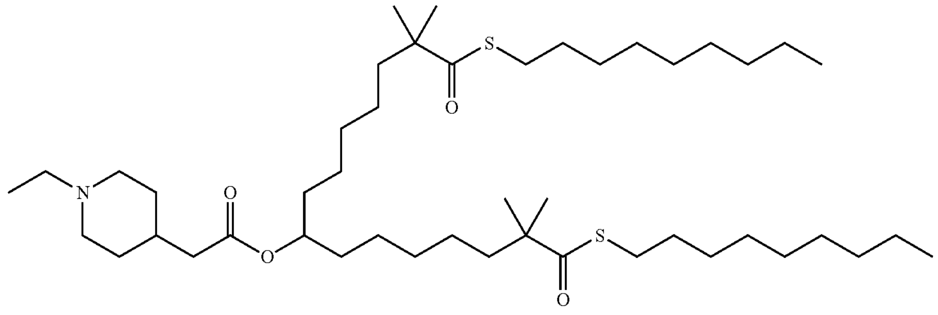
110
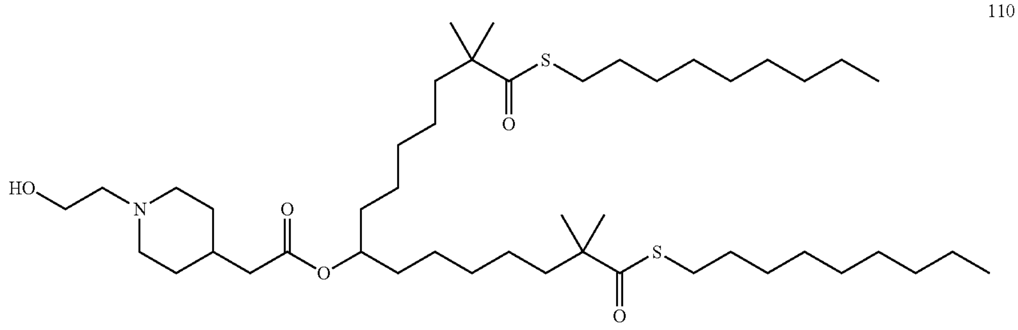
111
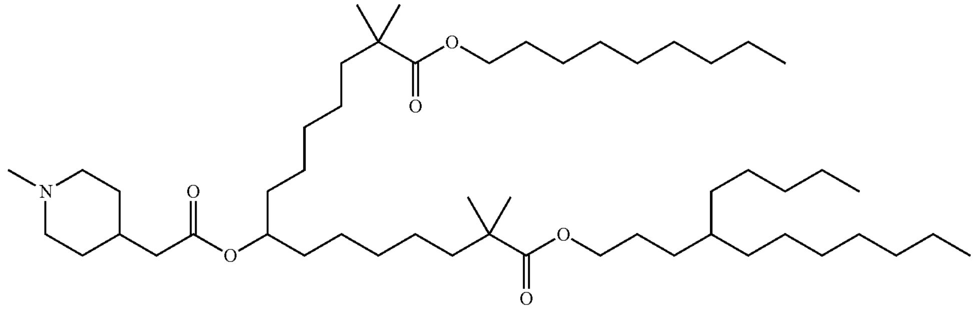

-continued
112
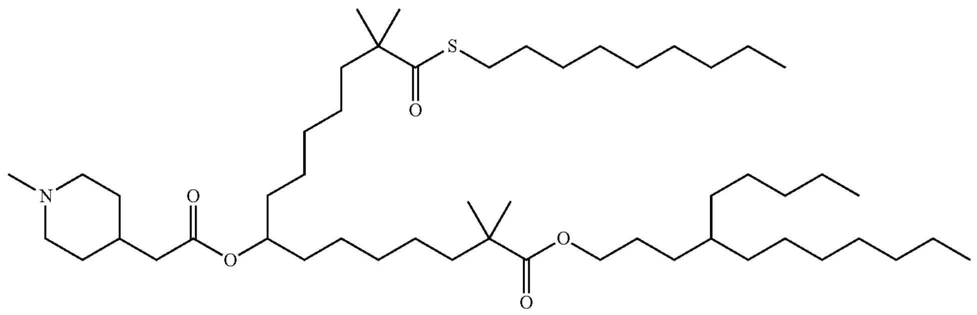
113
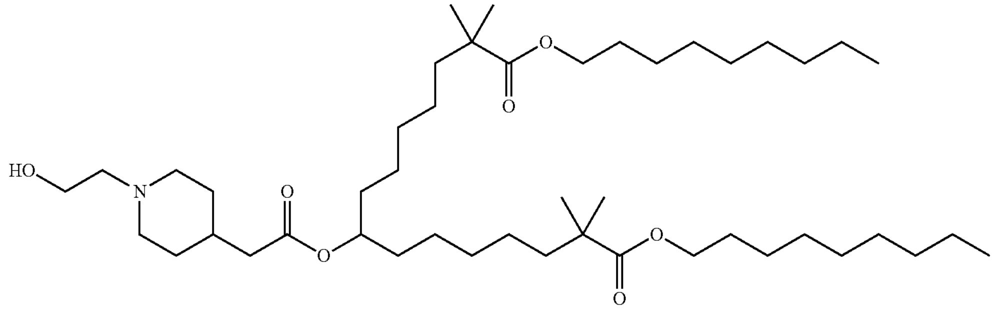
114
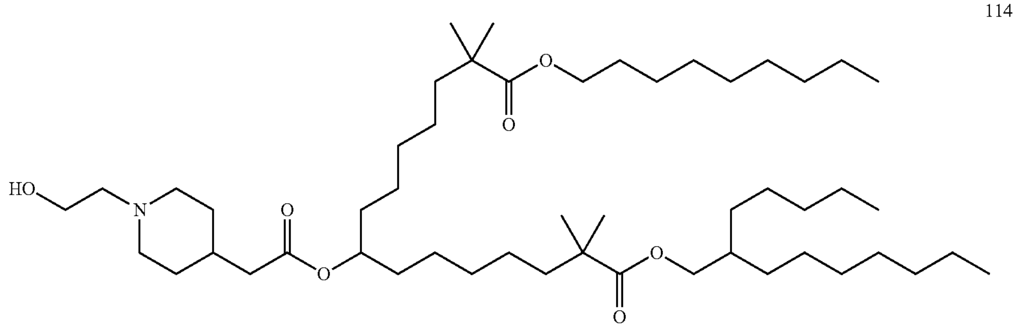
115
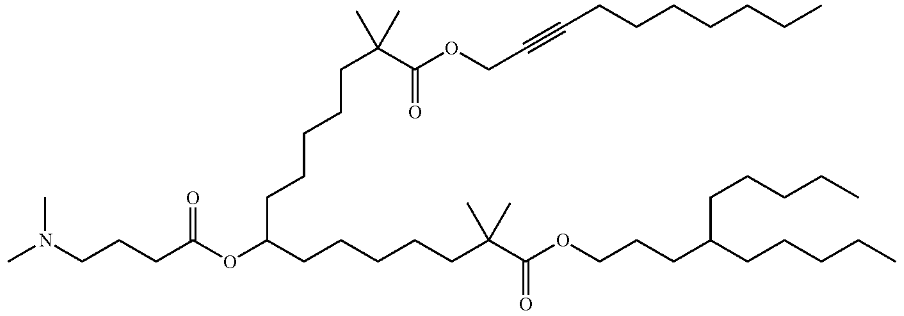
116
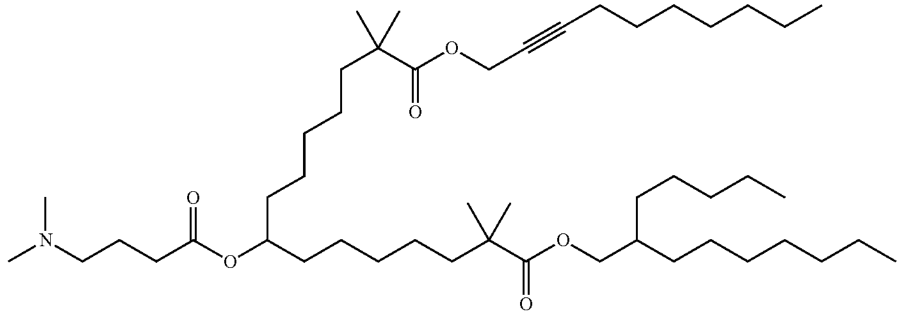

-continued
117
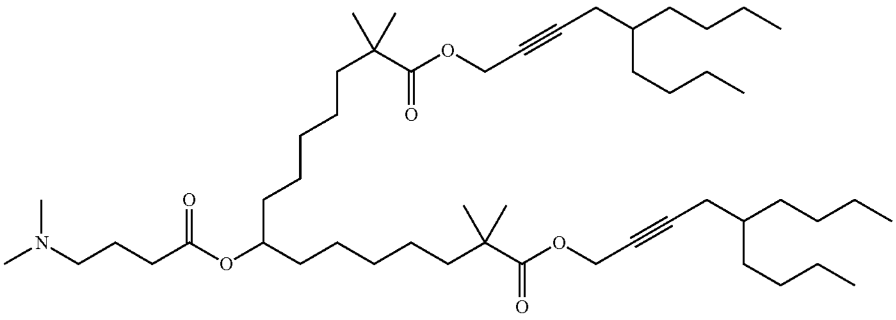
118
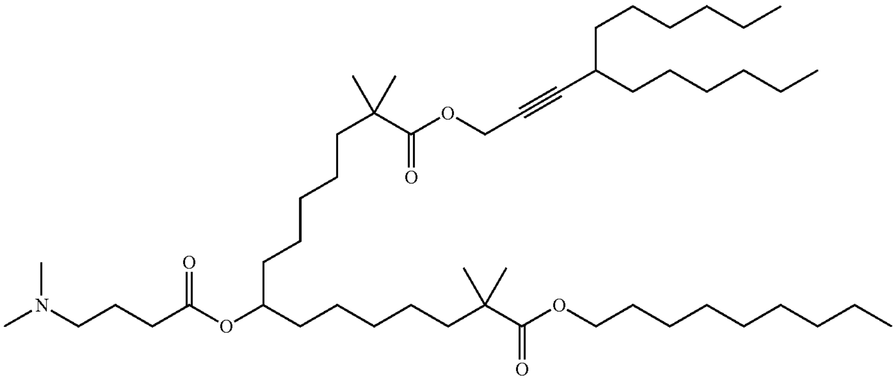
119
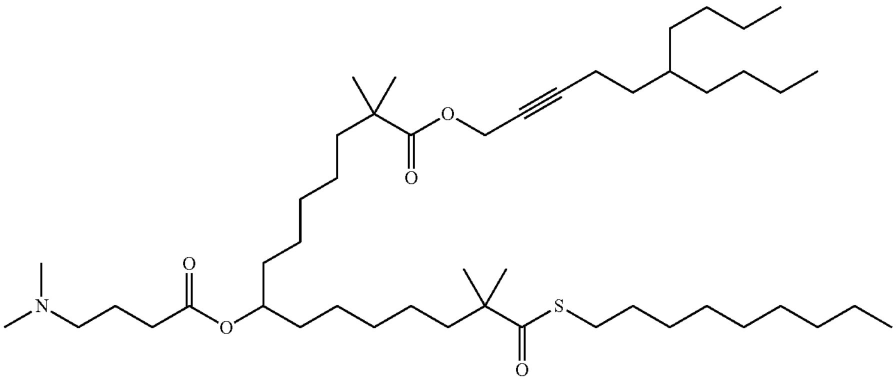
120
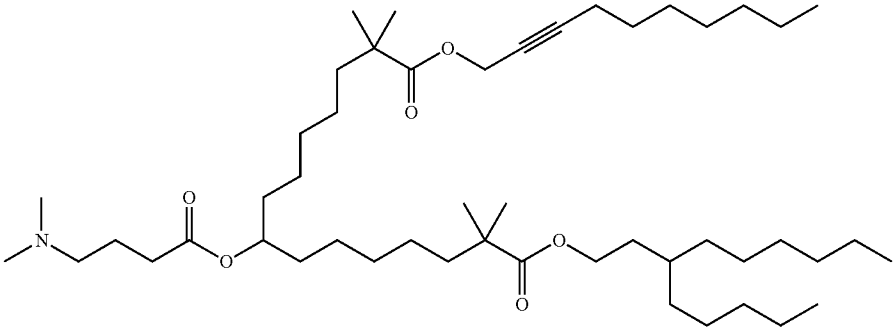

-continued
121
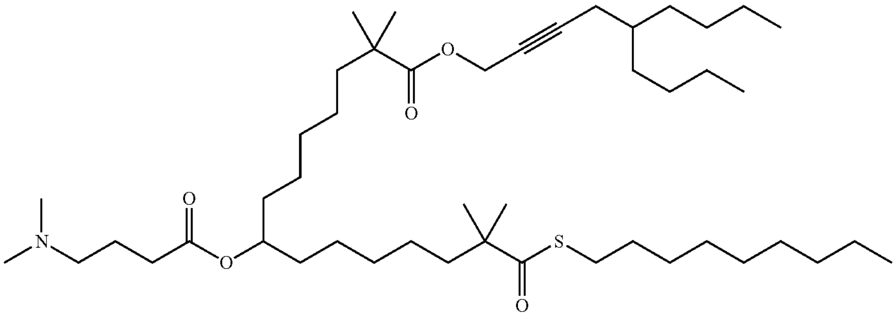
122
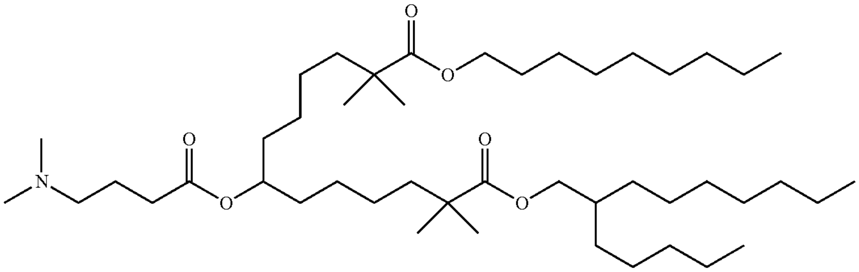
123
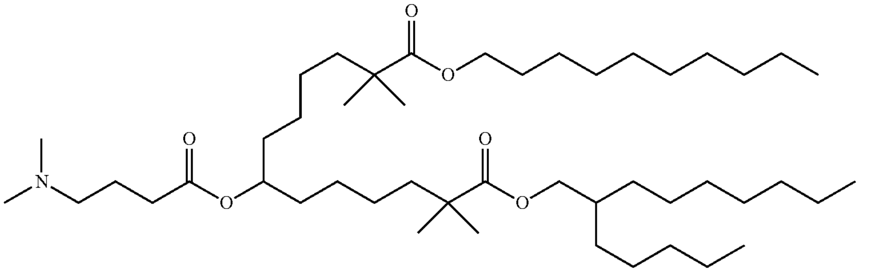
124
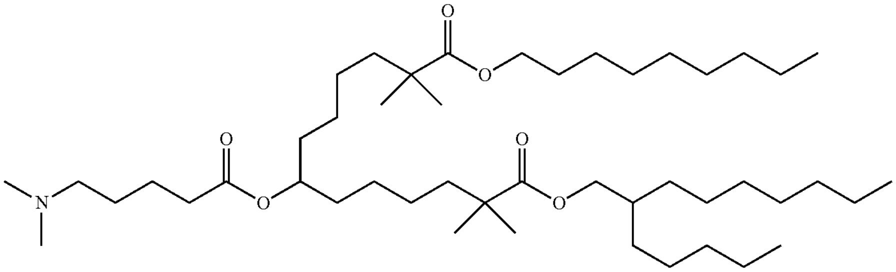
125
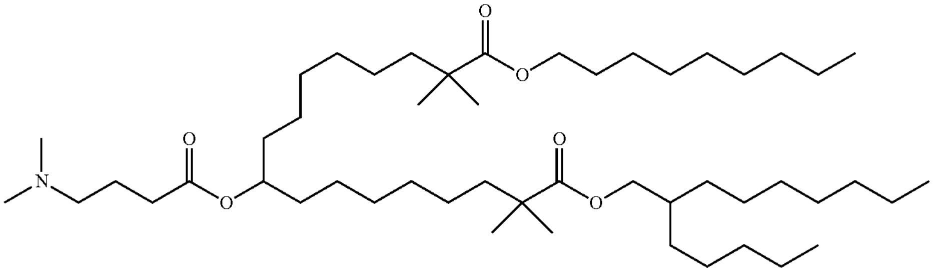

-continued

126

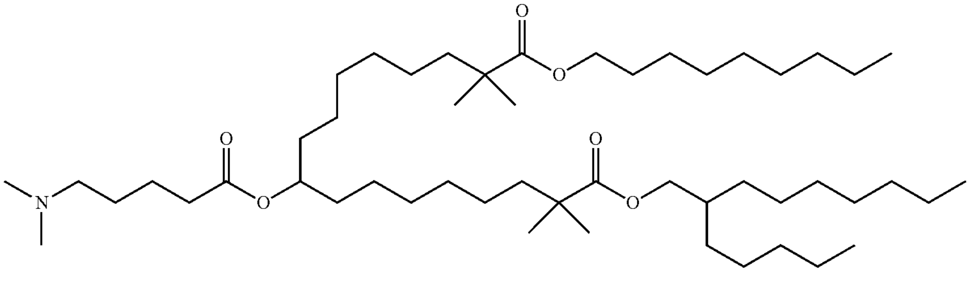

127

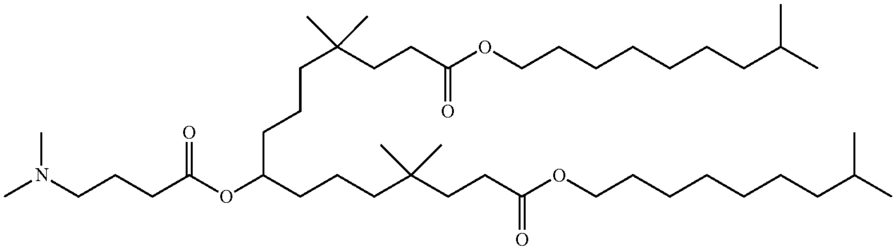

128

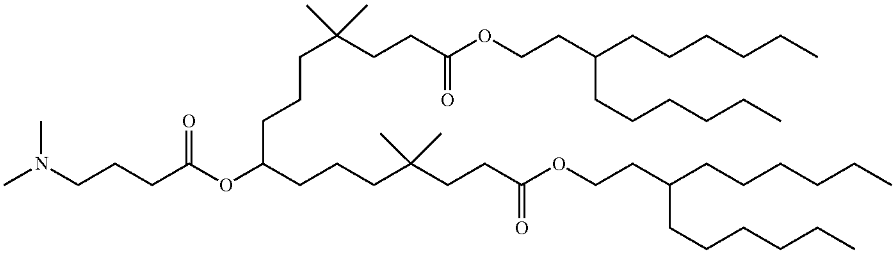

129

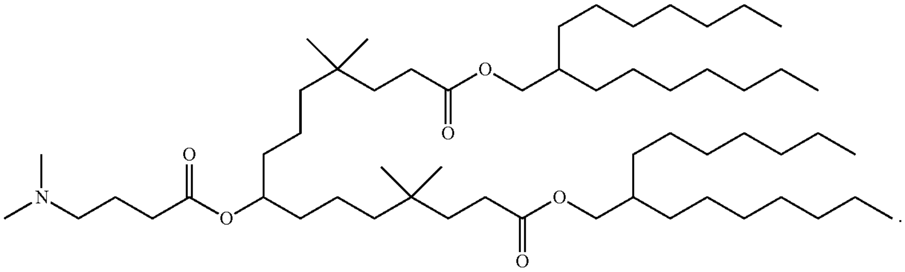

.

20. The nanoparticle composition of claim 1, wherein the load is present and comprises phosphorus atoms, and the N:P molar ratio of nitrogen (N) atoms in the ionizable cationic lipids to phosphorus (P) atoms in the load molecules is 1-15:1, alternatively 1-10:1 alternatively 3-12:1, alternatively 3-7:1, alternatively 3-6:1, alternatively 3-5:1, alternatively 6-12:1, alternatively 3-6:1, and alternatively 5:1.

21. The nanoparticle composition of claim 1, wherein the particle size of the nanoparticle is 65-200 nm, alternatively 65-180 nm, alternatively 70-170 nm, alternatively 70-130 nm, alternatively 70-180 nm, alternatively 80-180 nm, alternatively 90-180 nm, alternatively 100-135 nm, alternatively 65-160 nm, alternatively 65-150 nm, alternatively 65-140 nm, alternatively 65-130 nm alternatively 70-150 nm, alternatively 70-130 nm, alternatively 90-130 nm, alternatively 90-115 nm, and alternatively 65-75 nm.

22. The nanoparticle composition of claim 1, wherein the lipid ingredient comprises the following components in the molar percentages:

Ionizable cationic lipids 30 mol %-55 mol %, alternatively 32.5 mol %-50 mol %;

Structure lipids 28 mol %-64 mol %, alternatively 30.6 mol %-61 mol %;

Neutral lipids 5 mol %-20 mol %;

Polymer lipids 1 mol %-3 mol %, alternatively 1 mol %-2 mol %;

the ionizable cationic lipid is
46
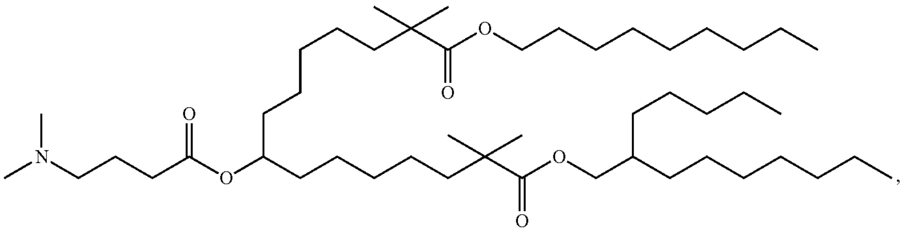,
122
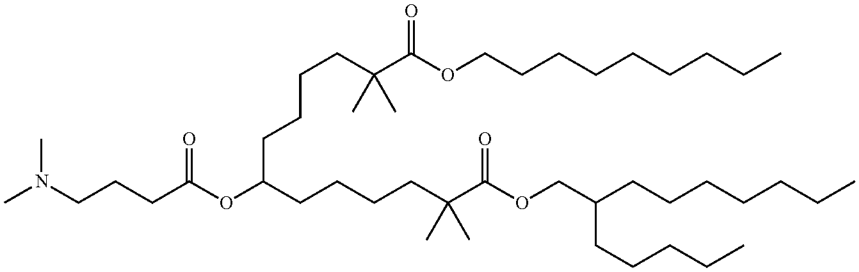,
123
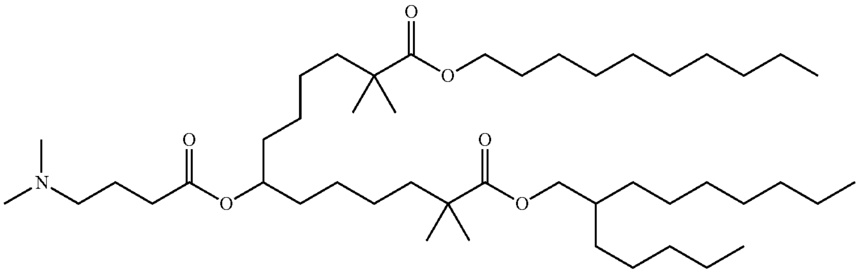 or
126
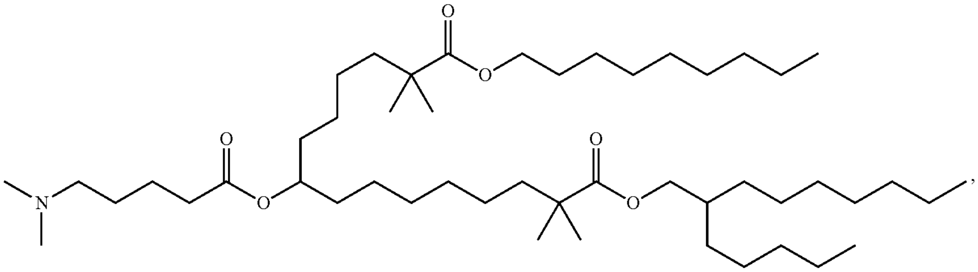,
alternatively is:
46
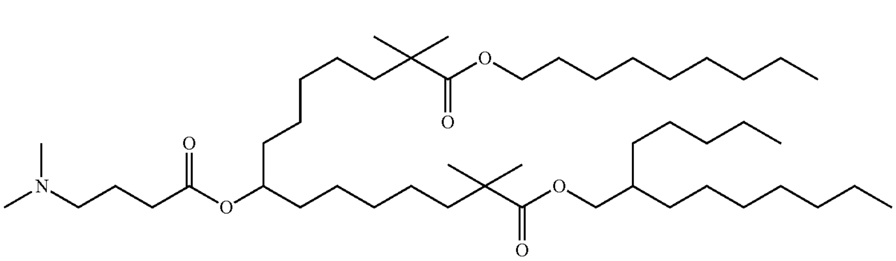;
alternatively, the lipid ingredient comprises the following components in the molar percentages:
Ionizable cationic lipids 40 mol %-52.5 mol %, alternatively 42.5 mol %-50 mol %;
Structure lipids 28 mol %-54 mol %, alternatively 30.6 mol %-51 mol %;
Neutral lipids 5 mol %-20 mol %;
Polymer lipids 1 mol %-3 mol %, alternatively 1 mol %-2 mol %.

23. The nanoparticle composition of claim 1, wherein the lipid ingredient comprises the following components in the molar percentages:

Ionizable cationic lipids 30 mol %-60 mol %;

Structure lipids 27.5 mol %-66 mol %;

Neutral lipids 1.5 mol %-20 mol %;

Polymer lipids 1.5 mol %-5 mol %;

The ionizable cationic

41

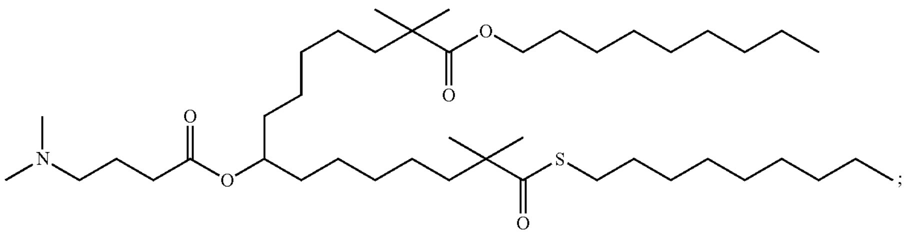

alternatively is:

18

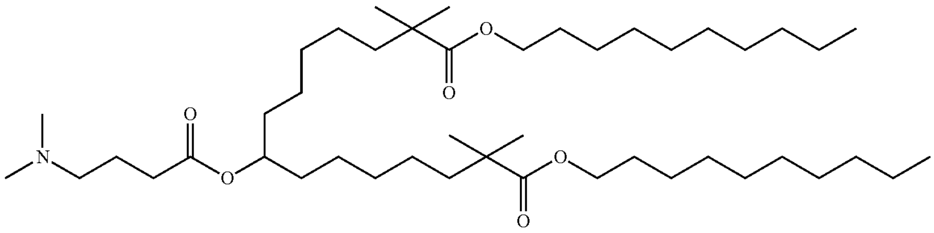

or

20

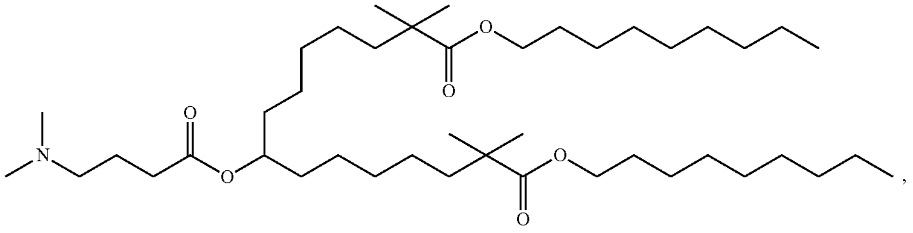

alternatively is:

20

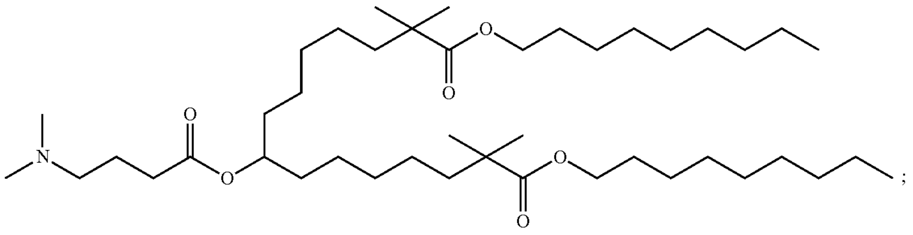

alternatively, the lipid ingredient comprises the following components in the molar percentages:

Ionizable cationic lipids 30 mol %-50 mol %;

Structure lipids 35 mol %-66 mol %;

Neutral lipids 1.5 mol %-20 mol %;

Polymer lipids 1.5 mol %-5 mol %;

alternatively, the lipid ingredient comprises the following components in the molar percentages:

Ionizable cationic lipids 30 mol %-50 mol %;

Structure lipids 38.5 mol %-63.5 mol %;

Neutral lipids 1.5 mol %-10 mol %;

Polymer lipids 1.5 mol %-4 mol %, alternatively 1.5 mol %-3.5 mol %;

alternatively, the lipid ingredient comprises the following components in the molar percentages:

Ionizable cationic lipids 30 mol %-50 mol %, alternatively 30 mol %-48.5 mol %;

Structure lipids 43 mol %-60 mol %, alternatively 45.5 mol %-57.5 mol %;

Neutral lipids 1.5 mol %-10 mol %;

Polymer lipids 1.5 mol %-4 mol %, alternatively 1.5 mol %-3.5 mol %.

24. The nanoparticle composition of claim 1, wherein the lipid ingredient comprises the following components in the molar percentages:

Ionizable cationic lipids 27.5 mol %-55 mol %, alternatively 30 mol %-50 mol %;

Structure lipids 35 mol %-68.5 mol %, alternatively 38.5 mol %-66 mol %;

Neutral lipids 1.5 mol %-20 mol %, alternatively 2.5 mol %-15 mol %;

Polymer lipids 1 mol %-5 mol %, alternatively 1.5 mol %-3.5 mol %;

the ionizable cationic lipid is

26

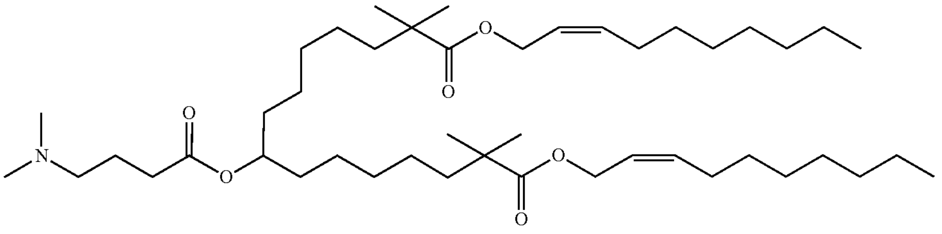

,

27

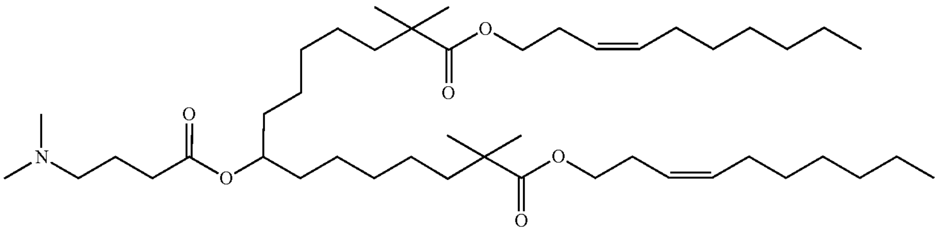

or

98

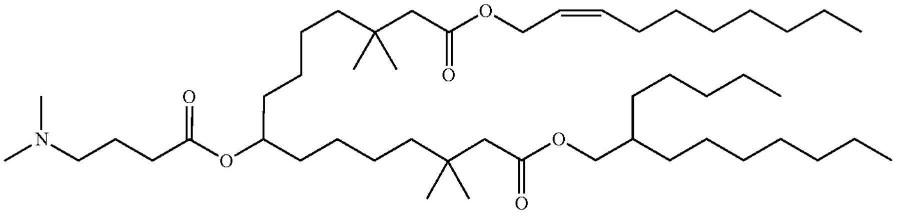

, alternatively is:

26

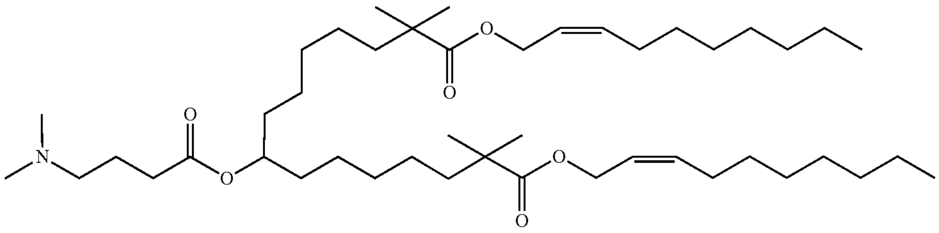

;

alternatively, the lipid ingredient comprises the following components in the molar percentages:

Ionizable cationic lipids 27.5 mol %-42.5 mol %, alternatively 30 mol %-40 mol %;

Structure lipids 41 mol %-68.5 mol %, alternatively 43.5 mol %-66 mol %;

Neutral lipids 2 mol %-18 mol %, alternatively 2.5 mol %-15 mol %;

Polymer lipids 1 mol %-4 mol %, alternatively 1.5 mol %-3.5 mol %.

25. The nanoparticle composition of claim 1, wherein the neutral lipids are selected from one or more of DSPC, DMPC, DOPC, DPPC, POPC, DOPE, DMPE, POPE and DPPE, alternatively DSPC and/or DOPE.

26. The nanoparticle composition of claim 1, wherein the structure lipids are selected from one or more of cholesterol, sitosterol, coprosterol, fucosterol, brassicasterol, ergosterol, tomatine, ursolic acid, α-tocopherol, stigmasterol, avenasterol, ergocalciferol and campesterol, alternatively cholesterol and/or β-sitosterol.

27. The nanoparticle composition of claim 1, wherein the polymer lipids are polyethylene glycolated lipids.

28. The nanoparticle composition of claim 1, wherein the load is present and is selected from one or more of therapeutic, prophylactic and diagnostic agents.

29. The nanoparticle composition of claim 27, wherein the polyethylene glycolated lipids are selected from one or more of DMPE-PEG1000, DPPE-PEG1000, DSPE-PEG1000, DOPE-PEG1000, DMG-PEG2000, Ceramide-PEG2000, DMPE-PEG2000, DPPE-PEG2000, DSPE-PEG2000, Azido-PEG2000, DSPE-PEG2000-Mannose, Ceramide-PEG5000, and DSPE-PEG5000.

30. The nanoparticle composition of claim 28, wherein the therapeutic, prophylactic or diagnostic agent is a nucleic acid.

31. A method for preparing the nanoparticle composition of claim 1, comprising: mixing the ionizable cationic lipids, the structure lipids, the neutral lipids, and the polymer lipids, and subsequently optionally mixing with a load.

32. A pharmaceutical composition, comprising the nanoparticle composition of claim 1, and pharmaceutically acceptable excipient(s).

33. The method of claim 31, wherein the mixing with a load occurs and the load is present, and the load is a nucleic acid, which is dissolved with a 20-30 mmol/L sodium acetate solution.

34. A method of treating, diagnosing, or preventing a disease in a subject, comprising administering to the subject the pharmaceutical composition of claim 32, wherein the load is present and is capable of treating, diagnosing, or preventing said disease.

35. A method of delivering a load in a subject, comprising administering to the subject the pharmaceutical composition of claim 32; wherein the load is present and is one or more of therapeutic, prophylactic or diagnostic agents.

* * * * *